(12) United States Patent
Liu et al.

(10) Patent No.: US 12,030,857 B2
(45) Date of Patent: Jul. 9, 2024

(54) GLUCOSE UPTAKE INHIBITORS

(71) Applicant: Kadmon Corporation, LLC, Bridgewater, NJ (US)

(72) Inventors: Kevin G. Liu, West Windsor, NJ (US); Kellen L. Olszewski, Brooklyn, NY (US); Ji-In Kim, Princeton, NJ (US); Masha V. Poyurovsky, New York, NY (US); Koi Morris, Plainsboro, NJ (US); Xuemei Yu, Livingston, NJ (US); Christophe Lamarque, Princeton, NJ (US)

(73) Assignee: Kadmon Corporation, LLC, Bridgewater, NJ (US)

( * ) Notice: Subject to any disclaimer, the term of this patent is extended or adjusted under 35 U.S.C. 154(b) by 2 days.

(21) Appl. No.: 16/973,941

(22) PCT Filed: Jun. 25, 2019

(86) PCT No.: PCT/US2019/038975
§ 371 (c)(1),
(2) Date: Dec. 10, 2020

(87) PCT Pub. No.: WO2020/005935
PCT Pub. Date: Jan. 2, 2020

(65) Prior Publication Data
US 2022/0363648 A1     Nov. 17, 2022

Related U.S. Application Data

(60) Provisional application No. 62/689,533, filed on Jun. 25, 2018.

(51) Int. Cl.
| | | |
|---|---|---|
| C07D 239/42 | (2006.01) |
| C07D 239/94 | (2006.01) |
| C07D 401/12 | (2006.01) |
| C07D 401/14 | (2006.01) |
| C07D 403/04 | (2006.01) |
| C07D 403/12 | (2006.01) |
| C07D 405/12 | (2006.01) |
| C07D 405/14 | (2006.01) |
| C07D 409/12 | (2006.01) |
| C07D 413/12 | (2006.01) |
| C07D 413/14 | (2006.01) |
| C07D 417/12 | (2006.01) |
| C07D 471/04 | (2006.01) |
| C07D 473/34 | (2006.01) |
| C07D 491/048 | (2006.01) |
| C07D 491/052 | (2006.01) |
| C07D 495/04 | (2006.01) |
| C07D 519/00 | (2006.01) |

(52) U.S. Cl.
CPC ......... *C07D 239/42* (2013.01); *C07D 239/94* (2013.01); *C07D 401/12* (2013.01); *C07D 401/14* (2013.01); *C07D 403/04* (2013.01); *C07D 403/12* (2013.01); *C07D 405/12* (2013.01); *C07D 405/14* (2013.01); *C07D 409/12* (2013.01); *C07D 413/12* (2013.01); *C07D 413/14* (2013.01); *C07D 417/12* (2013.01); *C07D 471/04* (2013.01); *C07D 473/34* (2013.01); *C07D 491/048* (2013.01); *C07D 491/052* (2013.01); *C07D 495/04* (2013.01); *C07D 519/00* (2013.01)

(58) Field of Classification Search
CPC ................ C07D 239/94; C07D 403/12; A61K 31/4155; A61K 31/517
See application file for complete search history.

(56) References Cited

U.S. PATENT DOCUMENTS

| | | | |
|---|---|---|---|
| 6,638,926 B2 * | 10/2003 | Davies ................... | A61P 37/06 |
| | | | 514/217.05 |
| 11,071,735 B2 * | 7/2021 | Kim ..................... | C07D 403/12 |
| 2012/0238540 A1 | 9/2012 | Holcomb et al. | |

FOREIGN PATENT DOCUMENTS

| | | | |
|---|---|---|---|
| WO | WO 2012/040499 | * | 3/2012 |
| WO | 2016210330 A1 | | 12/2016 |

OTHER PUBLICATIONS

Wang et al., Mtb PKNA/PKNB Dual Inhibition Provides Selectivity Advantages for Inhibitor Design To Minimize Host Kinase Interactions, ACS Medicinal Chemistry Letters, vol. 8, Issue 12, pp. 1224-1229 (2017).*

* cited by examiner

*Primary Examiner* — Deepak R Rao
(74) *Attorney, Agent, or Firm* — McNeill Baur PLLC

(57) ABSTRACT

This invention provides compounds that modulate glucose uptake activity and cellular transport/uptake of glucose, and particularly GLUTS3, but also including but not limited to GLUT1-14 (SLC2A1-SLC2A14). Compounds of the invention are useful for treating diseases, including cancer, autoimmune diseases and inflammation, infectious diseases, and metabolic diseases.

2 Claims, 4 Drawing Sheets

A.

B.

| Cell line | Example 122 IC50 (nM) |
|---|---|
| HT1080 | 1705 |
| DLD1 wild type | 5775 |
| DLD1-GLUT1-knockout | 58 |

A.

B.

A.

B.

C.

| CD4+ T cell assay | Example 122 IC50 (nM) |
|---|---|
| Glycolysis | 160 |
| IL-17A secretion | 3236 |

GLUCOSE UPTAKE INHIBITORS

FIELD OF THE INVENTION

This invention provides compounds that modulate glucose uptake activity and cellular transport/uptake of glucose, and particularly GLUT3, but also including but not limited to GLUT1-14 (SLC2A1-SLC2A14). Compounds of the invention are useful for treating diseases, including cancer, autoimmune diseases and inflammation, fibrosis, infectious diseases, and metabolic diseases.

BACKGROUND OF THE INVENTION

Glucose is an essential source of energy for mammalian cells, and is also used as a substrate in protein and lipid synthesis. Glucose transporters enable the movement of glucose across the cell membrane. GLUT1 (SLC2A1) is one of several transporters that facilitate the cellular uptake of glucose and several other monosaccharides, including 2-deoxyglucose, galactose, mannose, xylose and fucose. GLUT1 is ubiquitously expressed at low levels in human tissues, but its expression and activity is specifically elevated in the cells of the endothelial barriers, developing embryo and activated immune cells. GLUT3 (SLC2A3) is another member of the facilitative glucose transporter family that mediates glucose uptake in a more restricted subset of human tissues.

Glucose represents a central nutrient for many organisms, and control of glucose signaling and consumption is tightly regulated. Accordingly, many disease states are associated with defects in this regulation and therefore may be susceptible to therapeutic intervention using glucose uptake inhibitors. Certain glucose transporters facilitate glucose uptake by tumors, in which they are frequently overexpressed. In particular, increased GLUT1 and/or GLUT3 expression has been found to provide a mechanism for increased metabolism necessary for sustained tumor growth. Similar to cancer cells, certain immune cell subsets express high levels of GLUT transporters and require increased glucose metabolism for their growth, differentiation, and effector function.

Glucose uptake inhibitors may have utility in disease areas such as oncology, autoimmunity and inflammation, infection diseases/virology, and metabolic disease.

SUMMARY OF THE INVENTION

Compounds useful according to the present invention include those having the formula I:

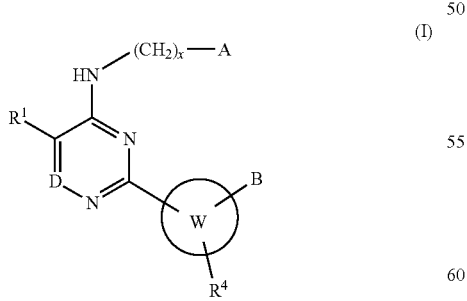

wherein:
A is selected from the group consisting of:
(i) a 4- to 7-membered heterocyclic ring having from 1 to 3 ring heteroatoms selected from O, S, and N, and which may be unsubstituted or substituted with up to three substituents selected from the group consisting of halo, hydroxy, oxo, —NR'R", —OR", CHR'R", —(CH$_2$)$_b$NR'R", —O—(CH$_2$)$_c$NR'R", —C(=O)—NR'R", —NR'C(=O)—R", —OC(=O)R', —OC(=O)NR'R", —SO$_2$NR'R", —OSO$_2$NR'R", —O—(CH$_2$)$_d$OR", —CO$_2$—R", cyano, C$_1$-C$_6$ alkyl, C$_1$-C$_6$ alkoxy, alkoxyalkyl, C$_3$-C$_6$ cycloalkyl, perfluoro C$_1$-C$_6$ alkyl, perfluoro C$_1$-C$_6$ alkoxy, and a 5- or 6-membered heterocyclic ring, which may be further substituted with 0 to 3 substituents selected from the group consisting of halo, hydroxy, oxo, —NR'R", —(CH$_2$)$_b$NR'R", —O—(CH$_2$)$_c$NR'R", —C(=O)—NR'R", —O—(CH$_2$)$_d$OR", cyano, C$_1$-C$_6$ alkyl, C$_1$-C$_6$ alkoxy, alkoxyalkyl, C$_3$-C$_6$ cyclic alkyl, perfluoro C$_1$-C$_6$ alkyl, and perfluoro C$_1$-C$_6$ alkoxy;

(ii) a phenyl group, unsubstituted or substituted with up to three substituents selected from the group consisting of halo, hydroxy, —NR'R", —OR", CHR'R", —(CH$_2$)$_b$NR'R", —O—(CH$_2$)$_c$NR'R", —C(=O)—NR'R", —NR'C(=O)—R", —OC(=O)R', —OC(=O)NR'R", —SO$_2$NR'R", —OSO$_2$NR'R", —O—(CH$_2$)$_d$OR", —CO$_2$—R", cyano, C$_1$-C$_6$ alkyl, C$_1$-C$_6$ alkoxy, alkoxyalkyl, C$_3$-C$_6$ cycloalkyl, perfluoro C$_1$-C$_6$ alkyl, perfluoro C$_1$-C$_6$ alkoxy, and a 5- or 6-membered heterocyclic ring, which may be further substituted with 0 to 3 substituents selected from the group consisting of halo, hydroxy, oxo, —NR'R", —OR", —(CH$_2$)$_b$NR'R", —O—(CH$_2$)$_c$NR'R", —C(=O)—NR'R", —OC(=O)R', —OC(=O)NR'R", —SO$_2$NR'R", —OSO$_2$NR'R", —O—(CH$_2$)$_d$OR", cyano, C$_1$-C$_6$ alkyl, C$_1$-C$_6$ alkoxy, alkoxyalkyl, C$_3$-C$_6$ cyclic alkyl, perfluoro C$_1$-C$_6$ alkyl, and perfluoro C$_1$-C$_6$ alkoxy;

(iii) a cyclic group selected from:

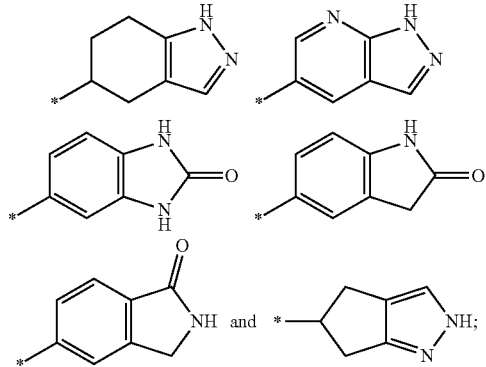

wherein each of the above structures may be optionally substituted with up to three substituents selected from the group consisting of halo, hydroxy, oxo, —NR'R", —(CH$_2$)$_b$NR'R", —O—(CH$_2$)$_c$NR'R", —C(=O)—NR'R", —NR'C(=O)—R", —OC(=O)R', —OC(=O)NR'R", —SO$_2$NR'R", —OSO$_2$NR'R", —O—(CH$_2$)$_d$OR", —CO$_2$—R", cyano, C$_1$-C$_6$ alkyl, C$_1$-C$_6$ alkoxy, alkoxyalkyl, C$_3$-C$_6$ cycloalkyl, perfluoro C$_1$-C$_6$ alkyl, perfluoro C$_1$-C$_6$ alkoxy, and a 5- or 6-membered heterocyclic ring, which may be further substituted with 0 to 3 substituents selected from the group consisting of halo, hydroxy, oxo, —NR'R", —(CH$_2$)$_b$NR'R", —O—(CH$_2$)$_c$NR'R", —C(=O)—NR'R", cyano, $C_1$-$C_6$ alkyl, $C_1$-$C_6$ alkoxy, alkoxyalkyl, $C_3$-$C_6$ cyclic alkyl, perfluoro $C_1$-$C_6$ alkyl, and perfluoro $C_1$-$C_6$ alkoxy;

each b is independently selected from 1 to 6;
each c is independently selected from 2 to 6;
each d is independently selected from 2 to 6;

x is 0 to 4;

$R^1$ is selected from the group consisting of H, halo, hydroxy, —NR'R", —OR", —(CH$_2$)$_b$NR'R", —O—(CH$_2$)$_f$NR'R", —C(=O)—NR'R", —NR'C(=O)—R", —OC(=O)R', —OC(=O)NR'R", —CO$_2$—R", —SO$_2$NR'R", —OSO$_2$NR'R", —O—(CH$_2$)$_g$OR", cyano, $C_1$-$C_6$ alkyl, $C_2$-$C_6$ alkenyl, $C_2$-$C_6$ alkynyl, $C_3$-$C_6$ cyclic alkyl, $C_1$-$C_6$ alkoxy, aryl, aralkyl, heterocycyl, $C_1$-$C_6$ perfluoro alkyl, and $C_1$-$C_6$ perfluoro alkoxy;

D is selected from N and C—$R^2$;

$R^2$ is selected from the group consisting of H, halo, hydroxy, —NR'R", —OR", —(CH$_2$)$_e$NR'R", —O—(CH$_2$)$_f$NR'R", —C(=O)—NR'R", —NR'C(=O)—R", —OC(=O)R', —OC(=O)NR'R", —CO$_2$—R", —SO$_2$NR'R", —OSO$_2$NR'R", —O—(CH$_2$)$_g$OR", cyano, $C_1$-$C_6$ alkyl, $C_2$-$C_6$ alkenyl, $C_2$-$C_6$ alkynyl, $C_3$-$C_6$ cyclic alkyl, $C_1$-$C_6$ alkoxy, aryl, aralkyl, heterocycyl, $C_1$-$C_6$ perfluoro alkyl, and $C_1$-$C_6$ perfluoro alkoxy;

alternatively, $R^1$ and $R^2$ are taken together to form a 5- to 7-membered fused ring having from 0 to 3 ring heteroatoms, and is unsubstituted or is substituted with up to 3 substituents selected from the group consisting of halo, hydroxy, cyano, amino, —CO$_2$—R", —SO$_2$—R", —NR'R", —OR", —S—R", —(CH$_2$)$_e$—R", —(CH$_2$)$_e$NR'R", —O—(CH$_2$)$_f$NR'R", —C(=O)—NR'R", —NRC(=O)—R", —OC(=O)R", —OC(=O)NR'R", —SO$_2$NR'R", —OSO$_2$NR'R", —O—(CH$_2$)$_g$OR", —O—(CH$_2$)$_e$R", —C(=O)—$C_1$-$C_6$ alkyl, $C_1$-$C_6$ alkyl, $C_1$-$C_6$ perfluoro alkyl, $C_1$-$C_6$ alkoxy and $C_1$-$C_6$ perfluoro alkoxy;

each e is independently selected from 1 to 6;
each f is independently selected from 2 to 6;
each g is independently selected from 2 to 6;

W is a five- or six-membered aryl or heteroaryl ring containing from 0 to 3 heteroatoms selected from the group consisting of N, O and S;

B is selected from the groups consisting of (i) a 4- to 7-membered heterocyclic ring having from 1 to 3 ring heteroatoms selected from O, S, and N, and which may be unsubstituted or substituted with up to three substituents selected from the group consisting of halo, hydroxy, oxo, —NR'R", —OR", —C(=O)—NR'R", —NRC(=O)—R", —OC(=O)R", —CO$_2$—R", —OC(=O)NR'R", —SO$_2$NR'R", —OSO$_2$NR'R", —O—(CH$_2$)$_d$OR", cyano, $C_1$-$C_6$ alkyl, $C_1$-$C_6$ alkoxy, alkoxyalkyl, $C_3$-$C_6$ cycloalkyl, perfluoro $C_1$-$C_6$ alkyl, and perfluoro $C_1$-$C_6$ alkoxy, and (ii) a group having the formula —X—Y—Z, wherein X is selected from the group consisting of O, NH and CH$_2$;

Y is selected from the group consisting of a single bond, —C(=O)— and —(CH$_2$)$_a$—, wherein a is from 1 to 6;

Z is selected from the group consisting of —NR'R", —C(=O)NR'R", —NRC(=O)R", and a 4- to 7-membered ring having from 0 to 3 ring heteroatoms selected from O, S, and N, which may be unsubstituted or substituted with up to three substituents selected from the group consisting of halo, hydroxy, oxo, —NR'R", —OR", —C(=O)—NR'R", —NRC(=O)—R", —OC(=O)R", —OC(=O)NR'R", —SO$_2$NR'R", —OSO$_2$NR'R", —CO$_2$—R", —O—(CH$_2$)$_d$OR", cyano, $C_1$-$C_6$ alkyl, $C_1$-$C_6$ alkoxy, alkoxyalkyl, $C_3$-$C_6$ cycloalkyl, perfluoro $C_1$-$C_6$ alkyl, and perfluoro $C_1$-$C_6$ alkoxy;

$R^4$ is selected from the group consisting of H, halo, hydroxy, oxo, —NR'R", cyano, $C_1$-$C_6$ alkyl, $C_1$-$C_6$ alkoxy, $C_3$-$C_6$ cyclic alkyl, perfluoro $C_1$-$C_6$ alkyl, and perfluoro $C_1$-$C_6$ alkoxy:

each R' is independently selected from the group consisting of H and $C_1$-$C_6$ alkyl;

each R" is independently selected from the group consisting of H, $C_1$-$C_6$ alkyl, $C_1$-$C_6$ fluoroalkyl, $C_1$-$C_6$ difluoroalkyl, $C_1$-$C_6$ perfluoroalkyl, aryl, aralkyl, $C_3$-$C_6$ cycloalkyl, and $C_3$-$C_7$ heterocyclyl having 1 to 3 heteroatoms selected from O, N, and S, wherein the aryl, aralkyl, $C_3$-$C_6$ cycloalkyl, and $C_3$-$C_7$ heterocyclyl may be further substituted with 0 to 3 substituents selected from halo, hydroxy, amino and $C_1$-$C_3$ alkyl; and alternatively, R' and R" attached to the same atom or to adjacent atoms may be taken together to form a 4- to 7-membered heterocylic ring having from 0 to 2 additional ring heteroatoms selected from N, O and S, and which may be unsubstituted or substituted with 1 to 3 substituents selected from the group consisting of halogen, cyano, $C_1$-$C_6$ alkyl, $C_3$-$C_6$ cycloalkyl, perfluoro $C_1$-$C_6$ alkyl, $C_1$-$C_6$ alkoxy, amino, amido and hydroxyl.

The present invention includes pharmaceutical compositions comprising the compounds of the invention and a pharmaceutically acceptable carrier. The present invention includes compositions comprising a substantially pure compound of the invention and a pharmaceutically acceptable salt, stereoisomer, or hydrate thereof, and a pharmaceutically acceptable carrier.

The glucose uptake inhibitors according to the Formula I have utility in disease areas such as oncology, autoimmunity and inflammation, infection diseases/virology, and metabolic disease.

DESCRIPTION OF THE DRAWINGS

In FIG. 2A, human CD4 positive T cells were activated for 24 hours in the presence of anti-CD3 and anti-CD28 antibodies, then mRNA was extracted and quantified by qRT-PCR. In FIG. 2B, human CD4 positive T cells were activated for 24, 48 or 72 hours in the presence of anti-CD3 and anti-CD28 antibodies, then protein was extracted and analyzed by Western blot. Activation of human CD4 positive T cells significantly induces the expression of both GLUT1 and GLUT3.

In FIG. 3A, human CD4 positive T cells were activated for 24 hours in the presence of anti-CD3 and anti-CD28 antibodies prior to a one hour treatment with compound of Ex. 122 combined with 10 μM oligomycin (glycolysis assay); alternately, the cells were activated for 5 days with anti- CD3, anti-CD28 and a cocktail of IL1β, TGFβ and IL6 to induce IL17 secretion in the presence of the indicated concentration of Ex. 122. In FIG. 3B, human CD4 T cells were for 5 days with anti-CD3 and anti-CD28 in the presence of Ex. 122 prior to being fixed, stained for CD25 expression and analyzed by flow cytometry. IL-17 secreted into the supernatant was measured with a MAGPIX xMAP instrument (Luminex). Glycolysis assays were carried out as described above. FIG. 3C lists the IC50 values (nM) for the glucose uptake inhibitors against activated T cell glycolysis and IL-17 secretion.

DETAILED DESCRIPTION OF THE INVENTION

Figure 1:
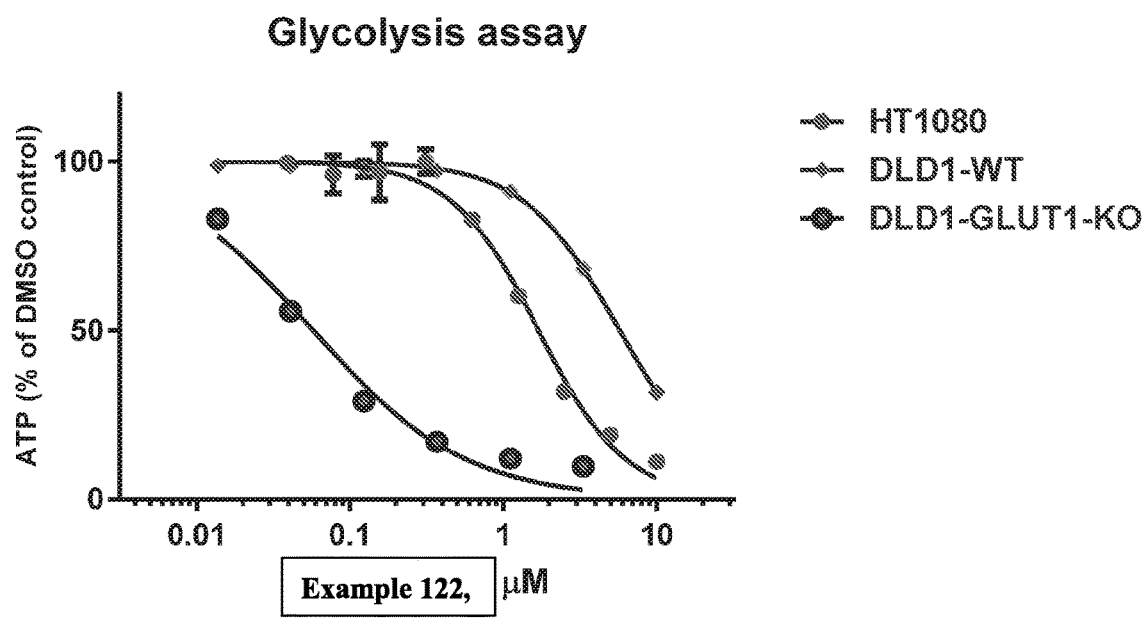
FIG. 1 shows the results from a glycolysis assay in HT1080 and syngeneic DLD1 cancer cells, either WT (wild-type) or GLUT1-KO (homozygous GLUT1 deletion). Cells were treated with GLUT inhibitors plus 10 μM oligomycin and subsequently ATP levels were determined using the Cell Titer Glo assay (Promega). The compounds of this invention selectively inhibit GLUT3 (A/B).

Glucose represents a central nutrient for many organisms, and control of glucose signaling and consumption is tightly regulated. Accordingly, many disease states are associated with defects in this regulation and therefore may be susceptible to therapeutic intervention using glucose uptake inhibitors. Glucose uptake inhibitors have utility in disease areas such as oncology, autoimmunity and inflammation, organ fibrosis, infection diseases/virology, and metabolic disease.

One of the emerging hallmarks of cancer is reprogramming of cancer cell metabolism. In order to meet the energetic demands of cell growth and division, cancer cells adopt the process of "aerobic glycolysis." While normal cells maintain a low rate of glycolysis, followed by full oxidization of pyruvate in the mitochondria, cancer cells rely on an increased rate of glycolysis followed by lactic acid fermentation (even in the presence of oxygen). Since mitochondrial oxidation phosphorylation generates more ATP than glycolysis alone, cancer cells rely heavily on increased rates of glucose consumption. One common way cancer cells achieve this goal is through the up-regulation of glucose transporters. In fact, many well-characterized oncogenes are thought to up-regulate both glycolytic enzymes and glucose transporters. Furthermore, the increased rate of glucose consumption displayed by the majority of tumors has already been employed in the field of diagnostics. Because of this cancer wide-phenomenon, one standard technique for imaging tumors is through the use of PET imaging of a radio-labelled glucose analog ($^{18}$FDG) (Hanahan, D. and R. A. Weinberg, *Hallmarks of cancer: the next generation. Cell,* 2011. 144(5): p. 646-74.) Taken together, it is predicted that inhibition of glucose uptake should affect cancer cells from a wide variety of tumor types while having little effect on normal cells.

As cellular metabolism is highly adaptable in general, targeting the initial entry of glucose into the cell is the most reliable way to disrupt glucose metabolism of abnormally proliferating cells in disease conditions.

Glucose transporter 3 (GLUT3) has recently been implicated in the initiation and survival of glioblastoma multiforme, a lethal and aggressive class of brain tumors (Flavahan, W. A. et al., *Brain tumor initiating cells adapt to restricted nutrition through preferential glucose uptake* Nat. Neurosci. 2013 October; 16(10):1373-82; Cosset, É. et al., *Glut3 Addiction Is a Druggable Vulnerability for a Molecularly Defined Subpopulation of Glioblastoma*, Cancer Cell. 2017 Dec. 11; 32(6):856-868). These cancers originate and grow in the nutrient-restricted compartment within the blood-brain barrier, which limits the diffusion of metabolic fuels such as glucose. To efficiently compete for limited glucose supplies, certain molecularly defined subsets of glioblastoma express the high-affinity GLUT3 isoform. GLUT3 levels correlate with poor prognosis in this disease, and genetic ablation of GLUT3 expression compromises the growth and viability of glioblastoma tumors in animal models. Thus it is likely that a brain-penetrant, GLUT3-specific inhibitor would show a therapeutic benefit in clinical glioblastoma multiforme. Compounds described in this invention are demonstrated to inhibit glucose transport and glycolysis in GLUT1 deficient, GLUT3 dependent cells.

The metabolism of immune cells is increasingly being recognized as major regulator of immune cell fate and function. The field of immunometabolism has made great insights into the precise metabolic pathways utilized by various immune cell subsets that allows for therapeutic intervention to control immune cell activity. Central to the activity of most pro-inflammatory immune cell subsets is glucose metabolism. Similar to cancer cells, certain activated immune cells adopt the process of "aerobic glycolysis." While normal cells maintain a low rate of glycolysis, followed by full oxidization of pyruvate in the mitochondria, the pro-inflammatory immune cells rely on an increased rate of glycolysis followed by lactic acid fermentation (even in the presence of oxygen). Since mitochondrial oxidative phosphorylation generates more ATP than glycolysis alone, activated pro-inflammatory cells rely heavily on increased rates of glucose consumption.

For example, activated T effector cells (both CD4 and CD8 positive T cells) switch to the process of aerobic glycolysis to meet their energetic demands (MacIver, N. J., R. D. Michalek, and J. C. Rathmell, *Metabolic regulation of T lymphocytes*. Annu Rev Immunol, 2013. 31: p. 259-83.) Since hyper-activation of helper T-cells (e.g. Th17, Th2, Th1) plays a large role in autoimmune disorders and inflammatory conditions, decreasing the rate of glycolysis in these cells would be predicted to curb secretion of inflammatory cytokines. In addition, as inhibition of glucose uptake activates AMPK, a master regulator of T regulatory cells (Michalek, R. D., et al., *Cutting edge: distinct glycolytic and lipid oxidative metabolic programs are essential for effector and regulatory CD4+ T cell subsets*. J Immunol, 2011. 186(6): p. 3299-303)), the use of glucose uptake inhibitors would also be predicted to increase the T regulatory cell population (which suppress inflammation), thereby "rebalancing" the immune system. In addition to CD4+ T cells, other cells of the immune system (including but not limited to CD8+ T cells, Gamma-Delta T cells, B cells, innate lymphoid cells, monocytes, macrophages, dendritic cells, neutrophils) rely heavily on glycolysis for their development, activation and effector functions.

Activated T cells upregulate GLUT1 upon activation and this has been shown to be essential for pro-inflammatory effector T cell function. For example, mouse GLUT1 KO CD4+ T cells are unable to differentiate (in vitro or in vivo) into Th1, Th2 or Th17 cells, but can still differentiate into T regulatory cells (anti-inflammatory). In addition, mouse GLUT1 KO CD4+ T cells are unable to cause disease pathology in mouse models of GVHD and Colitis (Cell Metab. 2014 Jul. 1; 20(1):61-72). Interestingly, additional GLUT transporters are also expressed in activated T cells, including but not limited to GLUT3 (Cell Metab. 2014 Jul. 1; 20(1):61-72).

Accordingly, we have investigated the use of inhibitors of GLUT transporters against activated pro-inflammatory immune cells, including but not limited to activated human CD4+ T cells. In order to understand what GLUT transporters are required to sustain glycolysis in activated T cells, we first utilized the syngeneic cancer cell lines DLD1 WT and DLD GLUT1−/− that rely on GLUT1 and GLUT3 expression, respectively, for glucose transport. Within this system, we have identified small molecules that are selective GLUT3 inhibitors, or simultaneously have the property of inhibiting both GLUT1 and GLUT3 mediated glucose transport.

In addition, glycolytic reprograming participates in the pathogenis of fibrotic conditions. Glycolysis is required for the initiation of sustainment of myofibroblast differentiation and together with additional profibrotic stimuli is responsible for the propagation of the fibrosis pathology (Am J Respir Crit Care Med. 2015 Dec. 15; 192(12): 1462-1474). Thus inhibition of glucose transport with the compounds in this invention could provide a therapeutic strategy for the treatment of organ fibrosis.

Compounds for use in the methods of the invention include small molecules. As used herein, the terms "chemical agent" and "small molecule" are used interchangeably, and both terms refer to substances that have a molecular weight up to about 4000 atomic mass units (Daltons), preferably up to about 2000 Daltons, and more preferably up to about 1000 Daltons. Unless otherwise stated herein, the term "small molecule" as used herein refers exclusively to chemical agents, and does not refer to biological agents. As used herein, "biological agents" are molecules which include proteins, polypeptides, and nucleic acids, and have molecular weights equal to or greater than about 2000 atomic mass units (Daltons). Compounds of the invention include salts, esters, and other pharmaceutically acceptable forms of such compounds.

Compounds useful according to the present invention include those having the formula I:

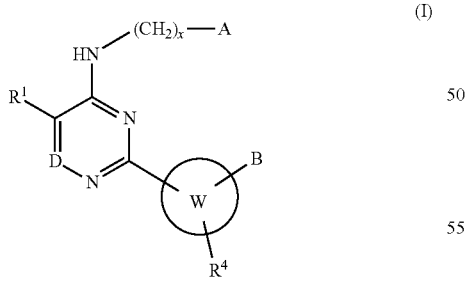

(I)

wherein:
A is selected from the group consisting of:
(i) a 4- to 7-membered heterocyclic ring having from 1 to 3 ring heteroatoms selected from O, S, and N, and which may be unsubstituted or substituted with up to three substituents selected from the group consisting of halo, hydroxy, oxo, —NR'R", —OR", CHR'R", —(CH$_2$)$_b$NR'R", —O—(CH$_2$)$_c$NR'R", —C(=O)—NR'R", —NR'C(=O)—R", —OC(=O)R', —OC(=O)NR'R", —SO$_2$NR'R", —OSO$_2$NR'R", —O—(CH$_2$)$_d$OR", —CO$_2$—R", cyano, C$_1$-C$_6$ alkyl, C$_1$-C$_6$ alkoxy, alkoxyalkyl, C$_3$-C$_6$ cycloalkyl, perfluoro C$_1$-C$_6$ alkyl, perfluoro C$_1$-C$_6$ alkoxy, and a 5- or 6-membered heterocyclic ring, which may be further substituted with 0 to 3 substituents selected from the group consisting of halo, hydroxy, oxo, —NR'R", —(CH$_2$)$_b$NR'R", —O—(CH$_2$)$_c$NR'R", —C(=O)—NR'R", —O—(CH$_2$)$_d$OR", cyano, C$_1$-C$_6$ alkyl, C$_1$-C$_6$ alkoxy, alkoxyalkyl, C$_3$-C$_6$ cyclic alkyl, perfluoro C$_1$-C$_6$ alkyl, and perfluoro C$_1$-C$_6$ alkoxy;

(ii) a phenyl group, unsubstituted or substituted with up to three substituents selected from the group consisting of halo, hydroxy, —NR'R", —OR", CHR'R", —(CH$_2$)$_b$NR'R", —O—(CH$_2$)$_c$NR'R", —C(=O)—NR'R", —NR'C(=O)—R", —OC(=O)R', —OC(=O)NR'R", —SO$_2$NR'R", —OSO$_2$NR'R", —O—(CH$_2$)$_d$OR", —CO$_2$—R", cyano, C$_1$-C$_6$ alkyl, C$_1$-C$_6$ alkoxy, alkoxyalkyl, C$_3$-C$_6$ cycloalkyl, perfluoro C$_1$-C$_6$ alkyl, perfluoro C$_1$-C$_6$ alkoxy, and a 5- or 6-membered heterocyclic ring, which may be further substituted with 0 to 3 substituents selected from the group consisting of halo, hydroxy, oxo, —NR'R", —OR", —(CH$_2$)$_b$NR'R", —O—(CH$_2$)$_c$NR'R", —C(=O)—NR'R", —OC(=O)R', —OC(=O)NR'R", —SO$_2$NR'R", —OSO$_2$NR'R", —O—(CH$_2$)$_d$OR", cyano, C$_1$-C$_6$ alkyl, C$_1$-C$_6$ alkoxy, alkoxyalkyl, C$_3$-C$_6$ cyclic alkyl, perfluoro C$_1$-C$_6$ alkyl, and perfluoro C$_1$-C$_6$ alkoxy;

(iii) a cyclic group selected from:

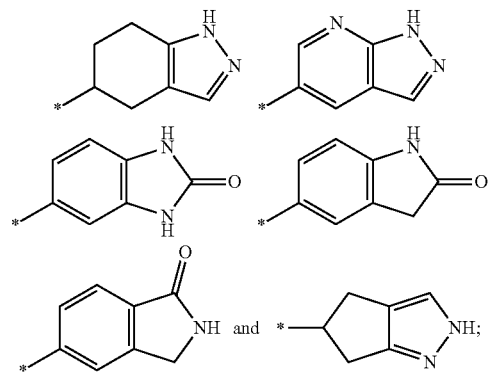

wherein each of the above structures may be optionally substituted with up to three substituents selected from the group consisting of halo, hydroxy, oxo, —NR'R", —(CH$_2$)$_b$NR'R", —O—(CH$_2$)$_c$NR'R", —C(=O)—NR'R", —NR'C(=O)—R", —OC(=O)R', —OC(=O)NR'R", —SO$_2$NR'R", —OSO$_2$NR'R", —O—(CH$_2$)$_d$OR", —CO$_2$—R", cyano, C$_1$-C$_6$ alkyl, C$_1$-C$_6$ alkoxy, alkoxyalkyl, C$_3$-C$_6$ cycloalkyl, perfluoro C$_1$-C$_6$ alkyl, perfluoro C$_1$-C$_6$ alkoxy, and a 5- or 6-membered heterocyclic ring, which may be further substituted with 0 to 3 substituents selected from the group consisting of halo, hydroxy, oxo, —NR'R", —(CH$_2$)$_b$NR'R", —O—(CH$_2$)$_c$NR'R", —C(=O)—NR'R", cyano, C$_1$-C$_6$ alkyl, C$_1$-C$_6$ alkoxy, alkoxyalkyl, C$_3$-C$_6$ cyclic alkyl, perfluoro C$_1$-C$_6$ alkyl, and perfluoro C$_1$-C$_6$ alkoxy;

each b is independently selected from 1 to 6;
each c is independently selected from 2 to 6;
each d is independently selected from 2 to 6;
x is 0 to 4;
$R^1$ is selected from the group consisting of H, halo, hydroxy, —NR'R", —OR", —$(CH_2)_e$NR'R", —O—$(CH_2)_f$NR'R", —C(=O)—NR'R", —NRC(=O)—R", —OC(=O)R', —OC(=O)NR'R", —$CO_2$—R", —$SO_2$NR'R", —$OSO_2$NR'R", —O—$(CH_2)_g$OR", cyano, $C_1$-$C_6$ alkyl, $C_2$-$C_6$ alkenyl, $C_2$-$C_6$ alkynyl, $C_3$-$C_6$ cyclic alkyl, $C_1$-$C_6$ alkoxy, aryl, aralkyl, heterocycyl, $C_1$-$C_6$ perfluoro alkyl, and $C_1$-$C_6$ perfluoro alkoxy;
D is selected from N and C—$R^2$;
$R^2$ is selected from the group consisting of H, halo, hydroxy, —NR'R", —OR", —$(CH_2)_e$NR'R", —O—$(CH_2)_f$NR'R", —C(=O)—NR'R", —NRC(=O)—R", —OC(=O)R', —OC(=O)NR'R", —$CO_2$—R", —$SO_2$NR'R", —$OSO_2$NR'R", —O—$(CH_2)_g$OR", cyano, $C_1$-$C_6$ alkyl, $C_2$-$C_6$ alkenyl, $C_2$-$C_6$ alkynyl, $C_3$-$C_6$ cyclic alkyl, $C_1$-$C_6$ alkoxy, aryl, aralkyl, heterocycyl, $C_1$-$C_6$ perfluoro alkyl, and $C_1$-$C_6$ perfluoro alkoxy;
alternatively, $R^1$ and $R^2$ are taken together to form a 5- to 7-membered fused ring having from 0 to 3 ring heteroatoms, and is unsubstituted or is substituted with up to 3 substituents selected from the group consisting of halo, hydroxy, cyano, amino, —$CO_2$—R", —$SO_2$—R", —NR'R", —OR", —S—R", —$(CH_2)_e$—R", —$(CH_2)_e$NR'R", —O—$(CH_2)_f$NR'R", —C(=O)—NR'R", —NRC(=O)—R", —OC(=O)R', —OC(=O)NR'R", —$SO_2$NR'R", —$OSO_2$NR'R", —O—$(CH_2)_g$OR", —O—$(CH_2)_e$R", —C(=O)—$C_1$-$C_6$ alkyl, $C_1$-$C_6$ alkyl, $C_1$-$C_6$ perfluoro alkyl, $C_1$-$C_6$ alkoxy and $C_1$-$C_6$ perfluoro alkoxy;
each e is independently selected from 1 to 6;
each f is independently selected from 2 to 6;
each g is independently selected from 2 to 6;
W is a five- or six-membered aryl or heteroaryl ring containing from 0 to 3 heteroatoms selected from the group consisting of N, O and S;
B is selected from the groups consisting of (i) a 4- to 7-membered heterocyclic ring having from 1 to 3 ring heteroatoms selected from O, S, and N, and which may be unsubstituted or substituted with up to three substituents selected from the group consisting of halo, hydroxy, oxo, —NR'R", —OR", —C(=O)—NR'R", —NRC(=O)—R", —OC(=O)R', —$CO_2$—R", —OC(=O)NR'R", —$SO_2$NR'R", —$OSO_2$NR'R", —O—$(CH_2)_d$OR", cyano, $C_1$-$C_6$ alkyl, $C_1$-$C_6$ alkoxy, alkoxyalkyl, $C_3$-$C_6$ cycloalkyl, perfluoro $C_1$-$C_6$ alkyl, and perfluoro $C_1$-$C_6$ alkoxy, and (ii) a group having the formula —X—Y—Z, wherein
X is selected from the group consisting of O, NH and $CH_2$;
Y is selected from the group consisting of a single bond, —C(=O)— and —$(CH_2)_a$—, wherein a is from 1 to 6;
Z is selected from the group consisting of —NR'R", —C(=O)NR'R", —NR'C(=O)R", and a 4- to 7-membered ring having from 0 to 3 ring heteroatoms selected from O, S, and N, which may be unsubstituted or substituted with up to three substituents selected from the group consisting of halo, hydroxy, oxo, —NR'R", —OR", —C(=O)—NR'R", —NR'C(=O)—R", —OC(=O)R', —OC(=O)NR'R", —$SO_2$NR'R", —$OSO_2$NR'R", —$CO_2$—R", —O—$(CH_2)_d$OR", cyano, $C_1$-$C_6$ alkyl, $C_1$-$C_6$ alkoxy, alkoxyalkyl, $C_3$-$C_6$ cycloalkyl, perfluoro $C_1$-$C_6$ alkyl, and perfluoro $C_1$-$C_6$ alkoxy;

$R^4$ is selected from the group consisting of H, halo, hydroxy, oxo, —NR'R", cyano, $C_1$-$C_6$ alkyl, $C_1$-$C_6$ alkoxy, $C_3$-$C_6$ cyclic alkyl, perfluoro $C_1$-$C_6$ alkyl, and perfluoro $C_1$-$C_6$ alkoxy:
each R' is independently selected from the group consisting of H and $C_1$-$C_6$ alkyl;
each R" is independently selected from the group consisting of H, $C_1$-$C_6$ alkyl, $C_1$-$C_6$ fluoroalkyl, $C_1$-$C_6$ difluoroalkyl, $C_1$-$C_6$ perfluoroalkyl, aryl, aralkyl, $C_3$-$C_6$ cycloalkyl, and $C_3$-$C_7$ heterocyclyl having 1 to 3 heteroatoms selected from O, N, and S, wherein the aryl, aralkyl, $C_3$-$C_6$ cycloalkyl, and $C_3$-$C_7$ heterocyclyl may be further substituted with 0 to 3 substituents selected from halo, hydroxy, amino and $C_1$-$C_3$ alkyl; and
alternatively, R' and R" attached to the same atom or to adjacent atoms may be taken together to form a 4- to 7-membered heterocylic ring having from 0 to 2 additional ring heteroatoms selected from N, O and S, and which may be unsubstituted or substituted with 1 to 3 substituents selected from the group consisting of halogen, cyano, $C_1$-$C_6$ alkyl, $C_3$-$C_6$ cycloalkyl, perfluoro $C_1$-$C_6$ alkyl, $C_1$-$C_6$ alkoxy, amino, amido and hydroxyl.

Compounds useful according to the present invention include those having the formula II:

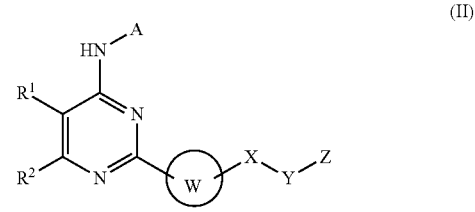

(II)

wherein:
A is selected from the group consisting of:
(i) a 4- to 7-membered heterocyclic ring having from 1 to 3 ring heteroatoms selected from O, S, and N, and which may be unsubstituted or substituted with up to three substituents selected from the group consisting of halo, hydroxy, oxo, —NR'R", —OR", CHR'R", —$(CH_2)_b$NR'R", —O—$(CH_2)_c$NR'R", —C(=O)—NR'R", —NR'C(=O)—R", —OC(=O)R', —OC(=O)NR'R", —$SO_2$NR'R", —$OSO_2$NR'R", —O—$(CH_2)_d$OR", —$CO_2$—R", cyano, $C_1$-$C_6$ alkyl, $C_1$-$C_6$ alkoxy, alkoxyalkyl, $C_3$-$C_6$ cycloalkyl, perfluoro $C_1$-$C_6$ alkyl, perfluoro $C_1$-$C_6$ alkoxy, and a 5- or 6-membered heterocyclic ring, which may be further substituted with 0 to 3 substituents selected from the group consisting of halo, hydroxy, oxo, —NR'R", —$(CH_2)_b$NR'R", —O—$(CH_2)_c$NR'R", —C(=O)—NR'R", —O—$(CH_2)_d$OR", cyano, $C_1$-$C_6$ alkyl, $C_1$-$C_6$ alkoxy, alkoxyalkyl, $C_3$-$C_6$ cyclic alkyl, perfluoro $C_1$-$C_6$ alkyl, and perfluoro $C_1$-$C_6$ alkoxy;
(ii) a phenyl group, unsubstituted or substituted with up to three substituents selected from the group consisting of halo, hydroxy, —NR'R", —OR", CHR'R", —$(CH_2)_b$NR'R", —O—$(CH_2)_c$NR'R", —C(=O)—NR'R", —NR'C(=O)—R", —OC(=O)R', —OC(=O)NR'R", —$SO_2$NR'R", —$OSO_2$NR'R", —O—$(CH_2)_d$OR", —$CO_2$—R", cyano, $C_1$-$C_6$ alkyl, $C_1$-$C_6$ alkoxy, alkoxyalkyl, $C_3$-$C_6$ cycloalkyl, perfluoro C₁-C₆ alkyl, perfluoro C₁-C₆ alkoxy, and a 5- or 6-membered heterocyclic ring, which may be further substituted with 0 to 3 substituents selected from the group consisting of halo, hydroxy, oxo, —NR'R", —OR", —(CH₂)$_b$NR'R", —O—(CH₂)$_c$NR'R", —C(=O)—NR'R", —OC(=O)R', —OC(=O)NR'R", —SO₂NR'R", —OSO₂NR'R", —O—(CH₂)$_d$OR", cyano, C₁-C₆ alkyl, C₁-C₆ alkoxy, alkoxyalkyl, C₃-C₆ cyclic alkyl, perfluoro C₁-C₆ alkyl, and perfluoro C₁-C₆ alkoxy;

(iii) a cyclic group selected from:

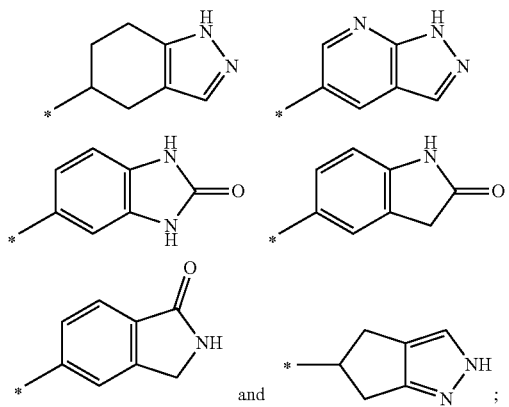

wherein each of the above structures may be optionally substituted with up to three substituents selected from the group consisting of halo, hydroxy, oxo, —NR'R", —(CH₂)$_b$NR'R", —O—(CH₂)$_c$NR'R", —C(=O)—NR'R", —NR'C(=O)—R", —OC(=O)R', —OC(=O)NR'R", —SO₂NR'R", —OSO₂NR'R", —O—(CH₂)$_d$OR", —CO₂—R", cyano, C₁-C₆ alkyl, C₁-C₆ alkoxy, alkoxyalkyl, C₃-C₆ cycloalkyl, perfluoro C₁-C₆ alkyl, perfluoro C₁-C₆ alkoxy, and a 5- or 6-membered heterocyclic ring, which may be further substituted with 0 to 3 substituents selected from the group consisting of halo, hydroxy, oxo, —NR'R", —(CH₂)$_b$NR'R", —O—(CH₂)$_c$NR'R", —C(=O)—NR'R", cyano, C₁-C₆ alkyl, C₁-C₆ alkoxy, alkoxyalkyl, C₃-C₆ cyclic alkyl, perfluoro C₁-C₆ alkyl, and perfluoro C₁-C₆ alkoxy;

each b is independently selected from 1 to 6;
each c is independently selected from 2 to 6;
each d is independently selected from 2 to 6;

$R^1$ is selected from the group consisting of H, halo, hydroxy, —NR'R", —OR", —(CH₂)$_e$NR'R", —O—(CH₂)$_f$NR'R", —C(=O)—NR'R", —NR'C(=O)—R", —OC(=O)R', —OC(=O)NR'R", —CO₂—R", —SO₂NR'R", —OSO₂NR'R", —O—(CH₂)$_g$OR", cyano, C₁-C₆ alkyl, C₂-C₆ alkenyl, C₂-C₆ alkynyl, C₃-C₆ cyclic alkyl, C₁-C₆ alkoxy, aryl, aralkyl, heterocycyl, C₁-C₆ perfluoro alkyl, and C₁-C₆ perfluoro alkoxy;

$R^2$ is selected from the group consisting of H, halo, hydroxy, —NR'R", —OR", —(CH₂)$_e$NR'R", —O—(CH₂)$_f$NR'R", —C(=O)—NR'R", —NR'C(=O)—R", —OC(=O)R', —OC(=O)NR'R", —CO₂—R", —SO₂NR'R", —OSO₂NR'R", —O—(CH₂)$_g$OR", cyano, C₁-C₆ alkyl, C₂-C₆ alkenyl, C₂-C₆ alkynyl, C₃-C₆ cyclic alkyl, C₁-C₆ alkoxy, aryl, aralkyl, heterocycyl, C₁-C₆ perfluoro alkyl, and C₁-C₆ perfluoro alkoxy;

alternatively, $R^1$ and $R^2$ are taken together to form a 5- to 7-membered fused ring having from 0 to 3 ring heteroatoms, and is unsubstituted or is substituted with up to 3 substituents selected from the group consisting of halo, hydroxy, cyano, amino, —CO₂—R", —SO₂—R", —NR'R", —OR", —S—R", —(CH₂)$_e$—R", —(CH₂)$_e$NR'R", —O—(CH₂)$_f$NR'R", —C(=O)—NR'R", —NR'C(=O)—R", —OC(=O)R", —OC(=O)NR'R", —SO₂NR'R", —OSO₂NR'R", —O—(CH₂)$_g$OR", —O—(CH₂)$_e$R", —C(=O)—C₁-C₆ alkyl, C₁-C₆ alkyl, C₁-C₆ perfluoro alkyl, C₁-C₆ alkoxy and C₁-C₆ perfluoro alkoxy;

each e is independently selected from 1 to 6;
each f is independently selected from 2 to 6;
each g is independently selected from 2 to 6;

W is a five- or six-membered aryl or heteroaryl ring containing from 0 to 3 heteroatoms selected from the group consisting of N, O and S;

X is selected from the group consisting of O, NH and CH₂;

Y is selected from the group consisting of a single bond, —C(=O)— and —(CH₂)$_a$—, wherein a is from 1 to 6;

Z is selected from the group consisting of —NR'R", —C(=O)NR'R", —NR'C(=O)R", and a 4- to 7-membered ring having from 0 to 3 ring heteroatoms selected from O, S, and N, which may be unsubstituted or substituted with up to three substituents selected from the group consisting of halo, hydroxy, oxo, —NR'R", —OR", —C(=O)—NR'R", —NR'C(=O)—R", —OC(=O)R", —OC(=O)NR'R", —SO₂NR'R", —OSO₂NR'R", —CO₂—R", —O—(CH₂)$_d$OR", cyano, C₁-C₆ alkyl, C₁-C₆ alkoxy, alkoxyalkyl, C₃-C₆ cycloalkyl, perfluoro C₁-C₆ alkyl, and perfluoro C₁-C₆ alkoxy;

each R' is independently selected from the group consisting of H and C₁-C₆ alkyl;

each R" is independently selected from the group consisting of H, C₁-C₆ alkyl, C₁-C₆ fluoroalkyl, C₁-C₆ difluoroalkyl, C₁-C₆ perfluoroalkyl, aryl, aralkyl, C₃-C₆ cycloalkyl, and C₃-C₇ heterocyclyl having 1 to 3 heteroatoms selected from O, N, and S, wherein the aryl, aralkyl, C₃-C₆ cycloalkyl, and C₃-C₇ heterocyclyl may be further substituted with 0 to 3 substituents selected from halo, hydroxy, amino and C₁-C₃ alkyl; and alternatively, R' and R" attached to the same atom or to adjacent atoms may be taken together to form a 4- to 7-membered heterocylic ring having from 0 to 2 additional ring heteroatoms selected from N, O and S, and which may be unsubstituted or substituted with 1 to 3 substituents selected from the group consisting of halogen, cyano, C₁-C₆ alkyl, C₃-C₆ cycloalkyl, perfluoro C₁-C₆ alkyl, C₁-C₆ alkoxy, amino, amido and hydroxyl.

Compounds useful according to the present invention include those having the formula II:

(II$_a$)

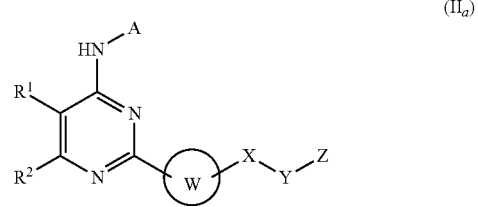

wherein:

A is selected from the group consisting of:

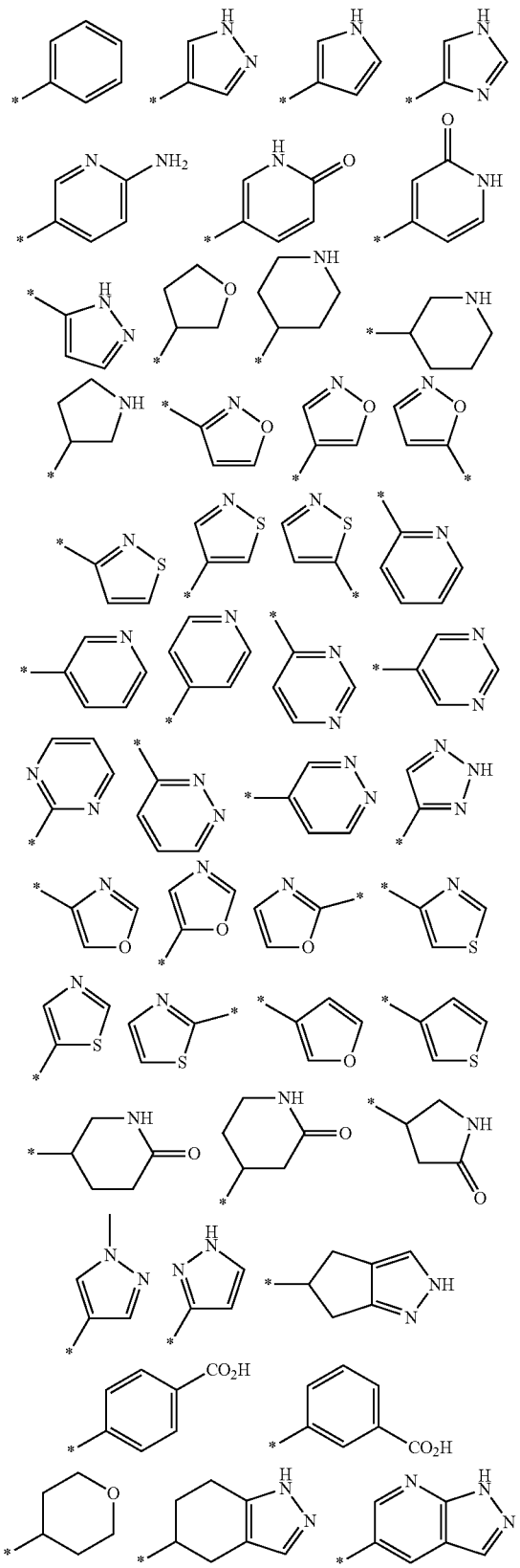

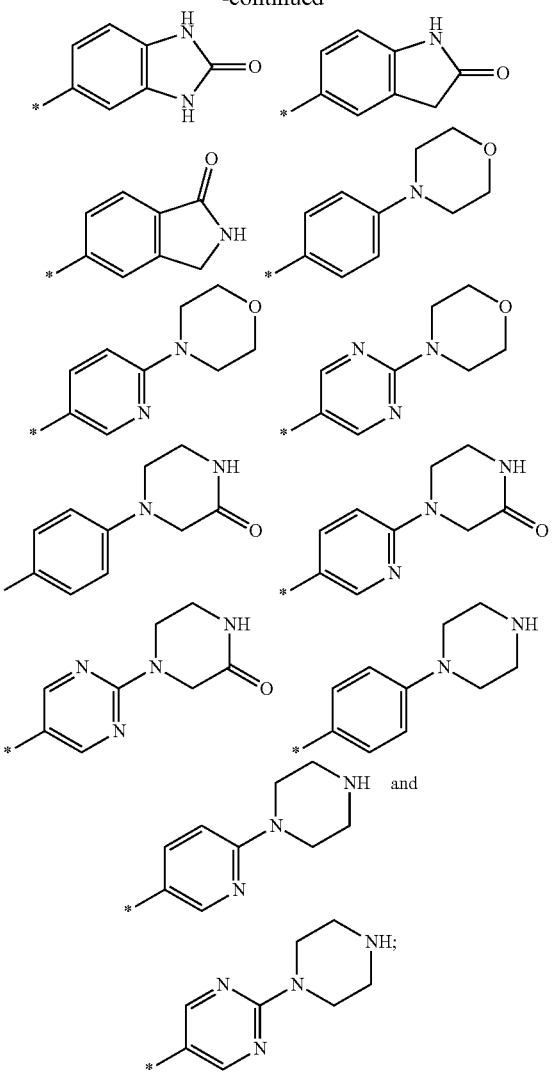

wherein each of the above structures for A may be optionally substituted with one to three substituents selected from the group consisting of halo, hydroxy, oxo, —NR'R", —(CH$_2$)$_b$NR'R", —O—(CH$_2$)—NR'R", —C(=O)—NR'R", —NRC(=O)—R", —OC(=O)R', —OC(=O)NR'R", —SO$_2$NR'R", —OSO$_2$NR'R", —O—(CH$_2$)$_d$OR", —CO$_2$—R", cyano, C$_1$-C$_6$ alkyl, C$_1$-C$_6$ alkoxy, alkoxyalkyl, C$_3$-C$_6$ cycloalkyl, perfluoro C$_1$-C$_6$ alkyl, and perfluoro C$_1$-C$_6$ alkoxy;

each b is independently selected from 1 to 6;
each c is independently selected from 2 to 6;
each d is independently selected from 2 to 6;

R$^1$ is selected from the group consisting of H, halo, hydroxy, —NR'R", —OR", —(CH$_2$)$_e$NR'R", —O—(CH$_2$)$_f$NR'R", —C(=O)—NR'R", —NRC(=O)—R", —OC(=O)R', —OC(=O)NR'R", —CO$_2$—R", —SO$_2$NR'R", —OSO$_2$NR'R", —O—(CH$_2$)$_g$OR", cyano, C$_1$-C$_6$ alkyl, C$_2$-C$_6$ alkenyl, C$_2$-C$_6$ alkynyl, C$_3$-C$_6$ cyclic alkyl, C$_1$-C$_6$ alkoxy, aryl, aralkyl, heterocycyl, C$_1$-C$_6$ perfluoro alkyl, and C$_1$-C$_6$ perfluoro alkoxy;

R$^2$ is selected from the group consisting of H, halo, hydroxy, —NR'R", —OR", —(CH$_2$)$_e$NR'R", —O—

—(CH$_2$)$_f$NR'R", —C(=O)—NR'R", —NRC(=O)—R",
—OC(=O)R', —OC(=O)NR'R", —CO$_2$—R",
—SO$_2$NR'R", —OSO$_2$NR'R", —O—(CH$_2$)$_g$OR",
cyano, C$_1$-C$_6$ alkyl, C$_2$-C$_6$ alkenyl, C$_2$-C$_6$ alkynyl,
C$_3$-C$_6$ cyclic alkyl, C$_1$-C$_6$ alkoxy, aryl, aralkyl, heterocycyl, C$_1$-C$_6$ perfluoro alkyl, and C$_1$-C$_6$ perfluoro alkoxy;

alternatively, R$^1$ and R$^2$ are taken together to form a 5- to 7-membered fused ring having from 0 to 3 ring heteroatoms, and is unsubstituted or is substituted with up to 3 substituents selected from the group consisting of halo, hydroxy, cyano, amino, —CO$_2$—R", —SO$_2$—R", —NR'R", —OR", —S—R", —(CH$_2$)$_e$—R", —(CH$_2$)$_e$NR'R", —O—(CH$_2$)$_f$NR'R", —C(=O)—NR'R", —NR'C(=O)—R", —OC(=O)R", —OC(=O)NR'R", —SO$_2$NR'R", —OSO$_2$NR'R", —O—(CH$_2$)$_g$OR", —O—(CH$_2$)$_e$R", —C(=O)—C$_1$-C$_6$ alkyl, C$_1$-C$_6$ alkyl, C$_1$-C$_6$ perfluoro alkyl, C$_1$-C$_6$ alkoxy and C$_1$-C$_6$ perfluoro alkoxy;

each e is independently selected from 1 to 6;
each f is independently selected from 2 to 6;
each g is independently selected from 2 to 6;

W is a five- or six-membered aryl or heteroaryl ring containing from 0 to 3 heteroatoms selected from the group consisting of N, O and S;

X is selected from the group consisting of O, NH and CH$_2$;

Y is selected from the group consisting of a single bond, —C(=O)— and —(CH$_2$)$_a$—, wherein a is from 1 to 6;

Z is selected from the group consisting of —NR'R", —C(=O)NR'R", —NR'C(=O)R", and a 4- to 7-membered ring having from 0 to 3 ring heteroatoms selected from O, S, and N, which may be unsubstituted or substituted with up to three substituents selected from the group consisting of halo, hydroxy, oxo, —NR'R", —OR", —C(=O)—NR'R", —NR'C(=O)—R", —OC(=O)R", —OC(=O)NR'R", —SO$_2$NR'R", —OSO$_2$NR'R", —CO$_2$—R", —O—(CH$_2$)$_d$OR", cyano, C$_1$-C$_6$ alkyl, C$_1$-C$_6$ alkoxy, alkoxyalkyl, C$_3$-C$_6$ cycloalkyl, perfluoro C$_1$-C$_6$ alkyl, and perfluoro C$_1$-C$_6$ alkoxy;

each R' is independently selected from the group consisting of H and C$_1$-C$_6$ alkyl;

each R" is independently selected from the group consisting of H, C$_1$-C$_6$ alkyl, C$_1$-C$_6$ fluoroalkyl, C$_1$-C$_6$ difluoroalkyl, C$_1$-C$_6$ perfluoroalkyl, aryl, aralkyl, C$_3$-C$_6$ cycloalkyl, and C$_3$-C$_7$ heterocyclyl having 1 to 3 heteroatoms selected from O, N, and S, wherein the aryl, aralkyl, C$_3$-C$_6$ cycloalkyl, and C$_3$-C$_7$ heterocyclyl may be further substituted with 0 to 3 substituents selected from halo, hydroxy, amino and C$_1$-C$_3$ alkyl; and alternatively, R' and R" attached to the same atom or to adjacent atoms may be taken together to form a 4- to 7-membered heterocylic ring having from 0 to 2 additional ring heteroatoms selected from N, O and S, and which may be unsubstituted or substituted with 1 to 3 substituents selected from the group consisting of halogen, cyano, C$_1$-C$_6$ alkyl, C$_3$-C$_6$ cycloalkyl, perfluoro C$_1$-C$_6$ alkyl, C$_1$-C$_6$ alkoxy, amino, amido and hydroxyl.

In certain embodiments, the present invention relates to a compound having the formula III:

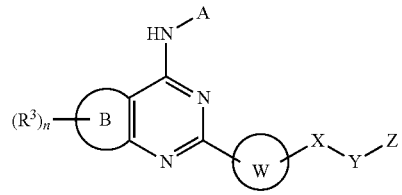

wherein:

A is selected from the group consisting of:
(i) a 4- to 7-membered heterocyclic ring having from 1 to 3 ring heteroatoms selected from O, S, and N, and which may be unsubstituted or substituted with up to three substituents selected from the group consisting of halo, hydroxy, oxo, —NR'R", —OR", CHR'R", —(CH$_2$)$_b$NR'R", —O—(CH$_2$)$_c$NR'R", —C(=O)—NR'R", —NR'C(=O)—R", —OC(=O)R', —OC(=O)NR'R", —SO$_2$NR'R", —OSO$_2$NR'R", —O—(CH$_2$)$_d$OR", —CO$_2$—R", cyano, C$_1$-C$_6$ alkyl, C$_1$-C$_6$ alkoxy, alkoxyalkyl, C$_3$-C$_6$ cycloalkyl, perfluoro C$_1$-C$_6$ alkyl, perfluoro C$_1$-C$_6$ alkoxy, and a 5- or 6-membered heterocyclic ring, which may be further substituted with 0 to 3 substituents selected from the group consisting of halo, hydroxy, oxo, —NR'R", —(CH$_2$)$_b$NR'R", —O—(CH$_2$)$_c$NR'R", —C(=O)—NR'R", —O—(CH$_2$)$_d$OR", cyano, C$_1$-C$_6$ alkyl, C$_1$-C$_6$ alkoxy, alkoxyalkyl, C$_3$-C$_6$ cyclic alkyl, perfluoro C$_1$-C$_6$ alkyl, and perfluoro C$_1$-C$_6$ alkoxy;

(ii) a phenyl group, unsubstituted or substituted with up to three substituents selected from the group consisting of halo, hydroxy, —NR'R", —OR", CHR'R", —(CH$_2$)$_b$NR'R", —O—(CH$_2$)$_c$NR'R", —C(=O)—NR'R", —NR'C(=O)—R", —OC(=O)R', —OC(=O)NR'R", —SO$_2$NR'R", —OSO$_2$NR'R", —O—(CH$_2$)$_d$OR", —CO$_2$—R", cyano, C$_1$-C$_6$ alkyl, C$_1$-C$_6$ alkoxy, alkoxyalkyl, C$_3$-C$_6$ cycloalkyl, perfluoro C$_1$-C$_6$ alkyl, perfluoro C$_1$-C$_6$ alkoxy, and a 5- or 6-membered heterocyclic ring, which may be further substituted with 0 to 3 substituents selected from the group consisting of halo, hydroxy, oxo, —NR'R", —OR", —(CH$_2$)$_b$NR'R", —O—(CH$_2$)$_c$NR'R", —C(=O)—NR'R", —OC(=O)R', —OC(=O)NR'R", —SO$_2$NR'R", —OSO$_2$NR'R", —O—(CH$_2$)$_d$OR", cyano, C$_1$-C$_6$ alkyl, C$_1$-C$_6$ alkoxy, alkoxyalkyl, C$_3$-C$_6$ cyclic alkyl, perfluoro C$_1$-C$_6$ alkyl, and perfluoro C$_1$-C$_6$ alkoxy;

(iii) a cyclic group selected from:

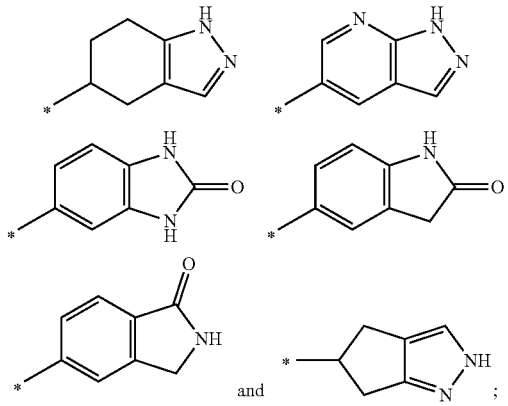

wherein each of the above structures may be optionally substituted with up to three substituents selected from the group consisting of halo, hydroxy, oxo, —NR'R", —(CH$_2$)$_b$NR'R", —O—(CH$_2$)$_c$NR'R", —C(=O)—NR'R", —NR'C(=O)—R", —OC(=O)R', —OC(=O)NR'R", —SO$_2$NR'R", —OSO$_2$NR'R", —O—(CH$_2$)$_d$OR", —CO$_2$—R", cyano, C$_1$-C$_6$ alkyl, C$_1$-C$_6$ alkoxy, alkoxyalkyl, C$_3$-C$_6$ cycloalkyl, perfluoro C$_1$-C$_6$ alkyl, perfluoro C$_1$-C$_6$ alkoxy, and a 5- or 6-membered heterocyclic ring, which may be further substituted with 0 to 3 substituents selected from the group consisting of halo, hydroxy, oxo, —NR'R", —(CH$_2$)$_b$NR'R", —O—(CH$_2$)$_c$NR'R", —C(=O)—NR'R", cyano, C$_1$-C$_6$ alkyl, C$_1$-C$_6$ alkoxy, alkoxyalkyl, C$_3$-C$_6$ cyclic alkyl, perfluoro C$_1$-C$_6$ alkyl, and perfluoro C$_1$-C$_6$ alkoxy;

B is a 5- to 7-membered fused ring having from 0 to 3 ring heteroatoms;

R$^3$ is selected from the group consisting of halo, hydroxy, cyano, amino, —CO$_2$—R", —SO$_2$—R", —NR'R", —OR", —S—R", —(CH$_2$)$_e$—R", —(CH$_2$)$_e$NR'R", —O—(CH$_2$)$_f$NR'R", —C(=O)—NR'R", —NR'C(=O)—R", —OC(=O)R", —OC(=O)NR'R", —SO$_2$NR'R", —OSO$_2$NR'R", —O—(CH$_2$)$_g$OR", —O—(CH$_2$)$_e$R", —C(=O)—C$_1$-C$_6$ alkyl, C$_1$-C$_6$ alkyl, C$_1$-C$_6$ perfluoro alkyl, C$_1$-C$_6$ alkoxy and C$_1$-C$_6$ perfluoro alkoxy;

each e is independently selected from 1 to 6;
each f is independently selected from 2 to 6;
each g is independently selected from 2 to 6;

n is 0 to 3

W is a five- or six-membered aryl or heteroaryl ring containing from 0 to 3 heteroatoms selected from the group consisting of N, O and S;

X is selected from the group consisting of O, NH and CH$_2$;

Y is selected from the group consisting of a single bond, —C(=O)— and —(CH$_2$)$_a$—, wherein a is from 1 to 6;

Z is selected from the group consisting of —NR'R", —C(=O)NR'R", —NR'C(=O)R", and a 4- to 7-membered ring having from 0 to 3 ring heteroatoms selected from O, S, and N, which may be unsubstituted or substituted with up to three substituents selected from the group consisting of halo, hydroxy, oxo, —NR'R", —OR", —C(=O)—NR'R", —NR'C(=O)—R", —OC(=O)R", —OC(=O)NR'R", —SO$_2$NR'R", —OSO$_2$NR'R", —CO$_2$—R", —O—(CH$_2$)$_d$OR", cyano, C$_1$-C$_6$ alkyl, C$_1$-C$_6$ alkoxy, alkoxyalkyl, C$_3$-C$_6$ cycloalkyl, perfluoro C$_1$-C$_6$ alkyl, and perfluoro C$_1$-C$_6$ alkoxy;

each R' is independently selected from the group consisting of H and C$_1$-C$_6$ alkyl;

each R" is independently selected from the group consisting of H, C$_1$-C$_6$ alkyl, C$_1$-C$_6$ fluoroalkyl, C$_1$-C$_6$ difluoroalkyl, C$_1$-C$_6$ perfluoroalkyl, aryl, aralkyl, C$_3$-C$_6$ cycloalkyl, and C$_3$-C$_7$ heterocyclyl having 1 to 3 heteroatoms selected from O, N, and S, wherein the aryl, aralkyl, C$_3$-C$_6$ cycloalkyl, and C$_3$-C$_7$ heterocyclyl may be further substituted with 0 to 3 substituents selected from halo, hydroxy, amino and C$_1$-C$_3$ alkyl; and alternatively, R' and R" attached to the same atom or to adjacent atoms may be taken together to form a 4- to 7-membered heterocylic ring having from 0 to 2 additional ring heteroatoms selected from N, O and S, and which may be unsubstituted or substituted with 1 to 3 substituents selected from the group consisting of halogen, cyano, C$_1$-C$_6$ alkyl, C$_3$-C$_6$ cycloalkyl, perfluoro C$_1$-C$_6$ alkyl, C$_1$-C$_6$ alkoxy, amino, amido and hydroxyl.

In certain embodiments, the present invention relates to a compound having the formula IIIa:

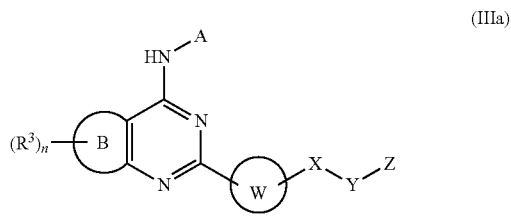

(IIIa)

wherein:

A is selected from the group consisting of:

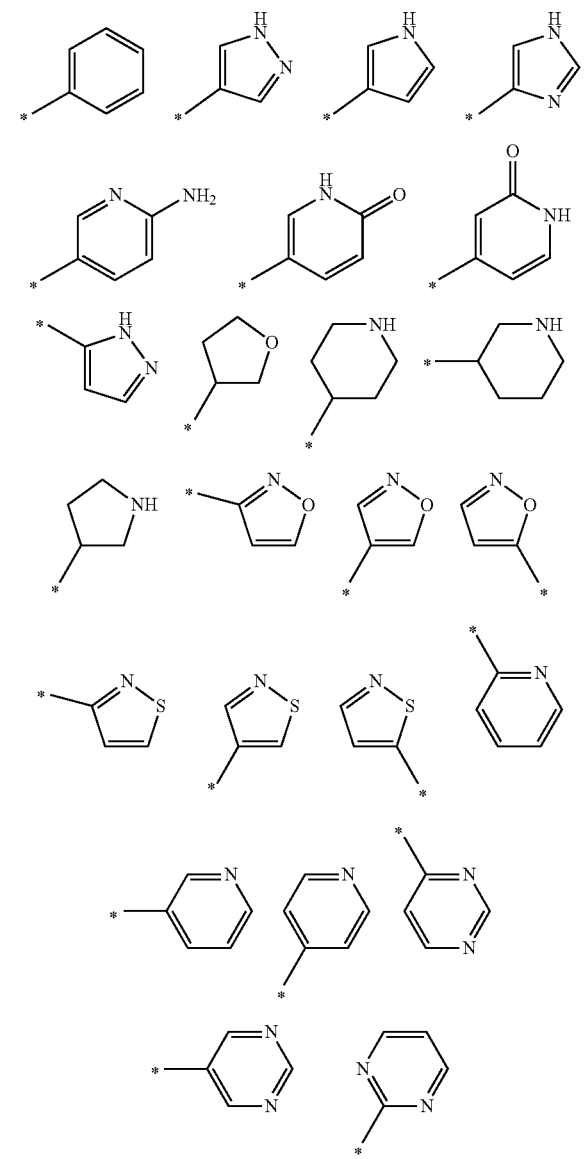

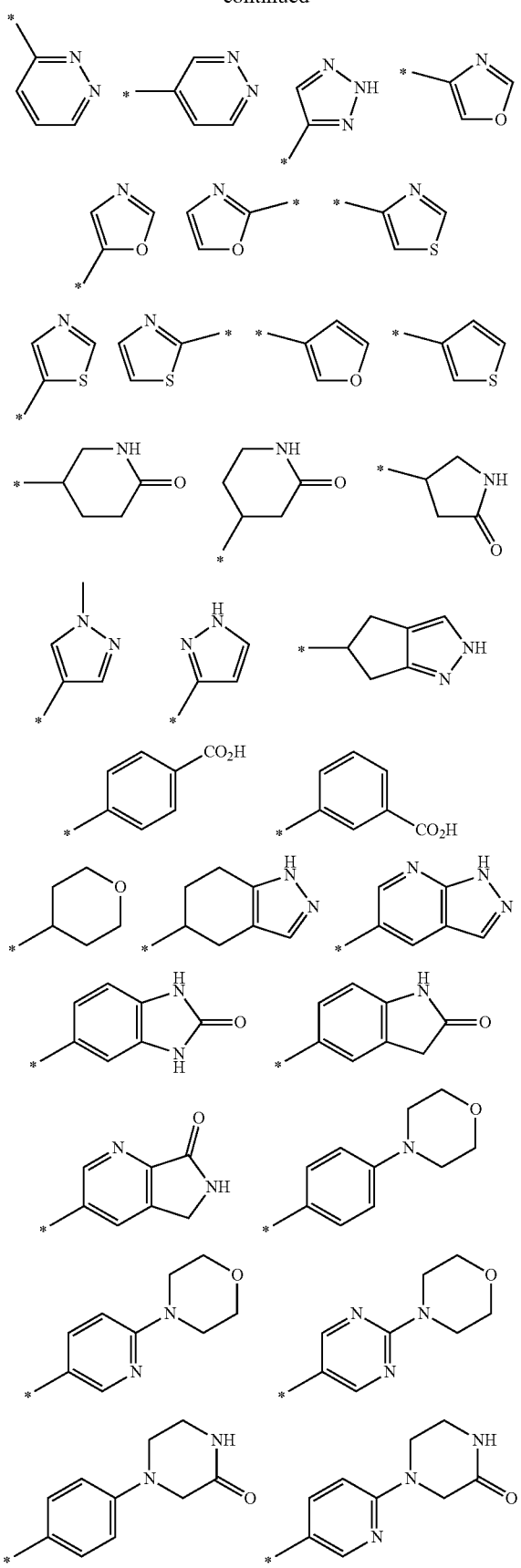

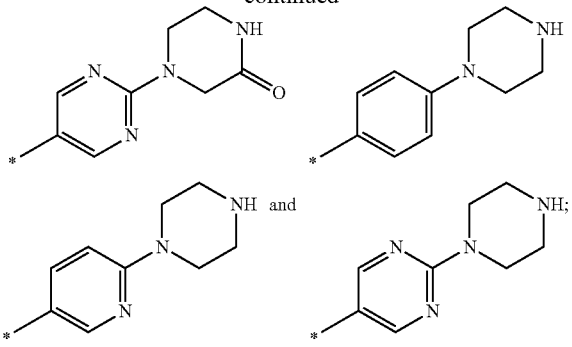

wherein each of the above structures for A may be optionally substituted with one to three substituents selected from the group consisting of halo, hydroxy, oxo, —NR'R", —(CH$_2$)$_b$NR'R", —O—(CH$_2$)$_c$NR'R", —C(=O)—NR'R", —NR'C(=O)—R", —OC(=O)R', —OC(=O)NR'R", —SO$_2$NR'R", —OSO$_2$NR'R", —O—(CH$_2$)$_d$OR", —CO$_2$—R", cyano, C$_1$-C$_6$ alkyl, C$_1$-C$_6$ alkoxy, alkoxyalkyl, C$_3$-C$_6$ cycloalkyl, perfluoro C$_1$-C$_6$ alkyl, and perfluoro C$_1$-C$_6$ alkoxy;

each b is independently selected from 1 to 6;
each c is independently selected from 2 to 6;
each d is independently selected from 2 to 6;

B is a 5- to 7-membered fused ring having from 0 to 3 ring heteroatoms:

R$^3$ is selected from the group consisting of halo, hydroxy, cyano, amino, —CO$_2$—R", —SO$_2$—R", —NR'R", —OR", —S—R", —(CH$_2$)$_e$—R", —(CH$_2$)$_e$NR'R", —O—(CH$_2$)$_f$NR'R", —C(=O)—NR'R", —NR'C(=O)—R", —OC(=O)R", —OC(=O)NR'R", —SO$_2$NR'R", —OSO$_2$NR'R", —O—(CH$_2$)$_g$OR", —O—(CH$_2$)$_e$R", —C(=O)—C$_1$-C$_6$ alkyl, C$_1$-C$_6$ alkyl, C$_1$-C$_6$ perfluoro alkyl, C$_1$-C$_6$ alkoxy and C$_1$-C$_6$ perfluoro alkoxy;

each e is independently selected from 1 to 6;
each f is independently selected from 2 to 6;
each g is independently selected from 2 to 6;

n is from 0 to 3;

W is a five- or six-membered aryl or heteroaryl ring containing from 0 to 3 heteroatoms selected from the group consisting of N, O and S;

X is selected from the group consisting of O, NH and CH$_2$;

Y is selected from the group consisting of a single bond, —C(=O)— and —(CH$_2$)$_a$—, wherein a is from 1 to 6;

Z is selected from the group consisting of —NR'R", —C(=O)NR'R", —NR'C(=O)R", and a 4- to 7-membered ring having from 0 to 3 ring heteroatoms selected from O, S, and N, which may be unsubstituted or substituted with up to three substituents selected from the group consisting of halo, hydroxy, oxo, —NR'R", —OR", —C(=O)—NR'R", —NR'C(=O)—R", —OC(=O)R", —OC(=O)NR'R", —SO$_2$NR'R", —OSO$_2$NR'R", —CO$_2$—R", —O—(CH$_2$)$_d$OR", cyano, C$_1$-C$_6$ alkyl, C$_1$-C$_6$ alkoxy, alkoxyalkyl, C$_3$-C$_6$ cycloalkyl, perfluoro C$_1$-C$_6$ alkyl, and perfluoro C$_1$-C$_6$ alkoxy;

each R' is independently selected from the group consisting of H and C$_1$-C$_6$ alkyl;

each R" is independently selected from the group consisting of H, C$_1$-C$_6$ alkyl, C$_1$-C$_6$ fluoroalkyl, C$_1$-C$_6$ difluoroalkyl, C$_1$-C$_6$ perfluoroalkyl, aryl, aralkyl, $C_3$-$C_6$ cycloalkyl, and $C_3$-$C_7$ heterocyclyl having 1 to 3 heteroatoms selected from O, N, and S, wherein the aryl, aralkyl, $C_3$-$C_6$ cycloalkyl, and $C_3$-$C_7$ heterocyclyl may be further substituted with 0 to 3 substituents selected from halo, hydroxy, amino and $C_1$-$C_3$ alkyl; and alternatively, R' and R" attached to the same atom or to adjacent atoms may be taken together to form a 4- to 7-membered heterocyclic ring having from 0 to 2 additional ring heteroatoms selected from N, O and S, and which may be unsubstituted or substituted with 1 to 3 substituents selected from the group consisting of halogen, cyano, $C_1$-$C_6$ alkyl, $C_3$-$C_6$ cycloalkyl, perfluoro $C_1$-$C_6$ alkyl, $C_1$-$C_6$ alkoxy, amino, amido and hydroxyl.

In certain embodiments, the present invention relates to a compound having the formula IV:

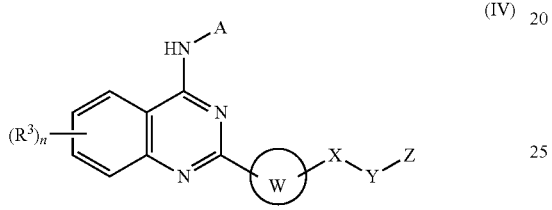

(IV)

wherein:

A is selected from the group consisting of:
(i) a 4- to 7-membered heterocyclic ring having from 1 to 3 ring heteroatoms selected from O, S, and N, and which may be unsubstituted or substituted with up to three substituents selected from the group consisting of halo, hydroxy, oxo, —NR'R", —OR", CHR'R", —($CH_2$)$_b$NR'R", —O—($CH_2$)$_c$NR'R", —C(=O)—NR'R", —NR'C(=O)—R", —OC(=O)R', —OC(=O)NR'R", —$SO_2$NR'R", —$OSO_2$NR'R", —O—($CH_2$)$_d$OR", —$CO_2$—R", cyano, $C_1$-$C_6$ alkyl, $C_1$-$C_6$ alkoxy, alkoxyalkyl, $C_3$-$C_6$ cycloalkyl, perfluoro $C_1$-$C_6$ alkyl, perfluoro $C_1$-$C_6$ alkoxy, and a 5- or 6-membered heterocyclic ring, which may be further substituted with 0 to 3 substituents selected from the group consisting of halo, hydroxy, oxo, —NR'R", —($CH_2$)$_b$NR'R", —O—($CH_2$)$_c$NR'R", —C(=O)—NR'R", —O—($CH_2$)$_d$OR", cyano, $C_1$-$C_6$ alkyl, $C_1$-$C_6$ alkoxy, alkoxyalkyl, $C_3$-$C_6$ cyclic alkyl, perfluoro $C_1$-$C_6$ alkyl, and perfluoro $C_1$-$C_6$ alkoxy;

(ii) a phenyl group, unsubstituted or substituted with up to three substituents selected from the group consisting of halo, hydroxy, —NR'R", —OR", CHR'R", —($CH_2$)$_b$NR'R", —O—($CH_2$)$_c$NR'R", —C(=O)—NR'R", —NR'C(=O)—R", —OC(=O)R', —OC(=O)NR'R", —$SO_2$NR'R", —$OSO_2$NR'R", —O—($CH_2$)$_d$OR", —$CO_2$—R", cyano, $C_1$-$C_6$ alkyl, $C_1$-$C_6$ alkoxy, alkoxyalkyl, $C_3$-$C_6$ cycloalkyl, perfluoro $C_1$-$C_6$ alkyl, perfluoro $C_1$-$C_6$ alkoxy, and a 5- or 6-membered heterocyclic ring, which may be further substituted with 0 to 3 substituents selected from the group consisting of halo, hydroxy, oxo, —NR'R", —OR", —($CH_2$)$_b$NR'R", —O—($CH_2$)$_c$NR'R", —C(=O)—NR'R", —OC(=O)R', —OC(=O)NR'R", —$SO_2$NR'R", —$OSO_2$NR'R", —O—($CH_2$)$_d$OR", cyano, $C_1$-$C_6$ alkyl, $C_1$-$C_6$ alkoxy, alkoxyalkyl, $C_3$-$C_6$ cyclic alkyl, perfluoro $C_1$-$C_6$ alkyl, and perfluoro $C_1$-$C_6$ alkoxy;

(iii) a cyclic group selected from:

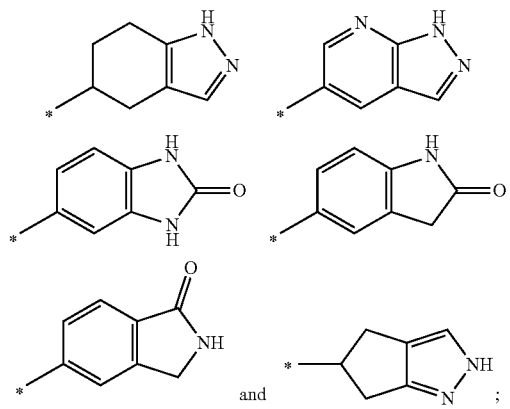

and wherein each of the above structures may be optionally substituted with up to three substituents selected from the group consisting of halo, hydroxy, oxo, —NR'R", —($CH_2$)$_b$NR'R", —O—($CH_2$)$_c$NR'R", —C(=O)—NR'R", —NR'C(=O)—R", —OC(=O)R', —OC(=O)NR'R", —$SO_2$NR'R", —$OSO_2$NR'R", —O—($CH_2$)$_d$OR", —$CO_2$—R", cyano, $C_1$-$C_6$ alkyl, $C_1$-$C_6$ alkoxy, alkoxyalkyl, $C_3$-$C_6$ cycloalkyl, perfluoro $C_1$-$C_6$ alkyl, perfluoro $C_1$-$C_6$ alkoxy, and a 5- or 6-membered heterocyclic ring, which may be further substituted with 0 to 3 substituents selected from the group consisting of halo, hydroxy, oxo, —NR'R", —($CH_2$)$_b$NR'R", —O—($CH_2$)$_c$NR'R", —C(=O)—NR'R", cyano, $C_1$-$C_6$ alkyl, $C_1$-$C_6$ alkoxy, alkoxyalkyl, $C_3$-$C_6$ cyclic alkyl, perfluoro $C_1$-$C_6$ alkyl, and perfluoro $C_1$-$C_6$ alkoxy;

each b is independently selected from 1 to 6;
each c is independently selected from 2 to 6;
each d is independently selected from 2 to 6;
$R^3$ is selected from the group consisting of halo, hydroxy, cyano, amino, —$CO_2$—R", —$SO_2$—R", —NR'R", —OR", —S—R", —($CH_2$)$_e$—R", —($CH_2$)$_e$NR'R", —O—($CH_2$)$_f$NR'R", —C(=O)—NR'R", —NR'C(=O)—R", —OC(=O)R", —OC(=O)NR'R", —$SO_2$NR'R", —$OSO_2$NR'R", —O—($CH_2$)$_g$OR", —O—($CH_2$)$_e$R", —C(=O)—$C_1$-$C_6$ alkyl, $C_1$-$C_6$ alkyl, $C_1$-$C_6$ perfluoro alkyl, $C_1$-$C_6$ alkoxy and $C_1$-$C_6$ perfluoro alkoxy;
each e is independently selected from 1 to 6;
each f is independently selected from 2 to 6;
each g is independently selected from 2 to 6;
n is from 0 to 3;
W is a five- or six-membered aryl or heteroaryl ring containing from 0 to 3 heteroatoms selected from the group consisting of N, O and S;
X is selected from the group consisting of O, NH and $CH_2$;
Y is selected from the group consisting of a single bond, —C(=O)— and —($CH_2$)$_a$—, wherein a is from 1 to 6;
Z is selected from the group consisting of —NR'R", —C(=O)NR'R", —NR'C(=O)R", and a 4- to 7-membered ring having from 0 to 3 ring heteroatoms selected from O, S, and N, which may be unsubstituted or substituted with up to three substituents selected from the group consisting of halo, hydroxy, oxo, —NR'R", —OR", —C(=O)—NR'R", —NR'C(=O)—R", —OC(=O)R", —OC(=O)NR'R", —$SO_2$NR'R", —$OSO_2$NR'R", —$CO_2$—R", —O—($CH_2$)$_d$OR", cyano, $C_1$-$C_6$ alkyl, $C_1$-$C_6$ alkoxy, alkoxyalkyl, $C_3$-$C_6$ cycloalkyl, perfluoro $C_1$-$C_6$ alkyl, and perfluoro $C_1$-$C_6$ alkoxy;

each R' is independently selected from the group consisting of H and $C_1$-$C_6$ alkyl;

each R" is independently selected from the group consisting of H, $C_1$-$C_6$ alkyl, $C_1$-$C_6$ fluoroalkyl, $C_1$-$C_6$ difluoroalkyl, $C_1$-$C_6$ perfluoroalkyl, aryl, aralkyl, $C_3$-$C_6$ cycloalkyl, and $C_3$-$C_7$ heterocyclyl having 1 to 3 heteroatoms selected from O, N, and S, wherein the aryl, aralkyl, $C_3$-$C_6$ cycloalkyl, and $C_3$-$C_7$ heterocyclyl may be further substituted with 0 to 3 substituents selected from halo, hydroxy, amino and $C_1$-$C_3$ alkyl; and alternatively, R' and R" attached to the same atom or to adjacent atoms may be taken together to form a 4- to 7-membered heterocylic ring having from 0 to 2 additional ring heteroatoms selected from N, O and S, and which may be unsubstituted or substituted with 1 to 3 substituents selected from the group consisting of halogen, cyano, $C_1$-$C_6$ alkyl, $C_3$-$C_6$ cycloalkyl, perfluoro $C_1$-$C_6$ alkyl, $C_1$-$C_6$ alkoxy, amino, amido and hydroxyl.

In certain embodiments, the present invention relates to a compound having the formula IVa:

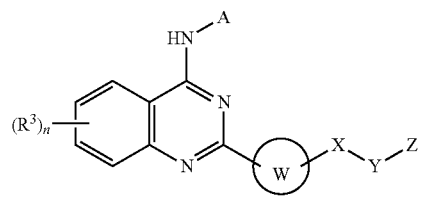

(IVa)

wherein:

A is selected from the group consisting of:

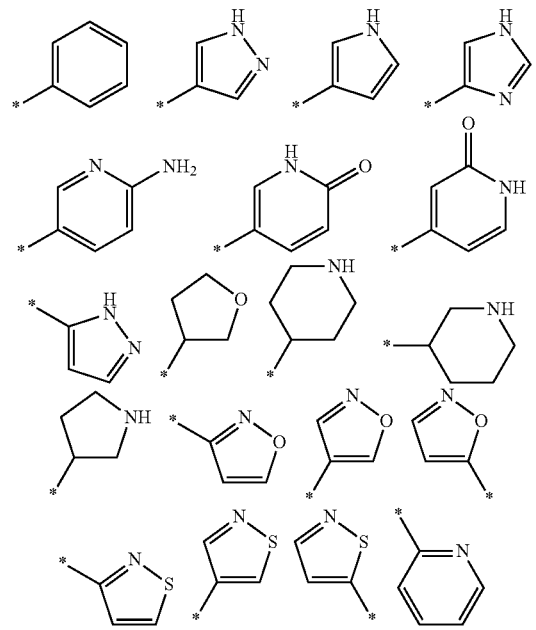

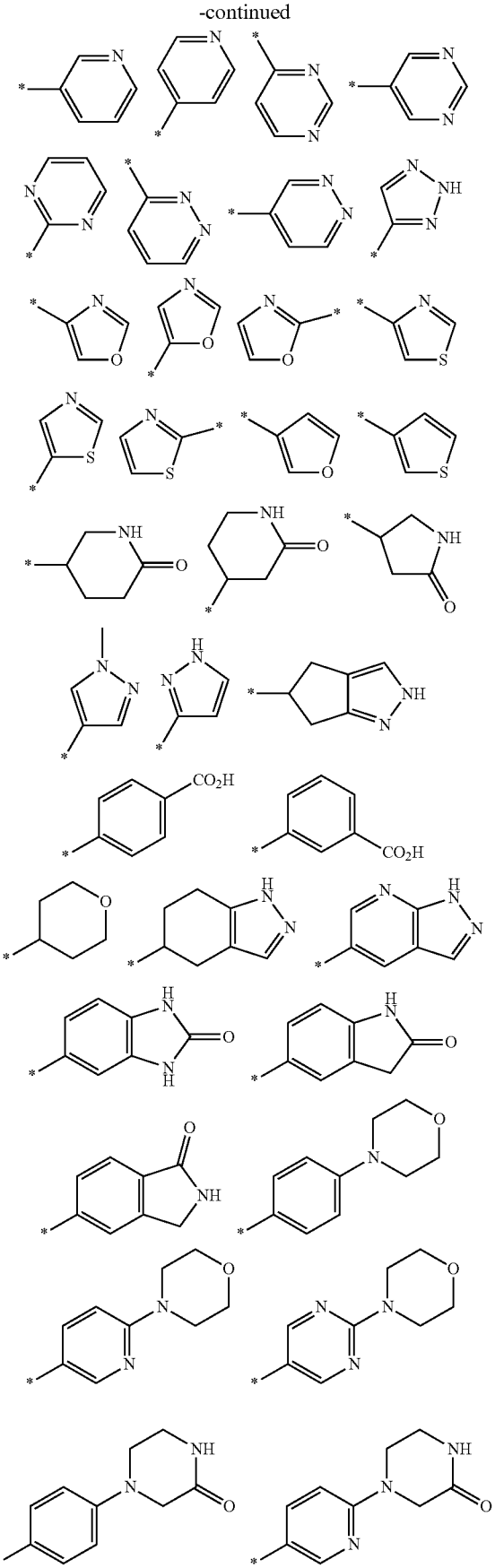

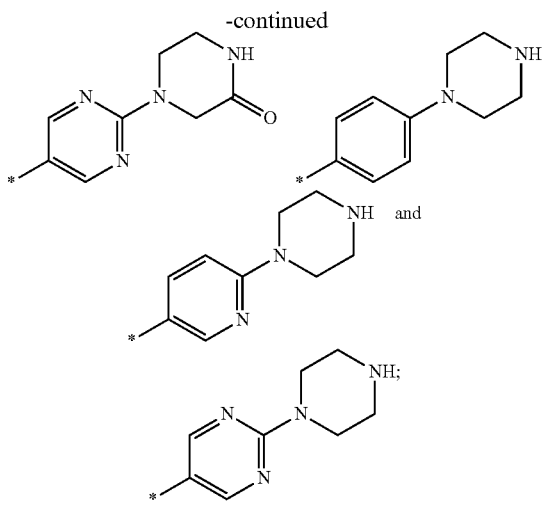

wherein each of the above structures for A may be optionally substituted with one to three substituents selected from the group consisting of halo, hydroxy, oxo, —NR'R", —(CH$_2$)$_b$NR'R", —O—(CH$_2$)$_c$NR'R", —C(═O)—NR'R", —NR'C(═O)—R", —OC(═O)R', —OC(═O)NR'R", —SO$_2$NR'R", —OSO$_2$NR'R", —O—(CH$_2$)$_d$OR", —CO$_2$—R", cyano, C$_1$-C$_6$ alkyl, C$_1$-C$_6$ alkoxy, alkoxyalkyl, C$_3$-C$_6$ cycloalkyl, perfluoro C$_1$-C$_6$ alkyl, and perfluoro C$_1$-C$_6$ alkoxy;

each b is independently selected from 1 to 6;
each c is independently selected from 2 to 6;
each d is independently selected from 2 to 6;

R$^3$ is selected from the group consisting of halo, hydroxy, cyano, amino, —CO$_2$—R", —SO$_2$—R", —NR'R", —OR", —S—R", —(CH$_2$)$_e$—R", —(CH$_2$)$_e$NR'R", —O—(CH$_2$)$_f$NR'R", —C(═O)—NR'R", —NR'C(═O)—R", —OC(═O)R", —OC(═O)NR'R", —SO$_2$NR'R", —OSO$_2$NR'R", —O—(CH$_2$)$_g$OR", —O—(CH$_2$)$_e$R", —C(═O)—C$_1$-C$_6$ alkyl, C$_1$-C$_6$ alkyl, C$_1$-C$_6$ perfluoro alkyl, C$_1$-C$_6$ alkoxy and C$_1$-C$_6$ perfluoro alkoxy;

each e is independently selected from 1 to 6;
each f is independently selected from 2 to 6;
each g is independently selected from 2 to 6 n is from 0 to 3;

W is a five- or six-membered aryl or heteroaryl ring containing from 0 to 3 heteroatoms selected from the group consisting of N, O and S;

X is selected from the group consisting of O, NH and CH$_2$;

Y is selected from the group consisting of a single bond, —C(═O)— and —(CH$_2$)$_a$—, wherein a is from 1 to 6;

Z is selected from the group consisting of —NR'R", —C(═O)NR'R", —NR'C(═O)R", and a 4- to 7-membered ring having from 0 to 3 ring heteroatoms selected from O, S, and N, which may be unsubstituted or substituted with up to three substituents selected from the group consisting of halo, hydroxy, oxo, —NR'R", —OR", —C(═O)—NR'R", —NR'C(═O)—R", —OC(═O)R", —OC(═O)NR'R", —SO$_2$NR'R", —OSO$_2$NR'R", —CO$_2$—R", —O—(CH$_2$)$_d$OR", cyano, C$_1$-C$_6$ alkyl, C$_1$-C$_6$ alkoxy, alkoxyalkyl, C$_3$-C$_6$ cycloalkyl, perfluoro C$_1$-C$_6$ alkyl, and perfluoro C$_1$-C$_6$ alkoxy;

each R' is independently selected from the group consisting of H and C$_1$-C$_6$ alkyl;

each R" is independently selected from the group consisting of H, C$_1$-C$_6$ alkyl, C$_1$-C$_6$ fluoroalkyl, C$_1$-C$_6$ difluoroalkyl, C$_1$-C$_6$ perfluoroalkyl, aryl, aralkyl, C$_3$-C$_6$ cycloalkyl, and C$_3$-C$_7$ heterocyclyl having 1 to 3 heteroatoms selected from O, N, and S, wherein the aryl, aralkyl, C$_3$-C$_6$ cycloalkyl, and C$_3$-C$_7$ heterocyclyl may be further substituted with 0 to 3 substituents selected from halo, hydroxy, amino and C$_1$-C$_3$ alkyl; and alternatively, R' and R" attached to the same atom or to adjacent atoms may be taken together to form a 4- to 7-membered heterocylic ring having from 0 to 2 additional ring heteroatoms selected from N, O and S, and which may be unsubstituted or substituted with 1 to 3 substituents selected from the group consisting of halogen, cyano, C$_1$-C$_6$ alkyl, C$_3$-C$_6$ cycloalkyl, perfluoro C$_1$-C$_6$ alkyl, C$_1$-C$_6$ alkoxy, amino, amido and hydroxyl.

In certain embodiments, the present invention relates to a compound having the formula IVb:

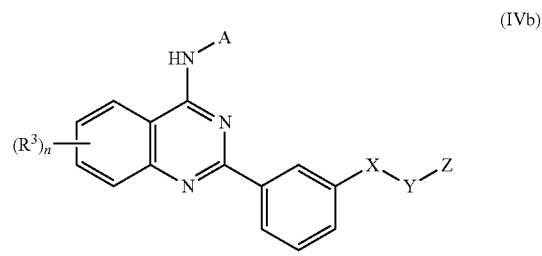

(IVb)

wherein:
A is selected from the group consisting of:
(i) a 4- to 7-membered heterocyclic ring having from 1 to 3 ring heteroatoms selected from O, S, and N, and which may be unsubstituted or substituted with up to three substituents selected from the group consisting of halo, hydroxy, oxo, —NR'R", —OR", CHR'R", —(CH$_2$)$_b$NR'R", —O—(CH$_2$)$_c$NR'R", —C(═O)—NR'R", —NR'C(═O)—R", —OC(═O)R', —OC(═O)NR'R", —SO$_2$NR'R", —OSO$_2$NR'R", —O—(CH$_2$)$_d$OR", —CO$_2$—R", cyano, C$_1$-C$_6$ alkyl, C$_1$-C$_6$ alkoxy, alkoxyalkyl, C$_3$-C$_6$ cycloalkyl, perfluoro C$_1$-C$_6$ alkyl, perfluoro C$_1$-C$_6$ alkoxy, and a 5- or 6-membered heterocyclic ring, which may be further substituted with 0 to 3 substituents selected from the group consisting of halo, hydroxy, oxo, —NR'R", —(CH$_2$)$_b$NR'R", —O—(CH$_2$)$_c$NR'R", —C(═O)—NR'R", —O—(CH$_2$)$_d$OR", cyano, C$_1$-C$_6$ alkyl, C$_1$-C$_6$ alkoxy, alkoxyalkyl, C$_3$-C$_6$ cyclic alkyl, perfluoro C$_1$-C$_6$ alkyl, and perfluoro C$_1$-C$_6$ alkoxy;

(ii) a phenyl group, unsubstituted or substituted with up to three substituents selected from the group consisting of halo, hydroxy, —NR'R", —OR", CHR'R", —(CH$_2$)$_b$NR'R", —O—(CH$_2$)$_c$NR'R", —C(═O)—NR'R", —NR'C(═O)—R", —OC(═O)R', —OC(═O)NR'R", —SO$_2$NR'R", —OSO$_2$NR'R", —O—(CH$_2$)$_d$OR", —CO$_2$—R", cyano, C$_1$-C$_6$ alkyl, C$_1$-C$_6$ alkoxy, alkoxyalkyl, C$_3$-C$_6$ cycloalkyl, perfluoro C$_1$-C$_6$ alkyl, perfluoro C$_1$-C$_6$ alkoxy, and a 5- or 6-membered heterocyclic ring, which may be further substituted with 0 to 3 substituents selected from the group consisting of halo, hydroxy, oxo, —NR'R", —OR", —(CH$_2$)$_b$NR'R", —O—(CH$_2$)$_c$NR'R", —C(═O)—NR'R", —OC(═O)R', —OC(═O)NR'R", —SO$_2$NR'R", —OSO$_2$NR'R", —O—

$(CH_2)_d$ OR", cyano, $C_1$-$C_6$ alkyl, $C_1$-$C_6$ alkoxy, alkoxyalkyl, $C_3$-$C_6$ cyclic alkyl, perfluoro $C_1$-$C_6$ alkyl, and perfluoro $C_1$-$C_6$ alkoxy;

(iii) a cyclic group selected from:

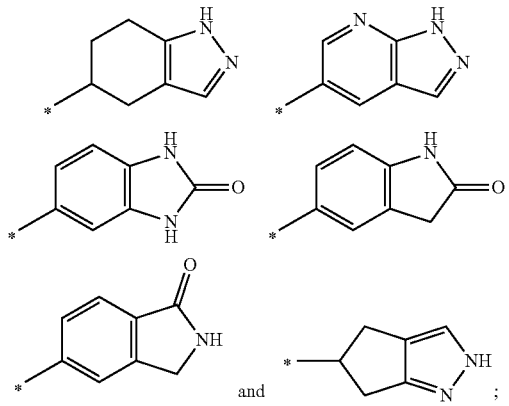

and wherein each of the above structures may be optionally substituted with up to three substituents selected from the group consisting of halo, hydroxy, oxo, —NR'R", —$(CH_2)_b$NR'R", —O—$(CH_2)_c$NR'R", —C(=O)—NR'R", —NR'C(=O)—R", —OC(=O)R', —OC(=O)NR'R", —SO$_2$NR'R", —OSO$_2$NR'R", —O—$(CH_2)_d$OR", —CO$_2$—R", cyano, $C_1$-$C_6$ alkyl, $C_1$-$C_6$ alkoxy, alkoxyalkyl, $C_3$-$C_6$ cycloalkyl, perfluoro $C_1$-$C_6$ alkyl, perfluoro $C_1$-$C_6$ alkoxy, and a 5- or 6-membered heterocyclic ring, which may be further substituted with 0 to 3 substituents selected from the group consisting of halo, hydroxy, oxo, —NR'R", —$(CH_2)_b$NR'R", —O—$(CH_2)_c$NR'R", —C(=O)—NR'R", cyano, $C_1$-$C_6$ alkyl, $C_1$-$C_6$ alkoxy, alkoxyalkyl, $C_3$-$C_6$ cyclic alkyl, perfluoro $C_1$-$C_6$ alkyl, and perfluoro $C_1$-$C_6$ alkoxy;

each b is independently selected from 1 to 6;
each c is independently selected from 2 to 6;
each d is independently selected from 2 to 6;
$R^3$ is selected from the group consisting of halo, hydroxy, cyano, amino, —CO$_2$—R", —SO$_2$—R", —NR'R", —OR", —S—R", —$(CH_2)_e$—R", —$(CH_2)_e$NR'R", —O—$(CH_2)_f$NR'R", —C(=O)—NR'R", —NR'C(=O)—R", —OC(=O)R", —OC(=O)NR'R", —SO$_2$NR'R", —OSO$_2$NR'R", —O—$(CH_2)_g$OR", —O—$(CH_2)_e$R", —C(=O)—$C_1$-$C_6$ alkyl, $C_1$-$C_6$ alkyl, $C_1$-$C_6$ perfluoro alkyl, $C_1$-$C_6$ alkoxy and $C_1$-$C_6$ perfluoro alkoxy;
each e is independently selected from 1 to 6;
each f is independently selected from 2 to 6;
each g is independently selected from 2 to 6;
n is from 0 to 3;
X is selected from the group consisting of O, NH and CH$_2$;
Y is selected from the group consisting of a single bond, —C(=O)— and —$(CH_2)_a$—, wherein a is from 1 to 6;
Z is selected from the group consisting of —NR'R", —C(=O)NR'R", —NR'C(=O)R", and a 4- to 7-membered ring having from 0 to 3 ring heteroatoms selected from O, S, and N, which may be unsubstituted or substituted with up to three substituents selected from the group consisting of halo, hydroxy, oxo, —NR'R", —OR", —C(=O)—NR'R", —NR'C(=O)—R", —OC(=O)R", —OC(=O)NR'R", —SO$_2$NR'R", —OSO$_2$NR'R", —CO$_2$—R", —O—$(CH_2)_d$OR", cyano, $C_1$-$C_6$ alkyl, $C_1$-$C_6$ alkoxy, alkoxyalkyl, $C_3$-$C_6$ cycloalkyl, perfluoro $C_1$-$C_6$ alkyl, and perfluoro $C_1$-$C_6$ alkoxy;

each R' is independently selected from the group consisting of H and $C_1$-$C_6$ alkyl;

each R" is independently selected from the group consisting of H, $C_1$-$C_6$ alkyl, $C_1$-$C_6$ fluoroalkyl, $C_1$-$C_6$ difluoroalkyl, $C_1$-$C_6$ perfluoroalkyl, aryl, aralkyl, $C_3$-$C_6$ cycloalkyl, and $C_3$-$C_7$ heterocyclyl having 1 to 3 heteroatoms selected from O, N, and S, wherein the aryl, aralkyl, $C_3$-$C_6$ cycloalkyl, and $C_3$-$C_7$ heterocyclyl may be further substituted with 0 to 3 substituents selected from halo, hydroxy, amino and $C_1$-$C_3$ alkyl; and alternatively, R' and R" attached to the same atom or to adjacent atoms may be taken together to form a 4- to 7-membered heterocylic ring having from 0 to 2 additional ring heteroatoms selected from N, O and S, and which may be unsubstituted or substituted with 1 to 3 substituents selected from the group consisting of halogen, cyano, $C_1$-$C_6$ alkyl, $C_3$-$C_6$ cycloalkyl, perfluoro $C_1$-$C_6$ alkyl, $C_1$-$C_6$ alkoxy, amino, amido and hydroxyl.

In certain embodiments, the present invention relates to a compound having the formula IVc:

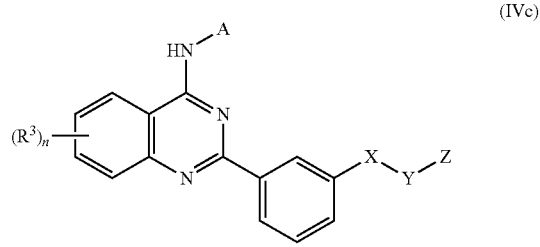

(IVc)

wherein:

A is selected from the group consisting of:

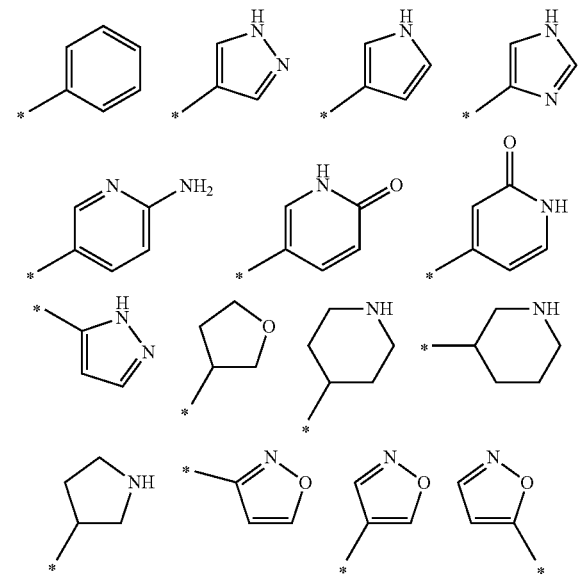

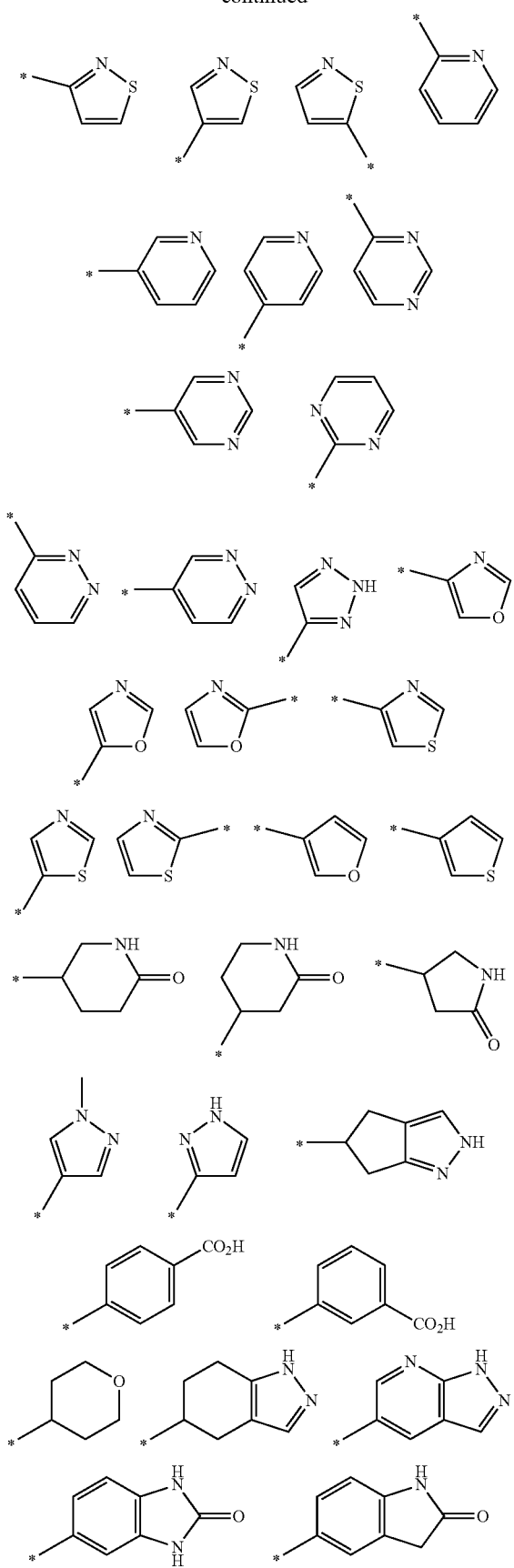
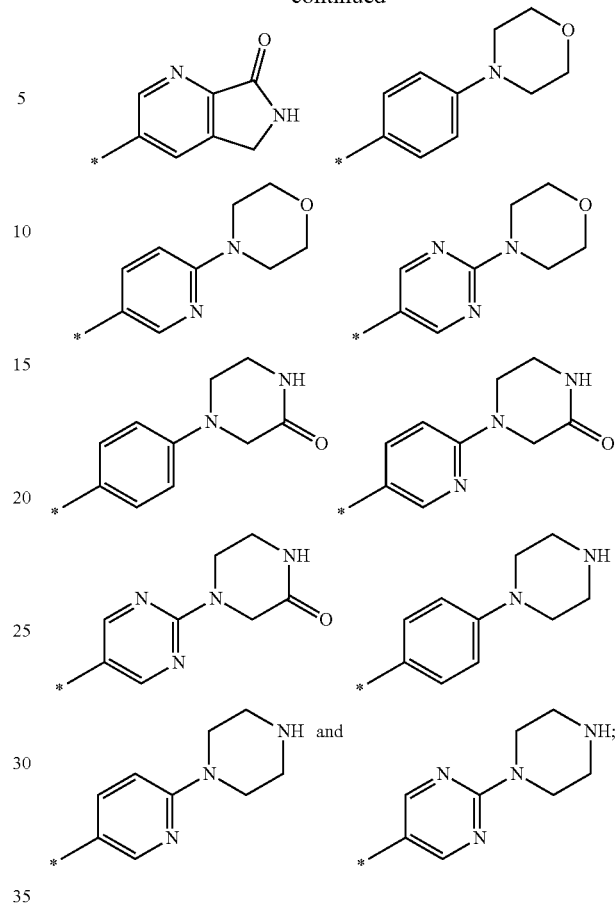

wherein each of the above structures for A may be optionally substituted with one to three substituents selected from the group consisting of halo, hydroxy, oxo, —NR'R", —(CH$_2$)$_b$NR'R", —O—(CH$_2$)$_c$NR'R", —C(=O)—NR'R", —NR'C(=O)—R", —OC(=O)R', —OC(=O)NR'R", —SO$_2$NR'R", —OSO$_2$NR'R", —O—(CH$_2$)$_d$OR", —CO$_2$—R", cyano, C$_1$-C$_6$ alkyl, C$_1$-C$_6$ alkoxy, alkoxyalkyl, C$_3$-C$_6$ cycloalkyl, perfluoro C$_1$-C$_6$ alkyl, and perfluoro C$_1$-C$_6$ alkoxy;

each b is independently selected from 1 to 6;
each c is independently selected from 2 to 6;
each d is independently selected from 2 to 6;

R$^3$ is selected from the group consisting of halo, hydroxy, cyano, amino, —CO$_2$—R", —SO$_2$—R", —NR'R", —OR", —S—R", —(CH$_2$)$_e$—R", —(CH$_2$)$_e$NR'R", —O—(CH$_2$)$_f$NR'R", —C(=O)—NR'R", —NR'C(=O)—R", —OC(=O)R", —OC(=O)NR'R", —SO$_2$NR'R", —OSO$_2$NR'R", —O—(CH$_2$)$_g$OR", —O—(CH$_2$)$_g$R", —C(=O)—C$_1$-C$_6$ alkyl, C$_1$-C$_6$ alkyl, C$_1$-C$_6$ perfluoro alkyl, C$_1$-C$_6$ alkoxy and C$_1$-C$_6$ perfluoro alkoxy;

each e is independently selected from 1 to 6;
each f is independently selected from 2 to 6;
each g is independently selected from 2 to 6;
n is from 0 to 3;
X is selected from the group consisting of O, NH and CH$_2$;
Y is selected from the group consisting of a single bond, —C(=O)— and —(CH$_2$)$_a$—, wherein a is from 1 to 6;
Z is selected from the group consisting of —NR'R", —C(=O)NR'R", —NR'C(=O)R", and a 4- to 7-membered ring having from 0 to 3 ring heteroatoms selected from O, S, and N, which may be unsubstituted or substituted with up to three substituents selected from the group consisting of halo, hydroxy, oxo, —NR'R", —OR", —C(=O)—NR'R", —NR'C(=O)—R", —OC(=O)R", —OC(=O)NR'R", —SO$_2$NR'R", —OSO$_2$NR'R", —CO$_2$—R", —O—(CH$_2$)$_d$OR", cyano, C$_1$-C$_6$ alkyl, C$_1$-C$_6$ alkoxy, alkoxyalkyl, C$_3$-C$_6$ cycloalkyl, perfluoro C$_1$-C$_6$ alkyl, and perfluoro C$_1$-C$_6$ alkoxy;

R is selected from the group consisting of each R' is independently selected from the group consisting of H and C$_1$-C$_6$ alkyl;

each R" is independently selected from the group consisting of H, C$_1$-C$_6$ alkyl, C$_1$-C$_6$ fluoroalkyl, C$_1$-C$_6$ difluoroalkyl, C$_1$-C$_6$ perfluoroalkyl, aryl, aralkyl, C$_3$-C$_6$ cycloalkyl, and C$_3$-C$_7$ heterocyclyl having 1 to 3 heteroatoms selected from O, N, and S, wherein the aryl, aralkyl, C$_3$-C$_6$ cycloalkyl, and C$_3$-C$_7$ heterocyclyl may be further substituted with 0 to 3 substituents selected from halo, hydroxy, amino and C$_1$-C$_3$ alkyl; and alternatively, R' and R" attached to the same atom or to adjacent atoms may be taken together to form a 4- to 7-membered heterocylic ring having from 0 to 2 additional ring heteroatoms selected from N, O and S, and which may be unsubstituted or substituted with 1 to 3 substituents selected from the group consisting of halogen, cyano, C$_1$-C$_6$ alkyl, C$_3$-C$_6$ cycloalkyl, perfluoro C$_1$-C$_6$ alkyl, C$_1$-C$_6$ alkoxy, amino, amido and hydroxyl.

In certain embodiments, the present invention relates to a compound having the formula IVd:

(IVd)

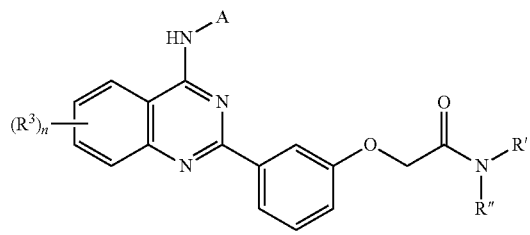

wherein:

A is selected from the group consisting of:
(i) a 4- to 7-membered heterocyclic ring having from 1 to 3 ring heteroatoms selected from O, S, and N, and which may be unsubstituted or substituted with up to three substituents selected from the group consisting of halo, hydroxy, oxo, —NR'R", —OR", CHR'R", —(CH$_2$)$_b$NR'R", —O—(CH$_2$)$_c$NR'R", —C(=O)—NR'R", —NR'C(=O)—R", —OC(=O)R', —OC(=O)NR'R", —SO$_2$NR'R", —OSO$_2$NR'R", —O—(CH$_2$)$_d$OR", —CO$_2$—R", cyano, C$_1$-C$_6$ alkyl, C$_1$-C$_6$ alkoxy, alkoxyalkyl, C$_3$-C$_6$ cyclic alkyl, perfluoro C$_1$-C$_6$ alkyl, and perfluoro C$_1$-C$_6$ alkoxy;

(ii) a phenyl group, unsubstituted or substituted with up to three substituents selected from the group consisting of halo, hydroxy, —NR'R", —OR", CHR'R", —(CH$_2$)$_b$NR'R", —O—(CH$_2$)$_c$NR'R", —C(=O)—NR'R", —NR'C(=O)—R", —OC(=O)R', —OC(=O)NR'R", —SO$_2$NR'R", —OSO$_2$NR'R", —O—(CH$_2$)$_d$OR", —CO$_2$—R", cyano, C$_1$-C$_6$ alkyl, C$_1$-C$_6$ alkoxy, alkoxyalkyl, C$_3$-C$_6$ cycloalkyl, perfluoro C$_1$-C$_6$ alkyl, perfluoro C$_1$-C$_6$ alkoxy, and a 5- or 6-membered heterocyclic ring, which may be further substituted with 0 to 3 substituents selected from the group consisting of halo, hydroxy, oxo, —NR'R", —OR", —(CH$_2$)$_b$NR'R", —O—(CH$_2$)$_c$NR'R", —C(=O)—NR'R", —OC(=O)R', —OC(=O)NR'R", —SO$_2$NR'R", —OSO$_2$NR'R", —O—(CH$_2$)$_d$OR", cyano, C$_1$-C$_6$ alkyl, C$_1$-C$_6$ alkoxy, alkoxyalkyl, C$_3$-C$_6$ cyclic alkyl, perfluoro C$_1$-C$_6$ alkyl, and perfluoro C$_1$-C$_6$ alkoxy;

(iii) a cyclic group selected from:

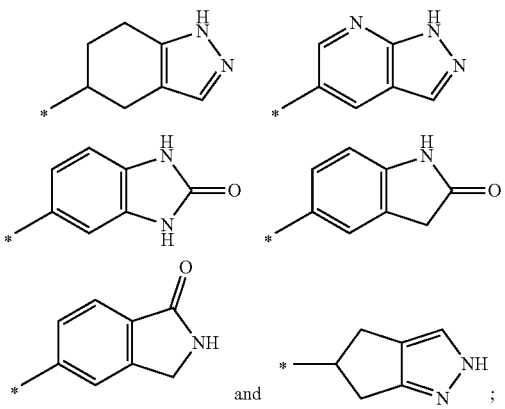

and ;

wherein each of the above structures may be optionally substituted with up to three substituents selected from the group consisting of halo, hydroxy, oxo, —NR'R", —(CH$_2$)$_b$NR'R", —O—(CH$_2$)$_c$NR'R", —C(=O)—NR'R", —NR'C(=O)—R", —OC(=O)R', —OC(=O)NR'R", —SO$_2$NR'R", —OSO$_2$NR'R", —O—(CH$_2$)$_d$OR", —CO$_2$—R", cyano, C$_1$-C$_6$ alkyl, C$_1$-C$_6$ alkoxy, alkoxyalkyl, C$_3$-C$_6$ cycloalkyl, perfluoro C$_1$-C$_6$ alkyl, perfluoro C$_1$-C$_6$ alkoxy, and a 5- or 6-membered heterocyclic ring, which may be further substituted with 0 to 3 substituents selected from the group consisting of halo, hydroxy, oxo, —NR'R", —(CH$_2$)$_b$NR'R", —O—(CH$_2$)$_c$NR'R", —C(=O)—NR'R", cyano, C$_1$-C$_6$ alkyl, C$_1$-C$_6$ alkoxy, alkoxyalkyl, C$_3$-C$_6$ cyclic alkyl, perfluoro C$_1$-C$_6$ alkyl, and perfluoro C$_1$-C$_6$ alkoxy;

each b is independently selected from 1 to 6;
each c is independently selected from 2 to 6;
each d is independently selected from 2 to 6;

R$^3$ is selected from the group consisting of halo, hydroxy, cyano, amino, —CO$_2$—R", —SO$_2$—R", —NR'R", —OR", —S—R", —(CH$_2$)$_e$—R", —(CH$_2$)$_e$NR'R", —O—(CH$_2$)$_f$NR'R", —C(=O)—NR'R", —NR'C(=O)—R", —OC(=O)R", —OC(=O)NR'R", —SO$_2$NR'R", —OSO$_2$NR'R", —O—(CH$_2$)$_g$OR", —O—(CH$_2$)$_e$R", —C(=O)—C$_1$-C$_6$ alkyl, C$_1$-C$_6$ alkyl, C$_1$-C$_6$ perfluoro alkyl, C$_1$-C$_6$ alkoxy and C$_1$-C$_6$ perfluoro alkoxy;

each e is independently selected from 1 to 6;
each f is independently selected from 2 to 6;
each g is independently selected from 2 to 6;
n is from 0 to 3;
each R' is independently selected from the group consisting of H and $C_1$-$C_6$ alkyl;
each R" is independently selected from the group consisting of H, $C_1$-$C_6$ alkyl, $C_1$-$C_6$ fluoroalkyl, $C_1$-$C_6$ difluoroalkyl, $C_1$-$C_6$ perfluoroalkyl, aryl, aralkyl, $C_3$-$C_6$ cycloalkyl, and $C_3$-$C_7$ heterocyclyl having 1 to 3 heteroatoms selected from O, N, and S, wherein the aryl, aralkyl, $C_3$-$C_6$ cycloalkyl, and $C_3$-$C_7$ heterocyclyl may be further substituted with 0 to 3 substituents selected from halo, hydroxy, amino and $C_1$-$C_3$ alkyl; and
alternatively, R' and R" attached to the same atom or to adjacent atoms may be taken together to form a 4- to 7-membered heterocylic ring having from 0 to 2 additional ring heteroatoms selected from N, O and S, and which may be unsubstituted or substituted with 1 to 3 substituents selected from the group consisting of halogen, cyano, $C_1$-$C_6$ alkyl, $C_3$-$C_6$ cycloalkyl, perfluoro $C_1$-$C_6$ alkyl, $C_1$-$C_6$ alkoxy, amino, amido and hydroxyl.

In certain embodiments, the present invention relates to a compound having the formula IVe:

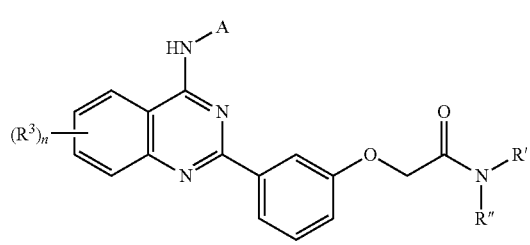

(IVe)

wherein:
A is selected from the group consisting of:

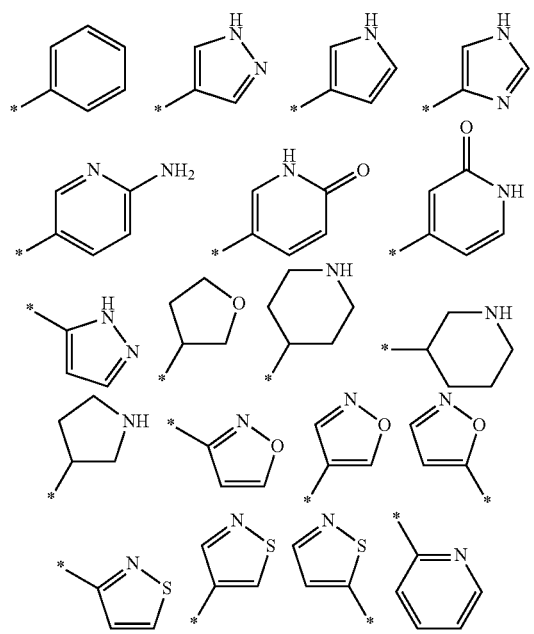

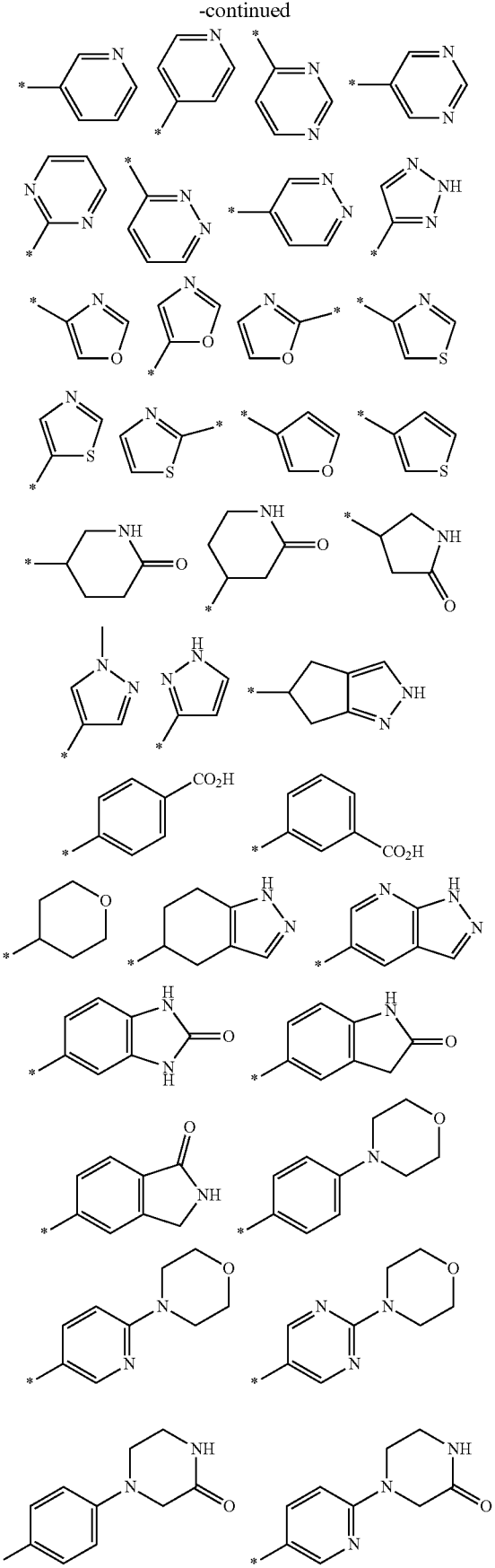

-continued

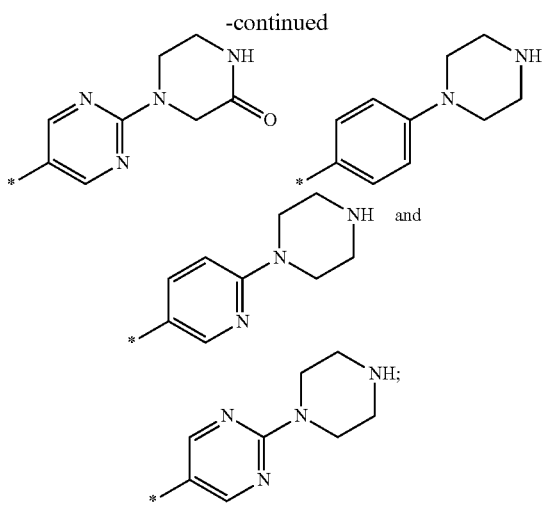

wherein each of the above structures for A may be optionally substituted with one to three substituents selected from the group consisting of halo, hydroxy, oxo, —NR'R", —(CH$_2$)$_b$NR'R", —O—(CH$_2$)$_c$NR'R", —C(=O)—NR'R", —NR'C(=O)—R", —OC(=O)R', —OC(=O)NR'R", —SO$_2$NR'R", —OSO$_2$NR'R", —O—(CH$_2$)$_d$OR", —CO$_2$—R", cyano, C$_1$-C$_6$ alkyl, C$_1$-C$_6$ alkoxy, alkoxyalkyl, C$_3$-C$_6$ cycloalkyl, perfluoro C$_1$-C$_6$ alkyl, and perfluoro C$_1$-C$_6$ alkoxy;
each b is independently selected from 1 to 6;
each c is independently selected from 2 to 6;
each d is independently selected from 2 to 6;
R$^3$ is selected from the group consisting of halo, hydroxy, cyano, amino, —CO$_2$—R", —SO$_2$—R", —NR'R", —OR", —S—R", —(CH$_2$)$_e$—R", —(CH$_2$)$_e$NR'R", —O—(CH$_2$)$_f$NR'R", —C(=O)—NR'R", —NR'C(=O)—R", —OC(=O)R", —OC(=O)NR'R", —SO$_2$NR'R", —OSO$_2$NR'R", —O—(CH$_2$)$_g$OR", —O—(CH$_2$)$_e$R", —C(=O)—C$_1$-C$_6$ alkyl, C$_1$-C$_6$ alkyl, C$_1$-C$_6$ perfluoro alkyl, C$_1$-C$_6$ alkoxy and C$_1$-C$_6$ perfluoro alkoxy;
each e is independently selected from 1 to 6;
each f is independently selected from 2 to 6;
each g is independently selected from 2 to 6;
n is from 0 to 3;
each R' is independently selected from the group consisting of H and C$_1$-C$_6$ alkyl;
each R" is independently selected from the group consisting of H, C$_1$-C$_6$ alkyl, C$_1$-C$_6$ fluoroalkyl, C$_1$-C$_6$ difluoroalkyl, C$_1$-C$_6$ perfluoroalkyl, aryl, aralkyl, C$_3$-C$_6$ cycloalkyl, and C$_3$-C$_7$ heterocyclyl having 1 to 3 heteroatoms selected from O, N, and S, wherein the aryl, aralkyl, C$_3$-C$_6$ cycloalkyl, and C$_3$-C$_7$ heterocyclyl may be further substituted with 0 to 3 substituents selected from halo, hydroxy, amino and C$_1$-C$_3$ alkyl; and
alternatively, R' and R" attached to the same atom or to adjacent atoms may be taken together to form a 4- to 7-membered heterocylic ring having from 0 to 2 additional ring heteroatoms selected from N, O and S, and which may be unsubstituted or substituted with 1 to 3 substituents selected from the group consisting of halogen, cyano, C$_1$-C$_6$ alkyl, C$_3$-C$_6$ cycloalkyl, perfluoro C$_1$-C$_6$ alkyl, C$_1$-C$_6$ alkoxy, amino, amido and hydroxyl.
In certain embodiments, the present invention relates to a compound having the formula IVf:

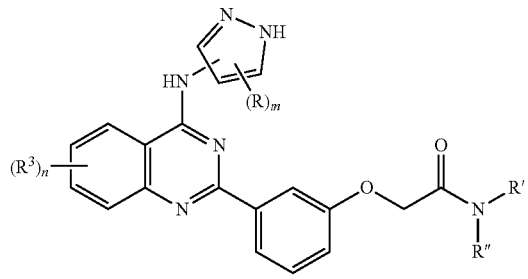

wherein:
R$^3$ is selected from the group consisting of halo, hydroxy, cyano, amino, —CO$_2$—R", —SO$_2$—R", —NR'R", —OR", —S—R", —(CH$_2$)$_e$—R", —(CH$_2$)$_e$NR'R", —O—(CH$_2$)$_f$NR'R", —C(=O)—NR'R", —NR'C(=O)—R", —OC(=O)R", —OC(=O)NR'R", —SO$_2$NR'R", —OSO$_2$NR'R", —O—(CH$_2$)$_g$OR", —O—(CH$_2$)$_e$R", —C(=O)—C$_1$-C$_6$ alkyl, C$_1$-C$_6$ alkyl, C$_1$-C$_6$ perfluoro alkyl, C$_1$-C$_6$ alkoxy and C$_1$-C$_6$ perfluoro alkoxy;
each e is independently selected from 1 to 6;
each f is independently selected from 2 to 6;
each g is independently selected from 2 to 6;
n is from 0 to 3;
each R' is independently selected from the group consisting of H and C$_1$-C$_6$ alkyl;
each R" is independently selected from the group consisting of H, C$_1$-C$_6$ alkyl, C$_1$-C$_6$ fluoroalkyl, C$_1$-C$_6$ difluoroalkyl, C$_1$-C$_6$ perfluoroalkyl, aryl, aralkyl, C$_3$-C$_6$ cycloalkyl, and C$_3$-C$_7$ heterocyclyl having 1 to 3 heteroatoms selected from O, N, and S, wherein the aryl, aralkyl, C$_3$-C$_6$ cycloalkyl, and C$_3$-C$_7$ heterocyclyl may be further substituted with 0 to 3 substituents selected from halo, hydroxy, amino and C$_1$-C$_3$ alkyl; and
alternatively, R' and R" attached to the same atom or to adjacent atoms may be taken together to form a 4- to 7-membered heterocylic ring having from 0 to 2 additional ring heteroatoms selected from N, O and S, and which may be unsubstituted or substituted with 1 to 3 substituents selected from the group consisting of halogen, cyano, C$_1$-C$_6$ alkyl, C$_3$-C$_6$ cycloalkyl, perfluoro C$_1$-C$_6$ alkyl, C$_1$-C$_6$ alkoxy, amino, amido and hydroxyl.
In certain embodiments of the present invention, there is provided a compound of the formula (V):

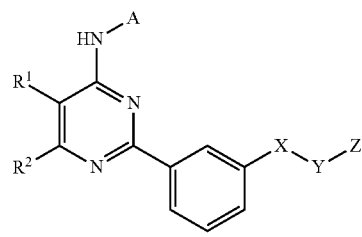

wherein:
A is selected from the group consisting of:
(i) a 4- to 7-membered heterocyclic ring having from 1 to 3 ring heteroatoms selected from O, S, and N, and which may be unsubstituted or substituted with up to three substituents selected from the group consisting of halo, hydroxy, oxo, —NR'R", —OR", CHR'R", —(CH$_2$)$_b$NR'R", —O—(CH$_2$)$_c$NR'R", —C(=O)—NR'R", —NR'C(=O)—R", —OC(=O)R', —OC(=O)NR'R", —SO$_2$NR'R", —OSO$_2$NR'R", —O—(CH$_2$)$_d$OR", —CO$_2$—R", cyano, C$_1$-C$_6$ alkyl, C$_1$-C$_6$ alkoxy, alkoxyalkyl, C$_3$-C$_6$ cycloalkyl, perfluoro C$_1$-C$_6$ alkyl, perfluoro C$_1$-C$_6$ alkoxy, and a 5- or 6-membered heterocyclic ring, which may be further substituted with 0 to 3 substituents selected from the group consisting of halo, hydroxy, oxo, —NR'R", —(CH$_2$)$_b$NR'R", —O—(CH$_2$)$_c$NR'R", —C(=O)—NR'R", —O—(CH$_2$)$_d$OR", cyano, C$_1$-C$_6$ alkyl, C$_1$-C$_6$ alkoxy, alkoxyalkyl, C$_3$-C$_6$ cyclic alkyl, perfluoro C$_1$-C$_6$ alkyl, and perfluoro C$_1$-C$_6$ alkoxy;

(ii) a phenyl group, unsubstituted or substituted with up to three substituents selected from the group consisting of halo, hydroxy, —NR'R", —OR", CHR'R", —(CH$_2$)$_b$NR'R", —O—(CH$_2$)$_c$NR'R", —C(=O)—NR'R", —NR'C(=O)—R", —OC(=O)R', —OC(=O)NR'R", —SO$_2$NR'R", —OSO$_2$NR'R", —O—(CH$_2$)$_d$OR", —CO$_2$—R", cyano, C$_1$-C$_6$ alkyl, C$_1$-C$_6$ alkoxy, alkoxyalkyl, C$_3$-C$_6$ cycloalkyl, perfluoro C$_1$-C$_6$ alkyl, perfluoro C$_1$-C$_6$ alkoxy, and a 5- or 6-membered heterocyclic ring, which may be further substituted with 0 to 3 substituents selected from the group consisting of halo, hydroxy, oxo, —NR'R", —OR", —(CH$_2$)$_b$NR'R", —O—(CH$_2$)$_c$NR'R", —C(=O)—NR'R", —OC(=O)R', —OC(=O)NR'R", —SO$_2$NR'R", —OSO$_2$NR'R", —O—(CH$_2$)$_d$OR", cyano, C$_1$-C$_6$ alkyl, C$_1$-C$_6$ alkoxy, alkoxyalkyl, C$_3$-C$_6$ cyclic alkyl, perfluoro C$_1$-C$_6$ alkyl, and perfluoro C$_1$-C$_6$ alkoxy;

(iii) a cyclic group selected from:

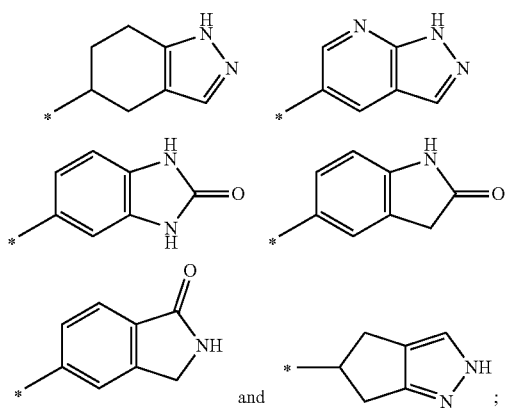

wherein each of the above structures may be optionally substituted with up to three substituents selected from the group consisting of halo, hydroxy, oxo, —NR'R", —(CH$_2$)$_b$NR'R", —O—(CH$_2$)$_c$NR'R", —C(=O)—NR'R", —NR'C(=O)—R", —OC(=O)R', —OC(=O)NR'R", —SO$_2$NR'R", —OSO$_2$NR'R", —O—(CH$_2$)$_d$OR", —CO$_2$—R", cyano, C$_1$-C$_6$ alkyl, C$_1$-C$_6$ alkoxy, alkoxyalkyl, C$_3$-C$_6$ cycloalkyl, perfluoro C$_1$-C$_6$ alkyl, perfluoro C$_1$-C$_6$ alkoxy, and a 5- or 6-membered heterocyclic ring, which may be further substituted with 0 to 3 substituents selected from the group consisting of halo, hydroxy, oxo, —NR'R", —(CH$_2$)$_b$NR'R", —O—(CH$_2$)$_c$NR'R", —C(=O)—NR'R", cyano, C$_1$-C$_6$ alkyl, C$_1$-C$_6$ alkoxy, alkoxyalkyl, C$_3$-C$_6$ cyclic alkyl, perfluoro C$_1$-C$_6$ alkyl, and perfluoro C$_1$-C$_6$ alkoxy;

each b is independently selected from 1 to 6;
each c is independently selected from 2 to 6;
each d is independently selected from 2 to 6;

R$^1$ is selected from the group consisting of H, halo, hydroxy, —NR'R", —OR", —(CH$_2$)$_e$NR'R", —O—(CH$_2$)$_f$NR'R", —C(=O)—NR'R", —NR'C(=O)—R", —OC(=O)R', —OC(=O)NR'R", —CO$_2$—R", —SO$_2$NR'R", —OSO$_2$NR'R", —O—(CH$_2$)$_g$OR", cyano, C$_1$-C$_6$ alkyl, C$_2$-C$_6$ alkenyl, C$_2$-C$_6$ alkynyl, C$_3$-C$_6$ cyclic alkyl, C$_1$-C$_6$ alkoxy, aryl, aralkyl, heterocycyl, C$_1$-C$_6$ perfluoro alkyl, and C$_1$-C$_6$ perfluoro alkoxy;

R$^2$ is selected from the group consisting of H, halo, hydroxy, —NR'R", —OR", —(CH$_2$)$_e$NR'R", —O—(CH$_2$)$_f$NR'R", —C(=O)—NR'R", —NR'C(=O)—R", —OC(=O)R', —OC(=O)NR'R", —CO$_2$—R", —SO$_2$NR'R", —OSO$_2$NR'R", —O—(CH$_2$)$_g$OR", cyano, C$_1$-C$_6$ alkyl, C$_2$-C$_6$ alkenyl, C$_2$-C$_6$ alkynyl, C$_3$-C$_6$ cyclic alkyl, C$_1$-C$_6$ alkoxy, aryl, aralkyl, heterocycyl, C$_1$-C$_6$ perfluoro alkyl, and C$_1$-C$_6$ perfluoro alkoxy;

alternatively, R$^1$ and R$^2$ are taken together to form a 5- to 7-membered fused ring having from 0 to 3 ring heteroatoms, and is unsubstituted or is substituted with up to 3 substituents selected from the group consisting of halo, hydroxy, cyano, amino, —CO$_2$—R", —SO$_2$—R", —NR'R", —OR", —S—R", —(CH$_2$)$_e$—R", —(CH$_2$)$_e$NR'R", —O—(CH$_2$)$_f$NR'R", —C(=O)—NR'R", —NR'C(=O)—R", —OC(=O)R", —OC(=O)NR'R", —SO$_2$NR'R", —OSO$_2$NR'R", —O—(CH$_2$)$_g$OR", —O—(CH$_2$)$_e$R", —C(=O)—C$_1$-C$_6$ alkyl, C$_1$-C$_6$ alkyl, C$_1$-C$_6$ perfluoro alkyl, C$_1$-C$_6$ alkoxy and C$_1$-C$_6$ perfluoro alkoxy;

each e is independently selected from 1 to 6;
each f is independently selected from 2 to 6;
each g is independently selected from 2 to 6;

X is selected from the group consisting of O, NH and CH$_2$;

Y is selected from the group consisting of a single bond, —C(=O)— and —(CH$_2$)$_a$—, wherein a is from 1 to 6;

Z is selected from the group consisting of —NR'R", —C(=O)NR'R", —NR'C(=O)R", and a 4- to 7-membered ring having from 0 to 3 ring heteroatoms selected from O, S, and N, which may be unsubstituted or substituted with up to three substituents selected from the group consisting of halo, hydroxy, oxo, —NR'R", —OR", —C(=O)—NR'R", —NR'C(=O)—R", —OC(=O)R", —OC(=O)NR'R", —SO$_2$NR'R", —OSO$_2$NR'R", —CO$_2$—R", —O—(CH$_2$)$_d$OR", cyano, C$_1$-C$_6$ alkyl, C$_1$-C$_6$ alkoxy, alkoxyalkyl, C$_3$-C$_6$ cycloalkyl, perfluoro C$_1$-C$_6$ alkyl, and perfluoro C$_1$-C$_6$ alkoxy;

each R' is independently selected from the group consisting of H and C$_1$-C$_6$ alkyl;

each R" is independently selected from the group consisting of H, C$_1$-C$_6$ alkyl, C$_1$-C$_6$ fluoroalkyl, C$_1$-C$_6$ difluoroalkyl, C$_1$-C$_6$ perfluoroalkyl, aryl, aralkyl, C$_3$-C$_6$ cycloalkyl, and C$_3$-C$_7$ heterocyclyl having 1 to 3 heteroatoms selected from O, N, and S, wherein the aryl, aralkyl, C$_3$-C$_6$ cycloalkyl, and C$_3$-C$_7$ heterocyclyl may be further substituted with 0 to 3 substituents selected from halo, hydroxy, amino and C$_1$-C$_3$ alkyl; and alternatively, R' and R" attached to the same atom or to adjacent atoms may be taken together to form a 4- to 7-membered heterocylic ring having from 0 to 2 additional ring heteroatoms selected from N, O and S, and which may be unsubstituted or substituted with 1 to 3 substituents selected from the group consisting of halogen, cyano, $C_1$-$C_6$ alkyl, $C_3$-$C_6$ cycloalkyl, perfluoro $C_1$-$C_6$ alkyl, $C_1$-$C_6$ alkoxy, amino, amido and hydroxyl.

In certain embodiments of the present invention, there is provided a compound of the formula (Va):

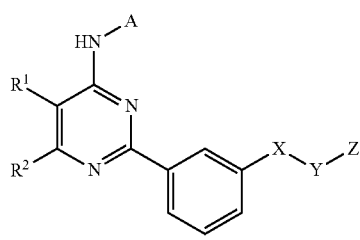

(Va)

wherein:

A is selected from the group consisting of:

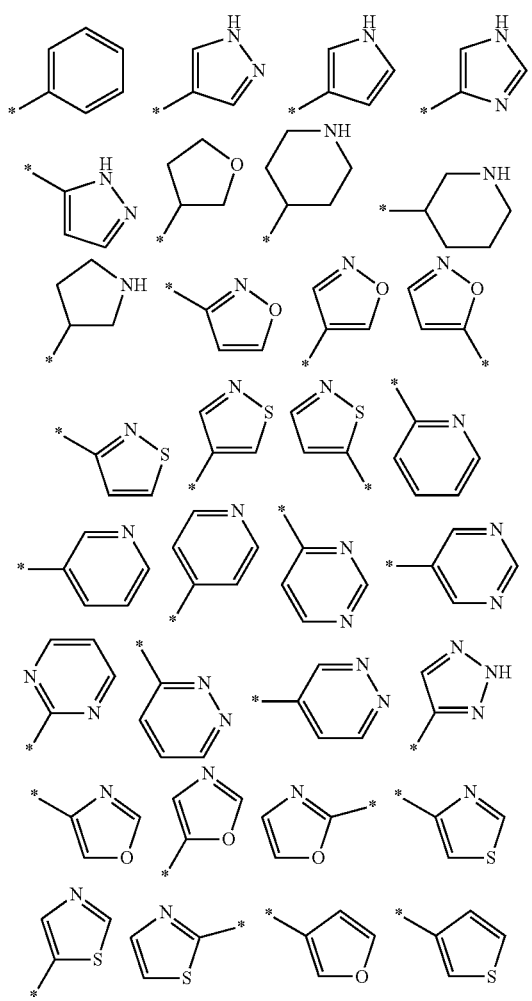

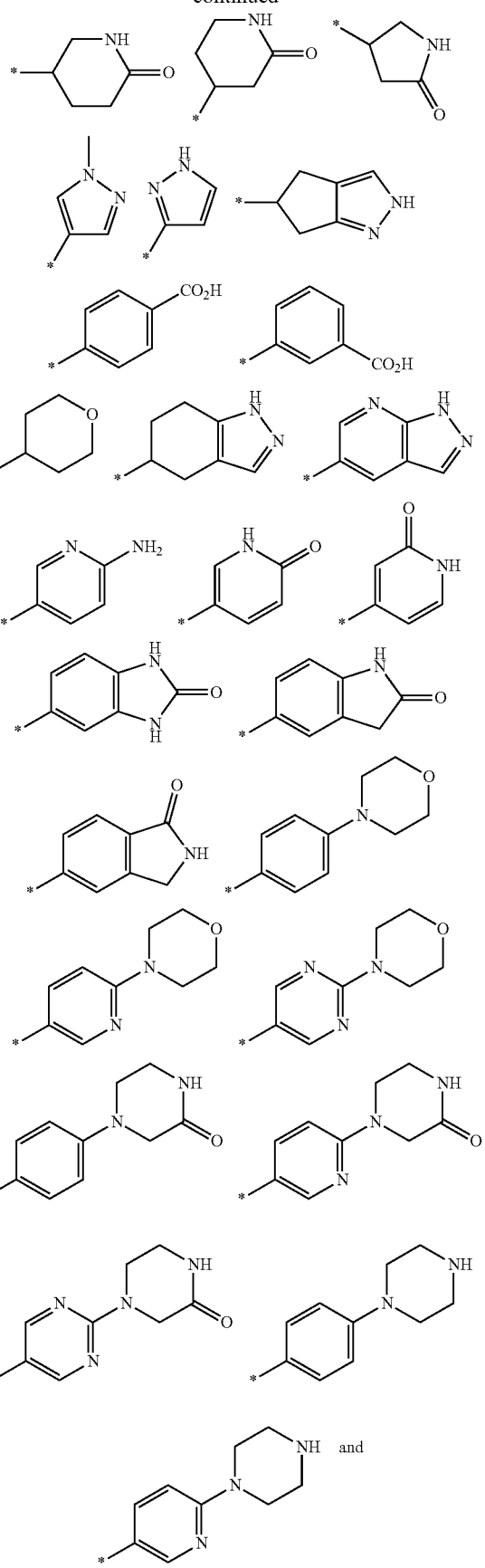

-continued

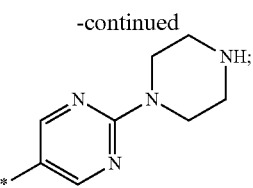

wherein each of the above structures for A may be optionally substituted with one to three substituents selected from the group consisting of halo, hydroxy, oxo, —NR'R", —(CH$_2$)$_b$NR'R", —O—(CH$_2$)$_c$NR'R", —C(=O)—NR'R", —NR'C(=O)—R", —OC(=O)R', —OC(=O)NR'R", —SO$_2$NR'R", —OSO$_2$NR'R", —O—(CH$_2$)$_d$OR", —CO$_2$—R", cyano, C$_1$-C$_6$ alkyl, C$_1$-C$_6$ alkoxy, alkoxyalkyl, C$_3$-C$_6$ cycloalkyl, perfluoro C$_1$-C$_6$ alkyl, and perfluoro C$_1$-C$_6$ alkoxy;

each b is independently selected from 1 to 6;
each c is independently selected from 2 to 6;
each d is independently selected from 2 to 6;

$R^1$ is selected from the group consisting of H, halo, hydroxy, —NR'R", —OR", —(CH$_2$)$_e$NR'R", —O—(CH$_2$)$_f$NR'R", —C(=O)—NR'R", —NR'C(=O)—R", —OC(=O)R', —OC(=O)NR'R", —CO$_2$—R", —SO$_2$NR'R", —OSO$_2$NR'R", —O—(CH$_2$)$_g$OR", cyano, C$_1$-C$_6$ alkyl, C$_2$-C$_6$ alkenyl, C$_2$-C$_6$ alkynyl, C$_3$-C$_6$ cyclic alkyl, C$_1$-C$_6$ alkoxy, aryl, aralkyl, heterocycyl, C$_1$-C$_6$ perfluoro alkyl, and C$_1$-C$_6$ perfluoro alkoxy;

$R^2$ is selected from the group consisting of H, halo, hydroxy, —NR'R", —OR", —(CH$_2$)$_e$NR'R", —O—(CH$_2$)$_f$NR'R", —C(=O)—NR'R", —NR'C(=O)—R", —OC(=O)R', —OC(=O)NR'R", —CO$_2$—R", —SO$_2$NR'R", —OSO$_2$NR'R", —O—(CH$_2$)$_g$OR", cyano, C$_1$-C$_6$ alkyl, C$_2$-C$_6$ alkenyl, C$_2$-C$_6$ alkynyl, C$_3$-C$_6$ cyclic alkyl, C$_1$-C$_6$ alkoxy, aryl, aralkyl, heterocycyl, C$_1$-C$_6$ perfluoro alkyl, and C$_1$-C$_6$ perfluoro alkoxy;

alternatively, $R^1$ and $R^2$ are taken together to form a 5- to 7-membered fused ring having from 0 to 3 ring heteroatoms, and is unsubstituted or is substituted with up to 3 substituents selected from the group consisting of halo, hydroxy, cyano, amino, —CO$_2$—R", —SO$_2$—R", —NR'R", —OR", —S—R", —(CH$_2$)$_e$—R", —(CH$_2$)$_e$NR'R", —O—(CH$_2$)$_f$NR'R", —C(=O)—NR'R", —NR'C(=O)—R", —OC(=O)R", —OC(=O)NR'R", —SO$_2$NR'R", —OSO$_2$NR'R", —O—(CH$_2$)$_g$OR", —O—(CH$_2$)$_e$R", —C(=O)—C$_1$-C$_6$ alkyl, C$_1$-C$_6$ alkyl, C$_1$-C$_6$ perfluoro alkyl, C$_1$-C$_6$ alkoxy and C$_1$-C$_6$ perfluoro alkoxy;

each e is independently selected from 1 to 6;
each f is independently selected from 2 to 6;
each g is independently selected from 2 to 6;

X is selected from the group consisting of O, NH and CH$_2$;

Y is selected from the group consisting of a single bond, —C(=O)— and —(CH$_2$)$_a$—, wherein a is from 1 to 6;

Z is selected from the group consisting of —NR'R", —C(=O)NR'R", —NR'C(=O)R", and a 4- to 7-membered ring having from 0 to 3 ring heteroatoms selected from O, S, and N, which may be unsubstituted or substituted with up to three substituents selected from the group consisting of halo, hydroxy, oxo, —NR'R", —OR", —C(=O)—NR'R", —NR'C(=O)—R", —OC(=O)R", —OC(=O)NR'R", —SO$_2$NR'R", —OSO$_2$NR'R", —CO$_2$—R", —O—(CH$_2$)$_d$OR", cyano, C$_1$-C$_6$ alkyl, C$_1$-C$_6$ alkoxy, alkoxyalkyl, C$_3$-C$_6$ cycloalkyl, perfluoro C$_1$-C$_6$ alkyl, and perfluoro C$_1$-C$_6$ alkoxy;

each R' is independently selected from the group consisting of H and C$_1$-C$_6$ alkyl;

each R" is independently selected from the group consisting of H, C$_1$-C$_6$ alkyl, C$_1$-C$_6$ fluoroalkyl, C$_1$-C$_6$ difluoroalkyl, C$_1$-C$_6$ perfluoroalkyl, aryl, aralkyl, C$_3$-C$_6$ cycloalkyl, and C$_3$-C$_7$ heterocyclyl having 1 to 3 heteroatoms selected from O, N, and S, wherein the aryl, aralkyl, C$_3$-C$_6$ cycloalkyl, and C$_3$-C$_7$ heterocyclyl may be further substituted with 0 to 3 substituents selected from halo, hydroxy, amino and C$_1$-C$_3$ alkyl; and alternatively, R' and R" attached to the same atom or to adjacent atoms may be taken together to form a 4- to 7-membered heterocylic ring having from 0 to 2 additional ring heteroatoms selected from N, O and S, and which may be unsubstituted or substituted with 1 to 3 substituents selected from the group consisting of halogen, cyano, C$_1$-C$_6$ alkyl, C$_3$-C$_6$ cycloalkyl, perfluoro C$_1$-C$_6$ alkyl, C$_1$-C$_6$ alkoxy, amino, amido and hydroxyl.

In certain embodiments of the present invention, there is provided a compound of the formula (Vb):

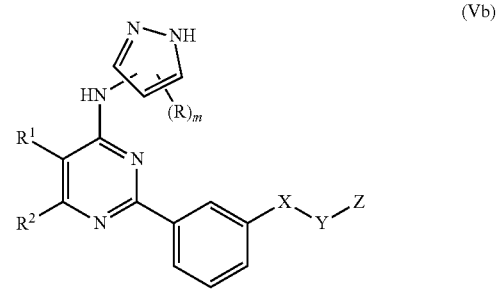

wherein:

each R is selected from the group consisting of halo, hydroxy, oxo, —NR'R", —(CH$_2$)$_b$NR'R", —O—(CH$_2$)$_c$ NR'R", —C(=O)—NR'R", —NR'C(=O)—R", —OC(=O)R', —OC(=O)NR'R", —SO$_2$NR'R", —OSO$_2$NR'R", —O—(CH$_2$)$_d$OR", —CO$_2$—R", cyano, C$_1$-C$_6$ alkyl, C$_1$-C$_6$ alkoxy, alkoxyalkyl, C$_3$-C$_6$ cycloalkyl, perfluoro C$_1$-C$_6$ alkyl, perfluoro C$_1$-C$_6$ alkoxy;

each b is independently selected from 1 to 6;
each c is independently selected from 2 to 6;
each d is independently selected from 2 to 6;
m is selected from 0 to 2;

$R^1$ is selected from the group consisting of H, halo, hydroxy, —NR'R", —OR", —(CH$_2$)$_e$NR'R", —O—(CH$_2$)$_f$NR'R", —C(=O)—NR'R", —NR'C(=O)—R", —OC(=O)R', —OC(=O)NR'R", —CO$_2$—R", —SO$_2$NR'R", —OSO$_2$NR'R", —O—(CH$_2$)$_g$OR", cyano, C$_1$-C$_6$ alkyl, C$_2$-C$_6$ alkenyl, C$_2$-C$_6$ alkynyl, C$_3$-C$_6$ cyclic alkyl, C$_1$-C$_6$ alkoxy, aryl, aralkyl, heterocycyl, C$_1$-C$_6$ perfluoro alkyl, and C$_1$-C$_6$ perfluoro alkoxy;

$R^2$ is selected from the group consisting of H, halo, hydroxy, —NR'R", —OR", —(CH$_2$)$_e$NR'R", —O—(CH$_2$)$_f$NR'R", —C(=O)—NR'R", —NR'C(=O)—R", —OC(=O)R', —OC(=O)NR'R", —CO$_2$—R", —SO$_2$NR'R", —OSO$_2$NR'R", —O—(CH$_2$)$_g$OR", cyano, C$_1$-C$_6$ alkyl, C$_2$-C$_6$ alkenyl, C$_2$-C$_6$ alkynyl, $C_3$-$C_6$ cyclic alkyl, $C_1$-$C_6$ alkoxy, aryl, aralkyl, heterocycyl, $C_1$-$C_6$ perfluoro alkyl, and $C_1$-$C_6$ perfluoro alkoxy;

alternatively, $R^1$ and $R^2$ are taken together to form a 5- to 7-membered fused ring having from 0 to 3 ring heteroatoms, and is unsubstituted or is substituted with up to 3 substituents selected from the group consisting of halo, hydroxy, cyano, amino, —CO$_2$—R", —SO$_2$—R", —NR'R", —OR", —S—R", —(CH$_2$)$_e$—R", —(CH$_2$)$_e$NR'R", —O—(CH$_2$)$_f$NR'R", —C(=O)—NR'R", —NR'C(=O)—R", —OC(=O)R", —OC(=O)NR'R", —SO$_2$NR'R", —OSO$_2$NR'R", —O—(CH$_2$)$_g$OR", —O—(CH$_2$)$_e$R", —C(=O)—$C_1$-$C_6$ alkyl, $C_1$-$C_6$ alkyl, $C_1$-$C_6$ perfluoro alkyl, $C_1$-$C_6$ alkoxy and $C_1$-$C_6$ perfluoro alkoxy;

each e is independently selected from 1 to 6;

each f is independently selected from 2 to 6;

each g is independently selected from 2 to 6;

X is selected from the group consisting of O, NH and CH$_2$;

Y is selected from the group consisting of a single bond, —C(=O)— and —(CH$_2$)$_a$—, wherein a is from 1 to 6;

Z is selected from the group consisting of —NR'R", —C(=O)NR'R", —NR'C(=O)R", and a 4- to 7-membered ring having from 0 to 3 ring heteroatoms selected from O, S, and N, which may be unsubstituted or substituted with up to three substituents selected from the group consisting of halo, hydroxy, oxo, —NR'R", —OR", —C(=O)—NR'R", —NR'C(=O)—R", —OC(=O)R", —OC(=O)NR'R", —SO$_2$NR'R", —OSO$_2$NR'R", —CO$_2$—R", —O—(CH$_2$)$_d$OR", cyano, $C_1$-$C_6$ alkyl, $C_1$-$C_6$ alkoxy, alkoxyalkyl, $C_3$-$C_6$ cycloalkyl, perfluoro $C_1$-$C_6$ alkyl, and perfluoro $C_1$-$C_6$ alkoxy;

each R' is independently selected from the group consisting of H and $C_1$-$C_6$ alkyl;

each R" is independently selected from the group consisting of H, $C_1$-$C_6$ alkyl, $C_1$-$C_6$ fluoroalkyl, $C_1$-$C_6$ difluoroalkyl, $C_1$-$C_6$ perfluoroalkyl, aryl, aralkyl, $C_3$-$C_6$ cycloalkyl, and $C_3$-$C_7$ heterocyclyl having 1 to 3 heteroatoms selected from O, N, and S, wherein the aryl, aralkyl, $C_3$-$C_6$ cycloalkyl, and $C_3$-$C_7$ heterocyclyl may be further substituted with 0 to 3 substituents selected from halo, hydroxy, amino and $C_1$-$C_3$ alkyl; and alternatively, R' and R" attached to the same atom or to adjacent atoms may be taken together to form a 4- to 7-membered heterocylic ring having from 0 to 2 additional ring heteroatoms selected from N, O and S, and which may be unsubstituted or substituted with 1 to 3 substituents selected from the group consisting of halogen, cyano, $C_1$-$C_6$ alkyl, $C_3$-$C_6$ cycloalkyl, perfluoro $C_1$-$C_6$ alkyl, $C_1$-$C_6$ alkoxy, amino, amido and hydroxyl.

a certain embodiments of the present invention, there is provided a compound of the formula (Vc):

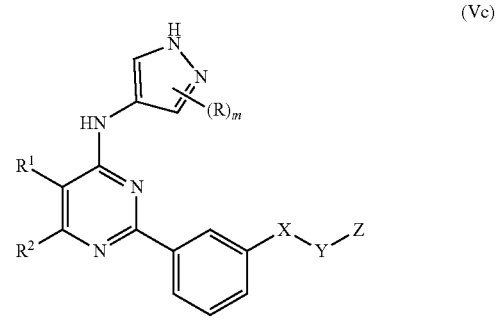

wherein:

each R is selected from the group consisting of halo, hydroxy, oxo, —NR'R", —(CH$_2$)$_b$NR'R", —O—(CH$_2$)$_c$NR'R", —C(=O)—NR'R", —NR'C(=O)—R", —OC(=O)R', —OC(=O)NR'R", —SO$_2$NR'R", —OSO$_2$NR'R", —O—(CH$_2$)$_d$OR", —CO$_2$—R", cyano, $C_1$-$C_6$ alkyl, $C_1$-$C_6$ alkoxy, alkoxyalkyl, $C_3$-$C_6$ cycloalkyl, perfluoro $C_1$-$C_6$ alkyl, perfluoro $C_1$-$C_6$ alkoxy;

each b is independently selected from 1 to 6;

each c is independently selected from 2 to 6;

each d is independently selected from 2 to 6;

m is selected from 0 to 2;

$R^1$ is selected from the group consisting of H, halo, hydroxy, —NR'R", —OR", —(CH$_2$)$_e$NR'R", —O—(CH$_2$)$_f$NR'R", —C(=O)—NR'R", —NR'C(=O)—R", —OC(=O)R', —OC(=O)NR'R", —CO$_2$—R", —SO$_2$NR'R", —OSO$_2$NR'R", —O—(CH$_2$)$_g$OR", cyano, $C_1$-$C_6$ alkyl, $C_2$-$C_6$ alkenyl, $C_2$-$C_6$ alkynyl, $C_3$-$C_6$ cyclic alkyl, $C_1$-$C_6$ alkoxy, aryl, aralkyl, heterocycyl, $C_1$-$C_6$ perfluoro alkyl, and $C_1$-$C_6$ perfluoro alkoxy;

$R^2$ is selected from the group consisting of H, halo, hydroxy, —NR'R", —OR", —(CH$_2$)$_e$NR'R", —O—(CH$_2$)$_f$NR'R", —C(=O)—NR'R", —NR'C(=O)—R", —OC(=O)R', —OC(=O)NR'R", —CO$_2$—R", —SO$_2$NR'R", —OSO$_2$NR'R", —O—(CH$_2$)$_g$OR", cyano, $C_1$-$C_6$ alkyl, $C_2$-$C_6$ alkenyl, $C_2$-$C_6$ alkynyl, $C_3$-$C_6$ cyclic alkyl, $C_1$-$C_6$ alkoxy, aryl, aralkyl, heterocycyl, $C_1$-$C_6$ perfluoro alkyl, and $C_1$-$C_6$ perfluoro alkoxy;

alternatively, $R^1$ and $R^2$ are taken together to form a 5- to 7-membered fused ring having from 0 to 3 ring heteroatoms, and is unsubstituted or is substituted with up to 3 substituents selected from the group consisting of halo, hydroxy, cyano, amino, —CO$_2$—R", —SO$_2$—R", —NR'R", —OR", —S—R", —(CH$_2$)$_e$—R", —(CH$_2$)$_e$NR'R", —O—(CH$_2$)$_f$NR'R", —C(=O)—NR'R", —NR'C(=O)—R", —OC(=O)R", —OC(=O)NR'R", —SO$_2$NR'R", —OSO$_2$NR'R", —O—(CH$_2$)$_g$OR", —O—(CH$_2$)$_e$R", —C(=O)—$C_1$-$C_6$ alkyl, $C_1$-$C_6$ alkyl, $C_1$-$C_6$ perfluoro alkyl, $C_1$-$C_6$ alkoxy and $C_1$-$C_6$ perfluoro alkoxy;

each e is independently selected from 1 to 6;

each f is independently selected from 2 to 6;

each g is independently selected from 2 to 6;

X is selected from the group consisting of O, NH and CH$_2$;

Y is selected from the group consisting of a single bond, —C(=O)— and —(CH$_2$)$_a$—, wherein a is from 1 to 6;

Z is selected from the group consisting of —NR'R", —C(=O)NR'R", —NR'C(=O)R", and a 4- to 7-membered ring having from 0 to 3 ring heteroatoms selected from O, S, and N, which may be unsubstituted or substituted with up to three substituents selected from the group consisting of halo, hydroxy, oxo, —NR'R", —OR", —C(=O)—NR'R", —NR'C(=O)—R", —OC(=O)R", —OC(=O)NR'R", —SO$_2$NR'R", —OSO$_2$NR'R", —CO$_2$—R", —O—(CH$_2$)$_d$OR", cyano, $C_1$-$C_6$ alkyl, $C_1$-$C_6$ alkoxy, alkoxyalkyl, $C_3$-$C_6$ cycloalkyl, perfluoro $C_1$-$C_6$ alkyl, and perfluoro $C_1$-$C_6$ alkoxy;

each R' is independently selected from the group consisting of H and $C_1$-$C_6$ alkyl;

each R" is independently selected from the group consisting of H, $C_1$-$C_6$ alkyl, $C_1$-$C_6$ fluoroalkyl, $C_1$-$C_6$ difluoroalkyl, $C_1$-$C_6$ perfluoroalkyl, aryl, aralkyl, $C_3$-$C_6$ cycloalkyl, and $C_3$-$C_7$ heterocyclyl having 1 to 3 heteroatoms selected from O, N, and S, wherein the aryl, aralkyl, $C_3$-$C_6$ cycloalkyl, and $C_3$-$C_7$ heterocyclyl may be further substituted with 0 to 3 substituents selected from halo, hydroxy, amino and $C_1$-$C_3$ alkyl; and alternatively, R' and R" attached to the same atom or to adjacent atoms may be taken together to form a 4- to 7-membered heterocylic ring having from 0 to 2 additional ring heteroatoms selected from N, O and S, and which may be unsubstituted or substituted with 1 to 3 substituents selected from the group consisting of halogen, cyano, $C_1$-$C_6$ alkyl, $C_3$-$C_6$ cycloalkyl, perfluoro $C_1$-$C_6$ alkyl, $C_1$-$C_6$ alkoxy, amino, amido and hydroxyl.

In certain embodiments of the present invention, there is provided a compound of the formula VI:

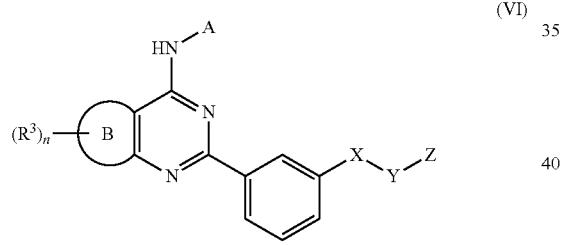

(VI)

wherein:
A is selected from the group consisting of:
  (i) a 4- to 7-membered heterocyclic ring having from 1 to 3 ring heteroatoms selected from O, S, and N, and which may be unsubstituted or substituted with up to three substituents selected from the group consisting of halo, hydroxy, oxo, —NR'R", —OR", CHR'R", —(CH$_2$)$_b$NR'R", —O—(CH$_2$)$_c$NR'R", —C(=O)—NR'R", —NR'C(=O)—R", —OC(=O)R', —OC(=O)NR'R", —SO$_2$NR'R", —OSO$_2$NR'R", —O—(CH$_2$)$_d$OR", —CO$_2$—R", cyano, $C_1$-$C_6$ alkyl, $C_1$-$C_6$ alkoxy, alkoxyalkyl, $C_3$-$C_6$ cycloalkyl, perfluoro $C_1$-$C_6$ alkyl, perfluoro $C_1$-$C_6$ alkoxy, and a 5- or 6-membered heterocyclic ring, which may be further substituted with 0 to 3 substituents selected from the group consisting of halo, hydroxy, oxo, —NR'R", —(CH$_2$)$_b$NR'R", —O—(CH$_2$)$_c$NR'R", —C(=O)—NR'R", —O—(CH$_2$)$_d$OR", cyano, $C_1$-$C_6$ alkyl, $C_1$-$C_6$ alkoxy, alkoxyalkyl, $C_3$-$C_6$ cyclic alkyl, perfluoro $C_1$-$C_6$ alkyl, and perfluoro $C_1$-$C_6$ alkoxy;
  (ii) a phenyl group, unsubstituted or substituted with up to three substituents selected from the group consisting of halo, hydroxy, —NR'R", —OR", CHR'R", —(CH$_2$)$_b$NR'R", —O—(CH$_2$)$_c$NR'R", —C(=O)—NR'R", —NR'C(=O)—R", —OC(=O)R', —OC(=O)NR'R", —SO$_2$NR'R", —OSO$_2$NR'R", —O—(CH$_2$)$_d$OR", —CO$_2$—R", cyano, $C_1$-$C_6$ alkyl, $C_1$-$C_6$ alkoxy, alkoxyalkyl, $C_3$-$C_6$ cycloalkyl, perfluoro $C_1$-$C_6$ alkyl, perfluoro $C_1$-$C_6$ alkoxy, and a 5- or 6-membered heterocyclic ring, which may be further substituted with 0 to 3 substituents selected from the group consisting of halo, hydroxy, oxo, —NR'R", —OR", —(CH$_2$)$_b$NR'R", —O—(CH$_2$)$_c$NR'R", —C(=O)—NR'R", —OC(=O)R', —OC(=O)NR'R", —SO$_2$NR'R", —OSO$_2$NR'R", —O—(CH$_2$)$_d$OR", cyano, $C_1$-$C_6$ alkyl, $C_1$-$C_6$ alkoxy, alkoxyalkyl, $C_3$-$C_6$ cyclic alkyl, perfluoro $C_1$-$C_6$ alkyl, and perfluoro $C_1$-$C_6$ alkoxy;

(iii) a cyclic group selected from:

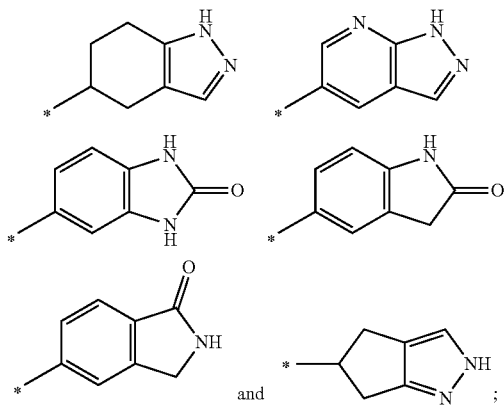

wherein each of the above structures may be optionally substituted with up to three substituents selected from the group consisting of halo, hydroxy, oxo, —NR'R", —(CH$_2$)$_b$NR'R", —O—(CH$_2$)$_c$NR'R", —C(=O)—NR'R", —NR'C(=O)—R", —OC(=O)R', —OC(=O)NR'R", —SO$_2$NR'R", —OSO$_2$NR'R", —O—(CH$_2$)$_d$OR", —CO$_2$—R", cyano, $C_1$-$C_6$ alkyl, $C_1$-$C_6$ alkoxy, alkoxyalkyl, $C_3$-$C_6$ cycloalkyl, perfluoro $C_1$-$C_6$ alkyl, perfluoro $C_1$-$C_6$ alkoxy, and a 5- or 6-membered heterocyclic ring, which may be further substituted with 0 to 3 substituents selected from the group consisting of halo, hydroxy, oxo, —NR'R", —(CH$_2$)$_b$NR'R", —O—(CH$_2$)$_c$NR'R", —C(=O)—NR'R", cyano, $C_1$-$C_6$ alkyl, $C_1$-$C_6$ alkoxy, alkoxyalkyl, $C_3$-$C_6$ cyclic alkyl, perfluoro $C_1$-$C_6$ alkyl, and perfluoro $C_1$-$C_6$ alkoxy;

each b is independently selected from 1 to 6;
each c is independently selected from 2 to 6;
each d is independently selected from 2 to 6;
B is a 5- to 7-membered fused ring having from 0 to 3 ring heteroatoms:
$R^3$ is selected from the group consisting of halo, hydroxy, cyano, amino, —CO$_2$—R", —SO$_2$—R", —NR'R", —OR", —S—R", —(CH$_2$)$_e$—R", —(CH$_2$)$_e$NR'R", —O—(CH$_2$)$_f$NR'R", —C(=O)—NR'R", —NR'C(=O)—R", —OC(=O)R", —OC(=O)NR'R", —SO$_2$NR'R", —OSO$_2$NR'R", —O—(CH$_2$)$_g$OR", —O—(CH$_2$)$_e$R", —C(=O)—$C_1$-$C_6$ alkyl, $C_1$-$C_6$ alkyl, $C_1$-$C_6$ perfluoro alkyl, $C_1$-$C_6$ alkoxy and $C_1$-$C_6$ perfluoro alkoxy;

each e is independently selected from 1 to 6;
each f is independently selected from 2 to 6;
each g is independently selected from 2 to 6;
n is 0 to 3;
X is selected from the group consisting of O, NH and $CH_2$;
Y is selected from the group consisting of a single bond, —C(=O)— and —$(CH_2)_a$—, wherein a is from 1 to 6;
Z is selected from the group consisting of —NR'R", —C(=O)NR'R", —NR'C(=O)R", and a 4- to 7-membered ring having from 0 to 3 ring heteroatoms selected from O, S, and N, which may be unsubstituted or substituted with up to three substituents selected from the group consisting of halo, hydroxy, oxo, —NR'R", —OR", —C(=O)—NR'R", —NR'C(=O)—R", —OC(=O)R", —OC(=O)NR'R", —$SO_2$NR'R", —$OSO_2$NR'R", —$CO_2$—R", —O—$(CH_2)_d$OR", cyano, $C_1$-$C_6$ alkyl, $C_1$-$C_6$ alkoxy, alkoxyalkyl, $C_3$-$C_6$ cycloalkyl, perfluoro $C_1$-$C_6$ alkyl, and perfluoro $C_1$-$C_6$ alkoxy;
each R' is independently selected from the group consisting of H and $C_1$-$C_6$ alkyl;
each R" is independently selected from the group consisting of H, $C_1$-$C_6$ alkyl, $C_1$-$C_6$ fluoroalkyl, $C_1$-$C_6$ difluoroalkyl, $C_1$-$C_6$ perfluoroalkyl, aryl, aralkyl, $C_3$-$C_6$ cycloalkyl, and $C_3$-$C_7$ heterocyclyl having 1 to 3 heteroatoms selected from O, N, and S, wherein the aryl, aralkyl, $C_3$-$C_6$ cycloalkyl, and $C_3$-$C_7$ heterocyclyl may be further substituted with 0 to 3 substituents selected from halo, hydroxy, amino and $C_1$-$C_3$ alkyl; and
alternatively, R' and R" attached to the same atom or to adjacent atoms may be taken together to form a 4- to 7-membered heterocylic ring having from 0 to 2 additional ring heteroatoms selected from N, O and S, and which may be unsubstituted or substituted with 1 to 3 substituents selected from the group consisting of halogen, cyano, $C_1$-$C_6$ alkyl, $C_3$-$C_6$ cycloalkyl, perfluoro $C_1$-$C_6$ alkyl, $C_1$-$C_6$ alkoxy, amino, amido and hydroxyl.

In certain embodiments of the present invention, there is provided a compound of the formula VIa:

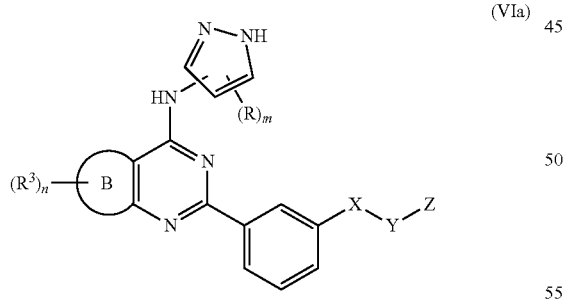

(VIa)

wherein:
each R is selected from the group consisting of halo, hydroxy, oxo, —NR'R", —$(CH_2)_b$NR'R", —O—$(CH_2)_c$NR'R", —C(=O)—NR'R", —NR'C(=O)—R", —OC(=O)R', —OC(=O)NR'R", —$SO_2$NR'R", —$OSO_2$NR'R", —O—$(CH_2)_d$OR", —$CO_2$—R", cyano, $C_1$-$C_6$ alkyl, $C_1$-$C_6$ alkoxy, alkoxyalkyl, $C_3$-$C_6$ cycloalkyl, perfluoro $C_1$-$C_6$ alkyl, perfluoro $C_1$-$C_6$ alkoxy;
each b is independently selected from 1 to 6;
each c is independently selected from 2 to 6;
each d is independently selected from 2 to 6;
m is selected from 0 to 2;
B is a 5- to 7-membered fused ring having from 0 to 3 ring heteroatoms;
$R^3$ is selected from the group consisting of halo, hydroxy, cyano, amino, —$CO_2$—R", —$SO_2$—R", —NR'R", —OR", —S—R", —$(CH_2)_e$—R", —$(CH_2)_e$NR'R", —O—$(CH_2)_f$NR'R", —C(=O)—NR'R", —NR'C(=O)—R", —OC(=O)R", —OC(=O)NR'R", —$SO_2$NR'R", —$OSO_2$NR'R", —O—$(CH_2)_g$OR", —O—$(CH_2)_e$R", —C(=O)—$C_1$-$C_6$ alkyl, $C_1$-$C_6$ alkyl, $C_1$-$C_6$ perfluoro alkyl, $C_1$-$C_6$ alkoxy and $C_1$-$C_6$ perfluoro alkoxy;
each e is independently selected from 1 to 6;
each f is independently selected from 2 to 6;
each g is independently selected from 2 to 6;
n is 0 to 3;
X is selected from the group consisting of O, NH and $CH_2$;
Y is selected from the group consisting of a single bond, —C(=O)— and —$(CH_2)_a$—, wherein a is from 1 to 6;
Z is selected from the group consisting of —NR'R", —C(=O)NR'R", —NR'C(=O)R", and a 4- to 7-membered ring having from 0 to 3 ring heteroatoms selected from O, S, and N, which may be unsubstituted or substituted with up to three substituents selected from the group consisting of halo, hydroxy, oxo, —NR'R", —OR", —C(=O)—NR'R", —NR'C(=O)—R", —OC(=O)R", —OC(=O)NR'R", —$SO_2$NR'R", —$OSO_2$NR'R", —$CO_2$—R", —O—$(CH_2)_d$OR", cyano, $C_1$-$C_6$ alkyl, $C_1$-$C_6$ alkoxy, alkoxyalkyl, $C_3$-$C_6$ cycloalkyl, perfluoro $C_1$-$C_6$ alkyl, and perfluoro $C_1$-$C_6$ alkoxy;
each R' is independently selected from the group consisting of H and $C_1$-$C_6$ alkyl;
each R" is independently selected from the group consisting of H, $C_1$-$C_6$ alkyl, $C_1$-$C_6$ fluoroalkyl, $C_1$-$C_6$ difluoroalkyl, $C_1$-$C_6$ perfluoroalkyl, aryl, aralkyl, $C_3$-$C_6$ cycloalkyl, and $C_3$-$C_7$ heterocyclyl having 1 to 3 heteroatoms selected from O, N, and S, wherein the aryl, aralkyl, $C_3$-$C_6$ cycloalkyl, and $C_3$-$C_7$ heterocyclyl may be further substituted with 0 to 3 substituents selected from halo, hydroxy, amino and $C_1$-$C_3$ alkyl; and
alternatively, R' and R" attached to the same atom or to adjacent atoms may be taken together to form a 4- to 7-membered heterocylic ring having from 0 to 2 additional ring heteroatoms selected from N, O and S, and which may be unsubstituted or substituted with 1 to 3 substituents selected from the group consisting of halogen, cyano, $C_1$-$C_6$ alkyl, $C_3$-$C_6$ cycloalkyl, perfluoro $C_1$-$C_6$ alkyl, $C_1$-$C_6$ alkoxy, amino, amido and hydroxyl.

In certain embodiments of the present invention, there is provided a compound of the formula VIb:

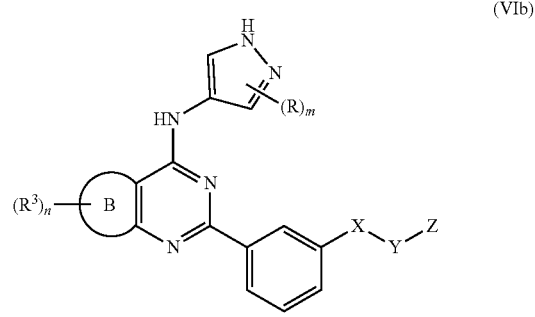

(VIb)

wherein:
each R is selected from the group consisting of halo, hydroxy, oxo, —NR'R", —(CH$_2$)$_b$NR'R", —O—(CH$_2$)$_c$NR'R", —C(=O)—NR'R", —NR'C(=O)—R", —OC(=O)R', —OC(=O)NR'R", —SO$_2$NR'R", —OSO$_2$NR'R", —O—(CH$_2$)$_d$OR", —CO$_2$—R", cyano, C$_1$-C$_6$ alkyl, C$_1$-C$_6$ alkoxy, alkoxyalkyl, C$_3$-C$_6$ cycloalkyl, perfluoro C$_1$-C$_6$ alkyl, perfluoro C$_1$-C$_6$ alkoxy;
each b is independently selected from 1 to 6;
each c is independently selected from 2 to 6;
each d is independently selected from 2 to 6;
m is selected from 0 to 2;
B is a 5- to 7-membered fused ring having from 0 to 3 ring heteroatoms:
halo, hydroxy, cyano, amino, —NR'R", —OR", —(CH$_2$)$_e$NR'R", —O—(CH$_2$)$_f$NR'R", —C(=O)—NR'R", —NR'C(=O)—R", —O—(CH$_2$)$_g$OR", —C(=O)—C$_1$-C$_6$ alkyl, C$_1$-C$_6$ alkyl, C$_1$-C$_6$ perfluoro alkyl, C$_1$-C$_6$ alkoxy and C$_1$-C$_6$ perfluoro alkoxy;
R$^3$ is selected from the group consisting of halo, hydroxy, cyano, amino, —CO$_2$—R", —SO$_2$—R", —NR'R", —OR", —S—R", —(CH$_2$)$_e$—R", —(CH$_2$)$_e$NR'R", —O—(CH$_2$)$_f$NR'R", —C(=O)—NR'R", —NR'C(=O)—R", —OC(=O)R", —OC(=O)NR'R", —SO$_2$NR'R", —OSO$_2$NR'R", —O—(CH$_2$)$_g$OR", —O—(CH$_2$)$_e$R", —C(=O)—C$_1$-C$_6$ alkyl, C$_1$-C$_6$ alkyl, C$_1$-C$_6$ perfluoro alkyl, C$_1$-C$_6$ alkoxy and C$_1$-C$_6$ perfluoro alkoxy;
each e is independently selected from 1 to 6;
each f is independently selected from 2 to 6;
each g is independently selected from 2 to 6;
n is 0 to 3;
X is selected from the group consisting of O, NH and CH$_2$;
Y is selected from the group consisting of a single bond, —C(=O)— and —(CH$_2$)$_a$—, wherein a is from 1 to 6;
Z is selected from the group consisting of —NR'R", —C(=O)NR'R", —NR'C(=O)R", and a 4- to 7-membered ring having from 0 to 3 ring heteroatoms selected from O, S, and N, which may be unsubstituted or substituted with up to three substituents selected from the group consisting of halo, hydroxy, oxo, —NR'R", —OR", —C(=O)—NR'R", —NR'C(=O)—R", —OC(=O)R", —OC(=O)NR'R", —SO$_2$NR'R", —OSO$_2$NR'R", —CO$_2$—R", —O—(CH$_2$)$_d$OR", cyano, C$_1$-C$_6$ alkyl, C$_1$-C$_6$ alkoxy, alkoxyalkyl, C$_3$-C$_6$ cycloalkyl, perfluoro C$_1$-C$_6$ alkyl, and perfluoro C$_1$-C$_6$ alkoxy;
each R' is independently selected from the group consisting of H and C$_1$-C$_6$ alkyl;
each R" is independently selected from the group consisting of H, C$_1$-C$_6$ alkyl, C$_1$-C$_6$ fluoroalkyl, C$_1$-C$_6$ difluoroalkyl, C$_1$-C$_6$ perfluoroalkyl, aryl, aralkyl, C$_3$-C$_6$ cycloalkyl, and C$_3$-C$_7$ heterocyclyl having 1 to 3 heteroatoms selected from O, N, and S, wherein the aryl, aralkyl, C$_3$-C$_6$ cycloalkyl, and C$_3$-C$_7$ heterocyclyl may be further substituted with 0 to 3 substituents selected from halo, hydroxy, amino and C$_1$-C$_3$ alkyl; and
alternatively, R' and R" attached to the same atom or to adjacent atoms may be taken together to form a 4- to 7-membered heterocylic ring having from 0 to 2 additional ring heteroatoms selected from N, O and S, and which may be unsubstituted or substituted with 1 to 3 substituents selected from the group consisting of halogen, cyano, C$_1$-C$_6$ alkyl, C$_3$-C$_6$ cycloalkyl, perfluoro C$_1$-C$_6$ alkyl, C$_1$-C$_6$ alkoxy, amino, amido and hydroxyl.

In certain embodiments of the present invention, there is provided a compound of the formula VII:

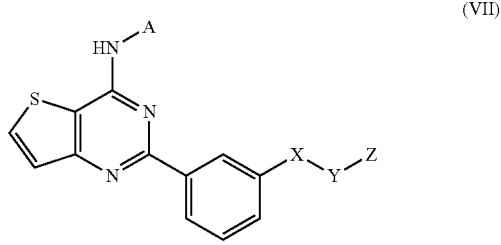

(VII)

wherein:
A is selected from the group consisting of:
(i) a 4- to 7-membered heterocyclic ring having from 1 to 3 ring heteroatoms selected from O, S, and N, and which may be unsubstituted or substituted with up to three substituents selected from the group consisting of halo, hydroxy, oxo, —NR'R", —OR", CHR'R", —(CH$_2$)$_b$NR'R", —O—(CH$_2$)$_c$NR'R", —C(=O)—NR'R", —NR'C(=O)—R", —OC(=O)R', —OC(=O)NR'R", —SO$_2$NR'R", —OSO$_2$NR'R", —O—(CH$_2$)$_d$OR", —CO$_2$—R", cyano, C$_1$-C$_6$ alkyl, C$_1$-C$_6$ alkoxy, alkoxyalkyl, C$_3$-C$_6$ cycloalkyl, perfluoro C$_1$-C$_6$ alkyl, perfluoro C$_1$-C$_6$ alkoxy, and a 5- or 6-membered heterocyclic ring, which may be further substituted with 0 to 3 substituents selected from the group consisting of halo, hydroxy, oxo, —NR'R", —(CH$_2$)$_b$NR'R", —O—(CH$_2$)$_c$NR'R", —C(=O)—NR'R", —O—(CH$_2$)$_d$OR", cyano, C$_1$-C$_6$ alkyl, C$_1$-C$_6$ alkoxy, alkoxyalkyl, C$_3$-C$_6$ cyclic alkyl, perfluoro C$_1$-C$_6$ alkyl, and perfluoro C$_1$-C$_6$ alkoxy;
(ii) a phenyl group, unsubstituted or substituted with up to three substituents selected from the group consisting of halo, hydroxy, —NR'R", —OR", CHR'R", —(CH$_2$)$_b$NR'R", —O—(CH$_2$)$_c$NR'R", —C(=O)—NR'R", —NR'C(=O)—R", —OC(=O)R', —OC(=O)NR'R", —SO$_2$NR'R", —OSO$_2$NR'R", —O—(CH$_2$)$_d$OR", —CO$_2$—R", cyano, C$_1$-C$_6$ alkyl, C$_1$-C$_6$ alkoxy, alkoxyalkyl, C$_3$-C$_6$ cycloalkyl, perfluoro C$_1$-C$_6$ alkyl, perfluoro C$_1$-C$_6$ alkoxy, and a 5- or 6-membered heterocyclic ring, which may be further substituted with 0 to 3 substituents selected from the group consisting of halo, hydroxy, oxo, —NR'R", —OR", —(CH$_2$)$_b$NR'R", —O—(CH$_2$)$_c$NR'R", —C(=O)—NR'R", —OC(=O)R', —OC(=O)NR'R", —SO$_2$NR'R", —OSO$_2$NR'R", —O—(CH$_2$)$_d$OR", cyano, C$_1$-C$_6$ alkyl, C$_1$-C$_6$ alkoxy, alkoxyalkyl, C$_3$-C$_6$ cyclic alkyl, perfluoro C$_1$-C$_6$ alkyl, and perfluoro C$_1$-C$_6$ alkoxy;
(iii) a cyclic group selected from:

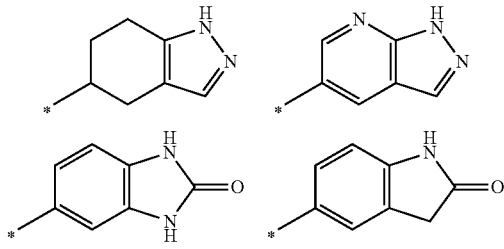

-continued

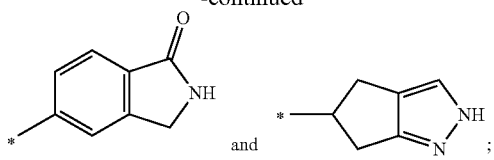
and wherein each of the above structures may be optionally substituted with up to three substituents selected from the group consisting of halo, hydroxy, oxo, —NR'R", —(CH$_2$)$_b$NR'R", —O—(CH$_2$)$_c$NR'R", —C(=O)—NR'R", —NR'C(=O)—R", —OC(=O)R', —OC(=O)NR'R", —SO$_2$NR'R", —OSO$_2$NR'R", —O—(CH$_2$)$_d$OR", —CO$_2$—R", cyano, C$_1$-C$_6$ alkyl, C$_1$-C$_6$ alkoxy, alkoxyalkyl, C$_3$-C$_6$ cycloalkyl, perfluoro C$_1$-C$_6$ alkyl, perfluoro C$_1$-C$_6$ alkoxy, and a 5- or 6-membered heterocyclic ring, which may be further substituted with 0 to 3 substituents selected from the group consisting of halo, hydroxy, oxo, —NR'R", —(CH$_2$)$_b$NR'R", —O—(CH$_2$)$_c$NR'R", —C(=O)—NR'R", cyano, C$_1$-C$_6$ alkyl, C$_1$-C$_6$ alkoxy, alkoxyalkyl, C$_3$-C$_6$ cyclic alkyl, perfluoro C$_1$-C$_6$ alkyl, and perfluoro C$_1$-C$_6$ alkoxy;
each b is independently selected from 1 to 6;
each c is independently selected from 2 to 6;
each d is independently selected from 2 to 6;
X is selected from the group consisting of O, NH and CH$_2$;
Y is selected from the group consisting of a single bond, —C(=O)— and —(CH$_2$)$_a$—, wherein a is from 1 to 6;
Z is selected from the group consisting of —NR'R", —C(=O)NR'R", —NR'C(=O)R", and a 4- to 7-membered ring having from 0 to 3 ring heteroatoms selected from O, S, and N, which may be unsubstituted or substituted with up to three substituents selected from the group consisting of halo, hydroxy, oxo, —NR'R", —OR", —C(=O)—NR'R", —NR'C(=O)—R", —OC(=O)R", —OC(=O)NR'R", —SO$_2$NR'R", —OSO$_2$NR'R", —CO$_2$—R", —O—(CH$_2$)$_d$OR", cyano, C$_1$-C$_6$ alkyl, C$_1$-C$_6$ alkoxy, alkoxyalkyl, C$_3$-C$_6$ cycloalkyl, perfluoro C$_1$-C$_6$ alkyl, and perfluoro C$_1$-C$_6$ alkoxy;
each R' is independently selected from the group consisting of H and C$_1$-C$_6$ alkyl;
each R" is independently selected from the group consisting of H, C$_1$-C$_6$ alkyl, C$_1$-C$_6$ fluoroalkyl, C$_1$-C$_6$ difluoroalkyl, C$_1$-C$_6$ perfluoroalkyl, aryl, aralkyl, C$_3$-C$_6$ cycloalkyl, and C$_3$-C$_7$ heterocyclyl having 1 to 3 heteroatoms selected from O, N, and S, wherein the aryl, aralkyl, C$_3$-C$_6$ cycloalkyl, and C$_3$-C$_7$ heterocyclyl may be further substituted with 0 to 3 substituents selected from halo, hydroxy, amino and C$_1$-C$_3$ alkyl; and
alternatively, R' and R" attached to the same atom or to adjacent atoms may be taken together to form a 4- to 7-membered heterocylic ring having from 0 to 2 additional ring heteroatoms selected from N, O and S, and which may be unsubstituted or substituted with 1 to 3 substituents selected from the group consisting of halogen, cyano, C$_1$-C$_6$ alkyl, C$_3$-C$_6$ cycloalkyl, perfluoro C$_1$-C$_6$ alkyl, C$_1$-C$_6$ alkoxy, amino, amido and hydroxyl.

In certain embodiments of the present invention, there is provided a compound of the formula VIIa:

(VIIa)

wherein:
A is selected from the group consisting of:

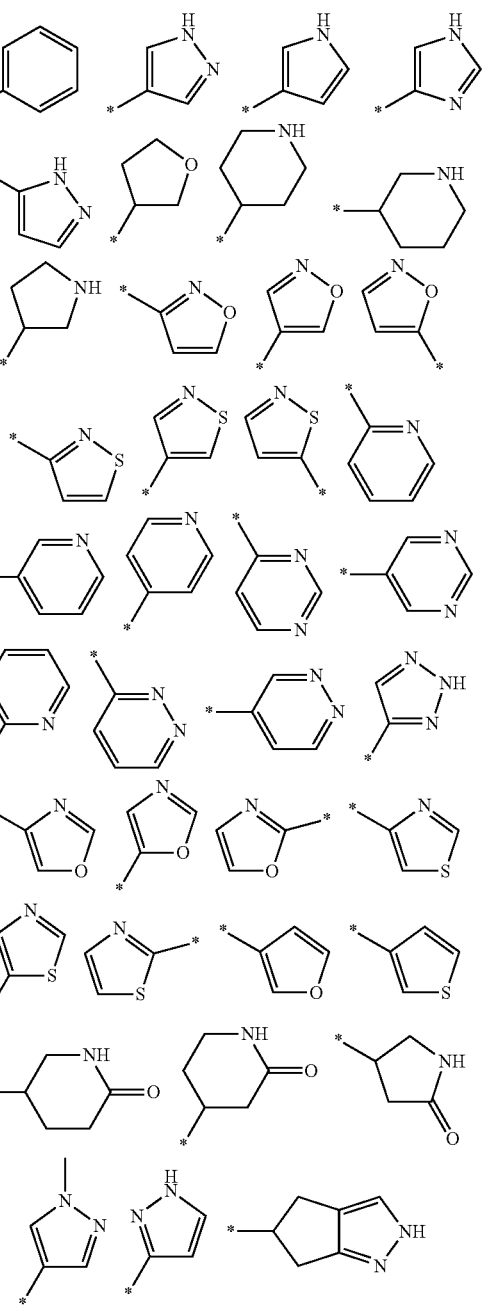

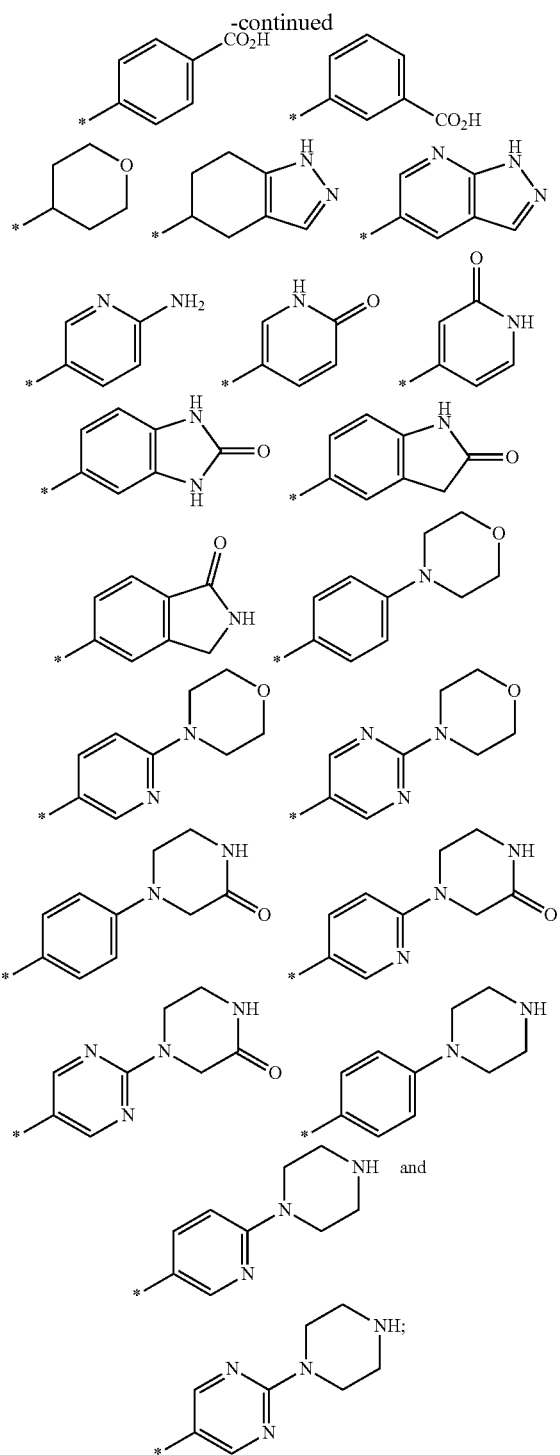

wherein each of the above structures for A may be optionally substituted with one to three substituents selected from the group consisting of halo, hydroxy, oxo, —NR'R", —(CH$_2$)$_b$NR'R", —O—(CH$_2$)$_c$NR'R", —C(=O)—NR'R", —NR'C(=O)—R", —OC(=O)R', —OC(=O)NR'R", —SO$_2$NR'R", —OSO$_2$NR'R", —O—(CH$_2$)$_d$OR", —CO$_2$—R", cyano, C$_1$-C$_6$ alkyl, C$_1$-C$_6$ alkoxy, alkoxyalkyl, C$_3$-C$_6$ cycloalkyl, perfluoro C$_1$-C$_6$ alkyl, and perfluoro C$_1$-C$_6$ alkoxy;

each b is independently selected from 1 to 6;
each c is independently selected from 2 to 6;
each d is independently selected from 2 to 6;

X is selected from the group consisting of O, NH and CH$_2$;

Y is selected from the group consisting of a single bond, —C(=O)— and —(CH$_2$)$_a$—, wherein a is from 1 to 6;

Z is selected from the group consisting of —NR'R", —C(=O)NR'R", —NR'C(=O)R", and a 4- to 7-membered ring having from 0 to 3 ring heteroatoms selected from O, S, and N, which may be unsubstituted or substituted with up to three substituents selected from the group consisting of halo, hydroxy, oxo, —NR'R", —OR", —C(=O)—NR'R", —NR'C(=O)—R", —OC(=O)R", —OC(=O)NR'R", —SO$_2$NR'R", —OSO$_2$NR'R", —CO$_2$—R", —O—(CH$_2$)$_d$OR", cyano, C$_1$-C$_6$ alkyl, C$_1$-C$_6$ alkoxy, alkoxyalkyl, C$_3$-C$_6$ cycloalkyl, perfluoro C$_1$-C$_6$ alkyl, and perfluoro C$_1$-C$_6$ alkoxy;

each R' is independently selected from the group consisting of H and C$_1$-C$_6$ alkyl;

each R" is independently selected from the group consisting of H, C$_1$-C$_6$ alkyl, C$_1$-C$_6$ fluoroalkyl, C$_1$-C$_6$ difluoroalkyl, C$_1$-C$_6$ perfluoroalkyl, aryl, aralkyl, C$_3$-C$_6$ cycloalkyl, and C$_3$-C$_7$ heterocyclyl having 1 to 3 heteroatoms selected from O, N, and S, wherein the aryl, aralkyl, C$_3$-C$_6$ cycloalkyl, and C$_3$-C$_7$ heterocyclyl may be further substituted with 0 to 3 substituents selected from halo, hydroxy, amino and C$_1$-C$_3$ alkyl; and alternatively, R' and R" attached to the same atom or to adjacent atoms may be taken together to form a 4- to 7-membered heterocylic ring having from 0 to 2 additional ring heteroatoms selected from N, O and S, and which may be unsubstituted or substituted with 1 to 3 substituents selected from the group consisting of halogen, cyano, C$_1$-C$_6$ alkyl, C$_3$-C$_6$ cycloalkyl, perfluoro C$_1$-C$_6$ alkyl, C$_1$-C$_6$ alkoxy, amino, amido and hydroxyl.

In certain embodiments of the present invention, there is provided a compound of the formula VIIb:

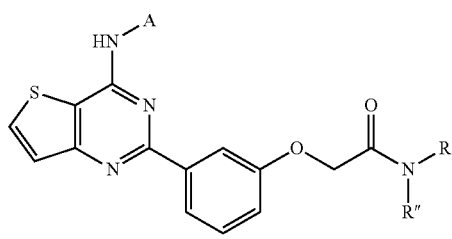

(VIIb)

wherein:
A is selected from the group consisting of:
(i) a 4- to 7-membered heterocyclic ring having from 1 to 3 ring heteroatoms selected from O, S, and N, and which may be unsubstituted or substituted with up to three substituents selected from the group consisting of halo, hydroxy, oxo, —NR'R", —OR", CHR'R", —(CH$_2$)$_b$NR'R", —O—(CH$_2$)$_c$NR'R", —C(=O)—NR'R", —NR'C(=O)—R", —OC(=O)R', —OC(=O)NR'R", —SO$_2$NR'R", —OSO$_2$NR'R", —O—(CH$_2$)$_d$OR", —CO$_2$—R", cyano, C$_1$-C$_6$ alkyl, C$_1$-C$_6$ alkoxy, alkoxyalkyl, C$_3$-C$_6$ cycloalkyl, perfluoro C$_1$-C$_6$ alkyl, perfluoro C$_1$-C$_6$ alkoxy, and a 5- or 6-membered heterocyclic ring, which may be further substituted with 0 to 3 substituents selected from the group consisting of halo, hydroxy, oxo, —NR'R", —(CH₂)_bNR'R", —O—(CH₂)_cNR'R", —C(=O)—NR'R", —O—(CH₂)_dOR", cyano, C₁-C₆ alkyl, C₁-C₆ alkoxy, alkoxyalkyl, C₃-C₆ cyclic alkyl, perfluoro C₁-C₆ alkyl, and perfluoro C₁-C₆ alkoxy;

(ii) a phenyl group, unsubstituted or substituted with up to three substituents selected from the group consisting of halo, hydroxy, —NR'R", —OR", CHR'R", —(CH₂)_bNR'R", —O—(CH₂)_cNR'R", —C(=O)—NR'R", —NR'C(=O)—R", —OC(=O)R', —OC(=O)NR'R", —SO₂NR'R", —OSO₂NR'R", —O—(CH₂)_dOR", —CO₂—R", cyano, C₁-C₆ alkyl, C₁-C₆ alkoxy, alkoxyalkyl, C₃-C₆ cycloalkyl, perfluoro C₁-C₆ alkyl, perfluoro C₁-C₆ alkoxy, and a 5- or 6-membered heterocyclic ring, which may be further substituted with 0 to 3 substituents selected from the group consisting of halo, hydroxy, oxo, —NR'R", —OR", —(CH₂)_bNR'R", —O—(CH₂)_cNR'R", —C(=O)—NR'R", —OC(=O)R', —OC(=O)NR'R", —SO₂NR'R", —OSO₂NR'R", —O—(CH₂)_dOR", cyano, C₁-C₆ alkyl, C₁-C₆ alkoxy, alkoxyalkyl, C₃-C₆ cyclic alkyl, perfluoro C₁-C₆ alkyl, and perfluoro C₁-C₆ alkoxy; (iii) a cyclic group selected from:

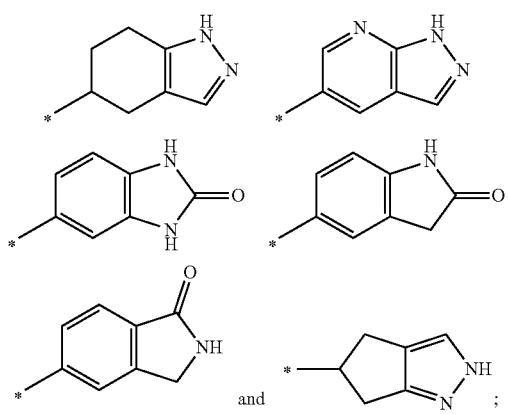

and wherein each of the above structures may be optionally substituted with up to three substituents selected from the group consisting of halo, hydroxy, oxo, —NR'R", —(CH₂)_bNR'R", —O—(CH₂)_cNR'R", —C(=O)—NR'R", —NR'C(=O)—R", —OC(=O)R', —OC(=O)NR'R", —SO₂NR'R", —OSO₂NR'R", —O—(CH₂)_dOR", —CO₂—R", cyano, C₁-C₆ alkyl, C₁-C₆ alkoxy, alkoxyalkyl, C₃-C₆ cycloalkyl, perfluoro C₁-C₆ alkyl, perfluoro C₁-C₆ alkoxy, and a 5- or 6-membered heterocyclic ring, which may be further substituted with 0 to 3 substituents selected from the group consisting of halo, hydroxy, oxo, —NR'R", —(CH₂)_bNR'R", —O—(CH₂)_cNR'R", —C(=O)—NR'R", cyano, C₁-C₆ alkyl, C₁-C₆ alkoxy, alkoxyalkyl, C₃-C₆ cyclic alkyl, perfluoro C₁-C₆ alkyl, and perfluoro C₁-C₆ alkoxy;

each b is independently selected from 1 to 6;
each c is independently selected from 2 to 6;
each d is independently selected from 2 to 6;
each R' is independently selected from the group consisting of H and C₁-C₆ alkyl;
each R" is independently selected from the group consisting of H, C₁-C₆ alkyl, C₁-C₆ fluoroalkyl, C₁-C₆ difluoroalkyl, C₁-C₆ perfluoroalkyl, aryl, aralkyl, C₃-C₆ cycloalkyl, and C₃-C₇ heterocyclyl having 1 to 3 heteroatoms selected from O, N, and S, wherein the aryl, aralkyl, C₃-C₆ cycloalkyl, and C₃-C₇ heterocyclyl may be further substituted with 0 to 3 substituents selected from halo, hydroxy, amino and C₁-C₃ alkyl; and alternatively, R' and R" attached to the same atom or to adjacent atoms may be taken together to form a 4- to 7-membered heterocylic ring having from 0 to 2 additional ring heteroatoms selected from N, O and S, and which may be unsubstituted or substituted with 1 to 3 substituents selected from the group consisting of halogen, cyano, C₁-C₆ alkyl, C₃-C₆ cycloalkyl, perfluoro C₁-C₆ alkyl, C₁-C₆ alkoxy, amino, amido and hydroxyl.

In certain embodiments of the present invention, there is provided a compound of the formula VIIc:

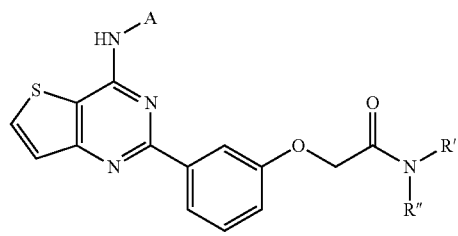

(VIIc)

wherein:

A is selected from the group consisting of:

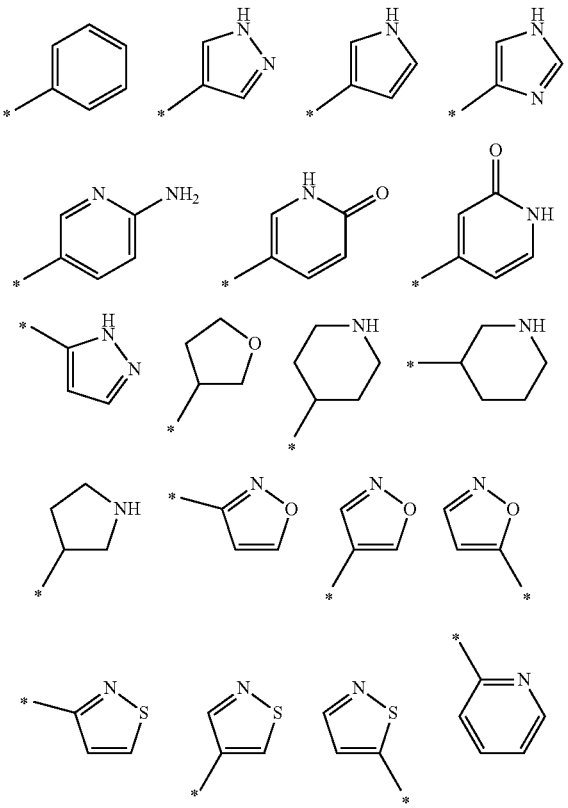

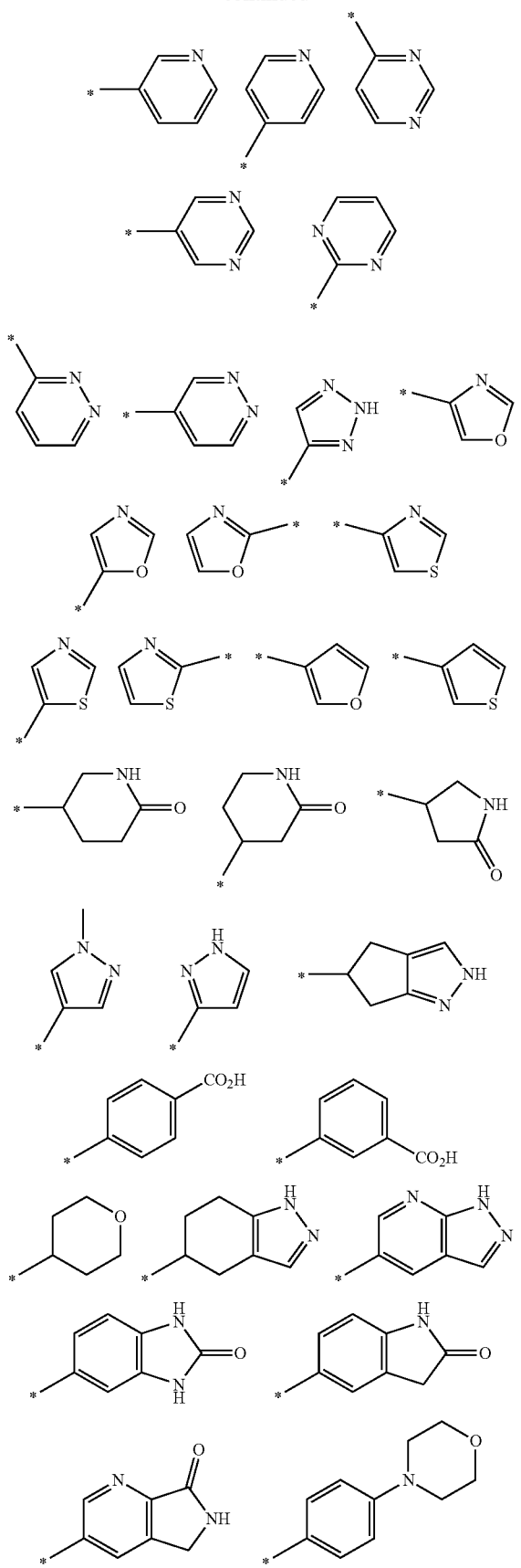
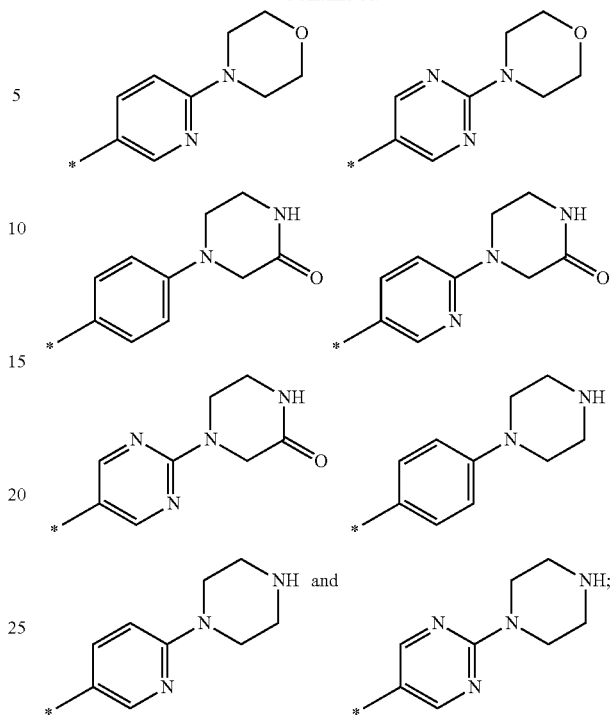

wherein each of the above structures for A may be optionally substituted with one to three substituents selected from the group consisting of halo, hydroxy, oxo, —NR'R", —(CH$_2$)$_b$NR'R", —O—(CH$_2$)$_c$NR'R", —C(=O)—NR'R", —NR'C(=O)—R", —OC(=O)R', —OC(=O)NR'R", —SO$_2$NR'R", —OSO$_2$NR'R", —O—(CH$_2$)$_d$OR", —CO$_2$—R", cyano, C$_1$-C$_6$ alkyl, C$_1$-C$_6$ alkoxy, alkoxyalkyl, C$_3$-C$_6$ cycloalkyl, perfluoro C$_1$-C$_6$ alkyl, and perfluoro C$_1$-C$_6$ alkoxy;

each b is independently selected from 1 to 6;

each c is independently selected from 2 to 6;

each d is independently selected from 2 to 6;

each R' is independently selected from the group consisting of H and C$_1$-C$_6$ alkyl;

each R" is independently selected from the group consisting of H, C$_1$-C$_6$ alkyl, C$_1$-C$_6$ fluoroalkyl, C$_1$-C$_6$ difluoroalkyl, C$_1$-C$_6$ perfluoroalkyl, aryl, aralkyl, C$_3$-C$_6$ cycloalkyl, and C$_3$-C$_7$ heterocyclyl having 1 to 3 heteroatoms selected from O, N, and S, wherein the aryl, aralkyl, C$_3$-C$_6$ cycloalkyl, and C$_3$-C$_7$ heterocyclyl may be further substituted with 0 to 3 substituents selected from halo, hydroxy, amino and C$_1$-C$_3$ alkyl; and alternatively, R' and R" attached to the same atom or to adjacent atoms may be taken together to form a 4- to 7-membered heterocylic ring having from 0 to 2 additional ring heteroatoms selected from N, O and S, and which may be unsubstituted or substituted with 1 to 3 substituents selected from the group consisting of halogen, cyano, C$_1$-C$_6$ alkyl, C$_3$-C$_6$ cycloalkyl, perfluoro C$_1$-C$_6$ alkyl, C$_1$-C$_6$ alkoxy, amino, amido and hydroxyl.

In certain embodiments of the present invention, there is provided a compound of the formula VIId:

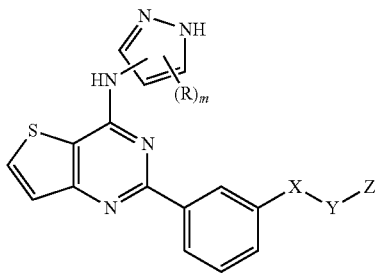

(VIId)

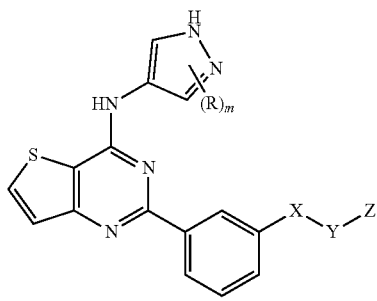

(VIIe)

wherein:
- each R is selected from the group consisting of halo, hydroxy, oxo, —NR'R", —(CH$_2$)$_b$NR'R", —O—(CH$_2$)$_c$ NR'R", —C(=O)—NR'R", —NR'C(=O)—R", —OC(=O)R', —OC(=O)NR'R", —SO$_2$NR'R", —OSO$_2$NR'R", —O—(CH$_2$)$_d$OR", —CO$_2$—R", cyano, C$_1$-C$_6$ alkyl, C$_1$-C$_6$ alkoxy, alkoxyalkyl, C$_3$-C$_6$ cycloalkyl, perfluoro C$_1$-C$_6$ alkyl, perfluoro C$_1$-C$_6$ alkoxy;
- each b is independently selected from 1 to 6;
- each c is independently selected from 2 to 6;
- each d is independently selected from 2 to 6;
- m is selected from 0 to 2;
- X is selected from the group consisting of O, NH and CH$_2$;
- Y is selected from the group consisting of a single bond, —C(=O)— and —(CH$_2$)$_a$—, wherein a is from 1 to 6;
- Z is selected from the group consisting of —NR'R", —C(=O)NR'R", —NR'C(=O)R", and a 4- to 7-membered ring having from 0 to 3 ring heteroatoms selected from O, S, and N, which may be unsubstituted or substituted with up to three substituents selected from the group consisting of halo, hydroxy, oxo, —NR'R", —OR", —C(=O)—NR'R", —NR'C(=O)—R", —OC(=O)R", —OC(=O)NR'R", —SO$_2$NR'R", —OSO$_2$NR'R", —CO$_2$—R", —O—(CH$_2$)$_d$OR", cyano, C$_1$-C$_6$ alkyl, C$_1$-C$_6$ alkoxy, alkoxyalkyl, C$_3$-C$_6$ cycloalkyl, perfluoro C$_1$-C$_6$ alkyl, and perfluoro C$_1$-C$_6$ alkoxy;
- each R' is independently selected from the group consisting of H and C$_1$-C$_6$ alkyl;
- each R" is independently selected from the group consisting of H, C$_1$-C$_6$ alkyl, C$_1$-C$_6$ fluoroalkyl, C$_1$-C$_6$ difluoroalkyl, C$_1$-C$_6$ perfluoroalkyl, aryl, aralkyl, C$_3$-C$_6$ cycloalkyl, and C$_3$-C$_7$ heterocyclyl having 1 to 3 heteroatoms selected from O, N, and S, wherein the aryl, aralkyl, C$_3$-C$_6$ cycloalkyl, and C$_3$-C$_7$ heterocyclyl may be further substituted with 0 to 3 substituents selected from halo, hydroxy, amino and C$_1$-C$_3$ alkyl; and alternatively, R' and R" attached to the same atom or to adjacent atoms may be taken together to form a 4- to 7-membered heterocylic ring having from 0 to 2 additional ring heteroatoms selected from N, O and S, and which may be unsubstituted or substituted with 1 to 3 substituents selected from the group consisting of halogen, cyano, C$_1$-C$_6$ alkyl, C$_3$-C$_6$ cycloalkyl, perfluoro C$_1$-C$_6$ alkyl, C$_1$-C$_6$ alkoxy, amino, amido and hydroxyl.

In certain embodiments of the present invention, there is provided a compound of the formula VIIe:

wherein:
- each R is selected from the group consisting of halo, hydroxy, oxo, —NR'R", —(CH$_2$)$_b$NR'R", —O—(CH$_2$)$_c$ NR'R", —C(=O)—NR'R", —NR'C(=O)—R", —OC(=O)R', —OC(=O)NR'R", —SO$_2$NR'R", —OSO$_2$NR'R", —O—(CH$_2$)$_d$OR", —CO$_2$—R", cyano, C$_1$-C$_6$ alkyl, C$_1$-C$_6$ alkoxy, alkoxyalkyl, C$_3$-C$_6$ cycloalkyl, perfluoro C$_1$-C$_6$ alkyl, perfluoro C$_1$-C$_6$ alkoxy;
- each b is independently selected from 1 to 6;
- each c is independently selected from 2 to 6;
- each d is independently selected from 2 to 6;
- m is selected from 0 to 2;
- X is selected from the group consisting of O, NH and CH$_2$;
- Y is selected from the group consisting of a single bond, —C(=O)— and —(CH$_2$)$_a$—, wherein a is from 1 to 6;
- Z is selected from the group consisting of —NR'R", —C(=O)NR'R", —NR'C(=O)R", and a 4- to 7-membered ring having from 0 to 3 ring heteroatoms selected from O, S, and N, which may be unsubstituted or substituted with up to three substituents selected from the group consisting of halo, hydroxy, oxo, —NR'R", —OR", —C(=O)—NR'R", —NR'C(=O)—R", —OC(=O)R", —OC(=O)NR'R", —SO$_2$NR'R", —OSO$_2$NR'R", —CO$_2$—R", —O—(CH$_2$)$_d$OR", cyano, C$_1$-C$_6$ alkyl, C$_1$-C$_6$ alkoxy, alkoxyalkyl, C$_3$-C$_6$ cycloalkyl, perfluoro C$_1$-C$_6$ alkyl, and perfluoro C$_1$-C$_6$ alkoxy;
- each R' is independently selected from the group consisting of H and C$_1$-C$_6$ alkyl;
- each R" is independently selected from the group consisting of H, C$_1$-C$_6$ alkyl, C$_1$-C$_6$ fluoroalkyl, C$_1$-C$_6$ difluoroalkyl, C$_1$-C$_6$ perfluoroalkyl, aryl, aralkyl, C$_3$-C$_6$ cycloalkyl, and C$_3$-C$_7$ heterocyclyl having 1 to 3 heteroatoms selected from O, N, and S, wherein the aryl, aralkyl, C$_3$-C$_6$ cycloalkyl, and C$_3$-C$_7$ heterocyclyl may be further substituted with 0 to 3 substituents selected from halo, hydroxy, amino and C$_1$-C$_3$ alkyl; and alternatively, R' and R" attached to the same atom or to adjacent atoms may be taken together to form a 4- to 7-membered heterocylic ring having from 0 to 2 additional ring heteroatoms selected from N, O and S, and which may be unsubstituted or substituted with 1 to 3 substituents selected from the group consisting of halogen, cyano, C$_1$-C$_6$ alkyl, C$_3$-C$_6$ cycloalkyl, perfluoro C$_1$-C$_6$ alkyl, C$_1$-C$_6$ alkoxy, amino, amido and hydroxyl.

In certain embodiments of the present invention, there is provided a compound of the formula VIIf:

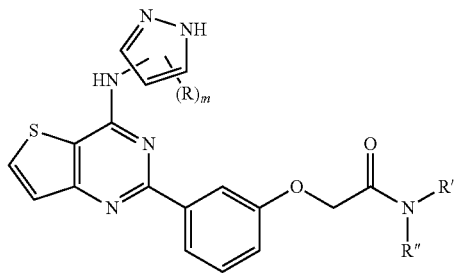

(VIIf)

wherein:
each R is selected from the group consisting of halo, hydroxy, oxo, —NR'R", —(CH$_2$)$_b$NR'R", —O—(CH$_2$)$_c$ NR'R", —C(=O)—NR'R", —NR'C(=O)—R", —OC(=O)R', —OC(=O)NR'R", —SO$_2$NR'R", —OSO$_2$NR'R", —O—(CH$_2$)$_d$OR", —CO$_2$—R", cyano, C$_1$-C$_6$ alkyl, C$_1$-C$_6$ alkoxy, alkoxyalkyl, C$_3$-C$_6$ cycloalkyl, perfluoro C$_1$-C$_6$ alkyl, perfluoro C$_1$-C$_6$ alkoxy;
each b is independently selected from 1 to 6;
each c is independently selected from 2 to 6;
each d is independently selected from 2 to 6;
m is selected from 0 to 2;
each R' is independently selected from the group consisting of H and C$_1$-C$_6$ alkyl;
each R" is independently selected from the group consisting of H, C$_1$-C$_6$ alkyl, C$_1$-C$_6$ fluoroalkyl, C$_1$-C$_6$ difluoroalkyl, C$_1$-C$_6$ perfluoroalkyl, aryl, aralkyl, C$_3$-C$_6$ cycloalkyl, and C$_3$-C$_7$ heterocyclyl having 1 to 3 heteroatoms selected from O, N, and S, wherein the aryl, aralkyl, C$_3$-C$_6$ cycloalkyl, and C$_3$-C$_7$ heterocyclyl may be further substituted with 0 to 3 substituents selected from halo, hydroxy, amino and C$_1$-C$_3$ alkyl; and
alternatively, R' and R" attached to the same atom or to adjacent atoms may be taken together to form a 4- to 7-membered heterocylic ring having from 0 to 2 additional ring heteroatoms selected from N, O and S, and which may be unsubstituted or substituted with 1 to 3 substituents selected from the group consisting of halogen, cyano, C$_1$-C$_6$ alkyl, C$_3$-C$_6$ cycloalkyl, perfluoro C$_1$-C$_6$ alkyl, C$_1$-C$_6$ alkoxy, amino, amido and hydroxyl.

In certain embodiments of the present invention, there is provided a compound of the formula VIIg:

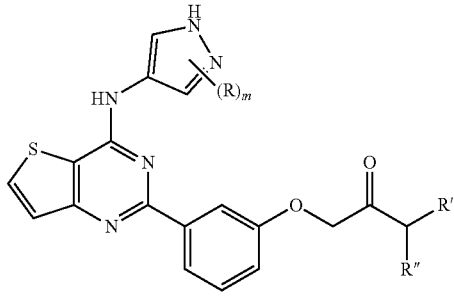

(VIIg)

wherein:
each R is selected from the group consisting of halo, hydroxy, oxo, —NR'R", —(CH$_2$)$_b$NR'R", —O—(CH$_2$)$_c$ NR'R", —C(=O)—NR'R", —NR'C(=O)—R", —OC(=O)R', —OC(=O)NR'R", —SO$_2$NR'R", —OSO$_2$NR'R", —O—(CH$_2$)$_d$OR", —CO$_2$—R", cyano, C$_1$-C$_6$ alkyl, C$_1$-C$_6$ alkoxy, alkoxyalkyl, C$_3$-C$_6$ cycloalkyl, perfluoro C$_1$-C$_6$ alkyl, perfluoro C$_1$-C$_6$ alkoxy;
each b is independently selected from 1 to 6;
each c is independently selected from 2 to 6;
each d is independently selected from 2 to 6;
m is selected from 0 to 2;
each R' is independently selected from the group consisting of H and C$_1$-C$_6$ alkyl;
each R" is independently selected from the group consisting of H, C$_1$-C$_6$ alkyl, C$_1$-C$_6$ fluoroalkyl, C$_1$-C$_6$ difluoroalkyl, C$_1$-C$_6$ perfluoroalkyl, aryl, aralkyl, C$_3$-C$_6$ cycloalkyl, and C$_3$-C$_7$ heterocyclyl having 1 to 3 heteroatoms selected from O, N, and S, wherein the aryl, aralkyl, C$_3$-C$_6$ cycloalkyl, and C$_3$-C$_7$ heterocyclyl may be further substituted with 0 to 3 substituents selected from halo, hydroxy, amino and C$_1$-C$_3$ alkyl; and
alternatively, R' and R" attached to the same atom or to adjacent atoms may be taken together to form a 4- to 7-membered heterocylic ring having from 0 to 2 additional ring heteroatoms selected from N, O and S, and which may be unsubstituted or substituted with 1 to 3 substituents selected from the group consisting of halogen, cyano, C$_1$-C$_6$ alkyl, C$_3$-C$_6$ cycloalkyl, perfluoro C$_1$-C$_6$ alkyl, C$_1$-C$_6$ alkoxy, amino, amido and hydroxyl.

In embodiments of the invention according to above formulae, A may be selected from the groups having the following structures:

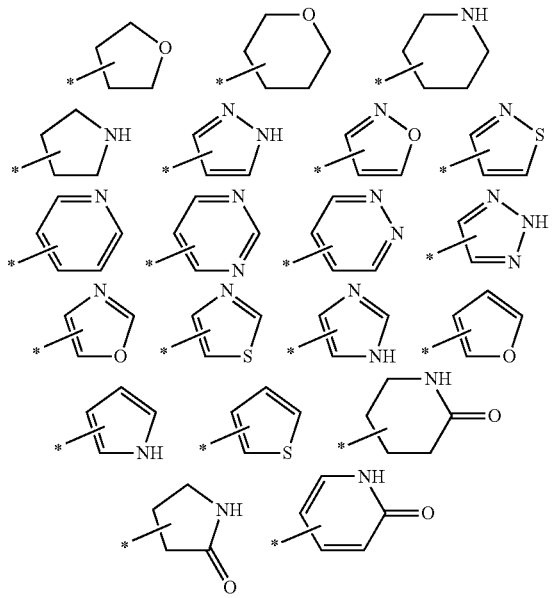

which may be unsubstituted or substituted with one to three substituents selected from the group consisting of halo, hydroxy, oxo, —NR'R", —(CH$_2$)$_b$NR'R", —O—(CH$_2$)$_c$ NR'R", —C(=O)—NR'R", —NR'C(=O)—R", —OC(=O)R', —OC(=O)NR'R", —SO$_2$NR'R", —OSO$_2$NR'R", —O—(CH$_2$)$_d$OR", —CO$_2$—R", cyano, C$_1$-C$_6$ alkyl, C$_1$-C$_6$ alkoxy, alkoxyalkyl, C$_3$-C$_6$ cycloalkyl, perfluoro C$_1$-C$_6$ alkyl, and perfluoro C$_1$-C$_6$ alkoxy.

In embodiments of the invention according to above formulae, A may be selected from the groups having the following structures:

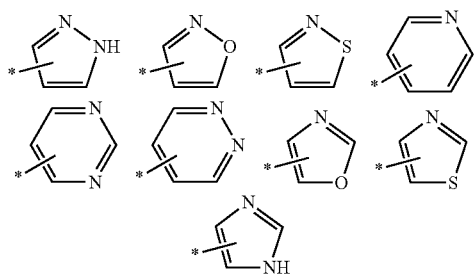

which may be unsubstituted or substituted with one to three substituents selected from the group consisting of halo, hydroxy, oxo, —NR'R", —(CH$_2$)$_b$NR'R", —O—(CH$_2$)$_c$NR'R", —C(=O)—NR'R", —NR'C(=O)—R", —OC(=O)R', —OC(=O)NR'R", —SO$_2$NR'R", —OSO$_2$NR'R", —O—(CH$_2$)$_d$OR", —CO$_2$—R", cyano, C$_1$-C$_6$ alkyl, C$_1$-C$_6$ alkoxy, alkoxyalkyl, C$_3$-C$_6$ cycloalkyl, perfluoro C$_1$-C$_6$ alkyl, and perfluoro C$_1$-C$_6$ alkoxy.

In embodiments of the invention according to above formulae, A may be a phenyl group which may be unsubstituted or substituted with up to three substituents selected from the group consisting of halo, hydroxy, —NR'R", —OR", CHR'R", —(CH$_2$)$_b$NR'R", —O—(CH$_2$)$_c$NR'R", —C(=O)—NR'R", —NR'C(=O)—R", —OC(=O)R', —OC(=O)NR'R", —SO$_2$NR'R", —OSO$_2$NR'R", —O—(CH$_2$)$_d$OR", —CO$_2$—R", cyano, C$_1$-C$_6$ alkyl, C$_1$-C$_6$ alkoxy, alkoxyalkyl, C$_3$-C$_6$ cycloalkyl, perfluoro C$_1$-C$_6$ alkyl, perfluoro C$_1$-C$_6$ alkoxy, and a 5- or 6-membered heterocyclic ring, which may be further substituted with 0 to 3 substituents selected from the group consisting of halo, hydroxy, oxo, —NR'R", —OR", —(CH$_2$)$_b$NR'R", —O—(CH$_2$)$_c$NR'R", —C(=O)—NR'R", —OC(=O)R', —OC(=O)NR'R", —SO$_2$NR'R", —OSO$_2$NR'R", —O—(CH$_2$)$_d$OR", cyano, C$_1$-C$_6$ alkyl, C$_1$-C$_6$ alkoxy, alkoxyalkyl, C$_3$-C$_6$ cyclic alkyl, perfluoro C$_1$-C$_6$ alkyl, and perfluoro C$_1$-C$_6$ alkoxy.

In embodiments of the invention according to the above formulae, A may be a selected from the groups having the following structures:

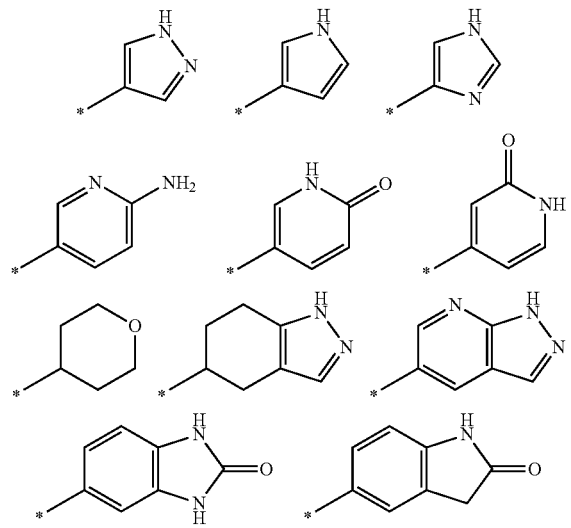

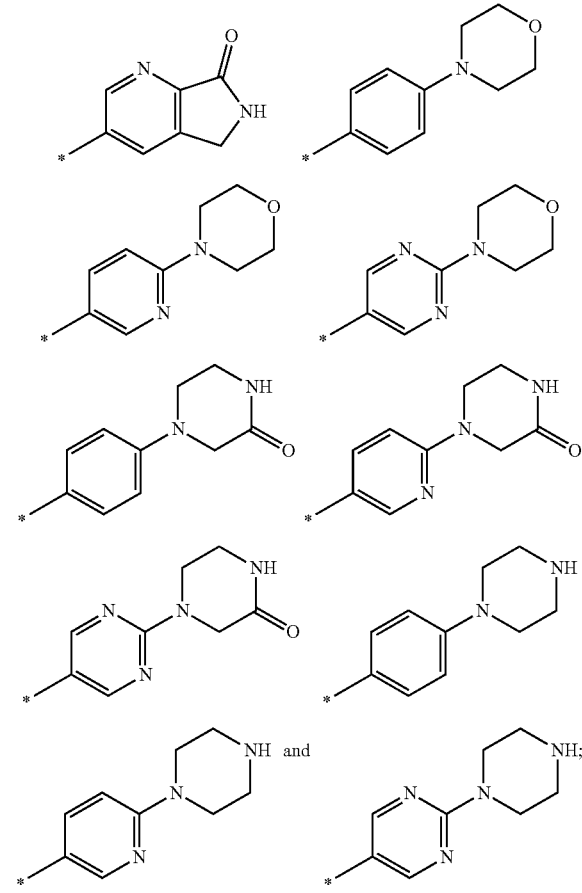

which may be unsubstituted or substituted with one to three substituents selected from the group consisting of halo, hydroxy, oxo, —NR'R", —(CH$_2$)$_b$NR'R", —O—(CH$_2$)$_c$NR'R", —C(=O)—NR'R", —NR'C(=O)—R", —OC(=O)R', —OC(=O)NR'R", —SO$_2$NR'R", —OSO$_2$NR'R", —O—(CH$_2$)$_d$OR", —CO$_2$—R", cyano, C$_1$-C$_6$ alkyl, C$_1$-C$_6$ alkoxy, alkoxyalkyl, C$_3$-C$_6$ cycloalkyl, perfluoro C$_1$-C$_6$ alkyl, and perfluoro C$_1$-C$_6$ alkoxy.

In embodiments of the invention according to above formulae, A may be selected from the groups having the following structures:

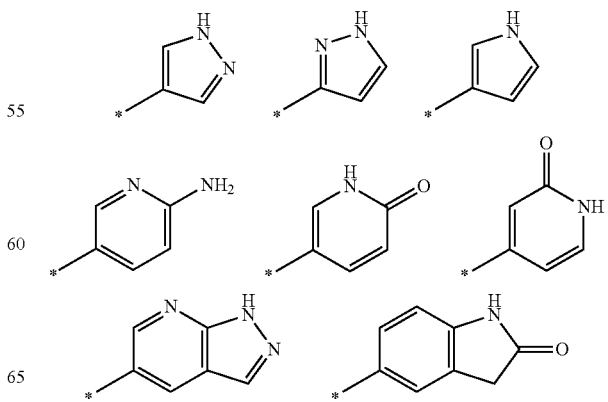

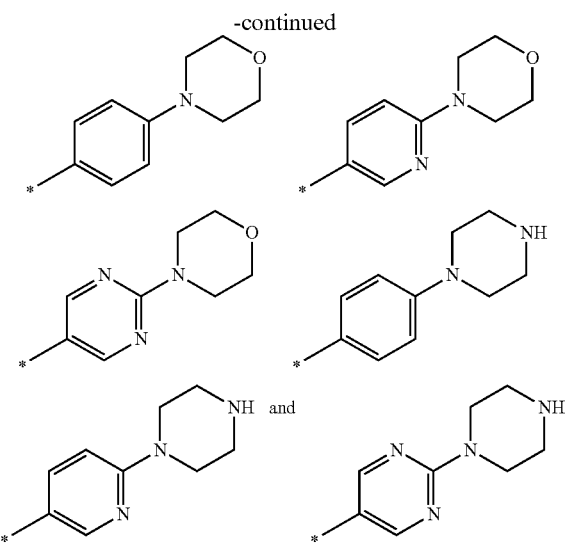

which may be unsubstituted or substituted with one to three substituents selected from the group consisting of halo, hydroxy, oxo, —NR'R", —(CH$_2$)$_b$NR'R", —O—(CH$_2$)$_c$NR'R", —C(=O)—NR'R", —NR'C(=O)—R", —OC(=O)R', —OC(=O)NR'R", —SO$_2$NR'R", —OSO$_2$NR'R", —O—(CH$_2$)$_d$OR", —CO$_2$—R", cyano, C$_1$-C$_6$ alkyl, C$_1$-C$_6$ alkoxy, alkoxyalkyl, C$_3$-C$_6$ cycloalkyl, perfluoro C$_1$-C$_6$ alkyl, and perfluoro C$_1$-C$_6$ alkoxy.

In other embodiments of the invention according to above formulae, A may be selected from the groups having the following structures:

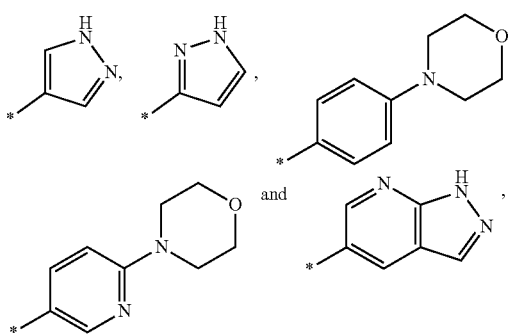

which may be unsubstituted or substituted with one to three substituents selected from the group consisting of halo, hydroxy, oxo, —NR'R", —(CH$_2$)$_b$NR'R", —O—(CH$_2$)$_c$NR'R", —C(=O)—NR'R", —NR'C(=O)—R", —OC(=O)R', —OC(=O)NR'R", —SO$_2$NR'R", —OSO$_2$NR'R", —O—(CH$_2$)$_d$OR", —CO$_2$—R", cyano, C$_1$-C$_6$ alkyl, C$_1$-C$_6$ alkoxy, alkoxyalkyl, C$_3$-C$_6$ cycloalkyl, perfluoro C$_1$-C$_6$ alkyl, and perfluoro C$_1$-C$_6$ alkoxy.

In other embodiments of the invention according to the above formulae, A may be selected from the groups having the following structures:

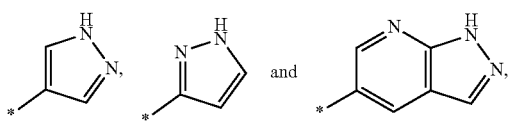 [SMILES: *c1cn[nH]c1 ; *c1cc[nH]n1 ; *c1cnc2[nH]ncc2c1]

which may be unsubstituted or substituted with substituents selected from the group consisting of halo, hydroxy, oxo, —NR'R", —(CH$_2$)$_b$NR'R", —O—(CH$_2$)$_c$NR'R", —C(=O)—NR'R", —NR'C(=O)—R", —OC(=O)R', —OC(=O)NR'R", —SO$_2$NR'R", —OSO$_2$NR'R", —O—(CH$_2$)$_d$OR", —CO$_2$—R", cyano, C$_1$-C$_6$ alkyl, C$_1$-C$_6$ alkoxy, alkoxyalkyl, C$_3$-C$_6$ cycloalkyl, perfluoro C$_1$-C$_6$ alkyl, and perfluoro C$_1$-C$_6$ alkoxy.

The term "heteroatom" as used herein means an atom of any element other than carbon or hydrogen. Preferred heteroatoms are boron, nitrogen, oxygen, phosphorus, sulfur and selenium. Most preferred are nitrogen, sulfur and oxygen.

The term "alkyl" refers to the radical of saturated aliphatic groups, including straight-chain alkyl groups, branched-chain alkyl groups, cycloalkyl (alicyclic) groups, alkyl substituted cycloalkyl groups, and cycloalkyl substituted alkyl groups. In preferred embodiments, a straight chain or branched chain alkyl has 10 or fewer carbon atoms in its backbone (e.g., C$_1$-C$_{10}$ for straight chain, C$_3$-C$_{10}$ for branched chain), and more preferably 6 or fewer. Likewise, preferred cycloalkyls have from 3-10 carbon atoms in their ring structure, and more preferably have 3, 4, 5, or 6 carbons in the ring structure.

Unless the number of carbons is otherwise specified, "lower alkyl" as used herein means an alkyl group, as defined above, but having from one to four carbons, and more preferably from one to three carbon atoms. Likewise, "lower alkenyl" and "lower alkynyl" have similar chain lengths. Preferred alkyl groups are lower alkyls. In preferred embodiments, a substituent designated herein as alkyl is a lower alkyl.

The term "cycloalkyl" refers to saturated, carbocyclic groups having from 3 to 7 carbons in the ring. Preferred cycloalkyl groups include cyclopropyl, cyclobutyl, cyclopentyl and cyclohexyl.

The term "aralkyl", as used herein, refers to an alkyl group, and preferably a lower alkyl group, substituted with an aryl group (e.g., an aromatic or heteroaromatic group).

The terms "alkenyl" and "alkynyl" refer to unsaturated aliphatic groups analogous in length and possible substitution to the alkyls described above, but that contain at least one double or triple bond respectively.

The term "aryl" as used herein includes 5- and 6-membered single-ring aromatic groups that may include from zero to four heteroatoms, for example, benzene, pyrene, pyrrole, furan, thiophene, imidazole, oxazole, thiazole, triazole, pyrazole, pyridine, pyrazine, pyridazine and pyrimidine, and the like. Those aryl groups having heteroatoms in the ring structure may also be referred to as "aryl heterocycles" or "heteroaromatics." The aromatic ring can be substituted at one or more ring positions with such substituents as described above, for example, halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —CF$_3$, —CN, or the like. The term "aryl" also includes polycyclic ring systems having two or more cyclic rings in which two or more carbons are common to two adjoining rings (the rings are "fused rings") wherein at least one of the rings is aromatic, e.g., the other cyclic rings can be cycloalkyls, cycloalkenyls, aryls and/or heterocyclic groups.

The terms "heterocyclyl" or "heterocyclic group" refer to 3- to 10-membered ring structures, more preferably 5- or 6-membered rings, whose ring structures include one to four heteroatoms. Heterocyclic groups may be saturated, unsaturated or aromatic. Heterocycles can also be polycycles. Heterocyclic groups include, for example, thiophene, thianthrene, furan, pyran, isobenzofuran, chromene, xanthene, phenoxathiin, pyrrole, imidazole, pyrazole, isothiazole, isoxazole, pyridine, pyrazine, pyrimidine, pyridazine, indolizine, isoindole, indole, indazole, purine, quinolizine, isoquinoline, quinoline, phthalazine, naphthyridine, quinoxaline, quinazoline, cinnoline, pteridine, carbazole, carboline, phenanthridine, acridine, pyrimidine, phenanthroline, phenazine, phenarsazine, phenothiazine, furazan, phenoxazine, pyrrolidine, oxolane, thiolane, oxazole, piperidine, piperazine, morpholine, lactones, lactams such as azetidinones and pyrrolidinones, sultams, sultones, and the like. The heterocyclic ring can be substituted at one or more positions with such substituents as described above, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, —$CF_3$, —CN, or the like.

The terms "polycyclyl" or "polycyclic group" refer to two or more rings (e.g., cycloalkyls, cycloalkenyls, aryls and/or heterocyclyls) in which two or more carbons are common to two adjoining rings, e.g., the rings are "fused rings". Rings that are joined through non-adjacent atoms are termed "bridged" rings. Each of the rings of the polycyclic group can be substituted with such substituents as described above, for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, —$CF_3$, —CN, or the like.

As used herein, the term "nitro" means —$NO_2$; the term "halogen" or "halo" designates —F, —Cl, —Br or —I; the term "sulfhydryl" means —SH; the term "hydroxyl" means —OH; and the term "sulfonyl" means —$SO_2$—.

The terms "amine" and "amino" are art-recognized and refer to both unsubstituted and substituted amines, e.g., a moiety that can be represented by the general formula:

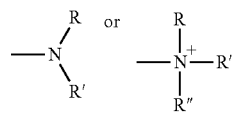

wherein R, R' and R" each independently represent a group permitted by the rules of valence, preferably H, alkyl, alkenyl, alkynyl, aralkyl, aryl, and heterocyclic groups, a more preferably are selected from H and lower alkyl.

The terms "alkoxyl" or "alkoxy" as used herein refers to an alkyl group, as defined above, having an oxygen radical attached thereto. Representative alkoxyl groups include methoxy, ethoxy, propyloxy, tert-butoxy and the like. The term lower alkoxy refers to an alkoxy group having from 1 to 4 carbon atoms, and more preferably from 1 to 3 carbon atoms.

The term "oxo" as used herein refers to an oxygen atom that has a double bond to a carbon.

The abbreviations Me, Et, Ph, Tf, Nf, Ts, Ms represent methyl, ethyl, phenyl, trifluoromethanesulfonyl, nonafluorobutanesulfonyl, p-toluenesulfonyl and methanesulfonyl, respectively. A more comprehensive list of the abbreviations utilized by organic chemists of ordinary skill in the art appears in the first issue of each volume of the Journal of Organic Chemistry; this list is typically presented in a table entitled Standard List of Abbreviations. The abbreviations contained in said list, and all abbreviations utilized by organic chemists of ordinary skill in the art are hereby incorporated by reference.

As used herein, the definition of each expression, e.g. alkyl, m, n, R, R", $R^3$, etc., when it occurs more than once in any structure, is intended to be independent of its definition elsewhere in the same structure.

It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc.

As used herein, the term "substituted" is contemplated to include all permissible substituents of organic compounds. In a broad aspect, the permissible substituents include acyclic and cyclic, branched and unbranched, carbocyclic and heterocyclic, aromatic and non-aromatic substituents of organic compounds. Illustrative substituents include, for example, those described herein above. The permissible substituents can be one or more and the same or different for appropriate organic compounds. For purposes of this invention, the heteroatoms such as nitrogen may have hydrogen substituents and/or any permissible substituents of organic compounds described herein which satisfy the valences of the heteroatoms. This invention is not intended to be limited in any manner by the permissible substituents of organic compounds.

The phrase "protecting group" as used herein means temporary substituents which protect a potentially reactive functional group from undesired chemical transformations. Examples of such protecting groups include esters of carboxylic acids, silyl ethers of alcohols, and acetals and ketals of aldehydes and ketones, respectively. The field of protecting group chemistry has been reviewed (Greene, T. W.; Wuts, P. G. M. *Protective Groups in Organic Synthesis*, 2$^{nd}$ ed.; Wiley: New York, 1991).

Certain compounds of the present invention may exist in particular geometric or stereoisomeric forms. The present invention contemplates all such compounds, including cis- and trans-isomers, R- and S-enantiomers, diastereomers, (D)-isomers, (L)-isomers, the racemic mixtures thereof, and other mixtures thereof, as falling within the scope of the invention. Additional asymmetric carbon atoms may be present in a substituent such as an alkyl group. All such isomers, as well as mixtures thereof, are included in this invention. The invention provides a method of inhibiting one or more glucose transporters in a mammal. In particular, the invention provides a method of inhibiting GLUT1 and GLUT3 in a mammal. The invention provides a method of treating a patient suffering from a disease comprising administering to the patient in need of such treatment a therapeutically effective amount of a compound of Formulas I, II, IIa, III, IIIa, IV, IVa, IVb, IVc, IVd, IVe, IVf, V, Va, Vb, Vc, VI, VIa, VIb, VII, VIIa, VIIb, VIIc, VIId, VIIe, VIIf, or VIIg. In certain such embodiments, the compounds of Formulas I, II, IIa, III, IIIa, IV, IVa, IVb, IVc, IVd, IVe, IVf, V, Va, Vb, Vc, VI, VIa, VIb, VII, VIIa, VIIb, VIIc, VIId, VIIe, VIIf, or VIIg inhibit GLUT1 and GLUT3.

Glucose uptake inhibitors of the invention inhibit tumor cell growth and metastasis and angiogenesis, and are useful for treating neoplastic diseases. Neoplastic diseases include any malignant growth or tumor caused by abnormal or uncontrolled cell division, and may spread to other parts of the body through the lymphatic system or the blood stream. Neoplastic disease includes, without limitation, lymphoma (a neoplasm of lymph tissue that is usually malignant), carcinoma (any malignant tumor derived from epithelial tissue), leukemia (malignant neoplasm of blood-forming tissues; characterized by abnormal proliferation of leukocytes), sarcoma (a usually malignant tumor arising from connective tissue (bone or muscle etc.), and blastoma (malignancy in precursor cells). Nonlimiting examples include squamous cell cancer, small-cell lung cancer, pituitary cancer, esophageal cancer, astrocytoma, soft tissue sarcoma, non-small cell lung cancer, adenocarcinoma of the lung, squamous carcinoma of the lung, cancer of the peritoneum, hepatocellular cancer, gastrointestinal cancer, pancreatic cancer, glioblastoma, cervical cancer, ovarian cancer, liver cancer, bladder cancer, hepatoma, breast cancer, colon cancer, colorectal cancer, endometrial or uterine carcinoma, salivary gland carcinoma, kidney cancer, liver cancer, prostate cancer, vulval cancer, thyroid cancer, hepatic carcinoma, brain cancer, endometrial cancer, testis cancer, cholangiocarcinoma, gallbladder carcinoma, gastric cancer, melanoma, and various types of head and neck cancer. In particular, the compounds of the present invention inhibit tumors with a defined genetic background that render cancer cells more reliant on glycolysis. Non-limiting examples include genetic mutations in TCA cycle components Fumarate Hydratase (FH), Succinate Dehydrogenase (SDH), and mitochondrial encoded complex I mutations. Mutations in FH underlie an inherited cancer disease termed leiomyomatosis renal cell carcinoma (HLRCC). Kidney tumors associated with this disease are aggressive and have the tendency to metastasize early. Tumor cell lines derived from such tumors are extremely dependent on glucose uptake for survival (Yang et al, *Cancer Genet Cytogenet.* 2010 Jan. 1; 196(1): 45-55.). Germline mutations in SDH have been observed in patients with hereditary paragangliomas and phaeochromocytomas (Belinksi et al, *Front Oncol.* 2013 May 17; 3:117.). Germline mutations in SDH have also been associated with renal neoplasia (Gill, *Pathology* (June 2012) 44(4), pp. 285-292) and cell lines derived from such tumors consume very little oxygen and thus are predicted to be completely dependent on glycolysis for survival.

In certain embodiments, a glucose uptake inhibitor of the invention is used as part of a rational combination therapy. Other compounds or therapies to be used with a glucose uptake inhibitor of the invention include, but are not limited to, $H_2O_2$, Vitamin C (pharmacological-dose), Ionizing Radiation, Beta-lapachone, AEQ501, ARQ761 (prodrug), Elesclemol, Menadione, Bleomycin, Cisplatinum, Apatone (IC-MedTech) (Menadione+Vitamin C), Imexon, Antamycin A, Paraquat, MPP, Caged H2O2, Mustard Gas—Mustargen, methchlorethamine), Melphalan (ALkeran), NOV-002, Pyrogallol, Acetaminophen, Dimethylfumarate (DMF) and its metabolite methylhydrogenfumarate (MHF), Apaziquone/E0quin, E09, and CPI-613 (AKGDH inhibitor).

Glucose uptake inhibitors of the invention may be co-administered with other antineoplastic agents, including chemotherapeutic agents and radiation. Anti-neoplastic agents can be grouped into a variety of classes including, for example, mitotic inhibitors, alkylating agents, anti-metabolites, intercalating antibiotics, growth factor inhibitors, cell cycle inhibitors, enzymes, topoisomerase inhibitors, anti-survival agents, biological response modifiers, anti-hormones, steroids and anti-angiogenesis agents. Examples of alkylating agents include, but are not limited to, cisplatin, cyclophosphamide, melphalan, and dacarbazine. Examples of antimetabolites include, but are not limited to, doxorubicin, daunorubicin, and paclitaxel, gemcitabine. Non-limiting examples of topoisomerase inhibitors are irinotecan (CPT-11), aminocamptothecin, camptothecin, DX-8951f, and topotecan (topoisomerase I) and etoposide (VP-16) and teniposide (VM-26) (topoisomerase II). When the antineoplastic agent is radiation, the source of the radiation can be either external (e.g., external beam radiation therapy—EBRT) or internal (i.e., brachytherapy—BT) to the patient being treated. The dose of anti-neoplastic agent administered depends on numerous factors, including, for example, the type of agent, the type and severity tumor being treated and the route of administration of the agent. It should be emphasized, however, that the present invention is not limited to any particular dose.

Glucose uptake inhibitors in this invention may be co-administered with an anti-angiogenic agent, for example a small molecule or biological molecule that targets a vascular endothelial growth factor (e.g., VEGF) or its receptor (e.g., VEGFR1, VEGFR2). In another embodiment, the compound is co-administered with an antagonist of the human EGFR related family of receptor tyrosine kinases (HER1/EGFR (epidermal growth factor receptor)/c-erbB1, HER2/c-erbB2, HER3/c-erbB3 and HER4/c-erbB4).

Glucose uptake inhibitors in this invention may be further co-administered with other agents that deplete cellular ATP or energy. Examples of such agents include, but are not limited to: metformin, phenformin, pyrvinium, rotenone.

The glucose uptake inhibitors may be co-administered with cell death inducing agents, which could include but are not limited to: BCL2 family inhibitors (e.g.: ABT737, ABT263, ABT199, obatoclax), SMAC family mimetics, TRAIL agonists, ferroptosis inducing agents (e.g.: sorafenib, erastin) and ER stress inducers.

The invention provides a method of treating an autoimmune disorder in a subject comprising administering to the subject a therapeutically effective amount of a compound of Formulas I, II, IIa, III, IIIa, IV, IVa, IVb, IVc, IVd, IVe, IVf, V, Va, Vb, Vc, VI, VIa, VIb, VII, VIIa, VIIb, VIIc, VIId, VIIe, VIIf, or VIIg. Autoimmune disorders include, without limitation, rheumatoid arthritis, multiple sclerosis, systemic lupus erythematosus (SLE; lupus), psoriasis, Crohn's disease, atopic dermatitis, eczema, or graft-versus-host disease (GVHD), Acute Disseminated Encephalomyelitis (ADEM), Acute necrotizing hemorrhagic leukoencephalitis, Addison's disease, Agammaglobulinemia, Alopecia areata, Amyloidosis, Ankylosing spondylitis, Anti-GBM/Anti-TBM nephritis, Antiphospholipid syndrome (APS), Autoimmune angioedema, Autoimmune aplastic anemia, Autoimmune dysautonomia, Autoimmune hepatitis, Autoimmune hyperlipidemia, Autoimmune immunodeficiency, Autoimmune inner ear disease (AIED), Autoimmune myocarditis, Autoimmune oophoritis, Autoimmune pancreatitis, Autoimmune retinopathy, Autoimmune thrombocytopenic purpura (ATP), Autoimmune thyroid disease, Autoimmune urticaria, Axonal & neuronal neuropathies, Balo disease, Behcet's disease, Bullous pemphigoid, Cardiomyopathy, Castleman disease, Celiac disease, Chagas disease, Chronic fatigue syndrome, Chronic inflammatory demyelinating polyneuropathy (CIDP), Chronic recurrent multifocal ostomyelitis (CRMO), Churg-Strauss syndrome, Cicatricial pemphigoid/benign mucosal pemphigoid, Crohn's disease, Cogans syndrome, Cold agglutinin disease, Congenital heart block, Coxsackie myocarditis, CREST disease, Essential mixed cryoglobulinemia, Demyelinating neuropathies, Dermatitis herpetiformis, Dermatomyositis, Devic's disease (neuromyelitis optica), Discoid lupus, Dressler's syndrome, Endometriosis, Eosinophilic esophagitis, Eosinophilic fasciitis, Erythema nodosum, Experimental allergic encephalomyelitis, Evans syndrome, Fibromyalgia**, Fibrosing alveolitis, Giant cell arteritis (temporal arteritis), Giant cell myocarditis, Glomerulonephritis, Goodpasture's syndrome, Granulomatosis with Polyangiitis (GPA) (formerly called Wegener's Granulomatosis), Graves' disease, Guillain-Barre syndrome, Hashimoto's encephalitis, Hashimoto's thyroiditis, Hemolytic anemia, Henoch-Schonlein purpura, Herpes gestationis, Hypogammaglobulinemia, Idiopathic thrombocytopenic purpura (ITP), IgA nephropathy, IgG4-related sclerosing disease, Immunoregulatory lipoproteins, Inclusion body myositis, Interstitial cystitis, Juvenile arthritis, Juvenile diabetes (Type 1 diabetes), Juvenile myositis, Kawasaki syndrome, Lambert-Eaton syndrome, Leukocytoclastic vasculitis, Lichen planus, Lichen sclerosus, Ligneous conjunctivitis, Linear IgA disease (LAD), Lupus (SLE), Lyme disease, chronic, Meniere's disease, Microscopic polyangiitis, Mixed connective tissue disease (MCTD), Mooren's ulcer, Mucha-Habermann disease, Multiple sclerosis, Myasthenia gravis, Myositis, Narcolepsy, Neuromyelitis optica (Devic's), Neutropenia, Ocular cicatricial pemphigoid, Optic neuritis, Palindromic rheumatism, PANDAS (Pediatric Autoimmune Neuropsychiatric Disorders Associated with *Streptococcus*), Paraneoplastic cerebellar degeneration, Paroxysmal nocturnal hemoglobinuria (PNH), Parry Romberg syndrome, Parsonnage-Turner syndrome, Pars planitis (peripheral uveitis), Pemphigus, Peripheral neuropathy, Perivenous encephalomyelitis, Pernicious anemia, POEMS syndrome, Polyarteritis nodosa, Type I, II, & III autoimmune polyglandular syndromes, Polymyalgia rheumatica, Polymyositis, Postmyocardial infarction syndrome, Postpericardiotomy syndrome, Progesterone dermatitis, Primary biliary cirrhosis, Primary sclerosing cholangitis, Psoriasis, Psoriatic arthritis, Idiopathic pulmonary fibrosis, Pyoderma gangrenosum, Pure red cell aplasia, Raynauds phenomenon, Reactive Arthritis, Reflex sympathetic dystrophy, Reiter's syndrome, Relapsing polychondritis, Restless legs syndrome, Retroperitoneal fibrosis, Rheumatic fever, Rheumatoid arthritis, Sarcoidosis, Schmidt syndrome, Scleritis, Scleroderma, Sjogren's syndrome, Sperm & testicular autoimmunity, Stiff person syndrome, Subacute bacterial endocarditis (SBE), Susac's syndrome, Sympathetic ophthalmia, Takayasu's arteritis, Temporal arteritis/Giant cell arteritis, Thrombocytopenic purpura (TTP), Tolosa-Hunt syndrome, Transverse myelitis, Type 1 diabetes, Ulcerative colitis, Undifferentiated connective tissue disease (UCTD), Uveitis, Vasculitis, Vesiculobullous dermatosis, Vitiligo, Wegener's granulomatosis (now termed Granulomatosis with Polyangiitis (GPA).

The invention provides a method of treating inflammation in a subject comprising administering to the subject a therapeutically effective amount of a compound of Formulas I, II, IIa, III, IIIa, IV, IVa, IVb, IVc, IVd, IVe, IVf, V, Va, Vb, Vc, VI, VIa, VIb, VII, VIIa, VIIb, VIIc, VIId, VIIe, VIIf, or VIIg. Inflammation includes, without limitation, asthma, cardiovascular inflammation, renal inflammation, arteriosclerosis and sepsis. Other inflammatory conditions that can be treated by methods of the invention include fibrotic conditions (including, e.g., idiopathic pulmonary fibrosis, renal fibrosis, kidney fibrosis, ocular fibrosis, cardiac fibrosis, NASH, scleroderma, systemic sclerosis, and cirrhosis).

In certain embodiments of the invention, glucose uptake inhibitors are used to treat parasitic or viral infections, including, but not limited to, malaria, leishmaniasis, African trypanosomiasis, tuberculosis, HIV, HCMV and herpes virus.

Many intracellular pathogens (including viruses, parasites, etc.) radically alter the metabolic program of the infected cell. For example, the malaria parasites of the genus *Plasmodium*, upon invading an erythrocyte, increase the cell's glucose consumption by up to 100-fold relative to a normal erythrocyte (Roth, E., Jr., *Plasmodium falciparum carbohydrate metabolism: a connection between host cell and parasite*. Blood Cells, 1990. 16(2-3): p. 453-60). While the plasmodial genome encodes a hexose transporter that is expressed to the parasite's plasma membrane and mediates glucose uptake into the parasite cell (Woodrow, C. J., J. I. Penny, and S. Krishna, *Intraerythrocytic Plasmodium falciparum expresses a high affinity facilitative hexose transporter*. J Biol Chem, 1999. 274(11): p. 7272-7), this glucose must first enter the host cell cytoplasm in a transport process that depends primarily on the host erythrocyte glucose transporter GLUT-1 (Kirk, K., H. A. Homer, and J. Kirk, *Glucose uptake in Plasmodium falciparum-infected erythrocytes is an equilibrative not an active process*. Mol Biochem Parasitol, 1996. 82(2): p. 195-205). Since glucose starvation rapidly induces the death of intraerythrocytic *Plasmodium* parasites (Babbitt, S. E., et al., *Plasmodium falciparum responds to amino acid starvation by entering into a hibernatory state*. Proc Natl Acad Sci USA, 2012. 109(47): p. E3278-87), and since inhibitors of the parasite hexose transporter inhibit parasite growth and viability in vitro and in vivo (Joet, T., et al., *Validation of the hexose transporter of Plasmodium falciparum as a novel drug target*. Proc Natl Acad Sci USA, 2003. 100(13): p. 7476-9), we investigated the use of inhibitors of GLUT-1-mediated glucose uptake against the most lethal of the human malaria parasites, *Plasmodium falciparum*.

Inhibitors of GLUT-1-mediated glucose uptake are extremely potent against cultured *P. falciparum*, as they rapidly induce a loss of viability of the parasite cell. This is consistent with the absolute dependence of *Plasmodium* parasites on glucose import, first into the host cell cytosol (through GLUT-1) and then into the parasite cell (through parasite hexose transporters). These data also suggest that inhibitors of other host transporters essential for glucose metabolism will provide a beneficial therapeutic effect in malaria patients.

Figure 2:
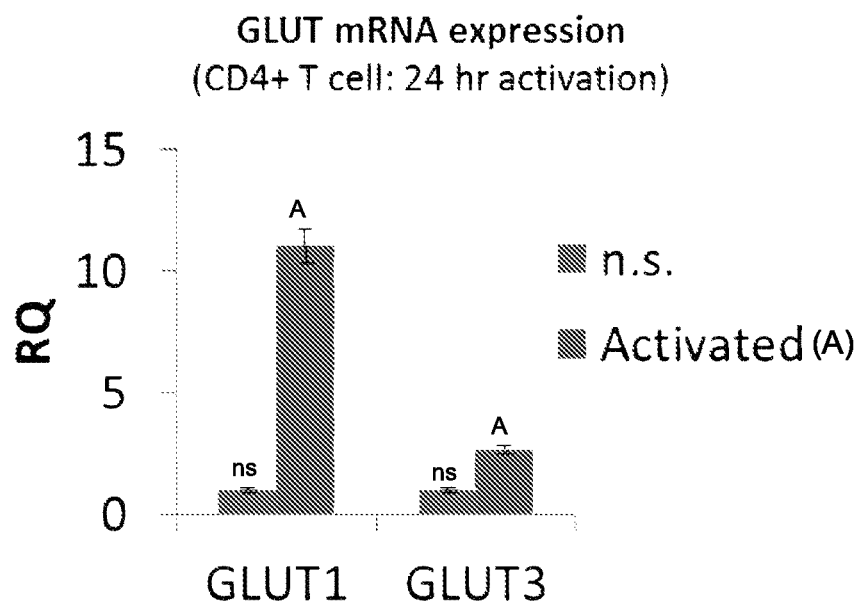
FIG. 2 shows that T cell activation induces both GLUT1 and GLUT3.
Figure 2:
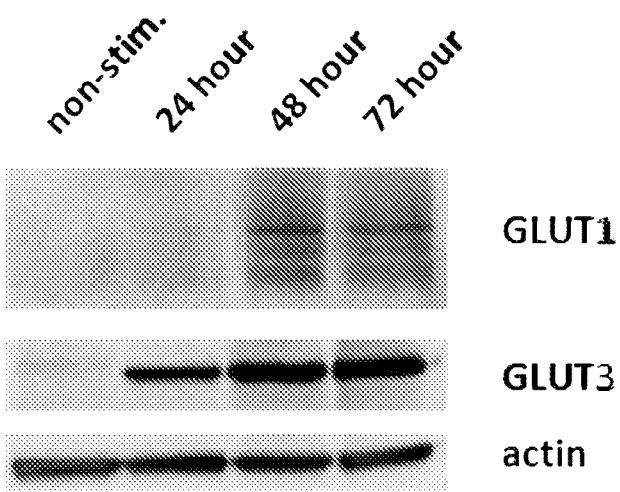
Figure 3:
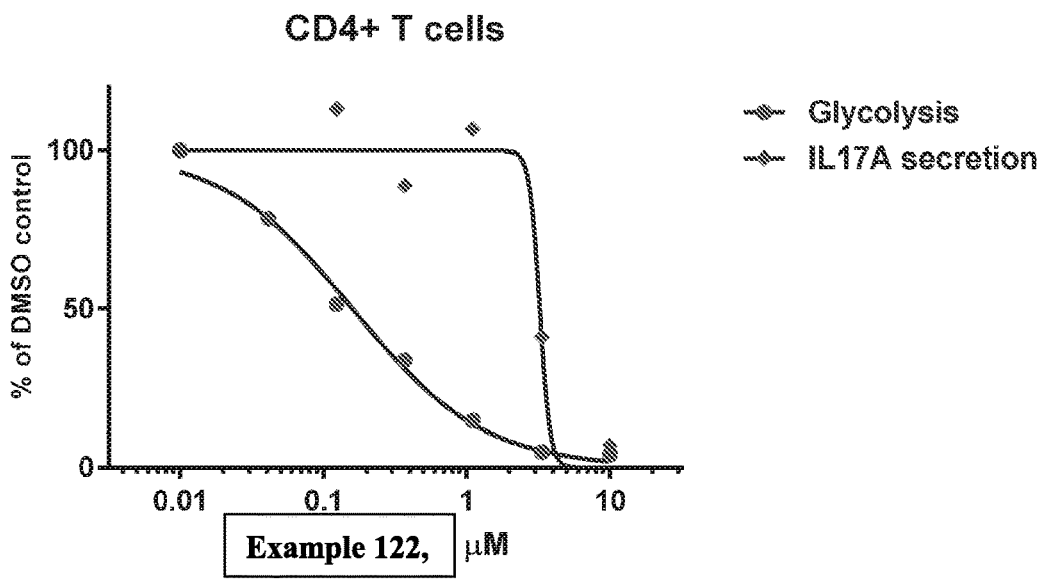
FIG. 3 shows that the metabolism and function of activated T cells are suppressed by compounds disclosed herein.
Figure 3:
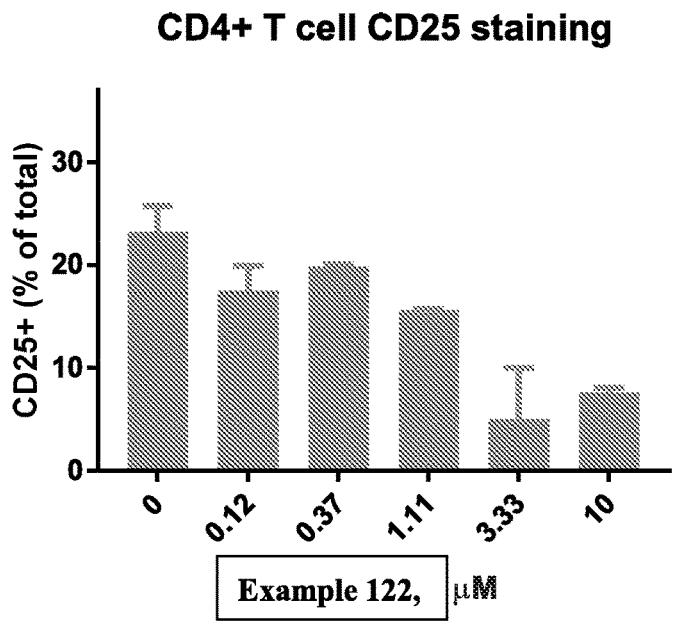
Figure 4:
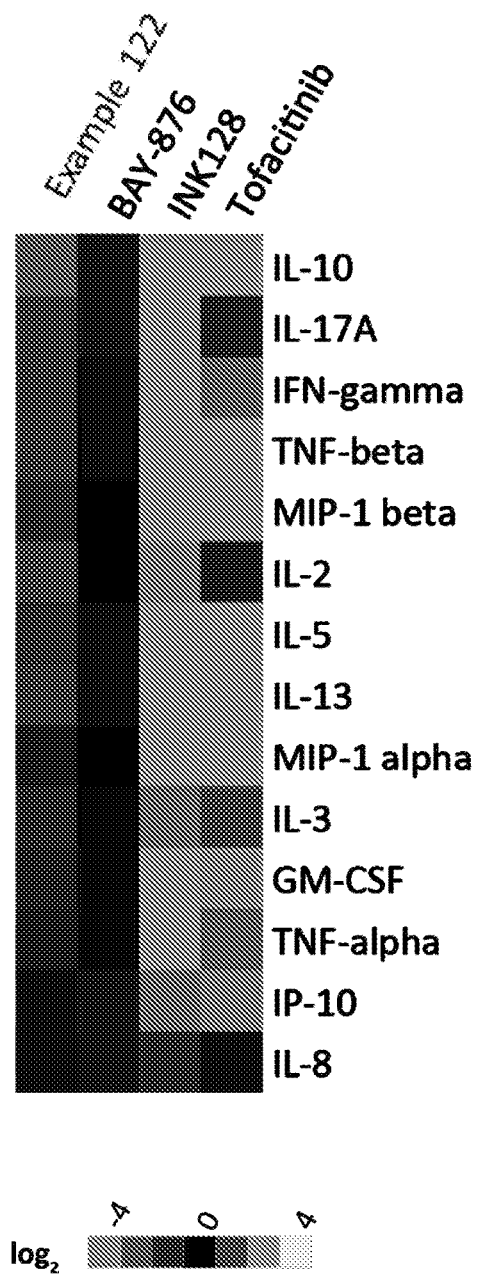
FIG. 4 shows that cytokine secretion of activated T cells is broadly suppressed by compounds disclosed herein. Human CD4 positive T cells were activated for 72 hours in the presence of anti-CD3 and anti-CD28 antibodies and 1 μM of either Ex. 122, the GLUT1-specific inhibitor Bay876, the mTOR inhibitor INK128 or the JAK inhibitor tofacitinib. Secreted cytokine levels in the culture supernatant were quantified by MAGPIX xMAP assay using the Human Cytokine Premixed 29 Plex Kit (EMD Millipore) and plotted as a heat map showing $log_2$ fold changes relative to vehicle-treated control cultures. The compounds of this invention inhibit the secretion of the majority of cytokines assayed, whereas a GLUT1-specific inhibitor does not.

As previously discussed, malaria parasites rely on glucose imported by host transporters in the erythrocyte membrane (i.e. GLUT-1). At low nanomolar concentrations, the glucose uptake inhibitors display striking inhibition of both parasite proliferation and lactate excretion, a downstream maker of glucose consumption/glycolysis. Moreover, microscopic examination of the parasites reveals that treated parasites condense and shrink, characteristics of parasite cell death, within 6 hours of inhibitor treatment (FIG. 2) and that cellular ATP levels are depleted within 15 minutes.

Human immunodeficiency virus (HIV): AIDS, one of the most important diseases in terms of global health burden, is caused by HIV infection of the host immune cells. Several reports indicate that a successful infection and replication cycle depends on GLUT-1-mediated glucose import (Loisel-Meyer, S., et al., *Glut1-mediated glucose transport regulates HIV infection*. Proc Natl Acad Sci USA, 2012. 109(7): p. 2549-54), and GLUT-1 levels serve as a disease marker in chronically HIV-infected patients (Palmer, C. S., et al., *Increased glucose metabolic activity is associated with CD4+ T-cell activation and depletion during chronic HIV infection*. AIDS, 2014. 28(3): p. 297-309). GLUT-1 inhibitors may suppress viral replication in a manner that does not elicit the drug resistance that otherwise necessitates combination therapy with multiple direct-acting antivirals.

*Mycobacterium tuberculosis*: Tuberculosis is caused by infection with a *Mycobacterium* that replicates within host macrophages. *M. tuberculosis* infection in culture induces a significant increase in GLUT-1-mediated glucose uptake, and treatment with glycolysis inhibitors such as 3-bromopyruvate induce death of both the host cell and the infecting bacterium (Mehrotra, P., et al., *Pathogenicity of Mycobacterium tuberculosis is expressed by regulating metabolic thresholds of the host macrophage.* PLoS Pathog, 2014. 10(7): p. e1004265). This strongly suggests that GLUT-1 inhibitors would exert a similar suppression of infected macrophage viability.

*Leishmania donovani*: Infection with parasites of the genus *Leishmania* causes leishmaniasis, the most severe form of which is caused by the species *Leishmania donovani*. Like *M. tuberculosis, L. donovani* infects host macrophages, and induces an increase in the levels of the GLUT-1 transporter Singh, A. K., et al., *Intracellular pathogen Leishmania donovani activates hypoxia inducible factor-1 by dual mechanism for survival advantage within macrophage.* PLoS One, 2012. 7(6): p. e38489. GLUT-1 inhibition may provide a therapeutic benefit against this protozoan parasite as well.

In one aspect, the present invention provides pharmaceutically acceptable compositions which comprise a therapeutically-effective amount of one or more of the compounds of Formulas I, II, IIa, III, IIIa, IV, IVa, IVb, IVc, IVd, IVe, IVf, V, Va, Vb, Vc, VI, VIa, VIb, VII, VIIa, VIIb, VIIc, VIId, VIIe, VIIf, or VIIg, formulated together with one or more pharmaceutically excipients. As described below, the pharmaceutical compositions of the present invention may be specially formulated for administration in solid or liquid form, including those adapted for the following: (1) oral administration, for example, drenches (aqueous or non-aqueous solutions or suspensions), tablets, e.g., those targeted for buccal, sublingual, and systemic absorption, boluses, powders, granules, pastes for application to the tongue; (2) parenteral administration, for example, by subcutaneous, intramuscular, intravenous or epidural injection as, for example, a sterile solution or suspension, or sustained-release formulation; (3) topical application, for example, as a cream, ointment, or a controlled-release patch or spray applied to the skin; (4) intravaginally or intrarectally, for example, as a pessary, cream or foam; (5) sublingually; (6) ocularly; (7) transdermally; or (8) nasally.

The phrase "pharmaceutically acceptable" is employed herein to refer to those compounds, materials, compositions, and/or dosage forms which are, within the scope of sound medical judgment, suitable for use in contact with the tissues of human beings and animals with toxicity, irritation, allergic response, or other problems or complications, commensurate with a reasonable benefit/risk ratio.

The phrase "pharmaceutically-acceptable carrier" as used herein means a pharmaceutically-acceptable material, composition or vehicle, such as a liquid or solid filler, diluent, excipient, manufacturing aid (e.g., lubricant, talc magnesium, calcium or zinc stearate, or steric acid), or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; and (22) other non-toxic compatible substances employed in pharmaceutical formulations.

As set out above, certain embodiments of the present compounds may contain a basic functional group, such as amino or alkylamino, and are, thus, capable of forming pharmaceutically-acceptable salts with pharmaceutically-acceptable acids. The term "pharmaceutically-acceptable salts" in this respect, refers to the relatively non-toxic, inorganic and organic acid addition salts of compounds of the present invention. These salts can be prepared in situ in the administration vehicle or the dosage form manufacturing process, or by separately reacting a purified compound of the invention in its free base form with a suitable organic or inorganic acid, and isolating the salt thus formed during subsequent purification. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like (see, e.g., Berge et al. (1977) "Pharmaceutical Salts", *J. Pharm. Sci.* 66:1-19).

The pharmaceutically acceptable salts of the subject compounds include the conventional nontoxic salts or quaternary ammonium salts of the compounds, e.g., from non-toxic organic or inorganic acids. For example, such conventional nontoxic salts include those derived from inorganic acids such as hydrochloride, hydrobromic, sulfuric, sulfamic, phosphoric, nitric, and the like; and the salts prepared from organic acids such as acetic, propionic, succinic, glycolic, stearic, lactic, malic, tartaric, citric, ascorbic, palmitic, maleic, hydroxymaleic, phenylacetic, glutamic, benzoic, salicyclic, sulfanilic, 2-acetoxybenzoic, fumaric, toluenesulfonic, methanesulfonic, ethane disulfonic, oxalic, isothionic, and the like.

In other cases, the compounds of the present invention may contain one or more acidic functional groups and, thus, are capable of forming pharmaceutically-acceptable salts with pharmaceutically-acceptable bases. The term "pharmaceutically-acceptable salts" in these instances refers to the relatively non-toxic, inorganic and organic base addition salts of compounds of the present invention. These salts can likewise be prepared in situ in the administration vehicle or the dosage form manufacturing process, or by separately reacting the purified compound in its free acid form with a suitable base, such as the hydroxide, carbonate or bicarbonate of a pharmaceutically-acceptable metal cation, with ammonia, or with a pharmaceutically-acceptable organic primary, secondary or tertiary amine. Representative alkali or alkaline earth salts include the lithium, sodium, potassium, calcium, magnesium, and aluminum salts and the like. Representative organic amines useful for the formation of base addition salts include ethylamine, diethylamine, ethylenediamine, ethanolamine, diethanolamine, piperazine and the like (see, e.g., Berge et al., supra).

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Formulations of the present invention include those suitable for oral, nasal, topical (including buccal and sublingual), rectal, vaginal and/or parenteral administration. The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient which can be combined with a carrier material to produce a single dosage form will generally be that amount of the compound which produces a therapeutic effect. Generally, out of one hundred percent, this amount will range from about 0.1 percent to about ninety-nine percent of active ingredient, preferably from about 5 percent to about 70 percent, most preferably from about 10 percent to about 30 percent.

In certain embodiments, a formulation of the present invention comprises an excipient selected from the group consisting of cyclodextrins, celluloses, liposomes, micelle forming agents, e.g., bile acids, and polymeric carriers, e.g., polyesters and polyanhydrides; and a compound of the present invention. In certain embodiments, an aforementioned formulation renders orally bioavailable a compound of the present invention.

Methods of preparing these formulations or compositions include the step of bringing into association a compound of the present invention with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules, cachets, pills, tablets, lozenges, powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. A compound of the present invention may also be administered as a bolus, electuary or paste.

In solid dosage forms of the invention for oral administration (capsules, tablets, pills, dragees, powders, granules, trouches and the like), the active ingredient is mixed with one or more pharmaceutically-acceptable excipients including a pharmaceutically-acceptable carrier, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds and surfactants, such as poloxamer and sodium lauryl sulfate; (7) wetting agents, such as, for example, cetyl alcohol, glycerol monostearate, and non-ionic surfactants; (8) absorbents, such as kaolin and bentonite clay; (9) lubricants, such as talc, calcium stearate, magnesium stearate, solid polyethylene glycols, sodium lauryl sulfate, zinc stearate, sodium stearate, stearic acid, and mixtures thereof; (10) coloring agents; and (11) controlled release agents such as crospovidone or ethyl cellulose. In the case of capsules, tablets and pills, the pharmaceutical compositions may also comprise buffering agents. Solid compositions of a similar type may also be employed as fillers in soft and hard-shelled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be formulated for rapid release, e.g., freeze-dried. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above-described excipients.

Liquid dosage forms for oral administration of the compounds of the invention include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions of the invention for rectal or vaginal administration may be presented as a suppository, which may be prepared by mixing one or more compounds of the invention with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Formulations of the present invention which are suitable for vaginal administration also include pessaries, tampons, creams, gels, pastes, foams or spray formulations containing such carriers as are known in the art to be appropriate.

Dosage forms for the topical or transdermal administration of a compound of this invention include powders, sprays, ointments, pastes, creams, lotions, gels, solutions, patches and inhalants. The active compound may be mixed under sterile conditions with a pharmaceutically-acceptable carrier, and with any preservatives, buffers, or propellants which may be required.

The ointments, pastes, creams and gels may contain, in addition to an active compound of this invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a compound of this invention, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present invention to the body. Such dosage forms can be made by dissolving or dispersing the compound in the proper medium. Absorption enhancers can also be used to increase the flux of the compound across the skin. The rate of such flux can be controlled by either providing a rate controlling membrane or dispersing the compound in a polymer matrix or gel.

Ophthalmic formulations, eye ointments, powders, solutions and the like, are also contemplated as being within the scope of this invention.

Pharmaceutical compositions of this invention suitable for parenteral administration comprise one or more compounds of the invention in combination with one or more pharmaceutically-acceptable sterile isotonic aqueous or nonaqueous solutions, dispersions, suspensions or emulsions, or sterile powders which may be reconstituted into sterile injectable solutions or dispersions just prior to use, which may contain sugars, alcohols, antioxidants, buffers, bacteriostats, solutes which render the formulation isotonic with the blood of the intended recipient or suspending or thickening agents.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms upon the subject compounds may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally-administered drug form is accomplished by dissolving or suspending the drug in an oil vehicle.

Injectable depot forms are made by forming microencapsule matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissue.

When the compounds of the present invention are administered as pharmaceuticals, to humans and animals, they can be given per se or as a pharmaceutical composition containing, for example, 0.1 to 99% (more preferably, 10 to 30%) of active ingredient in combination with a pharmaceutically acceptable carrier.

The preparations of the present invention may be given orally, parenterally, topically, or rectally. They are of course given in forms suitable for each administration route. For example, they are administered in tablets or capsule form, by injection, inhalation, eye lotion, ointment, suppository, etc. administration by injection, infusion or inhalation; topical by lotion or ointment; and rectal by suppositories. Oral administrations are preferred.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticulare, subcapsular, subarachnoid, intraspinal and intrasternal injection and infusion.

The phrases "systemic administration," "administered systemically," "peripheral administration" and "administered peripherally" as used herein mean the administration of a compound, drug or other material other than directly into the central nervous system, such that it enters the patient's system and, thus, is subject to metabolism and other like processes, for example, subcutaneous administration.

These compounds may be administered to humans and other animals for therapy by any suitable route of administration, including orally, nasally, as by, for example, a spray, rectally, intravaginally, parenterally, intracisternally and topically, as by powders, ointments or drops, including buccally and sublingually.

Regardless of the route of administration selected, the compounds of the present invention, which may be used in a suitable hydrated form, and/or the pharmaceutical compositions of the present invention, are formulated into pharmaceutically-acceptable dosage forms by conventional methods known to those of skill in the art.

Actual dosage levels of the active ingredients in the pharmaceutical compositions of this invention may be varied so as to obtain an amount of the active ingredient which is effective to achieve the desired therapeutic response for a particular patient, composition, and mode of administration, without being toxic to the patient.

The selected dosage level will depend upon a variety of factors including the activity of the particular compound of the present invention employed, or the ester, salt or amide thereof, the route of administration, the time of administration, the rate of excretion or metabolism of the particular compound being employed, the rate and extent of absorption, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In general, a suitable daily dose of a compound of the invention will be that amount of the compound which is the lowest dose effective to produce a therapeutic effect. Such an effective dose will generally depend upon the factors described above. Generally, oral, intravenous, intracerebroventricular and subcutaneous doses of the compounds of this invention for a patient, when used for the indicated analgesic effects, will range from about 0.0001 to about 100 mg per kilogram of body weight per day.

In certain embodiments, a dose of a compound or a composition is administered to a subject every day, every other day, every couple of days, every third day, once a week, twice a week, three times a week, or once every two weeks. If desired, the effective daily dose of the active compound may be administered as two, three, four, five, six or more sub-doses administered separately at appropriate intervals throughout the day, optionally, in unit dosage forms. In some embodiments, a dose(s) of a compound or a composition is administered for 2 days, 3 days, 5 days, 7 days, 14 days, or 21 days. In certain embodiments, a dose of a compound or a composition is administered for 1 month, 1.5 months, 2 months, 2.5 months, 3 months, 4 months, 5 months, 6 months or more.

The above-described administration schedules are provided for illustrative purposes only and should not be considered limiting. A person of ordinary skill in the art will readily understand that all doses are within the scope of the invention.

While it is possible for a compound of the present invention to be administered alone, it is preferable to administer the compound as a pharmaceutical formulation (composition).

The patient receiving this treatment is any animal in need, including primates, in particular humans, and other mammals such as equines, cattle, swine and sheep; and poultry and pets in general.

The compounds for use in the methods of the invention can be administered as such or in admixtures with pharmaceutically acceptable carriers and can also be administered in conjunction with antimicrobial agents such as penicillins, cephalosporins, aminoglycosides and glycopeptides. Conjunctive therapy, thus includes sequential, simultaneous and separate administration of the active compound in a way that the therapeutical effects of the first administered one is not entirely disappeared when the subsequent is administered.

The addition of the active compound of the invention to animal feed is preferably accomplished by preparing an appropriate feed premix containing the active compound in an effective amount and incorporating the premix into the complete ration.

Alternatively, an intermediate concentrate or feed supplement containing the active ingredient can be blended into the feed. The way in which such feed premixes and complete rations can be prepared and administered are described in reference books (such as "Applied Animal Nutrition", W.H. Freedman and CO., San Francisco, U.S.A., 1969 or "Livestock Feeds and Feeding" O and B books, Corvallis, Ore., U.S.A., 1977).

Microemulsification technology may be employed to improve bioavailability of lipophilic (water insoluble) pharmaceutical agents. Examples include Trimetrine (Dordunoo, S. K., et al., Drug Development and Industrial Pharmacy, 17(12), 1685-1713, 1991) and REV 5901 (Sheen, P. C., et al., J Pharm Sci 80(7), 712-714, 1991). Among other things, microemulsification provides enhanced bioavailability by preferentially directing absorption to the lymphatic system instead of the circulatory system, which thereby bypasses the liver, and prevents destruction of the compounds in the hepatobiliary circulation.

In one aspect of invention, the formulations contain micelles formed from a compound of the present invention and at least one amphiphilic carrier, in which the micelles have an average diameter of less than about 100 nm. More preferred embodiments provide micelles having an average diameter less than about 50 nm, and even more preferred embodiments provide micelles having an average diameter less than about 30 nm, or even less than about 20 nm.

While all suitable amphiphilic carriers are contemplated, the presently preferred carriers are generally those that have Generally-Recognized-as-Safe (GRAS) status, and that can both solubilize the compound of the present invention and microemulsify it at a later stage when the solution comes into a contact with a complex water phase (such as one found in human gastro-intestinal tract). Usually, amphiphilic ingredients that satisfy these requirements have HLB (hydrophilic to lipophilic balance) values of 2-20, and their structures contain straight chain aliphatic radicals in the range of C-6 to C-20. Examples are polyethylene-glycolized fatty glycerides and polyethylene glycols.

Particularly preferred amphiphilic carriers are saturated and monounsaturated polyethyleneglycolyzed fatty acid glycerides, such as those obtained from fully or partially hydrogenated various vegetable oils. Such oils may advantageously consist of tri-, di- and mono-fatty acid glycerides and di- and mono-polyethyleneglycol esters of the corresponding fatty acids, with a particularly preferred fatty acid composition including capric acid 4-10, capric acid 3-9, lauric acid 40-50, myristic acid 14-24, palmitic acid 4-14 and stearic acid 5-15%. Another useful class of amphiphilic carriers includes partially esterified sorbitan and/or sorbitol, with saturated or mono-unsaturated fatty acids (SPAN-series) or corresponding ethoxylated analogs (TWEEN-series).

Commercially available amphiphilic carriers are particularly contemplated, including Gelucire-series, Labrafil, Labrasol, or Lauroglycol (all manufactured and distributed by Gattefosse Corporation, Saint Priest, France), PEG-mono-oleate, PEG-di-oleate, PEG-mono-laurate and di-laurate, Lecithin, Polysorbate 80, etc (produced and distributed by a number of companies in USA and worldwide).

Hydrophilic polymers suitable for use in the present invention are those which are readily water-soluble, can be covalently attached to a vesicle-forming lipid, and which are tolerated in vivo without toxic effects (i.e., are biocompatible). Suitable polymers include polyethylene glycol (PEG), polylactic (also termed polylactide), polyglycolic acid (also termed polyglycolide), a polylactic-polyglycolic acid copolymer, and polyvinyl alcohol. Preferred polymers are those having a molecular weight of from about 100 or 120 daltons up to about 5,000 or 10,000 daltons, and more preferably from about 300 daltons to about 5,000 daltons. In a particularly preferred embodiment, the polymer is polyethyleneglycol having a molecular weight of from about 100 to about 5,000 daltons, and more preferably having a molecular weight of from about 300 to about 5,000 daltons. In a particularly preferred embodiment, the polymer is polyethyleneglycol of 750 daltons (PEG(750)). The polymers used in the present invention have a significantly smaller molecular weight, approximately 100 daltons, compared to the large MW of 5000 daltons or greater that used in standard pegylation techniques. Polymers may also be defined by the number of monomers therein; a preferred embodiment of the present invention utilizes polymers of at least about three monomers, such PEG polymers consisting of three monomers (approximately 150 daltons).

Other hydrophilic polymers which may be suitable for use in the present invention include polyvinylpyrrolidone, polymethoxazoline, polyethyloxazoline, polyhydroxypropyl methacrylamide, polymethacrylamide, polydimethylacrylamide, and derivatized celluloses such as hydroxymethylcellulose or hydroxyethylcellulose.

In certain embodiments, a formulation of the present invention comprises a biocompatible polymer selected from the group consisting of polyamides, polycarbonates, polyalkylenes, polymers of acrylic and methacrylic esters, polyvinyl polymers, polyglycolides, polysiloxanes, polyurethanes and co-polymers thereof, celluloses, polypropylene, polyethylenes, polystyrene, polymers of lactic acid and glycolic acid, polyanhydrides, poly(ortho)esters, poly(butic acid), poly(valeric acid), poly(lactide-co-caprolactone), polysaccharides, proteins, polyhyaluronic acids, polycyanoacrylates, and blends, mixtures, or copolymers thereof.

The release characteristics of a formulation of the present invention depend on the encapsulating material, the concentration of encapsulated drug, and the presence of release modifiers. For example, release can be manipulated to be pH dependent, for example, using a pH sensitive coating that releases only at a low pH, as in the stomach, or a higher pH, as in the intestine. An enteric coating can be used to prevent release from occurring until after passage through the stomach. Multiple coatings or mixtures of cyanamide encapsulated in different materials can be used to obtain an initial release in the stomach, followed by later release in the intestine. Release can also be manipulated by inclusion of salts or pore forming agents, which can increase water uptake or release of drug by diffusion from the capsule. Excipients which modify the solubility of the drug can also be used to control the release rate. Agents which enhance degradation of the matrix or release from the matrix can also be incorporated. They can be added to the drug, added as a separate phase (i.e., as particulates), or can be co-dissolved in the polymer phase depending on the compound. In all cases the amount should be between 0.1 and thirty percent (w/w polymer). Types of degradation enhancers include inorganic salts such as ammonium sulfate and ammonium chloride, organic acids such as citric acid, benzoic acid, and ascorbic acid, inorganic bases such as sodium carbonate, potassium carbonate, calcium carbonate, zinc carbonate, and zinc hydroxide, and organic bases such as protamine sulfate, spermine, choline, ethanolamine, diethanolamine, and triethanolamine and surfactants such as Tween® and Pluronic®. Pore forming agents which add microstructure to the matrices (i.e., water soluble compounds such as inorganic salts and sugars) are added as particulates. The range should be between one and thirty percent (w/w polymer).

Uptake can also be manipulated by altering residence time of the particles in the gut. This can be achieved, for example, by coating the particle with, or selecting as the encapsulating material, a mucosal adhesive polymer. Examples include most polymers with free carboxyl groups, such as chitosan, celluloses, and especially polyacrylates (as used herein, polyacrylates refers to polymers including acrylate groups and modified acrylate groups such as cyanoacrylates and methacrylates).

The above-described administration schedules are provided for illustrative purposes only and should not be considered limiting. A person of ordinary skill in the art will readily understand that all doses are within the scope of the invention.

Compounds of the invention can be advantageously administered with second agents to patients in need thereof. When GLUT inhibitor is administered with a second agent, the GLUT inhibitor and the second agent can be administered sequentially or concomitantly. Sequentially means that one agent is administered for a time followed by administration of the second agent, which may be followed by administration of the first agent. When agents are administered sequentially, the level or one agent may not be maintained at a therapeutically effective level when the second agent is administered, and vice versa. Concomitantly means that the first and second agent are administered according to a schedule that maintains both agents at a substantially therapeutically effective level, even though the agents are not administered simultaneously. Each agent can be administered in single or multiple doses, and the doses can be administered on any schedule, including, without limitation, twice daily, daily, weekly, every two weeks, and monthly.

The invention also includes adjunctive administration. Adjunctive administration means that a second agent is administered to a patient in addition to a first agent that is already being administered to treat a disease or disease symptom. In some embodiments, adjunctive administration involves administering a second agent to a patient in which administration of the first agent did not sufficiently treat a disease or disease symptom. In other embodiments, adjunctive administration involves administration of the second agent to a patient whose disease has been effectively treated by administration of the first agent, with the expectation that the adjunctive treatment improves the outcome of the treatment. In some embodiments, the effect of administering the first and second agents is synergistic. In some embodiments, administration of the first and second agents prevents or lengthens the time until relapse, compared to administration of either of the agents alone. In some embodiments, administration of the first and second agents allows for reduced dosage and/or frequency of administration of the first and second agent.

Anti-inflammatories and immunosuppressants that can be administer in combination with the compounds of the present invention include steroid drugs such as glucocorticoids (e.g., dexamethasone), FK506 (tacrolimus), ciclosporin, fingolimod, interferon, such as IFNβ or IFNγ, a tumor necrosis factor-alpha (TNF-α) binding protein such as infliximab (Remicade), etanercept (Enbrel), or adalimumab (Humira), mycophenolic acid, MMF, Methotrexate, NSAID, Statins, Sirolimus/temsirolimus/everolimus, abatacept (Orencia), anakinra (Kineret), certolizumab (Cimzia). golimumab (Simponi), ixekizumab (Taltz), natalizumab (Tysabri), rituximab (Rituxan), secukinumab (Cosentyx), tocilizumab (Actemra), ustekinumab (Stelara), vedolizumab (Entyvio), basiliximab (Simulect), daclizumab (Zinbryta), muromonab (Orthoclone OKT3), Jakafi (Ruxolitinib), Xeljanz (Tofacitnib), and Otezla (Apremilast).

General Synthesis

Compounds of formula G may be prepared by reacting a compound of formula A where W is an aryl or a heteroaryl and a compound of formula B where X and Y are independent halogens in the presence of a base such as potassium carbonate to give the compound of formula C; Reacting said formula C compound with a compound of formula of D to give the compound of formula E; Reacting of said formula E compound and bis(pinacolato)diboron F in the presence a catalyst such as Pd(PPh$_3$)$_4$. The reaction sequence is shown in the scheme 1.

Scheme 1

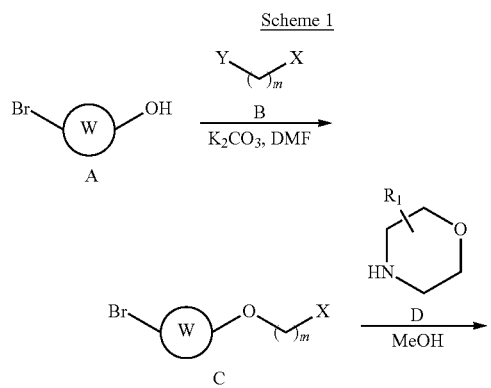

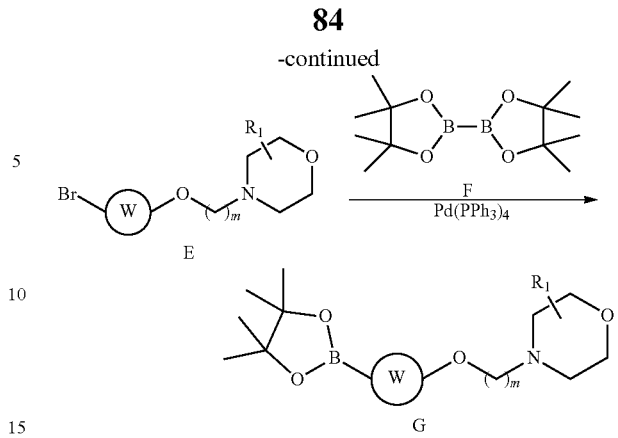

Compounds of formula K may be prepared by reacting a compound of formula H where X and Y are independent halogens and an amine in the presence of a base such as triethylamine to give the compound of formula I; Reacting said formula I compound with a compound of formula of A in the presence of a base such as potassium carbonate to give the compound of formula J; Reacting of said formula J compound and bis(pinacolato)diboron F in the presence a catalyst such as Pd(PPh$_3$)$_4$. The reaction sequence is shown in the scheme 2.

Scheme 2

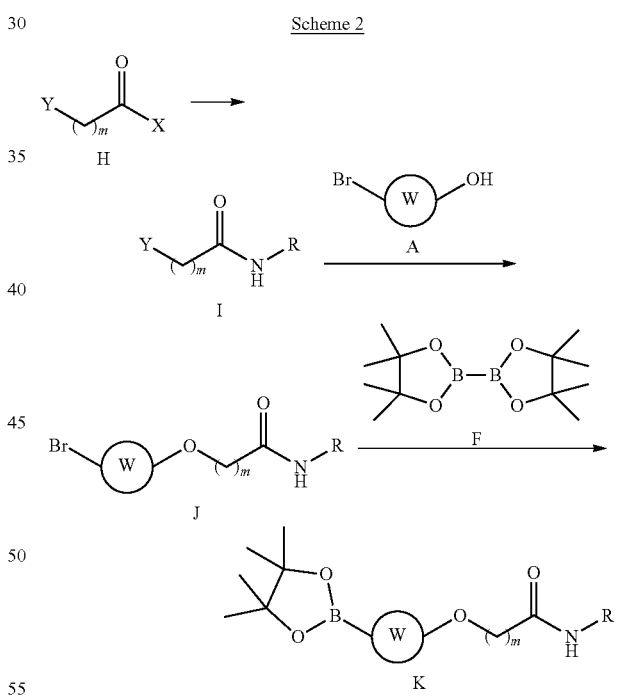

Compounds of formula O may be prepared by reacting a compound of formula L where X is a halogen such as Cl or Br and an aliphatic amine or an aromatic or heteroaryl amine of formula M to give the compound of formula N; Reacting said formula N compound with a compound of formula of K in the presence of a catalyst such as Pd(PPh$_3$)$_4$. Compounds of formula P may be prepared by reacting of said formula N compound and a compound of formula G in the presence a catalyst such as Pd(PPh$_3$)$_4$. The reaction sequence is shown in the reaction 3.

Scheme 3
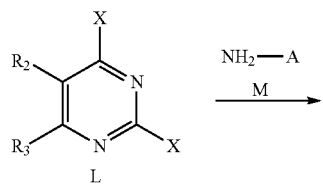
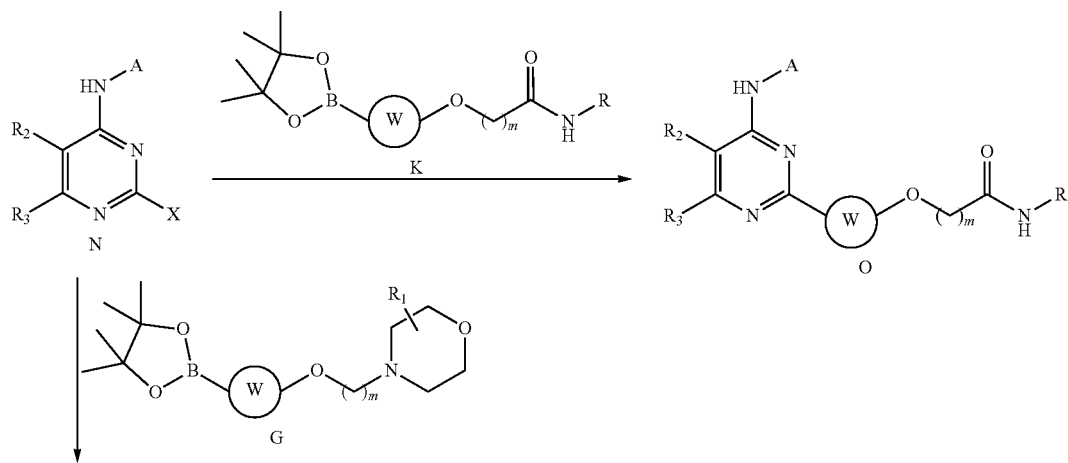
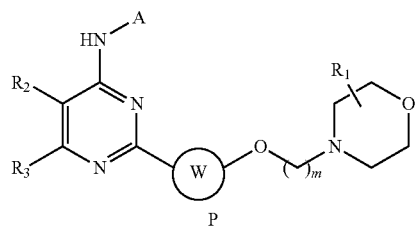
Compounds of formula S, T, W, X may be prepared in a similar fashion as that for compounds of formula O and P (Scheme 4 and 5).
Scheme 4
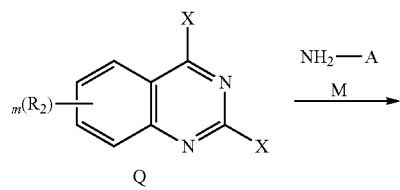

87 88
-continued
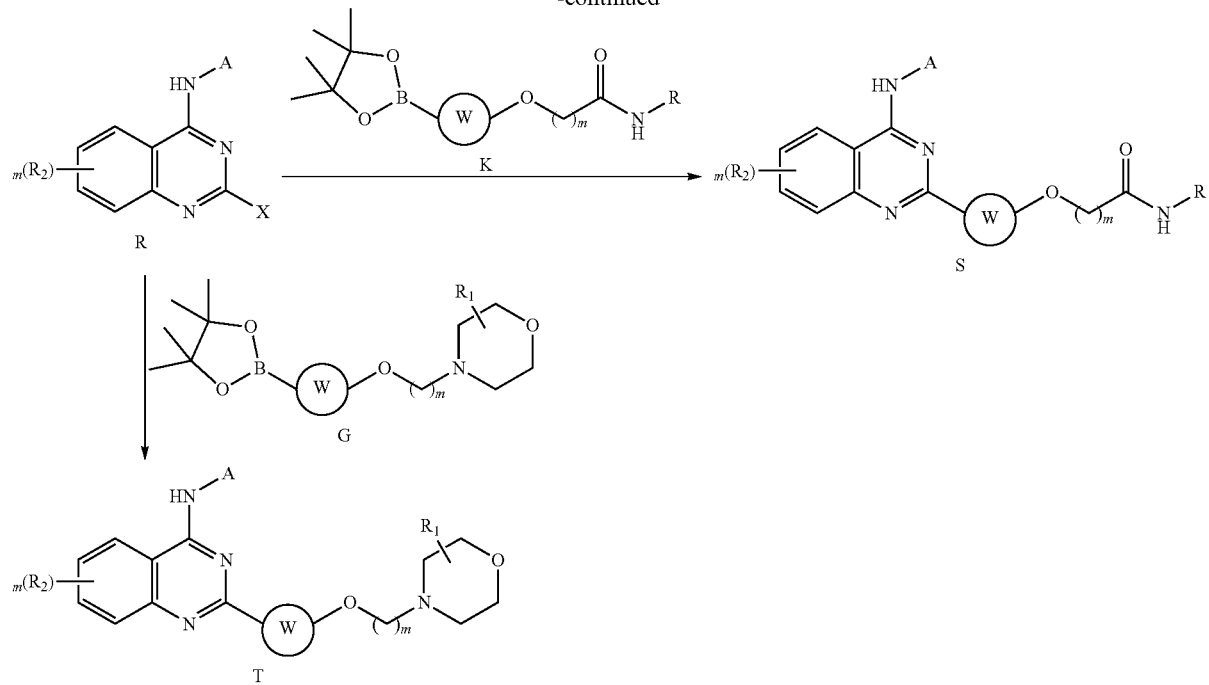
Scheme 5
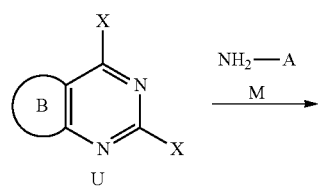
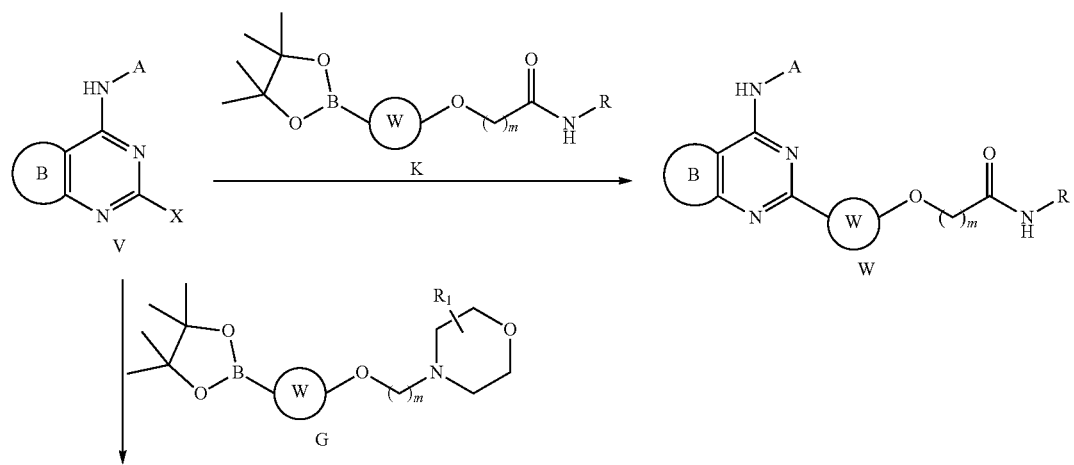

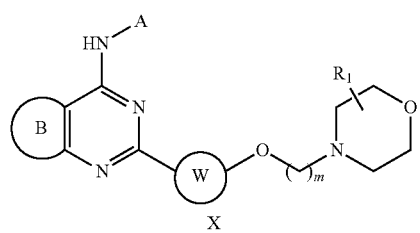

Alternatively, formula S compounds may also be prepared according a synthetic sequence depicted in Scheme 6. In this sequence, formula S compounds may be prepared by reacting a compound of formula Y with a compound of formula I to provide a compound of formula Z; hydrolysis of formula Z compound to provide formula AA compound; Reaction of the said formula AA compound with formula AB compound to provide formula AC compound; Cyclization of said formula AC compound followed by reacting with POCl$_3$ or SOCl$_2$ to provide formula AE compound; Reacting of said formula AE compound with a variety of amines A-NH$_2$.

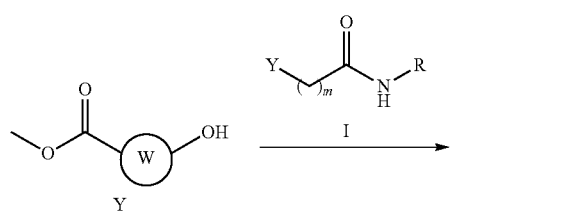

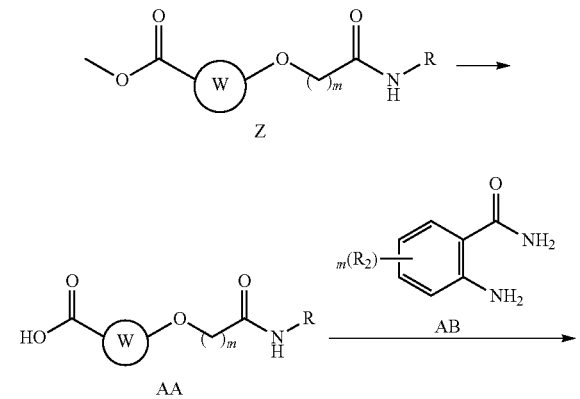

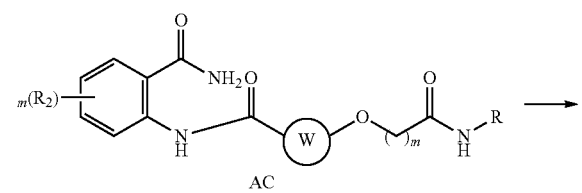

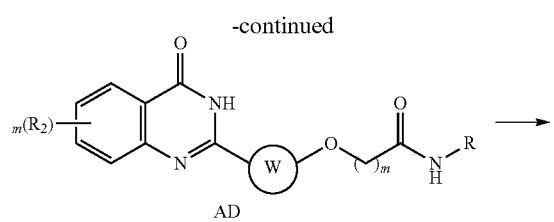

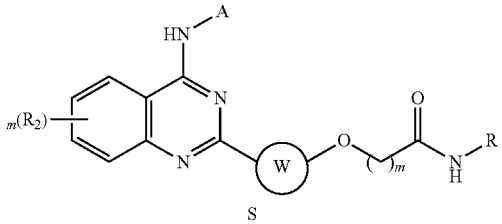

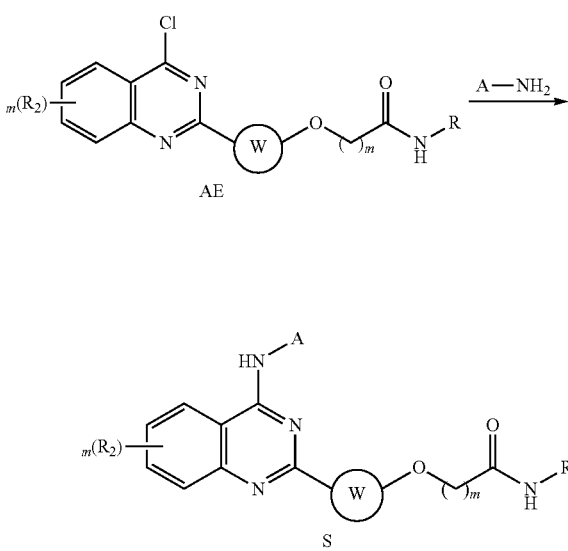

Formula AM compounds may be prepared according to a synthetic sequence depicted in Scheme 7. In this sequence, formula AM compounds may be prepared by reacting a compound of formula AF with a compound of formula R$_3$—X to provide a compound of formula AG; Hydrolysis of formula AG compound to provide formula AH compound; Reaction of the said formula AH compound with a suitable rhodium catalyst to provide formula AI compound; Cyclization of said formula AI compound by reacting with SOCl$_2$ to provide formula AJ compound; Reacting of said formula AJ compound with a compound of formula AK to provide a compound of formula AL which can then be reacted with a variety of amines A-NH$_2$, after suitable activation.

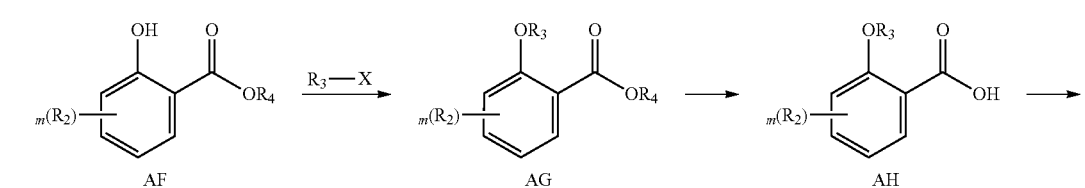

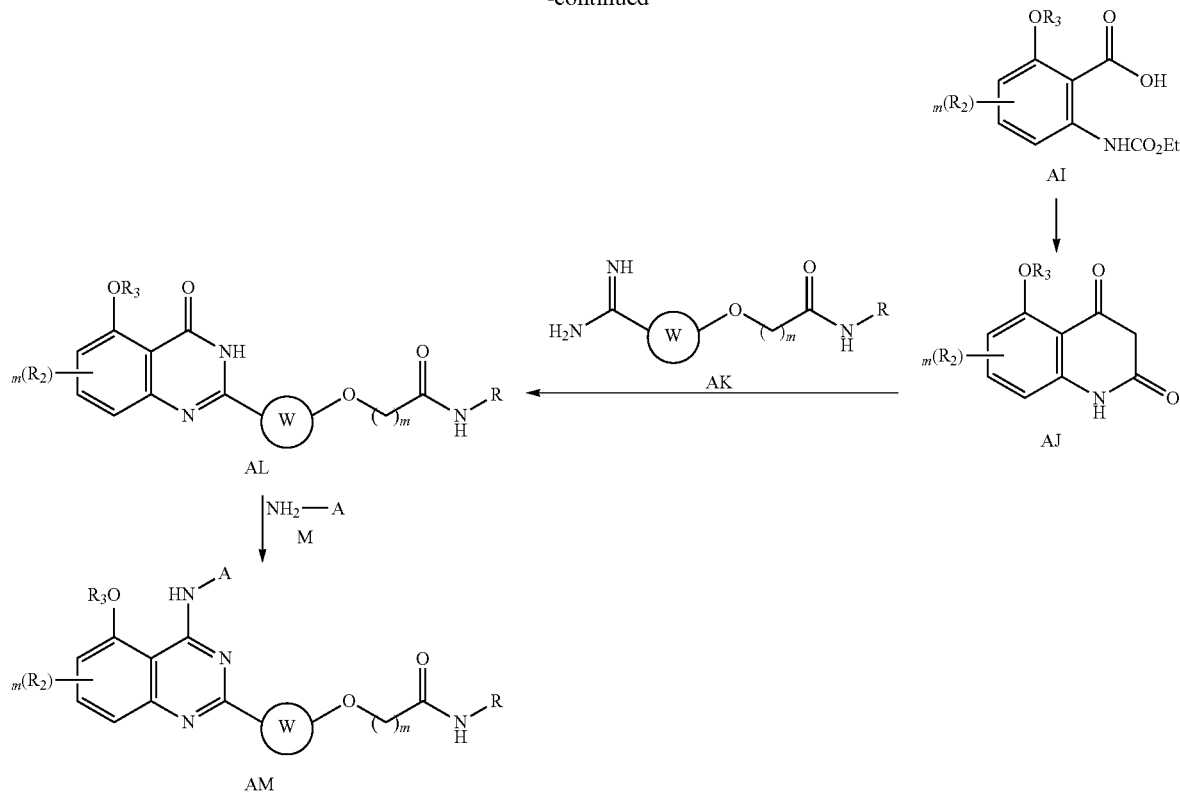

Alternatively, formula AM compounds may also be prepared according a synthetic sequence depicted in Schemes 8 or 9. In the sequence of Scheme 8, formula AM compounds may be prepared by reacting a compound of formula AN with an alkylating agent to provide a compound of formula AO; Aromatic substitution with an alcohol $R_3OH$ to provide formula AP compound; Nitro reduction of the said formula AP compound to provide formula AQ compound; Reaction of formula AQ compound with urea to provide formula AR compound; Reaction of formula AR with $POCl_3$ or $SOCl_2$ to provide formula AS compound; Reaction of the said formula AS compound with an amine A-$NH_2$ to provide formula AT compound; Coupling of formula AT compound with a boronic acid or ester bearing an amide moiety.

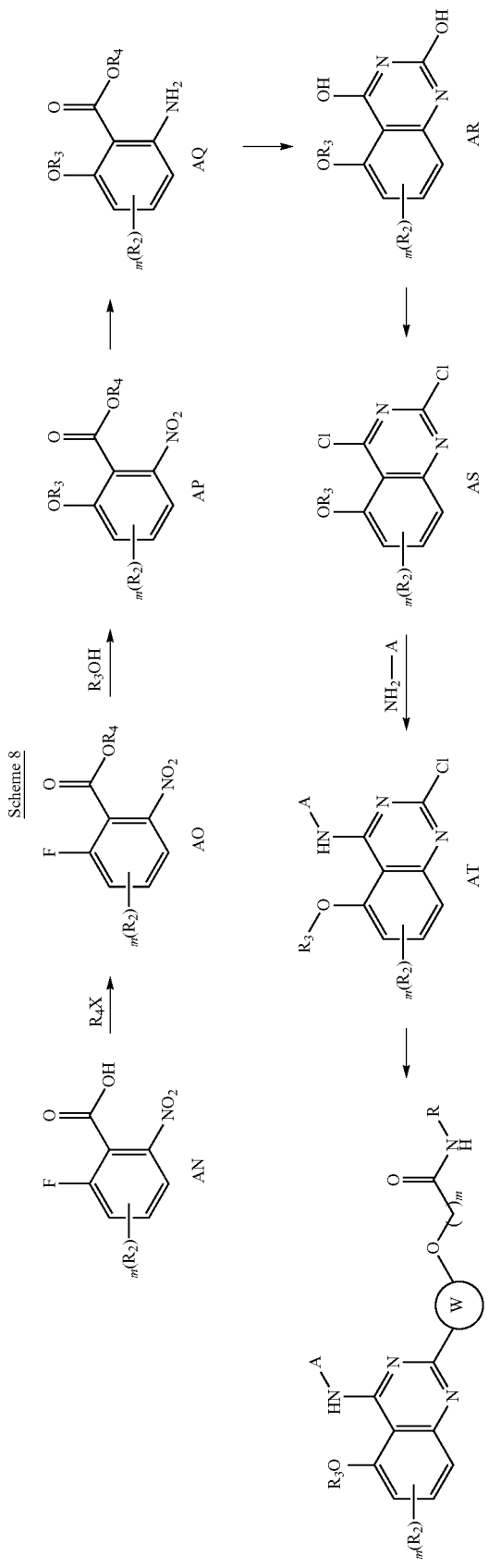

In the sequence of Scheme 9, formula AM compounds may be prepared by hydrolysis of a compound of formula AP to provide compound of formula A U; Amide formation of formula AU compound to provide formula AV compound; Nitro reduction of formula AV compound to provide formula AW compound; Amide coupling of the said formula AW compound with formulation AX compound to provide formula AY compound; Cyclization of formula A Y compound followed by chlorination and subsequent aromatic substitution with an amine $NH_2$-A.

Scheme 9
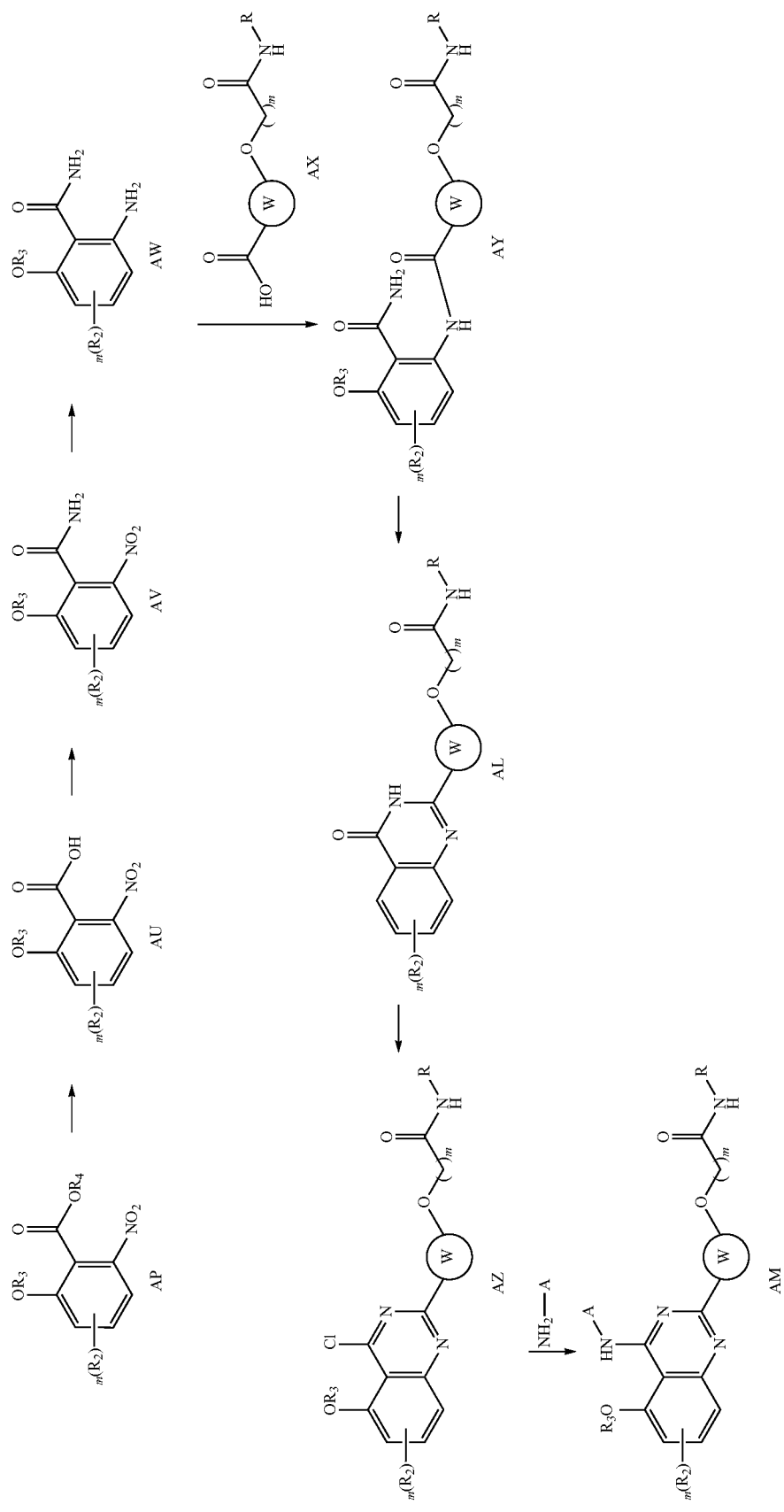

Compounds of formula Q (Scheme 10) may be prepared by bromination of a formula BA compound to give the compound of formula BB; Amination of the said formula BB compound to give the compound of formula BC; Deprotection of formula BC compound to provide formula BD compound; Cyclization of formula BD compound with urea followed by chlorination with $POCl_3$ or $SOCl_2$. Formula compound BE may also be synthesized from formula compound BB.

Scheme 10

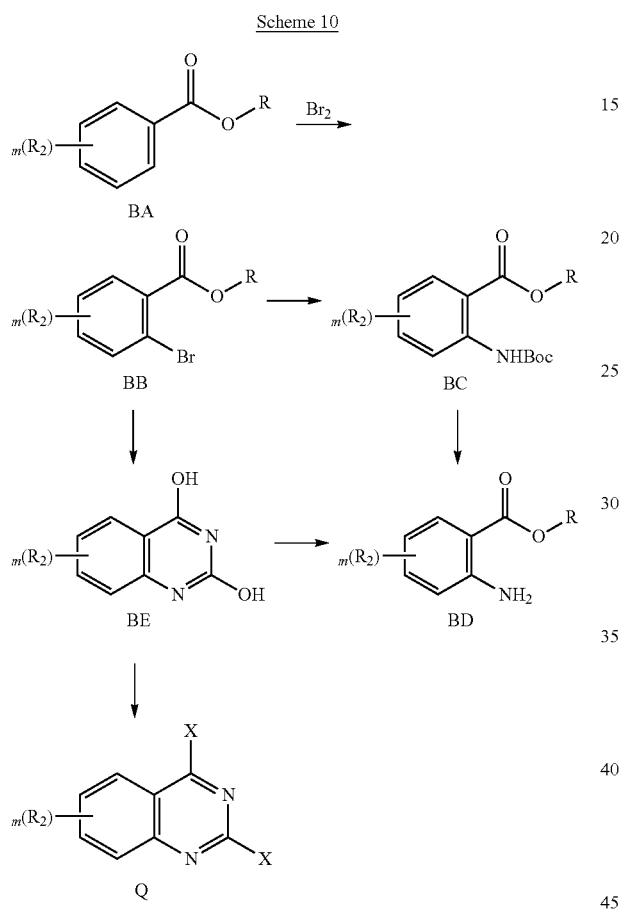

Formula BJ compounds may be prepared according to a synthetic sequence depicted in Scheme 10. In this sequence, formula BJ compounds may be prepared by reacting a compound of formula BE with a compound of formula $(R_3)_2NH$ to provide a compound of formula BF; Nitro reduction of formula BF compounds to provide formula BG compounds; Amide coupling of the said formula compounds BG and a compound of formula AA to lead to compounds of formula BH. Cyclization of said formula BH compound by reaction with NaOH to provide a compound of formula BI which can then be reacted with a variety of amines $A-NH_2$ after suitable activation.

EXAMPLES

All solvents and reagents were obtained commercially and used as received. $^1H$ NMR spectra were recorded on a Bruker instrument in the cited deuterated solvents. Chemical shifts are given in ppm, and coupling constants are in Hertz. All final compounds were purified by flash chromatography using 220-400 mesh silica gel or reverse-phase HPLC with $CH_3CN$/water as the solvents. Thin-layer chromatography was done on silica gel 60 F-254 (0.25-nm thickness) plates. Visualization was accomplished with UV light and/or 10% phosphomolybdic acid in ethanol. Nominal (low resolution) mass spectra were acquired on either a Waters LCT or an Applied Biosystems API 3000 mass spectrometer. High resolution mass spectra (FIRMS) were acquired on either a Waters LCT or an Agilent TOF mass spectrometer. All other LC-MS experiments were done on an Agilent 1100 HPLC coupled with an Agilent single quadrupole mass spectrometer. Compound purity was determined by a LC-MS with 230 nm and 254 nm wavelengths. All final compounds reported here have purity ≥95%.

Example 1

Preparation of Intermediate INT-1

4-(3-(3-(4,4,5,5-Tetramethyl-1,3,2-dioxaborolan-2-yl)phenoxy)propyl) morpholine

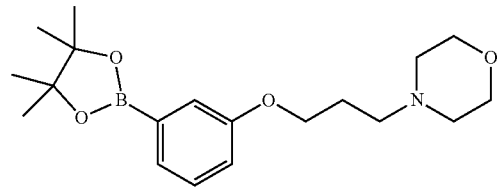 [SMILES: CC1(C)OB(c2cccc(OCCCN3CCOCC3)c2)OC1(C)C]

Step 1

4-(3-(3-Bromophenoxy)propyl)morpholine

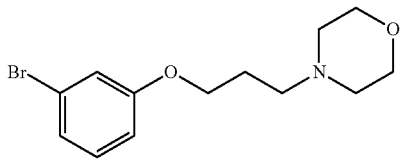 [SMILES: Brc1cccc(OCCCN2CCOCC2)c1]

To a mixture of 3-bromophenol (5.00 g, 28.90 mmol) in DMF (20.00 mL) was added 4-(3-chloropropyl)morpholine (7.09 g, 35.43 mmol, HCl), $K_2CO_3$ (9.99 g, 72.25 mmol) and KI (479.74 mg, 2.89 mmol). The mixture was stirred at 40° C. for 88 hr. LCMS showed that about 67% of desired product formed. TLC (petroleum ether/EtOAc=2:1) showed that 3-bromophenol ($R_f$=0.7) was consumed completely and one new spot ($R_f$=0.3) formed. The reaction mixture was cooled to room temperature and diluted with $H_2O$ (50 mL). The resulted mixture was extracted with EtOAc (50 mL×3). The combined organic layers were washed with brine (50 mL), dried over $Na_2SO_4$, filtered and concentrated under reduced pressure to give a residue. The residue was purified by column chromatography ($SiO_2$, Petroleum ether/Ethyl acetate=1/0 to 0:1) and was further purified by reverse phase MPLC (FA conditions). The solution was concentrated under reduced pressure to remove MeCN and the mixture was extracted with EtOAc (50 mL×3). The combined organic layers were washed with brine (50 mL), dried over $Na_2SO_4$, filtered and concentrated under reduced pressure to provide the title compound (3.77 g, 38%, FA salt) as a yellow solid. MS (ES+) m/e 300 (M+H)⁺. ¹H NMR (400 MHz, DMSO-d₆) δ 7.25 (t, J=8.4 Hz, 1H), 7.15-7.11 (m, 2H), 6.97-6.94 (m, 1H), 4.05 (t, J=6.0 Hz, 2H), 3.72 (t, J=4.4 Hz, 4H), 2.79-2.67 (m, 6H), 2.04-1.97 (m, 2H).

Step 2

4-(3-(3-(4,4,5,5-Tetramethyl-1,3,2-dioxaborolan-2-yl)phenoxy)propyl) morpholine

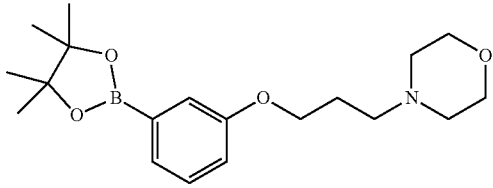 [SMILES: CC1(C)OB(c2cccc(OCCCN3CCOCC3)c2)OC1(C)C]

To a mixture of 4-(3-(3-bromophenoxy)propyl)morpholine (3.10 g, 10.33 mmol) in dioxane (30.00 mL) was added B₂(Pin)₂ (3.15 g, 12.39 mmol), AcOK (2.03 g, 20.65 mmol) and Pd(dppf)Cl₂ (377.81 mg, 516.34 μmol). The mixture was stirred under N₂ at 90° C. for 16 hr. LCMS showed that one new main peak formed and was the desired product. The reaction mixture was cooled to room temperature and diluted with H₂O (100 mL). The mixture was extracted with EtOAc (100 mL×3). The combined organic layers were washed with brine (100 mL), dried over Na₂SO₄, filtered and concentrated under reduced pressure to give a residue. The residue was purified by column chromatography (SiO₂, Petroleum ether/Ethyl acetate=100/1 to 0:1) to provide the title compound (3.67 g) as a brown oil. MS (ES+) m/e 348 (M+H)⁺.

Example 2

Preparation of Intermediate INT-2

3-Methyl-4-(2-(3-(4,4,5,5-tetramethyl-1,3,2-dioxaborolan-2-yl)phenoxy)ethyl) morpholine

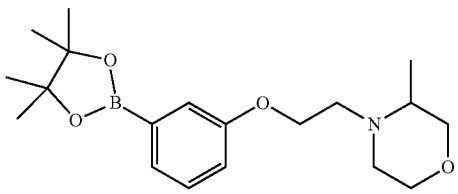 [SMILES: CC1COCCN1CCOc1cccc(B2OC(C)(C)C(C)(C)O2)c1]

Step 1

1-Bromo-3-(2-chloroethoxy)benzene

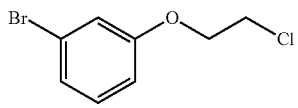 [SMILES: ClCCOc1cccc(Br)c1]

To K₂CO₃ (5.53 g, 40.00 mmol) in a 250 mL RBF was added dry EtOH (67 mL) followed by 3-bromophenol (3.46 g, 20.00 mmol, 2.12 mL) and the mixture was stirred for 15 min at rt. Then 1-bromo-2-chloroethane (5.74 g, 40.00 mmol, 3.33 mL) was added and the mixture was refluxed overnight then checked by LC-MS and tlc. This mixture was cooled to rt, poured into water, extracting with EtOAc once, separating the aqueous layer and extracting once with EtOAc, and washing the combined organic layers with water once then saturated NaCl once. The organic layer was then dried with sodium sulfate, and concentrated in vacuo to give the crude product as an oil. Column chromatography (Hexanes to 10% Ethyl Acetate/Hexanes gradient) gave the title compound (2.90 g, 62%).

Step 2

4-(2-(3-Bromophenoxy)ethyl)-3-methylmorpholine

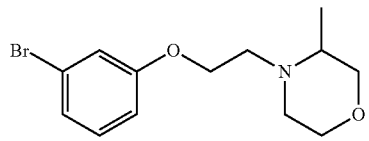 [SMILES: CC1COCCN1CCOc1cccc(Br)c1]

A solution of 1-bromo-3-(2-chloroethoxy)benzene (1.41 g, 6.00 mmol), 3-methylmorpholine (1.82 g, 18.00 mmol, 1.36 mL), and DMA (6.0 mL) was heated at 100° C. overnight. The reaction mixture was cooled to rt, poured into water, and extracted once with EtOAc. The aqueous layer was separated and extracted twice with EtOAc. The combined organic layers were washed twice with water and once with saturated NaCl, dried over sodium sulfate, and concentrated in vacuo to give 1.60 g of the crude product as an orange oil. The oil was dissolved in DCM and loaded onto an 80 g silica gel column. Column chromatography (DCM to 6% MeOH/DCM gradient) gave the title compound (1.40 g, 78%) as a light orange oil. MS (ES+) m/e 300 (M+H)⁺.

Step 3

3-Methyl-4-(2-(3-(4,4,5,5-tetramethyl-1,3,2-dioxaborolan-2-yl)phenoxy)ethyl)morpholine

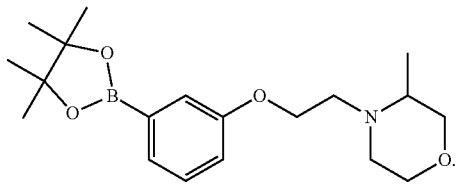 [SMILES: CC1COCCN1CCOc1cccc(B2OC(C)(C)C(C)(C)O2)c1]

To a solution of 4-(2-(3-bromophenoxy)ethyl)-3-methylmorpholine (1.40 g, 4.66 mmol) in dry DMSO (13.3 mL) in a 100 mL RBF was added bis(pinacolato)diboron (3.55 g, 13.99 mmol) and KOAc (1.93 g, 13.99 mmol). Then the vial was flushed with nitrogen and PdCl₂(dppf) (170.6 mg, 0.233 mmol) was added. The reaction was heated at 80° C. for 2 h under nitrogen. The reaction was cooled to rt and poured into water. The aqueous mixture was extracted with EtOAc once. The aqueous layer was separated and extracted twice with EtOAc. The combined organic layers were washed twice with water, once with saturated NaCl, dried over sodium sulfate, decanted from the drying agent, and concentrated in vacuo to give 3.3 g of a dark brown solid. The solid was dissolved in DCM and loaded onto an 80 g silica gel column Column chromatography (30% DCM/70% EtOAc to 20% DCM/80% EtOAc gradient) gave the title compound (848 mg, 52%) as a dark orange-red oil. MS (ES+) m/e 348 (M+H)$^+$.

Example 3

Preparation of Intermediate INT-3

3-Methyl-4-(3-(3-(4,4,5,5-tetramethyl-1,3,2-dioxaborolan-2-yl)phenoxy)propyl) morpholine

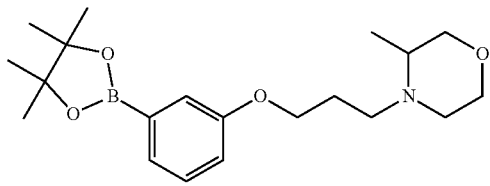 [SMILES: CC1COCCN1CCCOc1cccc(B2OC(C)(C)C(C)(C)O2)c1]

Step 1

1-Bromo-3-(3-chloropropoxy)benzene

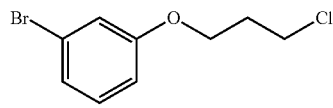 [SMILES: ClCCCOc1cccc(Br)c1]

To K$_2$CO$_3$ (5.53 g, 40.00 mmol) in a 250 mL RBF was added dry EtOH (67 mL) followed by 3-bromophenol (3.46 g, 20.00 mmol, 2.12 mL) and the mixture was stirred for 15 min at rt. Then 1-bromo-3-chloropropane (6.29 g, 40.00 mmol, 4.0 mL) was added and the mixture was refluxed overnight then checked by LC-MS and tlc. This mixture was cooled to rt, poured into water, extracting with EtOAc once, separating the aqueous layer and extracting once with EtOAc, and washing the combined organic layers with water once then saturated NaCl once. The organic layer was then dried with sodium sulfate, and concentrated in vacuo to give the crude product as an oil. Column chromatography (Hexanes to 10% Ethyl Acetate/Hexanes gradient) gave the title compound (4.2 g, 84%).

Step 2

4-(3-(3-Bromophenoxy)propyl)-3-methylmorpholine

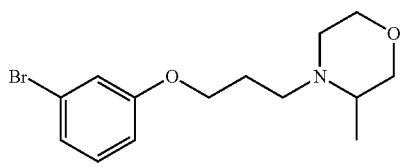 [SMILES: CC1COCCN1CCCOc1cccc(Br)c1]

A solution of 1-bromo-3-(3-chloropropoxy)benzene (944 mg, 3.78 mmol), B (1.21 g, 12.00 mmol, 1.36 mL), and DMA (4.0 mL) was heated at 90° C. for 5 h followed by overnight. The reaction mixture was cooled to rt, poured into water, and extracted once with EtOAc. The aqueous layer was separated and extracted twice with EtOAc. The combined organic layers were washed twice with water and once with saturated NaCl, dried over sodium sulfate, decanted from the drying agent and concentrated in vacuo to give 1.11 g of the crude product as an orange oil. The oil was dissolved in DCM and loaded onto a 80 g silica gel column. Column chromatography (DCM to 6% MeOH/DCM gradient) gave the title compound (998 mg, 84%) as a light orange oil. MS (ES+) m/e 314 (M+H)$^+$.

Step 3

3-Methyl-4-(3-(3-(4,4,5,5-tetramethyl-1,3,2-dioxaborolan-2-yl)phenoxy)propyl) morpholine

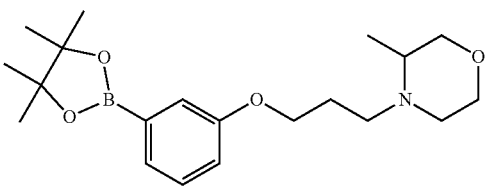 [SMILES: CC1COCCN1CCCOc1cccc(B2OC(C)(C)C(C)(C)O2)c1]

To a solution of 4-(3-(3-bromophenoxy)propyl)-3-methylmorpholine (998 mg, 3.18 mmol) in dry DMSO (9.1 mL) in a 100 mL RBF was added bis(pinacolato)diboron (2.42 g, 9.53 mmol) and KOAc (1.32 g, 9.53 mmol). Then the vial was flushed with nitrogen and PdCl$_2$(dppf) (116 mg, 0.159 mmol) was added. The reaction was heated at 80° C. for 2 h. The reaction was cooled to rt and poured into water. The aqueous mixture was extracted with EtOAc once. The aqueous layer was separated and extracted twice with EtOAc. The combined organic layers were washed twice with water, once with saturated NaCl, dried over sodium sulfate, decanted from the drying agent, and concentrated in vacuo to give 2.7 g of a brown semisolid. The crude was dissolved in DCM and loaded onto an 80 g silica gel column. Column chromatography (30% DCM/70% EtOAc to 20% DCM/80% EtOAc gradient) gave the title compound (644 mg, 56%). MS (ES+) m/e 362 (M+H)$^+$.

Example 4

Preparation of Intermediate INT-4

N-Isopropyl-2-(3-(4,4,5,5-tetramethyl-1,3,2-dioxaborolan-2-yl)phenoxy) acetamide

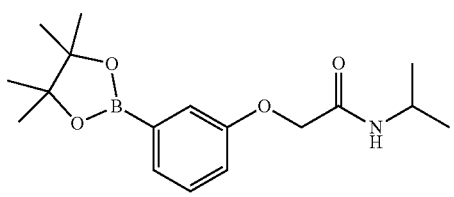 [SMILES: CC(C)NC(=O)COc1cccc(B2OC(C)(C)C(C)(C)O2)c1]

Step 1

2-Chloro-N-isopropylacetamide

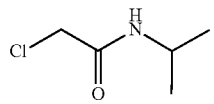

To a solution of propan-2-amine (5.9 g, 0.1 mol) in DCM (500 mL) was added 2-chloroacetyl chloride (11.1 g, 0.1 mol) drop wise at 0° C. The mixture was stirred at room temperature for 2 hrs. Then the mixture was quenched with water. The organic phase was washed with saturated brine, dried with anhydrous $Na_2SO_4$, filtered and concentrated in vacuo to give the product title compound (6.30 g) as a light yellow oil. $^1$H NMR (400 MHz, DMSO-$d_6$) δ 6.37 (b, 1H), 4.14-4.02 (m, 1H), 1.20 (d, J=6.8 Hz, 6H).

Step 2

2-(3-Bromophenoxy)-N-isopropylacetamide

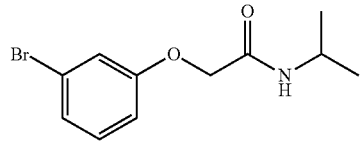

To a mixture of $K_2CO_3$ (13.8 g, 100 mmol) and 3-bromophenol (8.5 g, 50 mmol) in $CH_3CN$ (100 mL) was stirred at room temperature for 30 min. Then 2-chloro-N-isopropylacetamide (6.3 g, 46 mmol) was added. The mixture was heated at reflux overnight. After LCMS showed the reaction was completed, the mixture was filtered and the filtrate was concentrated. The residue was dissolved in DCM and washed with NaOH solution, the organic phase was dried and concentrated to give the title compound (8.0 g) as a white solid. $^1$H NMR (400 MHz, DMSO-$d_6$) δ 7.21-7.12 (m, 3H), 6.87-6.85 (m, 1H), 6.30 (b, 1H), 4.44 (s, 2H), 4.25-4.15 (m, 1H), 1.20 (d, J=6.8 Hz, 6H).

Step 3

N-Isopropyl-2-(3-(4,4,5,5-tetramethyl-1,3,2-dioxaborolan-2-yl)phenoxy) acetamide

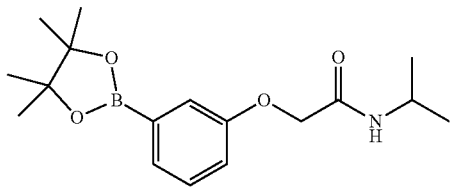 [SMILES: CC(C)NC(=O)COc1cccc(B2OC(C)(C)C(C)(C)O2)c1]

To a mixture of 2-(3-bromophenoxy)-N-isopropylacetamide (39.00 g, 143.31 mmol, 1.00 Eq), KOAc (28.13 g, 286.62 mmol) and 4,4,5,5-tetramethyl-2-(4,4,5,5-tetramethyl-1,3,2-dioxaborolan-2-yl)-1,3,2-dioxaborolane (47.31 g, 186.30 mmol) in dioxane (1 L) was added Pd(dppf)$Cl_2$ (5.32 g, 7.17 mmol) at room temperature under $N_2$. Then the reaction mixture was heated to 90° C. for 4 h. After LCMS showed the starting material was consumed completely, the mixture was filtered and the filtrate was concentrated. The residue was purified by column flash to provide the title compound (30 g) as a white solid. $^1$H NMR (400 MHz, DMSO-$d_6$) δ 7.48-7.27 (m, 3H), 7.03-7.01 (m, 1H), 6.41 (b, 1H), 4.48 (s, 2H), 4.24-4.15 (m, 1H), 1.20 (d, J=6.8 Hz, 6H). MS (ES+) m/e 320 (M+H)$^+$.

Example 5

Preparation of Intermediate INT-5

N-(tert-Butyl)-2-(3-(4,4,5,5-tetramethyl-1,3,2-dioxaborolan-2-yl)phenoxy) acetamide

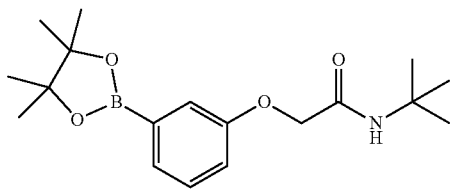 [SMILES: CC(C)(C)NC(=O)COc1cccc(B2OC(C)(C)C(C)(C)O2)c1]

Step 1

2-(3-Bromophenoxy)-N-(tert-butyl)acetamide

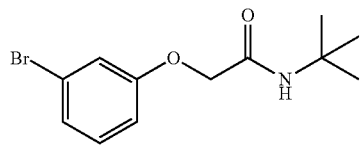 [SMILES: CC(C)(C)NC(=O)COc1cccc(Br)c1]

To a mixture of N-(tert-butyl)-2-chloroacetamide (3.48 g, 23.26 mmol) and 3-bromophenol (3.62 g, 20.93 mmol) in MeCN (40.00 mL) was added $K_2CO_3$ (6.43 g, 46.52 mmol). The mixture was stirred at 70° C. for 16 h. TLC (petroleum ether/EtOAc=5:1, $R_f$=0.62) showed one new main spot was detected. The reaction mixture was diluted with water (50 mL) and extracted with EtOAc (50 mL×3). The combined organic layers were dried over $Na_2SO_4$, filtered, and concentrated under reduced pressure to give a residue. The residue was purified by column chromatography ($SiO_2$) to give the title compound (3.52 g, 53%) as a white solid. $^1$H NMR (400 MHz, DMSO-$d_6$) δ 7.55 (s, 1H), 7.25 (t, J=8.4 Hz, 1H), 7.15-7.13 (m, 2H), 6.95-6.93 (m, 1H), 4.43 (s, 2H), 1.28 (m, 9H). MS (ES+) m/e 286 (M+H)$^+$.

Step 2

N-(tert-Butyl)-2-(3-(4,4,5,5-tetramethyl-1,3,2-dioxaborolan-2-yl)phenoxy) acetamide

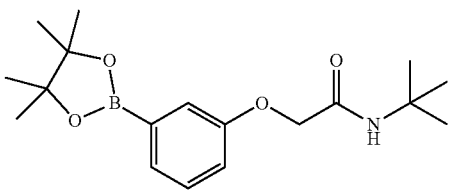 [SMILES: CC(C)(C)NC(=O)COc1cccc(B2OC(C)(C)C(C)(C)O2)c1]

To a mixture of 2-(3-bromophenoxy)-N-(tert-butyl)acetamide (3.50 g, 12.23 mmol) and 4,4,4',4',5,5,5',5'-octamethyl-2,2'-bi(1,3,2-dioxaborolane) (4.66 g, 18.35 mmol) in dioxane (70.00 mL) was added AcOK (2.40 g, 24.46 mmol), Pd(dppf)Cl$_2$ (447.44 mg, 611.50 μmol). The mixture was stirred under N$_2$ at 90° C. for 16 h. TLC (petroleum ether/EtOAc=5:1, R$_f$=0.61) showed that one main spot was detected. The reaction mixture was diluted with water (50 mL) and the mixture was extracted with EtOAc (50 mL×3). The combined organic layers were dried over Na$_2$SO$_4$, filtered and concentrated under reduced pressure to give a residue. The residue was purified by column chromatography (SiO$_2$, petroleum ether/EtOAc=1:0 to 10:1) to give the title compound (3.88 g, 95%) as a white solid. $^1$H NMR (400 MHz, DMSO-d$_6$) δ 7.55 (s, 1H), 7.33-7.25 (m, 2H), 7.20-7.19 (m, 1H), 7.07-7.05 (m, 1H), 4.40 (s, 2H), 1.29-1.28 (m, 21H). MS (ES+) m/e 334 (M+H)$^+$.

Example 6

Preparation of Intermediate INT-6

2,4-Dichloro-6-ethoxyquinazoline

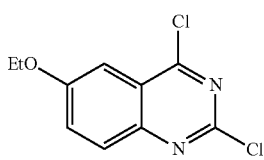

Step 1

Ethyl 5-ethoxy-2-nitrobenzoate

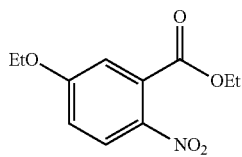 [SMILES: CCOC(=O)c1cc(OCC)ccc1[N+](=O)[O-]]

To a solution of compound 5-hydroxy-2-nitrobenzoic acid (130.00 g, 709.92 mmol) in DMF (800.00 mL) was added K$_2$CO$_3$ (196.24 g, 1.42 mol) and EtI (442.88 g, 2.84 mol). The mixture was stirred at 80° C. for 16 hour. LCMS showed starting material was consumed completely. The reaction mixture was cooled to room temperature and quenched by addition of water (1 L). The mixture was extracted with EtOAc (2×2 L). The combined organic layers were washed with brine (3×1 L), dried over Na$_2$SO$_4$, filtered, and concentrated under reduced pressure to provide the title compound (141.00 g, 83%) as a yellow solid. $^1$H NMR (400 MHz, DMSO-d$_6$) δ 8.15-8.09 (m, 1H), 7.29-7.19 (m, 2H), 4.31 (q, J=7.2 Hz, 2H), 4.20 (q, J=7.2 Hz, 2H), 1.35 (t, J=6.80 Hz, 3H), 1.27 (t, J=7.2 Hz, 3H). MS (ES+) m/e 240 (M+H)$^+$.

Step 2

Ethyl 2-amino-5-ethoxybenzoate

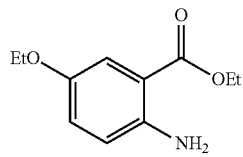

To a solution of compound ethyl 5-ethoxy-2-nitrobenzoate (75.00 g, 313.52 mmol, two batches) in MeOH (600.00 mL) was added Pd/C (8 g, 10% w/w %, wet) under N$_2$. The suspension was degassed under vacuum and purged with H$_2$ for several times. The mixture was stirred under H$_2$ (50 psi) at 40° C. for 16 hours. LCMS showed that a major peak formed and was the desired compound and TLC (petroleum ether/EtOAc=3:1 R$_f$=0.56) showed a new major spot. The reaction mixture was filtered and concentrated under reduced pressure to give the title compound (117.00 g, 89%) as an off-white solid. $^1$H NMR (400 MHz, DMSO-d$_6$) δ 7.18 (d, J=3.2 Hz, 1H), 6.97 (dd, J=8.8, 2.8 Hz, 1H), 6.73 (d, J=8.8 Hz, 1H), 6.25 (s, 2H), 4.25 (q, J=7.2 Hz, 2H), 3.89 (q, J=7.2 Hz, 2H), 1.28 (td, J=10.8, 7.2 Hz, 6H). MS (ES+) m/e 210 (M+H)$^+$. MS (ES+) m/e 210 (M+H)$^+$.

Step 3

6-Ethoxyquinazoline-2,4-diol

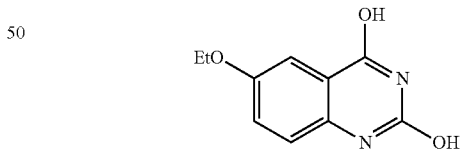

Ethyl 2-amino-5-ethoxybenzoate (100.00 g, 477.92 mmol) and urea (574.08 g, 9.56 mol) was stirred at 180° C. for 4 hour. LCMS showed that the desired compound was the major peak. The reaction mixture was cooled to room temperature and diluted with water (3 L). White solid precipitated and the mixture was stirred at room temperature for 16 hours. After filtration the cake was dispersed in toluene and dried under vacuum for 4 times to provide the title compound. (158.00 g) as a white solid that was used directly for next step reaction without further purification. $^1$H NMR (400 MHz, DMSO-d$_6$) δ 7.32-7.23 (m, 1H), 7.11

(d, J=8.8 Hz, 1H), 4.04 (q, J=6.8 Hz, 2H), 1.32 (t, J=7.2 Hz, 3H). MS (ES+) m/e 207 (M+H)⁺.

Step 4

2,4-Dichloro-6-ethoxyquinazoline

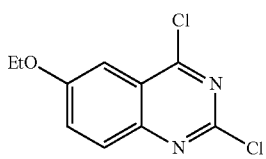 [SMILES: CCOc1ccc2nc(Cl)nc(Cl)c2c1]

To a mixture of 6-ethoxyquinazoline-2,4-diol (138.00 g, 669.25 mmol) in POCl₃ (350.00 mL) was added DIPEA (86.49 g, 669.25 mmol). The reaction was stirred at 90° C. for 20 hours. LCMS showed starting material was consumed completely and the desired compound was the major product. An additional batch was synthesized. The combined batches were concentrated under reduced pressure to remove volatiles. The residue was diluted with water (30 L) and basified by sat. NaHCO₃ at 0° C. to pH>10. The mixture was extracted with EtOAc (3×6 L). The organic layers were dried over Na₂SO₄, filtered, and concentrated under reduced pressure to give a residue. The residue was purified by column chromatography (SiO₂, Petroleum ether/Ethyl acetate: from 20/1 to 8/1) to afford the title compound as a yellow solid (90.3 g). ¹H NMR (400 MHz, DMSO-d₆) δ 7.97 (d, J=9.2 Hz, 1H), 7.79 (dd, J=9.2, 2.8 Hz, 1H), 7.44 (d, J=2.8 Hz, 1H), 4.25 (q, J=6.8 Hz, 2H), 1.42 (t, J=6.8 Hz, 3H). MS (ES+) m/e 243 (M+H)⁺. MS (ES+) m/e 243 (M+H)⁺.

Example 7

General procedure for synthesis of compounds according to the disclosure. The synthesis is being exemplified by synthesis of compounds with structure XVI.

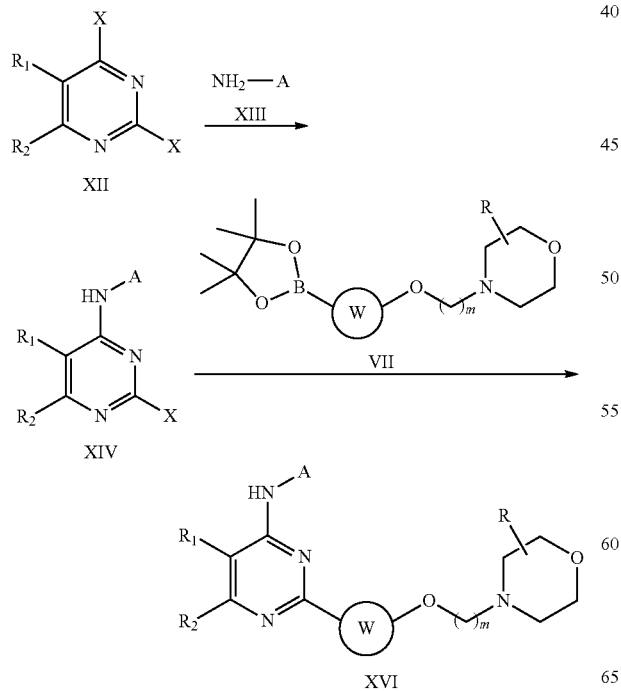

Step 1

A mixture of a compound of formula XII (1 equiv), amine XIII (1 equiv), and diisopropylethylamine (2 equiv) in DMF (0.3-0.5 M) was stirred at 80-100° C. for 3-12 h. The reaction was closely monitored by LCMS or TLC until starting material XIII was consumed. The reaction mixture was then poured into water, and the precipitate was then collected by filtration and washed with water and dried to provide the compound of formula XIV. In some cases, the product did not precipitate. For those reactions, the reaction mixture was extracted with EtOAc and the organic layer was backwashed with water and brine, dried over Na₂SO₄, and concentrated and purified by chromatography.

Step 2

A mixture of compound of formula XIV (1 equiv), compound of formula VII (1 equiv), Pd(PPh₃)₄ (0.1 equiv), and 1 N Na₂CO₃ solution and dioxane (1:5 v/v) was stirred at 100-180° C. in a sealed vessel for 2 h. The ° mixture was then concentrated. The residue was dissolved in DMSO and MeOH and purified by reverse-phase HPLC to provide compound of formula XVI as GLUT3 inhibitors.

Example 8

N-Isopropyl-2-(3-(4-((4-methoxyphenyl)amino)quinazolin-2-yl)phenoxy) acetamide

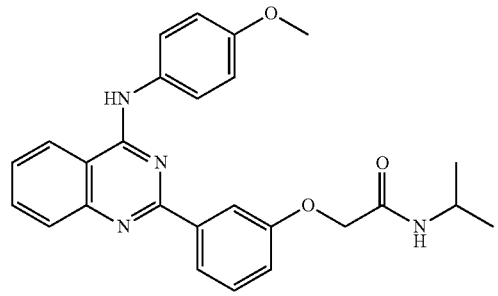 [SMILES: COc1ccc(Nc2nc(-c3cccc(OCC(=O)NC(C)C)c3)nc3ccccc23)cc1]

MS (ES+) m/e 443 (M+H)⁺.

Example 9

N-Isopropyl-2-(3-(4-((4-methoxyphenyl)amino)thieno[3,2-d]pyrimidin-2-yl) phenoxy)acetamide

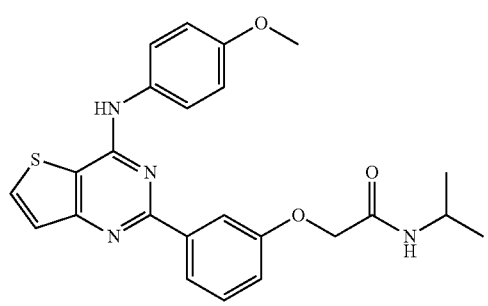 [SMILES: COc1ccc(Nc2nc(-c3cccc(OCC(=O)NC(C)C)c3)nc3ccsc23)cc1]

MS (ES+) m/e 449 (M+H)⁺.

Example 10

N-Isopropyl-2-(3-(4-((3-methoxyphenyl)amino)thieno[3,2-d]pyrimidin-2-yl) phenoxy)acetamide

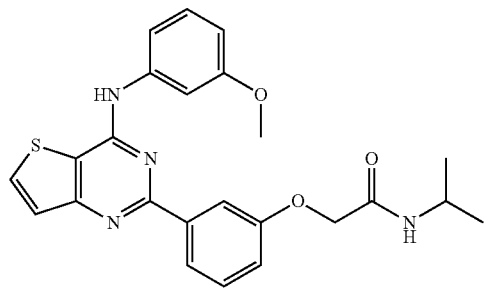 [SMILES: COc1cccc(Nc2nc(-c3cccc(OCC(=O)NC(C)C)c3)nc3ccsc23)c1]

MS (ES+) m/e 449 (M+H)+.

Example 11

2-(3-(4-((4-Aminophenyl)amino)thieno[3,2-d]pyrimidin-2-yl)phenoxy)-N-isopropylacetamide

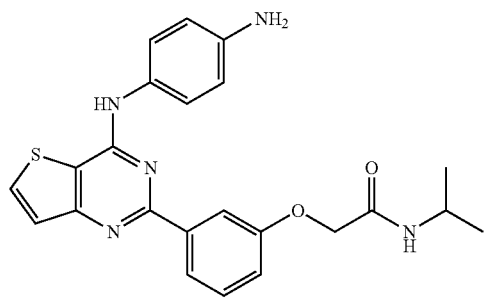 [SMILES: CC(C)NC(=O)COc1cccc(-c2nc(Nc3ccc(N)cc3)c3sccc3n2)c1]

MS (ES+) m/e 434 (M+H)+.

Example 12

2-(3-(4-((4-Hydroxyphenyl)amino)thieno[3,2-d]pyrimidin-2-yl)phenoxy)-N-isopropylacetamide

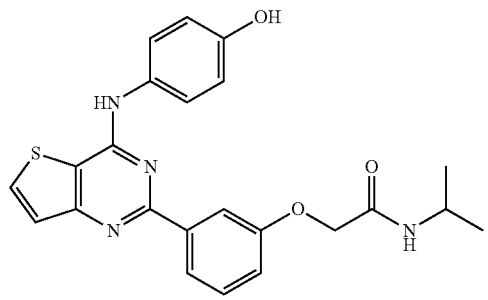 [SMILES: CC(C)NC(=O)COc1cccc(-c2nc(Nc3ccc(O)cc3)c3sccc3n2)c1]

MS (ES+) m/e 435 (M+H)+.

Example 13

2-(3-(4-((3-Hydroxyphenyl)amino)thieno[3,2-d]pyrimidin-2-yl)phenoxy)-N-isopropylacetamide

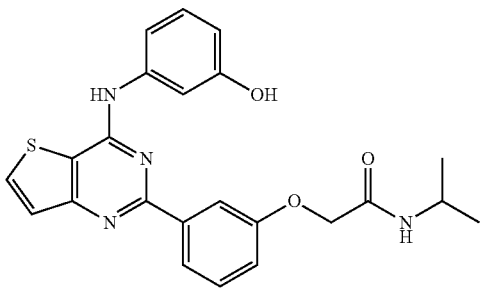 [SMILES: CC(C)NC(=O)COc1cccc(-c2nc(Nc3cccc(O)c3)c3sccc3n2)c1]

MS (ES+) m/e 435 (M+H)+.

Example 14

N-Isopropyl-2-(3-(4-((2-methoxyphenyl)amino)thieno[3,2-d]pyrimidin-2-yl) phenoxy)acetamide

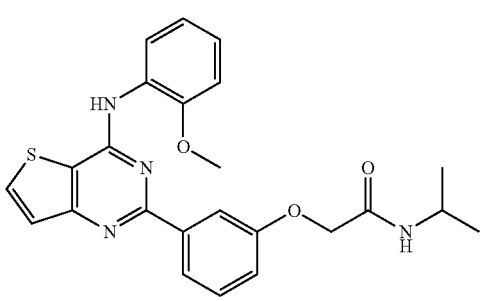 [SMILES: COc1ccccc1Nc1nc(-c2cccc(OCC(=O)NC(C)C)c2)nc2ccsc12]

MS (ES+) m/e xxx (M+H)+.

Example 15

2-(3-(4-((3-Aminophenyl)amino)thieno[3,2-d]pyrimidin-2-yl)phenoxy)-N-isopropylacetamide

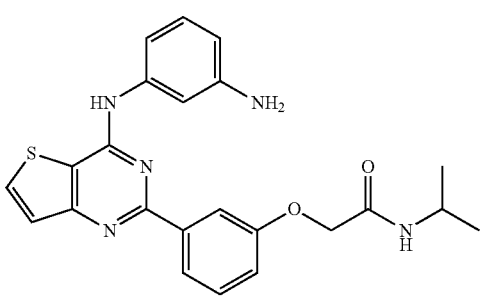 [SMILES: CC(C)NC(=O)COc1cccc(-c2nc(Nc3cccc(N)c3)c3sccc3n2)c1]

MS (ES+) m/e 449 (M+H)+.

Example 16

2-(3-(4-((4-Acetamidophenyl)amino)thieno[3,2-d]pyrimidin-2-yl)phenoxy)-N-isopropylacetamide

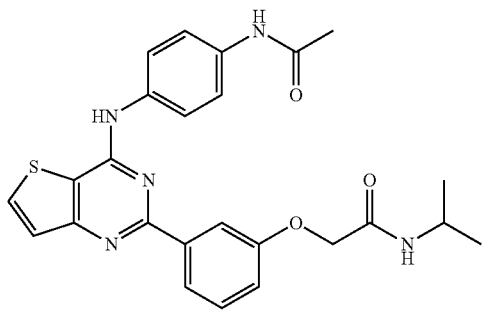 [SMILES: CC(=O)Nc1ccc(Nc2nc(-c3cccc(OCC(=O)NC(C)C)c3)nc3ccsc23)cc1]

MS (ES+) m/e 476 (M+H)+.

Example 17

2-(3-(4-((3-Acetamidophenyl)amino)thieno[3,2-d]pyrimidin-2-yl)phenoxy)-N-isopropylacetamide

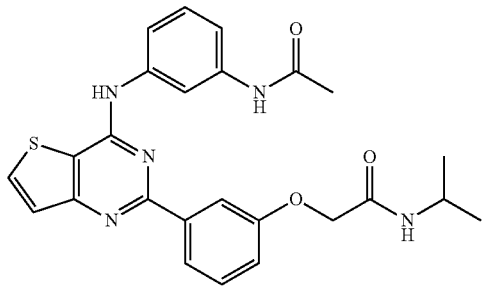 [SMILES: CC(=O)Nc1cccc(Nc2nc(-c3cccc(OCC(=O)NC(C)C)c3)nc3ccsc23)c1]

MS (ES+) m/e 476 (M+H)+.

Example 18

N-Isopropyl-2-(3-(4-((4-(piperazin-1-yl)phenyl)amino)thieno[3,2-d]pyrimidin-2-yl)phenoxy)acetamide

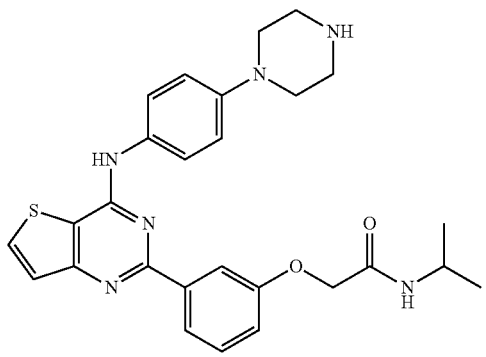 [SMILES: CC(C)NC(=O)COc1cccc(-c2nc(Nc3ccc(N4CCNCC4)cc3)c3sccc3n2)c1]

MS (ES+) m/e 503 (M+H)+.

Example 19

N-Isopropyl-2-(3-(4-((3-(piperazin-1-yl)phenyl)amino)thieno[3,2-d]pyrimidin-2-yl)phenoxy)acetamide

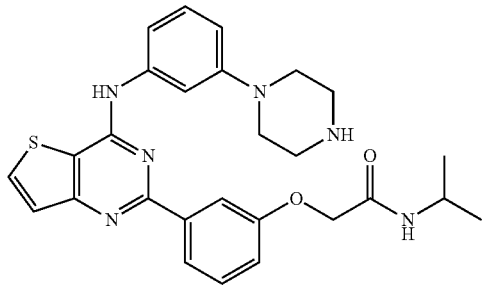 [SMILES: CC(C)NC(=O)COc1cccc(-c2nc(Nc3cccc(N4CCNCC4)c3)c3sccc3n2)c1]

MS (ES+) m/e 503 (M+H)+.

Example 20

2-(3-(4-((6-Aminopyridin-3-yl)amino)thieno[3,2-d]pyrimidin-2-yl)phenoxy)-N-isopropylacetamide

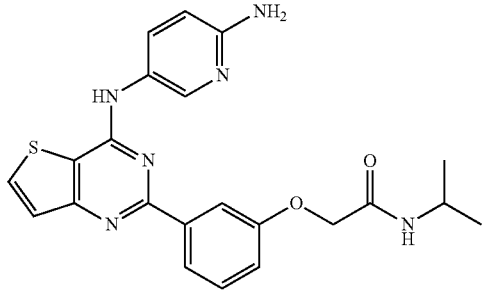 [SMILES: CC(C)NC(=O)COc1cccc(-c2nc(Nc3ccc(N)nc3)c3sccc3n2)c1]

MS (ES+) m/e 435 (M+H)+.

Example 21

N-Isopropyl-2-(3-(4-((4-morpholinophenyl)amino)thieno[3,2-d]pyrimidin-2-yl) phenoxy)acetamide

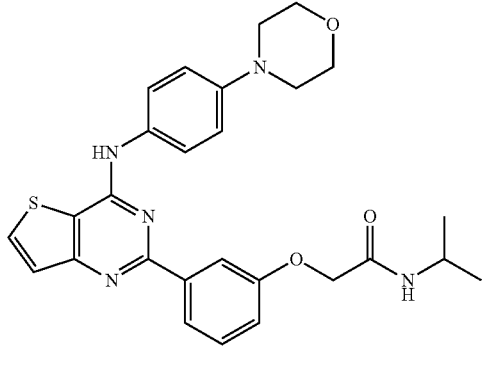 [SMILES: CC(C)NC(=O)COc1cccc(-c2nc(Nc3ccc(N4CCOCC4)cc3)c3sccc3n2)c1]

$^1$H NMR (500 MHz, DMSO-$d_6$) δ 9.76 (s, 1H), 8.24 (d, J=5.3 Hz, 1H), 8.08-7.91 (m, 4H), 7.68 (d, J=8.5 Hz, 2H), 7.49 (d, J=5.4 Hz, 1H), 7.44 (t, J=8.1 Hz, 1H), 7.10 (d, J=8.9 Hz, 1H), 7.06 (d, J=9.0 Hz, 2H), 4.52 (s, 2H), 4.00 (dp, J=14.4, 6.7 Hz, 1H), 3.83-3.73 (m, 4H), 3.22-3.10 (m, 4H), 1.12 (d, J=6.6 Hz, 6H). MS (ES+) m/e 504 (M+H)+.

Example 22

2-(3-(4-((1H-Pyrazol-4-yl)amino)thieno[3,2-d]pyrimidin-2-yl)phenoxy)-N-isopropylacetamide

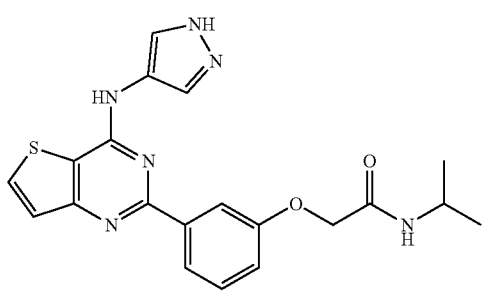 [SMILES: CC(C)NC(=O)COc1cccc(-c2nc(Nc3cn[nH]c3)c3sccc3n2)c1]

MS (ES+) m/e 409 (M+H)+.

Example 23

2-(3-(4-((1H-Pyrazolo[3,4-b]pyridin-5-yl)amino)thieno[3,2-d]pyrimidin-2-yl) phenoxy)-N-isopropylacetamide

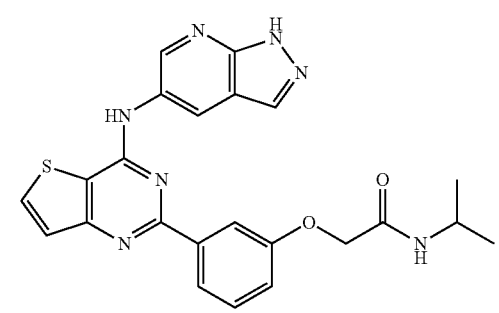 [SMILES: CC(C)NC(=O)COc1cccc(-c2nc(Nc3cnc4[nH]ncc4c3)c3sccc3n2)c1]

$^1$H NMR (500 MHz, DMSO-$d_6$) δ 13.68 (s, 1H), 10.23 (s, 1H), 8.86 (d, J=2.2 Hz, 1H), 8.64 (d, J=2.2 Hz, 1H), 8.31 (d, J=5.3 Hz, 1H), 8.24 (s, 1H), 8.05-7.91 (m, 3H), 7.56 (d, J=5.4 Hz, 1H), 7.44 (t, J=8.0 Hz, 1H), 7.10 (dd, J=8.1, 2.1 Hz, 1H), 4.52 (s, 2H), 3.98 (dq, J=13.3, 6.6 Hz, 1H), 1.11 (d, J=6.6 Hz, 6H). MS (ES+) m/e 500 (M+H)+.

Example 24

2-(3-(4-((1H-Pyrazolo[3,4-b]pyridin-5-yl)amino)thieno[3,2-d]pyrimidin-2-yl) phenoxy)-N-(tert-butyl)acetamide

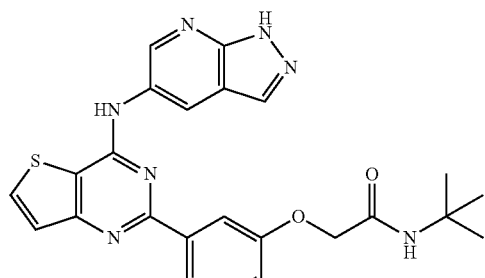

$^1$H NMR (500 MHz, DMSO-$d_6$) δ 13.72 (s, 1H), 10.29 (s, 1H), 8.86 (d, J=2.4 Hz, 1H), 8.63 (d, J=2.3 Hz, 1H), 8.32 (d, J=5.4 Hz, 1H), 8.24 (s, 1H), 7.98-7.90 (m, 2H), 7.62-7.52 (m, 2H), 7.44 (t, J=7.9 Hz, 1H), 7.14-7.05 (m, 1H), 4.49 (s, 2H), 1.31 (s, 9H). MS (ES+) m/e 474 (M+H)+.

Example 25

N-(6-Methoxypyridin-3-yl)-2-(3-(3-morpholinopropoxy)phenyl)-5,7-dihydrofuro[3,4-d]pyrimidin-4-amine

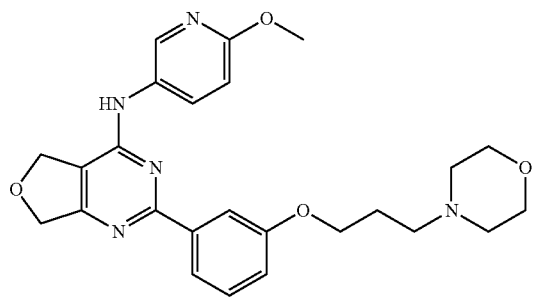 [SMILES: COc1ccc(Nc2nc(-c3cccc(OCCCN4CCOCC4)c3)nc3c2COC3)cn1]

MS (ES+) m/e 364 (M+H)+.

Example 26

N-(4-Morpholinophenyl)-2-(3-(3-morpholinopropoxy)phenyl)-5,7-dihydrofuro[3,4-d]pyrimidin-4-amine

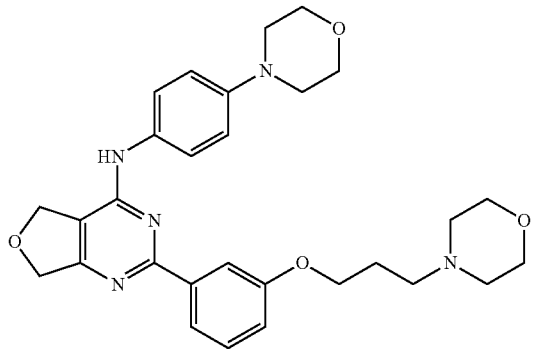 [SMILES: c1cc(OCCCN2CCOCC2)cc(-c2nc3c(c(Nc4ccc(N5CCOCC5)cc4)n2)COC3)c1]

MS (ES+) m/e 518 (M+H)+.

Example 27

N-(3,5-Dimethoxyphenyl)-2-(3-(3-morpholinopropoxy)phenyl)-5,7-dihydrofuro[3,4-d]pyrimidin-4-amine

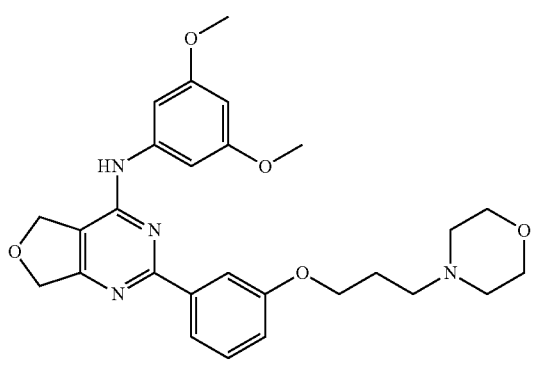 [SMILES: COc1cc(Nc2nc(-c3cccc(OCCCN4CCOCC4)c3)nc3c2COC3)cc(OC)c1]

MS (ES+) m/e 493 (M+H)+.

Example 28

N-(4-Chloro-3-methoxyphenyl)-2-(3-(3-morpholinopropoxy)phenyl)-5,7-dihydrofuro[3,4-d]pyrimidin-4-amine

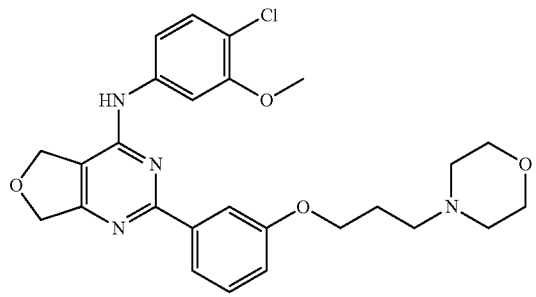 [SMILES: COc1cc(Nc2nc(-c3cccc(OCCCN4CCOCC4)c3)nc3c2COC3)ccc1Cl]

MS (ES+) m/e 497 (M+H)+.

Example 29

N-(Benzo[d][1,3]dioxol-5-yl)-2-(3-(3-morpholinopropoxy)phenyl)-5,7-dihydrofuro[3,4-d]pyrimidin-4-amine

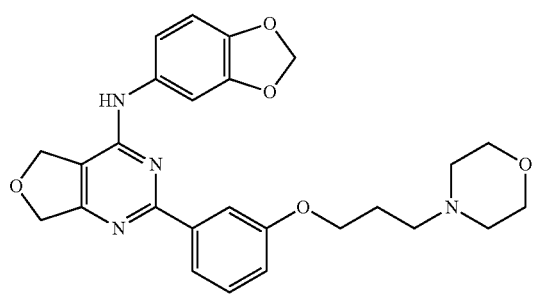 [SMILES: c1cc(OCCCN2CCOCC2)cc(-c2nc3c(c(Nc4ccc5c(c4)OCO5)n2)COC3)c1]

MS (ES+) m/e 477 (M+H)+.

Example 30

4-((2-(3-(3-Morpholinopropoxy)phenyl)-5,7-dihydrofuro[3,4-d]pyrimidin-4-yl)amino)benzamide

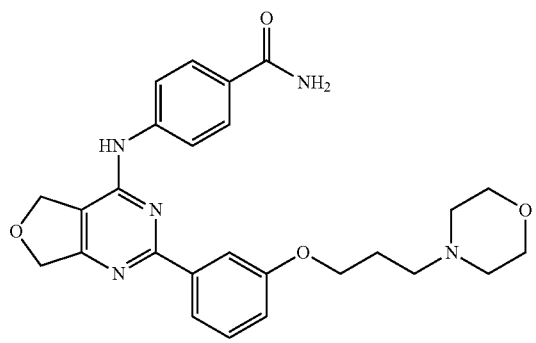 [SMILES: NC(=O)c1ccc(Nc2nc(-c3cccc(OCCCN4CCOCC4)c3)nc3c2COC3)cc1]

MS (ES+) m/e 476 (M+H)+.

Example 31

3-((2-(3-(3-Morpholinopropoxy)phenyl)-5,7-dihydrofuro[3,4-d]pyrimidin-4-yl)amino)benzamide

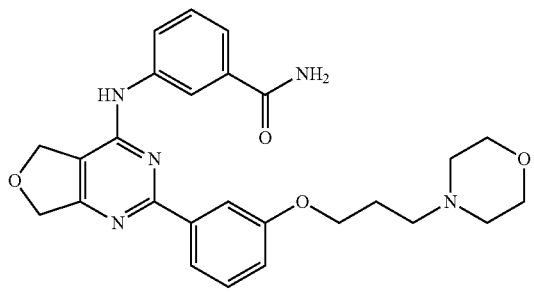 [SMILES: NC(=O)c1cccc(Nc2nc(-c3cccc(OCCCN4CCOCC4)c3)nc3c2COC3)c1]

MS (ES+) m/e 476 (M+H)+.

Example 32

N-Methyl-3-((2-(3-(3-morpholinopropoxy)phenyl)-5,7-dihydrofuro[3,4-d]pyrimidin-4-yl)amino)benzamide

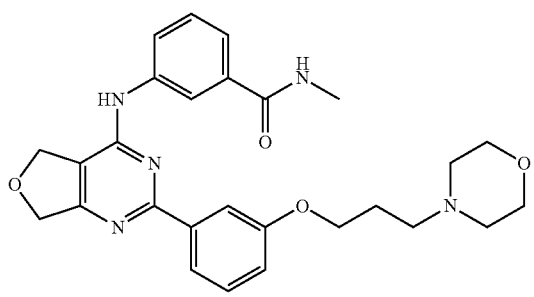 [SMILES: CNC(=O)c1cccc(Nc2nc(-c3cccc(OCCCN4CCOCC4)c3)nc3c2COC3)c1]

MS (ES+) m/e 490 (M+H)'.

Example 33

N-(4-Methoxy-3-methylphenyl)-2-(3-(3-morpholinopropoxy)phenyl)-5,7-dihydrofuro[3,4-d]pyrimidin-4-amine

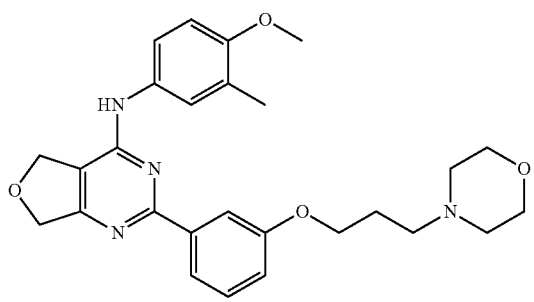 [SMILES: COc1ccc(Nc2nc(-c3cccc(OCCCN4CCOCC4)c3)nc3c2COC3)cc1C]

MS (ES+) m/e 477 (M+H)+.

Example 34

N-(tert-Butyl)-2-(3-(4-((2-oxo-2,3-dihydro-1H-benzo[d]imidazol-5-yl)amino) thieno[3,2-d]pyrimidin-2-yl)phenoxy)acetamide

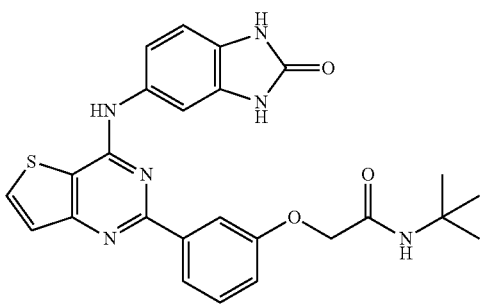 [SMILES: CC(C)(C)NC(=O)COc1cccc(-c2nc(Nc3ccc4[nH]c(=O)[nH]c4c3)c3sccc3n2)c1]

MS (ES+) m/e 489 (M+H)+.

Example 35

4-((2-(3-(2-(tert-Butylamino)-2-oxoethoxy)phenyl)thieno[3,2-d]pyrimidin-4-yl)amino)benzamide

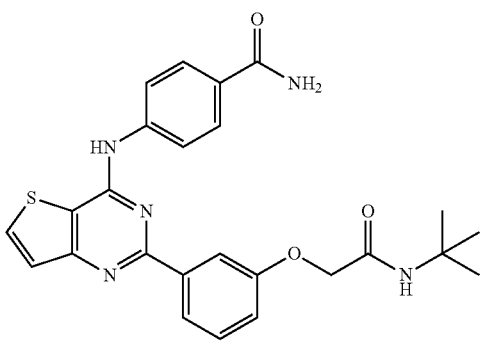 [SMILES: CC(C)(C)NC(=O)COc1cccc(-c2nc(Nc3ccc(C(N)=O)cc3)c3sccc3n2)c1]

MS (ES+) m/e 476 (M+H)+.

Example 36

2-(3-(4-((4-Amino-3-hydroxyphenyl)amino)thieno[3,2-d]pyrimidin-2-yl) phenoxy)-N-(tert-butyl)acetamide

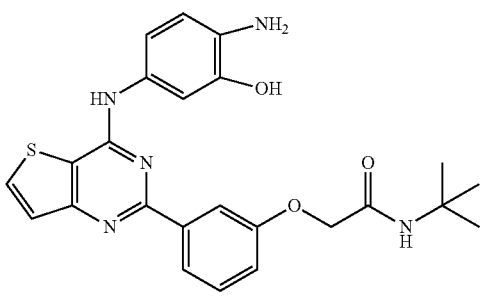 [SMILES: CC(C)(C)NC(=O)COc1cccc(-c2nc(Nc3ccc(N)c(O)c3)c3sccc3n2)c1]

MS (ES+) m/e 464 (M+H)+.

Example 37

4-((2-(3-(2-(tert-Butylamino)-2-oxoethoxy)phenyl)thieno[3,2-d]pyrimidin-4-yl)amino)-N-methylbenzamide

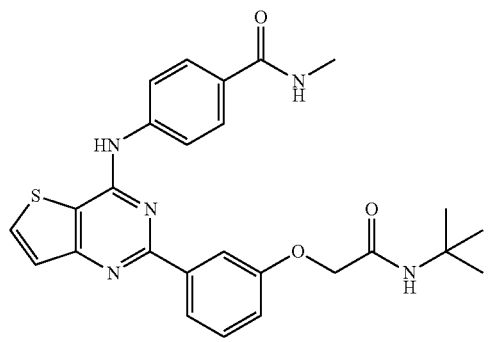 [SMILES: CNC(=O)c1ccc(Nc2nc(-c3cccc(OCC(=O)NC(C)(C)C)c3)nc3ccsc23)cc1]

¹H NMR (500 MHz, DMSO-d₆) δ 10.10 (s, 1H), 8.39 (q, J=4.2 Hz, 1H), 8.33 (d, J=5.4 Hz, 1H), 8.02 (d, J=8.7 Hz, 4H), 7.93 (d, J=8.8 Hz, 2H), 7.56 (d, J=5.4 Hz, 2H), 7.46 (t, J=7.9 Hz, 1H), 7.09 (dd, J=8.2, 1.9 Hz, 1H), 4.52 (s, 2H), 2.81 (d, J=4.5 Hz, 3H), 1.32 (s, 9H). MS (ES+) m/e 490 (M+H)⁺.

Example 38

N-(tert-Butyl)-2-(3-(4-((6-morpholinopyridin-3-yl)amino)thieno[3,2-d]pyrimidin-2-yl)phenoxy)acetamide

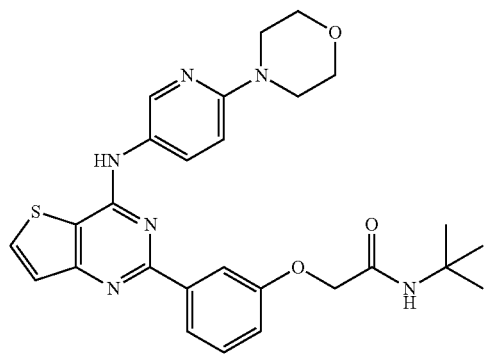 [SMILES: CC(C)(C)NC(=O)COc1cccc(-c2nc(Nc3ccc(N4CCOCC4)nc3)c3sccc3n2)c1]

¹H NMR (500 MHz, DMSO-d₆) δ 9.93 (s, 1H), 8.56 (s, 1H), 8.29 (d, J=5.4 Hz, 1H), 8.10 (s, 1H), 8.01-7.89 (m, 2H), 7.57 (s, 1H), 7.53 (d, J=5.4 Hz, 1H), 7.44 (t, J=7.9 Hz, 1H), 7.17-7.02 (m, 2H), 4.49 (s, 2H), 3.81-3.70 (m, 4H), 3.56-3.47 (m, 4H), 1.32 (s, 9H). MS (ES+) m/e 519 (M+H)⁺.

Example 39

N-(tert-Butyl)-2-(3-(4-((6-oxo-1,6-dihydropyridin-3-yl)amino)thieno[3,2-d]pyrimidin-2-yl)phenoxy)acetamide

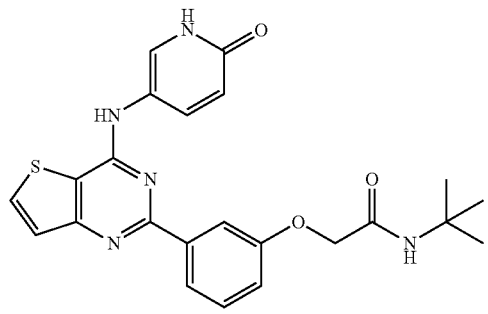 [SMILES: CC(C)(C)NC(=O)COc1cccc(-c2nc(Nc3ccc(=O)[nH]c3)c3sccc3n2)c1]

¹H NMR (500 MHz, DMSO-d₆) δ 9.88 (s, 1H), 8.65 (s, 2H), 8.29 (d, J=5.3 Hz, 1H), 7.91 (d, J=7.7 Hz, 2H), 7.59 (s, 1H), 7.53 (d, J=5.4 Hz, 1H), 7.48-7.40 (m, 1H), 7.07 (d, J=7.4 Hz, 1H), 4.49 (s, 2H), 1.31 (s, 9H). MS (ES+) m/e 450 (M+H)⁺.

Example 40

N-(tert-Butyl)-2-(3-(4-((2-oxoindolin-5-yl)amino)thieno[3,2-d]pyrimidin-2-yl) phenoxy)acetamide

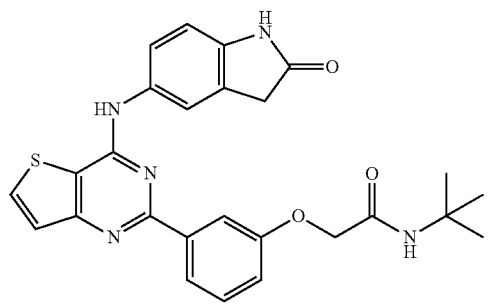 [SMILES: CC(C)(C)NC(=O)COc1cccc(-c2nc(Nc3ccc4c(c3)CC(=O)N4)c3sccc3n2)c1]

MS (ES+) m/e 488 (M+H)⁺.

Example 41

2-(3-(4-((2-Aminopyrimidin-5-yl)amino)thieno[3,2-d]pyrimidin-2-yl)phenoxy)-N-(tert-butyl)acetamide

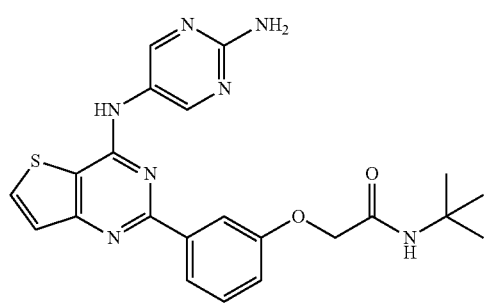 [SMILES: CC(C)(C)NC(=O)COc1cccc(-c2nc(Nc3cnc(N)nc3)c3sccc3n2)c1]

MS (ES+) m/e 450 (M+H)⁺.

Example 42

N-Methyl-4-((2-(3-(3-morpholinopropoxy)phenyl)-5,7-dihydrofuro[3,4-d]pyrimidin-4-yl)amino)benzamide

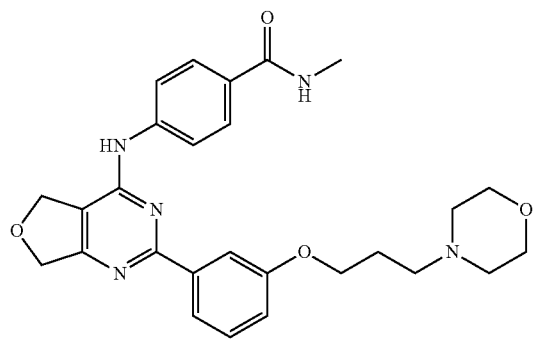 [SMILES: CNC(=O)c1ccc(Nc2nc(-c3cccc(OCCCN4CCOCC4)c3)nc3c2COC3)cc1]

MS (ES+) m/e 490 (M+H)+.

Example 43

N-(tert-Butyl)-2-(3-(4-((6-(piperazin-1-yl)pyridin-3-yl)amino)thieno[3,2-d]pyrimidin-2-yl)phenoxy)acetamide

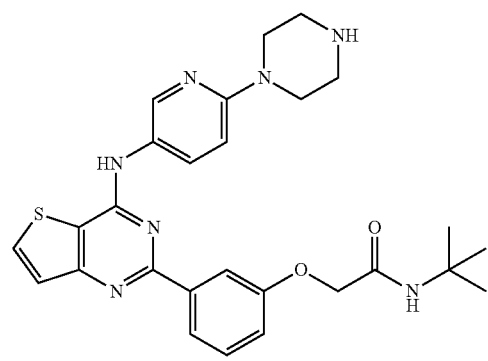 [SMILES: CC(C)(C)NC(=O)COc1cccc(-c2nc(Nc3ccc(N4CCNCC4)nc3)c3sccc3n2)c1]

$^1$H NMR (500 MHz, DMSO-$d_6$) δ 10.62 (s, 1H), 9.30 (s, 1H), 8.62 (s, 1H), 8.39 (d, J=5.3 Hz, 1H), 8.16 (s, 1H), 8.00-7.93 (m, 2H), 7.70-7.59 (m, 2H), 7.49 (t, J=7.9 Hz, 1H), 7.16 (d, J=8.1 Hz, 1H), 4.53 (s, 2H), 3.85 (s, 4H), 3.24 (s, 4H), 1.31 (s, 9H). MS (ES+) m/e 518 (M+H)+.

Example 44

N-(tert-Butyl)-2-(3-(4-((4-(3-oxopiperazin-1-yl)phenyl)amino)thieno[3,2-d]pyrimidin-2-yl)phenoxy)acetamide

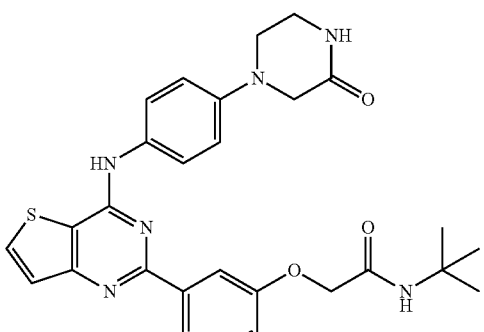

MS (ES+) m/e 531 (M+H)+.

Example 45

2-(3-(4-((1H-Pyrazolo[3,4-b]pyridin-5-yl)amino)thieno[3,2-d]pyrimidin-2-yl) phenoxy)-N-(tert-butyl)acetamide $^1$H NMR (500 MHz, DMSO-$d_6$) δ 10.10 (s, 1H), 8.86 (d, J=2.3 Hz, 1H), 8.63 (d, J=2.4 Hz, 1H), 8.29 (d, J=5.4 Hz, 1H), 8.23 (s, 1H), 7.99-7.92 (m, 2H), 7.54 (d, J=5.6 Hz, 2H), 7.42 (t, J=8.0 Hz, 1H), 7.11-7.00 (m, 1H), 4.48 (s, 2H), 1.31 (s, 9H). MS (ES+) m/e 474 (M+H)+.

Example 46

N-(tert-Butyl)-2-(3-(4-((4-morpholinophenyl)amino)thieno[3,2-d]pyrimidin-2-yl)phenoxy)acetamide

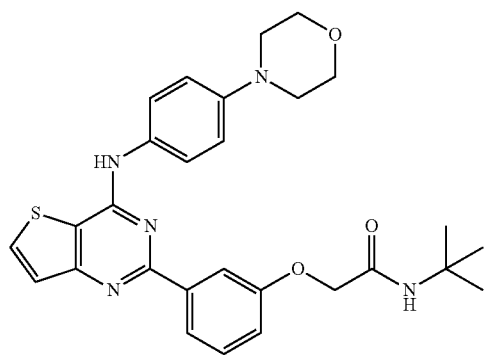 [SMILES: CC(C)(C)NC(=O)COc1cccc(-c2nc(Nc3ccc(N4CCOCC4)cc3)c3sccc3n2)c1]

$^1$H NMR (500 MHz, DMSO-d$_6$) δ 10.00 (s, 1H), 8.27 (d, J=5.4 Hz, 1H), 8.01-7.94 (m, 2H), 7.67 (d, J=8.3 Hz, 2H), 7.56 (s, 1H), 7.50 (d, J=5.4 Hz, 1H), 7.46 (t, J=7.9 Hz, 1H), 7.11 (dd, J=8.2, 2.6 Hz, 1H), 7.07 (d, J=8.7 Hz, 2H), 4.49 (s, 2H), 3.78 (t, J=4.7 Hz, 4H), 3.17 (t, J=4.8 Hz, 4H), 1.32 (s, 9H). MS (ES+) m/e 518 (M+H)$^+$.

Example 47

2-(3-(4-((1H-Pyrazolo[3,4-b]pyridin-5-yl)amino)-5,7-dihydrofuro[3,4-d]pyrimidin-2-yl)phenoxy)-N-(tert-butyl)acetamide

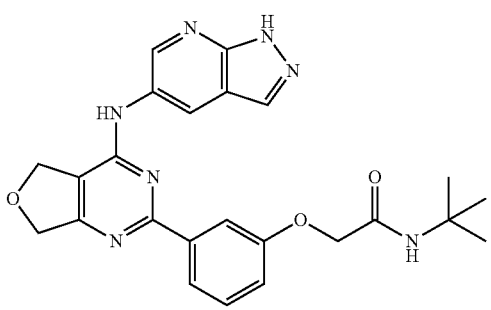 [SMILES: CC(C)(C)NC(=O)COc1cccc(-c2nc3c(c(Nc4cnc5[nH]ncc5c4)n2)COC3)c1]

MS (ES+) m/e 460 (M+H)$^+$.

Example 48

N-(tert-Butyl)-2-(3-(4-((4-(piperazin-1-yl)phenyl)amino)-5,7-dihydrofuro[3,4-d]pyrimidin-2-yl)phenoxy)acetamide

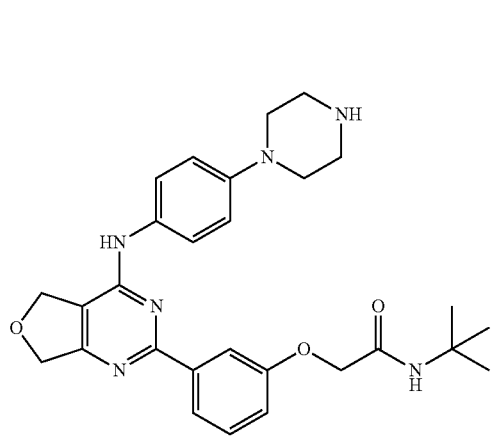 [SMILES: CC(C)(C)NC(=O)COc1cccc(-c2nc3c(c(Nc4ccc(N5CCNCC5)cc4)n2)COC3)c1]

MS (ES+) m/e 503 (M+H)$^+$.

Example 49

N-(tert-Butyl)-2-(3-(4-((4-(piperazin-1-yl)phenyl)amino)thieno[3,2-d]pyrimidin-2-yl)phenoxy)acetamide

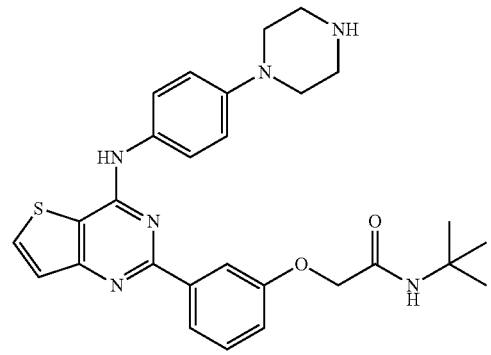 [SMILES: CC(C)(C)NC(=O)COc1cccc(-c2nc(Nc3ccc(N4CCNCC4)cc3)c3sccc3n2)c1]

MS (ES+) m/e 517 (M+H)$^+$.

Example 50

5-((2-(3-(3-Morpholinopropoxy)phenyl)thieno[3,2-d]pyrimidin-4-yl)amino)-1,3-dihydro-2H-benzo[d]imidazol-2-one

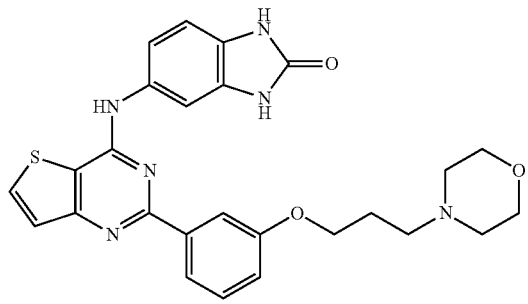 [SMILES: O=c1[nH]c2ccc(Nc3nc(-c4cccc(OCCCN5CCOCC5)c4)nc4ccsc34)cc2[nH]1]

MS (ES+) m/e 503 (M+H)+.

Example 51

4-((2-(3-(3-Morpholinopropoxy)phenyl)thieno[3,2-d]pyrimidin-4-yl)amino)benzamide

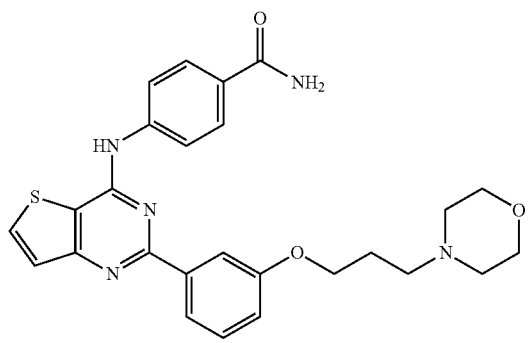 [SMILES: NC(=O)c1ccc(Nc2nc(-c3cccc(OCCCN4CCOCC4)c3)nc3ccsc23)cc1]

MS (ES+) m/e 489 (M+H)+.

Example 52

5-((2-(3-(3-Morpholinopropoxy)phenyl)thieno[3,2-d]pyrimidin-4-yl)amino) indolin-2-one

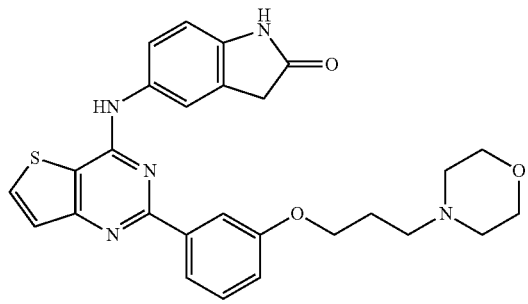 [SMILES: O=C1Cc2cc(Nc3nc(-c4cccc(OCCCN5CCOCC5)c4)nc4ccsc34)ccc2N1]

MS (ES+) m/e 502 (M+H)+.

Example 53

2-Amino-5-((2-(3-(3-morpholinopropoxy)phenyl)thieno[3,2-d]pyrimidin-4-yl)amino)phenol

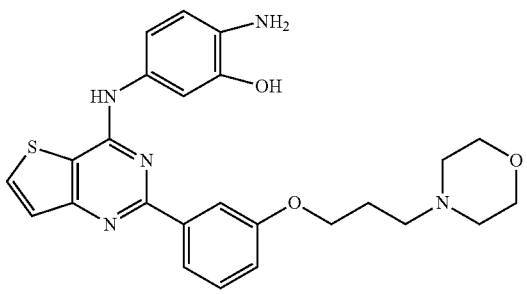 [SMILES: Nc1ccc(Nc2nc(-c3cccc(OCCCN4CCOCC4)c3)nc3ccsc23)cc1O]

MS (ES+) m/e 478 (M+H)+.

Example 54

2-(3-(3-Morpholinopropoxy)phenyl)-N-(6-morpholinopyridin-3-yl) thieno[3,2-d]pyrimidin-4-amine

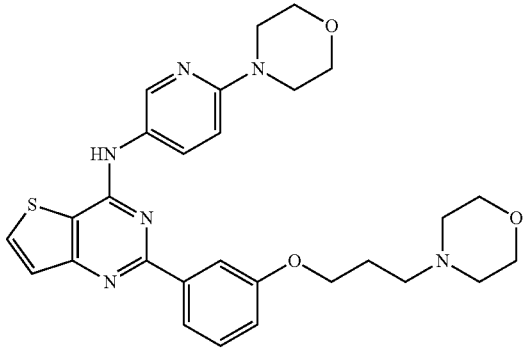 [SMILES: c1cc(OCCCN2CCOCC2)cc(-c2nc(Nc3ccc(N4CCOCC4)nc3)c3sccc3n2)c1]

MS (ES+) m/e 533 (M+H)+.

Example 55

N-Methyl-4-((2-(3-(3-morpholinopropoxy)phenyl)thieno[3,2-d]pyrimidin-4-yl)amino)benzamide

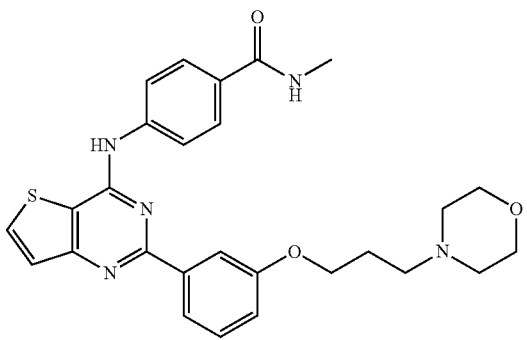 [SMILES: CNC(=O)c1ccc(Nc2nc(-c3cccc(OCCCN4CCOCC4)c3)nc3ccsc23)cc1]

MS (ES+) m/e 504 (M+H)+.

Example 56

2-(3-(4-((6-Aminopyridin-3-yl)amino)thieno[3,2-d]pyrimidin-2-yl)phenoxy)-N-(tert-butyl)acetamide

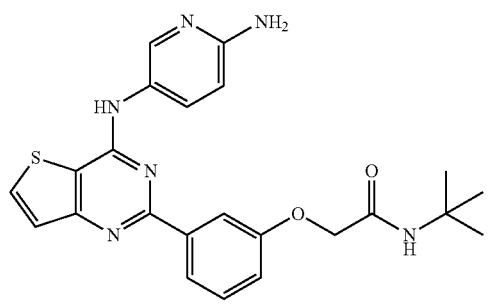

$^1$H NMR (500 MHz, DMSO-d$_6$) δ 10.00 (s, 1H), 8.60 (d, J=2.5 Hz, 1H), 8.32 (d, J=5.4 Hz, 1H), 8.27 (dd, J=9.5, 2.5 Hz, 1H), 7.99-7.92 (m, 3H), 7.62-7.52 (m, 2H), 7.43 (t, J=8.0 Hz, 1H), 7.13-7.05 (m, 2H), 4.51 (s, 2H), 1.31 (s, 9H). MS (ES+) m/e 449 (M+H)$^+$.

Example 57

4-((2-(3-(2-(tert-Butylamino)-2-oxoethoxy)phenyl)thieno[3,2-d]pyrimidin-4-yl)amino)-N-ethylbenzamide

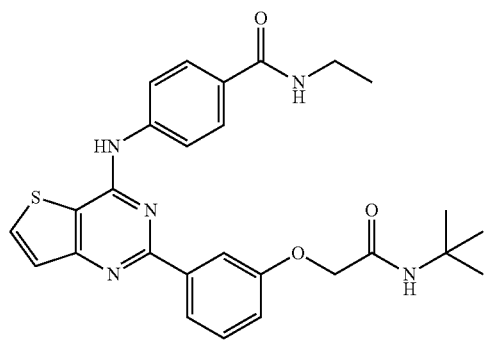 [SMILES: CCNC(=O)c1ccc(Nc2nc(-c3cccc(OCC(=O)NC(C)(C)C)c3)nc3ccsc23)cc1]

$^1$H NMR (500 MHz, DMSO-d$_6$) δ 10.08 (s, 1H), 8.42 (t, J=5.6 Hz, 1H), 8.33 (d, J=5.4 Hz, 1H), 8.06-7.99 (m, 4H), 7.97-7.91 (m, 2H), 7.56 (d, J=5.2 Hz, 2H), 7.46 (t, J=7.9 Hz, 1H), 7.09 (dd, J=8.3, 2.6 Hz, 1H), 4.52 (s, 2H), 3.36-3.23 (m, 2H), 1.32 (s, 9H), 1.15 (t, J=7.2 Hz, 3H). MS (ES+) m/e 504 (M+H)$^+$.

Example 58

N-(tert-Butyl)-2-(3-(4-((1-oxoisoindolin-5-yl)amino)thieno[3,2-d]pyrimidin-2-yl)phenoxy)acetamide

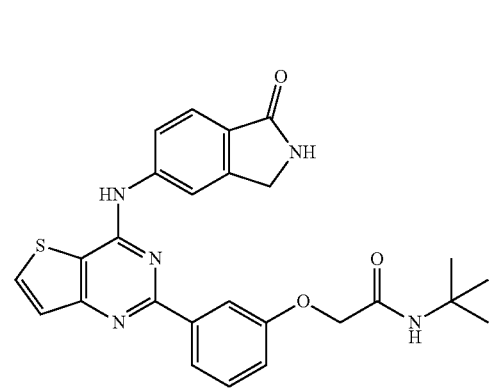 [SMILES: CC(C)(C)NC(=O)COc1cccc(-c2nc(Nc3ccc4c(c3)CNC4=O)c3sccc3n2)c1]

$^1$H NMR (500 MHz, DMSO-d$_6$) δ 10.15 (s, 1H), 8.48 (s, 1H), 8.33 (d, J=5.4 Hz, 1H), 8.24 (d, J=1.7 Hz, 1H), 8.05-7.99 (m, 2H), 7.96 (dd, J=8.3, 1.8 Hz, 1H), 7.73 (d, J=8.2 Hz, 1H), 7.59-7.53 (m, 2H), 7.46 (t, J=7.9 Hz, 1H), 7.10 (dd, J=8.3, 2.6 Hz, 1H), 4.51 (s, 2H), 4.46 (s, 2H), 1.31 (s, 9H). MS (ES+) m/e 488 (M+H)$^+$.

Example 59

2-(3-(4-((6-Aminopyridin-3-yl)amino)-5,7-dihydrofuro[3,4-d]pyrimidin-2-yl) phenoxy)-N-(tert-butyl)acetamide

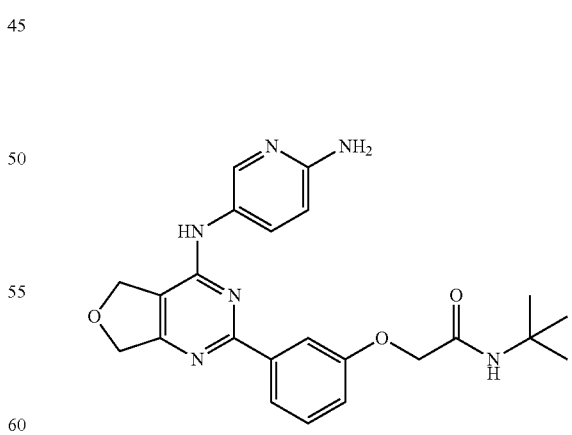

MS (ES+) m/e 435 (M+H)$^+$.

Example 60

N-(tert-Butyl)-2-(3-(6-methoxy-4-((4,5,6,7-tetra-hydro-1H-indazol-5-yl)amino) quinazolin-2-yl)phenoxy)acetamide

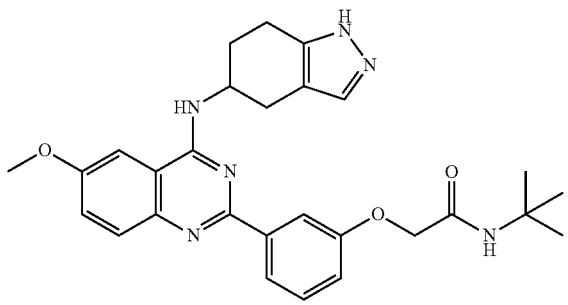 [SMILES: COc1ccc2nc(-c3cccc(OCC(=O)NC(C)(C)C)c3)nc(NC3CCc4[nH]ncc4C3)c2c1]

MS (ES+) m/e 501 (M+H)⁺.

Example 61

6-Methoxy-2-(3-(3-morpholinopropoxy)phenyl)-N-(4,5,6,7-tetrahydro-1H-indazol-5-yl)quinazolin-4-amine

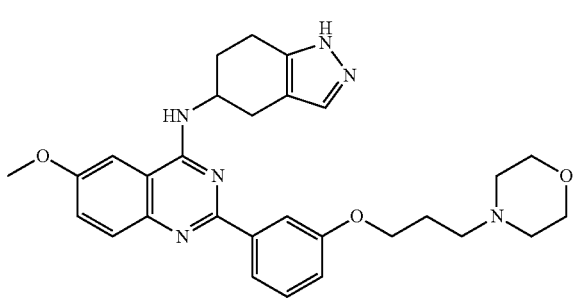 [SMILES: COc1ccc2nc(-c3cccc(OCCCN4CCOCC4)c3)nc(NC3CCc4[nH]ncc4C3)c2c1]

MS (ES+) m/e 515 (M+H).

Example 62

5-((2-(3-(3-Morpholinopropoxy)phenyl)thieno[3,2-d]pyrimidin-4-yl)amino)pyridin-2(1H)-one

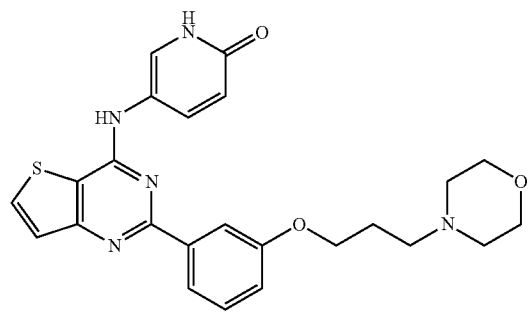 [SMILES: O=c1ccc(Nc2nc(-c3cccc(OCCCN4CCOCC4)c3)nc3ccsc23)c[nH]1]

MS (ES+) m/e 464 (M+H)⁺.

Example 63

N5-(2-(3-(3-Morpholinopropoxy)phenyl)thieno[3,2-d]pyrimidin-4-yl)pyrimidine-2,5-diamine

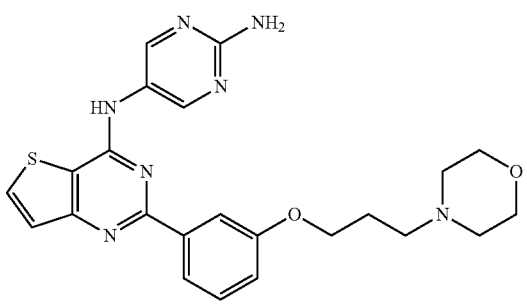 [SMILES: Nc1ncc(Nc2nc(-c3cccc(OCCCN4CCOCC4)c3)nc3ccsc23)cn1]

MS (ES+) m/e 464 (M+H)⁺.

Example 64

N-Ethyl-4-((2-(3-(3-morpholinopropoxy)phenyl)thieno[3,2-d]pyrimidin-4-yl)amino)benzamide

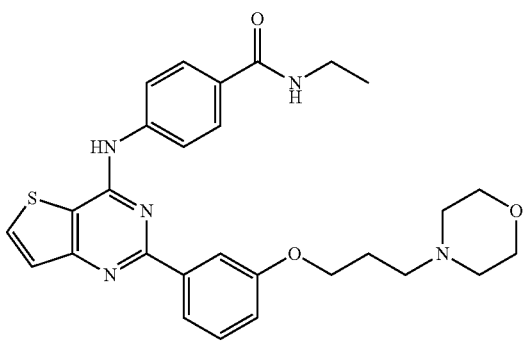 [SMILES: CCNC(=O)c1ccc(Nc2nc(-c3cccc(OCCCN4CCOCC4)c3)nc3ccsc23)cc1]

MS (ES+) m/e 518 (M+H)⁺.

Example 65

5-((2-(3-(3-Morpholinopropoxy)phenyl)thieno[3,2-d]pyrimidin-4-yl)amino) isoindolin-1-one

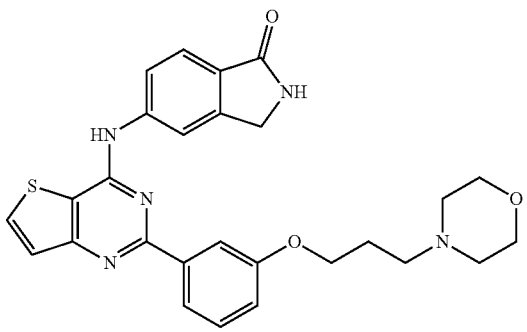 [SMILES: O=C1NCc2cc(Nc3nc(-c4cccc(OCCCN5CCOCC5)c4)nc4ccsc34)ccc21]

MS (ES+) m/e 502 (M+H)⁺.

Example 66

4-((2-(3-(2-Oxo-2-(tert-pentylamino)ethoxy)phenyl)thieno[3,2-d]pyrimidin-4-yl)amino)benzamide

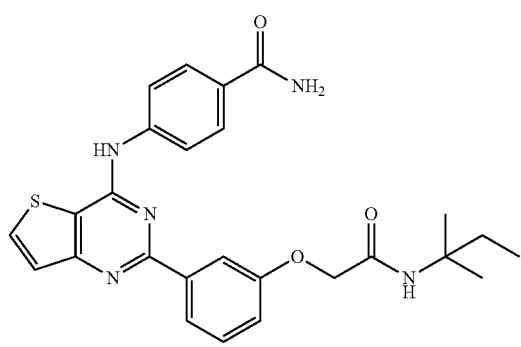 [SMILES: CCC(C)(C)NC(=O)COc1cccc(-c2nc(Nc3ccc(C(N)=O)cc3)c3sccc3n2)c1]

MS (ES+) m/e 490 (M+H)+.

Example 67

2-(3-(4-((6-Oxo-1,6-dihydropyridin-3-yl)amino)thieno[3,2-d]pyrimidin-2-yl) phenoxy)-N-(tert-pentyl)acetamide

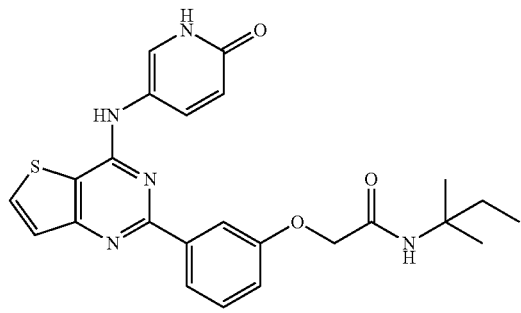 [SMILES: CCC(C)(C)NC(=O)COc1cccc(-c2nc(Nc3ccc(=O)[nH]c3)c3sccc3n2)c1]

¹H NMR (500 MHz, DMSO-d₆) δ 9.83 (s, 1H), 8.64 (s, 2H), 8.29 (d, J=5.4 Hz, 1H), 7.96-7.85 (m, 2H), 7.52 (d, J=5.4 Hz, 1H), 7.46-7.37 (m, 2H), 7.06 (dd, J=8.4, 2.6 Hz, 1H), 4.51 (s, 2H), 1.68 (q, J=7.4 Hz, 2H), 1.25 (s, 6H), 0.78 (t, J=7.5 Hz, 3H). MS (ES+) m/e 464 (M+H)+.

Example 68

2-(3-(4-((6-Morpholinopyridin-3-yl)amino)thieno[3,2-d]pyrimidin-2-yl) phenoxy)-N-(tert-pentyl)acetamide

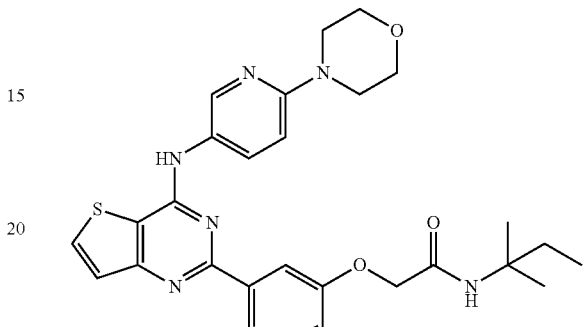

¹H NMR (500 MHz, DMSO-d₆) δ 9.93 (s, 1H), 8.56 (s, 1H), 8.28 (d, J=5.4 Hz, 1H), 8.10 (s, 1H), 7.99-7.91 (m, 2H), 7.52 (d, J=5.4 Hz, 1H), 7.47-7.35 (m, 2H), 7.16-7.04 (m, 2H), 4.51 (s, 2H), 3.76 (t, J=4.9 Hz, 4H), 3.51 (t, J=4.8 Hz, 4H), 1.68 (q, J=7.4 Hz, 2H), 1.25 (s, 6H), 0.78 (t, J=7.5 Hz, 3H). MS (ES+) m/e 533 (M+H)+.

Example 69

N-Methyl-4-((2-(3-(2-oxo-2-(tert-pentylamino)ethoxy)phenyl)thieno[3,2-d]pyrimidin-4-yl)amino)benzamide

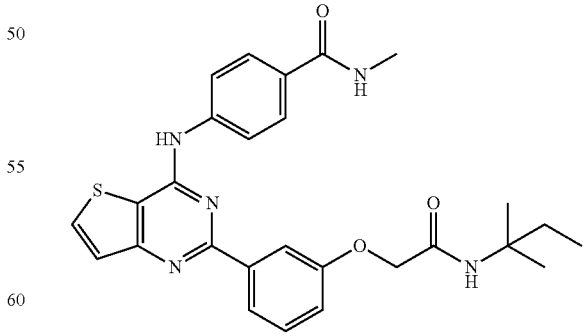

MS (ES+) m/e 504 (M+H)+.

Example 70

2-(3-(4-((2-Oxoindolin-5-yl)amino)thieno[3,2-d]pyrimidin-2-yl)phenoxy)-N-(tert-pentyl)acetamide

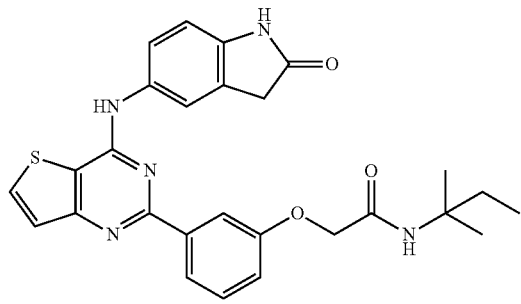 [SMILES: CCC(C)(C)NC(=O)COc1cccc(-c2nc(Nc3ccc4c(c3)CC(=O)N4)c3sccc3n2)c1]

MS (ES+) m/e 502 (M+H)+.

Example 71

2-(3-(4-((1H-Pyrazolo[3,4-b]pyridin-5-yl)amino)thieno[3,2-d]pyrimidin-2-yl) phenoxy)-N-(tert-pentyl)acetamide

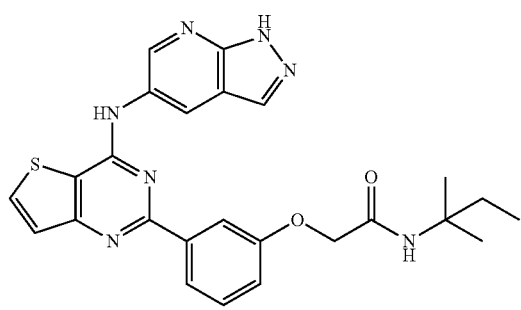 [SMILES: CCC(C)(C)NC(=O)COc1cccc(-c2nc(Nc3cnc4[nH]ncc4c3)c3sccc3n2)c1]

MS (ES+) m/e 488 (M+H)+.

Example 72

N-(tert-Butyl)-2-(3-(4-((6-(methylamino)pyridin-3-yl)amino)thieno[3,2-d]pyrimidin-2-yl)phenoxy)acetamide

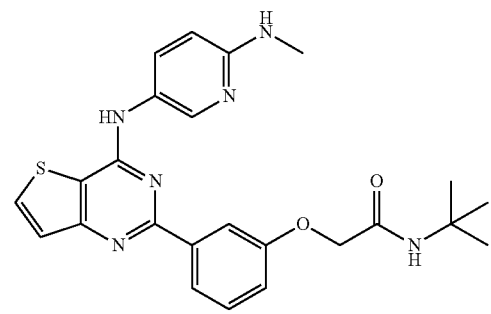 [SMILES: CNc1ccc(Nc2nc(-c3cccc(OCC(=O)NC(C)(C)C)c3)nc3ccsc23)cn1]

MS (ES+) m/e 463 (M+H)+.

Example 73

N-(tert-Butyl)-2-(3-(4-((4-morpholinophenyl)amino)-5,7-dihydrofuro[3,4-d]pyrimidin-2-yl)phenoxy)acetamide

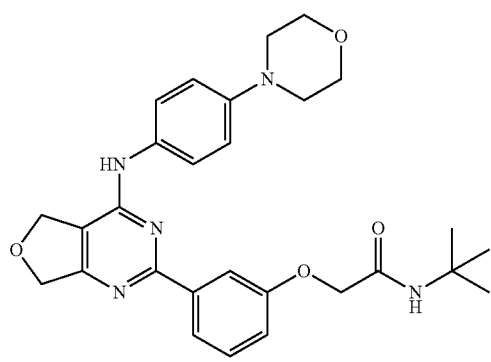 [SMILES: CC(C)(C)NC(=O)COc1cccc(-c2nc3c(c(Nc4ccc(N5CCOCC5)cc4)n2)COC3)c1]

MS (ES+) m/e 504 (M+H)+.

Example 74

4-((2-(3-(2-(tert-Butylamino)-2-oxoethoxy)phenyl)quinazolin-4-yl)amino)-N-methylbenzamide

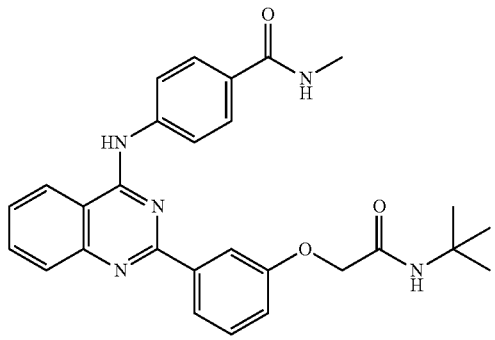 [SMILES: CNC(=O)c1ccc(Nc2nc(-c3cccc(OCC(=O)NC(C)(C)C)c3)nc3ccccc23)cc1]

$^1$H NMR (500 MHz, DMSO-$d_6$) δ 8.66 (d, J=8.3 Hz, 1H), 8.45 (q, J=4.3 Hz, 1H), 8.10-7.87 (m, 8H), 7.73 (t, J=7.4 Hz, 1H), 7.59 (s, 1H), 7.50 (t, J=7.9 Hz, 1H), 7.15 (dd, J=8.6, 2.5 Hz, 1H), 4.53 (s, 2H), 2.82 (d, J=4.5 Hz, 3H), 1.32 (s, 9H). MS (ES+) m/e 484 (M+H)+.

Example 75

4-((2-(3-(2-(tert-Butylamino)-2-oxoethoxy)phenyl)-6-ethoxyquinazolin-4-yl)amino)-N-methylbenzamide

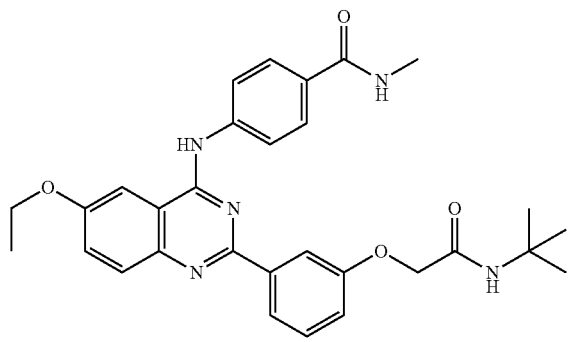 [SMILES: CCOc1ccc2nc(-c3cccc(OCC(=O)NC(C)(C)C)c3)nc(Nc3ccc(C(=O)NC)cc3)c2c1]

MS (ES+) m/e 528 (M+H)+.

Example 76

N-(tert-Butyl)-2-(3-(4,5-dimethyl-6-((6-morpholinopyridin-3-yl)amino)pyrimidin-2-yl)phenoxy)acetamide

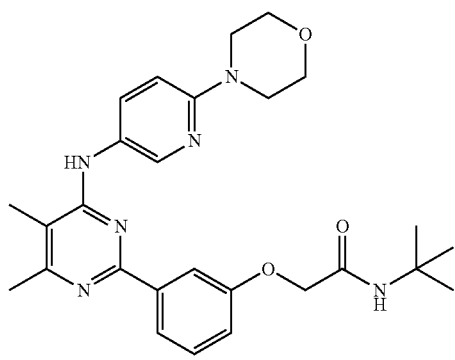 [SMILES: Cc1nc(-c2cccc(OCC(=O)NC(C)(C)C)c2)nc(Nc2ccc(N3CCOCC3)nc2)c1C]

MS (ES+) m/e 491 (M+H)+.

Example 77

N-(tert-Butyl)-2-(3-(6-((6-morpholinopyridin-3-yl)amino)pyrimidin-4-yl) phenoxy)acetamide

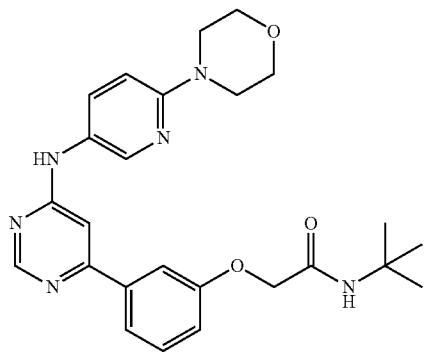 [SMILES: CC(C)(C)NC(=O)COc1cccc(-c2cc(Nc3ccc(N4CCOCC4)nc3)ncn2)c1]

MS (ES+) m/e 463 (M+H)+.

Example 78

N-(tert-Butyl)-2-(3-(4-((6-morpholinopyridin-3-yl)amino)quinazolin-2-yl) phenoxy)acetamide

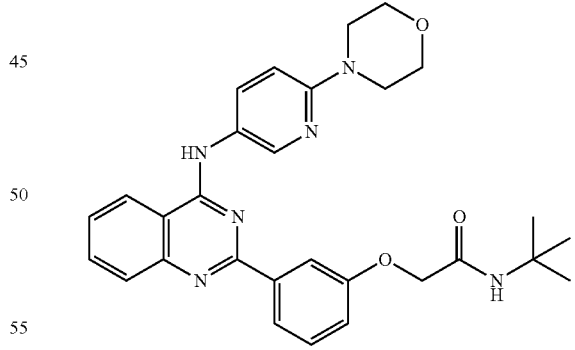

$^1$H NMR (500 MHz, DMSO-$d_6$) δ 8.67-8.53 (m, 2H), 8.13 (d, J=9.5 Hz, 1H), 8.04-7.87 (m, 4H), 7.74 (s, 1H), 7.60 (s, 1H), 7.51 (t, J=8.1 Hz, 1H), 7.18 (d, J=8.2 Hz, 1H), 7.09 (d, J=9.3 Hz, 1H), 4.51 (s, 2H), 3.76 (t, J=4.8 Hz, 4H), 3.52 (t, J=4.8 Hz, 4H), 1.31 (s, 9H). MS (ES+) m/e 513 (M+H)+.

Example 79

N-(tert-Butyl)-2-(3-(6-ethoxy-4-((6-morpholinopyridin-3-yl)amino)quinazolin-2-yl)phenoxy)acetamide

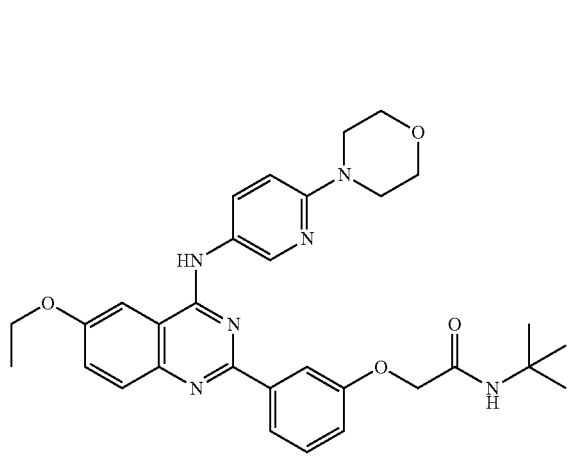 [SMILES: CCOc1ccc2nc(-c3cccc(OCC(=O)NC(C)(C)C)c3)nc(Nc3ccc(N4CCOCC4)nc3)c2c1]

¹H NMR (500 MHz, DMSO-d₆) δ 11.69 (s, 1H), 8.64 (s, 1H), 8.42 (s, 1H), 8.28 (d, J=12.0 Hz, 2H), 8.01-7.92 (m, 2H), 7.72 (dd, J=9.2, 2.5 Hz, 1H), 7.66 (s, 1H), 7.56 (t, J=8.0 Hz, 1H), 7.26 (d, J=8.0 Hz, 2H), 4.56 (s, 2H), 4.31 (q, J=7.0 Hz, 2H), 3.78 (t, J=4.7 Hz, 4H), 3.63 (t, J=4.8 Hz, 4H), 1.45 (t, J=6.9 Hz, 3H), 1.30 (s, 9H). MS (ES+) m/e 557 (M+H)⁺.

Example 80

4-((2-(3-(2-(tert-Butylamino)-2-oxoethoxy)phenyl)pyrimidin-4-yl)amino)-N-methylbenzamide

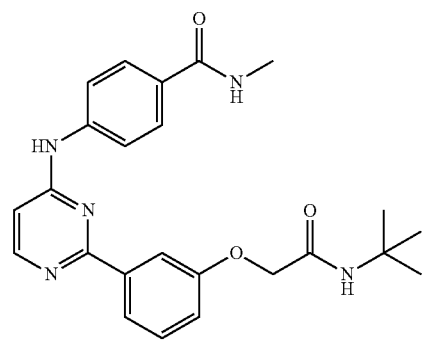 [SMILES: CNC(=O)c1ccc(Nc2ccnc(-c3cccc(OCC(=O)NC(C)(C)C)c3)n2)cc1]

MS (ES+) m/e 434 (M+H)⁺.

Example 81

N-(tert-Butyl)-2-(3-(4-((6-morpholinopyridin-3-yl)amino)pyrimidin-2-yl) phenoxy)acetamide

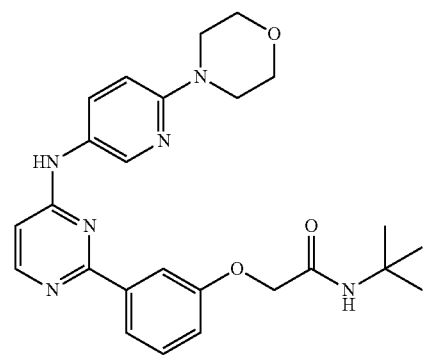 [SMILES: CC(C)(C)NC(=O)COc1cccc(-c2nccc(Nc3ccc(N4CCOCC4)nc3)n2)c1]

MS (ES+) m/e 463 (M+H)⁺.

Example 82

2-(3-(3-Morpholinopropoxy)phenyl)-N-(6-morpholinopyridin-3-yl)thieno[3,2-d]pyrimidin-4-amine

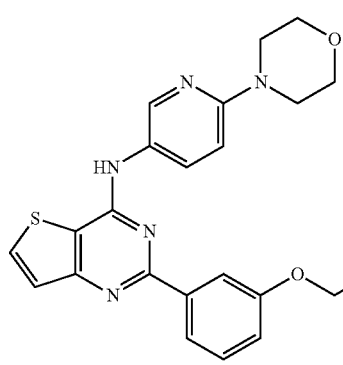

MS (ES+) m/e 533 (M+H)⁺.

Example 83

N-Ethyl-4-((2-(3-(3-morpholinopropoxy)phenyl)thieno[3,2-d]pyrimidin-4-yl)amino)benzamide

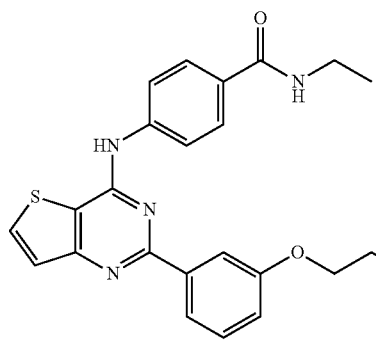

¹H NMR (500 MHz, DMSO-d₆) δ 10.07 (s, 1H), 9.71 (s, 1H), 8.44 (t, J=5.6 Hz, 1H), 8.33 (d, J=5.4 Hz, 1H), 8.07-8.00 (m, 3H), 7.94 (d, J=8.4 Hz, 1H), 7.57 (d, J=5.4 Hz, 1H), 7.47 (t, J=7.9 Hz, 1H), 7.10 (dd, J=8.2, 2.4 Hz, 1H), 4.19 (t, J=6.0 Hz, 2H), 4.07-3.96 (m, 3H), 3.67 (t, J=12.3 Hz, 2H), 3.54 (d, J=12.6 Hz, 2H), 3.34 (dp, J=27.3, 7.1, 6.1 Hz, 3H), 3.14 (d, J=11.5 Hz, 2H), 2.21 (dq, J=12.0, 6.3 Hz, 2H), 1.15 (t, J=7.2 Hz, 32H). MS (ES+) m/e 518 (M+H)⁺.

Example 84

5-((2-(3-(3-Morpholinopropoxy)phenyl)thieno[3,2-d]pyrimidin-4-yl)amino) isoindolin-1-one

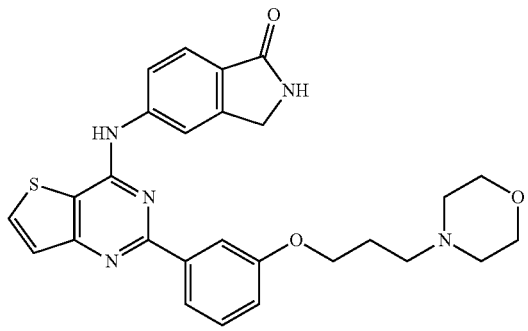 [SMILES: O=C1NCc2cc(Nc3nc(-c4cccc(OCCCN5CCOCC5)c4)nc4ccsc34)ccc21]

MS (ES+) m/e 502 (M+H)⁺.

Example 85

N2-Methyl-N5-(2-(3-(3-morpholinopropoxy)phenyl)thieno[3,2-d]pyrimidin-4-yl)pyridine-2,5-diamine

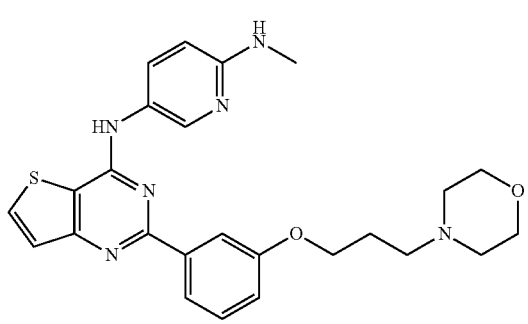 [SMILES: CNc1ccc(Nc2nc(-c3cccc(OCCCN4CCOCC4)c3)nc3ccsc23)cn1]

MS (ES+) m/e 477 (M+H)⁺.

Example 86

4-((2-(3-(2-(tert-Butylamino)-2-oxoethoxy)phenyl)-5-methoxypyrimidin-4-yl)amino)-N-methylbenzamide

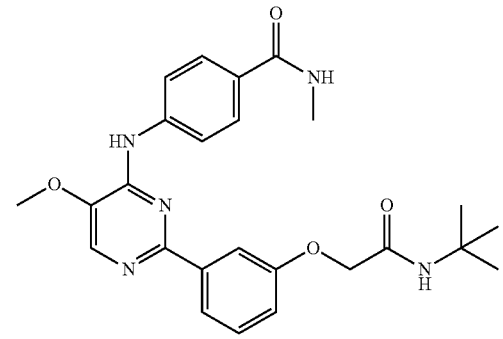 [SMILES: CNC(=O)c1ccc(Nc2nc(-c3cccc(OCC(=O)NC(C)(C)C)c3)ncc2OC)cc1]

MS (ES+) m/e 464 (M+H)⁺.

Example 87

N-(tert-Butyl)-2-(3-(5-methoxy-4-((6-morpholinopyridin-3-yl)amino)pyrimidin-2-yl)phenoxy)acetamide

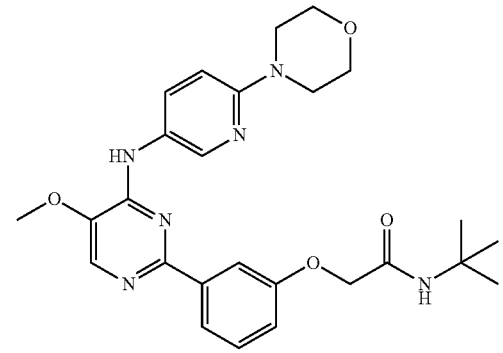 [SMILES: COc1cnc(-c2cccc(OCC(=O)NC(C)(C)C)c2)nc1Nc1ccc(N2CCOCC2)nc1]

MS (ES+) m/e 493 (M+H)⁺.

Example 88

N-Isopropyl-2-(3-(4-((6-morpholinopyridin-3-yl)amino)thieno[3,2-d]pyrimidin-2-yl)phenoxy)acetamide

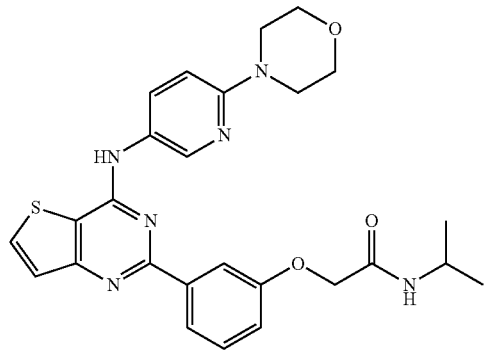

MS (ES+) m/e 505 (M+H)+.

Example 89

5-((2-(3-(3-Morpholinopropoxy)phenyl)thieno[3,2-d]pyrimidin-4-yl)amino)pyridin-2(1H)-one

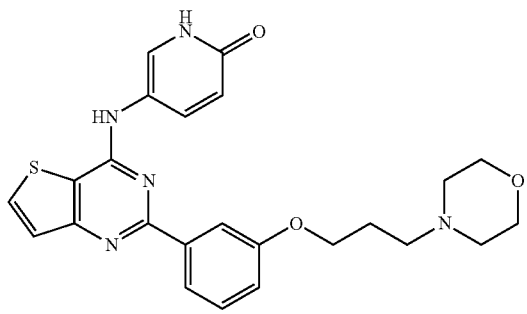 [SMILES: O=c1ccc(Nc2nc(-c3cccc(OCCCN4CCOCC4)c3)nc3ccsc23)c[nH]1]

MS (ES+) m/e 464 (M+H)+.

Example 90

2-(3-(3-Morpholinopropoxy)phenyl)-N-(6-(piperazin-1-yl)pyridin-3-yl)thieno[3,2-d]pyrimidin-4-amine

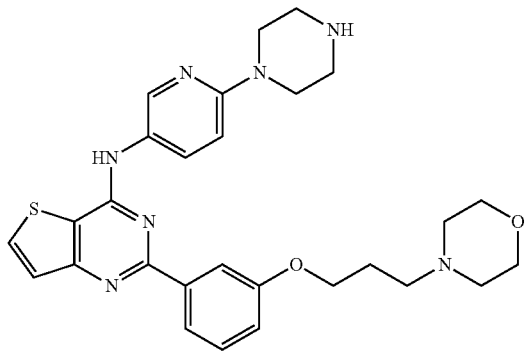 [SMILES: c1cc(OCCCN2CCOCC2)cc(-c2nc(Nc3ccc(N4CCNCC4)nc3)c3sccc3n2)c1]

MS (ES+) m/e 532 (M+H)+.

Example 91

4-(4-((2-(3-(3-Morpholinopropoxy)phenyl)thieno[3,2-d]pyrimidin-4-yl)amino)phenyl)piperazin-2-one

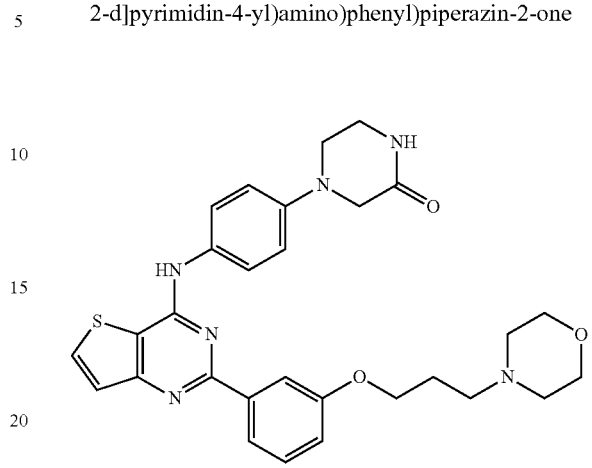

MS (ES+) m/e 545 (M+H)+.

Example 92

2-(3-(3-Morpholinopropoxy)phenyl)-N-(1H-pyrazolo[3,4-b]pyridin-5-yl) thieno[3,2-d]pyrimidin-4-amine

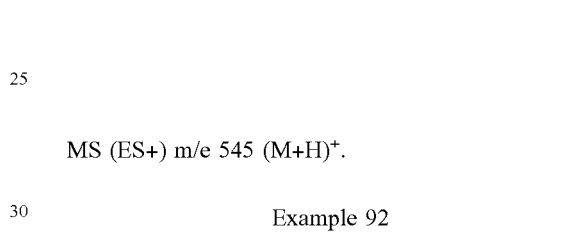

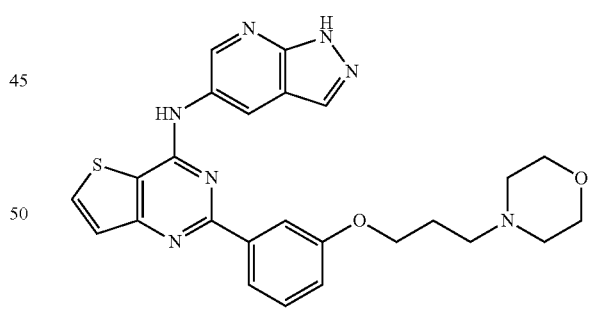

$^1$H NMR (500 MHz, DMSO-$d_6$) δ 13.71 (s, 1H), 10.08 (s, 1H), 9.69 (s, 1H), 8.86 (d, J=2.4 Hz, 1H), 8.61 (d, J=2.3 Hz, 1H), 8.29 (d, J=5.4 Hz, 1H), 8.22 (s, 1H), 8.00-7.91 (m, 2H), 7.55 (d, J=5.4 Hz, 1H), 7.43 (t, J=7.9 Hz, 1H), 7.06 (dd, J=8.1, 2.6 Hz, 1H), 4.13 (t, J=5.9 Hz, 2H), 4.02 (dd, J=12.8, 3.3 Hz, 2H), 3.66 (t, J=12.3 Hz, 2H), 3.51 (d, J=12.3 Hz, 2H), 3.32 (p, J=5.0 Hz, 2H), 3.20-3.05 (m, 2H), 2.17 (dq, J=11.7, 6.0 Hz, 2H). MS (ES+) m/e 488 (M+H)+.

Example 93

N-Isopropyl-2-(3-(4-(((6-morpholinopyridin-3-yl)amino)quinazolin-2-yl) phenoxy)acetamide

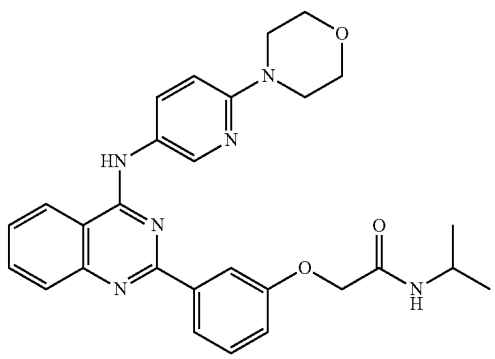 [SMILES: CC(C)NC(=O)COc1cccc(-c2nc(Nc3ccc(N4CCOCC4)nc3)c3ccccc3n2)c1]

$^1$H NMR (500 MHz, DMSO-d$_6$) δ 10.67 (s, 1H), 8.60 (dd, J=9.6, 5.3 Hz, 2H), 8.14 (d, J=9.0 Hz, 1H), 8.05-7.86 (m, 5H), 7.76 (s, 1H), 7.53 (t, J=8.0 Hz, 1H), 7.22 (d, J=8.3 Hz, 1H), 7.11 (d, J=9.2 Hz, 1H), 4.54 (s, 2H), 3.98 (dp, J=8.1, 6.5 Hz, 1H), 3.80-3.70 (m, 4H), 3.53 (t, J=4.9 Hz, 4H), 1.11 (d, J=6.6 Hz, 6H). MS (ES+) m/e 499 (M+H)$^+$.

Example 94

2-(3-(6-Ethoxy-4-(((6-morpholinopyridin-3-yl)amino)quinazolin-2-yl)phenoxy)-N-isopropylacetamide

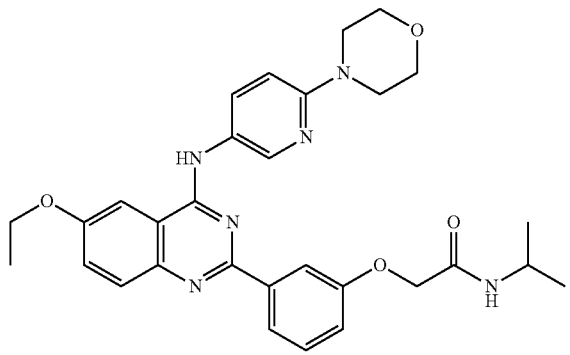 [SMILES: CCOc1ccc2nc(-c3cccc(OCC(=O)NC(C)C)c3)nc(Nc3ccc(N4CCOCC4)nc3)c2c1]

MS (ES+) m/e 543 (M+H)$^+$.

Example 95

4-((2-(3-(2-(Isopropylamino)-2-oxoethoxy)phenyl)thieno[3,2-d]pyrimidin-4-yl)amino)benzamide

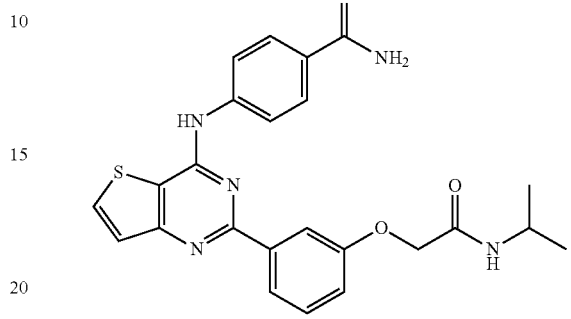

$^1$H NMR (500 MHz, DMSO-d$_6$) δ 10.11 (s, 1H), 8.33 (d, J=5.4 Hz, 1H), 8.07-7.91 (m, 8H), 7.57 (d, J=5.4 Hz, 1H), 7.47 (t, J=8.1 Hz, 1H), 7.31 (s, 1H), 7.14-7.06 (m, 1H), 4.55 (s, 3H), 3.99 (dp, J=8.1, 6.5 Hz, 1H), 1.11 (d, J=6.6 Hz, 6H). MS (ES+) m/e 462 (M+H)$^+$.

Example 96

4-((2-(3-(2-(Isopropylamino)-2-oxoethoxy)phenyl)thieno[3,2-d]pyrimidin-4-yl)amino)-N-methylbenzamide

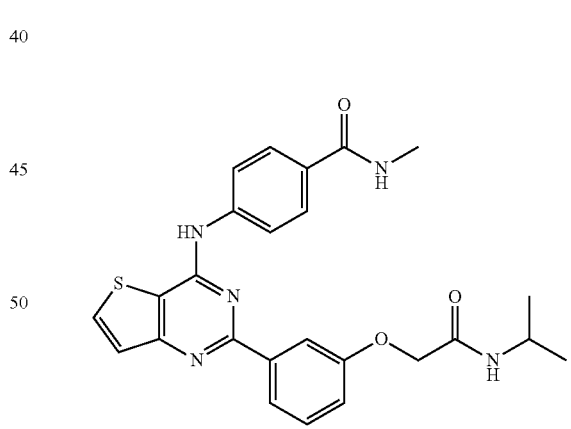

$^1$H NMR (500 MHz, DMSO-d$_6$) δ 10.09 (s, 1H), 8.40 (d, J=4.7 Hz, 1H), 8.33 (d, J=5.3 Hz, 1H), 8.08-7.96 (m, 5H), 7.92 (d, J=8.5 Hz, 2H), 7.57 (d, J=5.3 Hz, 1H), 7.46 (t, J=8.1 Hz, 1H), 7.10 (dd, J=8.4, 2.5 Hz, 1H), 6.36 (ddd, J=12.7, 5.6, 2.4 Hz, 1H), 4.55 (s, 2H), 3.97 (tq, J=13.8, 6.8 Hz, 1H), 2.81 (d, J=4.4 Hz, 3H), 1.11 (d, J=6.6 Hz, 6H). MS (ES+) m/e 476 (M+H)$^+$.

Example 97

N-Ethyl-4-((2-(3-(2-(isopropylamino)-2-oxoethoxy)phenyl)thieno[3,2-d]pyrimidin-4-yl)amino)benzamide

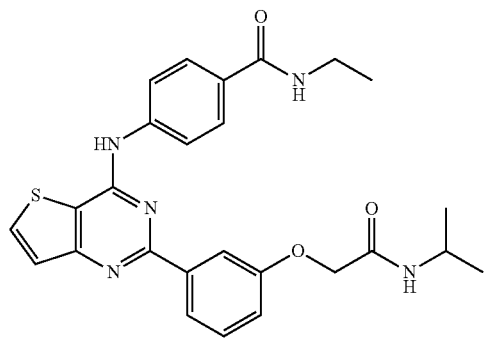 [SMILES: CCNC(=O)c1ccc(Nc2nc(-c3cccc(OCC(=O)NC(C)C)c3)nc3ccsc23)cc1]

MS (ES+) m/e 490 (M+H)+.

Example 98

N-Isopropyl-2-(3-(4-((1-oxoisoindolin-5-yl)amino)thieno[3,2-d]pyrimidin-2-yl) phenoxy)acetamide

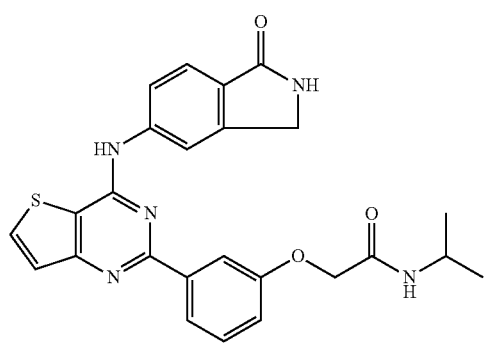 [SMILES: CC(C)NC(=O)COc1cccc(-c2nc(Nc3ccc4c(c3)CNC4=O)c3sccc3n2)c1]

$^1$H NMR (500 MHz, DMSO-$d_6$) δ 10.11 (s, 1H), 8.47 (s, 1H), 8.33 (d, J=5.4 Hz, 1H), 8.28 (d, J=1.7 Hz, 1H), 8.07-8.02 (m, 2H), 7.99 (d, J=8.1 Hz, 1H), 7.94 (dd, J=8.3, 1.8 Hz, 1H), 7.72 (d, J=8.2 Hz, 1H), 7.57 (d, J=5.4 Hz, 1H), 7.47 (t, J=8.1 Hz, 1H), 7.15-7.07 (m, 1H), 4.54 (s, 2H), 4.46 (s, 2H), 3.99 (dp, J=8.1, 6.5 Hz, 1H), 1.11 (d, J=6.6 Hz, 6H). MS (ES+) m/e 474 (M+H)+.

Example 99

N-(tert-Butyl)-2-(3-(4-((2-oxo-1,2-dihydropyridin-4-yl)amino)-7,8-dihydro-5H-pyrano[4,3-d]pyrimidin-2-yl)phenoxy)acetamide

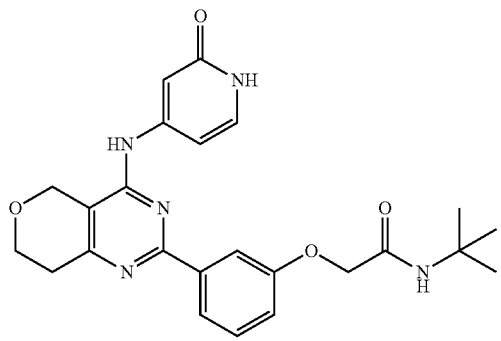 [SMILES: CC(C)(C)NC(=O)COc1cccc(-c2nc3c(c(Nc4cc[nH]c(=O)c4)n2)COCC3)c1]

MS (ES+) m/e 450 (M+H)+.

Example 100

N-(tert-Butyl)-2-(3-(4-((6-oxo-1,6-dihydropyridin-3-yl)amino)-7,8-dihydro-5H-pyrano[4,3-d]pyrimidin-2-yl)phenoxy)acetamide

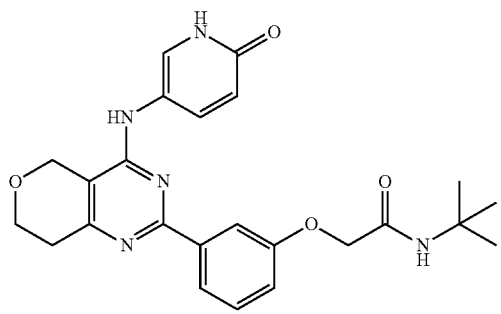 [SMILES: CC(C)(C)NC(=O)COc1cccc(-c2nc3c(c(Nc4ccc(=O)[nH]c4)n2)COCC3)c1]

MS (ES+) m/e 450 (M+H)+.

Example 101

N-(tert-Butyl)-2-(3-(5-methoxy-4-((6-oxo-1,6-dihydropyridin-3-yl)amino)pyrimidin-2-yl)phenoxy)acetamide

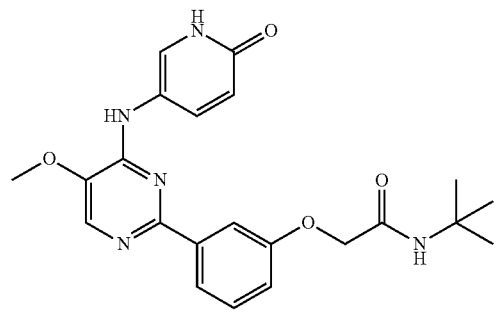 [SMILES: COc1cnc(-c2cccc(OCC(=O)NC(C)(C)C)c2)nc1Nc1ccc(=O)[nH]c1]

MS (ES+) m/e 424 (M+H)+.

Example 102

N-(tert-Butyl)-2-(3-(4-((tetrahydro-2H-pyran-4-yl)amino)thieno[3,2-d]pyrimidin-2-yl)phenoxy)acetamide

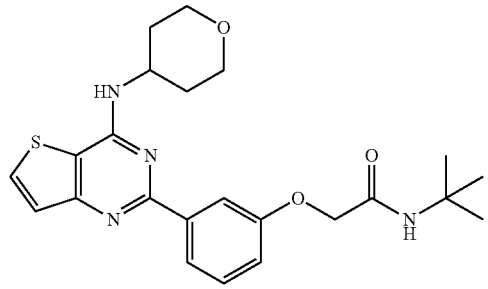 [SMILES: CC(C)(C)NC(=O)COc1cccc(-c2nc(NC3CCOCC3)c3sccc3n2)c1]

MS (ES+) m/e 441 (M+H)+.

Example 103

N-(tert-Butyl)-2-(3-(4-((tetrahydro-2H-pyran-4-yl)amino)quinazolin-2-yl) phenoxy)acetamide

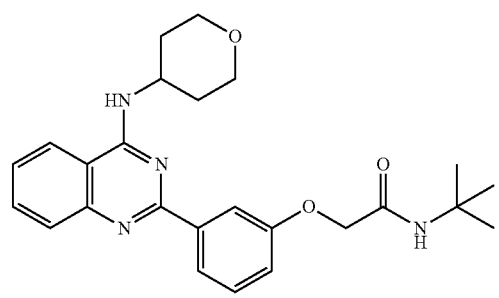 [SMILES: CC(C)(C)NC(=O)COc1cccc(-c2nc(NC3CCOCC3)c3ccccc3n2)c1]

MS (ES+) m/e 434 (M+H)+.

Example 104

4-((2-(3-(3-Morpholinopropoxy)phenyl)quinazolin-4-yl)amino)pyridin-2(1H)-one

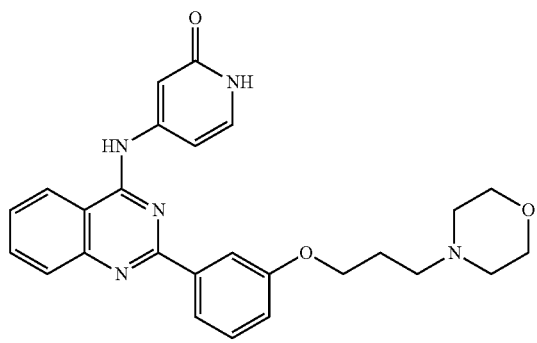 [SMILES: O=c1cc(Nc2nc(-c3cccc(OCCCN4CCOCC4)c3)nc3ccccc23)cc[nH]1]

MS (ES+) m/e 458 (M+H)+.

Example 105

5-((2-(3-(3-Morpholinopropoxy)phenyl)quinazolin-4-yl)amino)pyridin-2(1H)-one

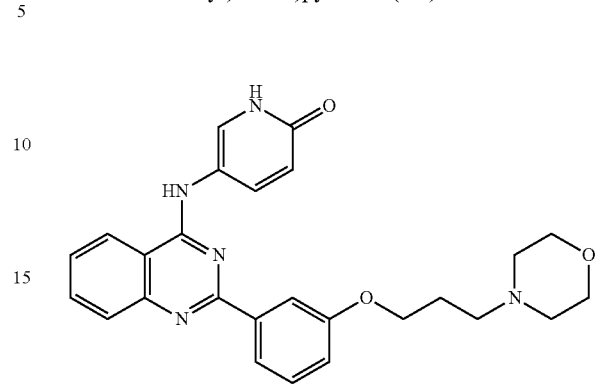

MS (ES+) m/e 458 (M+H)+.

Example 106

2-(3-(3-Morpholinopropoxy)phenyl)-N-(1H-pyrazolo[3,4-b]pyridin-5-yl) quinazolin-4-amine

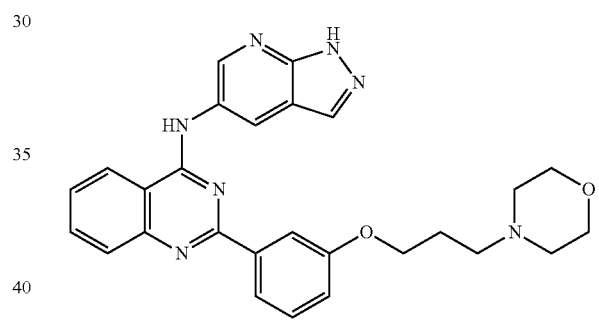

MS (ES+) m/e 482 (M+H)+.

Example 107

N-Ethyl-4-((2-(3-(3-morpholinopropoxy)phenyl)quinazolin-4-yl)amino)benzamide

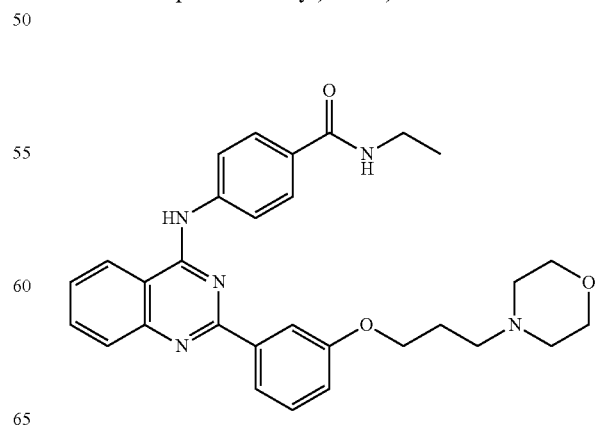

MS (ES+) m/e 512 (M+H)+.

Example 108

5-((2-(3-(3-Morpholinopropoxy)phenyl)quinazolin-4-yl)amino)isoindolin-1-one

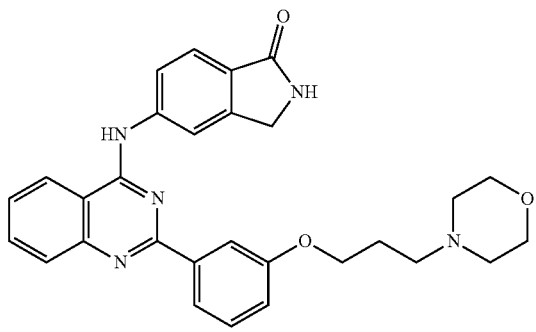 [SMILES: O=C1NCc2cc(Nc3nc(-c4cccc(OCCCN5CCOCC5)c4)nc4ccccc34)ccc21]

MS (ES+) m/e 496 (M+H)⁺.

Example 109

N-(tert-Butyl)-2-(3-(4-((2-oxo-1,2-dihydropyridin-4-yl)amino)quinazolin-2-yl) phenoxy)acetamide

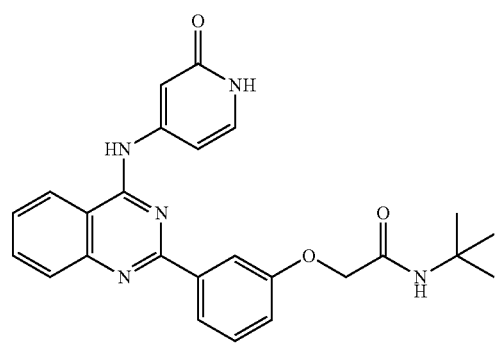 [SMILES: CC(C)(C)NC(=O)COc1cccc(-c2nc(Nc3cc[nH]c(=O)c3)c3ccccc3n2)c1]

MS (ES+) m/e 444 (M+H)⁺.

Example 110

N-(tert-Butyl)-2-(3-(4-((6-oxo-1,6-dihydropyridin-3-yl)amino)quinazolin-2-yl) phenoxy)acetamide

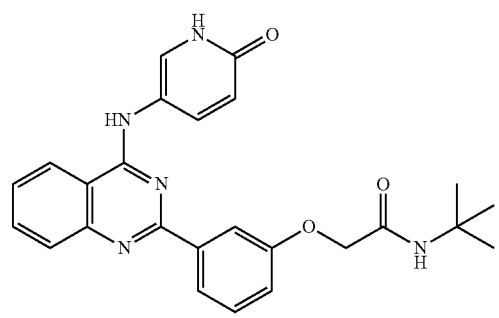 [SMILES: CC(C)(C)NC(=O)COc1cccc(-c2nc(Nc3ccc(=O)[nH]c3)c3ccccc3n2)c1]

MS (ES+) m/e 444 (M+H)⁺.

Example 111

2-(3-(4-((1H-Pyrazolo[3,4-b]pyridin-5-yl)amino)quinazolin-2-yl)phenoxy)-N-(tert-butyl)acetamide

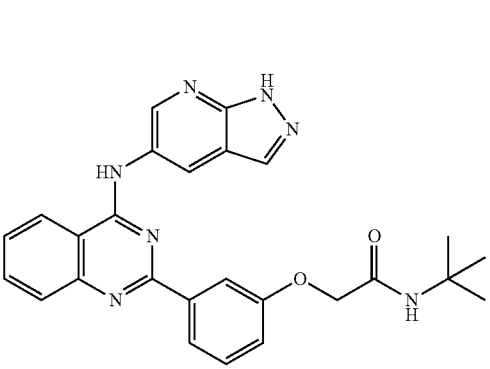 [SMILES: CC(C)(C)NC(=O)COc1cccc(-c2nc(Nc3cnc4[nH]ncc4c3)c3ccccc3n2)c1]

MS (ES+) m/e 468 (M+H)⁺.

Example 112

4-((2-(3-(2-(tert-Butylamino)-2-oxoethoxy)phenyl)quinazolin-4-yl)amino)-N-ethylbenzamide

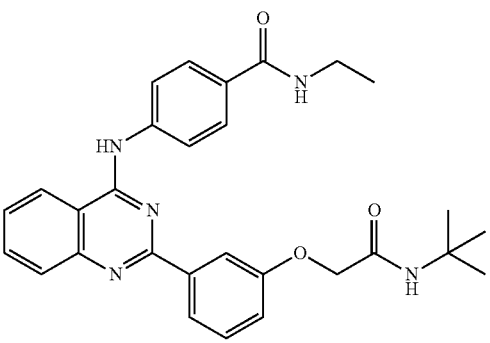 [SMILES: CCNC(=O)c1ccc(Nc2nc(-c3cccc(OCC(=O)NC(C)(C)C)c3)nc3ccccc23)cc1]

$^1$H NMR (500 MHz, DMSO-$d_6$) δ 10.41 (s, 1H), 8.66 (d, J=8.3 Hz, 1H), 8.48 (t, J=5.5 Hz, 1H), 8.16-7.89 (m, 8H), 7.73 (t, J=7.3 Hz, 1H), 7.59 (s, 1H), 7.51 (t, J=7.9 Hz, 1H), 7.20-7.08 (m, 1H), 4.54 (s, 2H), 3.41-3.18 (m, 2H), 1.32 (s, 9H), 1.16 (t, J=7.2 Hz, 3H). MS (ES+) m/e 498 (M+H)⁺.

Example 113

N-(tert-Butyl)-2-(3-(4-((1-oxoisoindolin-5-yl)amino)quinazolin-2-yl)phenoxy) acetamide

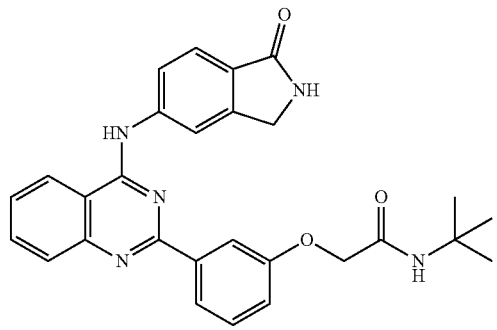 [SMILES: CC(C)(C)NC(=O)COc1cccc(-c2nc(Nc3ccc4c(c3)CNC4=O)c3ccccc3n2)c1]

¹H NMR (500 MHz, DMSO-d₆) δ 10.49 (s, 1H), 8.68 (d, J=8.4 Hz, 1H), 8.56 (s, 1H), 8.25 (s, 1H), 8.06-7.92 (m, 6H), 7.79 (d, J=8.2 Hz, 1H), 7.74 (t, J=7.2 Hz, 1H), 7.57 (s, 1H), 7.51 (t, J=7.9 Hz, 1H), 7.16 (dd, J=8.5, 2.6 Hz, 1H), 4.53 (s, 2H), 4.48 (s, 2H), 1.31 (s, 9H). MS (ES+) m/e 482 (M+H)⁺.

Example 114

5-((6-Ethoxy-2-(3-(2-(3-methylmorpholino)ethoxy)phenyl)quinazolin-4-yl)amino)isoindolin-1-one

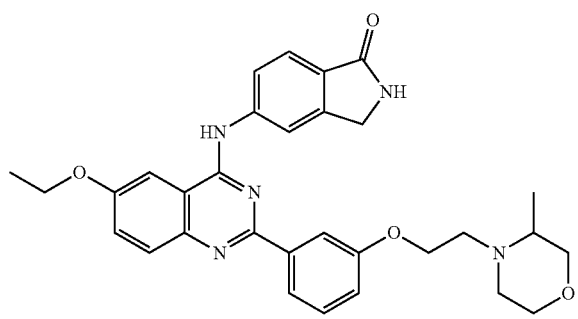 [SMILES: CCOc1ccc2nc(-c3cccc(OCCN4CCOCC4C)c3)nc(Nc3ccc4c(c3)CNC4=O)c2c1]

MS (ES+) m/e 540 (M+H)⁺.

Example 115

5-((6-Ethoxy-2-(3-(2-(3-methylmorpholino)ethoxy)phenyl)quinazolin-4-yl)amino)pyridin-2(1H)-one

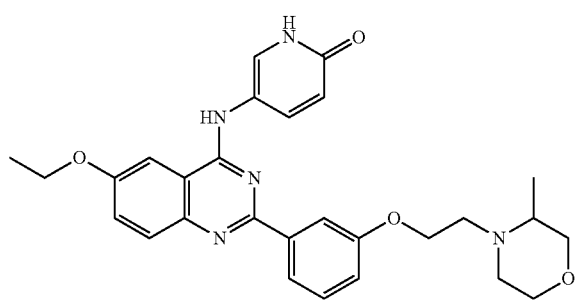 [SMILES: CCOc1ccc2nc(-c3cccc(OCCN4CCOCC4C)c3)nc(Nc3ccc(=O)[nH]c3)c2c1]

MS (ES+) m/e 502 (M+H)⁺.

Example 116

4-((6-Ethoxy-2-(3-(2-(3-methylmorpholino)ethoxy)phenyl)quinazolin-4-yl)amino)benzamide

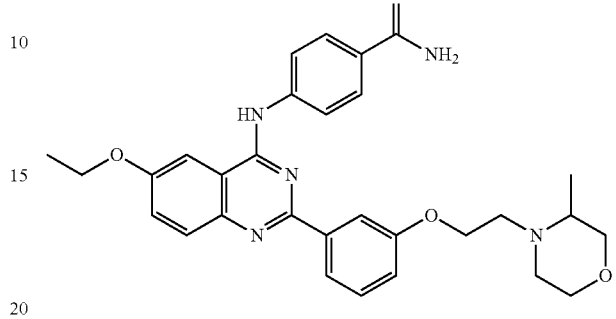

MS (ES+) m/e 528 (M+H)⁺.

Example 117

6-Ethoxy-2-(3-(2-(3-methylmorpholino)ethoxy)phenyl)-N-(1H-pyrazolo[3,4-b]pyridin-5-yl)quinazolin-4-amine

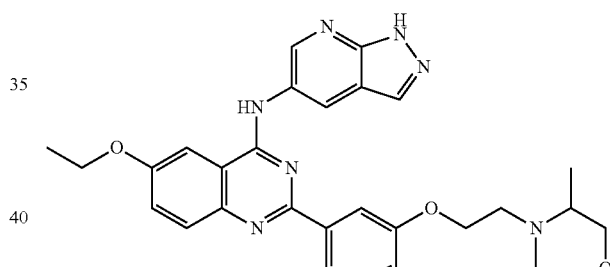

MS (ES+) m/e 526 (M+H)⁺.

Example 118

5-((6-Ethoxy-2-(3-(3-(3-methylmorpholino)propoxy)phenyl)quinazolin-4-yl)amino)pyridin-2(1H)-one

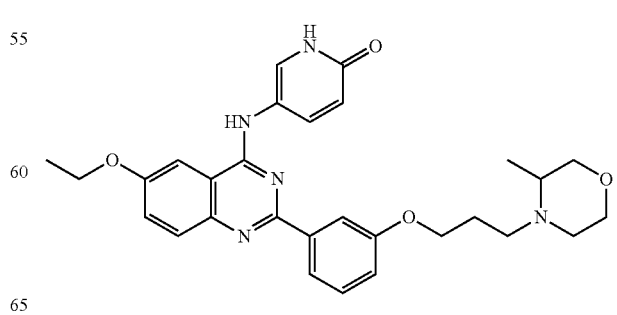

MS (ES+) m/e 516 (M+H)⁺.

Example 119

6-Ethoxy-2-(3-(3-(3-methylmorpholino)propoxy)phenyl)-N-(1H-pyrazolo[3,4-b]pyridin-5-yl)quinazolin-4-amine

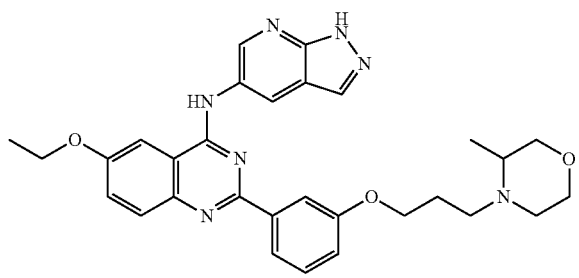 [SMILES: CCOc1ccc2nc(-c3cccc(OCCCN4CCOCC4C)c3)nc(Nc3cnc4[nH]ncc4c3)c2c1]

MS (ES+) m/e 540 (M+H)⁺.

Example 120

5-((6-Ethoxy-2-(3-(3-(3-methylmorpholino)propoxy)phenyl)quinazolin-4-yl)amino)isoindolin-1-one

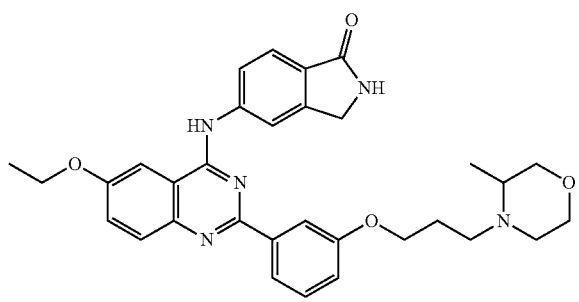 [SMILES: CCOc1ccc2nc(-c3cccc(OCCCN4CCOCC4C)c3)nc(Nc3ccc4c(c3)CNC4=O)c2c1]

MS (ES+) m/e 554 (M+H)⁺.

Example 121

4-((6-Ethoxy-2-(3-(3-(3-methylmorpholino)propoxy)phenyl)quinazolin-4-yl)amino)benzamide

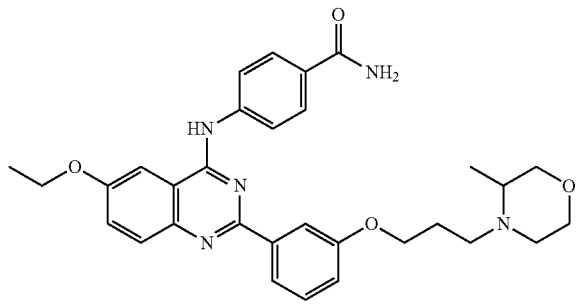 [SMILES: CCOc1ccc2nc(-c3cccc(OCCCN4CCOCC4C)c3)nc(Nc3ccc(C(N)=O)cc3)c2c1]

MS (ES+) m/e 542 (M+H)⁺.

Example 122

2-(3-(4-((1H-Pyrazol-4-yl)amino)-6-ethoxyquinazolin-2-yl)phenoxy)-N-(tert-butyl)acetamide

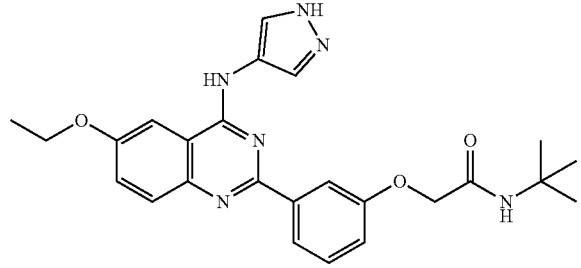 [SMILES: CCOc1ccc2nc(-c3cccc(OCC(=O)NC(C)(C)C)c3)nc(Nc3cn[nH]c3)c2c1]

¹H NMR (500 MHz, Methanol-d₄) δ 8.29 (s, 2H), 8.03 (d, J=2.6 Hz, 1H), 7.97 (d, J=9.2 Hz, 1H), 7.94 (dd, J=7.8, 1.7 Hz, 1H), 7.91 (t, J=2.1 Hz, 1H), 7.73 (dd, J=9.2, 2.6 Hz, 1H), 7.66 (t, J=8.0 Hz, 1H), 7.40 (dd, J=8.3, 2.5 Hz, 1H), 4.63 (s, 2H), 4.33 (q, J=7.0 Hz, 2H), 1.56 (t, J=7.0 Hz, 3H), 1.42 (s, 9H). MS (ES+) m/e 461 (M+H)⁺.

Example 123

N-(tert-Butyl)-2-(3-(6-ethoxy-4-((5-oxopyrrolidin-3-yl)amino)quinazolin-2-yl)phenoxy)acetamide

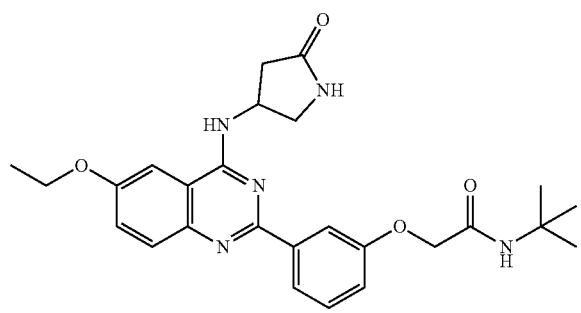 [SMILES: CCOc1ccc2nc(-c3cccc(OCC(=O)NC(C)(C)C)c3)nc(NC3CNC(=O)C3)c2c1]

MS (ES+) m/e 478 (M+H)⁺.

Example 124

N-(tert-Butyl)-2-(3-(6-ethoxy-4-((2-oxopiperidin-4-yl)amino)quinazolin-2-yl) phenoxy)acetamide

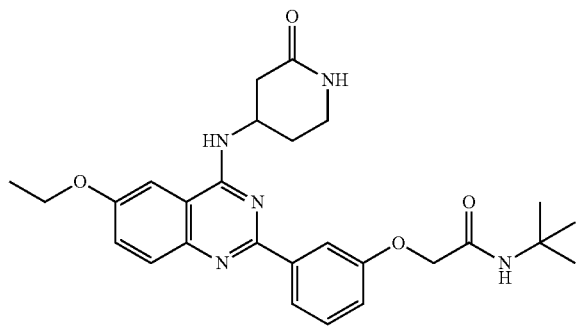 [SMILES: CCOc1ccc2nc(-c3cccc(OCC(=O)NC(C)(C)C)c3)nc(NC3CCNC(=O)C3)c2c1]

MS (ES+) m/e 492 (M+H)+.

Example 125

N-(tert-Butyl)-2-(3-(6-ethoxy-4-((2-oxopiperidin-4-yl)amino)quinazolin-2-yl) phenoxy)acetamide

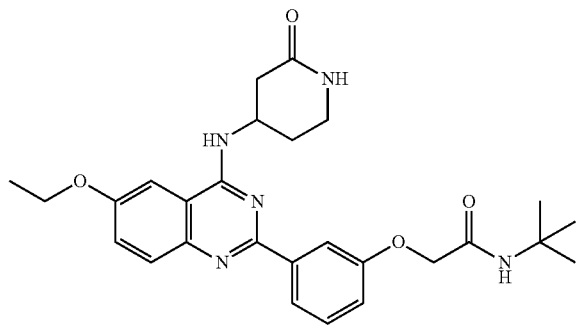 [SMILES: CCOc1ccc2nc(-c3cccc(OCC(=O)NC(C)(C)C)c3)nc(NC3CCNC(=O)C3)c2c1]

MS (ES+) m/e 492 (M+H)+.

Example 126

6-Ethoxy-2-(3-(2-(3-methylmorpholino)ethoxy)phenyl)-N-(1H-pyrazol-4-yl) quinazolin-4-amine

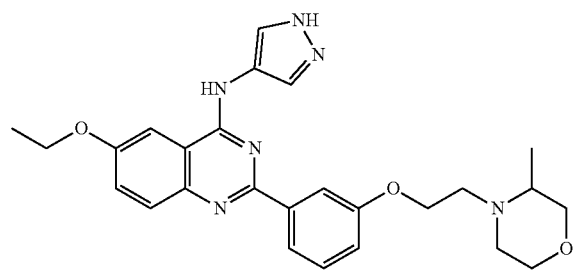 [SMILES: CCOc1ccc2nc(-c3cccc(OCCN4CCOCC4C)c3)nc(Nc3cn[nH]c3)c2c1]

$^1$H NMR (500 MHz, DMSO-d$_6$) δ 10.18 (s, 1H), 9.98 (s, 1H), 8.16 (s, 2H), 8.10-8.02 (m, 2H), 7.98 (s, 1H), 7.86 (d, J=8.8 Hz, 1H), 7.56 (d, J=8.3 Hz, 2H), 7.24 (s, 1H), 4.59-4.40 (m, 2H), 4.25 (q, J=7.0 Hz, 2H), 4.09-3.25 (m, 9H), 1.46 (t, J=6.9 Hz, 3H), 1.31 (d, J=5.1 Hz, 3H). MS (ES+) m/e 475 (M+H)+.

Example 127

4-((6-Ethoxy-2-(3-(2-(3-methylmorpholino)ethoxy) phenyl)quinazolin-4-yl)amino)pyrrolidin-2-one

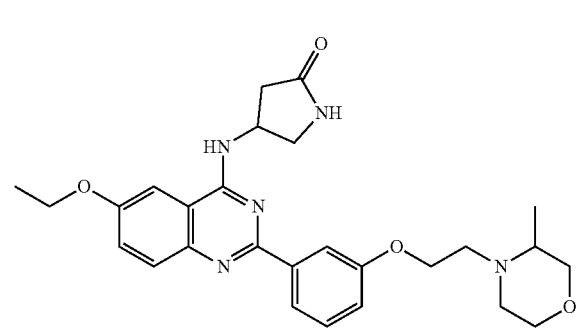 [SMILES: CCOc1ccc2nc(-c3cccc(OCCN4CCOCC4C)c3)nc(NC3CNC(=O)C3)c2c1]

MS (ES+) m/e 492 (M+H)+.

Example 128

4-((6-Ethoxy-2-(3-(2-(3-methylmorpholino)ethoxy) phenyl)quinazolin-4-yl)amino)piperidin-2-one

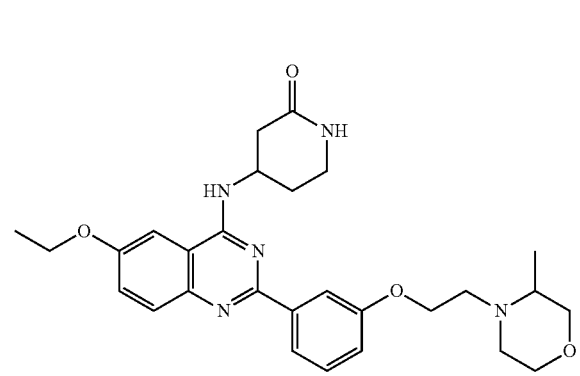 [SMILES: CCOc1ccc2nc(-c3cccc(OCCN4CCOCC4C)c3)nc(NC3CCNC(=O)C3)c2c1]

MS (ES+) m/e 506 (M+H)+.

Example 129

5-((6-Ethoxy-2-(3-(2-(3-methylmorpholino)ethoxy) phenyl)quinazolin-4-yl)amino)piperidin-2-one

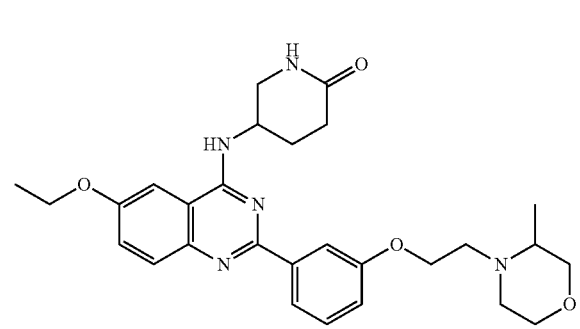 [SMILES: CCOc1ccc2nc(-c3cccc(OCCN4CCOCC4C)c3)nc(NC3CCC(=O)NC3)c2c1]

MS (ES+) m/e 506 (M+H)+.

Example 130

6-Ethoxy-2-(3-(3-(3-methylmorpholino)propoxy)phenyl)-N-(1H-pyrazol-4-yl) quinazolin-4-amine

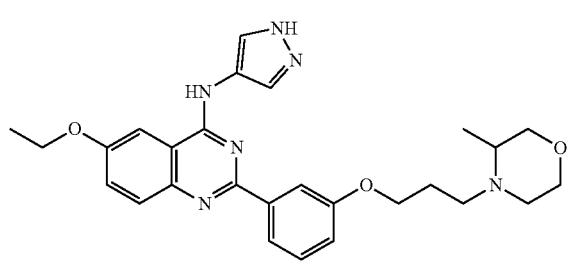 [SMILES: CCOc1ccc2nc(-c3cccc(OCCCN4CCOCC4C)c3)nc(Nc3cn[nH]c3)c2c1]

MS (ES+) m/e 489 (M+H)+.

Example 131

4-((6-Ethoxy-2-(3-(3-(3-methylmorpholino)propoxy)phenyl)quinazolin-4-yl)amino)pyrrolidin-2-one

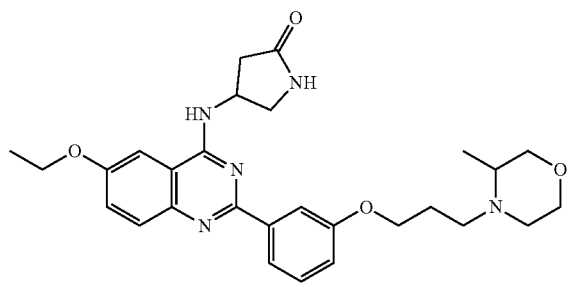 [SMILES: CCOc1ccc2nc(-c3cccc(OCCCN4CCOCC4C)c3)nc(NC3CNC(=O)C3)c2c1]

MS (ES+) m/e 506 (M+H)+.

Example 132

4-((6-Ethoxy-2-(3-(3-(3-methylmorpholino)propoxy)phenyl)quinazolin-4-yl)amino)piperidin-2-one

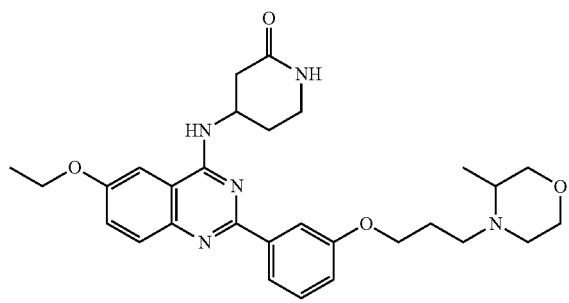 [SMILES: CCOc1ccc2nc(-c3cccc(OCCCN4CCOCC4C)c3)nc(NC3CCNC(=O)C3)c2c1]

MS (ES+) m/e 520 (M+H)+.

Example 133

5-((6-Ethoxy-2-(3-(3-(3-methylmorpholino)propoxy)phenyl)quinazolin-4-yl)amino)piperidin-2-one

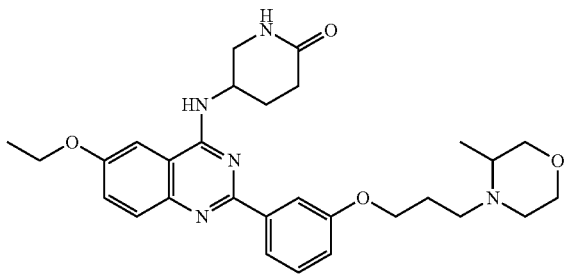 [SMILES: CCOc1ccc2nc(-c3cccc(OCCCN4CCOCC4C)c3)nc(NC3CCC(=O)NC3)c2c1]

MS (ES+) m/e 520 (M+H)+.

Example 134

N5-(6-Ethoxy-2-(3-(2-(3-methylmorpholino)ethoxy)phenyl)quinazolin-4-yl)pyridine-2,5-diamine

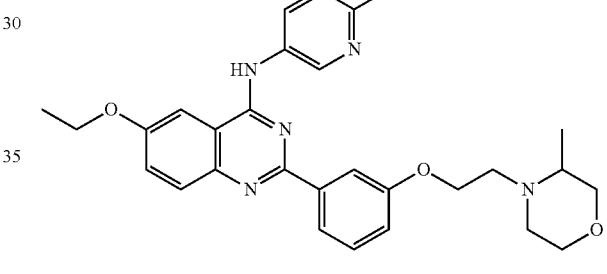

$^1$H NMR (500 MHz, DMSO-d$_6$) δ 10.92 (s, 1H), 9.99 (s, 1H), 8.55 (d, J=2.5 Hz, 1H), 8.35 (d, J=9.5 Hz, 1H), 8.04-7.97 (m, 3H), 7.92 (d, J=2.7 Hz, 1H), 7.84 (d, J=9.1 Hz, 1H), 7.57 (dd, J=9.1, 2.6 Hz, 1H), 7.47 (t, J=7.9 Hz, 1H), 7.19-7.06 (m, 2H), 4.56-4.39 (m, 2H), 4.24 (q, J=7.0 Hz, 2H), 4.02-3.24 (m, 9H), 1.46 (t, J=6.9 Hz, 3H), 1.32 (d, J=5.9 Hz, 3H). MS (ES+) m/e 501 (M+H)+.

Example 135

N5-(6-Ethoxy-2-(3-(3-(3-methylmorpholino)propoxy)phenyl)quinazolin-4-yl)pyridine-2,5-diamine

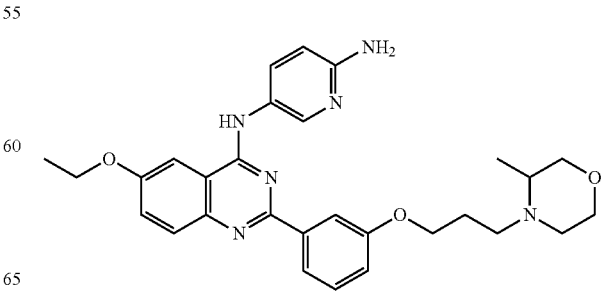

¹H NMR (500 MHz, DMSO-d₆) δ 9.98 (s, 1H), 9.87 (s, 1H), 8.57 (d, J=2.4 Hz, 1H), 8.34 (d, J=9.5 Hz, 1H), 8.01-7.91 (m, 4H), 7.84 (d, J=9.1 Hz, 1H), 7.57 (dd, J=9.1, 2.6 Hz, 1H), 7.44 (t, J=7.9 Hz, 1H), 7.16-7.04 (m, 2H), 4.24 (q, J=7.0 Hz, 2H), 4.18 (t, J=6.0 Hz, 2H), 4.10-3.07 (m, 11H), 1.46 (t, J=6.9 Hz, 3H), 1.26 (b, 3H). MS (ES+) m/e 515 (M+H)⁺.

Example 136

6-Ethoxy-2-(3-(2-(3-methylmorpholino)ethoxy)phenyl)-N-(tetrahydro-2H-pyran-4-yl)quinazolin-4-amine

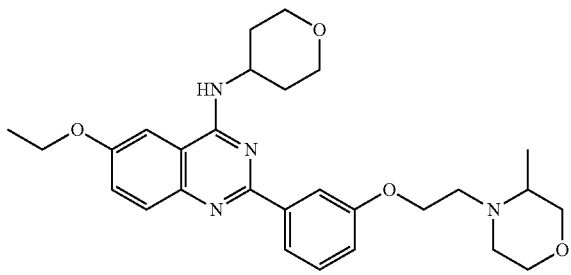 [SMILES: CCOc1ccc2nc(-c3cccc(OCCN4CCOCC4C)c3)nc(NC3CCOCC3)c2c1]

MS (ES+) m/e 493 (M+H)⁺.

Example 137

6-Ethoxy-2-(3-(3-(3-methylmorpholino)propoxy)phenyl)-N-(tetrahydro-2H-pyran-4-yl)quinazolin-4-amine

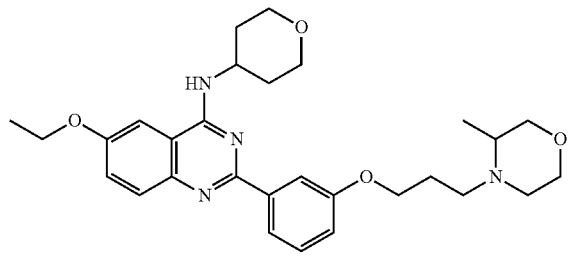 [SMILES: CCOc1ccc2nc(-c3cccc(OCCCN4CCOCC4C)c3)nc(NC3CCOCC3)c2c1]

MS (ES+) m/e 507 (M+H)⁺.

Example 138

5-((6-Ethoxy-2-(3-(2-(3-methylmorpholino)ethoxy)phenyl)quinazolin-4-yl)amino)-3-methylpyridin-2(1H)-one

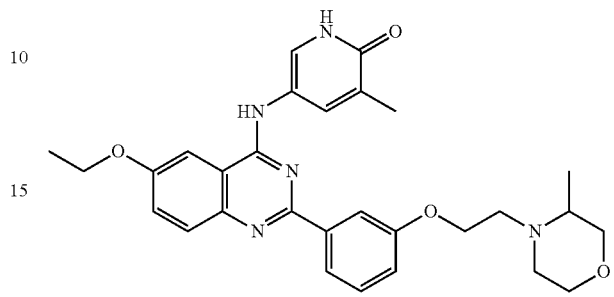

¹H NMR (500 MHz, DMSO-d₆) δ 9.93 (s, 1H), 7.97 (d, J=7.8 Hz, 1H), 7.93 (s, 2H), 7.85 (d, J=9.2 Hz, 1H), 7.77 (s, 2H), 7.61-7.54 (m, 1H), 7.51 (t, J=8.0 Hz, 1H), 7.20 (d, J=8.2 Hz, 1H), 4.44 (m, 2H), 4.23 (q, J=7.0 Hz, 2H), 4.08-3.17 (m, 9H), 2.09 (s, 3H), 1.45 (t, J=6.9 Hz, 3H), 1.29 (d, J=5.2 Hz, 3H). MS (ES+) m/e 516 (M+H)⁺.

Example 139

6-Ethoxy-2-(3-(2-(3-methylmorpholino)ethoxy)phenyl)-N-(tetrahydrofuran-3-yl) quinazolin-4-amine

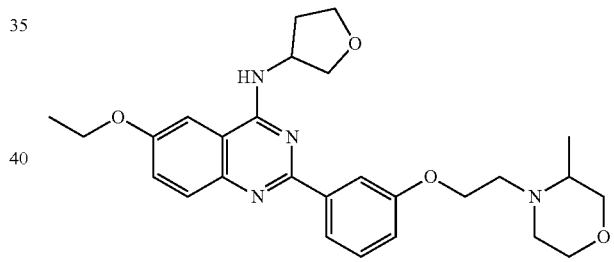

MS (ES+) m/e 479 (M+H).

Example 140

5-((6-Ethoxy-2-(3-(3-(3-methylmorpholino)propoxy)phenyl)quinazolin-4-yl)amino)-3-methylpyridin-2(1H)-one

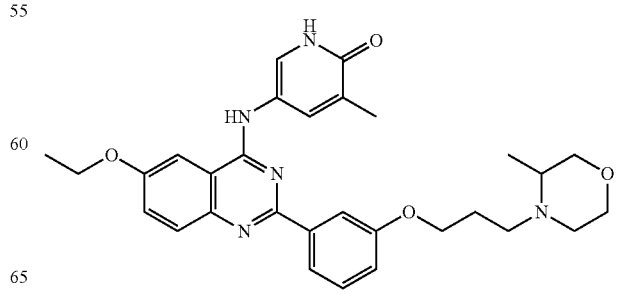

¹H NMR (500 MHz, DMSO-d₆) δ 9.95 (s, 1H), 9.78 (s, 1H), 7.94 (d, J=7.3 Hz, 2H), 7.87 (d, J=17.0 Hz, 2H), 7.81-7.70 (m, 2H), 7.58 (d, J=9.1 Hz, 1H), 7.48 (t, J=7.9 Hz, 1H), 7.14 (d, J=8.1 Hz, 1H), 4.23 (q, J=7.0 Hz, 2H), 4.16 (t, J=6.2 Hz, 2H), 4.10-3.13 (m, 11H), 2.09 (s, 3H), 1.45 (t, J=6.9 Hz, 3H), 1.25 (d, J=5.1 Hz, 3H). MS (ES+) m/e 530 (M+H)⁺.

Example 141

6-Ethoxy-2-(3-(3-(3-methylmorpholino)propoxy)phenyl)-N-(tetrahydrofuran-3-yl)quinazolin-4-amine

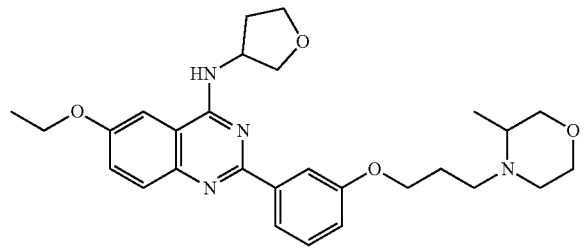 [SMILES: CCOc1ccc2nc(-c3cccc(OCCCN4CCOCC4C)c3)nc(NC3CCOC3)c2c1]

MS (ES+) m/e 493 (M+H)⁺.

Example 142

3-Chloro-5-((6-ethoxy-2-(3-(2-(3-methylmorpholino)ethoxy)phenyl) quinazolin-4-yl)amino)pyridin-2(1H)-one

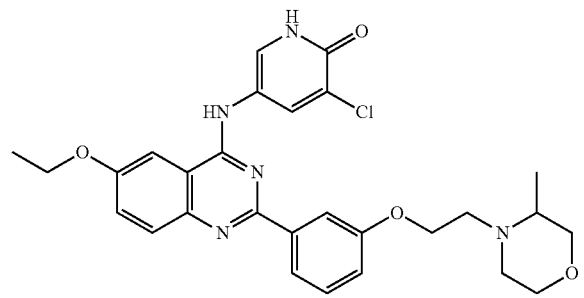 [SMILES: CCOc1ccc2nc(-c3cccc(OCCN4CCOCC4C)c3)nc(Nc3c[nH]c(=O)c(Cl)c3)c2c1]

MS (ES+) m/e 536 (M+H)⁺.

Example 143

3-Chloro-5-((6-ethoxy-2-(3-(3-(3-methylmorpholino)propoxy)phenyl) quinazolin-4-yl)amino)pyridin-2(1H)-one

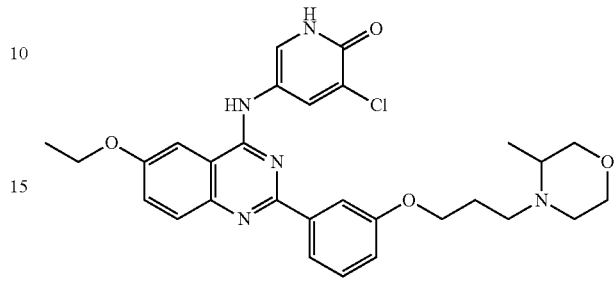

MS (ES+) m/e 550 (M+H)⁺.

Example 144

N-(tert-Butyl)-2-(3-(6-ethoxy-4-((5-methyl-6-oxo-1,6-dihydropyridin-3-yl)amino)quinazolin-2-yl)phenoxy)acetamide

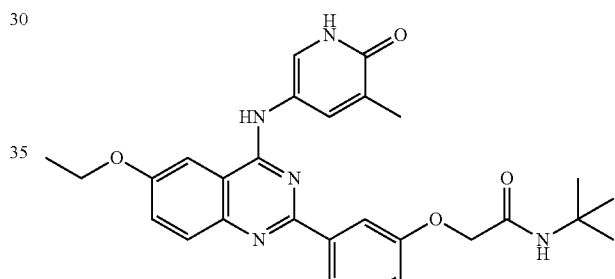

¹H NMR (500 MHz, Methanol-d₄) δ 8.02-7.96 (m, 3H), 7.90-7.84 (m, 3H), 7.75 (dd, J=9.2, 2.6 Hz, 1H), 7.61 (t, J=8.0 Hz, 1H), 7.35 (dd, J=8.2, 2.7 Hz, 1H), 4.58 (s, 2H), 4.32 (q, J=7.0 Hz, 2H), 2.25 (s, 3H), 1.56 (t, J=7.0 Hz, 3H), 1.41 (s, 9H). MS (ES+) m/e 502 (M+H)⁺.

Example 145

2-(3-(4-((6-Aminopyridin-3-yl)amino)-6-ethoxyquinazolin-2-yl)phenoxy)-N-(tert-butyl)acetamide

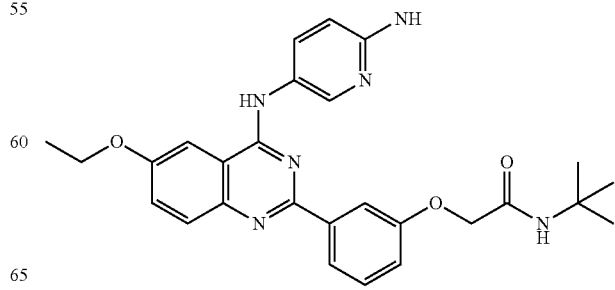

¹H NMR (500 MHz, Methanol-d₄) δ 8.61 (d, J=2.4 Hz, 1H), 8.36 (dd, J=9.5, 2.5 Hz, 1H), 8.02 (d, J=9.2 Hz, 1H), 7.98-7.93 (m, 2H), 7.90-7.88 (m, 1H), 7.76 (dd, J=9.1, 2.6 Hz, 1H), 7.60 (t, J=8.1 Hz, 1H), 7.34 (dd, J=8.0, 2.6 Hz, 1H), 7.22 (d, J=9.5 Hz, 1H), 4.60 (s, 2H), 4.32 (q, J=7.0 Hz, 2H), 1.56 (t, J=7.0 Hz, 3H), 1.40 (s, 9H). MS (ES+) m/e 487 (M+H)⁺.

Example 146

N-(tert-butyl)-2-(3-(6-ethoxy-4-((tetrahydrofuran-3-yl)amino)quinazolin-2-yl) phenoxy)acetamide

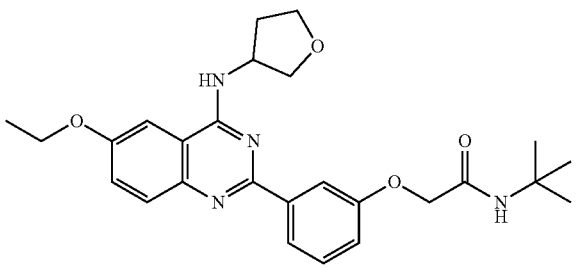 [SMILES: CCOc1ccc2nc(-c3cccc(OCC(=O)NC(C)(C)C)c3)nc(NC3CCOC3)c2c1]

MS (ES+) m/e 465 (M+H)⁺.

Example 147

2-(3-(6-Ethoxy-4-((5-methyl-6-oxo-1,6-dihydropyridin-3-yl)amino)quinazolin-2-yl)phenoxy)-N-isopropylacetamide

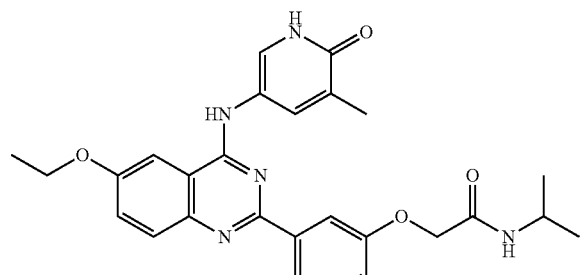

MS (ES+) m/e 488 (M+H)⁺.

Example 148

2-(3-(4-((6-Aminopyridin-3-yl)amino)-6-ethoxyquinazolin-2-yl)phenoxy)-N-isopropylacetamide

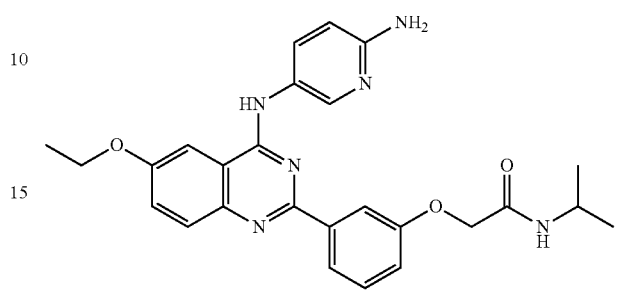

MS (ES+) m/e 473 (M+H)⁺.

Example 149

2-(3-(6-Ethoxy-4-((tetrahydrofuran-3-yl)amino)quinazolin-2-yl)phenoxy)-N-isopropylacetamide

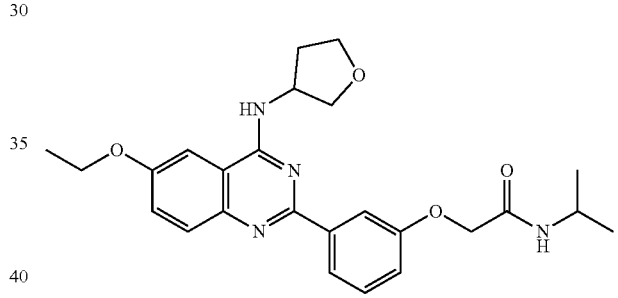

MS (ES+) m/e 451 (M+H)⁺.

Example 150

2-(3-(4-((1H-Pyrazol-4-yl)amino)-6-fluoroquinazolin-2-yl)phenoxy)-N-isopropylacetamide

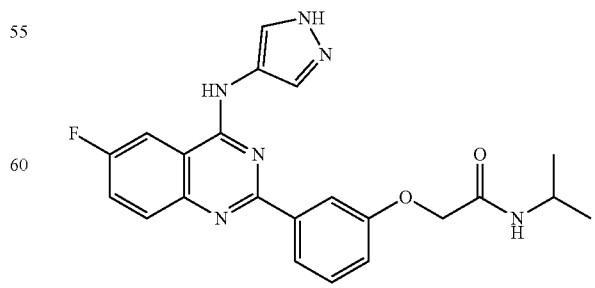

MS (ES+) m/e 421 (M+H)⁺.

Example 151

2-(3-(4-((1H-Pyrazol-4-yl)amino)-6-fluoroquinazo-lin-2-yl)phenoxy)-N-(tert-butyl)acetamide

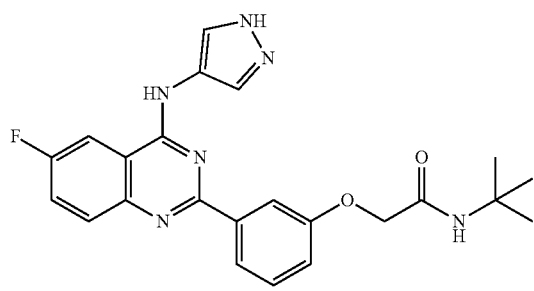 [SMILES: CC(C)(C)NC(=O)COc1cccc(-c2nc(Nc3cn[nH]c3)c3cc(F)ccc3n2)c1]

MS (ES+) m/e 435 (M+H)⁺.

Example 152

6-Fluoro-2-(3-(3-morpholinopropoxy)phenyl)-N-(1H-pyrazol-4-yl)quinazolin-4-amine

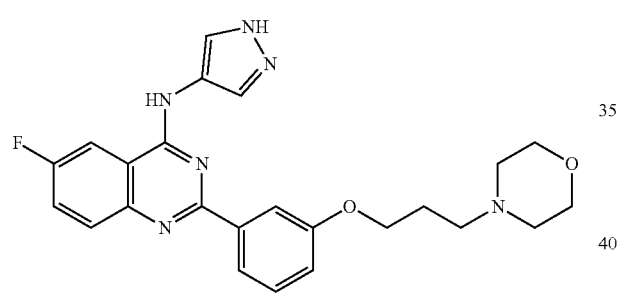

MS (ES+) m/e 449 (M+H)⁺.

Example 153

2-(3-(4-((1H-Pyrazol-4-yl)amino)pyrimidin-2-yl)phenoxy)-N-(tert-butyl) acetamide

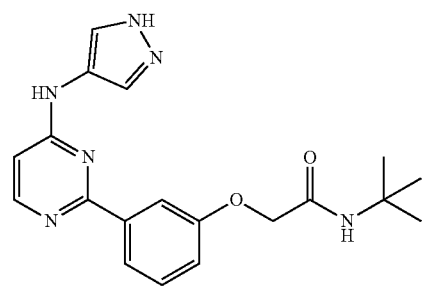 [SMILES: CC(C)(C)NC(=O)COc1cccc(-c2nccc(Nc3cn[nH]c3)n2)c1]

MS (ES+) m/e 367 (M+H)⁺.

Example 154

2-(3-(4-((1H-Pyrazol-4-yl)amino)-5-fluoropyrimi-din-2-yl)phenoxy)-N-(tert-butyl)acetamide

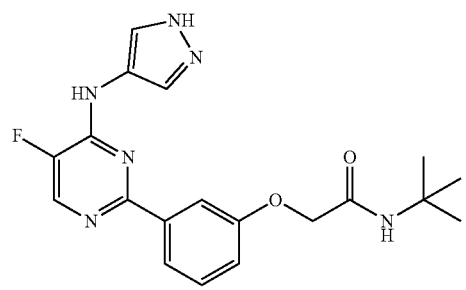 [SMILES: CC(C)(C)NC(=O)COc1cccc(-c2ncc(F)c(Nc3cn[nH]c3)n2)c1]

MS (ES+) m/e 385 (M+H)⁺.

Example 155

2-(3-(4-((1H-Pyrazol-4-yl)amino)-5-methoxypyrimi-din-2-yl)phenoxy)-N-(tert-butyl)acetamide

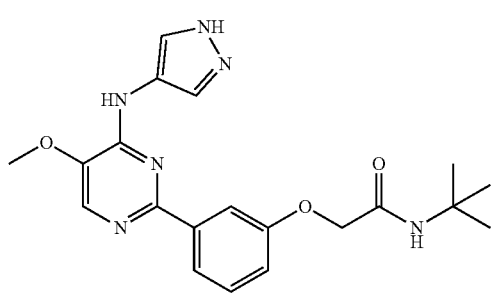 [SMILES: COc1cnc(-c2cccc(OCC(=O)NC(C)(C)C)c2)nc1Nc1cn[nH]c1]

MS (ES+) m/e 397 (M+H)⁺.

Example 156

2-(3-(4-((1H-Pyrazol-4-yl)amino)-5-ethoxypyrimi-din-2-yl)phenoxy)-N-(tert-butyl)acetamide

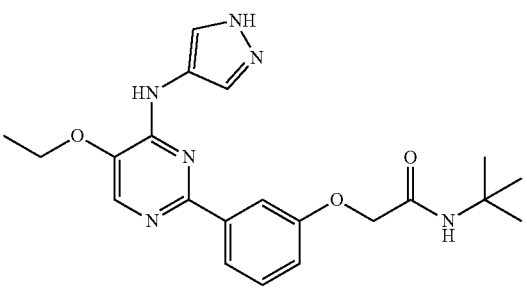 [SMILES: CCOc1cnc(-c2cccc(OCC(=O)NC(C)(C)C)c2)nc1Nc1cn[nH]c1]

MS (ES+) m/e 411 (M+H)⁺.

Example 157

2-(3-(4-((1H-Pyrazol-4-yl)amino)-5,6-dimethylpyrimidin-2-yl)phenoxy)-N-(tert-butyl)acetamide

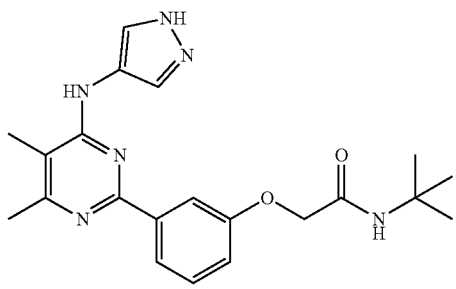 [SMILES: Cc1nc(-c2cccc(OCC(=O)NC(C)(C)C)c2)nc(Nc2cn[nH]c2)c1C]

MS (ES+) m/e 395 (M+H)$^+$.

Example 158

2-(3-(4-((1H-Pyrazol-4-yl)amino)quinazolin-2-yl)phenoxy)-N-(tert-butyl) acetamide

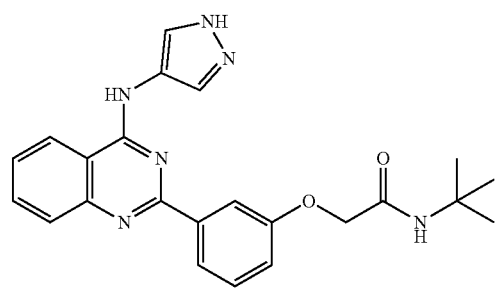 [SMILES: CC(C)(C)NC(=O)COc1cccc(-c2nc(Nc3cn[nH]c3)c3ccccc3n2)c1]

MS (ES+) m/e 417 (M+H)$^+$.

Example 159

2-(3-(4-((1H-Pyrazol-4-yl)amino)-7-fluoroquinazolin-2-yl)phenoxy)-N-(tert-butyl)acetamide

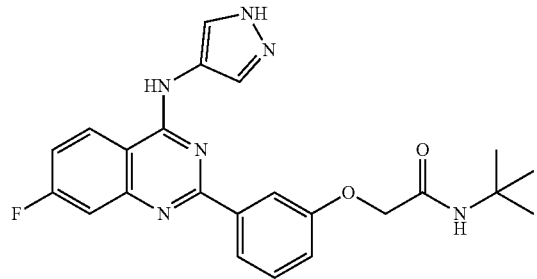 [SMILES: CC(C)(C)NC(=O)COc1cccc(-c2nc(Nc3cn[nH]c3)c3ccc(F)cc3n2)c1]

MS (ES+) m/e 435 (M+H)$^+$.

Example 160

2-(3-(4-((1H-Pyrazol-4-yl)amino)-5-fluoroquinazolin-2-yl)phenoxy)-N-(tert-butyl)acetamide

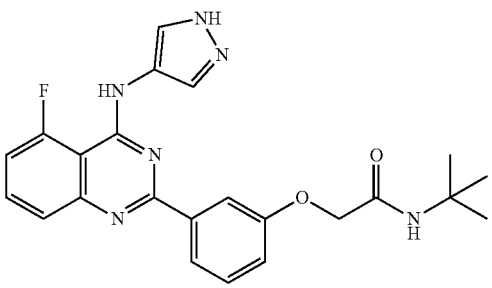

MS (ES+) m/e 435 (M+H)$^+$.

Example 161

2-(3-(4-((1H-Pyrazol-4-yl)amino)-6-methoxyquinazolin-2-yl)phenoxy)-N-(tert-butyl)acetamide

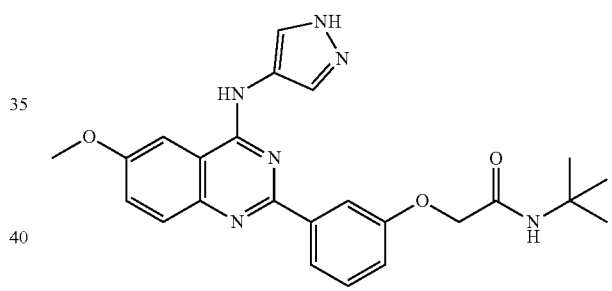

MS (ES+) m/e 447 (M+H)$^+$.

Example 162

N-(2-(3-(4-((1H-Pyrazol-4-yl)amino)-6-fluoroquinazolin-2-yl)phenoxy)ethyl) pivalamide

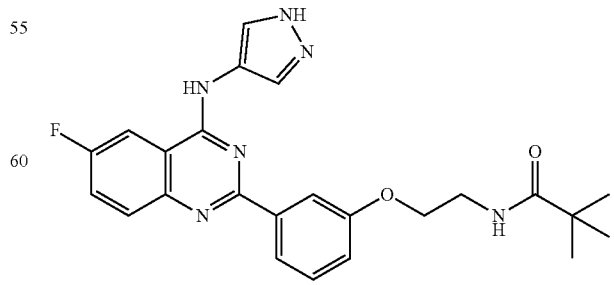

MS (ES+) m/e 449 (M+H)$^+$.

Example 163

N-(2-(3-(4-((1H-Pyrazol-4-yl)amino)-6-ethoxyquinazolin-2-yl)phenoxy)ethyl) pivalamide

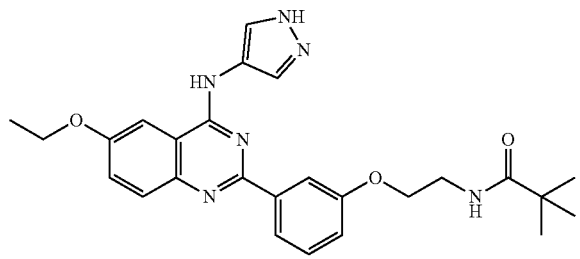 [SMILES: CCOc1ccc2nc(-c3cccc(OCCNC(=O)C(C)(C)C)c3)nc(Nc3cn[nH]c3)c2c1]

MS (ES+) m/e 475 (M+H)+.

Example 164

N-(4-(1H-Pyrazol-4-yl)phenyl)-2-(3-(3-morpholinopropoxy)phenyl)-6-(trifluoromethyl)pyrimidin-4-amine

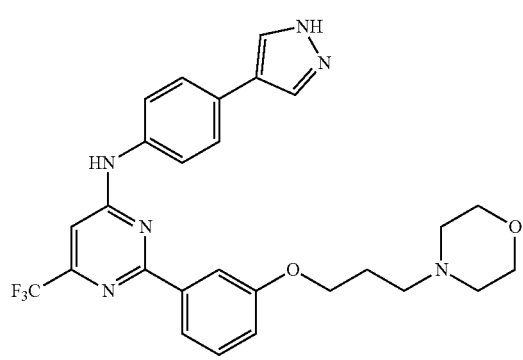 [SMILES: FC(F)(F)c1cc(Nc2ccc(-c3cn[nH]c3)cc2)nc(-c2cccc(OCCCN3CCOCC3)c2)n1]

MS (ES+) m/e 525 (M+H)+.

Example 165

6-Ethoxy-N-(5-methyl-1H-pyrazol-4-yl)-2-(3-(3-morpholinopropoxy)phenyl) quinazolin-4-amine

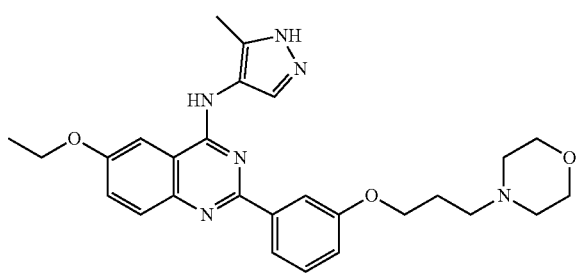 [SMILES: CCOc1ccc2nc(-c3cccc(OCCCN4CCOCC4)c3)nc(Nc3cn[nH]c3C)c2c1]

MS (ES+) m/e 489 (M+H)+.

Example 166

N-(tert-Butyl)-2-(3-(6-ethoxy-4-((5-methyl-1H-pyrazol-4-yl)amino) quinazolin-2-yl)phenoxy)acetamide

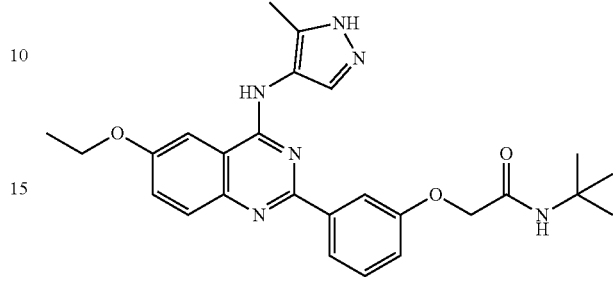

MS (ES+) m/e 475 (M+H)+.

Example 167

4-((2-(3-(2-(tert-Butylamino)-2-oxoethoxy)phenyl)-6-ethoxyquinazolin-4-yl)amino)benzamide

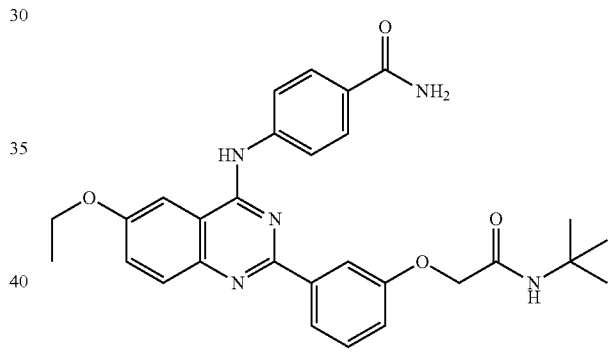

MS (ES+) m/e 514 (M+H)+.

Example 168

2-(3-(4-((1H-Pyrazol-4-yl)amino)-7-methoxyquinazolin-2-yl)phenoxy)-N-(tert-butyl)acetamide

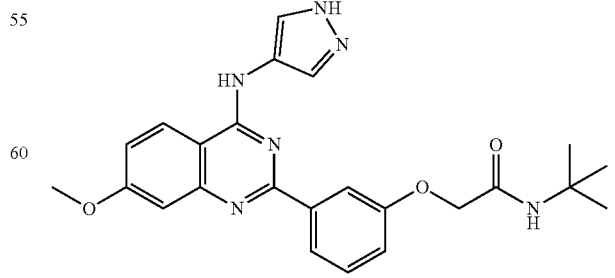

MS (ES+) m/e 447 (M+H)+.

Example 169

N-(tert-Butyl)-2-(3-(6-ethoxy-4-((1-methyl-1H-pyrazol-4-yl)amino) quinazolin-2-yl)phenoxy)acetamide

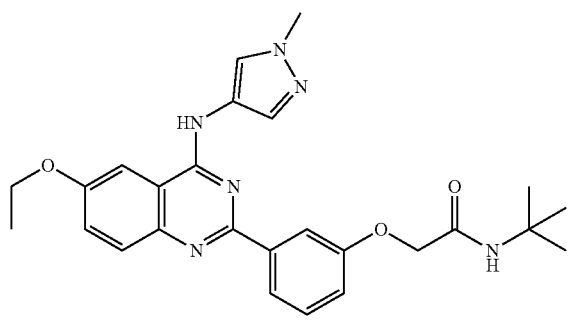 [SMILES: CCOc1ccc2nc(-c3cccc(OCC(=O)NC(C)(C)C)c3)nc(Nc3cnn(C)c3)c2c1]

MS (ES+) m/e 475 (M+H)⁺.

Example 170

2-(3-(4-((1H-Pyrazol-3-yl)amino)-6-ethoxyquinazolin-2-yl)phenoxy)-N-(tert-butyl)acetamide

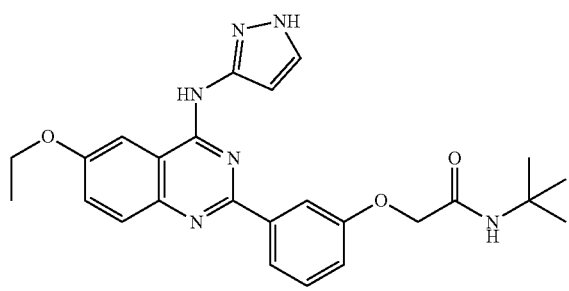 [SMILES: CCOc1ccc2nc(-c3cccc(OCC(=O)NC(C)(C)C)c3)nc(Nc3cc[nH]n3)c2c1]

MS (ES+) m/e 461 (M+H)⁺.

Example 171

N-(tert-Butyl)-2-(3-(6-ethoxy-4-((4-morpholinophenyl)amino) quinazolin-2-yl)phenoxy)acetamide

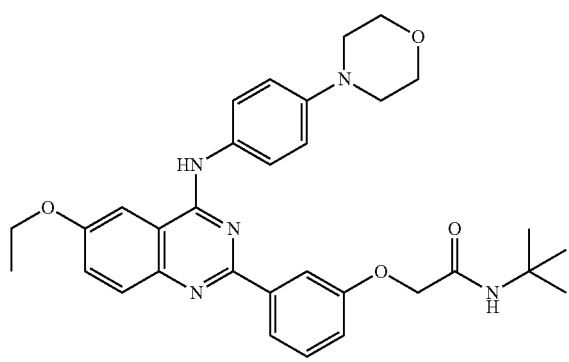 [SMILES: CCOc1ccc2nc(-c3cccc(OCC(=O)NC(C)(C)C)c3)nc(Nc3ccc(N4CCOCC4)cc3)c2c1]

MS (ES+) m/e 556 (M+H)⁺.

Example 172

N-(tert-Butyl)-2-(3-(6-ethoxy-4-(isothiazol-4-ylamino)quinazolin-2-yl) phenoxy)acetamide

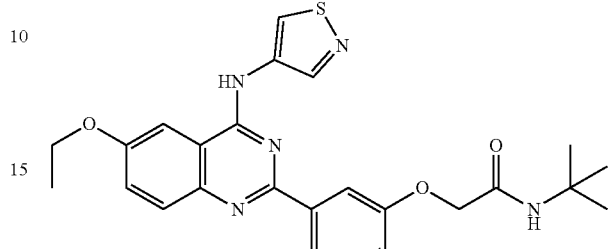

MS (ES+) m/e 478 (M+H)⁺.

Example 173

2-(3-(4-((1H-Pyrazol-4-yl)amino)-5-ethoxyquinazolin-2-yl)phenoxy)-N-(tert-butyl)acetamide

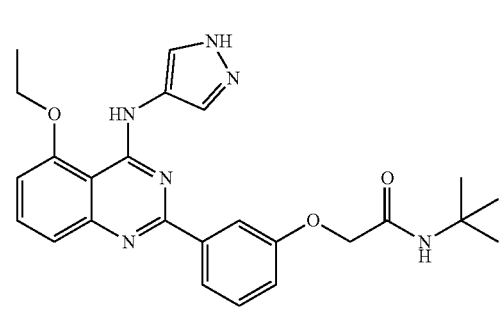 [SMILES: CCOc1cccc2nc(-c3cccc(OCC(=O)NC(C)(C)C)c3)nc(Nc3cn[nH]c3)c12]

MS (ES+) m/e 461 (M+H)⁺.

Example 174

2-(3-(4-((1H-Pyrazol-4-yl)amino)-5-phenoxypyrimidin-2-yl)phenoxy)-N-(tert-butyl)acetamide

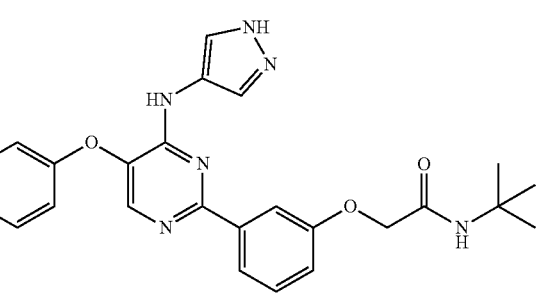

MS (ES+) m/e 459 (M+H)⁺.

Example 175

N-(tert-Butyl)-2-(3-(5-ethoxy-4-((1-methyl-1H-pyrazol-4-yl)amino) quinazolin-2-yl)phenoxy)acetamide

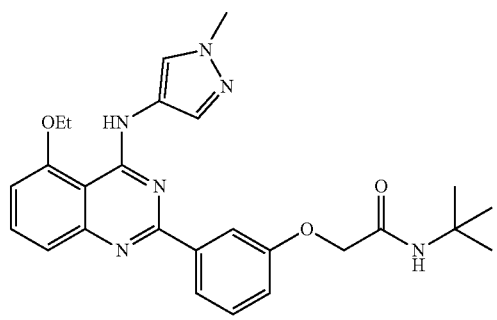 [SMILES: CCOc1cccc2nc(-c3cccc(OCC(=O)NC(C)(C)C)c3)nc(Nc3cnn(C)c3)c12]

MS (ES+) m/e 475 (M+H)+.

Example 176

2-(3-(4-((1H-Pyrazol-4-yl)amino)-6-phenoxypyrimidin-2-yl)phenoxy)-N-(tert-butyl)acetamide

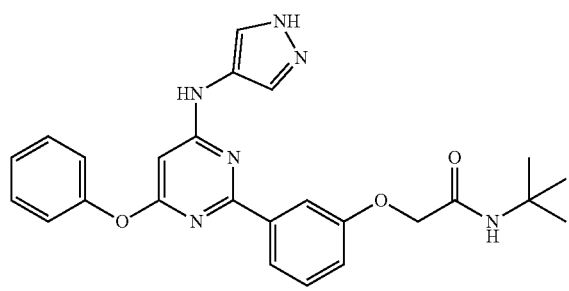 [SMILES: CC(C)(C)NC(=O)COc1cccc(-c2nc(Nc3cn[nH]c3)cc(Oc3ccccc3)n2)c1]

MS (ES+) m/e 459 (M+H)+.

Example 177

2-(3-(4-((1H-Pyrazol-4-yl)amino)-6-ethoxy-5-fluoroquinazolin-2-yl) phenoxy)-N-(tert-butyl)acetamide

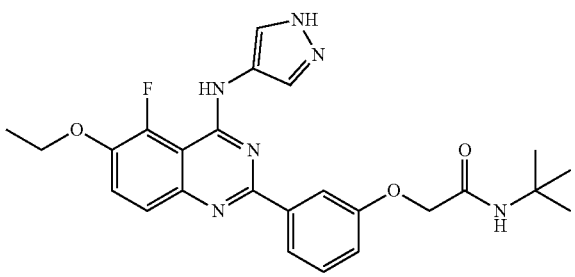 [SMILES: CCOc1ccc2nc(-c3cccc(OCC(=O)NC(C)(C)C)c3)nc(Nc3cn[nH]c3)c2c1F]

MS (ES+) m/e 479 (M+H)+.

Example 178

N-(tert-Butyl)-2-(3-(5-ethoxy-4-((1-ethyl-1H-pyrazol-4-yl)amino) quinazolin-2-yl)phenoxy)acetamide

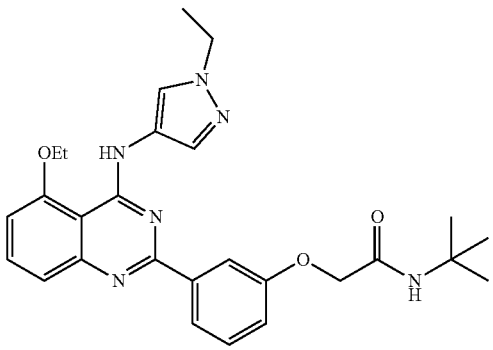 [SMILES: CCOc1cccc2nc(-c3cccc(OCC(=O)NC(C)(C)C)c3)nc(Nc3cnn(CC)c3)c12]

MS (ES+) m/e 489 (M+H)+.

Example 179

N-(tert-Butyl)-2-(3-(6-ethoxy-5-fluoro-4-((1-methyl-1H-pyrazol-4-yl)amino) quinazolin-2-yl)phenoxy)acetamide

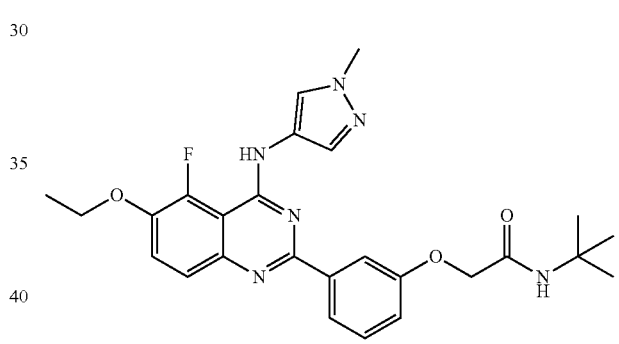

MS (ES+) m/e 493 (M+H)+.

Example 180

N-(tert-Butyl)-2-(3-(6-ethoxy-4-((1-ethyl-1H-pyrazol-4-yl)amino)-5-fluoroquinazolin-2-yl)phenoxy)acetamide

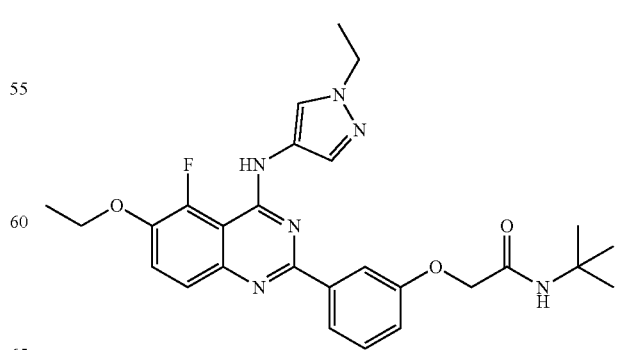

MS (ES+) m/e 507 (M+H)+.

Example 181

N-(tert-Butyl)-2-(3-(5-(3,6-dihydro-2H-pyran-4-yl)-4-((1-methyl-1H-pyrazol-4-yl)amino)pyrimidin-2-yl)phenoxy)acetamide

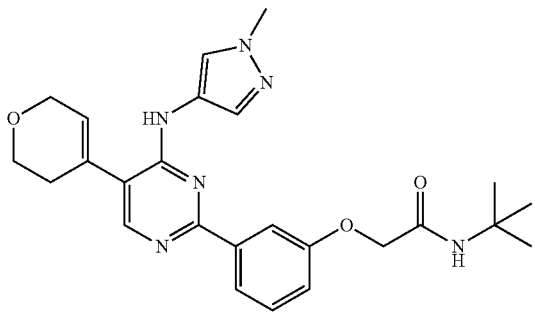 [SMILES: Cn1cc(Nc2nc(-c3cccc(OCC(=O)NC(C)(C)C)c3)ncc2C2=CCOCC2)cn1]

MS (ES+) m/e 463 (M+H)+.

Example 182

2-(3-(4-((1H-Pyrazol-4-yl)amino)-5-methoxyquinazolin-2-yl)phenoxy)-N-(tert-butyl)acetamide

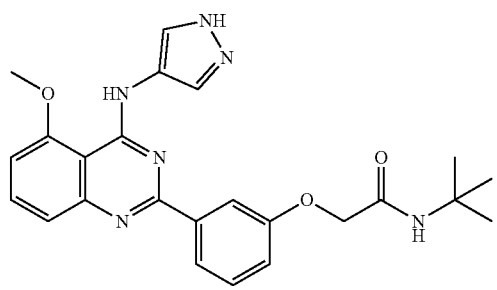 [SMILES: COc1cccc2nc(-c3cccc(OCC(=O)NC(C)(C)C)c3)nc(Nc3cn[nH]c3)c12]

MS (ES+) m/e 447 (M+H)+.

Example 183

N-(tert-Butyl)-2-(3-(4-((4-cyanophenyl)amino)-6-ethoxyquinazolin-2-yl) phenoxy)acetamide

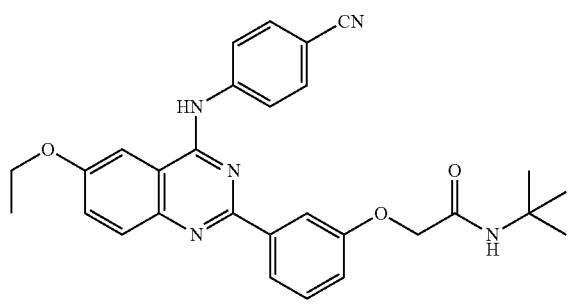 [SMILES: CCOc1ccc2nc(-c3cccc(OCC(=O)NC(C)(C)C)c3)nc(Nc3ccc(C#N)cc3)c2c1]

MS (ES+) m/e 496 (M+H)+.

Example 184

N-(tert-Butyl)-2-(3-(6-ethoxy-4-(pyrimidin-5-ylamino)quinazolin-2-yl) phenoxy)acetamide

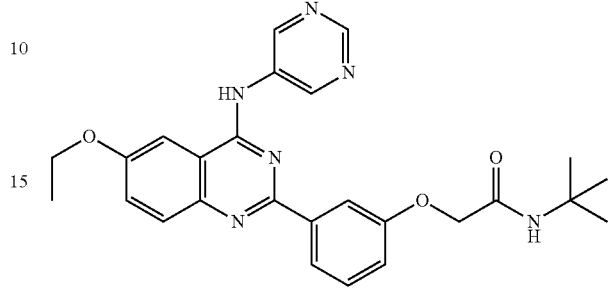

MS (ES+) m/e 473 (M+H)+.

Example 185

N-(tert-Butyl)-2-(3-(6-ethoxy-4-(isoxazol-4-ylamino)quinazolin-2-yl) phenoxy)acetamide

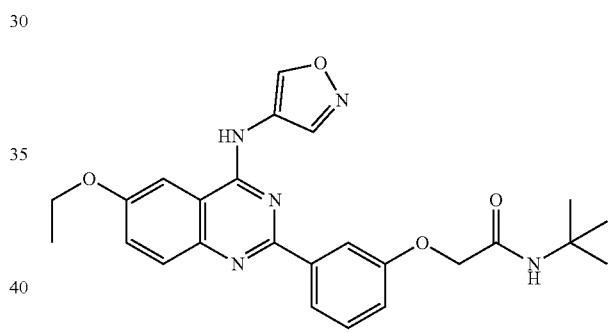

MS (ES+) m/e 462 (M+H)+.

Example 186

N-(tert-Butyl)-2-(3-(6-ethoxy-4-(pyridin-3-ylamino)quinazolin-2-yl) phenoxy)acetamide

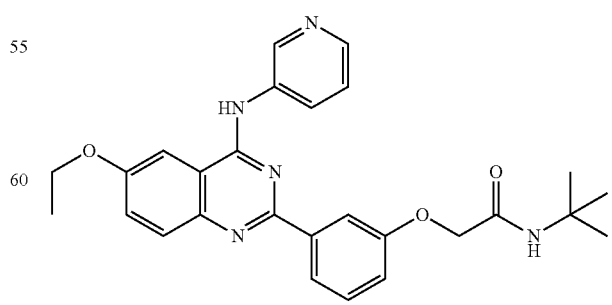

MS (ES+) m/e 472 (M+H)+.

Example 187

N-(tert-Butyl)-2-(3-(6-ethoxy-4-(pyridin-4-ylamino)quinazolin-2-yl) phenoxy)acetamide

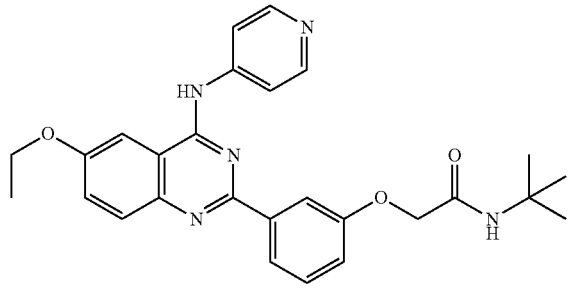 [SMILES: CCOc1ccc2nc(-c3cccc(OCC(=O)NC(C)(C)C)c3)nc(Nc3ccncc3)c2c1]

MS (ES+) m/e 472 (M+H)⁺.

Example 188

2-(3-(4-((1H-Pyrazol-4-yl)amino)-6-ethoxyquinazolin-2-yl)phenoxy)-N-(tert-pentyl)acetamide

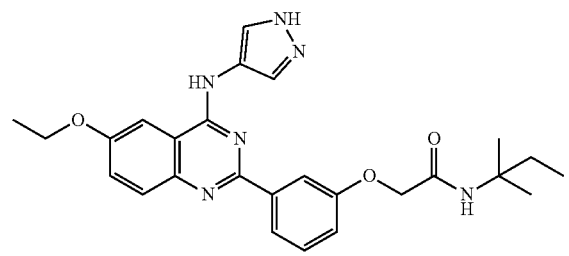 [SMILES: CCOc1ccc2nc(-c3cccc(OCC(=O)NC(C)(C)CC)c3)nc(Nc3cn[nH]c3)c2c1]

MS (ES+) m/e 475 (M+H)⁺.

Example 189

N-(tert-Butyl)-2-(3-(4-((3,5-dimethyl-1H-pyrazol-4-yl)amino)-6-ethoxyquinazolin-2-yl)phenoxy)acetamide

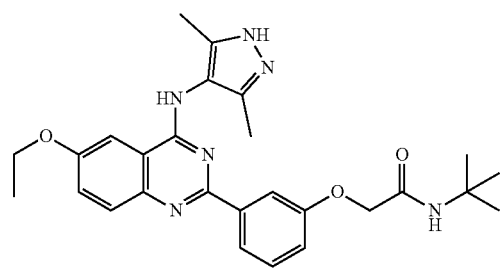 [SMILES: CCOc1ccc2nc(-c3cccc(OCC(=O)NC(C)(C)C)c3)nc(Nc3c(C)n[nH]c3C)c2c1]

MS (ES+) m/e 489 (M+H)⁺.

Example 190

N-(tert-Butyl)-2-(3-(6-ethoxy-4-((2-methylpyrimidin-5-yl)amino) quinazolin-2-yl)phenoxy)acetamide

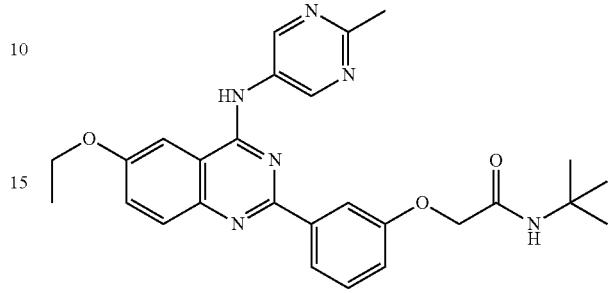

MS (ES+) m/e 487 (M+H)⁺.

Example 191

N-(tert-Butyl)-2-(3-(6-ethoxy-4-((5-phenyl-1H-pyrazol-3-yl)amino) quinazolin-2-yl)phenoxy)acetamide

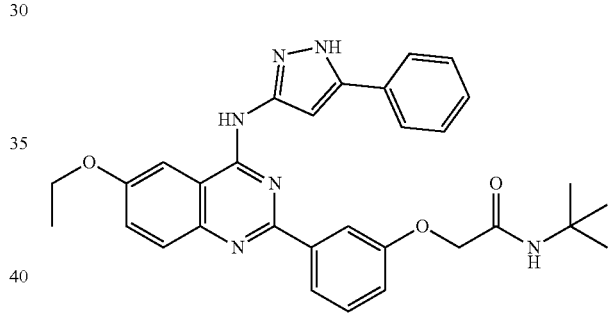

MS (ES+) m/e 537 (M+H)⁺.

Example 192

N-(tert-Butyl)-2-(3-(6-ethoxy-4-((5-isopropyl-1H-pyrazol-3-yl)amino) quinazolin-2-yl)phenoxy)acetamide

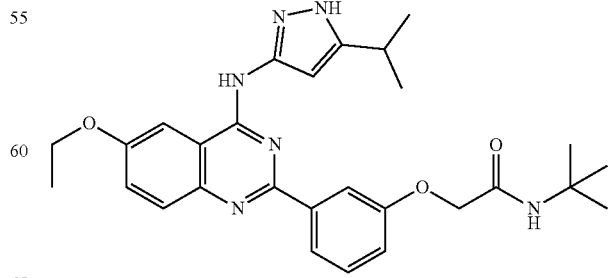

MS (ES+) m/e 503 (M+H)⁺.

Example 193

4-((2-(3-(2-(tert-Butylamino)-2-oxoethoxy)phenyl)-6-ethoxyquinazolin-4-yl)amino)-2-fluorobenzamide

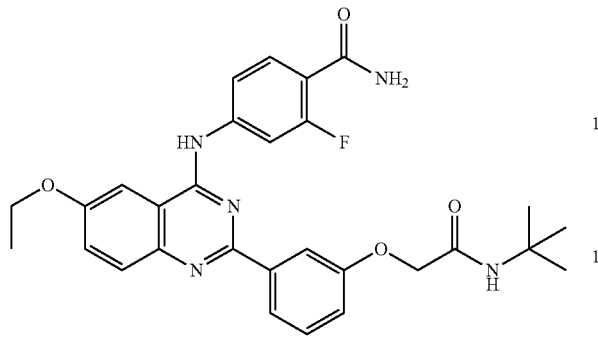

MS (ES+) m/e 532 (M+H)+.

Example 194

N-(tert-Butyl)-2-(3-(6-ethoxy-4-((1-(2-methoxyethyl)-1H-pyrazol-4-yl)amino) quinazolin-2-yl)phenoxy)acetamide

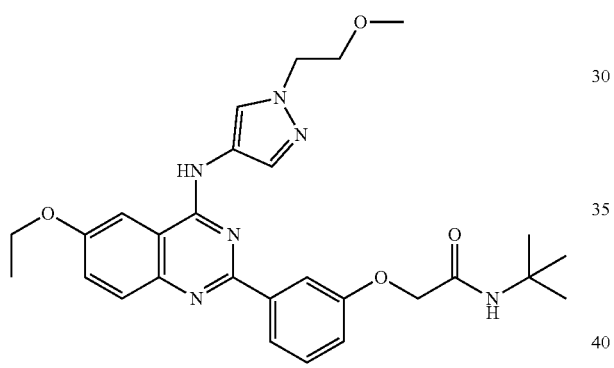

MS (ES+) m/e 519 (M+H)+.

Example 195

N-(tert-Butyl)-2-(3-(6-ethoxy-4-((1-(tetrahydrofuran-3-yl)-1H-pyrazol-4-yl)amino)quinazolin-2-yl)phenoxy)acetamide

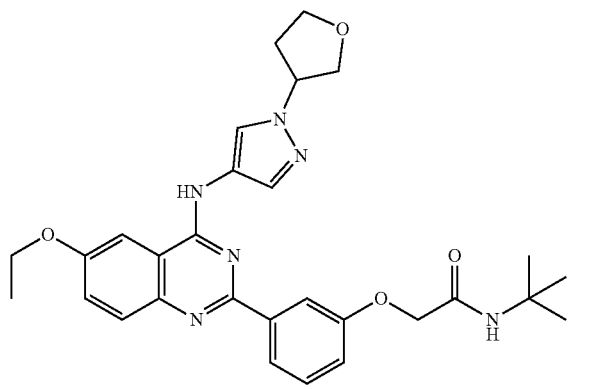

MS (ES+) m/e 531 (M+H)+.

Example 196

N-(tert-Butyl)-2-(3-(6-ethoxy-4-((1-(tetrahydro-2H-pyran-4-yl)-1H-pyrazol-4-yl)amino)quinazolin-2-yl)phenoxy)acetamide

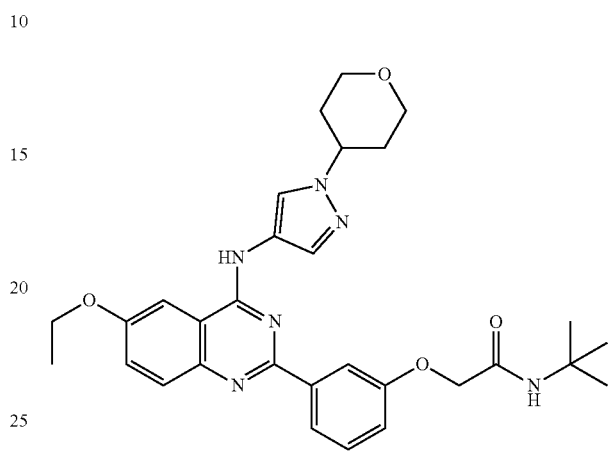

MS (ES+) m/e 545 (M+H)+.

Example 197

N-(tert-Butyl)-2-(3-(6-ethoxy-4-((1-(1-methylpiperidin-4-yl)-1H-pyrazol-4-yl)amino)quinazolin-2-yl)phenoxy)acetamide

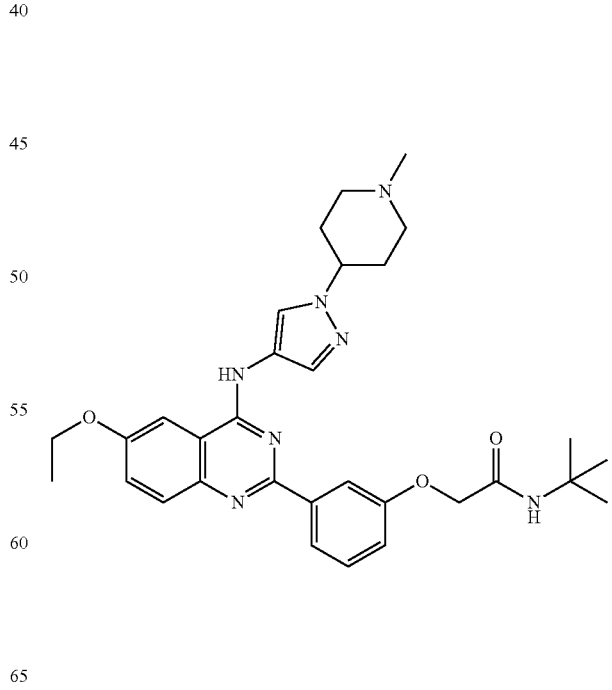

MS (ES+) m/e 558 (M+H)+.

Example 198

N-(tert-Butyl)-2-(3-(6-ethoxy-4-((1-ethyl-1H-pyrazol-4-yl)amino) quinazolin-2-yl)phenoxy)acetamide

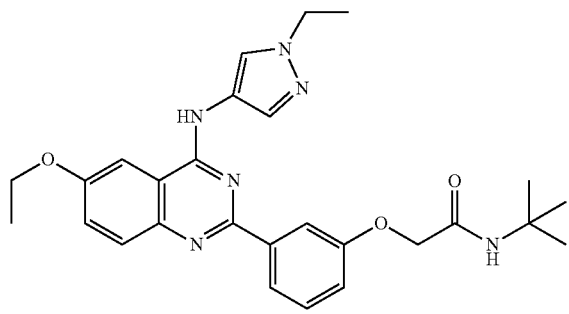

MS (ES+) m/e 489 (M+H)$^+$.

Example 199

2-(3-(4-((5-Benzyl-1H-pyrazol-3-yl)amino)-6-ethoxyquinazolin-2-yl) phenoxy)-N-(tert-butyl)acetamide

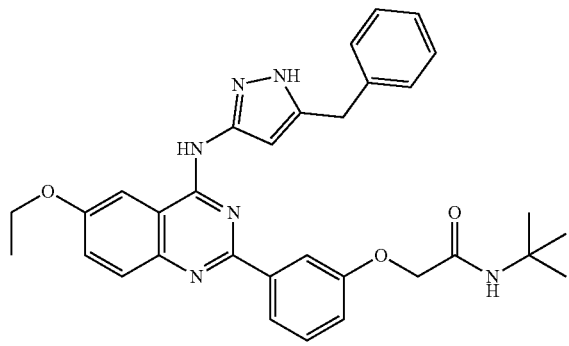 [SMILES: CCOc1ccc2nc(-c3cccc(OCC(=O)NC(C)(C)C)c3)nc(Nc3cc(Cc4ccccc4)[nH]n3)c2c1]

MS (ES+) m/e 551 (M+H)$^+$.

Example 200

N-(tert-Butyl)-2-(3-(5-(4-methoxyphenyl)-4-((1-methyl-1H-pyrazol-4-yl)amino)pyrimidin-2-yl)phenoxy)acetamide

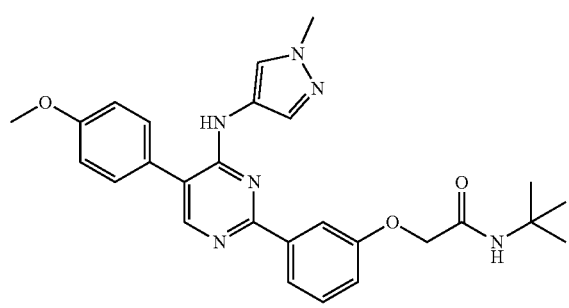

MS (ES+) m/e 487 (M+H)$^+$.

Example 201

2-(3-(4-((1H-Pyrazol-4-yl)amino)-6-(2-methoxyethoxy)quinazolin-2-yl) phenoxy)-N-(tert-butyl)acetamide

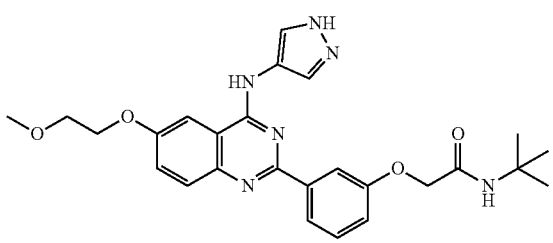 [SMILES: COCCOc1ccc2nc(-c3cccc(OCC(=O)NC(C)(C)C)c3)nc(Nc3cn[nH]c3)c2c1]

MS (ES+) m/e 491 (M+H)$^+$.

Example 202

N-(tert-Butyl)-2-(3-(6-(2-methoxyethoxy)-4-((1-methyl-1H-pyrazol-4-yl)amino)quinazolin-2-yl)phenoxy)acetamide

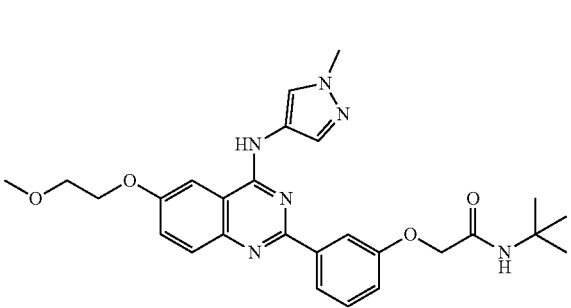

MS (ES+) m/e 505 (M+H)$^+$.

Example 203

2-(3-(4-((1H-Pyrazol-4-yl)amino)-5-(benzyloxy)pyrimidin-2-yl)phenoxy)-N-(tert-butyl)acetamide

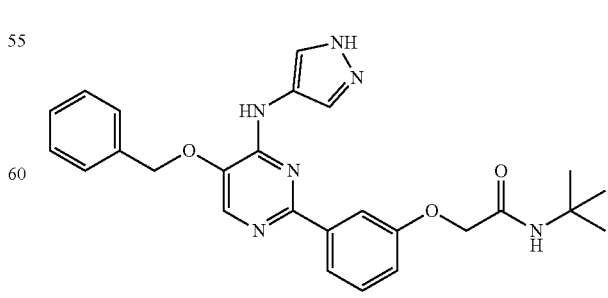

MS (ES+) m/e 473 (M+H)$^+$.

Example 204

2-(3-(5-(Benzyloxy)-4-((1-methyl-1H-pyrazol-4-yl)amino)pyrimidin-2-yl)phenoxy)-N-(tert-butyl)acetamide

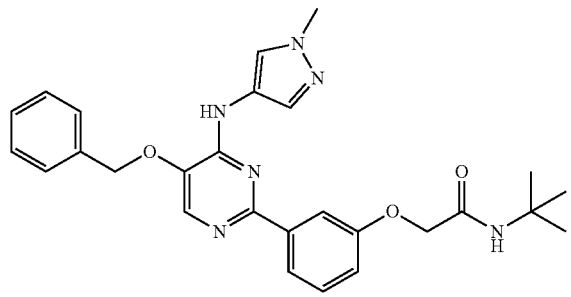 [SMILES: Cn1cc(Nc2nc(-c3cccc(OCC(=O)NC(C)(C)C)c3)ncc2OCc2ccccc2)cn1]

MS (ES+) m/e 487 (M+H)+.

Example 205

N-(tert-Butyl)-2-(3-(4-((1-methyl-1H-pyrazol-4-yl)amino)-5-(pyridin-4-yl)pyrimidin-2-yl)phenoxy)acetamide

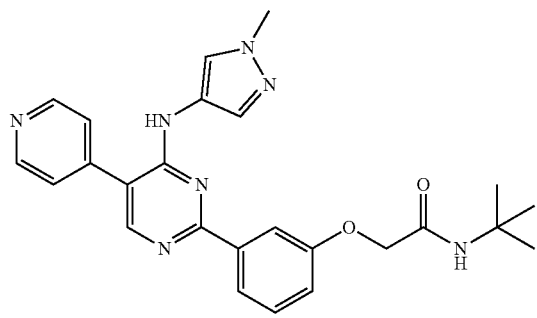 [SMILES: Cn1cc(Nc2nc(-c3cccc(OCC(=O)NC(C)(C)C)c3)ncc2-c2ccncc2)cn1]

MS (ES+) m/e 458 (M+H)+.

Example 206

N-(tert-Butyl)-2-(3-(4-((1-ethyl-1H-pyrazol-4-yl)amino)-5,7-dihydrofuro[3,4-d]pyrimidin-2-yl)phenoxy)acetamide

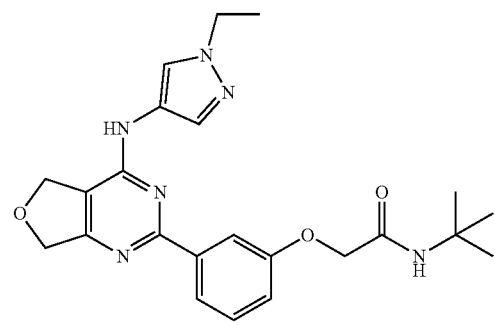 [SMILES: CCn1cc(Nc2nc(-c3cccc(OCC(=O)NC(C)(C)C)c3)nc3c2COC3)cn1]

MS (ES+) m/e 437 (M+H)+.

Example 207

N-(tert-Butyl)-2-(3-(4-((1-ethyl-1H-pyrazol-4-yl)amino)-7,8-dihydro-5H-pyrano[4,3-d]pyrimidin-2-yl)phenoxy)acetamide

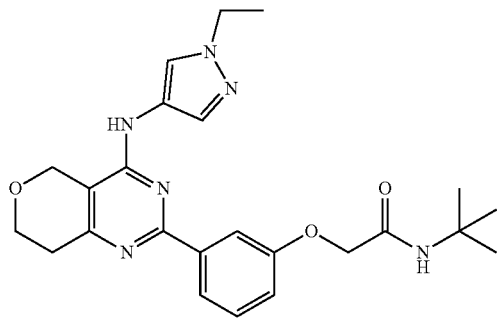 [SMILES: CCn1cc(Nc2nc(-c3cccc(OCC(=O)NC(C)(C)C)c3)nc3c2COCC3)cn1]

MS (ES+) m/e 451 (M+H)+.

Example 208

N-(tert-Butyl)-2-(3-(4-((1-(2-methoxyethyl)-1H-pyrazol-4-yl)amino)-5,7-dihydrofuro[3,4-d]pyrimidin-2-yl)phenoxy)acetamide

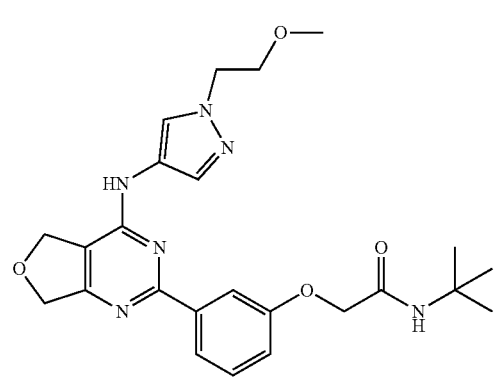 [SMILES: COCCn1cc(Nc2nc(-c3cccc(OCC(=O)NC(C)(C)C)c3)nc3c2COC3)cn1]

MS (ES+) m/e 467 (M+H)+.

Example 209

N-(tert-Butyl)-2-(3-(4-((4-cyano-3-fluorophenyl)amino)-6-ethoxyquinazolin-2-yl)phenoxy)acetamide

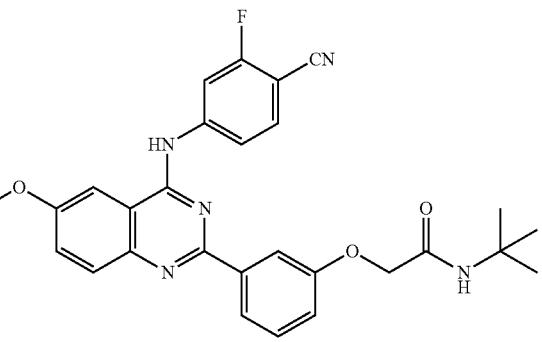

MS (ES+) m/e 514 (M+H)+.

Example 210

N-(tert-Butyl)-2-(3-(6-ethoxy-4-((6-fluoropyridin-3-yl)amino)quinazolin-2-yl) phenoxy)acetamide

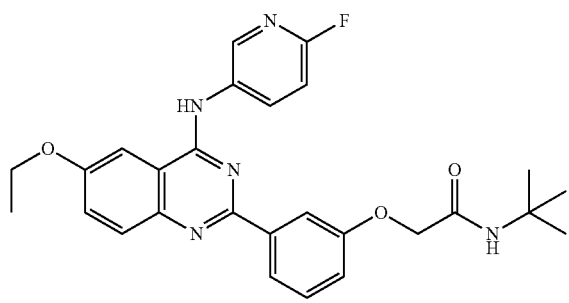

MS (ES+) m/e 490 (M+H)+.

Example 211

N-(tert-Butyl)-2-(3-(6-ethoxy-4-((2-fluoropyridin-4-yl)amino)quinazolin-2-yl) phenoxy)acetamide

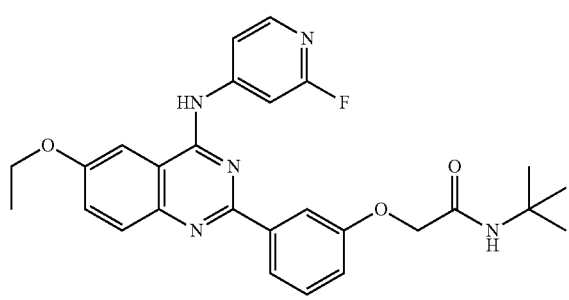 [SMILES: CCOc1ccc2nc(-c3cccc(OCC(=O)NC(C)(C)C)c3)nc(Nc3ccnc(F)c3)c2c1]

MS (ES+) m/e 490 (M+H)+.

Example 212

N-(tert-Butyl)-2-(3-(5-(3-methoxyprop-1-yn-1-yl)-4-((1-methyl-1H-pyrazol-4-yl)amino)pyrimidin-2-yl) phenoxy)acetamide

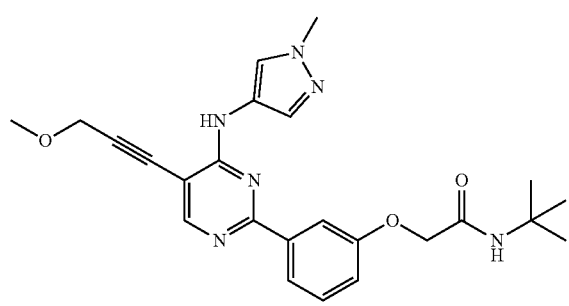 [SMILES: COCC#Cc1cnc(-c2cccc(OCC(=O)NC(C)(C)C)c2)nc1Nc1cnn(C)c1]

MS (ES+) m/e 449 (M+H)+.

Example 213

2-(3-(4-((1H-Pyrazol-4-yl)amino)-6-isopropoxyquinazolin-2-yl)phenoxy)-N-(tert-butyl)acetamide

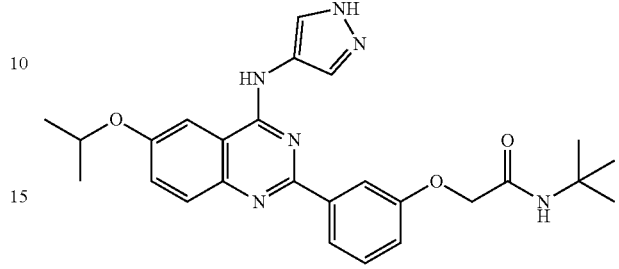

MS (ES+) m/e 475 (M+H)+.

Example 214

2-(3-(4-((1H-Pyrazol-4-yl)amino)-5-(2-methoxyethoxy)quinazolin-2-yl)-phenoxy)-N-(tert-butyl)acetamide

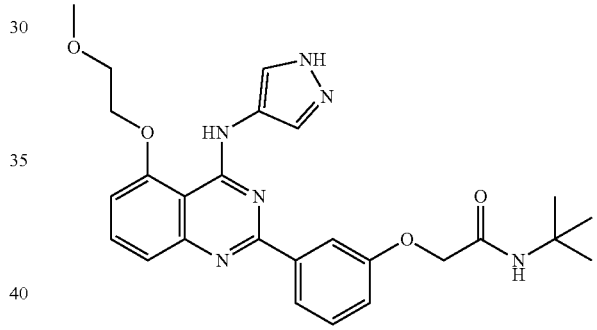

Step 1

2-Methoxyethyl 2-(2-methoxyethoxy)-6-nitrobenzoate

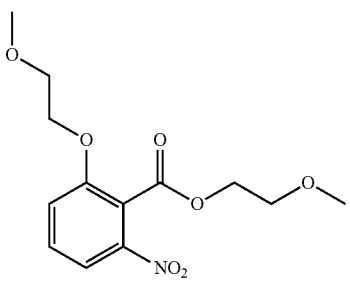 [SMILES: COCCOC(=O)c1c(OCCOC)cccc1[N+](=O)[O-]]

To a mixture of 2-hydroxy-6-nitrobenzoic acid (2 g, 10.92 mmol) and 1-bromo-2-methoxy-ethane (4.55 g, 32.77 mmol, 3.08 mL) in DMF (20 mL) was added K$_2$CO$_3$ (3.02 g, 21.84 mmol). The mixture was stirred at 80° C. for 16 h, cooled to room temperature, quenched by H$_2$O (100 mL)

and extracted with EtOAc (50 mL×2). The combined organic layers were washed by H₂O (100 mL×3), brine (100 mL×2), dried over Na₂SO₄, concentrated under reduced pressure to provide the title compound (3.3 g, crude) as a yellow oil. The crude product was used for the next step reaction without further purification. ¹H NMR (400 MHz, DMSO-d₆) δ 7.80 (d, J=8.0 Hz, 1H), 7.70 (t, J=8.4 Hz, 1H), 7.63 (d, J=8.4 Hz, 1H), 4.40 (t, J=8.4 Hz, 2H), 4.27 (t, J=8.4 Hz, 2H), 3.67-3.60 (m, 4H), 3.31 (s, 3H), 3.28 (s, 3H).

Step 2

2-Methoxyethyl 2-amino-6-(2-methoxyethoxy)benzoate

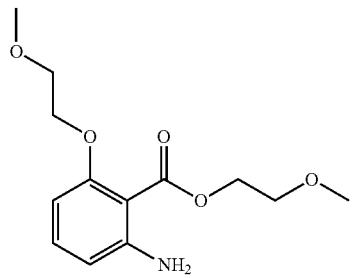 [SMILES: COCCOC(=O)c1c(N)cccc1OCCOC]

To a mixture of 2-methoxyethyl-2-(2-methoxyethoxy)-6-nitrobenzoate (3.3 g, crude) in MeOH (30 mL) was added dry Pd/C (400 mg, 10% purity). The mixture was stirred at 40° C. for 16 h under H₂ (50 psi) and filtered through celite pad and the filtrate was concentrated under reduced pressure to provide the title compound (3.2 g, crude) as a yellow oil. The crude product was used for the next step reaction without further purification. ¹H NMR (400 MHz, DMSO-d₆) δ 7.06 (t, J=8.4 Hz, 1H), 6.34 (dd, J=8.4, 2.0 Hz, 1H), 6.19 (d, J=8.0 Hz, 1H), 5.67 (m, 2H), 4.35-4.30 (m, 2H), 4.03-4.01 (m, 2H), 3.66-3.60 (m, 4H), 3.30 (d, J=5.6 Hz, 6H).

Step 3

5-(2-Methoxyethoxy)quinazoline-2,4-diol

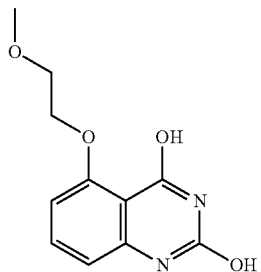 [SMILES: COCCOc1cccc2nc(O)nc(O)c12]

A mixture of 2-methoxyethyl 2-amino-6-(2-methoxyethoxy)-benzoate (3.2 g, crude) and urea (18 g, 299.72 mmol) was stirred at 180° C. for 4 h. The mixture was cooled to room temperature and to the mixture was added H₂O (400 mL). The mixture was stirred at 20° C. for 16 h, filtered, and dried to provide the title compound (4 g, crude) as a white solid. The crude product was used for the next step without further purification.

Step 4

2,4-Dichloro-5-(2-methoxyethoxy)quinazoline

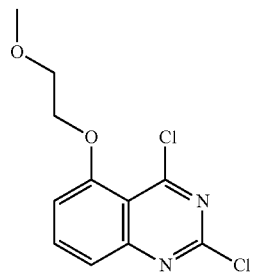 [SMILES: COCCOc1cccc2nc(Cl)nc(Cl)c12]

To POCl₃ (40 mL) was added compound 5-(2-methoxyethoxy)quinazoline-2,4-diol (4 g, crude) and DIPEA (4.38 g, 33.87 mmol, 5.90 mL). The mixture was stirred at 100° C. for 16 h, and concentrated under reduced pressure to give a residue. The residue was poured into ice-water (150 mL) slowly and carefully basified by sat. NaHCO₃ at 0° C. to about pH=8. The resulted mixture was extracted with EtOAc (300 mL×3). The combined organic layers were washed with brine (300 mL×2), dried over Na₂SO₄, filtered and concentrated under reduced pressure to give a residue. The residue was purified by column chromatography (SiO₂, Petroleum ether/Ethyl acetate=10/1 to 0:1) to provide the title compound (820 mg, crude) as a yellow solid.

Step 5

2-Chloro-5-(2-methoxyethoxy)-N-(1-(tetrahydro-2H-pyran-2-yl)-1H-pyrazol-4-yl)quinazolin-4-amine

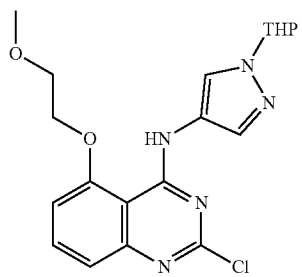

To a mixture of 2,4-dichloro-5-(2-methoxyethoxy)quinazoline (300 mg, crude) and 1-tetrahydropyran-2-ylpyrazol-4-amine (183.67 mg, crude) in DMF (3 mL) was added DIPEA (382.66 μL, 2.20 mmol). The mixture was stirred at 60° C. for 16 h. The reaction mixture was cooled to room temperature, quenched by H₂O (50 mL) and extracted with EtOAc (50 mL×2). The combined organic layers were washed by brine (50 mL×2), dried over Na₂SO₄, concentrated under reduced pressure to give a residue. The residue was purified by column chromatography (SiO₂, Petroleum ether/Ethyl acetate=1/1 to 0:1) to provide the title compound (total amount was 350 mg) as a brown solid. ¹H NMR (500 MHz, DMSO-d₆) δ 10.35 (s, 1H), 8.30-8.28 (m, 1H), 7.80-7.74 (m, 1H), 7.70 (s, 1H), 7.32-7.28 (m, 1H), 7.20-7.17 (m, 1H), 5.47 (dd, J=9.6, 2.0 Hz, 1H), 4.47-4.45 (m, 2H), 3.96-3.90 (m, 3H), 3.73-3.65 (m, 1H), 3.44 (s, 3H), 2.13-2.05 (m, 1H), 2.00-1.95 (m, 2H), 1.75-1.65 (m, 1H), 1.57-1.56 (m, 2H).

Step 6

N-(tert-Butyl)-2-(3-(5-(2-methoxyethoxy)-4-((1-(tetrahydro-2H-pyran-2-yl)-1H-pyrazol-4-yl)amino)quinazolin-2-yl)phenoxy)acetamide

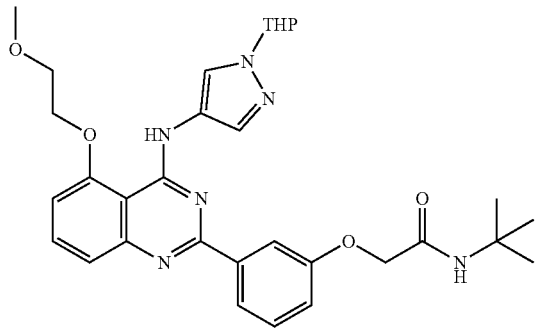

To a mixture of 2-chloro-5-(2-methoxyethoxy)-N-(1-(tetrahydro-2H-pyran-2-yl)-1H-pyrazol-4-yl)quinazolin-4-amine (350 mg, 866.63 µmol), N-(tert-butyl)-2-(3-(4,4,5,5-tetramethyl-1,3,2-dioxaborolan-2-yl)phenoxy)acetamide (346.54 mg, 1.04 mmol), and $K_2CO_3$ (239.55 mg, 1.73 mmol) in dioxane (5 mL) and $H_2O$ (0.5 mL) was added Pd(dppf)Cl$_2$ (63.41 mg, 86.66 µmol). The mixture was stirred at 100° C. for 16 h under N2, cooled to room temperature, quenched by $H_2O$ (50 mL) and extracted with EtOAc (50 mL×3). The combined organic layers were washed by brine (50 mL×2), dried over $Na_2SO_4$, concentrated under reduced pressure to give a residue. The residue was purified by column chromatography (SiO$_2$, Petroleum ether/Ethyl acetate=1/1 to 0:1) to provide the title compound (350 mg, 70%) as a brown solid.

Step 7

2-(3-(4-((1H-Pyrazol-4-yl)amino)-5-(2-methoxyethoxy)quinazolin-2-yl)-phenoxy)-N-(tert-butyl)acetamide

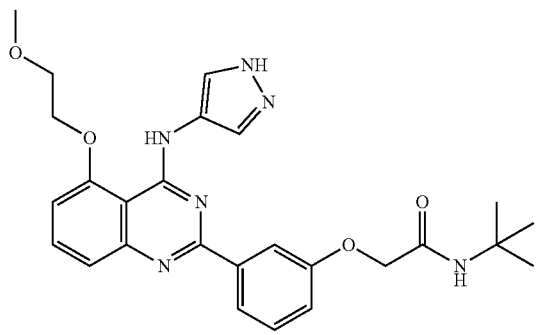 [SMILES: COCCOc1cccc2nc(-c3cccc(OCC(=O)NC(C)(C)C)c3)nc(Nc3cn[nH]c3)c12]

To a mixture of N-(tert-butyl)-2-(3-(5-(2-methoxyethoxy)-4-((1-(tetrahydro-2H-pyran-2-yl)-1H-pyrazol-4-yl)amino)quinazolin-2-yl)phenoxy)acetamide (350 mg, 609.05 µmol) in DCM (5 mL) was added HCl/dioxane (4 N, 5 mL). The mixture was stirred at 20° C. for 2 h and concentrated under reduced pressure to give a residue. The residue was purified by prep-HPLC (HCl conditions) to provide the title compound (84.2 mg, 26%, HCl salt) as a yellow solid. $^1$H NMR (500 MHz, DMSO-d$_6$) δ 11.00 (s, 1H), 8.12 (s, 2H), 8.00-7.94 (m, 3H), 7.80 (d, J=8.0 Hz, 1H), 7.69 (s, 1H), 7.62 (t, J=8.0 Hz, 1H), 7.38 (d, J=8.4 Hz, 1H), 7.30 (d, J=8.4 Hz, 1H), 4.62 (s, 2H), 4.56 (m, 2H), 3.96-3.94 (m, 2H), 3.45 (s, 3H), 1.30 (s, 9H). MS (ES+) m/e 491.2 (M+H)$^+$.

Example 215

2-(3-(4-((1H-Pyrazol-4-yl)amino)-5-(2-fluoroethoxy)quinazolin-2-yl)phenoxy)-N-(tert-butyl)acetamide

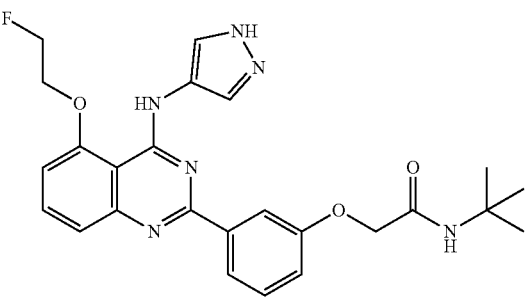 [SMILES: CC(C)(C)NC(=O)COc1cccc(-c2nc(Nc3cn[nH]c3)c3c(OCCF)cccc3n2)c1]

The title compound was synthesized following the same synthetic sequence described for Example 214 with the appropriate starting materials. $^1$H NMR (400 MHz, DMSO-d$_6$) δ 10.92 (s, 1H), 8.14 (s, 2H), 8.01-7.99 (m, 3H), 7.91 (d, J=8.4 Hz, 1H), 7.73 (s, 1H), 7.63 (t, J=8.4 Hz, 1H), 7.42 (d, J=8.0 Hz, 1H), 7.33-7.30 (m, 1H), 5.15-5.13 (m, 1H), 5.04-5.02 (m, 1H), 4.77-4.75 (m, 1H), 4.70-4.68 (m, 1H), 4.63 (s, 2H), 1.29 (s, 9H). MS (ES+) m/e 479.2 (M+H)$^+$.

Example 216

2-(3-(4-((1H-Pyrazol-3-yl)amino)-6-methoxyquinazolin-2-yl)phenoxy)-N-(tert-butyl)acetamide

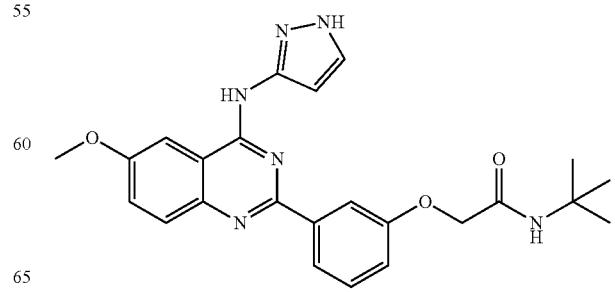

Step 1

3-Nitro-1-((2-(trimethylsilyl)ethoxy)methyl)-1H-pyrazole

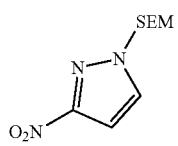

To a mixture of 3-nitro-1H-pyrazole (10 g, 88.44 mmol) in DMF (80 mL) was added NaH (4.24 g, 106.13 mmol, 60% purity) in portions at 0° C. Then to the mixture was added SEM-Cl (17.69 g, 106.13 mmol, 18.78 mL) dropwise at 0° C. The mixture was stirred at 25° C. for 1 h. The resulting mixture was diluted with water and extracted with EtOAc (50 mL×3). The combined organic layers were washed with brine (50 mL×3), dried over $Na_2SO_4$, filtered and concentrated under reduced pressure to give a residue. The residue was purified by column chromatography ($SiO_2$, Petroleum ether/Ethyl acetate=1:0 to 5:1, $R_f$=0.7, 0.75) to provide the title compound (29.5 g, crude) as a yellow oil.

Step 2

1-((2-(Trimethylsilyl)ethoxy)methyl)-1H-pyrazol-3-amine

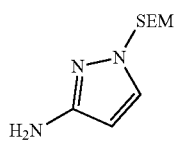

To a solution of 3-nitro-1-((2-(trimethylsilyl)ethoxy)methyl)-1H-pyrazole (10 g) in MeOH (150 mL) was added Pd/C (1.2 g, 10% purity, wet). The suspension was degassed under vacuum and purged with $H_2$ several times. The mixture was stirred under $H_2$ (15 psi) at 28° C. for 16 hours. The mixture was filtered. The filtrate was concentrated to provide the title compound (7.28 g, crude) as a yellow oil. The crude was used directly.

Step 3

2-Chloro-6-methoxy-N-(1-((2-(trimethylsilyl)ethoxy)methyl)-1H-pyrazol-3-yl)quinazolin-4-amine

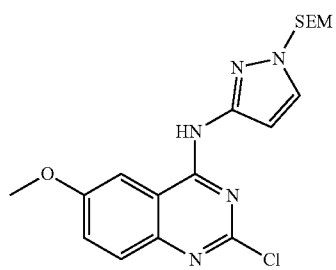 [SMILES: COc1ccc2nc(Cl)nc(Nc3ccn(COCC[Si](C)(C)C)n3)c2c1]

The title compound was synthesized following the procedure described for Example 214, step 5. $^1$H NMR (400 MHz, DMSO-$d_6$) δ 11.0 (s, 1H), 8.11 (d, J=2.8 Hz, 1H), 7.92 (d, J=2.4 Hz, 1H), 7.64 (d, J=8.8 Hz, 1H), 7.48 (dd, J=9.2, 2.8 Hz, 1H), 6.92 (d, J=2.4 Hz, 1H), 5.39 (s, 2H), 3.92 (s, 3H), 3.57-3.52 (m, 2H), 0.88-0.84 (m, 2H), 0.04-0.02 (m, 9H).

Step 4

2-Chloro-6-methoxy-N-(1-((2-(trimethylsilyl)ethoxy)methyl)-1H-pyrazol-3-yl)quinazolin-4-amine

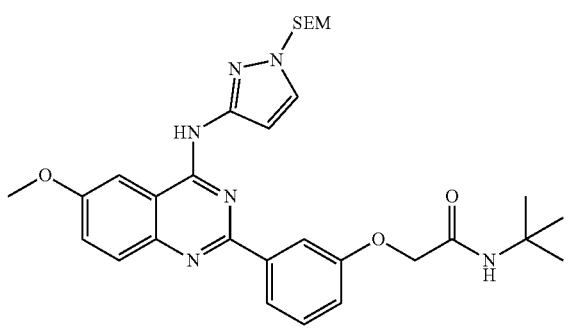 [SMILES: COc1ccc2nc(-c3cccc(OCC(=O)NC(C)(C)C)c3)nc(Nc3ccn(COCC[Si](C)(C)C)n3)c2c1]

The title compound was synthesized following the procedure described for Example 214, Step 6.

Step 5

2-(3-(4-((1H-Pyrazol-3-yl)amino)-6-methoxyquinazolin-2-yl)phenoxy)-N-(tert-butyl)acetamide

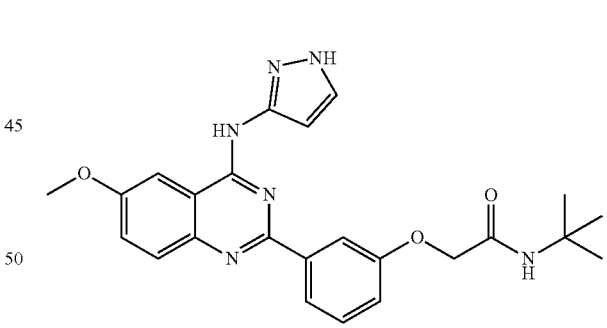

To a mixture of N-(tert-butyl)-2-(3-(6-methoxy-4-((1-((2-(trimethylsilyl)-ethoxy)methyl)-1H-pyrazol-3-yl)-amino)quinazolin-2-yl)phenoxy)acetamide (900 mg, crude) in DCM (20 mL) was added HCl/dioxane (4 N, 10 mL). The mixture was stirred at 25° C. for 1 h. The mixture was concentrated to give a residue. The residue was purified by prep-HPLC (HCl conditions) to provide the title compound (399.8 mg, HCl salt) as a yellow solid. $^1$H NMR (400 MHz, DMSO-$d_6$) δ 11.88 (s, 1H), 8.32 (s, 1H), 8.21 (s, 1H), 8.01-7.99 (m, 2H), 7.90 (d, J=2.0 Hz, 1H), 7.70 (d, J=9.2 Hz, 1H), 7.63-7.57 (m, 2H), 7.26 (d, J=7.6 Hz, 1H), 6.99 (d, J=2.4 Hz, 1H), 4.59 (s, 2H), 3.98 (s, 3H), 1.30 (s, 9H). MS (ES+) m/e 447.2 (M+H)$^+$.

Example 217

N-(tert-Butyl)-2-(3-(6-isopropoxy-4-((1-methyl-1H-pyrazol-4-yl)amino)-quinazolin-2-yl)phenoxy)acetamide

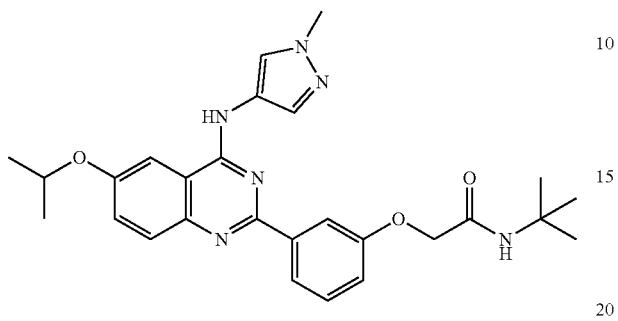

Step 1

Isopropyl 5-isopropoxy-2-nitrobenzoate

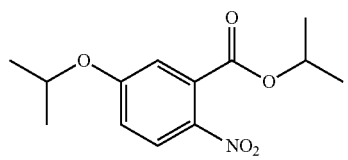 [SMILES: CC(C)OC(=O)c1cc(OC(C)C)ccc1[N+](=O)[O-]]

To a mixture of 5-hydroxy-2-nitrobenzoic acid (15 g, 81.91 mmol) and 2-iodopropane (55.70 g, 327.66 mmol, 32.76 mL) in DMF (150 mL) was added $K_2CO_3$ (28.30 g, 204.79 mmol). The mixture was stirred at 90° C. for 16 h. The mixture was cooled to room temperature and diluted with water (300 mL). The resulting mixture was extracted with EtOAc (300 mL×3). The combined organic layers were washed with brine (400 mL×5), dried over $Na_2SO_4$, filtered and concentrated under reduced pressure to provide the title compound (19 g, 87%) as a yellow solid.

Step 2

Isopropyl 2-amino-5-isopropoxybenzoate

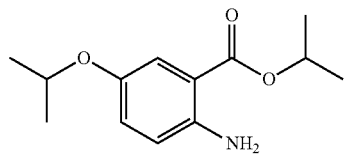

To a mixture of isopropyl 5-isopropoxy-2-nitrobenzoate (19.1 g, 71.46 mmol) in MeOH (180 mL) was added Pd/C (3 g, 10% purity, wet). The mixture was purged with $H_2$ several times. The mixture was stirred under $H_2$ (50 psi) at 40° C. for 16 hours. The mixture was filtered. The filtrate was concentrated to provide the title compound (17 g, crude) as a brown oil. $^1$H NMR (400 MHz, DMSO-$d_6$) δ 7.18 (d, J=2.8 Hz, 1H), 6.97 (dd, J=8.8, 3.2 Hz, 1H), 6.71 (d, J=9.2 Hz, 1H), 6.24 (s, 2H), 5.12-5.03 (m, 1H), 4.38-4.29 (m, 1H), 1.29 (d, J=6.4 Hz, 6H), 1.19 (d, J=6.0 Hz, 6H).

Step 3

6-Isopropoxyquinazoline-2,4-diol

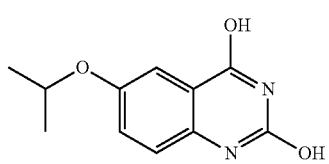 [SMILES: CC(C)Oc1ccc2nc(O)nc(O)c2c1]

The mixture of isopropyl 2-amino-5-isopropoxybenzoate (17 g) in urea (64.54 g, 1.07 mol, 57.63 mL) was heated to 180° C. The mixture was stirred at 180° C. for 4 h, cooled to about 50° C. and poured into water (2 L). The resulting mixture was stirred at 25° C. for 16 h, filtered to give the solid. The solid was washed with water (20 mL), dried with toluene to provide the title compound (14.3 g) as a yellow solid. $^1$H NMR (400 MHz, DMSO-$d_6$) δ 11.2-11.0 (m, 2H), 7.30 (d, J=2.8 Hz, 1H), 7.24 (d, J=8.8, 2.8 Hz, 1H), 7.10 (d, J=8.8 Hz, 1H), 4.63-4.54 (m, 1H), 1.26 (d, J=6.0 Hz, 6H).

Step 4

2,4-Dichloro-6-isopropoxyquinazoline

To $POCl_3$ (130 mL) was added 6-isopropoxyquinazoline-2,4-diol (14.3 g, 64.93 mmol) and DIPEA (16.78 g, 129.87 mmol, 22.62 mL). The mixture was stirred at 100° C. for 16 h under N2, cooled to rt, concentrated to remove most of $POCl_3$, poured into ice water (1 L), neutralized with sat. $NaHCO_3$ to adjust to pH=8 at 0° C., and the resulting mixture was extracted with EtOAc (800 mL×3). The combined organic layers were dried over $Na_2SO_4$, filtered and concentrated under reduced pressure to give a residue. The residue was purified by column chromatography ($SiO_2$, Petroleum ether/Ethyl acetate=1:0 to 10:1, $R_f$=0.95) to provide the title compound (14.5 g, 87%) as a white solid. $^1$H NMR (400 MHz, DMSO-$d_6$) δ 7.96 (d, J=9.2 Hz, 1H), 7.77 (dd, J=9.2, 2.8 Hz, 1H), 7.47 (d, J=2.8 Hz, 1H), 4.97-4.88 (m, 1H), 1.37 (d, J=6.0 Hz, 6H).

Step 5

2-Chloro-6-isopropoxy-N-(1-methyl-1H-pyrazol-4-yl)quinazolin-4-amine

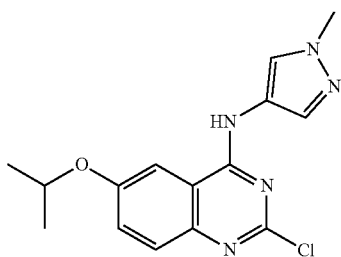 [SMILES: CC(C)Oc1ccc2nc(Cl)nc(Nc3cnn(C)c3)c2c1]

To a mixture of 2,4-dichloro-6-isopropoxyquinazoline (500 mg, 1.94 mmol) and 1-methylpyrazol-4-amine (259.76 mg, 1.94 mmol, HCl) in DMF (5 mL) was added DIPEA (754.00 mg, 5.83 mmol, 1.02 mL). The mixture was stirred at 60° C. for 16 h, cooled to room temperature and diluted with water (20 mL). The resulting mixture was extracted with EtOAc (20 mL×3). The combined organic layers were washed with brine (20 mL×2), dried over Na$_2$SO$_4$, filtered and concentrated under reduced pressure to give a residue. The residue was purified by column chromatography (SiO$_2$, Petroleum ether/Ethyl acetate=20/1 to 1:1, R$_f$=0.2) to provide the title compound (720 mg, crude) as a yellow solid.

Step 6

N-(tert-Butyl)-2-(3-(6-isopropoxy-4-((1-methyl-1H-pyrazol-4-yl)amino)-quinazolin-2-yl)phenoxy)acetamide

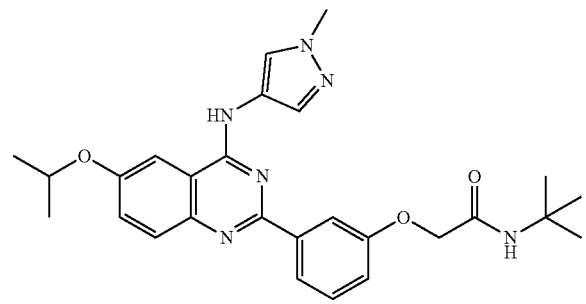 [SMILES: CC(C)Oc1ccc2nc(-c3cccc(OCC(=O)NC(C)(C)C)c3)nc(Nc3cnn(C)c3)c2c1]

To a mixture of 2-chloro-6-isopropoxy-N-(1-methyl-1H-pyrazol-4-yl)-quinazolin-4-amine (720 mg, crude) and N-(tert-butyl)-2-(3-(4,4,5,5-tetramethyl-1,3,2-dioxaborolan-2-yl)phenoxy)acetamide (981.53 mg, 2.95 mmol) in dioxane (7 mL) and H$_2$O (0.7 mL) was added K$_2$CO$_3$ (626.29 mg, 4.53 mmol) and Pd(dppf)Cl$_2$ (165.79 mg, 226.58 μmol). The mixture was stirred at 100° C. for 16 h under N2, cooled to room temperature and diluted with water (30 mL). The resulting mixture was extracted with EtOAc (30 mL×3). The combined organic layers were washed with brine (30 mL×2), dried over Na$_2$SO$_4$, filtered and concentrated under reduced pressure to give a residue. The residue was purified by column chromatography (SiO$_2$, Petroleum ether/Ethyl acetate=20:1 to 1:0, TLC:Petroleum ether/Ethyl acetate=1:1, R$_f$=0.3) to give crude solid. The solid was re-purified by prep-HPLC (HCl conditions) to provide the title compound (645.2 mg, 53%, HCl salt) as a yellow solid. $^1$H NMR (400 MHz, DMSO-d$_6$) δ 11.86 (s, 1H), 8.41 (s, 1H), 8.35 (s, 1H), 8.21-8.05 (m, 1H), 8.00 (s, 1H), 7.99-7.97 (m, 2H), 7.68-7.60 (m, 3H), 7.32-7.30 (m, 1H), 5.03-4.97 (m, 1H), 4.61 (s, 2H), 3.95 (s, 3H), 1.37 (d, J=6.0 Hz, 6H), 1.30 (s, 9H). MS (ES+) m/e 489.3 (M+H)$^+$.

Example 218

N-(tert-Butyl)-2-(3-(6-isopropoxy-4-((1-methyl-1H-pyrazol-3-yl)amino)-quinazolin-2-yl)phenoxy)acetamide

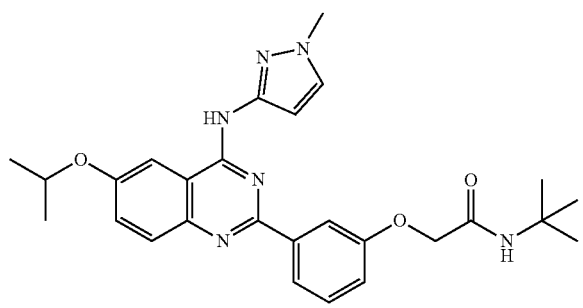 [SMILES: CC(C)Oc1ccc2nc(-c3cccc(OCC(=O)NC(C)(C)C)c3)nc(Nc3ccn(C)n3)c2c1]

Step 1

2-Chloro-6-isopropoxy-N-(1-methyl-1H-pyrazol-3-yl)quinazolin-4-amine

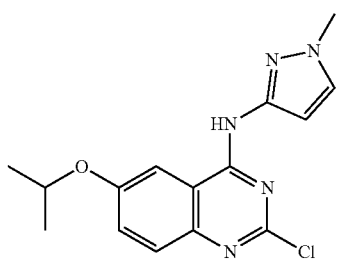 [SMILES: CC(C)Oc1ccc2nc(Cl)nc(Nc3ccn(C)n3)c2c1]

To a mixture of 2,4-dichloro-6-isopropoxyquinazoline (500 mg, 1.94 mmol) and 1-methylpyrazol-3-amine (188.86 mg, 1.94 mmol) in DMF (5 mL) was added DIPEA (502.66 mg, 3.89 mmol, 677.44 μL). The mixture was stirred at 60° C. for 16 h. The reaction mixture was cooled to room temperature and diluted with water (20 mL). The resulting mixture was extracted with EtOAc (20 mL×3). The combined organic layers were washed with brine (20 mL×2), dried over Na$_2$SO$_4$, filtered and concentrated under reduced pressure to give a residue. The residue was purified by column chromatography (SiO$_2$, Petroleum ether/Ethyl acetate=20/1 to 1:1, R$_f$=0.6) to provide the title compound (700 mg, crude) as a yellow solid.

Step 2

N-(tert-Butyl)-2-(3-(6-isopropoxy-4-((1-methyl-1H-pyrazol-3-yl)amino)-quinazolin-2-yl)phenoxy)acetamide

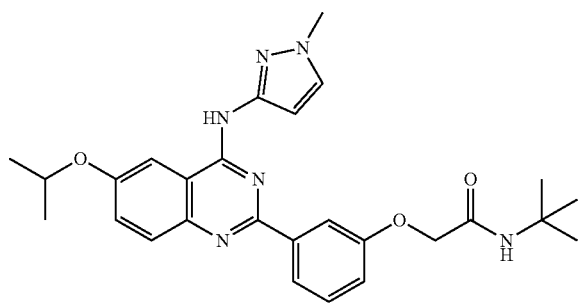 [SMILES: CC(C)Oc1ccc2nc(-c3cccc(OCC(=O)NC(C)(C)C)c3)nc(Nc3ccn(C)n3)c2c1]

To a mixture of 2-chloro-6-isopropoxy-N-(1-methyl-1H-pyrazol-3-yl)-quinazolin-4-amine (700 mg, crude) and N-(tert-butyl)-2-(3-(4,4,5,5-tetramethyl-1,3,2-dioxaborolan-2-yl)phenoxy)acetamide (954.26 mg, 2.86 mmol) in dioxane (7 mL) and H$_2$O (0.7 mL) was added K$_2$CO$_3$ (608.89 mg, 4.41 mmol) and Pd(dppf)Cl$_2$ (161.18 mg, 220.28 μmol). The mixture was stirred at 100° C. for 16 h under N2. The reaction mixture was cooled to room temperature and diluted with water (30 mL). The resulting mixture was extracted with EtOAc (30 mL×3). The combined organic layers were washed with brine (30 mL×2), dried over Na$_2$SO$_4$, filtered and concentrated under reduced pressure to give a residue. The residue was purified by column chromatography (SiO$_2$, Petroleum ether/Ethyl acetate=20:1 to 1:0, TLC:Petroleum ether/Ethyl acetate=1:1, R$_f$=0.5) to give crude solid. The solid was re-purified by prep-HPLC (HCl conditions) to provide the title compound (615.3 mg, 53%, HCl salt) as a yellow solid. $^1$H NMR (400 MHz, DMSO-d$_6$) δ 11.7 (s, 1H), 8.26-8.15 (m, 2H), 7.99-7.98 (m, 2H), 7.84 (s, 1H), 7.61-7.56 (m, 3H), 7.26-7.24 (m, 1H), 6.95 (d, J=2.0 Hz, 1H), 4.95-4.89 (m, 1H), 4.58 (s, 2H), 3.90 (s, 3H), 1.39 (d, J=5.6 Hz, 6H), 1.30 (s, 9H). MS (ES+) m/e 489.3 (M+H)$^+$.

Example 219

N-(tert-Butyl)-2-(3-(4-((1-methyl-1H-pyrazol-4-yl)amino)-6-propoxyquinazolin-2-yl)phenoxy)acetamide

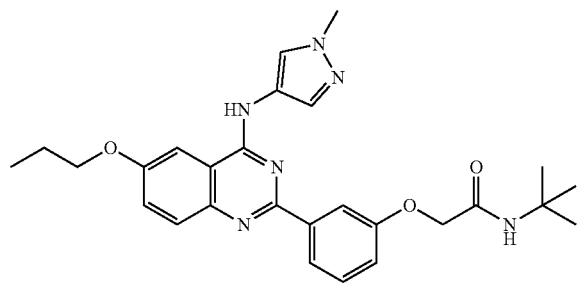 [SMILES: CCCOc1ccc2nc(-c3cccc(OCC(=O)NC(C)(C)C)c3)nc(Nc3cnn(C)c3)c2c1]

Step 1

2-Chloro-N-(1-methyl-1H-pyrazol-4-yl)-6-propoxy-quinazolin-4-amine

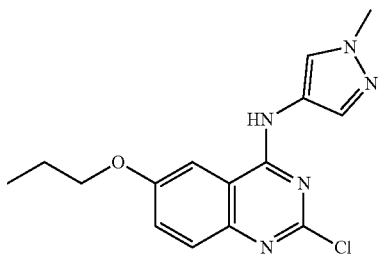 [SMILES: CCCOc1ccc2nc(Cl)nc(Nc3cnn(C)c3)c2c1]

To a solution of 2,4-dichloro-6-propoxyquinazoline (400 mg, 1.56 mmol) and 1-methyl-1H-pyrazol-4-amine (151.09 mg, 1.56 mmol) in DMF (4 mL) was added DIEA (402.13 mg, 3.11 mmol, 541.96 μL) at 25° C. and then the reaction mixture was heated to 60° C. and stirred for 15 hours. The mixture was cooled to room temperature and poured into H$_2$O (60 mL). The resulting mixture was extracted with EtOAc (20 mL×2). The combined organic phases were washed with brine (30 mL), dried over anhydrous Na$_2$SO$_4$, filtered and concentrated under reduced pressure. The residue was purified by column chromatography (SiO$_2$, Petroleum ether/Ethyl acetate=5/1 to 1/1) to provide the title compound (300 mg, 61%) as a yellow solid. $^1$H NMR (400 MHz, DMSO-d$_6$) δ 9.18 (s, 1H), 8.27 (s, 1H), 7.67 (d, J=8.8 Hz, 1H), 7.55 (s, 1H), 7.43 (d, J=2.4 Hz, 1H), 7.33 (dd, J=2.4, 9.2 Hz, 1H), 3.93 (s, 3H), 3.81 (t, J=6.8 Hz, 2H), 1.80-1.69 (m, 2H), 0.90-0.89 (m, 1H), 0.94 (t, J=7.6 Hz, 3H).

Step 2

N-(tert-Butyl)-2-(3-(4-((1-methyl-1H-pyrazol-4-yl)amino)-6-propoxyquinazolin-2-yl)phenoxy)acetamide

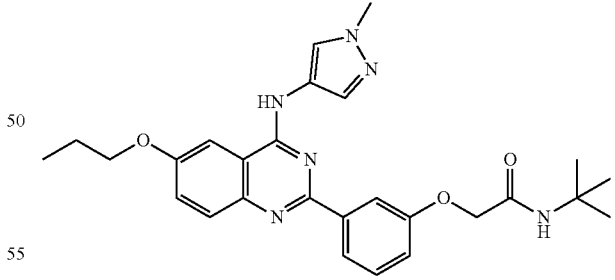

A mixture of 2-chloro-N-(1-methyl-1H-pyrazol-4-yl)-6-propoxyquinazolin-4-amine (300 mg, 944.07 μmol, 1 eq), N-(tert-butyl)-2-(3-(4,4,5,5-tetramethyl-1,3,2-dioxaborolan-2-yl)phenoxy)acetamide (408.97 mg, 1.23 mmol), K$_2$CO$_3$ (260.95 mg, 1.89 mmol) and Pd(dppf)Cl$_2$ (69.08 mg, 94.41 μmol) was suspended in dioxane (4 mL) and H$_2$O (0.4 mL) under nitrogen atmosphere. The resulting reaction mixture was heated to 100° C. and stirred for 15 hours, diluted with water and extracted with EtOAc (30 mL×3). The combined organic phases were washed with brine (30 mL), dried over anhydrous Na$_2$SO$_4$, filtered and concentrated under reduced pressure. The residue was purified by column chromatography (SiO$_2$, Petroleum ether/Ethyl acetate=5/1 to 2/1, R$_f$=0.3) and the further purification was carried out by prep-HPLC (HCl conditions) to provide the title compound (90 mg, 18%) as a light yellow solid. $^1$H NMR (400 MHz, DMSO-d$_6$) δ 11.30 (s, 1H), 8.33 (s, 1H), 8.18 (brs, 1H), 8.06 (d, J=9.2 Hz, 1H), 8.00-7.93 (m, 3H), 7.69 (d, J=8.0 Hz, 1H), 7.64-7.56 (m, 2H), 7.28 (d, J=7.6 Hz, 1H), 4.59 (s, 2H), 4.18 (t, J=6.4 Hz, 2H), 3.96 (s, 3H), 1.90-1.80 (m, 2H), 1.30 (s, 9H), 1.06 (t, J=7.2 Hz, 3H). MS (ES+) m/e 489.2 (M+H)$^+$.

Example 220

2-(3-(4-((1H-Pyrazol-3-yl)amino)-6-isopropoxyquinazolin-2-yl)phenoxy)-N-(tert-butyl)acetamide

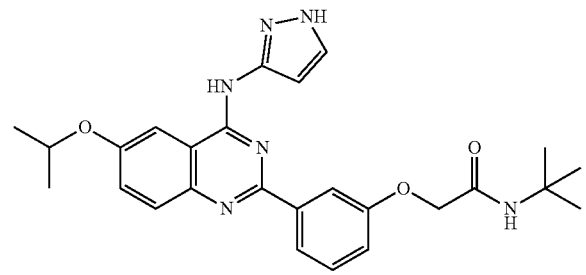 [SMILES: CC(C)Oc1ccc2nc(-c3cccc(OCC(=O)NC(C)(C)C)c3)nc(Nc3cc[nH]n3)c2c1]

Step 1

2-Chloro-6-isopropoxy-N-(1-((2-(trimethylsilyl)ethoxy)methyl)-1H-pyrazol-3-yl)quinazolin-4-amine

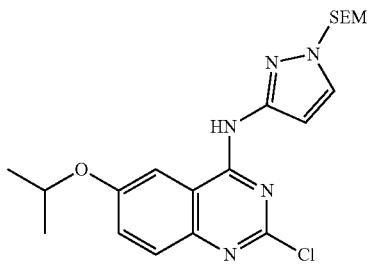 [SMILES: CC(C)Oc1ccc2nc(Cl)nc(Nc3ccn(COCC[Si](C)(C)C)n3)c2c1]

To a mixture of 2,4-dichloro-6-isopropoxyquinazoline (500 mg, 1.94 mmol) and 1-((2-(trimethylsilyl)ethoxy)methyl)-1H-pyrazol-3-amine (414.89 mg) in DMF (5 mL) was added DIPEA (502.67 mg, 3.89 mmol, 677.45 µL). The mixture was stirred at 60° C. for 16 h. The reaction mixture was cooled to room temperature and diluted with water (20 mL). The resulting mixture was extracted with EtOAc (20 mL×3). The combined organic layers were washed with brine (20 mL×2), dried over Na$_2$SO$_4$, filtered and concentrated under reduced pressure to give a residue. The residue was purified by column chromatography (SiO$_2$, Petroleum ether/Ethyl acetate=80/1 to 10:1, R$_f$=0.1) to provide the title compound (460 mg, crude) as a yellow solid.

Step 2

N-(tert-Butyl)-2-(3-(6-isopropoxy-4-((1-((2-(trimethylsilyl)ethoxy)methyl)-1H-pyrazol-3-yl)amino)quinazolin-2-yl)phenoxy)acetamide

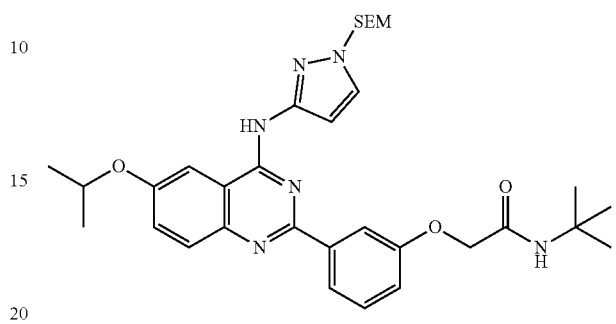

To a mixture of 2-chloro-6-isopropoxy-N-(1-((2-(trimethylsilyl)ethoxy)-methyl)-1H-pyrazol-3-yl)quinazolin-4-amine (460 mg) and N-(tert-butyl)-2-(3-(4,4,5,5-tetramethyl-1,3,2-dioxaborolan-2-yl)phenoxy)acetamide (423.82 mg, 1.27 mmol) in dioxane (5 mL) and H$_2$O (0.5 mL) was added K$_2$CO$_3$ (292.97 mg, 2.12 mmol, 2 eq) and Pd(dppf)Cl$_2$ (77.55 mg, 105.99 µmol). The mixture was stirred at 100° C. for 16 h under N2. The mixture was cooled to room temperature and diluted with water (30 mL). The resulting mixture was extracted with EtOAc (30 mL×3). The combined organic layers were dried over Na$_2$SO$_4$, filtered and concentrated under reduced pressure to give a residue. The residue was purified by column chromatography (SiO$_2$, Petroleum ether/Ethyl acetate=30:1 to 3:1, TLC:Petroleum ether/Ethyl acetate=2:1, R$_f$=0.7) to give compound 5 (600 mg, crude) as a yellow oil.

Step 3

2-(3-(4-((1H-Pyrazol-3-yl)amino)-6-isopropoxyquinazolin-2-yl)phenoxy)-N-(tert-butyl)acetamide

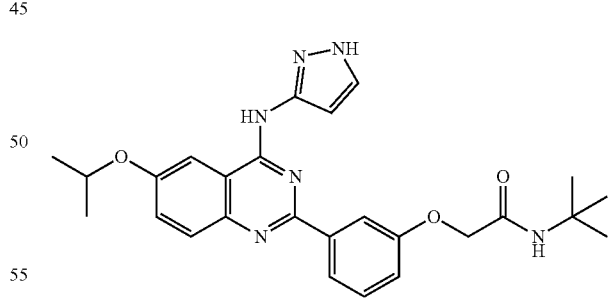

To a mixture of N-(tert-butyl)-2-(3-(6-isopropoxy-4-((1-((2-(trimethylsilyl)-ethoxy)methyl)-1H-pyrazol-3-yl)amino)quinazolin-2-yl)phenoxy)acetamide (600 mg, crude) in DCM (10 mL) was added HCl/dioxane (4 M, 5 mL). The mixture was stirred at 25° C. for 17 h, concentrated and purified by prep-HPLC (HCl conditions) to provide the title compound (170.8 mg, HCl salt) as a yellow solid. $^1$H NMR (400 MHz, DMSO-d$_6$) δ 11.9 (s, 1H), 8.31 (d, J=2.0 Hz, 1H), 8.21-8.19 (m, 1H), 7.98-7.96 (m, 2H), 7.90 (d, J=2.4 Hz, 1H), 7.67-7.58 (m, 3H), 7.28-7.26 (m, 1H), 6.97 (d, J=2.4 Hz, 1H), 4.96-4.90 (m, 1H), 4.58 (s, 2H), 1.39 (d, J=6.0 Hz, 6H), 1.29 (s, 9H). MS (ES+) m/e 475.2 (M+H)+.

Example 221

N-(tert-Butyl)-2-(3-(6-ethoxy-4-((2,4,5,6-tetrahydro-cyclopenta[c]pyrazol-5-yl)-amino)quinazolin-2-yl)phenoxy)acetamide

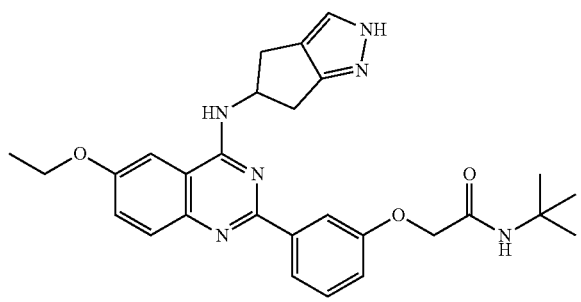 [SMILES: CCOc1ccc2nc(-c3cccc(OCC(=O)NC(C)(C)C)c3)nc(NC3Cc4c[nH]nc4C3)c2c1]

Step 1 tert-Butyl (Z)-(3-((dimethylamino)methylene)-4-oxocyclopentyl)carbamate

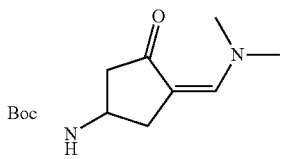

The mixture of tert-butyl (3-oxocyclopentyl)carbamate (2 g, 10.04 mmol) in 1,1-dimethoxy-N,N-dimethyl-methanamine (13.46 g, 112.91 mmol, 15.00 mL) was heated to 100° C. and stirred at 100° C. for 2 h. The mixture was concentrated to provide the title compound. The crude material was used directly for the next step reaction.

Step 2 tert-Butyl (2,4,5,6-tetrahydrocyclopenta[c]pyrazol-5-yl)carbamate

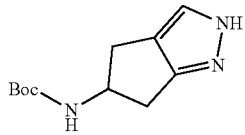

The mixture of tert-butyl (Z)-(3-((dimethylamino)methylene)-4-oxocyclopentyl)carbamate (the crude mixture) and N$_2$H$_4$·H$_2$O (12.79 g, 250.38 mmol, 12.42 mL, 98% purity) in EtOH (30 mL) was stirred at 25° C. for 16 h. The mixture was concentrated to give a residue. The residue was purified by column chromatography (SiO$_2$, Petroleum ether/Ethyl acetate=1:0 to 0:1, Rf=0.6, 0.55, 0.5) to provide the title compound (3.7 g crude). $^1$H NMR (400 MHz, DMSO-d$_6$) δ 7.29-7.24 (m, 2H), 4.53-4.47 (m, 1H), 2.92-2.85 (m, 2H), 2.46-2.38 (m, 2H), 1.39 (s, 9H).

Step 3

2,4,5,6-Tetrahydrocyclopenta[c]pyrazol-5-amine

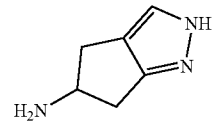

To a mixture of tert-butyl (2,4,5,6-tetrahydrocyclopenta[c]pyrazol-5-yl)-carbamate (35 mg, 156.76 μmol) in DCM (3 mL) was added HCl/dioxane (4 M, 1.5 mL). The mixture was stirred at 25° C. for 1 h and concentrated to provide the title compound (38 mg, crude, HCl salt) as a white solid. $^1$H NMR (400 MHz, DMSO-d$_6$) δ 8.37 (s, 3H), 7.46 (s, 1H), 4.26-4.23 (m, 1H), 3.09-2.99 (m, 2H), 2.76-2.67 (m, 2H).

Step 4

2-Chloro-6-ethoxy-N-(2,4,5,6-tetrahydrocyclopenta[c]pyrazol-5-yl)-quinazolin-4-amine

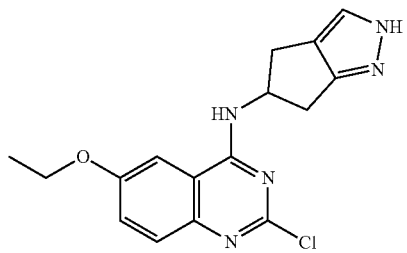 [SMILES: CCOc1ccc2nc(Cl)nc(NC3Cc4c[nH]nc4C3)c2c1]

To a mixture of 2,4-dichloro-6-ethoxyquinazoline (55 mg, 226.25 μmol) and 2,4,5,6-tetrahydrocyclopenta[c]pyrazol-5-amine (36.11 mg, HCl salt) in i-PrOH (1.5 mL) was added TEA (80.13 mg, 791.89 μmol, 110.22 μL). The mixture was stirred at 80° C. for 16 h, cooled to room temperature and diluted with water (10 mL). The resulting mixture was extracted with EtOAc (31 mL×3). The combined organic layers were dried over Na$_2$SO$_4$, filtered and concentrated under reduced pressure to give a residue. The residue was suspended in the mixed solvent (EtOAc:MeOH=20:1, 2 mL). The mixture was filtrate to give the solid. The solid was dried to provide the title compound (30 mg, 40%) as an off-white solid. $^1$H NMR (400 MHz, DMSO-d$_6$) δ 12.34 (s, 1H), 8.72 (d, J=7.2 Hz, 1H), 7.77 (s, 1H), 7.57 (d, J=8.8 Hz, 1H), 7.44-7.38 (m, 2H), 5.32-5.31 (m, 1H), 4.14 (q, J=6.8 Hz, 2H), 3.21-3.15 (m, 2H), 2.81-2.67 (m, 2H), 1.39 (t, J=6.8 Hz, 3H).

Step 5

N-(tert-Butyl)-2-(3-(6-ethoxy-4-((2,4,5,6-tetrahydro-cyclopenta[c]pyrazol-5-yl)-amino)quinazolin-2-yl)phenoxy)acetamide

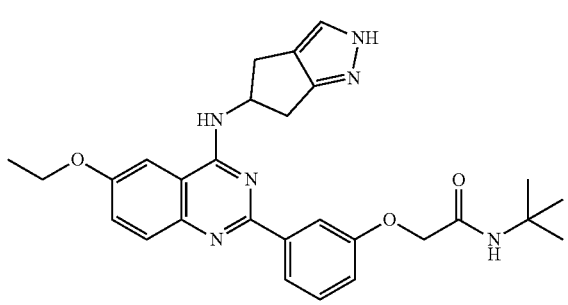 [SMILES: CCOc1ccc2nc(-c3cccc(OCC(=O)NC(C)(C)C)c3)nc(NC3Cc4c[nH]nc4C3)c2c1]

To a mixture of 2-chloro-6-ethoxy-N-(2,4,5,6-tetrahydro-cyclopenta[c]pyrazol-5-yl)-quinazolin-4-amine (30 mg, 90.97 μmol) and N-(tert-butyl)-2-(3-(4,4,5,5-tetramethyl-1,3,2-dioxaborolan-2-yl)phenoxy)acetamide (36.38 mg, 109.16 μmol) in dioxane (1 mL) was added $Na_2CO_3$ (2 M, 90.97 μL) and Pd(PPh$_3$)$_4$ (10.51 mg, 9.10 μmol). The mixture was purged with $N_2$, heated to 120° C. under microwave and stirred at 120° C. for 2 h under $N_2$, cooled to room temperature and diluted with water (15 mL). The resulting mixture was extracted with EtOAc (15 mL×3). The combined organic layers were dried over $Na_2SO_4$, filtered and concentrated under reduced pressure to give a residue. The residue was purified by column chromatography ($SiO_2$, EtOAc) to remove catalyst. The crude product was re-purified by prep-HPLC (HCl conditions) to provide the title compound (4.9 mg, 9%, HCl salt) as a white solid. $^1$H NMR (400 MHz, DMSO-d$_6$) δ 10.0 (s, 1H), 8.08-8.06 (m, 2H), 8.02-7.98 (m, 2H), 7.69-7.63 (m, 2H), 7.59-7.55 (m, 1H), 7.43 (s, 1H), 7.27-7.25 (m, 1H), 5.71-5.69 (m, 1H), 4.56 (s, 2H), 4.22 (q, J=6.8 Hz, 2H), 3.27-3.25 (m, 2H), 3.02-2.88 (m, 2H), 1.42 (t, J=7.2 Hz, 3H), 1.28 (s, 9H). MS (ES+) m/e 501.3 (M+H)$^+$.

Example 222

2-(3-(4-((1H-Pyrazol-4-yl)amino)-6-propoxyquinazolin-2-yl)phenoxy)-N-(tert-butyl)acetamide

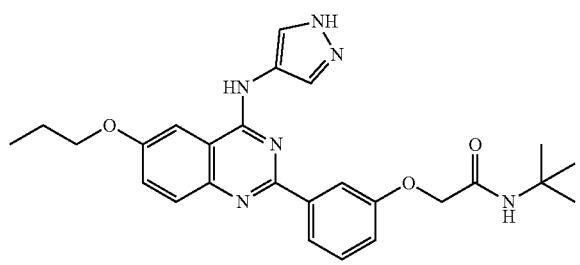

Step 1

Propyl 2-nitro-5-propoxybenzoate

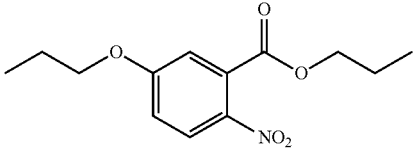

To a stirred solution of 5-hydroxy-2-nitrobenzoic acid (6.0 g, 32.77 mmol) and $K_2CO_3$ (11.32 g, 81.91 mmol) in DMF (60 mL) was added 1-bromopropane (16.12 g, 131.06 mmol, 11.94 mL) at 25° C. and then the resulting reaction mixture was heated to 90° C. and stirred for 15 hours. The mixture was cooled to room temperature and poured into $H_2O$ (250 mL). The resulting mixture was extracted with petroleum ether/ethyl acetate (3:1, 80 mL×3). The combined organic phases were washed with brine (100 mL), dried over $Na_2SO_4$, filtered and concentrated under reduced pressure to provide the title compound (10 g, crude) as a yellow oil. $^1$H NMR (400 MHz, DMSO-d$_6$) δ 7.95 (dd, J=9.2, 1.2 Hz, 1H), 7.01-6.92 (m, 2H), 4.24 (t, J=6.8 Hz, 2H), 3.97 (t, J=6.4 Hz, 2H), 1.84-1.76 (m, 2H), 1.75-1.65 (m, 2H), 0.99 (t, J=7.6 Hz, 3H), 0.93 (t, J=7.6 Hz, 3H).

Step 2

Propyl 2-amino-5-propoxybenzoate

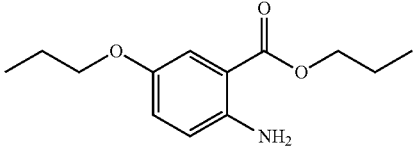 [SMILES: CCCOC(=O)c1cc(OCCC)ccc1N]

To a solution of propyl 2-nitro-5-propoxybenzoate (10 g, crude) in MeOH (100 mL) was added wet Pd/C (1.0 g, 10% purity) and then the reaction mixture was heated to 40° C. and stirred for 15 hours under $H_2$ (50 psi) atmosphere. The mixture was filtered and the solvent was removed under reduced pressure to give compound 3 (7.1 g, crude) as a brown oil. $^1$H NMR (400 MHz, DMSO-d$_6$) δ 7.39 (d, J=3.2 Hz, 1H), 6.95 (dd, J=8.8, 2.8 Hz, 1H), 6.62 (d, J=8.4 Hz, 1H), 5.42 (br s, 2H), 4.24 (t, J=6.4 Hz, 2H), 3.86 (t, J=6.4 Hz, 2H), 1.85-1.72 (m, 4H), 1.03 (t, J=7.2 Hz, 6H).

Step 3

6-Propoxyquinazoline-2,4-diol

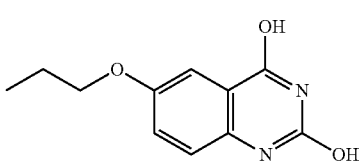 [SMILES: CCCOc1ccc2nc(O)nc(O)c2c1]

A mixture of propyl 2-amino-5-propoxybenzoate (7.1 g, crude) and urea (35.94 g, 598.41 mmol) was heated to 180° C. and stirred for 5 hours. The reaction mixture was cooled to 25° C. and H$_2$O (1000 mL) was added. The resulting suspension was stirred at 25° C. for 12 hours. The suspension was filtered and solid was dried over with toluene (40 mL×5) under reduced pressure to provide the title compound (7.2 g, crude) as a pink solid. $^1$H NMR (400 MHz, DMSO-d$_6$) δ 11.11 (brs, 2H), 7.36-7.22 (m, 2H), 7.11 (d, J=8.4 Hz, 1H), 3.94 (t, J=6.8 Hz, 2H), 1.79-1.67 (m, 2H), 0.98 (t, J=7.6 Hz, 3H).

Step 4

2,4-Dichloro-6-propoxyquinazoline

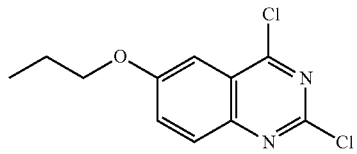 [SMILES: CCCOc1ccc2nc(Cl)nc(Cl)c2c1]

To a mixture of 6-propoxyquinazoline-2,4-diol (2.0 g, 9.08 mmol) in POCl$_3$ (20 mL) was added DIPEA (2.35 g, 18.16 mmol, 3.16 mL) at 25° C. and then the reaction mixture was heated to 90° C. and stirred for 15 hours under N$_2$. The reaction was cooled to room temperature and concentrated under reduced pressure to remove POCl$_3$. The mixture was poured into ice-water (80 mL) and carefully adjusted to pH=7~8 by sat. NaHCO$_3$. The aqueous layer was extracted with EtOAc (60 mL×3). The combined organic phases were washed with brine (60 mL), dried over anhydrous Na$_2$SO$_4$, filtered and concentrated under reduced pressure. The residue was purified by column chromatography (SiO$_2$, Petroleum ether/Ethyl acetate=20/1, R$_f$=0.95) provide the title compound (1.48 g, 63%) as a white solid. $^1$H NMR (400 MHz, DMSO-d$_6$) δ 7.89 (d, J=9.2 Hz, 1H), 7.61 (dd, J=9.2, 2.4 Hz, 1H), 7.39 (d, J=2.8 Hz, 1H), 4.10 (t, J=6.8 Hz, 2H), 1.98-1.86 (m, 2H), 1.11 (t, J=7.6 Hz, 3H).

Step 5

2-Chloro-6-propoxy-N-(1-(tetrahydro-2H-pyran-2-yl)-1H-pyrazol-4-yl)-quinazolin-4-amine

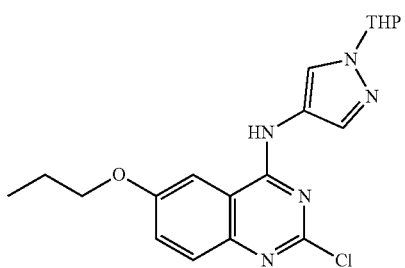

To a solution of 2,4-dichloro-6-propoxyquinazoline (500 mg, 1.94 mmol) and 1-(tetrahydro-2H-pyran-2-yl)-1H-pyrazol-4-amine (325.16 mg, crude) in DMF (5 mL) was added DIPEA (502.67 mg, 3.89 mmol, 677.45 µL) at 25° C., and then the reaction mixture was heated to 60° C. and stirred for 15 hours. The reaction mixture was cooled to room temperature and poured into H$_2$O (60 mL). The resulting mixture was extracted with EtOAc (20 mL×2). The combined organic phases were washed with brine (30 mL), dried over anhydrous Na$_2$SO$_4$, filtered and concentrated under reduced pressure. The residue was purified by column chromatography (SiO$_2$, Petroleum ether/Ethyl acetate=3/1 to 1/1, R$_f$=0.38) to provide the title compound (220 mg, 29%) as a light yellow solid. $^1$H NMR (400 MHz, DMSO-d$_6$) δ 10.26 (s, 1H), 8.30 (s, 1H), 7.86 (d, J=2.8 Hz, 1H), 7.81 (s, 1H), 7.64 (d, J=9.2 Hz, 1H), 7.50 (dd, J=2.8, 9.2 Hz, 1H), 5.46 (dd, J=2.0, 9.6 Hz, 1H), 4.09 (t, J=6.4 Hz, 2H), 3.99-3.89 (m, 1H), 3.73-3.62 (m, 1H), 2.15-2.03 (m, 1H), 2.00-1.92 (m, 2H), 1.87-1.79 (m, 2H), 1.75-1.62 (m, 1H), 1.60-1.49 (m, 2H), 1.05 (t, J=7.6 Hz, 3H).

Step 6

N-(tert-Butyl)-2-(3-(6-propoxy-4-((1-(tetrahydro-2H-pyran-2-yl)-1H-pyrazol-4-yl)amino)quinazolin-2-yl)phenoxy)acetamide

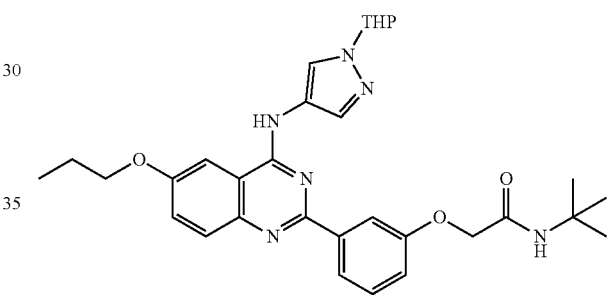

A mixture of 2-chloro-6-propoxy-N-(1-(tetrahydro-2H-pyran-2-yl)-1H-pyrazol-4-yl)quinazolin-4-amine (220 mg, 567.21 µmol), N-(tert-butyl)-2-(3-(4,4,5,5-tetramethyl-1,3,2-dioxaborolan-2-yl)phenoxy)acetamide (245.71 mg, 737.38 µmol), Pd(dppf)Cl$_2$ (41.50 mg, 56.72 µmol) and K$_2$CO$_3$ (156.78 mg, 1.13 mmol) was suspended in dioxane (3 mL) and H$_2$O (0.3 mL) under nitrogen atmosphere. The reaction mixture was cooled to room temperature and poured into H$_2$O (50 mL). The resulting mixture was extracted with EtOAc (20 mL×3). The combined organic phases were washed with brine (30 mL), dried over anhydrous Na$_2$SO$_4$, filtered and concentrated under reduced pressure. The residue was purified by column chromatography (SiO$_2$, Petroleum ether/Ethyl acetate=3/1 to 1:1, R$_f$=0.28) to provide the title compound (200 mg, 63%) as a yellow solid. $^1$H NMR (400 MHz, DMSO-d$_6$) δ 9.93 (s, 1H), 8.50 (s, 1H), 8.07-7.98 (m, 2H), 7.91-7.85 (m, 2H), 7.78 (d, J=10.0 1H), 7.55-7.48 (m, 2H), 7.45 (t, J=8.0 Hz, 1H), 7.07 (dd, J=2.4, 8.0 Hz, 1H), 5.50 (dd, J=2.0, 9.2 Hz, 1H), 4.51 (s, 2H), 4.12 (t, J=6.4 Hz, 2H), 4.00-3.92 (m, 1H), 3.77-3.65 (m, 1H), 2.22-2.08 (m, 1H), 2.06-1.94 (m, 2H), 1.90-1.80 (m, 2H), 1.78-1.66 (m, 1H), 1.62-1.52 (m, 2H), 1.30 (s, 9H), 1.06 (t, J=7.6 Hz, 3H).

Step 7

2-(3-(4-((1H-Pyrazol-4-yl)amino)-6-propoxyquinazolin-2-yl)phenoxy)-N-(tert-butyl)acetamide

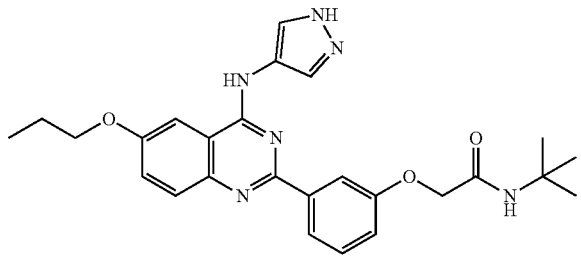 [SMILES: CCCOc1ccc2nc(-c3cccc(OCC(=O)NC(C)(C)C)c3)nc(Nc3cn[nH]c3)c2c1]

To a solution of N-(tert-butyl)-2-(3-(6-propoxy-4-((1-(tetrahydro-2H-pyran-2-yl)-1H-pyrazol-4-yl)amino)quinazolin-2-yl)phenoxy)acetamide (200 mg, 357.99 μmol) in DCM (2 mL) was added HCl/dioxane (4 M, 2 mL) at 25° C. The resulting mixture was stirred at 25° C. for 15 hours. The solvent was removed under reduce pressure and the resulting residue was purified by prep-HPLC (HCl conditions) to provide the title compound (123 mg, 67%) as a yellow solid. $^1$H NMR (400 MHz, DMSO-d$_6$) δ 11.62 (br s, 1H), 8.31-8.21 (m, 3H), 8.13 (d, J=9.2 Hz, 1H), 7.98-7.91 (m, 2H), 7.70 (dd, J=2.4, 9.2 Hz, 1H), 7.67-7.59 (m, 2H), 7.32-7.24 (m, 1H), 4.60 (s, 2H), 4.18 (t, J=6.4 Hz, 2H), 1.90-1.79 (m, 2H), 1.29 (s, 9H), 1.06 (t, J=7.6 Hz, 3H). MS (ES+) m/e 475.1 (M+H)$^+$.

Example 223

2-(3-(4-((1H-Pyrazol-3-yl)amino)-6-propoxyquinazolin-2-yl)phenoxy)-N-(tert-butyl)acetamide

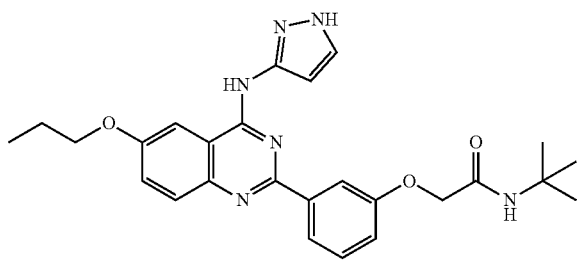 [SMILES: CCCOc1ccc2nc(-c3cccc(OCC(=O)NC(C)(C)C)c3)nc(Nc3cc[nH]n3)c2c1]

Step 1

2-Chloro-6-Propoxy-N-(1-((2-(trimethylsilyl)ethoxy)methyl)-1H-pyrazol-3-yl)-quinazolin-4-amine

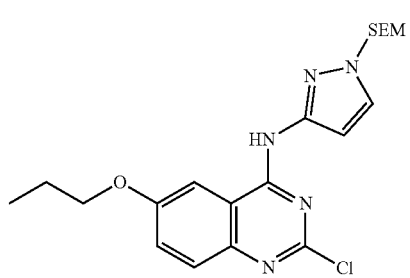 [SMILES: CCCOc1ccc2nc(Cl)nc(Nc3ccn(COCC[Si](C)(C)C)n3)c2c1]

To a solution of 2,4-dichloro-6-propoxyquinazoline (500 mg, 1.94 mmol) and 1-((2-(trimethylsilyl)ethoxy)methyl)-1H-pyrazol-3-amine (414.89 mg, crude) in DMF (7 mL) was added DIEA (502.67 mg, 3.89 mmol, 677.45 μL) at 25° C., and then the reaction mixture was heated to 60° C. and stirred for 15 hours. The reaction mixture was cooled to room temperature and poured into H$_2$O (60 mL) and the aqueous layer was extracted with EtOAc (20 mL×3). The combined organic phases were washed with brine (30 mL), dried over anhydrous Na$_2$SO$_4$, filtered and concentrated under reduced pressure. The residue was purified by column chromatography (SiO$_2$, Petroleum ether/Ethyl acetate=10/1) to provide the title compound (330 mg, 39%) as a light yellow solid. $^1$H NMR (400 MHz, DMSO-d$_6$) δ 8.29 (s, 1H), 7.76 (d, J=9.2 Hz, 1H), 7.56 (d, J=2.4 Hz, 1H), 7.43 (dd, J=2.4, 9.2 Hz, 1H), 7.23 (d, J=2.4 Hz, 1H), 7.07 (d, J=2.4 Hz, 1H), 5.35 (s, 2H), 3.99 (t, J=6.4 Hz, 2H), 3.60-3.53 (m, 2H), 1.94-1.83 (m, 2H), 1.09 (t, J=7.6 Hz, 3H), 0.97-0.89 (m, 2H), 0.01 (s, 9H).

Step 2

N-(tert-Butyl)-2-(3-(6-propoxy-4-((1-((2-(trimethylsilyl)ethoxy)methyl)-1H-pyrazol-3-yl)amino)quinazolin-2-yl)phenoxy)acetamide

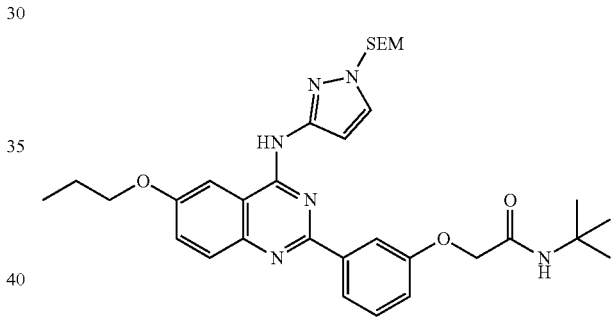

A mixture of 2-chloro-6-propoxy-N-(1-((2-(trimethylsilyl)ethoxy)methyl)-1H-pyrazol-3-yl)quinazolin-4-amine (330 mg, 760.36 μmol), N-(tert-butyl)-2-(3-(4,4,5,5-tetramethyl-1,3,2-dioxaborolan-2-yl)phenoxy)acetamide (329.39 mg, 988.47 μmol), Pd(dppf)Cl$_2$ (55.64 mg, 76.04 μmol) and K$_2$CO$_3$ (210.17 mg, 1.52 mmol) was dissolved in dioxane (4 mL) and H$_2$O (0.4 mL) under nitrogen atmosphere. The resulting reaction mixture was heated to 100° C. and stirred for 15 hours. The reaction mixture was poured into H$_2$O (50 mL) and the aqueous layer was extracted with EtOAc (20 mL×3). The combined organic phases were washed with brine (30 mL), dried over anhydrous Na$_2$SO$_4$, filtered and concentrated under reduced pressure. The residue was purified by column chromatography (SiO$_2$, Petroleum ether/Ethyl acetate=5/1 to 2/1, R$_f$=0.33) to provide the title compound (376 mg, 82%) as a brown oil. $^1$H NMR (400 MHz, DMSO-d$_6$) δ 8.41 (s, 1H), 8.20 (d, J=7.6 Hz, 1H), 8.15-8.11 (m, 1H), 7.90 (d, J=9.2 Hz, 1H), 7.64 (d, J=2.4 Hz, 1H), 7.48-7.41 (m, 2H), 7.33 (d, J=2.8 Hz, 1H), 7.24-7.21 (m, 1H), 7.02 (dd, J=2.4, 8.4 Hz, 1H), 6.55-6.47 (m, 1H), 5.36 (s, 2H), 4.51 (s, 2H), 4.04 (t, J=6.4 Hz, 2H), 3.62-3.55 (m, 2H), 1.92-1.85 (m, 2H), 1.23 (s, 9H), 1.09 (t, J=7.6 Hz, 3H), 0.97-0.91 (m, 2H), −0.01 (s, 9H).

Step 3

2-(3-(4-((1H-Pyrazol-3-yl)amino)-6-propoxyquinazolin-2-yl)phenoxy)-N-(tert-butyl)acetamide

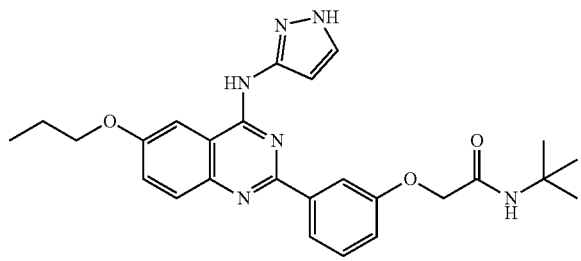 [SMILES: CCCOc1ccc2nc(-c3cccc(OCC(=O)NC(C)(C)C)c3)nc(Nc3cc[nH]n3)c2c1]

To a solution of N-(tert-butyl)-2-(3-(6-propoxy-4-((1-((2-(trimethylsilyl)-ethoxy)methyl)-1H-pyrazol-3-yl)amino)quinazolin-2-yl)phenoxy)acetamide (370 mg, 611.76 μmol) in DCM (4 mL) was added HCl/dioxane (4 M, 4 mL) at 25° C. The resulting mixture was stirred at 25° C. for 15 hours. The solvent was removed under reduced pressure. The residue was purified by prep-HPLC (HCl conditions) to provide the title compound (155 mg, 49%) as a yellow solid. $^1$H NMR (400 MHz, DMSO-$d_6$) δ 11.75 (brs, 1H), 8.28 (d, J=2.0 Hz, 1H), 8.11 (d, J=9.2 Hz, 1H), 8.00-7.94 (m, 2H), 7.89 (d, J=2.4 Hz, 1H), 7.67 (dd, J=2.0, 9.2 Hz, 1H), 7.64-7.55 (m, 2H), 7.27-7.21 (m, 1H), 6.99 (d, J=2.4 Hz, 1H), 4.57 (s, 2H), 4.15 (t, J=6.4 Hz, 2H), 1.91-1.79 (m, 2H), 1.29 (s, 9H), 1.06 (t, J=7.2 Hz, 3H). MS (ES+) m/e 475.1 (M+H)$^+$.

Example 224

2-(3-(4-((1H-Pyrazol-4-yl)amino)-6-cyclopropoxyquinazolin-2-yl)phenoxy)-N-(tert-butyl)acetamide

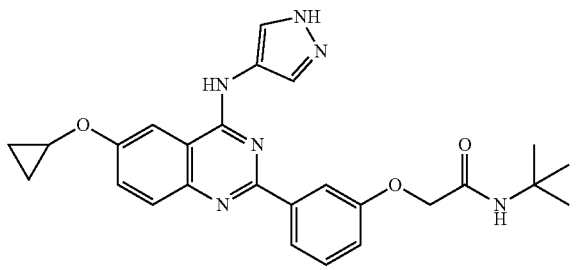 [SMILES: CC(C)(C)NC(=O)COc1cccc(-c2nc(Nc3cn[nH]c3)c3cc(OC4CC4)ccc3n2)c1]

Step 1

Methyl 5-cyclopropoxy-2-nitrobenzoate

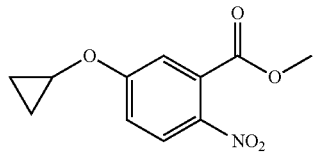 [SMILES: COC(=O)c1cc(OC2CC2)ccc1[N+](=O)[O-]]

To a solution of NaH (5.22 g, 130.56 mmol, 60% purity) in THF (130 mL) was added cyclopropanol (7.58 g, 130.56 mmol) in THF (5 mL) dropwise at 0° C. The reaction mixture was stirred at 0° C. for 30 min. The solution of methyl 5-fluoro-2-nitrobenzoate (13 g, 65.28 mmol) in THF (20 mL) was added dropwise at 0° C. The resulting reaction mixture was stirred at 0° C. for 1 hr. The reaction mixture was poured into H$_2$O (200 mL) and the aqueous layer was extracted with EtOAc (60 mL×3). The combined organic phases were washed with brine (50 mL), dried over anhydrous Na$_2$SO$_4$, filtered and concentrated under reduced pressure. The residue was purified by column chromatography (SiO$_2$, Petroleum ether/Ethyl acetate=50:1) to provide the title compound (6.65 g, 43%) as a yellow oil. $^1$H NMR (400 MHz, DMSO-$d_6$) δ 7.99 (d, J=8.8 Hz, 1H), 7.21-7.11 (m, 2H), 3.90 (s, 3H), 3.85-3.80 (m, 1H), 0.89-0.82 (m, 2H), 0.80-0.75 (m, 2H).

Step 2

5-Cyclopropoxy-2-nitrobenzoic Acid

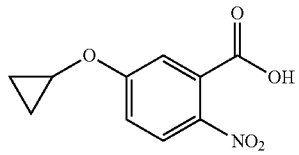 [SMILES: O=C(O)c1cc(OC2CC2)ccc1[N+](=O)[O-]]

To a solution of methyl 5-cyclopropoxy-2-nitrobenzoate (4.5 g, 18.97 mmol) in MeOH (20 mL) and H$_2$O (20 mL) was added LiOH·H$_2$O (2.39 g, 56.91 mmol) at 25° C. The resulting reaction mixture was heated to 35° C. and stirred for 15 hrs. The reaction mixture was poured into H$_2$O (80 mL) and adjusted to pH=2~3 by 1N HCl solution. The aqueous layer was extracted with EtOAc (60 mL×3). The combined organic phases were washed with brine (20 mL), dried over anhydrous Na$_2$SO$_4$, filtered and concentrated under reduced pressure to provide the title compound (4.6 g, crude) as a brown solid. $^1$H NMR (400 MHz, CDCl$_3$) δ 8.74 (brs, 1H), 7.98 (d, J=9.2 Hz, 1H), 7.31 (d, J=2.8 Hz, 1H), 7.18 (dd, J=9.2, 2.8 Hz, 1H), 3.89-3.81 (m, 1H), 0.93-0.85 (m, 2H), 0.84-0.77 (m, 2H).

Step 3

5-Cyclopropoxy-2-nitrobenzamide

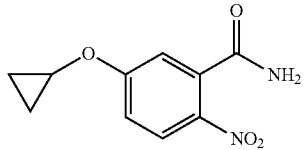 [SMILES: NC(=O)c1cc(OC2CC2)ccc1[N+](=O)[O-]]

To a solution of 5-cyclopropoxy-2-nitrobenzoic acid (4.6 g, 20.61 mmol) in DCM (45 mL) was added (COCl)$_2$ (5.23 g, 41.22 mmol, 3.61 mL) dropwise at 0° C., followed by DMF (80 μL). The mixture was then stirred at 25° C. for 30 min and concentrated. The residue was dissolved in THF (40 mL). DIEA (5.33 g, 41.22 mmol, 7.18 mL) and NH$_3$/THF (80 mL) was then added at 0° C. The mixture was then stirred at 25° C. for 12 hrs. The solvent was removed under reduced pressure. The residue was poured into H$_2$O (120 mL) and the aqueous layer was extracted with EtOAc (50 mL×3). The combined organic phases were washed with brine (50 mL), dried over anhydrous Na$_2$SO$_4$, filtered and concentrated under reduced pressure. The residue was purified by column chromatography (SiO$_2$, Petroleum ether/Ethyl acetate=3/1 to 1/1) to provide the title compound (3.4 g, 74%) as an off-white solid. $^1$H NMR (400 MHz, CDCl$_3$) δ 8.14-8.04 (m, 1H), 7.17-7.09 (m, 2H), 6.34 (s, 1H), 6.06 (s, 1H), 3.90-3.80 (m, 1H), 0.92-0.86 (m, 2H), 0.85-0.79 (m, 2H).

Step 4

2-Amino-5-cyclopropoxybenzamide

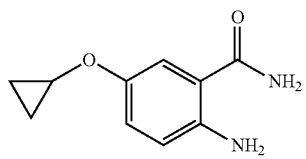

To a mixture of 5-cyclopropoxy-2-nitrobenzamide (3.4 g, 15.30 mmol) and NH$_4$Cl (4.50 g, 84.16 mmol) in EtOH (40 mL) and H$_2$O (20 mL) was added Fe (4.27 g, 76.51 mmol) at 50~60° C. The resulting reaction mixture was heated to 80° C. and stirred for 2 hours. The reaction mixture was cooled to 25° C. and filtered through celite. The filtrate was poured into H$_2$O (50 mL) and the aqueous layer was extracted with EtOAc (30 mL×3). The combined organic phases were washed with brine (30 mL), dried over anhydrous Na$_2$SO$_4$, filtered and concentrated under reduced pressure. The residue was purified by column chromatography (SiO$_2$, Petroleum ether/Ethyl acetate=1/2, R$_f$=0.28) to provide the title compound (2.9 g, 97%) as an off-white solid. $^1$H NMR (400 MHz, CDCl$_3$) δ 7.09-7.00 (m, 2H), 6.67 (d, J=8.8 Hz, 1H), 5.84 (brs, 2H), 5.24 (brs, 2H), 3.72-3.64 (m, 1H), 0.77-0.72 (m, 4H).

Step 5

3-(2-(tert-Butylamino)-2-oxoethoxy)-N-(2-carbamoyl-4-cyclopropoxyphenyl)-benzamide

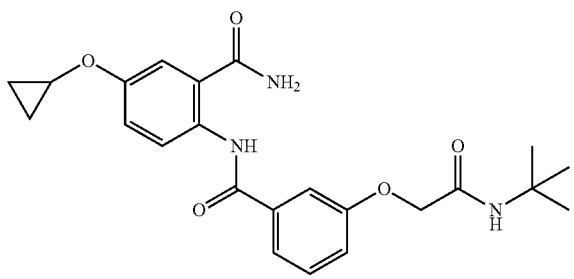 [SMILES: CC(C)(C)NC(=O)COc1cccc(C(=O)Nc2ccc(OC3CC3)cc2C(N)=O)c1]

To a mixture of 3-(2-(tert-butylamino)-2-oxoethoxy)benzoic acid (3.57 g, 14.20 mmol) and HATU (7.71 g, 20.29 mmol) in EtOAc (30 mL) was added 2-amino-5-cyclopropoxybenzamide (2.6 g, 13.53 mmol) and DIEA (5.24 g, 40.58 mmol, 7.07 mL). The reaction mixture was stirred at 25° C. for 12 hours. The mixture was poured into H$_2$O (120 mL) and the aqueous layer was extracted with EtOAc (50 mL×3). The combined organic phases were washed with brine (50 mL), dried over anhydrous Na$_2$SO$_4$, filtered and concentrated under reduced pressure. The residue was purified by column chromatography (SiO$_2$, Petroleum ether/Ethyl acetate=2/1 to 1/1 to 0/1, R$_f$=0.32) to provide the title compound (8.6 g, crude) as a yellow solid. $^1$H NMR (400 MHz, DMSO-d$_6$) δ 12.56 (s, 1H), 8.58 (d, J=9.2 Hz, 1H), 8.40 (s, 1H), 7.85 (s, 1H), 7.58 (s, 1H), 7.53 (d, J=2.8 Hz, 1H), 7.51-7.45 (m, 3H), 7.31 (dd, J=9.2, 2.8 Hz, 1H), 7.19-7.14 (m, 1H), 4.48 (s, 2H), 3.95-3.88 (m, 1H), 1.30 (s, 9H), 0.84-0.78 (m, 2H), 0.72-0.60 (m, 2H).

Step 6

N-(tert-Butyl)-2-(3-(6-cyclopropoxy-4-hydroxyquinazolin-2-yl)phenoxy)-acetamide

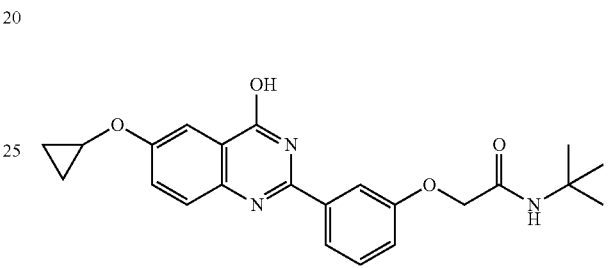

To a solution of 3-(2-(tert-butylamino)-2-oxoethoxy)-N-(2-carbamoyl-4-cyclopropoxyphenyl)benzamide (8.5 g, 19.98 mmol) in EtOH (40 mL) and H$_2$O (40 mL) was added K$_2$CO$_3$ (9.66 g, 69.92 mmol) at 25° C. The resulting reaction mixture was heated to 80° C. and stirred for 2 hours. The mixture was cooled to 25° C. and concentrated under reduced pressure to remove EtOH. A white solid was formed and filtered. The aqueous layer was extracted with EtOAc (30 mL×3). The combined organic layer was washed with brine, dried over Na$_2$SO$_4$, and concentrated to provide a solid. The solids were then combined with toluene and concentrated under reduced pressure three times to provide the title compound (8.5 g, crude) as a light yellow solid, which was used for the next step without the further purification. $^1$H NMR (400 MHz, DMSO-d$_6$) δ 7.91-7.85 (m, 2H), 7.75 (d, J=3.2 Hz, 1H), 7.59 (d, J=8.8 Hz, 1H), 7.54 (s, 1H), 7.39 (t, J=8.0 Hz, 1H), 7.34 (dd, J=2.8, 8.8 Hz, 1H), 7.06 (dd, J=1.6, 7.6 Hz, 1H), 4.51 (s, 2H), 3.98-3.91 (m, 1H), 1.32 (s, 9H), 0.89-0.81 (m, 2H), 0.75-0.69 (m, 2H).

Step 7

N-(tert-Butyl)-2-(3-(4-chloro-6-cyclopropoxyquinazolin-2-yl)phenoxy)-acetamide

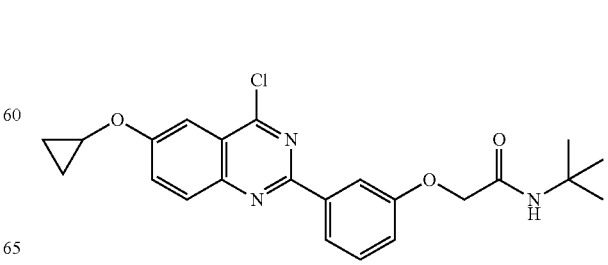

215

To a solution of N-(tert-butyl)-2-(3-(6-cyclopropoxy-4-hydroxyquinazolin-2-yl)phenoxy)acetamide (300 mg, 736.27 μmol) in DMF (3 mL) was added SOCl$_2$ (131.39 mg, 1.10 mmol, 80.12 μL) dropwise at 0° C. The resulting reaction mixture was stirred at 0° C. for 1 hr. The mixture was poured into ice-H$_2$O (50 mL) and adjusted to pH=7-8 by sat. NaHCO$_3$. The aqueous layer was extracted with EtOAc (20 mL×3). The combined organic phases were washed with brine (30 mL×2), dried over anhydrous Na$_2$SO$_4$, filtered and concentrated under reduced pressure to give compound 9 (180 mg, crude) as a yellow solid, which was used for the next step without the further purification.

Step 8

2-(3-(4-((1H-Pyrazol-4-yl)amino)-6-cyclopropoxy-quinazolin-2-yl)phenoxy)-N-(tert-butyl)acetamide

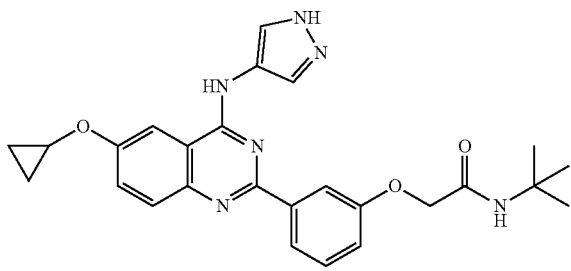 [SMILES: CC(C)(C)NC(=O)COc1cccc(-c2nc(Nc3cn[nH]c3)c3cc(OC4CC4)ccc3n2)c1]

To a solution of N-(tert-butyl)-2-(3-(4-chloro-6-cyclopropoxyquinazolin-2-yl)-phenoxy)acetamide (180 mg, crude) and 1H-pyrazol-4-amine (35.12 mg, 422.63 μmol) in DMF (2 mL) was added DIEA (109.24 mg, 845.25 μmol, 147.23 μL) at 25° C., and then the reaction mixture was heated to 60° C. and stirred for 12 hours. The mixture was poured into H$_2$O (70 mL) and the aqueous layer was extracted with EtOAc (30 mL×3). The combined organic phases were washed with brine (30 mL×2), dried over anhydrous Na$_2$SO$_4$, filtered and concentrated under reduced pressure. The residue was purified by prep-HPLC (HCl conditions) to provide the title compound (128.8 mg) as a yellow solid. $^1$H NMR (400 MHz, DMSO-d$_6$) δ 11.82 (brs, 1H), 8.52 (s, 1H), 8.31-8.16 (m, 3H), 8.00-7.92 (m, 2H), 7.77 (dd, J=9.2, 2.4 Hz, 1H), 7.68-7.57 (m, 2H), 7.29 (d, J=7.2 Hz, 1H), 4.61 (s, 2H), 4.21-4.10 (m, 1H), 1.29 (s, 9H), 1.03-0.92 (m, 2H), 0.81-0.72 (m, 2H). MS (ES+) m/e 473.3 (M+H)$^+$.

Example 225

2-(3-(4-((1H-Pyrazol-4-yl)amino)-5-chloro-6-ethoxyquinazolin-2-yl)phenoxy)-N-(tert-butyl)acet-amide

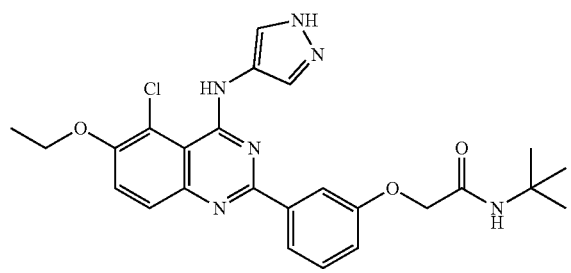

Step 1

Methyl 2-chloro-3-hydroxybenzoate

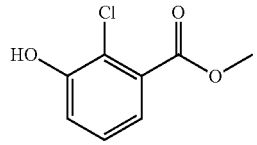

To a solution of methyl 3-hydroxybenzoate (10 g, 65.73 mmol) and i-Pr$_2$NH·HCl (90.47 mg, 657.26 μmol) in toluene (350 mL) was added 1,3-dichloro-5,5-dimethylhydantion (13.60 g, 69.01 mmol) at 0° C. in the absence of light. The mixture was stirred at 0-25° C. for 4 hrs. The mixture was filtered and the solvent was removed under reduced pressure. The residue was purified by column chromatography (SiO$_2$, Petroleum ether/Ethyl acetate=50/1 to 20/1, monitored by TLC (Petroleum ether/Ethyl acetate=5:1), R$_f$=0.46) to provide the title compound (12.2 g, 99%) as a yellow oil. $^1$H NMR (400 MHz, CDCl$_3$) δ 7.37 (dd, J=7.2, 2.0 Hz, 1H), 7.20-7.11 (m, 2H), 6.70 (s, 1H), 3.89 (s, 3H).

Step 2

Methyl 2-chloro-3-ethoxybenzoate

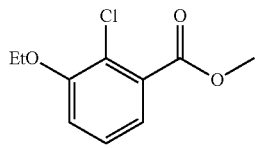

To a stirred solution of methyl 2-chloro-3-hydroxybenzoate (12.2 g, 65.38 mmol) and K$_2$CO$_3$ (13.55 g, 98.07 mmol) in DMF (100 mL) was added EtI (20.39 g, 130.77 mmol, 10.46 mL) at 25° C. And then the reaction mixture was heated to 90° C. and stirred for 15 hrs. The mixture was cooled to room temperature and poured into H$_2$O (300 mL). The resulting mixture was extracted with petroleum ether/ethyl acetate (v/v=3/1, 60 mL×3). The combined organic phases were washed with brine (100 mL), dried over anhydrous Na$_2$SO$_4$, filtered and concentrated under reduced pressure. The residue was purified by column chromatography (SiO$_2$, Petroleum ether/Ethyl acetate=I/O to 40/1) to provide the title compound (6.0 g, 43%) as a yellow oil. $^1$H NMR (400 MHz, CDCl$_3$) δ 7.31-7.27 (m, 1H), 7.22 (t, J=8.0 Hz, 1H), 7.02 (dd, J=8.0, 1.2 Hz, 1H), 4.10 (q, J=6.8 Hz, 2H), 3.91 (s, 3H), 1.45 (t, J=6.8 Hz, 3H).

Step 3

Methyl 6-bromo-2-chloro-3-ethoxybenzoate

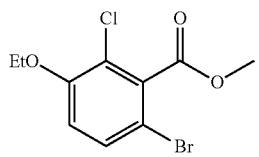

To a solution of methyl 2-chloro-3-ethoxybenzoate (3.8 g, 17.70 mmol) in HOAc (20 mL) was added Br$_2$ (5.66 g, 35.41 mmol, 1.83 mL) at 25° C. and then the reaction mixture was heated to 65° C. and stirred for 12 hours. The reaction mixture was cooled to 25° C. and poured into H$_2$O (120 mL), then the aqueous layer was extracted with EtOAc (50 mL×2). The combined organic phases were washed with sat. aq. NaHCO$_3$ (50 mL×2), dried over anhydrous Na$_2$SO$_4$, filtered and concentrated under reduced pressure. The residue was purified by column chromatography (SiO$_2$, Petroleum ether/Ethyl acetate=I/O to 40/1) to provide the title compound (4.0 g, 77%) as a yellow oil. $^1$H NMR (400 MHz, CDCl$_3$) δ 7.36 (d, J=8.8 Hz, 1H), 6.80 (d, J=8.8 Hz, 1H), 4.10 (q, J=6.8 Hz, 2H), 3.95 (s, 3H), 1.43 (t, J=6.8 Hz, 3H).

Step 4

5-Chloro-6-ethoxyquinazoline-2,4-diol

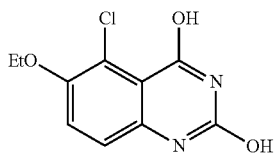

To a solution of methyl 6-bromo-2-chloro-3-ethoxybenzoate (2.0 g, 6.81 mmol) in dioxane (20 mL) was added Cs$_2$CO$_3$ (4.44 g, 13.63 mmol), Pd$_2$(dba)$_3$ (311.96 mg, 340.67 μmol), Xantphos (197.12 mg, 340.67 μmol) and urea (1.23 g, 20.44 mmol) at 25° C. The resulting reaction mixture was heated to 100° C. and stirred for 15 hours. The mixture was cooled to 25° C. and the solvent was removed under reduced pressure to give a residue. To the residue was added water (30 mL) and the mixture was acidized with HCl (1 N) until pH=2~3. Precipitate formed was suspended in EtOAc (30 mL) and the mixture was stirred at 25° C. for 20 min, filtered to provide the title compound (800 mg, crude) as a black solid. $^1$H NMR (400 MHz, DMSO-d$_6$) δ 11.28-10.98 (m, 2H), 7.49 (d, J=8.8 Hz, 1H), 7.11 (d, J=8.8 Hz, 1H), 4.08 (q, J=7.2 Hz, 2H), 1.33 (t, J=6.8 Hz, 3H).

Step 5

2,4,5-Trichloro-6-ethoxyquinazoline

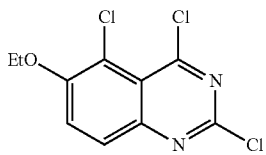 [SMILES: CCOc1ccc2nc(Cl)nc(Cl)c2c1Cl]

To a solution of 5-chloro-6-ethoxyquinazoline-2,4-diol (700 mg, 2.91 mmol) in POCl$_3$ (6 mL) was added DIEA (751.89 mg, 5.82 mmol, 1.01 mL) at 25° C. and then the reaction mixture was heated to 90° C. and stirred for 15 hours. The reaction mixture was cooled to room temperature and concentrated to remove POCl$_3$. The residue was poured into ice-H$_2$O (60 mL) and carefully adjusted to pH to 7~8 by sat. NaHCO$_3$. The aqueous layer was extracted with EtOAc (40 mL×4). The combined organic phases were washed with brine (40 mL), dried over anhydrous Na$_2$SO$_4$, filtered and concentrated under reduced pressure. The residue was purified by column chromatography (SiO$_2$, Petroleum ether/Ethyl acetate=5/1) to provide the title compound (280 mg, 35%) as a yellow solid. $^1$H NMR (400 MHz, CDCl$_3$) δ 7.95 (d, J=9.2 Hz, 1H), 7.72 (d, J=9.6 Hz, 1H), 4.31 (q, J=7.2 Hz, 2H), 1.56 (t, J=6.8 Hz, 3H).

Step 6

2,5-Dichloro-6-ethoxy-N-(1-(tetrahydro-2H-pyran-2-yl)-1H-pyrazol-4-yl)-quinazolin-4-amine

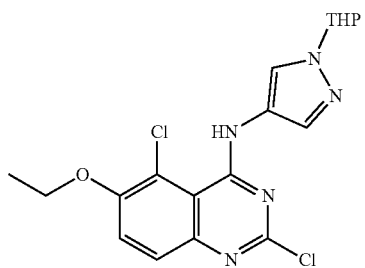

To a solution of 2,4,5-trichloro-6-ethoxyquinazoline (260 mg, 936.82 μmol) and 1-(tetrahydro-2H-pyrazol-2-yl)-1H-pyrazol-4-amine (172.31 mg, crude) in DMF (3 mL) was added DIEA (242.16 mg, 1.87 mmol, 326.35 μL) at 25° C., and then the reaction mixture was heated to 65° C. and stirred for 15 hours. The mixture which was poured into H$_2$O (80 mL) and the aqueous layer was extracted with EtOAc (20 mL×3). The combined organic phases were washed with H$_2$O (30 mL×2) and brine (30 mL), dried over anhydrous Na$_2$SO$_4$, filtered and concentrated under reduced pressure. The residue was purified by column chromatography (SiO$_2$, Petroleum ether/Ethyl acetate=3/1) to provide the title compound (330 mg, 84%) as a yellow solid. $^1$H NMR (400 MHz, DMSO-d$_6$) δ 9.95 (s, 1H), 8.32 (s, 1H), 7.92 (s, 1H), 7.80 (d, J=9.2 Hz, 1H), 7.69 (d, J=9.2 Hz, 1H), 5.44 (dd, J=9.6, 2.0 Hz, 1H), 4.27 (q, J=6.8 Hz, 2H), 3.96-3.89 (m, 1H), 3.73-3.62 (m, 1H), 2.12-2.01 (m, 1H), 2.00-1.91 (m, 2H), 1.75-1.63 (m, 1H), 1.60-1.50 (m, 2H), 1.40 (t, J=6.8 Hz, 3H).

Step 7

N-(tert-Butyl)-2-(3-(5-chloro-6-ethoxy-4-((1-(tetrahydro-2H-pyran-2-yl)-1H-pyrazol-4-yl)amino)quinazolin-2-yl)phenoxy)acetamide

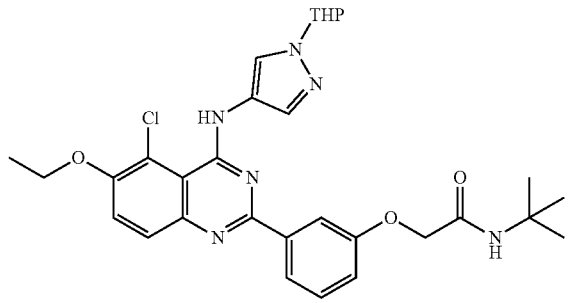

A mixture of 2,5-dichloro-6-ethoxy-N-(1-(tetrahydro-2H-pyran-2-yl)-1H-pyrazol-4-yl)-quinazolin-4-amine (200 mg, 489.86 µmol), N-(tert-butyl)-2-(3-(4,4,5,5-tetramethyl-1,3,2-dioxaborolan-2-yl)phenoxy)acetamide (195.88 mg, 587.83 µmol), Pd(dppf)Cl$_2$ (35.84 mg, 48.99 µmol) and K$_2$CO$_3$ (135.40 mg, 979.72 µmol) was dissolved in dioxane (3 mL) and H$_2$O (0.3 mL) under nitrogen atmosphere. The resulting reaction mixture was heated to 65° C. and stirred for 16 hours. The mixture was poured into H$_2$O (60 mL) and the aqueous layer was extracted with EtOAc (30 mL×3). The combined organic phases were washed with brine (30 mL), dried over anhydrous Na$_2$SO$_4$, filtered and concentrated under reduced pressure. The residue was purified by column chromatography (SiO$_2$, Petroleum ether/Ethyl acetate=4/1 to 2/1) to provide the title compound (100 mg, 35%) as a yellow gum. $^1$H NMR (400 MHz, DMSO-d$_6$) δ 9.66 (s, 1H), 8.41 (s, 1H), 8.15-8.11 (m, 1H), 8.09-8.06 (m, 1H), 7.92-7.86 (m, 2H), 7.50 (d, J=9.2 Hz, 1H), 7.44 (t, J=8.0 Hz, 1H), 7.06-7.02 (m, 1H), 6.49 (brs, 1H), 5.47 (dd, J=3.2, 9.2 Hz, 1H), 4.51 (s, 2H), 4.26 (q, J=7.2 Hz, 2H), 4.11-4.07 (m, 1H), 3.81-3.73 (m, 1H), 1.90-1.60 (m, 6H), 1.53 (t, J=6.8 Hz, 3H), 1.42 (s, 9H).

Step 8

2-(3-(4-((1H-Pyrazol-4-yl)amino)-5-chloro-6-ethoxyquinazolin-2-yl)phenoxy)-N-(tert-butyl)acetamide

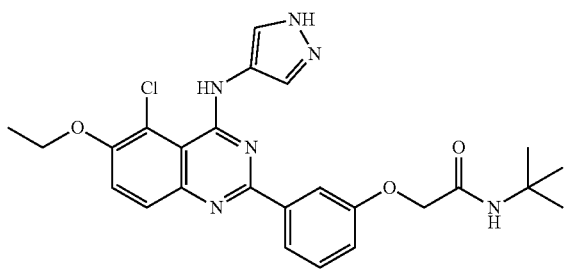

To a mixture of N-(tert-butyl)-2-(3-(5-chloro-6-ethoxy-4-((1-(tetrahydro-2H-pyran-2-yl)-1H-pyrazol-4-yl)amino)quinazolin-2-yl)phenoxy)acetamide (148 mg, 255.57 µmol) in DCM (3 mL) was added HCl/dioxane (4 M, 3 mL). The mixture was stirred at 25° C. for 2 h, concentrated and purified by prep-HPLC (HCl conditions) to provide the title compound (101.1 mg, 74%) as a yellow solid. $^1$H NMR (400 MHz, Methanol-d$_4$) δ 8.36 (s, 2H), 8.07 (d, J=9.2 Hz, 1H), 7.99 (d, J=9.2 Hz, 1H), 7.93-7.88 (m, 2H), 7.65 (t, J=8.4 Hz, 1H), 7.40 (d, J=8.4, 2.4 Hz, 1H), 4.61 (s, 2H), 4.40 (q, J=6.8 Hz, 2H), 1.56 (t, J=6.8 Hz, 3H), 1.41 (s, 9H). MS (ES+) m/e 496.0 (M+H)$^+$.

Example 226

2-(3-(4-((1H-Pyrazol-4-yl)amino)-6-chloro-5-methoxyquinazolin-2-yl)-phenoxy)-N-(tert-butyl)acetamide

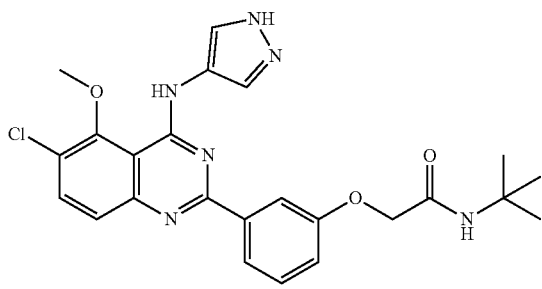 [SMILES: COc1c(Cl)ccc2nc(-c3cccc(OCC(=O)NC(C)(C)C)c3)nc(Nc3cn[nH]c3)c12]

Step 1

2,6-Dichloro-5-methoxy-N-(1-(tetrahydro-2H-pyran-2-yl)-1H-pyrazol-4-yl)-quinazolin-4-amine

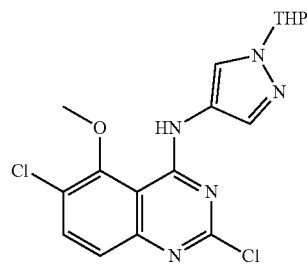

The mixture of 2,4,6-trichloro-5-methoxyquinazoline (500 mg, 1.90 mmol), 1-(tetrahydro-2H-pyran-2-yl)-1H-pyrazol-4-amine (317.27 mg, crude) and DIPEA (490.47 mg, 3.79 mmol) in n-BuOH (5 mL) was stirred 80° C. for 16 h. The reaction mixture was cooled to room temperature and diluted with H$_2$O (30 mL), and the resulting mixture was extracted with Ethyl acetate (30 mL×2). The organic phases were washed with brine (30 mL×2). The organic phase was dried with anhydrous Na$_2$SO$_4$, filtered and concentrated in vacuo to give a residue. The residue was purified by silica gel chromatography (Petroleum ether/Ethyl acetate=3/1 to 1/1, TLC:Petroleum ether/Ethyl acetate=1/1, R$_f$=0.2) to provide the title compound (310 mg, 38%) as a yellow oil. $^1$H NMR (400 MHz, DMSO-d$_6$) δ 10.12 (s, 1H), 8.34 (s, 1H), 7.98 (s, 1H), 7.93 (d, J=9.2 Hz, 1H), 7.51 (d, J=8.8 Hz, 1H), 5.48-5.41 (m, 1H), 4.03 (s, 3H), 3.94 (m, 1H), 3.71-3.61 (m, 1H), 2.12-2.00 (m, 1H), 1.99-1.89 (m, 2H), 1.78-1.62 (m, 1H), 1.60-1.49 (m, 2H).

Step 2

N-(tert-Butyl)-2-(3-(6-chloro-5-methoxy-4-((1-(tetrahydro-2H-pyran-2-yl)-1H-pyrazol-4-yl)amino)quinazolin-2-yl)phenoxy)acetamide

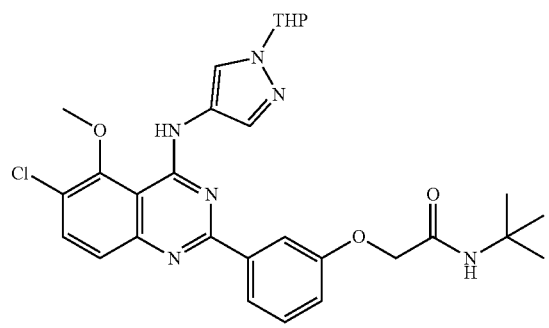

To a mixture of 2,6-dichloro-5-methoxy-N-(1-(tetrahydro-2H-pyran-2-yl)-1H-pyrazol-4-yl)quinazolin-4-amine (290 mg, 735.57 µmol), N-(tert-butyl)-2-(3-(4,4,5,5-tetramethyl-1,3,2-dioxaborolan-2-yl)phenoxy)acetamide (269.62 mg, 809.12 µmol), K$_2$CO$_3$ (203.32 mg, 1.47 mmol) in dioxane (3 mL), H$_2$O (0.3 mL) was added Pd(dppf)Cl$_2$ (53.82 mg, 73.56 µmol). The mixture was stirred 65° C. for 16 h under N$_2$. The reaction mixture was cooled to room temperature and diluted with H₂O (30 mL), and the resulting mixture was extracted with ethyl acetate (30 mL×2). The organic phases were washed with brine (30 mL×2). The organic phase was dried with anhydrous Na₂SO₄, filtered and concentrated in vacuo to give a residue. The residue was purified by silica gel chromatography (Petroleum ether/Ethyl acetate=1/0 to 4/1, $R_f$=0.45) to provide the title compound (300 mg, 72%) as a yellow oil. ¹H NMR (400 MHz, DMSO-d₆) δ 9.94 (s, 1H), 8.52 (s, 1H), 8.07 (s, 1H), 8.05 (d, J=7.6 Hz, 1H), 8.00 (s, 1H), 7.92 (d, J=8.8 Hz, 1H), 7.66 (d, J=8.8 Hz, 1H), 7.57 (s, 1H), 7.48 (t, J=8.0 Hz, 1H), 7.13 (dd, J=8.0, 2.4 Hz, 1H), 5.49 (dd, J=9.2, 2.0 Hz, 1H), 4.52 (s, 2H), 4.06 (s, 3H), 4.01-3.93 (m, 1H), 3.75-3.65 (m, 1H), 2.19-2.06 (m, 1H), 2.05-1.94 (m, 2H), 1.79-1.67 (m, 1H), 1.62-1.54 (m, 2H), 1.30 (s, 9H).

Step 3

2-(3-(4-((1H-Pyrazol-4-yl)amino)-6-chloro-5-methoxyquinazolin-2-yl)-phenoxy)-N-(tert-butyl)acetamide

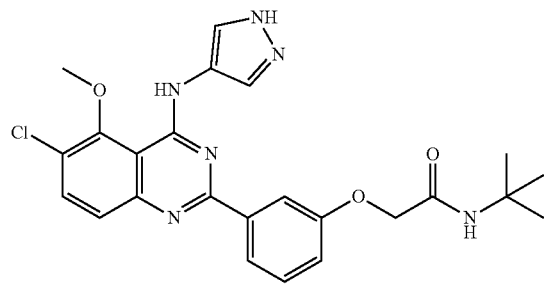 [SMILES: COc1c(Cl)ccc2nc(-c3cccc(OCC(=O)NC(C)(C)C)c3)nc(Nc3cn[nH]c3)c12]

The mixture of N-(tert-butyl)-2-(3-(6-chloro-5-methoxy-4-((1-(tetrahydro-2H-pyran-2-yl)-1H-pyrazol-4-yl)amino)quinazolin-2-yl)phenoxy)acetamide (350 mg, 619.40 µmol) in DCM (4 mL) added to HCl/dioxane (4 N, 4 mL) was stirred at 25° C. for 2 h, concentrated and purified by prep-HPLC (basic conditions) to provide the title compound (90 mg, 29%) as a white solid. ¹H NMR (400 MHz, DMSO-d₆) δ 12.80 (brs, 1H), 9.91 (s, 1H), 8.31-8.04 (m, 3H), 7.99 (s, 1H), 7.90 (d, J=9.2 Hz, 1H), 7.64 (d, J=9.2 Hz, 1H), 7.57 (s, 1H), 7.47 (t, J=8.0 Hz, 1H), 7.10 (dd, J=8.4, 2.4 Hz, 1H), 4.51 (s, 2H), 4.06 (s, 3H), 1.31 (s, 9H). MS (ES+) m/e 481.3 (M+H)⁺.

Example 227

2-(3-(4-((1H-Pyrazol-4-yl)amino)-6-cyclobutoxyquinazolin-2-yl)phenoxy)-N-(tert-butyl)acetamide

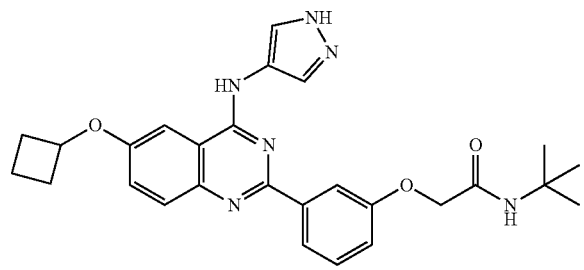 [SMILES: CC(C)(C)NC(=O)COc1cccc(-c2nc(Nc3cn[nH]c3)c3cc(OC4CCC4)ccc3n2)c1]

Step 1

2-Chloro-6-cyclobutoxy-N-(1-(tetrahydro-2H-pyran-2-yl)-1H-pyrazol-4-yl)-quinazolin-4-amine

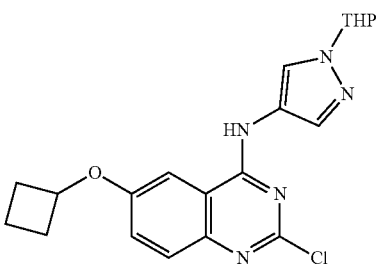

To a solution of 2,4-dichloro-6-cyclobutoxyquinazoline (500 mg, 1.86 mmol) and 1-tetrahydropyran-2-ylpyrazol-4-amine (341.71 mg, crude) in DMF (5 mL) was added DIEA (480.23 mg, 3.72 mmol, 647.21 µL) at 25° C. The reaction mixture was heated to 60° C. and stirred for 15 hours. The mixture was cooled to room temperature and poured into H₂O (60 mL). The resulting mixture was extracted with EtOAc (30 mL×3). The combined organic phases were washed with brine (30 mL×2), dried over anhydrous Na₂SO₄, filtered and concentrated under reduced pressure. The residue was purified by column chromatography (SiO₂, Petroleum ether/Ethyl acetate=2/1) to provide the title compound (580 mg, 78%) as a pink solid. ¹H NMR (400 MHz, DMSO-d₆) δ 10.24 (s, 1H), 8.29 (s, 1H), 7.82 (s, 1H), 7.70 (d, J=2.4 Hz, 1H), 7.63 (d, J=9.2 Hz, 1H), 7.42 (dd, J=2.4, 8.8 Hz, 1H), 5.46 (dd, J=2.0, 10.0 Hz, 1H), 4.92-4.81 (m, 1H), 3.98-3.88 (m, 1H), 3.73-3.61 (m, 1H), 2.62-2.52 (m, 2H), 2.15-2.02 (m, 3H), 2.00-1.90 (m, 2H), 1.88-1.78 (m, 1H), 1.77-1.63 (m, 2H), 1.60-1.50 (m, 2H).

Step 2

N-(tert-Butyl)-2-(3-(6-cyclobutoxy-4-((1-(tetrahydro-2H-pyran-2-yl)-1H-pyrazol-4-yl)amino)quinazolin-2-yl)phenoxy)acetamide

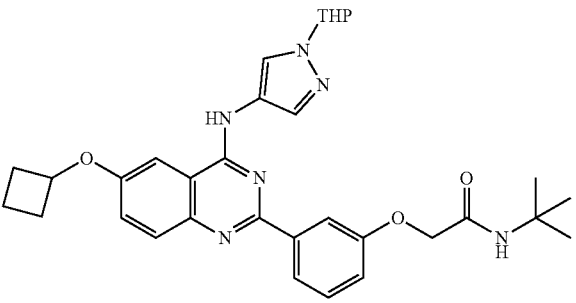

A mixture of 2-chloro-6-cyclobutoxy-N-(1-(tetrahydro-2H-pyran-2-yl)-1H-pyrazol-4-yl)quinazolin-4-amine (580 mg, 1.45 mmol), N-(tert-butyl)-2-(3-(4,4,5,5-tetramethyl-1,3,2-dioxaborolan-2-yl)phenoxy)acetamide (628.34 mg, 1.89 mmol), Pd(dppf)Cl₂ (106.13 mg, 145.05 µmol) and K₂CO₃ (400.92 mg, 2.90 mmol) was suspended in dioxane (6 mL) and H₂O (0.6 mL) under nitrogen atmosphere. The resulting reaction mixture was heated to 100° C. and stirred for 15 hours. The mixture was poured into H₂O (60 mL) and the aqueous layer was extracted with EtOAc (20 mL×4). The combined organic phases were washed with brine (30 mL), dried over anhydrous Na₂SO₄, filtered and concentrated under reduced pressure. The residue was purified by column chromatography (SiO₂, Petroleum ether/Ethyl acetate=3/1 to 1/2) to provide the title compound (605 mg, 73%) as a yellow solid.

Step 3

2-(3-(4-((1H-Pyrazol-4-yl)amino)-6-cyclobutoxyquinazolin-2-yl)phenoxy)-N-(tert-butyl)acetamide

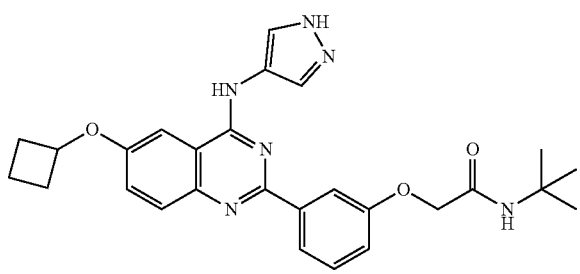 [SMILES: CC(C)(C)NC(=O)COc1cccc(-c2nc(Nc3cn[nH]c3)c3cc(OC4CCC4)ccc3n2)c1]

To a stirred solution of N-(tert-butyl)-2-(3-(6-cyclobutoxy-4-((1-(tetrahydro-2H-pyran-2-yl)-1H-pyrazol-4-yl)amino)quinazolin-2-yl)phenoxy)acetamide (250 mg, 438.07 μmol) in DCM (2.5 mL) was added HCl/dioxane (4 M, 2.5 mL) at 25° C. The resulting reaction mixture was stirred at 25° C. for 15 hours. The solvent was removed under reduced pressure. The residue was purified by prep-HPLC (HCl conditions) to provide the title compound (157.4 mg, 68%) as a yellow solid. ¹H NMR (400 MHz, DMSO-d₆) δ 11.79 (brs, 1H), 8.26 (s, 2H), 8.23-8.16 (m, 2H), 7.98-7.93 (m, 2H), 7.69 (s, 1H), 7.65-7.57 (m, 2H), 7.31-7.24 (m, 1H), 5.07-4.95 (m, 1H), 4.61 (s, 2H), 2.68-2.59 (m, 2H), 2.12-2.04 (m, 2H), 1.91-1.78 (m, 1H), 1.76-1.62 (m, 1H), 1.29 (s, 9H). MS (ES+) m/e 487.3 (M+H)⁺.

Example 228

2-(3-(4-((1H-Pyrazol-4-yl)amino)-5-isopropoxyquinazolin-2-yl)phenoxy)-N-(tert-butyl)acetamide

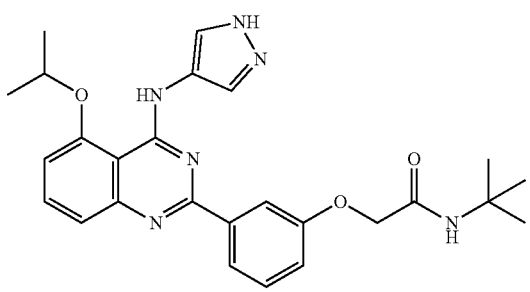 [SMILES: CC(C)Oc1cccc2nc(-c3cccc(OCC(=O)NC(C)(C)C)c3)nc(Nc3cn[nH]c3)c12]

Step 1

Isopropyl 2-fluoro-6-nitrobenzoate

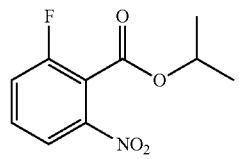 [SMILES: CC(C)OC(=O)c1c(F)cccc1[N+](=O)[O-]]

To a mixture of 2-fluoro-6-nitrobenzoic acid (15 g, 81.03 mmol) in DMF (90 mL) was added Cs₂CO₃ (31.68 g, 97.24 mmol). Then to the mixture was added 2-iodopropane (17.91 g, 105.34 mmol, 10.53 mL). The mixture was stirred at 70° C. for 3.5 h, diluted with water (150 mL) and extracted with EtOAc (150 mL×3). The combined organic layers were washed with brine (100 mL×4), dried over Na₂SO₄, filtered and concentrated under reduced pressure to provide the title compound (20.6 g, crude) as a yellow oil.

Step 2

Isopropyl 2-isopropoxy-6-nitrobenzoate

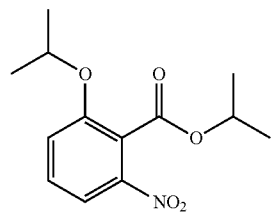 [SMILES: CC(C)OC(=O)c1c(OC(C)C)cccc1[N+](=O)[O-]]

To THF (220 mL) was added NaH (4.44 g, 60% purity) at 0° C. followed by propan-2-ol (19.44 g, 323.52 mmol, 24.77 mL). The mixture was stirred at 0° C. for 5 min. Then to the mixture was added isopropyl 2-fluoro-6-nitrobenzoate (21 g). The mixture was stirred at 0° C. for 1 h. The resulting mixture was extracted with EtOAc (400 mL×3). The combined organic layers were washed with brine (200 mL×2), dried over Na₂SO₄, filtered and concentrated under reduced pressure to give a residue. The residue was purified by column chromatography (SiO₂, Petroleum ether/Ethyl acetate=1:0 to 5:1, R$_f$=0.6) to provide the title compound (7.78 g) as a yellow oil.

Step 3

Isopropyl 2-amino-6-isopropoxybenzoate

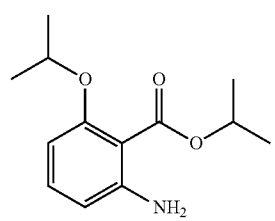

To a mixture of isopropyl 2-isopropoxy-6-nitrobenzoate (7.78 g) in MeOH (70 mL) was added Pd/C (1.5 g, 10%, wet). The mixture was purged with $H_2$ several times, stirred under $H_2$ (50 psi) at 40° C. for 16 hours and was filtered. The filtrate was concentrated to provide the title compound (6.76 g, crude) as a black brown oil.

Step 4

5-Isopropoxyquinazoline-2,4-diol

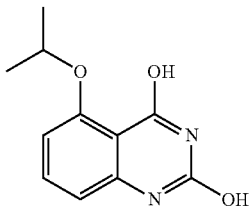 [SMILES: CC(C)Oc1cccc2nc(O)nc(O)c12]

The mixture of isopropyl 2-amino-6-isopropoxybenzoate (6.76 g) in urea (34.22 g, 569.81 mmol, 30.55 mL) was heated to 180° C. The mixture was stirred at 180° C. for 4 h, cooled to about 40° C. and poured into water (400 mL). The solid formed was collected and dried with toluene to provide the title compound (5.44 g) as a yellow solid Step 5

2,4-Dichloro-5-isopropoxyquinazoline

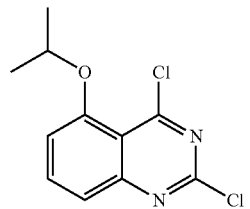 [SMILES: CC(C)Oc1cccc2nc(Cl)nc(Cl)c12]

To $POCl_3$ (46.3 mL) was added 5-isopropoxyquinazoline-2,4-diol (5.44 g, 24.70 mmol) and DIPEA (6.39 g, 49.40 mmol, 8.61 mL). The mixture was stirred at 100° C. for 16 h under $N_2$. The mixture was cooled to room temperature and concentrated to remove most of $POCl_3$. The resulting mixture was poured into ice water (500 mL). The mixture was carefully neutralized with sat. $NaHCO_3$ to about pH=8 at 0° C., then the mixture was extracted with EtOAc (500 mL×3). The combined organic layers were dried over $Na_2SO_4$, filtered and concentrated under reduced pressure to give a residue. The residue was purified by column chromatography (SiO$_2$, petroleum ether/ethyl acetate=50:1 to 5:1, R$_f$=0.8) to provide the title compound (5.6 g, 88%) as a white solid.

Step 6

2-Chloro-5-isopropoxy-N-(1-(tetrahydro-2H-pyran-2-yl)-1H-pyrazol-4-yl)-quinazolin-4-amine

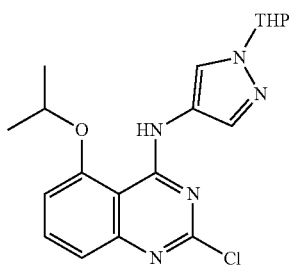

To a mixture of 2,4-dichloro-5-isopropoxyquinazoline (500 mg, 1.94 mmol) and compound 7 (341.42 mg) in DMF (5 mL) was added DIPEA (502.67 mg, 3.89 mmol, 677.45 µL). The mixture was stirred at 60° C. for 16 h, cooled to room temperature and diluted with water (40 mL). The resulting mixture was extracted with EtOAc (40 mL×3). The combined organic layers were washed with brine (40 mL), dried over $Na_2SO_4$, filtered and concentrated under reduced pressure to give a residue. The residue was purified by column chromatography (SiO$_2$, Petroleum ether/Ethyl acetate=50:1 to 1:1, TLC:Petroleum ether/Ethyl acetate=1:1, R$_f$=0.4) to provide the title compound (0.7 g, crude) as a light pink solid.

Step 7

N-(tert-Butyl)-2-(3-(5-isopropoxy-4-((1-(tetrahydro-2H-pyran-2-yl)-1H-pyrazol-4-yl)amino)quinazolin-2-yl)phenoxy)acetamide

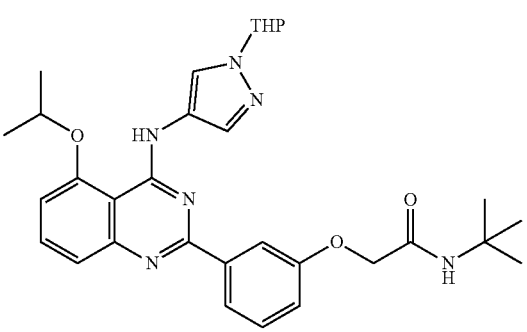

To a mixture of 2-chloro-5-isopropoxy-N-(1-(tetrahydro-2H-pyran-2-yl)-1H-pyrazol-4-yl)quinazolin-4-amine (400 mg) and N-(tert-butyl)-2-(3-(4,4,5,5-tetramethyl-1,3,2-dioxaborolan-2-yl)phenoxy)acetamide (412.39 mg, 1.24 mmol) in dioxane (5 mL) and $H_2O$ (0.5 mL) was added $K_2CO_3$ (285.06 mg, 2.06 mmol) and Pd(dppf)Cl$_2$ (75.46 mg, 103.13 µmol). The mixture was stirred at 100° C. for 16 h under $N_2$, cooled to room temperature and diluted with water (40 mL). The resulting mixture was extracted with EtOAc (40 mL×3). The combined organic layers were washed with brine (40 mL), dried over $Na_2SO_4$, filtered and concentrated under reduced pressure to give a residue. The residue was purified by column chromatography (SiO$_2$, Petroleum ether/

Ethyl acetate=20:1 to 1:1) to provide the title compound (310 mg, 54%) as a yellow oil.

Step 8

2-(3-(4-((1H-Pyrazol-4-yl)amino)-5-isopropoxyquinazolin-2-yl)phenoxy)-N-(tert-butyl)acetamide

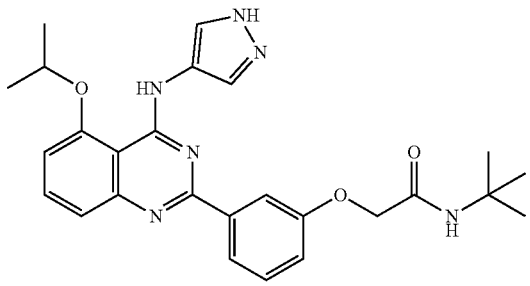 [SMILES: CC(C)Oc1cccc2nc(-c3cccc(OCC(=O)NC(C)(C)C)c3)nc(Nc3cn[nH]c3)c12]

To a mixture of N-(tert-butyl)-2-(3-(5-isopropoxy-4-((1-(tetrahydro-2H-pyran-2-yl)-1H-pyrazol-4-yl)amino)quinazolin-2-yl)phenoxy)acetamide (310 mg, 554.89 µmol) in DCM (5 mL) was added HCl/dioxane (4 N, 4 mL). The mixture was stirred at 25° C. for 16 h and concentrated to give a residue. The residue was purified by prep-HPLC (HCl conditions) twice to provide the title compound (79.0 mg, 27%, HCl salt) as a yellow solid. $^1$H NMR (400 MHz, DMSO-$d_6$) δ 11.0 (s, 1H), 8.20 (s, 2H), 8.04-7.82 (m, 4H), 7.74-7.73 (m, 1H), 7.63 (t, J=8.0 Hz, 1H), 7.42 (d, J=8.0 Hz, 1H), 7.33-7.31 (m, 1H), 5.13-5.07 (m 1H), 4.64 (s, 2H), 1.56 (d, J=6.0 Hz, 6H), 1.29 (s, 9H). MS (ES+) m/e 475.3 (M+H)$^+$.

Example 229

2-(3-(4-((1H-Pyrazol-3-yl)amino)-5-chloro-6-ethoxyquinazolin-2-yl)phenoxy)-N-(tert-butyl)acetamide

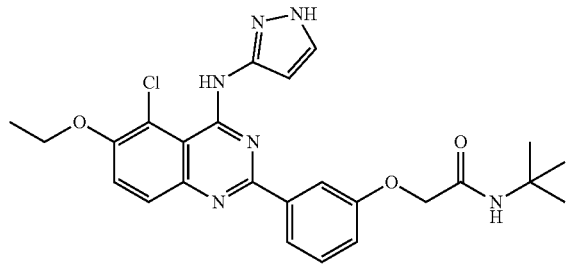 [SMILES: CCOc1ccc2nc(-c3cccc(OCC(=O)NC(C)(C)C)c3)nc(Nc3cc[nH]n3)c2c1Cl]

The title compound was synthesized following the synthetic sequence and the procedures described for Example 220. $^1$H NMR (400 MHz, DMSO-$d_6$) δ 10.49 (brs, 1H), 8.10 (d, J=9.2 Hz, 1H), 8.03-7.99 (m, 2H), 7.95 (d, J=9.2 Hz, 1H), 7.88 (d, J=2.4 Hz, 1H), 7.62 (s, 1H), 7.53 (t, J=8.0 Hz, 1H), 7.20-7.14 (m, 1H), 6.98 (d, J=2.4 Hz, 1H), 4.55 (s, 2H), 4.33 (q, J=7.2 Hz, 2H), 1.43 (t, J=7.2 Hz, 3H), 1.30 (s, 9H). MS (ES+) m/e 495.3 (M+H)$^+$.

Example 230

2-(3-(4-((1H-Pyrazol-3-yl)amino)-6-cyclobutoxyquinazolin-2-yl)phenoxy)-N-(tert-butyl)acetamide

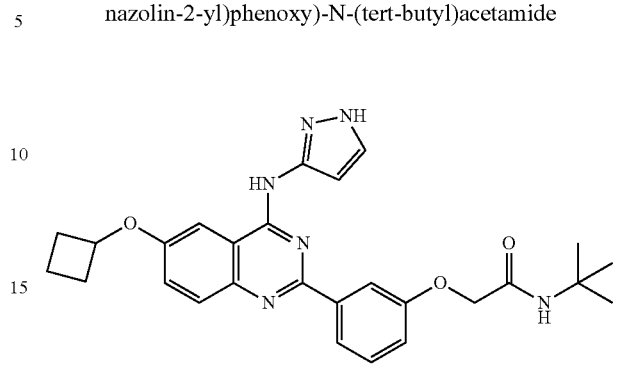

The title compound was synthesized following the synthetic sequence and the procedures described for Example 220. $^1$H NMR (400 MHz, DMSO-$d_6$) δ 11.68 (brs, 1H), 8.22 (d, J=5.6 Hz, 1H), 8.10-7.98 (m, 3H), 7.89 (d, J=2.4 Hz, 1H), 7.67-7.59 (m, 2H), 7.55 (t, J=8.0 Hz, 1H), 7.22 (d, J=6.4 Hz, 1H), 6.96 (d, J=2.4 Hz, 1H), 5.00-4.90 (m, 1H), 4.58 (s, 2H), 2.69-2.57 (m, 2H), 2.15-2.03 (m, 2H), 1.93-1.81 (m, 1H), 1.76-1.64 (m, 1H), 1.29 (s, 9H). MS (ES+) m/e 487.3 (M+H)$^+$.

Example 231

2-(3-(4-((1H-Pyrazol-4-yl)amino)-6-isopropoxyquinazolin-2-yl)phenoxy)-N-isopropylacetamide

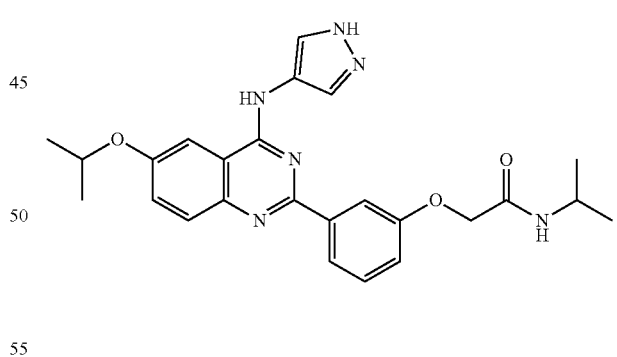

The title compound was synthesized following the synthetic sequence and the procedures described for Example 222. $^1$H NMR (400 MHz, DMSO-$d_6$) δ 11.95 (brs, 1H), 8.46-8.42 (m, 1H), 8.27 (s, 2H), 8.23 (d, J=9.2 Hz, 1H), 8.06 (d, J=8.0 Hz, 1H), 8.00-7.93 (m, 2H), 7.68 (dd, J=9.2, 2.4 Hz, 1H), 7.63 (t, J=7.6 Hz, 1H), 7.37-7.28 (m, 1H), 5.05-4.99 (m, 1H), 4.65 (s, 2H), 3.97-3.95 (m, 1H), 1.38 (d, J=6.0 Hz, 6H), 1.09 (d, J=7.2 Hz, 6H). MS (ES+) m/e 461.3 (M+H)$^+$.

Example 232

2-(3-(4-((1H-Pyrazol-4-yl)amino)-6-isopropoxyqui-
nazolin-2-yl)phenoxy)-N-cyclobutylacetamide

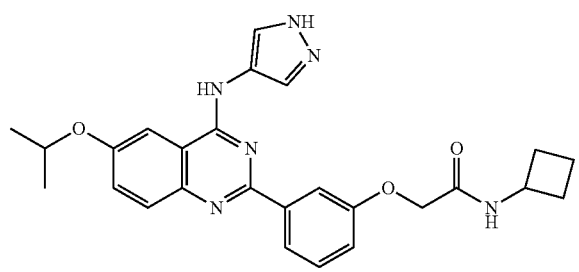 [SMILES: CC(C)Oc1ccc2nc(-c3cccc(OCC(=O)NC4CCC4)c3)nc(Nc3cn[nH]c3)c2c1]

The title compound was synthesized following the synthetic sequence and the procedures described for Example 222. $^1$H NMR (400 MHz, DMSO-d$_6$) δ 11.82 (brs, 1H), 8.45 (d, J=7.6 Hz, 1H), 8.39 (s, 1H), 8.26 (s, 2H), 8.19 (d, J=9.2 Hz, 1H), 8.00-7.92 (m, 2H), 7.68 (dd, J=9.2, 2.4 Hz, 1H), 7.63 (t, J=8.4 Hz, 1H), 7.35-7.28 (m, 1H), 5.05-4.96 (m, 1H), 4.64 (s, 2H), 4.33-4.25 (m, 1H), 2.20-2.09 (m, 2H), 2.06-1.93 (m, 2H), 1.69-1.56 (m, 2H), 1.38 (d, J=6.0 Hz, 6H). MS (ES+) m/e 473.3 (M+H)$^+$.

Example 233

2-(3-(4-((1H-Pyrazol-4-yl)amino)-6-isopropoxyqui-
nazolin-2-yl)phenoxy)-N-cyclopentylacetamide

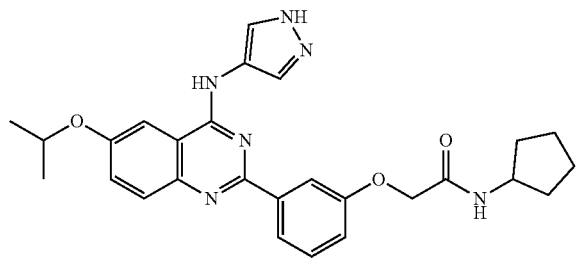 [SMILES: CC(C)Oc1ccc2nc(-c3cccc(OCC(=O)NC4CCCC4)c3)nc(Nc3cn[nH]c3)c2c1]

The title compound was synthesized following the synthetic sequence and the procedures described for Example 222. $^1$H NMR (400 MHz, DMSO-d$_6$) δ 11.73 (s, 1H), 8.34 (s, 1H), 8.24 (s, 2H), 8.16 (d, J=9.2 Hz, 1H), 8.12 (d, J=7.2 Hz, 1H), 8.00-7.90 (m, 2H), 7.68 (dd, J=9.2, 2.4 Hz, 1H), 7.63 (t, J=8.0 Hz, 1H), 7.33-7.28 (m, 1H), 5.05-4.93 (m, 1H), 4.65 (s, 2H), 4.13-4.06 (m, 1H), 1.88-1.75 (m, 2H), 1.70-1.58 (m, 2H), 1.56-1.42 (m, 4H), 1.39 (d, J=6.0 Hz, 6H). MS (ES+) m/e 487.5 (M+H)$^+$.

Example 234

2-(3-(4-((1H-Pyrazol-4-yl)amino)-6-isopropoxyqui-
nazolin-2-yl)phenoxy)-N-(1-methylcyclopropyl)
acetamide

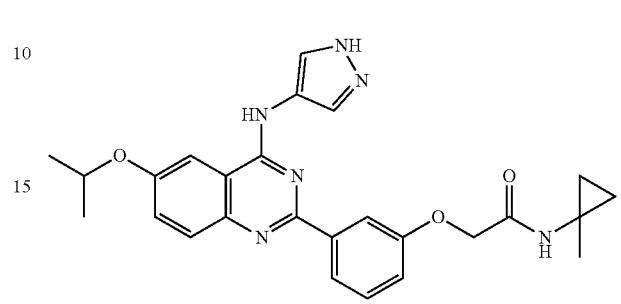

The title compound was synthesized following the synthetic sequence and the procedures described for Example 222. $^1$H NMR (400 MHz, DMSO-d$_6$) δ 11.80 (brs, 1H), 8.44 (s, 1H), 8.39 (s, 1H), 8.26 (s, 2H), 8.19 (d, J=9.2 Hz, 1H), 8.00-7.93 (m, 2H), 7.69 (dd, J=9.2, 2.4 Hz, 1H), 7.63 (t, J=8.2 Hz, 1H), 7.33-7.28 (m, 1H), 5.05-4.96 (m, 1H), 4.59 (s, 2H), 1.39 (d, J=6.0 Hz, 6H), 1.30 (s, 3H), 0.70-0.64 (m, 2H), 0.58-0.52 (m, 2H). MS (ES+) m/e 473.3 (M+H)$^+$.

Example 235

2-(3-(4-((1H-Pyrazol-4-yl)amino)-6-cyclobutoxyqui-
nazolin-2-yl)phenoxy)-N-isopropylacetamide

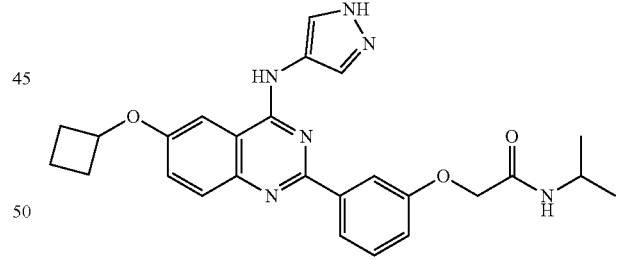

The title compound was synthesized following the synthetic sequence and the procedures described for Example 222. $^1$H NMR (400 MHz, DMSO-d$_6$) δ 12.00 (brs, 1H), 8.30-8.22 (m, 4H), 8.07 (d, J=7.6 Hz, 1H), 8.00-7.94 (m, 2H), 7.69-7.60 (m, 2H), 7.33 (dd, J=8.0, 2.0 Hz, 1H), 5.10-4.98 (m, 1H), 4.65 (s, 2H), 3.96-3.95 (m, 1H), 2.70-2.62 (m, 2H), 2.15-2.02 (m, 2H), 1.91-1.80 (m, 1H), 1.78-1.64 (m, 1H), 1.09 (d, J=6.8 Hz, 6H). MS (ES+) m/e 473.3 (M+H)$^+$.

Example 236

2-(3-(4-((1H-Pyrazol-4-yl)amino)-6-cyclobutoxyquinazolin-2-yl)phenoxy)-N-(sec-butyl)acetamide

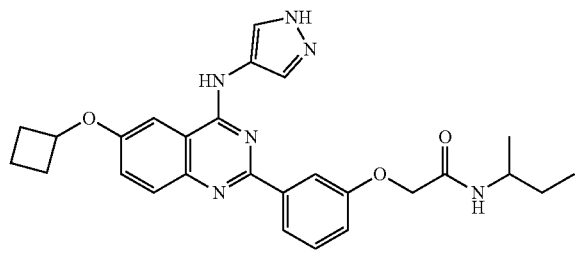 [SMILES: CCC(C)NC(=O)COc1cccc(-c2nc(Nc3cn[nH]c3)c3cc(OC4CCC4)ccc3n2)c1]

The title compound was synthesized following the synthetic sequence and the procedures described for Example 222. $^1$H NMR (400 MHz, DMSO-$d_6$) δ 11.81 (brs, 1H), 8.25 (s, 2H), 8.21-8.15 (m, 2H), 7.99-7.92 (m, 3H), 7.69-7.60 (m, 2H), 7.34-7.28 (m, 1H), 5.06-4.96 (m, 1H), 4.66 (s, 2H), 3.77 (m, 1H), 2.67-2.59 (m, 2H), 2.16-2.04 (m, 2H), 1.91-1.81 (m, 1H), 1.77-1.66 (m, 1H), 1.47-1.37 (m, 2H), 1.06 (d, J=6.4 Hz, 3H), 0.80 (t, J=7.2 Hz, 3H). MS (ES+) m/e 487.3 (M+H)$^+$.

Example 237

2-(3-(4-((1H-Pyrazol-4-yl)amino)-6-cyclobutoxyquinazolin-2-yl)phenoxy)-N-(1-methylcyclopropyl)acetamide

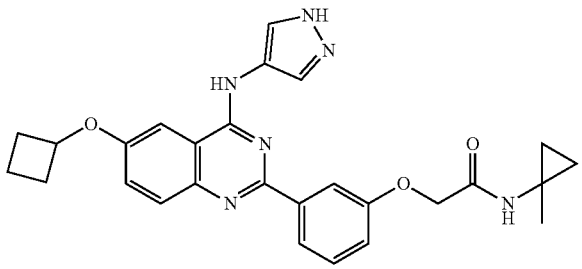 [SMILES: CC1(NC(=O)COc2cccc(-c3nc(Nc4cn[nH]c4)c4cc(OC5CCC5)ccc4n3)c2)CC1]

The title compound was synthesized following the synthetic sequence and the procedures described for Example 222. $^1$H NMR (400 MHz, DMSO-$d_6$) δ 12.00 (brs, 1H), 8.47 (s, 1H), 8.31-8.21 (m, 4H), 7.99-7.91 (m, 2H), 7.69-7.60 (m, 2H), 7.31 (dd, J=8.0, 1.6 Hz, 1H), 5.09-4.98 (m, 1H), 4.59 (s, 2H), 2.70-2.61 (m, 2H), 2.17-2.03 (m, 2H), 1.91-1.79 (m, 1H), 1.77-1.65 (m, 1H), 0.70-0.63 (m, 2H), 0.58-0.51 (m, 2H). MS (ES+) m/e 485.3 (M+H)$^+$.

Example 238

2-(3-(4-((1H-Pyrazol-4-yl)amino)-6-propoxyquinazolin-2-yl)phenoxy)-N-isopropylacetamide

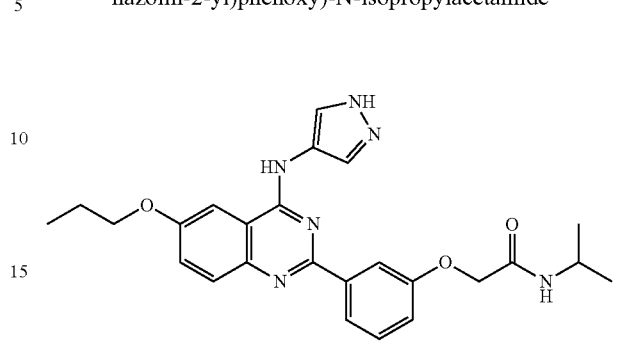

The title compound was synthesized following the synthetic sequence and the procedures described for Example 222. $^1$H NMR (400 MHz, DMSO-$d_6$) δ 11.58 (s, 1H), 8.23 (m, 3H), 8.10 (m, 1H), 8.02 (d, J=8.0 Hz, 1H), 7.98-7.90 (m, 2H), 7.73 (d, J=9.2 Hz, 1H), 7.64 (t, J=8.0 Hz, 1H), 7.32 (d, J=8.0 Hz, 1H), 4.63 (s, 2H), 4.19 (t, J=6.4 Hz, 2H), 3.98-3.94 (m, 1H), 1.87 (m, 2H), 1.11-1.05 (m, 9H). MS (ES+) m/e 461.3 (M+H)$^+$.

Example 239

2-(3-(4-((1H-Pyrazol-4-yl)amino)-6-propoxyquinazolin-2-yl)phenoxy)-N-(1-methylcyclopropyl)acetamide

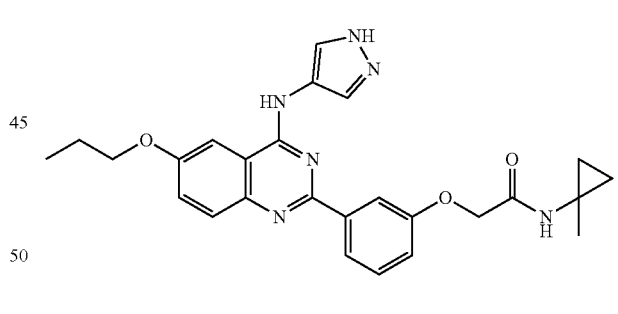

The title compound was synthesized following the synthetic sequence and the procedures described for Example 222. $^1$H NMR (400 MHz, DMSO-$d_6$) δ 12.03-11.70 (m, 1H), 8.49-8.31 (m, 2H), 8.29-8.14 (m, 3H), 7.96-7.95 (m, 2H), 7.71 (d, J=9.2 Hz, 1H), 7.63 (t, J=8.4 Hz, 1H), 7.30 (d, J=8.4 Hz, 1H), 4.59 (s, 2H), 4.20 (t, J=6.4 Hz, 2H), 1.89-1.78 (m, 2H), 1.29 (s, 3H), 1.06 (t, J=7.4 Hz, 3H), 0.71-0.62 (m, 2H), 0.57-0.47 (m, 2H). MS (ES+) m/e 473.3 (M+H)$^+$.

Example 240

2-(3-(4-((1H-Pyrazol-4-yl)amino)-6-propoxyquinazolin-2-yl)phenoxy)-N-cyclopentylacetamide

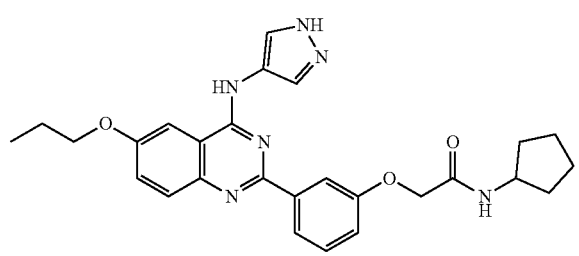 [SMILES: CCCOc1ccc2nc(-c3cccc(OCC(=O)NC4CCCC4)c3)nc(Nc3cn[nH]c3)c2c1]

The title compound was synthesized following the synthetic sequence and the procedures described for Example 222. $^1$H NMR (400 MHz, DMSO-d$_6$) δ 11.74 (s, 1H), 8.34 (s, 1H), 8.26 (s, 2H), 8.22-8.12 (m, 2H), 7.98-7.96 (m, 2H), 7.70 (dd, J=9.2, 2.4 Hz, 1H), 7.63 (t, J=8.0 Hz, 1H), 7.31 (d, J=7.6 Hz, 1H), 4.66 (s, 2H), 4.20 (t, J=6.8 Hz, 2H), 4.12-4.09 (m, 1H), 1.92-1.75 (m, 4H), 1.71-1.60 (m, 2H), 1.55-1.41 (m, 4H), 1.06 (t, J=7.6 Hz, 3H). MS (ES+) m/e 487.3 (M+H)$^+$.

Example 241

2-(3-(4-((1H-Pyrazol-4-yl)amino)-6-propoxyquinazolin-2-yl)phenoxy)-N-(1-fluoro-2-methylpropan-2-yl)acetamide

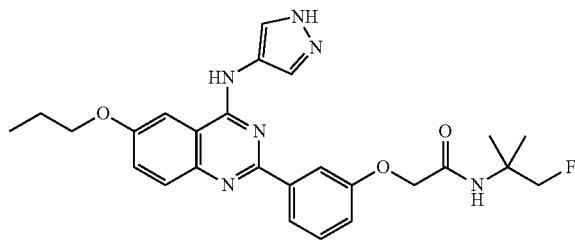 [SMILES: CCCOc1ccc2nc(-c3cccc(OCC(=O)NC(C)(C)CF)c3)nc(Nc3cn[nH]c3)c2c1]

The title compound was synthesized following the synthetic sequence and the procedures described for Example 222. $^1$H NMR (400 MHz, DMSO-d$_6$) δ 11.86 (s, 1H), 8.38 (s, 1H), 8.26-8.22 (m, 3H), 7.98-7.96 (m, 2H), 7.86 (s, 1H), 7.71 (dd, J=9.2, 3.2 Hz, 1H), 7.63 (t, J=8.0 Hz, 1H), 7.29 (dd, J=9.2, 3.2 Hz, 1H), 4.67 (s, 2H), 4.53 (s, 1H), 4.41 (s, 1H), 4.20 (t, J=6.4 Hz, 2H), 1.87-1.82 (m, 2H), 1.28 (d, J=2.0 Hz, 6H), 1.06 (t, J=7.2 Hz, 3H). MS (ES+) m/e 493.3 (M+H)$^+$.

Example 242

2-(3-(4-((1H-Pyrazol-4-yl)amino)-6-isopropoxyquinazolin-2-yl)phenoxy)-N-(1-fluoro-2-methylpropan-2-yl)acetamide

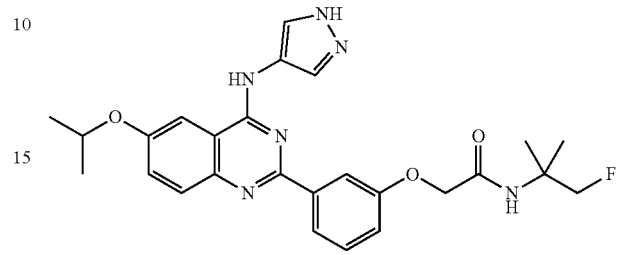

The title compound was synthesized following the synthetic sequence and the procedures described for Example 222. $^1$H NMR (400 MHz, DMSO-d$_6$) δ 11.88 (brs, 1H), 8.41 (d, J=1.6 Hz, 1H), 8.26 (s, 2H), 8.22 (d, J=9.2 Hz, 1H), 7.99-7.93 (m, 2H), 7.87 (s, 1H), 7.69 (dd, J=9.2, 2.4 Hz, 1H), 7.63 (t, J=8.0 Hz, 1H), 7.33-7.27 (m, 1H), 5.05-4.97 (m, 1H), 4.67 (s, 2H), 4.53 (s, 1H), 4.41 (s, 1H), 1.38 (d, J=6.0 Hz, 6H), 1.28 (s, 3H), 1.27 (s, 3H). MS (ES+) m/e 493.5 (M+H)$^+$.

Example 243

2-(3-(4-((1H-Pyrazol-4-yl)amino)-6-ethoxyquinazolin-2-yl)phenoxy)-N-(1-fluoro-2-methylpropan-2-yl)acetamide

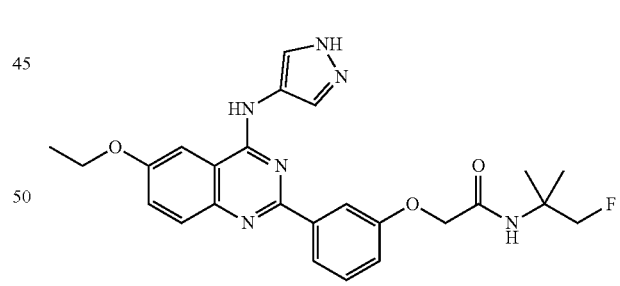

The title compound was synthesized following the synthetic sequence and the procedures described for Example 222. $^1$H NMR (400 MHz, DMSO-d$_6$) δ 11.68 (brs, 1H), 8.29 (s, 1H), 8.24 (s, 2H), 8.14 (d, J=9.2 Hz, 1H), 7.99-7.91 (m, 2H), 7.84 (s, 1H), 7.69 (d, J=7.2 Hz, 1H), 7.62 (t, J=8.0 Hz, 1H), 7.28 (d, J=7.6 Hz, 1H), 4.65 (s, 2H), 4.53 (s, 1H), 4.41 (s, 1H), 4.29 (q, J=6.8 Hz, 2H), 1.45 (t, J=6.8 Hz, 3H), 1.28 (s, 3H), 1.27 (s, 3H). MS (ES+) m/e 479.1 (M+H)$^+$.

Example 244

2-(3-(4-((1H-Pyrazol-3-yl)amino)-6-ethoxyquinazolin-2-yl)phenoxy)-N-(1-fluoro-2-methylpropan-2-yl)acetamide

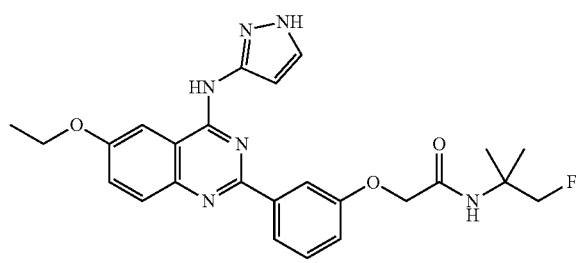 [SMILES: CCOc1ccc2nc(-c3cccc(OCC(=O)NC(C)(C)CF)c3)nc(Nc3cc[nH]n3)c2c1]

The title compound was synthesized following the synthetic sequence and the procedures described for Example 220. $^1$H NMR (400 MHz, DMSO-d$_6$) δ 11.92 (s, 1H), 8.32 (m, 2H), 8.00-7.95 (m, 2H), 7.90 (d, J=2.0 Hz, 1H), 7.83 (s, 1H), 7.69 (d, J=8.8 Hz, 1H), 7.59 (t, J=8.0 Hz, 1H), 7.26 (d, J=7.6 Hz, 1H), 6.99 (d, J=2.0 Hz, 1H), 4.64 (s, 2H), 4.53 (s, 1H), 4.41 (s, 1H), 4.27-4.25 (m, 2H), 1.45 (t, J=6.8 Hz, 3H), 1.28 (s, 6H). MS (ES+) m/e 479.3 (M+H)$^+$.

Example 245

2-(3-(4-((1H-Pyrazol-4-yl)amino)-6-propoxyquinazolin-2-yl)phenoxy)-N-(sec-butyl)acetamide

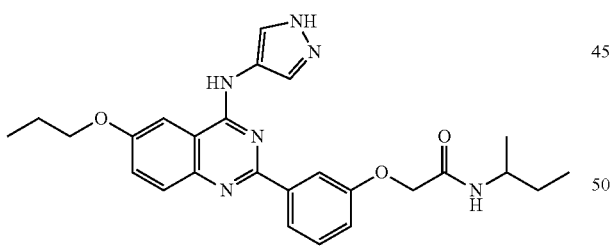

The title compound was synthesized following the synthetic sequence and the procedures described for Example 222. $^1$H NMR (400 MHz, DMSO-d$_6$) δ 11.78 (s, 1H), 8.32 (s, 1H), 8.24 (s, 2H), 8.15 (s, 1H), 8.00-7.99 (m, 3H), 7.66 (d, J=8.8 Hz, 1H), 7.59 (t, J=7.6 Hz, 1H), 7.27 (d, J=6.8 Hz, 1H), 4.66 (s, 2H), 4.19 (t, J=6.4 Hz, 2H), 3.82-3.75 (m, 1H), 1.89-1.78 (m, 2H), 1.50-1.36 (m, 2H), 1.11-1.0 (m, 6H), 0.79 (t, J=7.2 Hz, 3H). MS (ES+) m/e 475.3 (M+H)$^+$.

Example 246

2-(3-(4-((1H-Pyrazol-3-yl)amino)-6-isopropoxyquinazolin-2-yl)phenoxy)-N-(1-fluoro-2-methylpropan-2-yl)acetamide

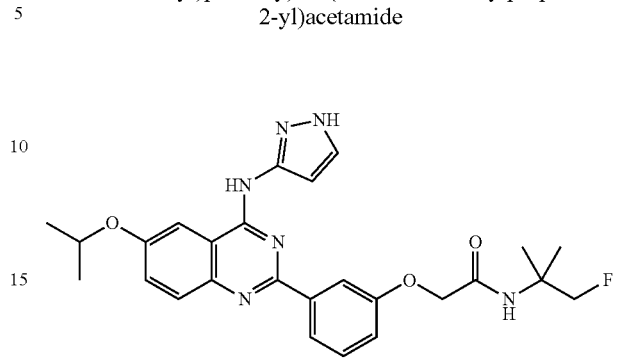

The title compound was synthesized following the synthetic sequence and the procedures described for Example 220. $^1$H NMR (400 MHz, DMSO-d$_6$) δ 12.99 (brs, 1H), 11.88 (brs, 1H), 8.31 (d, J=2.0 Hz, 1H), 8.22 (d, J=9.2 Hz, 1H), 8.04-7.96 (m, 2H), 7.90 (d, J=2.0 Hz, 1H), 7.83 (s, 1H), 7.69-7.56 (m, 2H), 7.26 (dd, J=8.0, 1.6 Hz, 1H), 6.98 (d, J=2.4 Hz, 1H), 4.98-4.89 (m, 1H), 4.64 (s, 2H), 4.53 (s, 1H), 4.41 (s, 1H), 1.39 (d, J=7.0 Hz, 6H), 1.28 (s, 6H). MS (ES+) m/e 493.3 (M+H)$^+$.

Example 247

2-(3-(4-((1H-Pyrazol-4-yl)amino)-6-(methylthio)quinazolin-2-yl)phenoxy)-N-(tert-butyl)acetamide

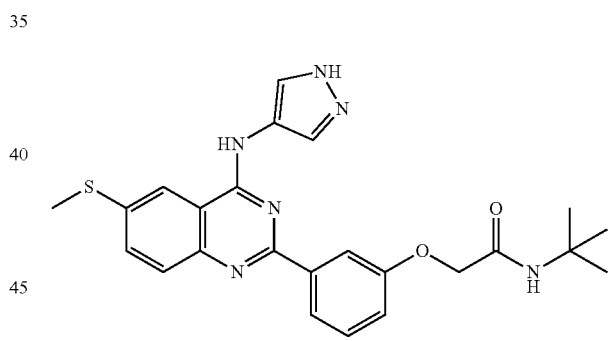

Step 1

2-Amino-5-(methylthio)benzoic acid

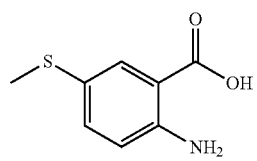

To a mixture of methyl 2-amino-5-(methylthio)benzoate (5 g, 24.81 mmol) in H$_2$O (50 mL) was added NaOH (1 g, 25.00 mmol) in H$_2$O (25 mL). The mixture (pH=7.5) was heated to 50° C. To the mixture was added Na$_2$S·9H$_2$O (20.14 g, 83.84 mmol) in H$_2$O (33.5 mL) in one portion.

After the initial exotherm had subsided, the mixture was stirred at 50-55° C. for 2.5 hr. To the mixture was added NaOH (1.25 g, 31.25 mmol) in H₂O (5 mL). To the mixture was added Me₂SO₄ (6.25 g, 49.61 mmol) drop-wise. The mixture was heated to 100° C. and stirred for 1 hr. The mixture was cooled to 0° C. To the mixture was added HCl (2 N) to adjust to pH=2. Some solid were formed. The mixture was filtered to give the solid and a filtrate. The solid was dried with toluene (20 mL×5) to afford a yellow solid (6 g, crude).

To a mixture of the yellow solid (0.9 g, crude) in MeOH (10 mL) was added Pd/C (0.1 g, 10%). The mixture was purged with H₂ several times. The mixture was stirred under H₂ (15 psi) at 40° C. for 16 hours. The mixture was filtered with celite to give a filtrate. The filtrate was concentrated under vacuum to provide the title compound (1.2 g, crude) as a yellow solid.

Step 2

6-(Methylthio)quinazoline-2,4-diol

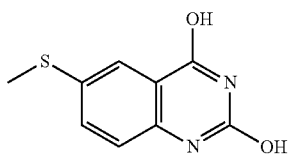

The mixture of 2-amino-5-(methylthio)benzoic acid (700 mg, crude) and AcOH (688.27 mg, 11.46 mmol) in H₂O (7 mL) was stirred for 30 min at 35° C. A solution of KOCN (929.67 mg, 11.46 mmol) in H₂O (5 mL) was added drop-wise to the mixture above. The mixture was stirred at 35° C. for 3 hr. Then NaOH (4.58 g, 114.51 mmol) was added to the reaction mixture slowly. The mixture was stirred for 2.5 hr at 35° C., cooled to room temperature and acidified with HCl (1 N) to adjust to pH=3. The solid was collected by filtration and dried with toluene (50 mL×3) to provide the title compound (680 mg, crude). ¹H NMR (400 MHz, DMSO-d₆) δ 11.31 (s, 1H), 11.14 (s, 1H), 7.68 (s, 1H), 7.58 (d, J=8.8 Hz, 1H), 7.13 (d, J=8.4 Hz, 1H), 2.49 (s, 3H).

Step 3

2,4-Dichloro-6-(methylthio)quinazoline

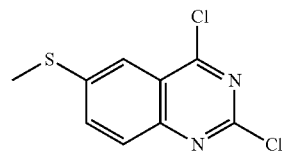

To POCl₃ (20 mL) were added 6-(methylthio)quinazoline-2,4-diol (923 mg, 4.43 mmol) and DIPEA (1.15 g, 8.86 mmol). The mixture was heated to 90° C. and stirred for 16 hr, cooled to room temperature and concentrated under vacuum to give a residue. To the ice saturated NaHCO₃ (200 mL) was added the residue slowly to adjust to pH=8 and the resulting mixture was diluted with H₂O (100 mL) and extracted with EtOAc (100 mL×3). The combined organic layers were washed with brine (100 mL×2), dried over Na₂SO₄, filtered and concentrated under reduced pressure to give a residue. The residue was purified by column chromatography (SiO₂, Petroleum ether/Ethyl acetate=5/1, R$_f$=0.7) to provide the title compound (956 mg, 87%) as a yellow solid. ¹H NMR (400 MHz, CDCl₃) δ 7.80-7.72 (m, 3H), 2.57 (s, 3H).

Step 4

2-Chloro-6-(methylthio)-N-(1-(tetrahydro-2H-pyran-2-yl)-1H-pyrazol-4-yl)-quinazolin-4-amine

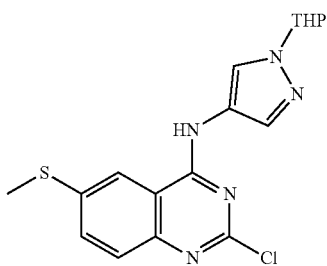

To a mixture of 2,4-dichloro-6-(methylthio)quinazoline (900 mg, 3.67 mmol) and 1-(tetrahydro-2H-pyran-2-yl)-1H-pyrazol-4-amine (613.91 mg) in DMF (9 mL) was added DIPEA (949.04 mg, 7.34 mmol). The mixture was heated to 60° C., stirred at 60° C. for 16 hr and cooled to room temperature. The reaction mixture was diluted with H₂O (60 mL) and extracted with EtOAc (30 mL×4). The combined organic layers were washed with brine (40 mL×2), dried over Na₂SO₄, filtered and concentrated under reduced pressure to give a residue. The residue was purified by column chromatography (SiO₂, Petroleum ether/Ethyl acetate=1/1, R$_f$=0.4) to provide the title compound (1.2 g, 86%) as a red solid.

Step 5

N-(tert-Butyl)-2-(3-(6-(methylthio)-4-((1-(tetrahydro-2H-pyran-2-yl)-1H-pyrazol-4-yl)amino)quinazolin-2-yl)phenoxy)acetamide

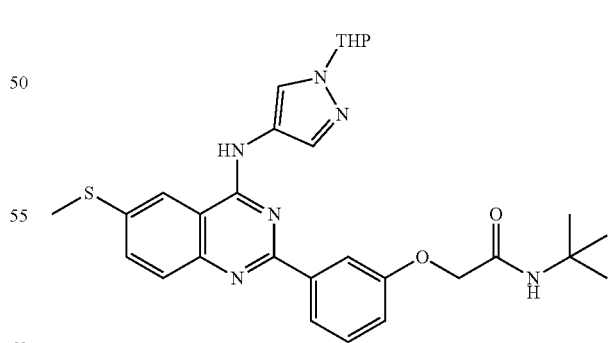

To a mixture of 2-chloro-6-(methylthio)-N-(1-(tetrahydro-2H-pyran-2-yl)-1H-pyrazol-4-yl)quinazolin-4-amine (600 mg, 1.60 mmol), and N-(tert-butyl)-2-(3-(4,4,5,5-tetramethyl-1,3,2-dioxaborolan-2-yl)phenoxy)acetamide (691.50 mg, 2.08 mmol) in dioxane (6 mL) and H₂O (0.6 mL) were added K₂CO₃ (441.23 mg, 3.19 mmol) and Pd(dppf)Cl$_2$ (58.40 mg, 79.81 μmol). The mixture was degassed under vacuum and purged with N$_2$ several times. The mixture was heated to 100° C. and stirred at 100° C. for 16 hr followed by addition of K$_2$CO$_3$ (100 mg) and Pd(dppf)Cl$_2$ (58.4 mg) and was stirred at 100° C. for 5 additional hours. The reaction mixture was cooled to room temperature, diluted with H$_2$O (20 mL) and extracted with EtOAc (30 mL×4). The combined organic layers were washed with brine (50 mL×2), dried over Na$_2$SO$_4$, filtered and concentrated under reduced pressure to give a residue. The residue was purified by column chromatography (SiO$_2$, Petroleum ether/Ethyl acetate=0/1, R$_f$=0.6) to provide the title compound (564 mg, 56%) as a yellow solid. $^1$H NMR (400 MHz, DMSO-d$_6$) δ 10.10 (s, 1H), 8.48 (s, 1H), 8.25 (s, 1H), 8.05 (d, J=8.0 Hz, 1H), 8.01-8.00 (m, 1H), 7.91 (s, 1H), 7.77 (s, 2H), 7.53 (s, 1H), 7.46 (t, J=8.0 Hz, 1H), 7.09 (dd, J=8.0, 2.4 Hz, 1H), 5.51 (dd, J=9.6, 2.4 Hz, 1H), 4.52 (s, 2H), 3.98-7.95 (m, 1H), 3.73-7.67 (m, 1H), 2.66 (s, 3H), 2.10-2.10 (m, 1H), 2.04-1.97 (m, 2H), 1.77-1.67 (m, 1H), 1.60-1.57 (m, 2H), 1.30 (s, 9H).

Step 6

2-(3-(4-((1H-Pyrazol-4-yl)amino)-6-(methylthio)quinazolin-2-yl)phenoxy)-N-(tert-butyl)acetamide

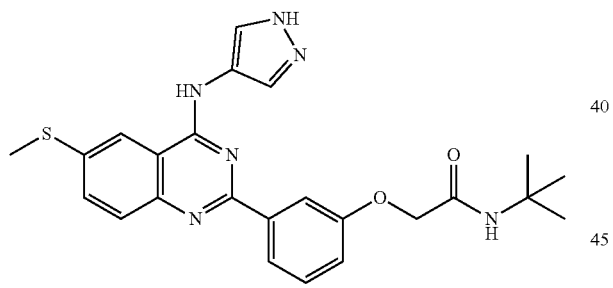

To a mixture of N-(tert-butyl)-2-(3-(6-(methylthio)-4-((1-(tetrahydro-2H-pyran-2-yl)-1H-pyrazol-4-yl)amino)quinazolin-2-yl)phenoxy)acetamide (564 mg, 907.88 μmol) in DCM (6 mL) was added HCl/dioxane (4 N, 6 mL). The mixture was heated to 40° C. and stirred at 40° C. for 11 hr and cooled to room temperature. The solids formed was collected by filtration, basidified with NaHCO$_3$ aqueous solution and extracted with EtOAc. The combined organic layers were dried over Na$_2$SO$_4$ and concentrated to provide a residue. The residue was purified by prep-HPLC (HCl conditions) to provide the title compound (374.53 mg, 81%, HCl salts) as a yellow solid. $^1$H NMR (400 MHz, DMSO-d$_6$) δ 11.91 (s, 1H), 8.61 (s, 1H), 8.26 (s, 2H), 8.17 (d, J=7.6 Hz, 1H), 7.99-7.95 (m, 3H), 7.68 (s, 1H), 7.63 (t, J=8.4 Hz, 1H), 7.31 (d, J=8.0 Hz, 1H), 4.62 (s, 2H), 2.73 (s, 3H), 1.30 (s, 9H). MS (ES+) m/e 463.3 (M+H)$^+$.

Example 248

2-(3-(4-((1H-Pyrazol-4-yl)amino)-6-(methylthio)quinazolin-2-yl)phenoxy)-N-isopropylacetamide

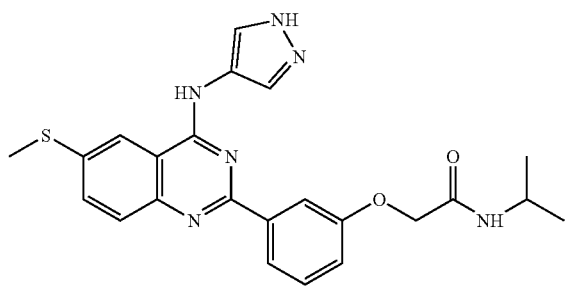 [SMILES: CSc1ccc2nc(-c3cccc(OCC(=O)NC(C)C)c3)nc(Nc3cn[nH]c3)c2c1]

The title compound was synthesized following the synthetic sequence and the procedures described for Example 247. $^1$H NMR (400 MHz, DMSO-d$_6$) δ 12.07 (s, 1H), 8.67 (s, 1H), 8.28 (s, 2H), 8.22 (d, J=8.8 Hz, 1H), 8.07 (d, J=8.0 Hz, 1H), 8.00-7.95 (m, 3H), 7.64 (t, J=8.0 Hz, 1H), 7.34 (d, J=8.0 Hz, 1H), 4.66 (s, 2H), 4.01-3.94 (m, 1H), 2.74 (s, 3H), 1.10 (d, J=2.8 Hz, 6H). MS (ES+) m/e 449.3 (M+H)$^+$.

Example 249

2-(3-(4-((1H-Pyrazol-3-yl)amino)-5-isopropoxyquinazolin-2-yl)phenoxy)-N-(tert-butyl)acetamide

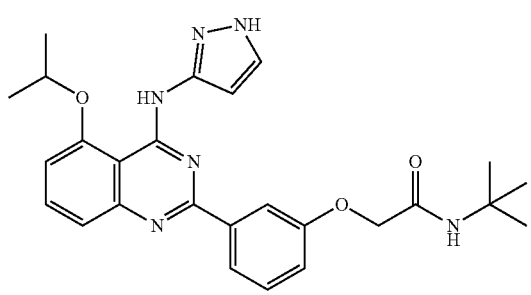 [SMILES: CC(C)Oc1cccc2nc(-c3cccc(OCC(=O)NC(C)(C)C)c3)nc(Nc3cc[nH]n3)c12]

The title compound was synthesized following the synthetic sequence and the procedures described for Example 222. $^1$H NMR (400 MHz, DMSO-d$_6$) δ 12.95 (brs, 1H), 11.35 (s, 1H), 8.02-8.00 (m, 2H), 7.96 (t, J=8.4 Hz, 1H), 7.91 (d, J=2.4 Hz, 1H), 7.77 (d, J=7.2 Hz, 1H), 7.67 (s, 1H), 7.61 (t, J=8.0 Hz, 1H), 7.41 (d, J=8.4 Hz, 1H), 7.28 (d, J=8.8 Hz, 1H), 7.03 (d, J=2.4 Hz, 1H), 5.17-5.11 (m, 1H), 4.60 (s, 2H), 1.54 (s, 6H), 1.30 (s, 9H). MS (ES+) m/e 475.4 (M+H)$^+$.

Example 250

2-(3-(4-((1H-Pyrazol-4-yl)amino)-6-(2,2,2-trifluoroethoxy)quinazolin-2-yl)-phenoxy)-N-(tert-butyl)acetamide

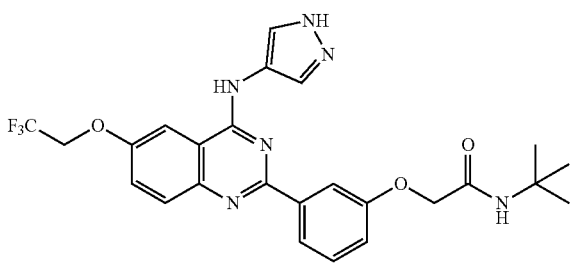 [SMILES: CC(C)(C)NC(=O)COc1cccc(-c2nc(Nc3cn[nH]c3)c3cc(OCC(F)(F)F)ccc3n2)c1]

The title compound was synthesized following the synthetic sequence and the procedures described for Example 222. ¹H NMR (400 MHz, DMSO-$d_6$) δ 11.99 (brs, 1H), 8.69 (s, 1H), 8.32-8.20 (m, 3H), 8.02-7.95 (m, 2H), 7.87-7.77 (m, 1H), 7.67 (s, 1H), 7.63 (t, J=8.0 Hz, 1H, 2H), 7.30 (d, J=7.2 Hz, 1H), 5.06 (q, J=8.4 Hz, 2H), 4.61 (s, 2H), 1.29 (s, 9H). MS (ES+) m/e 515.3 (M+H)⁺.

Example 251

2-(3-(4-((1H-Pyrazol-4-yl)amino)-6-(methylsulfonyl)quinazolin-2-yl)phenoxy)-N-(tert-butyl)acetamide

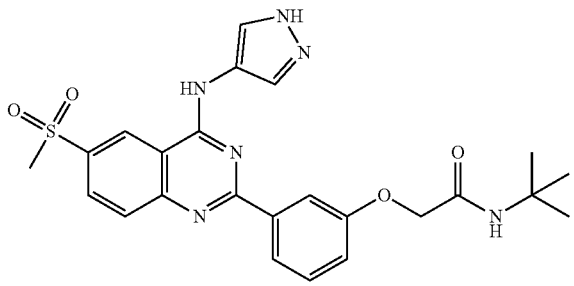 [SMILES: CC(C)(C)NC(=O)COc1cccc(-c2nc(Nc3cn[nH]c3)c3cc(S(C)(=O)=O)ccc3n2)c1]

To a mixture of 2-(3-(4-((1H-pyrazol-4-yl)amino)-6-(methylthio)quinazolin-2-yl)phenoxy)-N-(tert-butyl)acetamide (200 mg, 396.77 μmol, HCl salt) in dioxane (6 mL) was added Oxone® (526.3 mg, 856.10 μmol) in H₂O (5 mL). The mixture was stirred at 20° C. for 30 min. To the mixture was added saturated NaHCO₃ to adjust to pH=8. The mixture (combine with EW14729-71) was extracted with EtOAc (30 mL×3). The combined organic layers were washed with brine (20 mL×2), dried over Na₂SO₄, filtered and concentrated under reduced pressure to give a residue. The residue was purified by prep-HPLC (HCl conditions) to afford provide the title compound (110.8 mg, 52%, HCl salt) as a yellow solid. ¹H NMR (400 MHz, DMSO-$d_6$) δ 11.49 (brs, 1H), 9.32 (s, 1H), 8.38 (d, J=8.4 Hz, 1H), 8.21-8.19 (m, 3H), 8.07-8.03 (m, 2H), 7.63 (s, 1H), 7.58 (t, J=8.0 Hz, 1H), 7.24 (dd, J=8.8, 1.6 Hz, 1H), 4.58 (s, 2H), 3.38 (s, 3H), 1.30 (s, 9H). MS (ES+) m/e 495.3 (M+H)⁺.

Example 252

2-(3-(4-((1H-Pyrazol-4-yl)amino)-6-(methylsulfonyl)quinazolin-2-yl)phenoxy)-N-isopropylacetamide

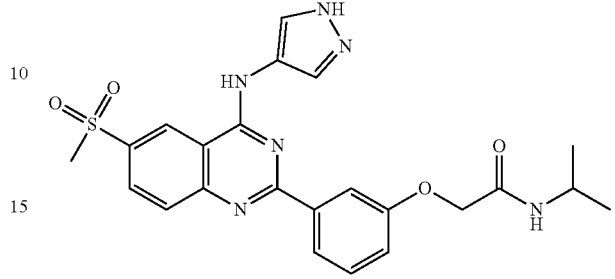

To a mixture of 2-(3-(4-((1H-pyrazol-4-yl)amino)-6-(methylthio)-quinazolin-2-yl)phenoxy)-N-isopropylacetamide (155 mg, 316.39 μmol, HCl) in dioxane (5 mL) was added Oxone (420.63 mg, 684.21 μmol) in H₂O (4 mL). The mixture was stirred at 20° C. for 30 min. To the mixture was added saturated NaHCO₃ to adjust to pH=8. The mixture was extracted with EtOAc (30 mL×3). The combined organic layers were washed with brine (20 mL×2), dried over Na₂SO₄, filtered and concentrated under reduced pressure to give a residue. The residue was purified by prep-HPLC (HCl conditions) to provide the title compound (93.2 mg, 56%, HCl salt) as a yellow solid. ¹H NMR (400 MHz, DMSO-$d_6$) δ 11.60 (brs, 1H), 9.33 (s, 1H), 8.38 (d, J=8.4 Hz, 1H), 8.21-8.19 (m, 3H), 8.07-8.01 (m, 3H), 7.58 (t, J=8.0 Hz, 1H), 7.26 (d, J=8.4, 1.6 Hz, 1H), 4.61 (s, 2H), 4.01-3.95 (m, 1H), 3.38 (s, 3H), 1.10 (d, J=6.8, 6H). MS (ES+) m/e 481.3 (M+H)⁺.

Example 253

2-(3-(4-((1H-Pyrazol-4-yl)amino)-6-ethoxy-5-methylquinazolin-2-yl)phenoxy)-N-(tert-butyl)acetamide

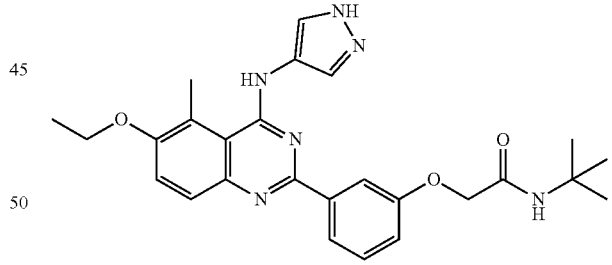

Step 1

Ethyl 6-bromo-3-ethoxy-2-methylbenzoate

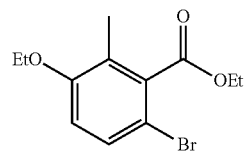 [SMILES: CCOC(=O)c1c(Br)ccc(OCC)c1C]

To a solution of ethyl 3-ethoxy-2-methylbenzoate (10 g, 48.02 mmol) in HOAc (50 mL) was added Br$_2$ (15.35 g, 96.04 mmol, 4.95 mL) at 25° C. The resulting mixture was stirred at 25° C. for 12 hrs, poured into H$_2$O (150 mL) and the aqueous layer was extracted with EtOAc (60 mL×3). The combined organic phases were washed with sat. Na$_2$HCO$_3$ (60 mL×2) and brine (60 mL), dried over anhydrous Na$_2$SO$_4$, filtered and concentrated under reduced pressure. The residue was purified by column chromatography (SiO$_2$, Petroleum ether/Ethyl acetate=1/0 to 50/1) to provide the title compound (13.0 g, 94%) as light yellow oil. $^1$H NMR (400 MHz, CDCl$_3$) δ 7.21 (d, J=8.8 Hz, 1H), 6.61 (d, J=8.8 Hz, 1H), 4.33 (q, J=7.2 Hz, 2H), 3.89 (q, J=6.8 Hz, 2H), 2.09 (s, 3H), 1.31 (t, J=7.2 Hz, 6H).

Step 2

Ethyl 6-((tert-butoxycarbonyl)amino)-3-ethoxy-2-methylbenzoate

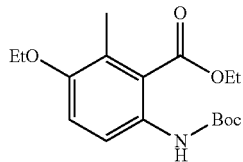 [SMILES: CCOC(=O)c1c(NC(=O)OC(C)(C)C)ccc(OCC)c1C]

To a solution of ethyl 6-bromo-3-ethoxy-2-methylbenzoate (5.0 g, 17.41 mmol) in dioxane (50 mL) was added Pd(OAc)$_2$ (390.93 mg, 1.74 mmol), Xantphos (1.01 g, 1.74 mmol), Cs$_2$CO$_3$ (11.35 g, 34.83 mmol) and NH$_2$Boc (3.06 g, 26.12 mmol) at 25° C. The resulting reaction mixture was heated to 100° C. and stirred for 15 h under nitrogen atmosphere. The solvent was removed under reduced pressure. The residue was suspended in H$_2$O (80 mL) and extracted with EtOAc (40 mL×3). The combined organic phases were washed with brine (50 mL), dried over anhydrous Na$_2$SO$_4$, filtered and concentrated under reduced pressure. The residue was purified by column chromatography (SiO$_2$, Petroleum ether:Ethyl acetate=1/0, monitored by TLC (Petroleum ether:Ethyl acetate=20:1, R$_f$=0.35) to provide the title compound (4.6 g, 812%) as a colourless oil.

Step 3

Ethyl 6-amino-3-ethoxy-2-methylbenzoate

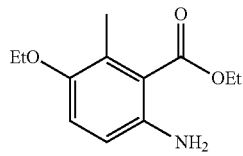

To a solution of ethyl 6-((tert-butoxycarbonyl)amino)-3-ethoxy-2-methylbenzoate (3.5 g, 10.82 mmol) in CH$_2$Cl$_2$ (30 mL) was added HCl/EtOAc (4 M, 30 mL). The reaction was stirred at 20° C. for 2 h. The solid was collected and was suspended in sat. NaHCO$_3$(50 mL) and extracted with EtOAc (30 mL×3). The organic layer was dried over Na$_2$SO$_4$, filtered and concentrated to provide the title compound (1.4 g, 58%) as a light yellow oil.

Step 4

6-Ethoxy-5-methylquinazoline-2,4-diol

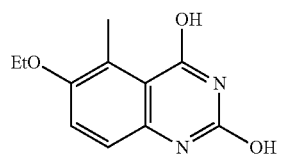 [SMILES: CCOc1ccc2nc(O)nc(O)c2c1C]

A mixture of ethyl 6-amino-3-ethoxy-2-methylbenzoate (0.9 g, 4.03 mmol) and urea (4.84 g, 80.62 mmol) was stirred at 180° C. for 4 h, cooled to room temperature, suspended with H$_2$O (150 mL) and the resulting mixture was stirred at room temperature for 16 h. The mixture was filtered and solid was collected, dried over with toluene to provide the title compound (1.2 g, crude) as a white solid. $^1$H NMR (400 MHz, DMSO-d$_6$) δ 11.20-10.70 (m, 2H), 7.32 (d, J=8.8 Hz, 1H), 6.99 (d, J=8.8 Hz, 1H), 6.99 (d, J=9.2, 1.6 Hz, 2H), 2.66 (s, 3H), 1.33 (t, J=6.4 Hz, 3H).

Step 5

2,4-Dichloro-6-ethoxy-5-methylquinazoline

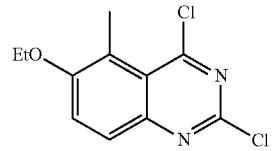 [SMILES: CCOc1ccc2nc(Cl)nc(Cl)c2c1C]

To the POCl$_3$ (10 mL) was added 6-ethoxy-5-methylquinazoline-2,4-diol (1.2 g), DIPEA (1.41 g, 10.91 mmol, 1.9 mL). The mixture was stirred at 100° C. for 16 h, cooled to room temperature and concentrated under reduced pressure to give a residue. The residue was added to ice water (100 mL), carefully neutralized with NaHCO$_3$ to pH=8. Then the resulting mixture was extracted with EtOAc (100 mL×3). The combined organic layers were washed by brine (100 mL×2), dried over Na$_2$SO$_4$, concentrated under reduced pressure to give a residue. The residue was purified by column chromatography (SiO$_2$, Petroleum ether:Ethyl acetate=10:1 to 5:1) to provide the title compound (400 mg) as a white solid. $^1$H NMR (400 MHz, DMSO-d$_6$) δ 7.62-7.45 (m, 1H), 7.45-7.25 (m, 1H), 4.28-4.13 (m, 2H), 2.66 (s, 3H), 1.37 (t, J=7.2 Hz, 3H).

Step 6

2-Chloro-6-ethoxy-5-methyl-N-(1-(tetrahydro-2H-pyran-2-yl)-1H-pyrazol-4-yl)-quinazolin-4-amine

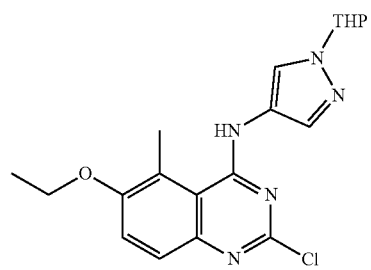

To a solution of 2,4-dichloro-6-ethoxy-5-methylquinazoline (400 mg, 1.56 mmol) in DMF (4 mL) was added DIPEA (402.13 mg, 3.11 mmol, 541.96 μL) and 1-tetrahydropyran-2-ylpyrazol-4-amine (260.13 mg). The mixture was stirred at 60° C. for 16 h, diluted with water (50 mL) and extracted with Ethyl acetate (40 mL×2). The combined organic layers were dried over $Na_2SO_4$, filtered and concentrated under reduced pressure to give a residue. The residue was purified by column chromatography ($SiO_2$, Petroleum ether:Ethyl acetate=1:0 to 0:1; TLC:Petroleum ether:Ethyl acetate=1:1, $R_f$=0.3) to provide the title compound (280 mg, 46%) as a yellow solid.

Step 7

N-(tert-Butyl)-2-(3-(6-ethoxy-5-methyl-4-((1-(tetrahydro-2H-pyran-2-yl)-1H-pyrazol-4-yl)amino)quinazolin-2-yl)phenoxy)acetamide

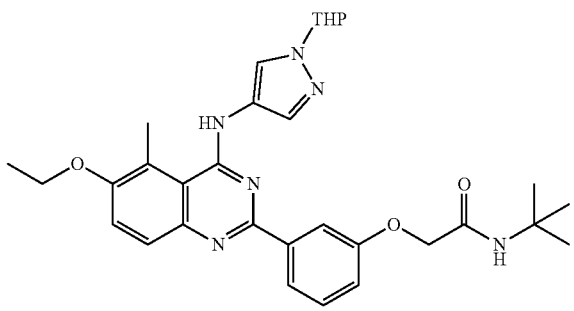

To a solution of 2-chloro-6-ethoxy-5-methyl-N-(1-(tetrahydro-2H-pyran-2-yl)-1H-pyrazol-4-yl)quinazolin-4-amine (280 mg, 721.91 μmol) in dioxane (3 mL) and $H_2O$ (0.3 mL) was added $K_2CO_3$ (199.54 mg, 1.44 mmol), N-tert-butyl-2-[3-(4,4,5,5-tetramethyl-1,3,2-dioxaborolan-2-yl)phenoxy]acetamide (288.67 mg, 866.29 μmol) and Pd(dppf)$Cl_2$ (52.82 mg, 72.19 μmol). The mixture was stirred at 100° C. for 16 h under $N_2$. The mixture was diluted with water (50 mL) and extracted with Ethyl acetate (40 mL×2). The combined organic layers were dried over $Na_2SO_4$ and concentrated under reduced pressure to give a residue. The residue was purified by column chromatography ($SiO_2$, Petroleum ether:ethylacetate=1:0 to 0:1) to provide the title compound (330 mg, 82%) as a yellow solid. $^1$H NMR (400 MHz, DMSO-$d_6$) δ 8.81 (s, 1H), 8.41 (s, 2H), 8.03-7.92 (m, 2H), 7.90 (s, 1H), 7.73-7.62 (m, 2H), 7.55-7.51 (s, 1H), 7.44 (t, J=8.0 Hz, 1H), 7.06 (dd, J=8.4, 2.4 Hz, 1H), 5.48 (dd, J=6.4, 2.4 Hz, 1H), 4.5 (s, 2H), 4.25-4.15 (m, 2H), 3.99-3.89 (m, 1H), 3.74-3.63 (m, 1H), 2.82-2.72 (m, 3H), 2.18-2.05 (m, 1H), 4.25-4.15 (m, 2H), 2.03-2.00 (m, 1H), 1.98-1.93 (m, 1H), 1.77-1.65 (m, 1H), 1.61-1.52 (m, 2H), 1.40 (t, J=6.8 Hz, 3H), 1.34-1.25 (m, 2H).

Step 8

2-(3-(4-((1H-Pyrazol-4-yl)amino)-6-ethoxy-5-methylquinazolin-2-yl)phenoxy)-N-(tert-butyl)acetamide

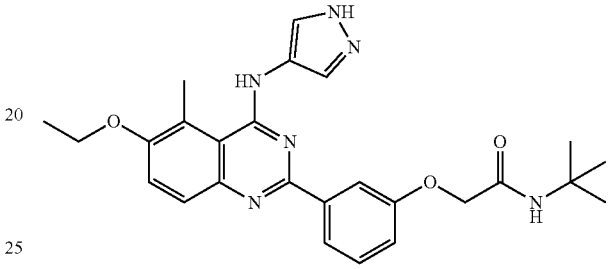

To a solution of N-(tert-butyl)-2-(3-(6-ethoxy-5-methyl-4-((1-(tetrahydro-2H-pyran-2-yl)-1H-pyrazol-4-yl)amino)quinazolin-2-yl)phenoxy)acetamide (330 mg, 590.69 μmol) in $CH_2Cl_2$ (4 mL) was added HCl/dioxane (4 M, 4 mL). The mixture was stirred at 40° C. for 2 h. The solid formed was collected and purified by prep-HPLC (HCl conditions) to provide the title compound (132.1 mg, 43%, HCl) as a yellow solid. $^1$H NMR (400 MHz, DMSO-$d_6$) δ 14.51 (s, 1H), 10.53 (s, 1H), 8.22-8.14 (m, 3H), 8.00-7.93 (m, 2H), 7.84 (d, J=9.6 Hz, 1H), 7.70 (s, 1H), 7.62 (t, J=8.4 Hz, 1H), 7.30 (dd, J=8.0, 2.0 Hz, 1H), 4.62 (s, 2H), 4.29-4.19 (m, 2H), 2.78 (s, 3H), 1.42 (t, J=7.2 Hz, 3H), 1.29 (s, 9H). MS (ES+) m/e 461.3 (M+H)$^+$.

Example 254

2-(3-(4-((1H-Pyrazol-3-yl)amino)-6-(2,2,2-trifluoroethoxy)quinazolin-2-yl)-phenoxy)-N-(tert-butyl)acetamide

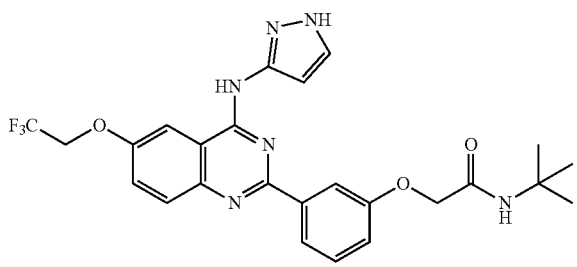 [SMILES: CC(C)(C)NC(=O)COc1cccc(-c2nc(Nc3cc[nH]n3)c3cc(OCC(F)(F)F)ccc3n2)c1]

The title compound was synthesized following the synthetic sequence and the procedures described for Example 222. $^1$H NMR (400 MHz, Methanol-$d_4$) δ 8.26 (d, J=2.4 Hz, 1H), 8.06 (d, J=8.8 Hz, 1H), 7.98-7.91 (m, 2H), 7.87-7.80 (m, 2H), 7.62 (t, J=8.0 Hz, 1H), 7.39-7.33 (m, 1H), 7.00 (d, J=2.4 Hz, 1H), 4.58 (s, 2H), 1.39 (s, 9H). MS (ES+) m/e 515.2 (M+H)$^+$.

Example 255

N-(tert-Butyl)-2-(3-(4-((1-methyl-1H-pyrazol-4-yl)amino)-pyrido[4,3-d]pyrimidin-2-yl)phenoxy)acetamide

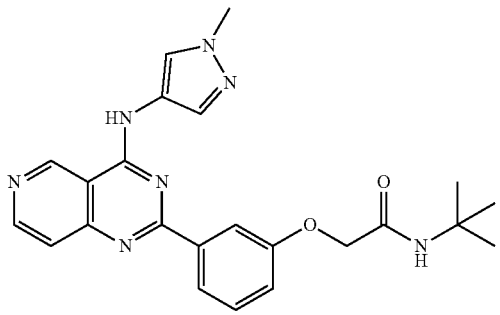 [SMILES: Cn1cc(Nc2nc(-c3cccc(OCC(=O)NC(C)(C)C)c3)nc3ccncc23)cn1]

Step 1

4-Chloro-2-(3-methoxyphenyl)pyrido[4,3-d]pyrimidine

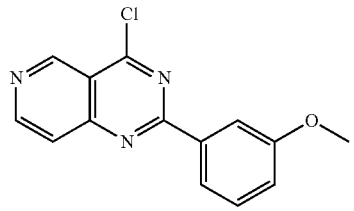 [SMILES: COc1cccc(-c2nc(Cl)c3cnccc3n2)c1]

To a mixture of 2-(3-methoxyphenyl)pyrido[4,3-d]pyrimidin-4(3H)-one (5 g, 19.74 mmol) in POCl$_3$ (50 mL) was added DIPEA (5.10 g, 39.49 mmol). The mixture was heated to 90° C. and stirred at 90° C. for 16 hr. The mixture was cooled to room temperature and concentrated under vacuum to give a residue. To the ice saturated NaHCO$_3$ (300 mL) was slowly added the residue to adjust to pH=8. The mixture was extracted with EtOAc (500 mL×3). The combined organic layers were washed with brine (300 mL×2), dried over Na$_2$SO$_4$, filtered and concentrated under reduced pressure to provide the title compound (5.06 g, crude) as a brown solid.

Step 2

2-(3-Methoxyphenyl)-N-(1-methyl-1H-pyrazol-4-yl)pyrido[4,3-d]pyrimidin-4-amine

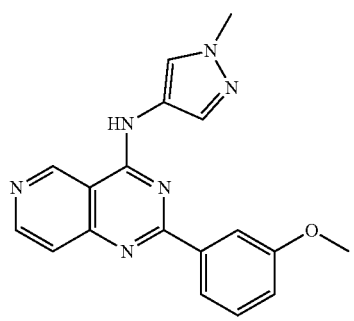 [SMILES: COc1cccc(-c2nc(Nc3cnn(C)c3)c3cnccc3n2)c1]

To a mixture of 4-chloro-2-(3-methoxyphenyl)pyrido[4,3-d]pyrimidine (2 g, crude), 1-methyl-1H-pyrazol-4-amine (1.08 g, 8.10 mmol, HCl salt) in DMF (20 mL) was added DIPEA (2.85 g, 22.08 mmol). The mixture was heated to 70° C. and stirred at 70° C. for 14 hr, cooled to room temperature and diluted with H$_2$O (150 mL) and extracted with EtOAc (80 mL×3). The combined organic layers were washed with brine (150 mL×2), dried over Na$_2$SO$_4$, filtered and concentrated under reduced pressure to give a residue. The residue was purified by column chromatography (SiO$_2$, EtOAc/MeOH=10/1, R$_f$=0.3) to provide the title compound (1.47 g, 58%) as a brown solid.

Step 3

3-(4-((1-Methyl-1H-pyrazol-4-yl)amino)pyrido[4,3-d]pyrimidin-2-yl)phenol

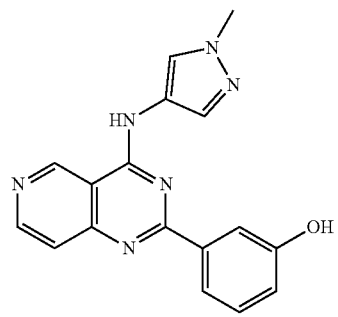 [SMILES: Cn1cc(Nc2nc(-c3cccc(O)c3)nc3ccncc23)cn1]

A mixture of 2-(3-methoxyphenyl)-N-(1-methyl-1H-pyrazol-4-yl)-pyrido[4,3-d]pyrimidin-4-amine (1.37 g, 4.00 mmol) was dissolved in DCM (10 mL) at 0° C. To the mixture was added BBr$_3$ (3.01 g, 12.00 mmol) in DCM (5 mL). The mixture was stirred at 20° C. for 4 hr followed by 30° C. for 3 hr, added slowly to ice-water. To the mixture was added NaOH (1 M) to pH=13. The resulting mixture was extracted with DCM (100 mL×2). The aqueous phase was acidified with HCl (1 N) to adjust to pH=9 and was extracted with EtOAc (100 mL×5). The combined organic layers were washed with brine (100 mL×2), dried over Na$_2$SO$_4$, filtered and concentrated under vacuum to give a residue. The residue was purified by prep-HPLC (neutral conditions) to provide the title compound (180 mg, 14%) as a brown solid. $^1$H NMR (400 MHz, DMSO-d$_6$) δ 10.53 (s, 1H), 9.73 (s, 1H), 9.66 (s, 1H), 8.75 (d, J=5.6 Hz, 1H), 8.21 (s, 1H), 7.94-7.93 (m, 3H), 7.64 (d, J=5.6 Hz, 1H), 7.36 (t, J=8.0 Hz, 1H), 6.95 (dd, J=8.0, 1.2 Hz, 1H), 3.94 (s, 3H).

Step 4

N-(tert-Butyl)-2-(3-(4-((1-methyl-1H-pyrazol-4-yl)amino)-pyrido[4,3-d]pyrimidin-2-yl)phenoxy)acetamide

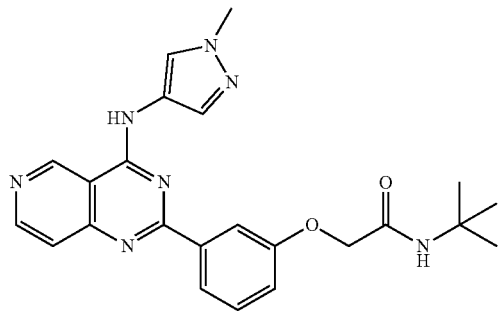 [SMILES: Cn1cc(Nc2nc(-c3cccc(OCC(=O)NC(C)(C)C)c3)nc3ccncc23)cn1]

To a mixture of 3-(4-((1-methyl-1H-pyrazol-4-yl)amino)pyrido[4,3-d]pyrimidin-2-yl)phenol (180 mg, 565.45 μmol) in THF (3 mL) was added NaH (27.14 mg, 678.54 μmol, 60% purity) at 20° C. The mixture was stirred at 20° C. for 30 min. A solution of 2-bromo-N-(tert-butyl)acetamide (120.71 mg, 621.99 μmol) in THF (1 mL) was added to the mixture slowly at 0° C. The mixture was stirred at 0° C. for 15 min, then stirred at 20° C. for 5 h, quenched with MeOH and concentrated under vacuum to give a residue. The residue was purified by prep-HPLC (HCl conditions) to provide the title compound (76.8 mg, 28%, HCl salts) as a yellow solid. $^1$H NMR (400 MHz, DMSO-d$_6$) δ 12.00 (s, 1H), 10.36 (s, 1H), 8.86 (d, J=6.4 Hz, 1H), 8.35 (s, 1H), 8.13 (d, J=7.6 Hz, 1H), 8.07 (d, J=2.0 Hz, 1H), 8.03 (d, J=6.4 Hz, 1H), 8.01 (s, 1H), 7.60-7.54 (m, 2H), 7.26 (dd, J=8.0, 2.4 Hz, 1H), 4.57 (s, 2H), 3.96 (s, 3H), 1.31 (s, 9H). MS (ES+) m/e 432.3 (M+H)$^+$.

Example 256

2-(3-(4-((1H-Pyrazol-4-yl)amino)pyrido[4,3-d]pyrimidin-2-yl)phenoxy)-N-(tert-butyl)acetamide

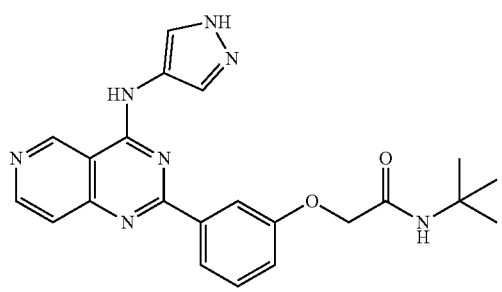 [SMILES: CC(C)(C)NC(=O)COc1cccc(-c2nc(Nc3cn[nH]c3)c3cnccc3n2)c1]

Step 1

2-(3-Methoxyphenyl)-N-(1-(tetrahydro-2H-pyran-2-yl)-1H-pyrazol-4-yl)-pyrido[4,3-d]pyrimidin-4-amine

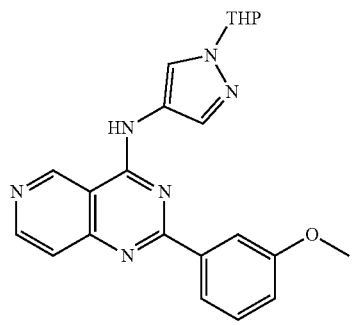

To a mixtures of 4-chloro-2-(3-methoxyphenyl)pyrido[4,3-d]pyrimidine (2 g, crude), 1-(tetrahydro-2H-pyran-2-yl)-1H-pyrazol-4-amine (1.35 g, crude) in DMF (20 mL) was added DIPEA (1.90 g, 14.72 mmol). The mixture was heated to 70° C. and stirred at 70° C. for 14 hr, cooled to room temperature, diluted with H$_2$O (150 mL) and extracted with EtOAc (80 mL×3). The combined organic layers were washed with brine (150 mL×2), dried over Na$_2$SO$_4$, filtered and concentrated under reduced pressure to give a residue. The residue was purified by column chromatography (SiO$_2$, Petroleum ether/Ethyl acetate=0/1, R$_f$=0.2) to provide the title compound (1.67 g) as a brown solid. $^1$H NMR (400 MHz, DMSO-d$_6$) δ 10.63 (s, 1H), 9.74 (s, 1H), 8.77 (d, J=2.0 Hz, 1H), 8.47 (s, 1H), 8.08 (d, J=7.6 Hz, 1H), 8.03 (dd, J=6.4, 2.0 Hz, 1H), 7.93 (s, 1H), 7.69 (d, J=5.6 Hz, 1H), 7.48 (t, J=8.0 Hz, 1H), 7.16-7.13 (m, 1H), 5.49 (dd, J=5.6, 2.4 Hz, 1H), 3.97-3.95 (m, 1H), 3.90 (s, 3H), 3.71-3.65 (m, 1H), 2.17-2.10 (m, 1H), 2.03-1.96 (m, 2H), 1.74-1.69 (m, 1H), 1.60-1.57 (m, 2H).

Step 2

3-(4-((1-(Tetrahydro-2H-pyran-2-yl)-1H-pyrazol-4-yl)amino)-pyrido[4,3-d]pyrimidin-2-yl)phenol

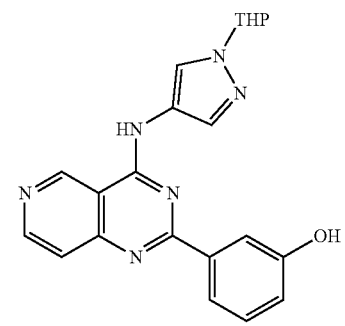

To a mixture of 2-(3-methoxyphenyl)-N-(1-(tetrahydro-2H-pyran-2-yl)-1H-pyrazol-4-yl)pyrido[4,3-d]pyrimidin-4-amine (1.37 g, 3.23 mmol) in DMF (14 mL) was added NaSEt (2.72 g, 32.34 mmol). The mixture was heated to 140° C. and stirred at 140° C. for 14 hr, cooled to room temperature and concentrated under vacuum to give a residue. The residue was diluted with H₂O (50 mL), MeOH (5 mL) and extracted with EtOAc (50 mL×5). The combined organic layers were washed with brine (100 mL×2), dried over Na₂SO₄, filtered and concentrated under reduced pressure to give a residue. The residue was purified by prep-HPLC (neutral conditions) to provide the title compound (800 mg, 63%) as a brown solid. $^1$H NMR (400 MHz, DMSO-d₆) δ 10.59 (s, 1H), 9.73 (s, 1H), 9.66 (s, 1H), 8.76 (d, J=6.0 Hz, 1H), 8.40 (s, 1H), 8.01 (s, 1H), 7.93-7.91 (m, 2H), 7.66 (d, J=5.6 Hz, 1H), 7.36 (t, J=8.0 Hz, 1H), 6.98-6.95 (m, 1H), 5.50 (dd, J=9.6, 2.4 Hz, 1H), 3.97-3.95 (m, 1H), 3.73-3.66 (m, 1H), 2.17-2.11 (m, 1H), 2.03-1.96 (m, 2H), 1.75-1.70 (m, 1H), 1.60-1.57 (m, 2H).

Step 3

N-(tert-Butyl)-2-(3-(4-((1-(tetrahydro-2H-pyran-2-yl)-1H-pyrazol-4-yl)amino)-pyrido[4,3-d]pyrimidin-2-yl)phenoxy)acetamide

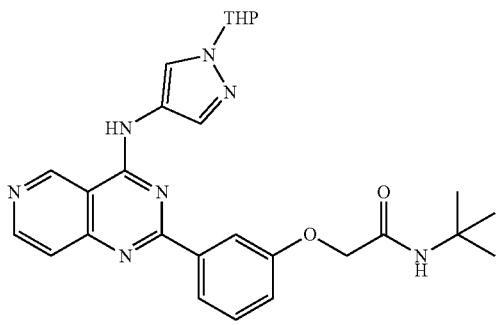

To a mixture of 3-(4-((1-(tetrahydro-2H-pyran-2-yl)-1H-pyrazol-4-yl)amino)-pyrido[4,3-d]pyrimidin-2-yl)phenol (200 mg, 514.90 μmol) in THF (3 mL) was added NaH (26.77 mg, 669.38 μmol, 60% purity) at 20° C. The mixture was stirred at 20° C. for 30 min. A solution of 2-bromo-N-(tert-butyl)acetamide (109.92 mg, 566.39 μmol) in THF (1 mL) was added to the mixture slowly at 0° C. The mixture was stirred at 0° C. for 15 min followed by at 20° C. for 4 h. The mixture was quenched with MeOH and concentrated under vacuum to give a residue. The residue was recrystallized with petroleum ether (10 mL), ethyl acetate (3 mL) to provide the title compound (208 mg, 74%) as a brown solid. $^1$H NMR (400 MHz, DMSO-d₆) δ 10.68 (s, 1H), 9.74 (s, 1H), 8.76 (d, J=6.0 Hz, 1H), 8.47 (s, 1H), 8.08 (d, J=7.6 Hz, 1H), 8.03 (s, 1H), 7.93 (s, 1H), 7.64 (d, J=6.0 Hz, 1H), 7.55 (s, 1H), 7.48 (t, J=8.0 Hz, 1H), 7.14 (dd, J=8.0, 2.4 Hz, 1H), 5.51 (dd, J=9.6, 2.0 Hz, 1H), 4.53 (s, 2H), 3.97-3.95 (m, 1H), 3.73-3.67 (m, 1H), 2.16-2.09 (m, 1H), 2.03-1.97 (m, 2H), 1.74-1.70 (m, 1H), 1.60-1.56 (m, 2H), 1.30 (s, 9H).

Step 4

2-(3-(4-((1H-Pyrazol-4-yl)amino)pyrido[4,3-d]pyrimidin-2-yl)phenoxy)-N-(tert-butyl)acetamide

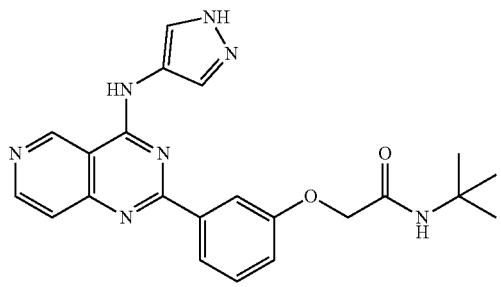 [SMILES: CC(C)(C)NC(=O)COc1cccc(-c2nc(Nc3cn[nH]c3)c3cnccc3n2)c1]

To a mixture of N-(tert-butyl)-2-(3-(4-((1-(tetrahydro-2H-pyran-2-yl)-1H-pyrazol-4-yl)amino)pyrido[4,3-d]pyrimidin-2-yl)phenoxy)acetamide (360 mg, 717.73 μmol) in DCM (5 mL) was added HCl/dioxane (4 N, 5 mL). The mixture was heated to 40° C. and stirred for 2 hr. The solid formed was collected and was purified by prep-HPLC (HCl conditions) to provide the title compound (239 mg, 72%, HCl salt) as a yellow solid. $^1$H NMR (400 MHz, DMSO-d₆) δ 11.85 (s, 1H), 10.26 (s, 1H), 8.86 (d, J=6.4 Hz, 1H), 8.23 (s, 2H), 8.10 (d, J=7.6 Hz, 1H), 8.04 (s, 1H), 8.00 (d, J=6.4 Hz, 1H), 7.65 (s, 1H), 7.56 (t, J=8.0 Hz, 1H), 7.23 (dd, J=8.0, 2.4 Hz, 1H), 4.57 (s, 2H), 1.30 (s, 9H). MS (ES+) m/e 418.3 (M+H)⁺.

Example 257

2-(3-(4-((1H-Pyrazol-3-yl)amino)-5-ethoxyquinazolin-2-yl)phenoxy)-N-(tert-butyl)acetamide

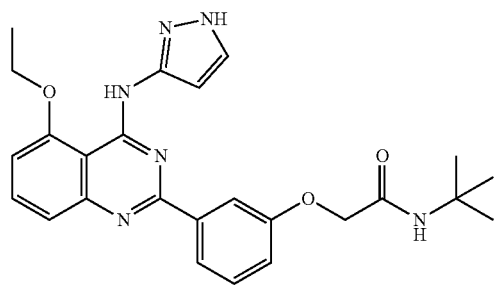 [SMILES: CCOc1cccc2nc(-c3cccc(OCC(=O)NC(C)(C)C)c3)nc(Nc3cc[nH]n3)c12]

Step 1

Ethyl 2-fluoro-6-nitrobenzoate

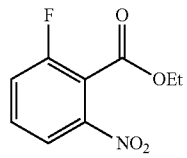

To a mixture of 2-fluoro-6-nitrobenzoic acid (20 g, 108.04 mmol), $K_2CO_3$ (29.86 g, 216.09 mmol) in DMF (200 mL) was added EtI (33.70 g, 216.09 mmol, 17.28 mL). The mixture was stirred at 80° C. for 16 h, cooled to room temperature, quenched by $H_2O$ (500 mL) and extracted with EtOAc (500 mL×2). The combined organic layers were washed by brine (400 mL), dried over $Na_2SO_4$, concentrated under reduced pressure to give a residue. The residue was purified by column chromatography ($SiO_2$, Petroleum ether/Ethyl acetate=10/1) to provide the title compound (35 g) as a yellow oil. $^1$H NMR (400 MHz, DMSO-$d_6$) δ 8.14-8.06 (m, 1H), 7.91-7.81 (m, 2H), 4.40 (q, J=7.2 Hz, 2H), 1.30 (t, J=7.2 Hz, 3H).

Step 2

Ethyl 2-ethoxy-6-nitrobenzoate

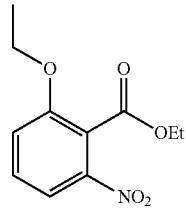

To a mixture of ethyl 2-fluoro-6-nitrobenzoate (35 g, 164.19 mmol) in THF (300 mL) was added NaOEt (22.35 g, 328.39 mmol) by portions at 0° C. The mixture was stirred at 25° C. for 2 h, quenched by $H_2O$ (500 mL) and extracted with EtOAc (500 mL×3). The combined organic layers were washed by brine (500 mL×2), dried over $Na_2SO_4$, concentrated under reduced pressure to give a residue. The residue was purified by column chromatography ($SiO_2$, Petroleum ether/Ethyl acetate=10/1 to 0:1) to provide the title compound (7.3 g, 19%) as a yellow oil.

Step 3

2-Ethoxy-6-nitrobenzoic Acid

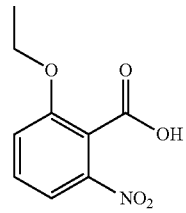

To a mixture of ethyl 2-ethoxy-6-nitrobenzoate (7.3 g, 30.52 mmol) in MeOH (70 mL), $H_2O$ (8 mL) was added NaOH (2.44 g, 61.03 mmol). The mixture was stirred at 25° C. for 18 h, quenched by $H_2O$ (500 mL) and extracted with EtOAc (200 mL×2). The aqueous layer was adjusted with HCl (1 N) to pH=6. The resulting mixture was extracted with EtOAc (200 mL×2). The combined organic layers were washed by brine (100 mL), dried over $Na_2SO_4$, concentrated under reduced pressure to provide the title compound (5 g, 78%) as a yellow solid. $^1$H NMR (400 MHz, DMSO-$d_6$) δ 7.73 (dd, J=8.0, 0.8 Hz, 1H), 7.63 (t, J=8.0 Hz, 1H), 7.57-7.52 (m, 1H), 4.18 (q, J=7.2 Hz, 2H), 1.32 (t, J=7.2 Hz, 3H).

Step 4

2-Ethoxy-6-nitrobenzamide

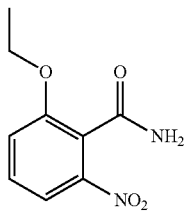

To a mixture of 2-ethoxy-6-nitrobenzoic acid (4 g, 18.94 mmol) in DCM (40 mL) was added drop-wise $(COCl)_2$ (4.81 g, 37.88 mmol, 3.32 mL) followed by DMF (40 μL) (4 drops) at 0° C. under $N_2$. The mixture was stirred at 25° C. for 1 h and concentrated under reduced pressure to give a residue. The residue was dissolved with THF (40 mL), DIPEA (4.90 g, 37.88 mmol, 6.60 mL) and $NH_3$·THF (50 mL, About 10 g $NH_3$ was bubbled to THF) were added at −30° C. The reaction mixture was then stirred at 25° C. for 16 h, diluted with $H_2O$ (50 mL) and EtOAc (50 mL). The solid formed was collected and dried with toluene (20 mL×3) to provide the title compound (2 g, 50%) as a gray solid. $^1$H NMR (400 MHz, DMSO-$d_6$) δ 7.88 (s, 1H), 7.63-7.53 (m, 3H), 7.47 (d, J=8.0 Hz, 1H), 4.14 (q, J=6.8 Hz, 2H), 1.37 (t, J=6.8 Hz, 3H).

Step 5

2-Amino-6-ethoxybenzamide

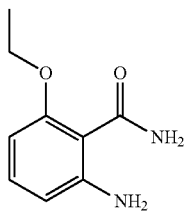

To a mixture of 2-ethoxy-6-nitrobenzamide (1 g, 4.76 mmol) in MeOH (10 mL) was added wet. Pd/C (100 mg, 10% purity). The mixture was stirred at 40° C. for 16 h under $H_2$ (15 psi) and was filtered through celite pad. The filtrate was concentrated under reduced pressure to provide the title compound (the total amount was 2.5 g, crude) as a gray solid. $^1$H NMR (400 MHz, DMSO-$d_6$) δ 7.53 (s, 1H), 7.29 (s, 1H), 7.00 (t, J=8.0 Hz, 1H), 6.37 (s, 2H), 6.30 (d, J=8.0 Hz, 1H), 6.17 (d, J=8.0 Hz, 1H), 4.02 (q, J=7.2 Hz, 2H), 1.34 (t, J=6.8 Hz, 3H).

Step 6

3-(2-(tert-Butylamino)-2-oxoethoxy)-N-(2-carbamoyl-3-ethoxyphenyl)-benzamide

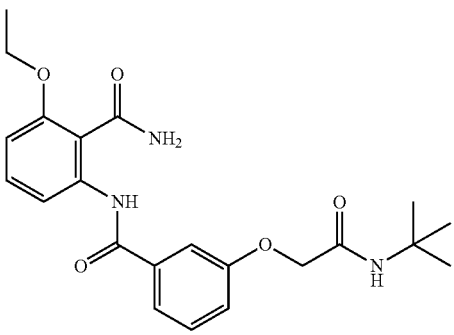 [SMILES: CCOc1cccc(NC(=O)c2cccc(OCC(=O)NC(C)(C)C)c2)c1C(N)=O]

To a mixture of 3-[2-(tert-butylamino)-2-oxo-ethoxy]benzoic acid (2 g, 7.96 mmol), 2-amino-6-ethoxybenzamide (1.29 g, crude), HATU (3.63 g, 9.55 mmol) in EtOAc (20 mL) was added DIPEA (2.06 g, 15.92 mmol, 2.77 mL). The mixture was stirred at 25° C. for 16 h, quenched by $H_2O$ (100 mL) and extracted with EtOAc (100 mL×3). The combined organic layers were washed with brine (100 mL), dried over $Na_2SO_4$, concentrated under reduced pressure to give a residue. The residue was purified by column chromatography ($SiO_2$, Petroleum ether/Ethyl acetate=50/1 to 0:1 to DCM/MeOH=10/1) to provide the title compound (3 g, 91%) as a white solid.

Step 7

N-(tert-Butyl)-2-(3-(5-ethoxy-4-hydroxyquinazolin-2-yl)phenoxy)acetamide

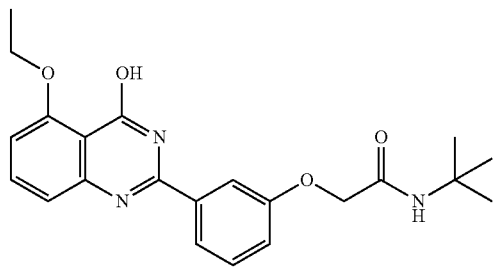 [SMILES: CCOc1cccc2nc(-c3cccc(OCC(=O)NC(C)(C)C)c3)nc(O)c12]

To a mixture of 3-(2-(tert-butylamino)-2-oxoethoxy)-N-(2-carbamoyl-3-ethoxyphenyl)benzamide (3 g, 7.26 mmol) in EtOH (20 mL), $H_2O$ (15 mL) was added $K_2CO_3$ (3.01 g, 21.77 mmol). The mixture was stirred at 80° C. for 16 h. The reaction mixture was cooled to room temperature, concentrated under reduced pressure to remove most of the solvent. The solid formed was collected and dried over toluene (40 mL×5) to provide the title compound (1.5 g, crude) as a white solid.

Step 8

N-(tert-Butyl)-2-(3-(5-ethoxy-4-((1-((2-(trimethylsilyl)ethoxy)methyl)-1H-pyrazol-3-yl)amino)quinazolin-2-yl)phenoxy)acetamide

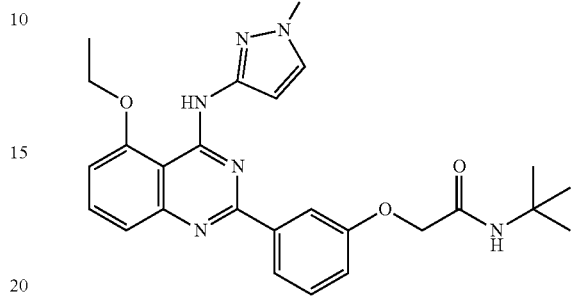

To a mixture of N-(tert-butyl)-2-(3-(5-ethoxy-4-hydroxyquinazolin-2-yl)-phenoxy)acetamide (200 mg, 505.75 µmop, BOP (335.53 mg, 758.63 µmol) in MeCN (4 mL) was added DIPEA (130.73 mg, 1.01 mmol, 176.19 µL). The mixture was stirred at 20° C. for 16 h. The mixture was concentrated under reduced pressure to give a residue. The residue was dissolved into NMP (4 mL), 1-(2-trimethylsilylethoxymethyl)pyrazol-3-amine (215.81 mg, crude) was added. The mixture was stirred at 80° C. for 16 h. The reaction mixture was cooled to room temperature, quenched by $H_2O$ (100 mL) and extracted with EtOAc (100 mL×3). The combined organic layers were washed by brine (100 mL), dried over $Na_2SO_4$, concentrated under reduced pressure to give a residue. The residue was purified by prep-TLC ($SiO_2$, Petroleum ether/Ethyl acetate=0/1) to provide the title compound (300 mg, 56%, 56% purity) as a yellow oil.

Step 9

2-(3-(4-((1H-Pyrazol-3-yl)amino)-5-ethoxyquinazolin-2-yl)phenoxy)-N-(tert-butyl)acetamide

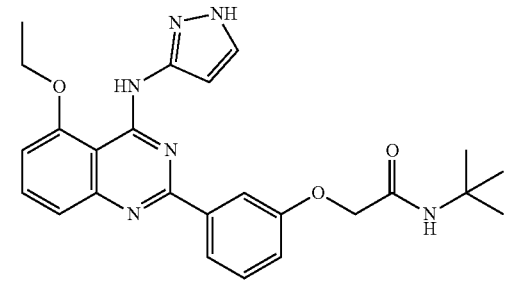 [SMILES: CCOc1cccc2nc(-c3cccc(OCC(=O)NC(C)(C)C)c3)nc(Nc3cc[nH]n3)c12]

To a mixture of N-(tert-butyl)-2-(3-(5-ethoxy-4-((1-((2-(trimethylsilyl)-ethoxy)methyl)-1H-pyrazol-3-yl)amino)quinazolin-2-yl)phenoxy)acetamide (380 mg, 405.22 µmol) in DCM (5 mL) was added HCl/dioxane (4 N, 5 mL). The mixture was stirred at 40° C. for 2 h, concentrated and purified by prep-HPLC (HCl conditions) to provide the title compound (58.3 mg, 28%, 98% purity, HCl salt) as a yellow solid. $^1$H NMR (400 MHz, DMSO-$d_6$) δ 13.03 (brs, 1H), 11.26 (s, 1H), 8.07-8.01 (m, 3H), 7.94 (d, J=2.4 Hz, 1H), 7.87 (d, J=7.6 Hz, 1H), 7.69 (s, 1H), 7.65 (t, J=8.0 Hz, 1H), 7.40 (d, J=8.0 Hz, 1H), 7.33 (d, J=7.2 Hz, 1H), 7.05 (d, J=2.4 Hz, 1H), 4.64 (s, 2H), 4.51 (q, J=6.8 Hz, 2H), 1.64 (t, J=6.8 Hz, 3H), 1.33 (s, 9H). MS (ES+) m/e 461.2 (M+H)$^+$.

Example 258

2-(3-(4-((1H-Pyrazol-4-yl)amino)-6-cyclopropoxy-quinazolin-2-yl)phenoxy)-N-isopropylacetamide

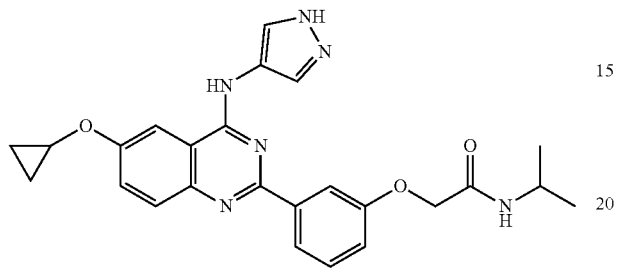

The title compound was synthesized following the synthetic sequence and the procedures described for Example 222. $^1$H NMR (400 MHz, DMSO-d$_6$) δ 11.89 (s, 1H), 8.55-8.53 (m, 1H), 8.27 (s, 2H), 8.23-8.19 (m, 1H), 8.07 (d, J=8.0 Hz, 1H), 7.97-7.96 (m, 2H), 7.79 (dd, J=9.2, 2.4 Hz, 1H), 7.65 (t, J=8.4 Hz, 1H), 7.34 (dd, J=8.4, 2.0 Hz, 1H), 4.65 (s, 2H), 4.18-4.15 (m, 1H), 4.01-3.93 (m, 2H), 1.10 (d, J=6.8 Hz, 6H), 1.01-0.96 (m, 2H), 0.80-0.76 (m, 2H). MS (ES+) m/e 459.2 (M+H)$^+$.

Example 259

Preparation of Intermediate INT-7

N-(tert-Butyl)-2-(3-carbamimidoylphenoxy)acetamide

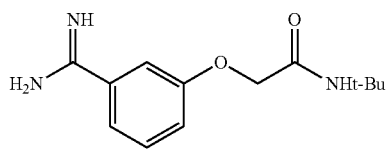

Step 1

N-(tert-Butyl)-2-(3-cyanophenoxy)acetamide

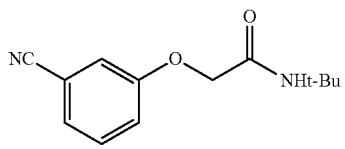

A stirred suspension of 3-cyanophenol (12.1 g, 102 mmol) and K$_2$CO$_3$ (26.8 g, 194 mmol) in anhydrous DMF (65 mL) was heated up to 70° C. for 5 minutes before N-(tert-butyl)-2-chloroacetamide (14.5 g, 96.9 mmol) was added. The reaction mixture was stirred at 70° C. for 5 hours after which, LCMS showed complete conversion to the desired product. The reaction mixture was cooled down to room temperature, diluted with sat. aq. Na$_2$CO$_3$ (150 mL) and extracted with MTBE (3×75 mL). The combined organic layers were washed with sat. aq. NaCl (100 mL), dried over Na$_2$SO$_4$, filtered and the solvents were evaporated under reduced pressure to afford N-(tert-butyl)-2-(3-cyanophenoxy)acetamide (22.2 g, 98%) as a white powder. The material was used in the next step without further purification.

Step 2

N-(tert-Butyl)-2-(3-(N-hydroxycarbamimidoyl)phenoxy)acetamide

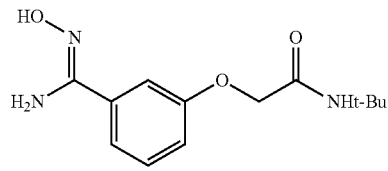

A 500 mL round-bottom flask equipped with a Teflon septum and magnetic stir bar was charged with N-(tert-butyl)-2-(3-cyanophenoxy)acetamide (22.0 g, 94.7 mmol) and absolute ethanol (118 mL). Diisopropylethylamine (26.4 mL, 152 mmol) and hydroxylamine hydrochloride (9.9 g, 142 mmol) were then added and the reaction mixture was stirred at 25° C. for 2 h. After 2 h, LC-MS showed that the starting material had almost completely disappeared, so the reaction time was extended to 3 h before volatiles were evaporated under reduced pressure. The crude residue was suspended in EtOAc (400 mL) and washed with water (100 mL) and sat. aq. NaCl (100 mL). The organic phase was dried over Na$_2$SO$_4$, filtered and evaporated under reduced pressure to give 24.8 g of N-(tert-butyl)-2-(3-(N'-hydroxycarbamimidoyl)phenoxy)acetamide as white needles. The material was used in the next step without further purification.

Step 3

N-(tert-Butyl)-2-(3-carbamimidoylphenoxy)acetamide

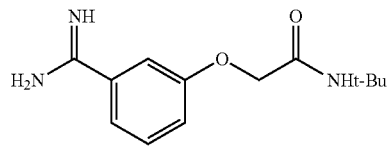

To a solution of N-(tert-butyl)-2-(3-(N'-hydroxycarbamimidoyl)phenoxy)-acetamide (6.2 g, 23.4 mmol) in acetic acid (95 mL) was added ammonium formate (10.5 g, 166 mmol). Under a nitrogen atmosphere, 10% Pd/C (825 mg) was added and the reaction mixture was stirred for 5 h at 120° C. After 5 h, LC-MS showed that the starting material had been consumed and that a large UV peak with the desired m/z had been formed. The reaction mixture was evaporated to minimum volume under reduced pressure and the crude residue was basified with 1N aq. NaOH (200 mL), followed by solid NaOH until pH>9. The aqueous layer was saturated with solid NaCl and then extracted with 30% iPrOH in EtOAc (3×150 mL). The combined organic layers were washed with water (2×150 mL) and sat. aq. NaCl (1×150 mL), dried over $Na_2SO_4$, filtered and the solvent was evaporated under reduced pressure. The crude residue was triturated with acetone to afford N-(tert-butyl)-2-(3-carbamimidoylphenoxy)-acetamide (4.22 g, 72%) as a white powder.

Example 260

2-(3-(4-((1H-Pyrazol-4-yl)amino)-5-ethoxy-6-methylquinazolin-2-yl)phenoxy)-N-(tert-butyl)acetamide

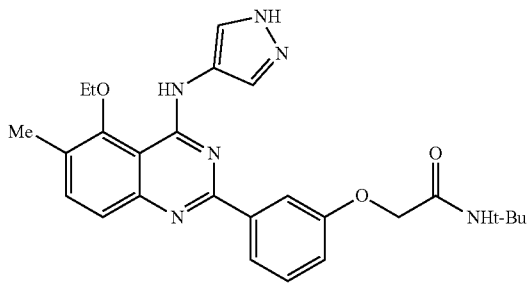

Step 1

Ethyl 2-ethoxy-3-methylbenzoate

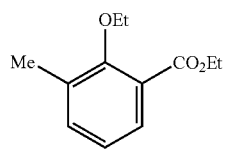 [SMILES: CCOC(=O)c1cccc(C)c1OCC]

To a solution of 3-methylsalicylic acid (10.0 g, 65.7 mmol) in MeOH (150 mL) was added concentrated sulfuric acid (8 mL) and the reaction mixture was refluxed for 16 h. The reaction mixture was cooled down to room temperature and volatiles were evaporated. The residue was diluted with water (100 mL) and extracted with EtOAc (3×100 mL). The combined organic layers were washed with sat. aq. NaCl (1×100 mL), dried over $Na_2SO_4$, filtered and the solvents were evaporated under reduced pressure. The crude residue was dissolved in DMSO (65.7 mL) and $K_2CO_3$ (18.2 g, 131 mmol) was added to the reaction mixture. After stirring for 5 minutes at 50° C. iodoethane (21.1 mL, 263 mmol) was added dropwise. The reaction mixture was stirred at 50° C. for 2 hours. TLC ($R_f$=0.54 @ 10% EtOAc in hexanes for starting material and $R_f$=0.79 @ 10% EtOAc in hexanes for product) showed that starting material was consumed completely. The reaction mixture was cooled to room temperature and quenched by addition of 1N aq. HCl (100 mL). The reaction mixture was extracted with MTBE (2×50 mL). The combined organic layers were washed with sat. aq. $Na_2CO_3$ (50 mL) and sat. aq. NaCl (50 mL), dried over $Na_2SO_4$, filtered through a short pad of silica and concentrated under reduced pressure to afford ethyl 2-ethoxy-3-methylbenzoate (12.1 g, 95%) as a yellow liquid. $^1H$ NMR (500 MHz, Chloroform-d) δ 7.62 (dd, J=7.7, 1.8 Hz, 1H), 7.32 (ddd, J=7.6, 1.9, 0.9 Hz, 1H), 7.03 (t, J=7.6 Hz, 1H), 4.37 (q, J=7.1 Hz, 2H), 3.96 (q, J=7.0 Hz, 2H), 2.31 (s, 3H), 1.41 (t, J=7.1 Hz, 3H), 1.39 (t, J=7.0 Hz, 4H).

Step 2

2-Ethoxy-3-methylbenzoic Acid

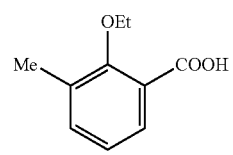

To a solution of methyl 2-ethoxy-3-methylbenzoate (12.1 g, 62.3 mmol) in MeOH (17 mL) and THF (69 mL) was added a solution of LiOH (2.98 g, 125 mmol) in $H_2O$ (69 mL). The reaction mixture was stirred at room temperature until complete hydrolysis. After 6 h, TLC showed that starting material ($R_f$=0.53 @ 10% EtOAc in hexanes) was consumed completely. Volatiles were evaporated under reduced pressure and the aqueous phase was washed with $Et_2O$ (1×50 mL) before being acidified to pH 2 with conc. aq. HCl in an ice bath and then extracted with $Et_2O$ (4×70 mL). The combined organic layers were washed with sat. aq. NaCl (1×100 mL), dried over $Na_2SO_4$, filtered and concentrated under reduced pressure. The crude residue was dissolved in hexane which was evaporated under reduced pressure to give 2-ethoxy-3-methylbenzoic acid (11.4 g, 100%) as a pale yellow waxy solid. MS (ES−) m/e 179 (M−H)⁻. $^1H$ NMR (500 MHz, Chloroform-d) δ 7.98 (dd, J=7.9, 1.7 Hz, 1H), 7.43 (ddd, J=7.5, 1.8, 0.9 Hz, 1H), 7.18 (t, J=7.7 Hz, 1H), 4.09 (q, J=7.1 Hz, 2H), 2.36 (s, 3H), 1.51 (t, J=7.1 Hz, 3H).

Step 3

2-Ethoxy-6-((ethoxycarbonyl)amino)-3-methylbenzoic Acid

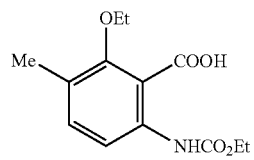

A 250 mL round-bottom flask equipped with a Teflon septum and magnetic stir bar was charged with 2-ethoxy-3-methylbenzoic acid (900 mg, 5.0 mmol), pentamethylcyclopentadienylrhodium(III) chloride dimer (123 mg, 200 μmol), silver acetate (1.25 g, 7.5 mmol) and t-BuOH (50.0 mL). The reaction mixture was then sparged with nitrogen for 20 min before ethyl chlorocarbamate (740 mg, 6.0 mmol) was quickly added. The reaction mixture was then stirred at 60° C. for 15 h. After 15 h, the reaction mixture was analyzed by LC-MS, which showed that starting material had been almost completely consumed and that a new large UV peak with the desired m/z had been formed. After cooling down to room temperature, the reaction mixture was poured in 50 mL of 2N aq. HCl and extracted with EtOAc (3×70 mL). The combined organic layers were dried over Na$_2$SO$_4$, filtered and the solvents were evaporated under reduced pressure. The crude residue was purified by flash column chromatography (15% to 80% EtOAc in hexane) to afford 2-ethoxy-6-((ethoxycarbonyl)-amino)-3-methylbenzoic acid (1.04 g, 80% purity, 67% corrected yield) as a yellow thick oil. MS (ES−) m/e 266 (M−H)$^−$. $^1$H NMR (500 MHz, DMSO-d$_6$) δ 13.07 (s, 1H), 8.95 (s, 1H), 7.24 (s, 2H), 4.06 (q, J=7.1 Hz, 2H), 3.88 (q, J=7.0 Hz, 2H), 2.19 (s, 2H), 1.27 (t, J=7.0 Hz, 2H), 1.20 (t, J=7.1 Hz, 2H).

Step 4

5-Ethoxy-6-methyl-2H-benzo[d][1,3]oxazine-2,4 (1H)-dione

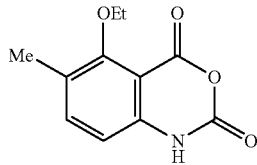 [SMILES: CCOc1c(C)ccc2[nH]c(=O)oc(=O)c12]

A 40 mL vial equipped with a Teflon septum and magnetic stir bar was charged with 2-ethoxy-6-((ethoxycarbonyl) amino)-3-methylbenzoic acid (1.0 g, 3.74 mmol, 90% purity) and anhydrous dioxane (11.3 mL). The reaction mixture was stirred at 60° C. for 5 minutes before thionyl chloride (440 µL, 6.0 mmol) was added dropwise. The reaction mixture was stirred at the same temperature for 1 h, after which, LC-MS showed complete conversion to the desired product. Volatiles were evaporated under reduced pressure. The crude residue was triturated with acetonitrile and filtered to afford 5-ethoxy-6-methyl-2H-benzo[d][1,3] oxazine-2,4(1H)-dione (555 mg, 75%) as an off-white powder. MS (ES−) m/e 220 (M−H)$^−$. $^1$H NMR (500 MHz, DMSO-d$_6$) δ 11.58 (s, 1H), 7.57 (d, J=8.4 Hz, 1H), 6.82 (d, J=8.3 Hz, 1H), 3.92 (q, J=6.9 Hz, 2H), 2.20 (s, 3H), 1.35 (t, J=7.0 Hz, 3H).

Step 5

N-(tert-Butyl)-2-(3-(5-ethoxy-6-methyl-4-oxo-3,4-dihydroquinazolin-2-yl)-phenoxy)acetamide

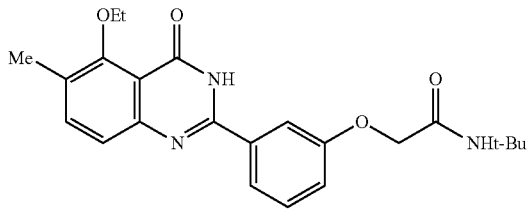

An 8 mL vial equipped with a Teflon septum and magnetic stir bar was charged with 5-ethoxy-6-methyl-2H-benzo[d] [1,3]oxazine-2,4(1H)-dione (255 mg, 1.15 mmol), N-(tert-butyl)-2-(3-carbamimidoylphenoxy)acetamide (431 mg, 1.73 mmol), potassium phosphate tribasic (367 mg, 1.73 mmol) and DMSO (5.8 mL). The reaction mixture was stirred at 25° C. for 16 h. LCMS showed complete consumption of the starting material and the presence of a large UV peak with the desired m/z. Volatiles were evaporated under reduced pressure and the crude residue was triturated with MTBE to afford N-(tert-butyl)-2-(3-(5-ethoxy-6-methyl-4-oxo-3,4-dihydroquinazolin-2-yl)phenoxy)acetamide (212 mg, 45%) as a white powder. MS (ES+) m/e 410 (M+H)$^+$. $^1$H NMR (500 MHz, Chloroform-d) δ 7.75 (s, 2H), 7.71 (d, J=7.7 Hz, 1H), 7.65 (d, J=8.0 Hz, 1H), 7.49 (t, J=8.0 Hz, 1H), 7.11 (dd, J=8.6, 1.9 Hz, 1H), 4.56 (s, 2H), 4.06 (q, J=7.0 Hz, 2H), 2.40 (s, 3H), 1.43 (t, J=7.1 Hz, 3H), 1.43 (s, 9H).

Step 6

2-(3-(4-((1H-Pyrazol-4-yl)amino)-5-ethoxy-6-methylquinazolin-2-yl)phenoxy)-N-(tert-butyl)acetamide

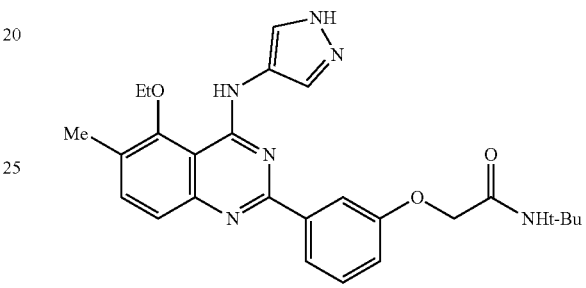

An 8 mL vial equipped with a Teflon septum and magnetic stir bar was charged with N-(tert-butyl)-2-(3-(5-ethoxy-6-methyl-4-oxo-3,4-dihydroquinazolin-2-yl)phenoxy)-acetamide (71 mg, 0.17 mmol) and BOP (100 mg, 0.23 mmol) followed by dry acetonitrile (2.6 mL) and DBU (39 µL, 0.26 mmol). The reaction mixture was stirred at room temperature for 5 minutes before 1-(tetrahydro-2H-pyran-2-yl)-1H-pyrazol-4-amine (43 mg, 0.26 mmol) was added dropwise. Stirring was continued for 15 h at room temperature. After 15 h, LC-MS showed that some product had been formed but that most of the material was as the Bt-activated intermediate. More 1-(tetrahydro-2H-pyran-2-yl)-1H-pyrazol-4-amine was added (20 mg, 0.12 mmol) and DBU (39 µL, 0.26 mmol) were added and the reaction mixture was stirred for 10 hours. LC-MS showed complete disappearance of the starting material and its activated form. Solvent was evaporated and the crude residue was purified by flash column chromatography (20% to 100% EtOAc in hexane, R$_f$=0.68 @ 100% EtOAc). The desired fractions were collected and evaporated and the residue was dissolved in 10 mL of 4.0 N HCl in dioxane and stirred at room temperature for 1 h. LCMS showed that the product had been completely deprotected so volatiles were evaporated under reduced pressure and the crude residue was purified by HPLC to afford 2-(3-(4-((1H-pyrazol-4-yl)amino)-5-ethoxy-6-methylquinazolin-2-yl) phenoxy)-N-(tert-butyl)acetamide (28 mg, 25%) as a bright yellow powder. MS (ES+) m/e 475 (M+H)$^+$. $^1$H NMR (500 MHz, DMSO-d$_6$) δ 8.22 (s, 2H), 7.97 (d, J=7.7 Hz, 1H), 7.92 (s, 1H), 7.83 (d, J=8.5 Hz, 1H), 7.65 (d, J=8.5 Hz, 1H), 7.63 (s, 1H), 7.56 (t, J=7.9 Hz, 1H), 7.20 (d, J=8.3 Hz, 1H), 4.55 (s, 2H), 4.13 (q, J=7.0 Hz, 2H), 2.45 (s, 3H), 1.50 (t, J=7.0 Hz, 3H), 1.30 (s, 9H).

Example 261

2-(3-(4-((1H-Pyrazol-4-yl)amino)-5-ethoxy-7-methylquinazolin-2-yl)phenoxy)-N-(tert-butyl)acetamide Bis Trifluoroacetic Acid Salt

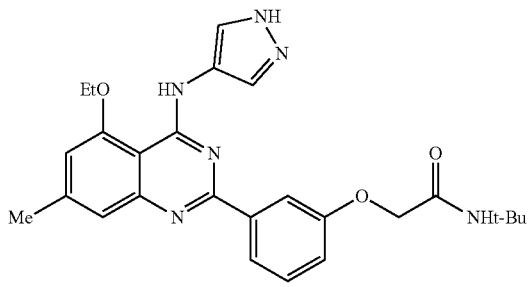

Step 1

Ethyl 2-ethoxy-4-methylbenzoate

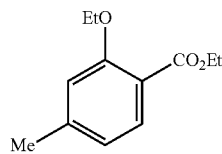 [SMILES: CCOC(=O)c1ccc(C)cc1OCC]

To a solution of 4-methylsalicylic acid (2.5 g, 16.4 mmol) in DMF (16.4 mL) was added $K_2CO_3$ (4.6 g, 32.9 mmol) and the reaction mixture was stirred at 25° C. for 30 min before EtI (5.3 mL, 65.7 mmol) was added. The mixture was stirred at 55° C. for 20 hours, after which LC-MS showed that starting material was consumed completely and that a new UV peak with the desired m/z was the major peak. The reaction mixture was cooled down to room temperature, poured into water (75 mL) and aqueous phase was extracted with EtOAc (3×35 mL). The combined organic layers were dried over $Na_2SO_4$, filtered and concentrated under reduced pressure to afford ethyl 2-ethoxy-4-methylbenzoate (3.4 g, 99%) as an amber oil.

Step 2

2-Ethoxy-4-methylbenzoic Acid

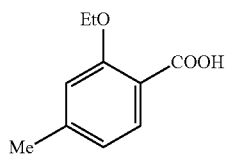

Following the synthetic sequence described for Example 260, step 2, 2-ethoxy-4-methylbenzoic acid was obtained (3.0 g, 99%) as a beige solid. MS (ES−) m/e 179 (M−H)⁻.
$^1$H NMR (500 MHz, Chloroform-d) δ 8.06 (d, J=8.0 Hz, 1H), 6.94 (d, J=8.0 Hz, 1H), 6.83 (s, 1H), 4.31 (q, J=7.0 Hz, 2H), 2.41 (s, 3H), 1.56 (t, J=7.0 Hz, 3H).

Step 3

2-Ethoxy-6-((ethoxycarbonyl)amino)-4-methylbenzoic Acid

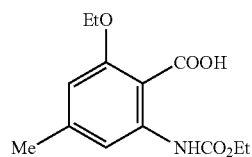

Following the synthetic sequence described for Example 260, step 3, 2-ethoxy-6-((ethoxycarbonyl)amino)-4-methylbenzoic acid was obtained (883 mg, 83%) as a beige solid. MS (ES−) m/e 266 (M−H)⁻.

Step 4

5-Ethoxy-7-methyl-2H-benzo[d][1,3]oxazine-2,4(1H)-dione

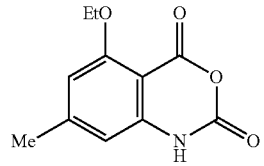

Following the synthetic sequence described for Example 260, step 4, 5-ethoxy-7-methyl-2H-benzo[d][1,3]oxazine-2,4(1H)-dione was obtained (527 mg, 72%) as a fluffy off-white solid. MS (ES−) m/e 220 (M−H)⁻.

Step 5

N-(tert-Butyl)-2-(3-(5-ethoxy-7-methyl-4-oxo-3,4-dihydroquinazolin-2-yl)-phenoxy)acetamide

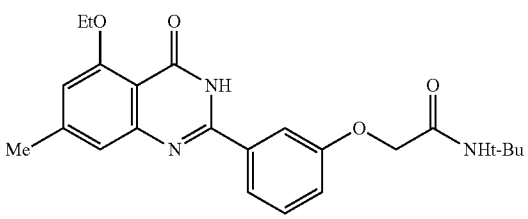

Following the synthetic sequence described for Example 260, step 5, N-(tert-butyl)-2-(3-(5-ethoxy-7-methyl-4-oxo-3,4-dihydroquinazolin-2-yl)phenoxy)-acetamide was obtained (127 mg, 69%) as a yellow powder. MS (ES+) m/e 410 (M+H)⁺.

Step 6

2-(3-(4-((1H-Pyrazol-4-yl)amino)-5-ethoxy-7-methylquinazolin-2-yl)phenoxy)-N-(tert-butyl)acetamide Bis Trifluoroacetic Acid Salt

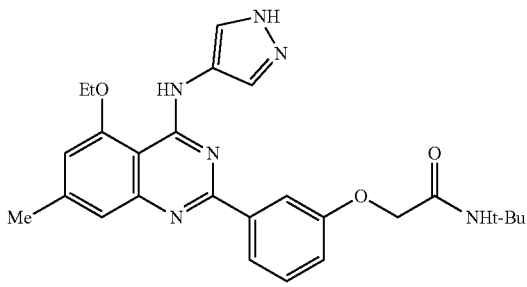

Following the synthetic sequence described for Example 260, step 6, 2-(3-(4-((1H-pyrazol-4-yl)amino)-5-ethoxy-7-methylquinazolin-2-yl)phenoxy)-N-(tert-butyl)acetamide bis trifluoroacetic acid salt was obtained (41.2 mg, 42%) as a bright yellow powder. MS (ES+) m/e 475 (M+H)$^+$.

Example 262

2-(3-(4-((1H-Pyrazol-3-yl)amino)-5-ethoxy-7-methylquinazolin-2-yl)phenoxy)-N-(tert-butyl)acetamide Bis Trifluoroacetic Acid Salt

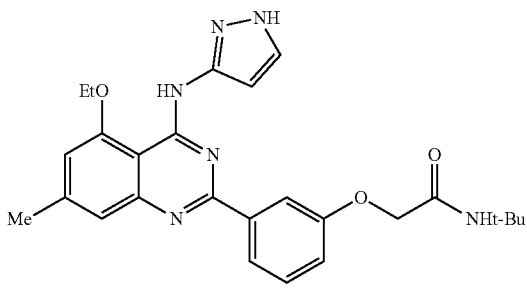

Following the synthetic sequence described for Example 261, 1-((2-(trimethylsilyl)ethoxy)methyl)-1H-pyrazol-3-amine was used in step 6 and SEM deprotection was carried out similarly (16 h reaction time) to afford 2-(3-(4-((1H-pyrazol-3-yl)amino)-5-ethoxy-7-methylquinazolin-2-yl)phenoxy)-N-(tert-butyl)acetamide bis trifluoroacetic acid salt (31.0 mg, 32%) as a bright yellow powder. MS (ES+) m/e 475 (M+H)$^+$.

Example 263

2-(3-(4-((1H-Pyrazol-4-yl)amino)-6-chloro-5-ethoxyquinazolin-2-yl)phenoxy)-N-(tert-butyl)acetamide Bis Trifluoroacetic Acid Salt

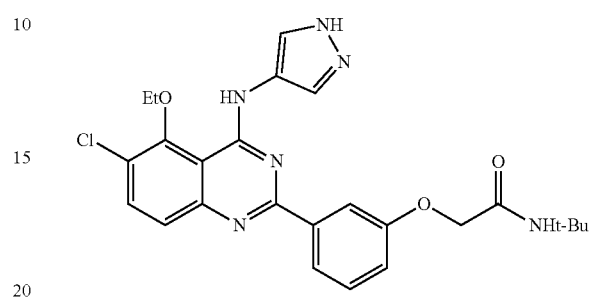

Step 1

Ethyl 3-chloro-2-ethoxybenzoate

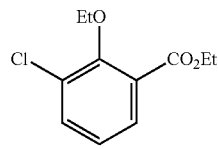 [SMILES: CCOC(=O)c1cccc(Cl)c1OCC]

Following the synthetic sequence described for Example 261, step 1, starting from 3-chloro-2-hydroxybenzoic acid (2.8 g, 16.2 mmol), ethyl 3-chloro-2-ethoxybenzoate was obtained (3.55 g, 96%) as a yellow oil.

Step 2

3-Chloro-2-ethoxybenzoic Acid

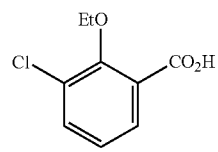 [SMILES: CCOc1c(Cl)cccc1C(=O)O]

Following the synthetic sequence described for Example 261, step 2, 3-chloro-2-ethoxybenzoic acid was obtained (3.1 g, 99%) as a beige solid. MS (ES−) m/e 199 ($^{35}$Cl M−H)$^-$, 201 ($^{37}$Cl M−H)$^-$. $^1$H NMR (500 MHz, Chloroform-d) δ 8.04 (dd, J=7.9, 1.6 Hz, 1H), 7.62 (dd, J=8.0, 1.6 Hz, 1H), 7.22 (t, J=7.9 Hz, 1H), 4.31 (q, J=7.1 Hz, 2H), 1.53 (t, J=7.1 Hz, 3H).

Step 3

3-Chloro-2-ethoxy-6-((ethoxycarbonyl)amino)-benzoic Acid

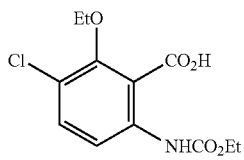

Following the synthetic sequence described for Example 261, step 3, 3-chloro-2-ethoxy-6-((ethoxycarbonyl)amino)-benzoic acid was obtained (887 mg, 77%) as an orange solid. MS (ES−) m/e 286 ($^{35}$Cl M−H)$^−$, 288 ($^{37}$Cl M−H)$^−$.

Step 4

6-Chloro-5-ethoxy-2H-benzo[d][1,3]oxazine-2,4(1H)-dione

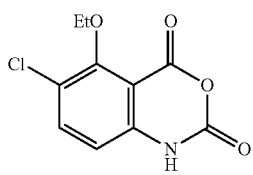

Following the synthetic sequence described for Example 261, step 4, 6-chloro-5-ethoxy-2H-benzo[d][1,3]oxazine-2,4(1H)-dione was obtained (524 mg, 71%) as a fluffy off-white solid. MS (ES−) m/e 240 ($^{35}$Cl M−H)$^−$, 242 ($^{37}$Cl M−H)$^−$.

Step 5

N-(tert-Butyl)-2-(3-(6-chloro-5-ethoxy-4-oxo-3,4-dihydroquinazolin-2-yl)-phenoxy)acetamide

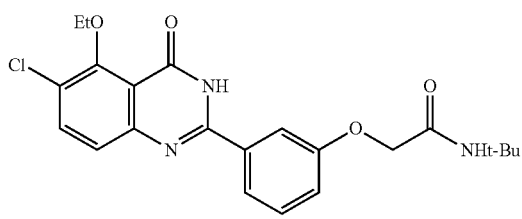

Following the synthetic sequence described for Example 261, step 5, N-(tert-butyl)-2-(3-(6-chloro-5-ethoxy-4-oxo-3,4-dihydroquinazolin-2-yl)phenoxy)-acetamide was obtained (76 mg, 39%) as a white powder. MS (ES+) m/e 430 ($^{35}$Cl M+H)$^+$, 432 ($^{37}$Cl M+H)$^+$.

Step 6

2-(3-(4-((1H-Pyrazol-4-yl)amino)-6-chloro-5-ethoxyquinazolin-2-yl)phenoxy)-N-(tert-butyl)acetamide Bis Trifluoroacetic Acid Salt

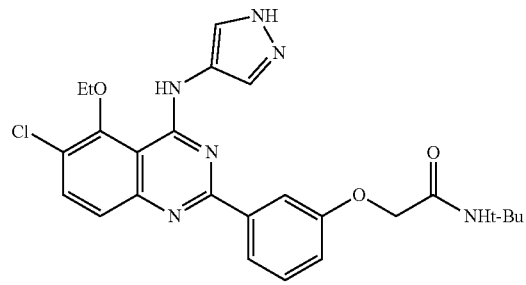

Following the synthetic sequence described for Example 261, step 6, 2-(3-(4-((1H-pyrazol-4-yl)amino)-6-chloro-5-ethoxyquinazolin-2-yl)phenoxy)-N-(tert-butyl)acetamide bis trifluoroacetic acid salt was obtained (3.5 mg, 3%) as a bright yellow powder. MS (ES+) m/e 495 ($^{35}$Cl M+H)$^+$, 497 ($^{37}$Cl M+H)$^+$.

Example 264

2-(3-(4-((1H-Pyrazol-4-yl)amino)-5-ethoxy-6-fluoroquinazolin-2-yl)phenoxy)-N-(tert-butyl)acetamide Bis Trifluoroacetic Acid Salt

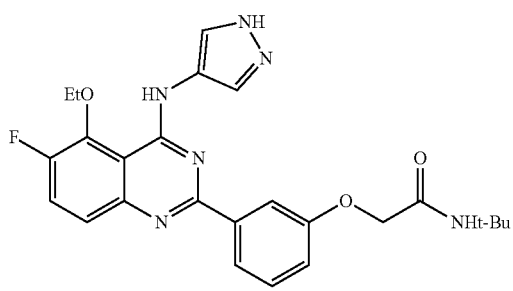

Step 1

Ethyl 2-ethoxy-3-fluorobenzoate

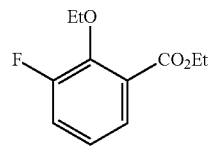

Following the synthetic sequence described for Example 261, step 1, starting from 3-fluoro-2-hydroxybenzoic acid (2.5 g, 16.0 mmol), ethyl 2-ethoxy-3-fluorobenzoate was obtained (2.68 g, 79%) as an amber liquid.

Step 2

2,2-Ethoxy-3-fluorobenzoic Acid

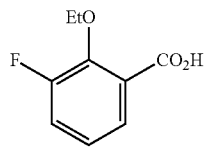

Following the synthetic sequence described for Example 261, step 2, 2-ethoxy-3-fluorobenzoic acid was obtained (2.37 g, 99%) as a dark orange oil. MS (ES−) m/e 183 (M−H)⁻, ¹H NMR (500 MHz, Chloroform-d) δ 7.93 (d, J=8.0 Hz, 1H), 7.34 (ddd, J=11.3, 8.2, 1.6 Hz, 1H), 7.17 (td, J=8.1, 4.7 Hz, 1H), 4.46 (qd, J=7.1, 1.4 Hz, 2H), 1.51 (t, J=7.1 Hz, 3H).

Step 3

2-Ethoxy-6-((ethoxycarbonyl)amino)-3-fluorobenzoic Acid

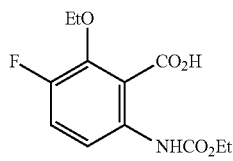

Following the synthetic sequence described for Example 261, step 3, 2-ethoxy-6-((ethoxycarbonyl)amino)-3-fluorobenzoic acid was obtained (807 mg, 74%) as a yellow solid. MS (ES−) m/e 270 (M−H)⁻.

Step 4

5-Ethoxy-6-fluoro-2H-benzo[d][1,3]oxazine-2,4(1H)-dione

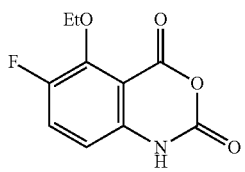

Following the synthetic sequence described for Example 261, step 4, 5-ethoxy-6-fluoro-2H-benzo[d][1,3]oxazine-2,4(1H)-dione was obtained (526 mg, 79%) as a white powder. MS (ES−) m/e 224 (M−H)⁻.

Step 5

N-(tert-Butyl)-2-(3-(5-ethoxy-6-fluoro-4-oxo-3,4-dihydroquinazolin-2-yl)-phenoxy)acetamide

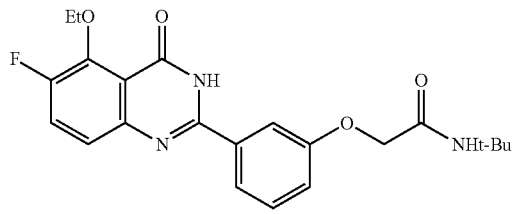

Following the synthetic sequence described for Example 261, step 5, N-(tert-butyl)-2-(3-(5-ethoxy-6-fluoro-4-oxo-3,4-dihydroquinazolin-2-yl)phenoxy)acetamide was obtained (55 mg, 30%) as a white powder. MS (ES+) m/e 412 (M+H)⁺.

Step 6

2-(3-(4-((1H-Pyrazol-4-yl)amino)-5-ethoxy-6-fluoroquinazolin-2-yl)phenoxy)-N-(tert-butyl)acetamide Bis Trifluoroacetic Acid Salt

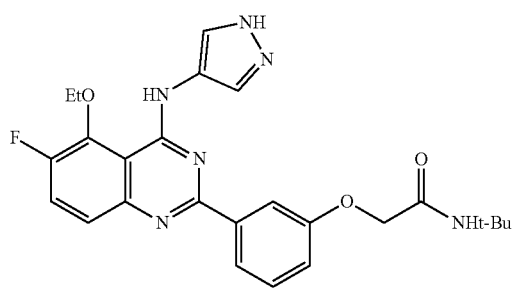

Following the synthetic sequence described for Example 261, step 6, 2-(3-(4-((1H-pyrazol-4-yl)amino)-5-ethoxy-6-fluoroquinazolin-2-yl)phenoxy)-N-(tert-butyl)acetamide bis trifluoroacetic acid salt was obtained (6.8 mg, 8%) as a bright yellow powder. MS (ES+) m/e 479 (M+H)⁺.

Example 265

2-(3-(4-((1H-Pyrazol-4-yl)amino)-5-ethoxy-7-fluoroquinazolin-2-yl)phenoxy)-N-(tert-butyl)acetamide Bis Trifluoroacetic Acid Salt

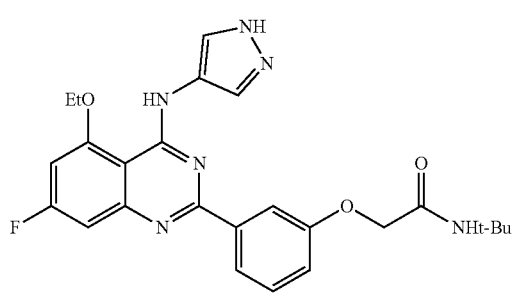

Step 1

Ethyl 2-ethoxy-4-fluorobenzoate

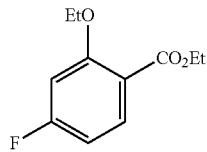 [SMILES: CCOC(=O)c1ccc(F)cc1OCC]

Following the synthetic sequence described for Example 261, step 1, starting from 4-fluoro-2-hydroxybenzoic acid (2.5 g, 16.0 mmol), ethyl 2-ethoxy-4-fluorobenzoate was obtained (1.83 g, 54%) as an amber oil.

Step 2

2-Ethoxy-4-fluorobenzoic acid

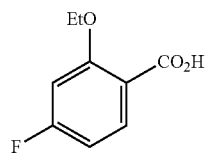

Following the synthetic sequence described for Example 261, step 2, 2-ethoxy-4-fluorobenzoic acid was obtained (1.57 g, 99%) as a beige solid. MS (ES−) m/e 183 (M−H)⁻, ¹H NMR (500 MHz, Chloroform-d) δ 8.21 (dd, J=8.8, 6.8 Hz, 1H), 6.84 (ddd, J=8.8, 7.8, 2.3 Hz, 1H), 6.75 (dd, J=10.1, 2.2 Hz, 1H), 4.31 (q, J=7.0 Hz, 2H), 1.59 (t, J=7.0 Hz, 3H).

Step 3

2-Ethoxy-6-((ethoxycarbonyl)amino)-4-fluorobenzoic Acid

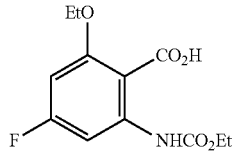

Following the synthetic sequence described for Example 261, step 3, 2-ethoxy-6-((ethoxycarbonyl)amino)-4-fluorobenzoic acid was obtained (773 mg, 71%) as an orange thick oil. MS (ES−) m/e 270 (M−H)⁻.

Step 4

5-Ethoxy-7-fluoro-2H-benzo[d][1,3]oxazine-2,4 (1H)-dione

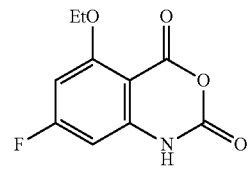

Following the synthetic sequence described for Example 261, step 4, 5-ethoxy-7-fluoro-2H-benzo[d][1,3]oxazine-2, 4(1H)-dione was obtained (291 mg, 45%) as a beige powder. MS (ES−) m/e 224 (M−H)⁻.

Step 5

N-(tert-Butyl)-2-(3-(5-ethoxy-7-fluoro-4-oxo-3,4-dihydroquinazolin-2-yl)-phenoxy)acetamide

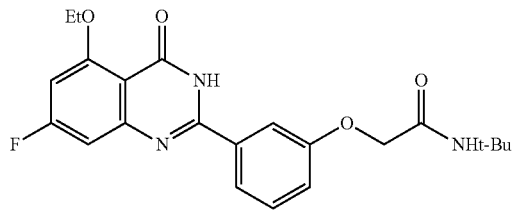

Following the synthetic sequence described for Example 261, step 5, N-(tert-butyl)-2-(3-(5-ethoxy-7-fluoro-4-oxo-3, 4-dihydroquinazolin-2-yl)phenoxy)-acetamide was obtained (170 mg, 46%) as a pale yellow solid. MS (ES+) m/e 412 (M+H)⁺.

Step 6

2-(3-(4-((1H-Pyrazol-4-yl)amino)-5-ethoxy-7-fluoroquinazolin-2-yl)phenoxy)-N-(tert-butyl)acetamide Bis Trifluoroacetic Acid Salt

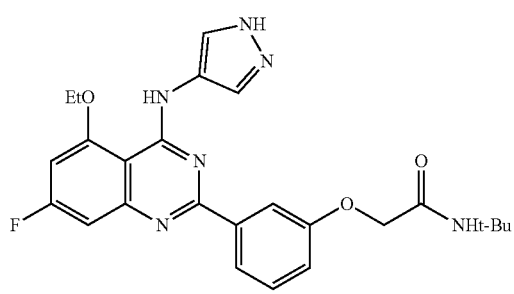

Following the synthetic sequence described for Example 261, step 6, 2-(3-(4-((1H-pyrazol-4-yl)amino)-5-ethoxy-7-fluoroquinazolin-2-yl)phenoxy)-N-(tert-butyl)acetamide bis trifluoroacetic acid salt was obtained (22 mg, 17%) as a bright yellow powder. MS (ES+) m/e 479 (M+H)⁺.

Example 266

2-(3-(4-((1H-Pyrazol-3-yl)amino)-5-(2,2-difluoro-ethoxy)-6-methylquinazolin-2-yl)phenoxy)-N-(tert-butyl)acetamide Bis Trifluoroacetic Acid Salt

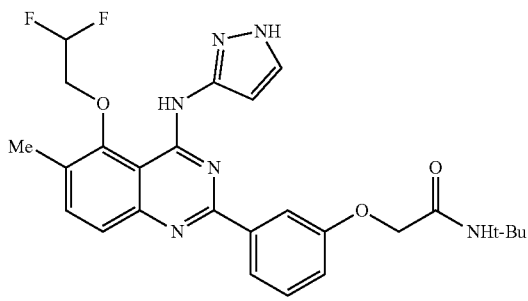

Step 1

Methyl 2-(2,2-difluoroethoxy)-3-methylbenzoate

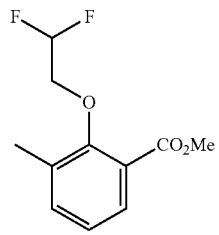 [SMILES: COC(=O)c1cccc(C)c1OCC(F)F]

To a stirred suspension of $K_2CO_3$ (3.33 g, 24.1 mmol) in DMSO (12.0 mL) was added methyl 3-methylsalicylate (2.0 g, 12.0 mmol) at room temperature. After 5 minutes at 50° C., 2,2-difluoroethyltrifluoromethanesulfonate (3.1 g, 14.4 mmol) was added dropwise. After 1 h at 50° C., more 2,2-difluoroethyltrifluoromethanesulfonate (1.1 g, 5.1 mmol) was added dropwise. After 1 h 30 at the same temperature, LC-MS showed complete conversion to the desired product. The reaction mixture was cooled to room temperature and quenched by addition of 1N aq. HCl (100 mL). The mixture was extracted with MTBE (2×50 mL). The combined organic layers were washed with sat. aq. $Na_2CO_3$ (50 mL) and sat. aq. NaCl (50 mL), dried over $Na_2SO_4$ and concentrated under reduced pressure. The crude residue was purified by flash column chromatography (0% to 20% EtOAc in hexane) to afford methyl 2-(2,2-difluoro-ethoxy)-3-methylbenzoate (2.57 g, 93%) as a colorless liquid. $^1$H NMR (500 MHz, Chloroform-d) δ 7.69 (dd, J=7.8, 1.2 Hz, 1H), 7.37 (d, J=7.4 Hz, 1H), 7.10 (t, J=7.7 Hz, 1H), 6.16 (tt, J=55.4, 4.1 Hz, 1H), 4.15 (td, J=13.5, 4.1 Hz, 1H), 3.91 (s, 2H), 2.34 (s, 2H).

Step 2

2-(2,2-Difluoroethoxy)-3-methylbenzoic Acid

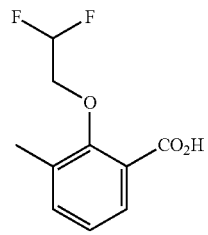

To a solution of methyl 2-(2,2-difluoroethoxy)-3-methyl-benzoate (2.6 g, 11.2 mmol) in THF (9.9 mL) and MeOH (2.5 mL) was added a solution of LiOH (802 mg, 33.5 mmol) in $H_2O$ (9.9 mL). The reaction mixture was stirred at room temperature. After 8 h, LC-MS showed complete conversion. Volatiles were evaporated under reduced pressure and the aqueous phase (30 mL) was acidified to pH 2 with conc. aq. HCl (~2.8 mL) in an ice bath and then extracted with MTBE (2×50 mL). The combined organic layers were dried over $Na_2SO_4$, filtered and concentrated under reduced pressure and the crude residue was dried under high vacuum to give 2.4 g (99%) of 2-(2,2-difluoro-ethoxy)-3-methylbenzoic acid as a white powder. MS (ES−) m/e 215 (M−H)⁻.

Step 3

2-(2,2-Difluoroethoxy)-6-((ethoxycarbonyl)amino)-3-methylbenzoic Acid

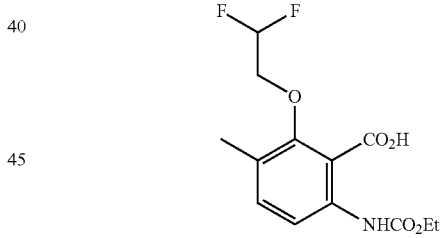

A 100 mL round-bottom flask equipped with a Teflon septum and magnetic stir bar was charged with 2-(2,2-difluoroethoxy)-3-methylbenzoic acid (865 mg, 4.0 mmol), ethyl chlorocarbamate (593 mg, 4.8 mmol) and t-BuOH (40 mL). Pentamethylcyclopentadienyl-rhodium(III) chloride dimer (99 mg, 160 μmol) and silver acetate (1.00 g, 6.0 mmol) were then added at once with stirring. The reaction mixture was sparged with nitrogen for 20 min and then stirred at 60° C. for 20 h after which, LC-MS showed complete conversion to the desired product. After cooling down to room temperature, the reaction mixture was poured in 70 mL of 2N aq. HCl and extracted with EtOAc (2×70 mL). The combined organic layers were dried over $Na_2SO_4$ and passed through a silica cartridge eluting with EtOAc. The solvents were evaporated under reduced pressure to afford 2-(2,2-difluoroethoxy)-6-((ethoxycarbonyl)-amino)-3-methylbenzoic acid (1.1 g, 93%) as an orange-brown powder. MS (ES−) m/e 302 (M−H)⁻.

Step 4

5-(2,2-Difluoroethoxy)-6-methyl-2H-benzo[d][1,3]oxazine-2,4(1H)-dione

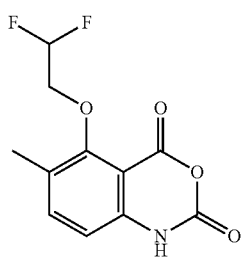

A 40 mL vial equipped with a Teflon septum and magnetic stir bar was charged with 2-(2,2-difluoroethoxy)-6-((ethoxycarbonyl)amino)-3-methylbenzoic acid (1.13 g, 3.7 mmol) and anhydrous dioxane (11.2 mL). Thionyl chloride (1.08 mL, 14.9 mmol) was added dropwise and the reaction mixture was stirred at 60° C. for 1 hour after which, LC-MS showed complete conversion to the desired product. Volatiles were evaporated under reduced pressure and the crude residue was triturated with MTBE and filtered to afford 900 mg (94%) of 5-(2,2-difluoroethoxy)-6-methyl-2H-benzo[d][1,3]oxazine-2,4(1H)-dione as an ocher powder. MS (ES−) m/e 256 (M−H)⁻.

Step 5

N-(tert-Butyl)-2-(3-(5-(2,2-difluoroethoxy)-6-methyl-4-oxo-3,4-dihydroquinazolin-2-yl)phenoxy)acetamide

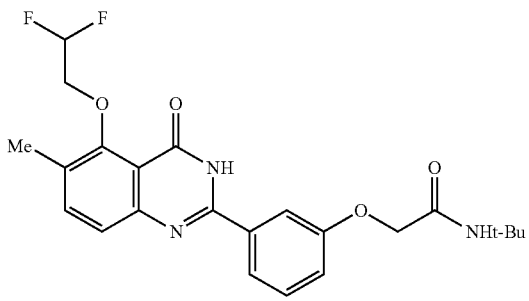

A 40 mL vial opened to air and equipped with a magnetic stir bar was charged with 5-(2,2-difluoroethoxy)-6-methyl-2H-benzo[d][1,3]oxazine-2,4(1H)-dione (310 mg, 1.20 mmol), N-(tert-butyl)-2-(3-carbamimidoylphenoxy)acetamide (421 mg, 1.69 mmol), potassium phosphate tribasic (768 mg, 3.61 mmol) and DMSO (12.1 mL). The reaction mixture was stirred at 25° C. After 90 min, LC-MS showed complete conversion of the starting material to a major UV peak with the desired m/z. The reaction mixture was poured into water (50 mL) and extracted with EtOAc (2×50 mL). The combined organic layers were washed with sat. aq. NaCl, dried over Na₂SO₄, and evaporated under reduced pressure. The crude residue was purified by flash column chromatography (0% to 15% MeOH in DCM, $R_f$=0.36 @10% MeOH in DCM) to afford N-(tert-butyl)-2-(3-(5-(2,2-difluoroethoxy)-6-methyl-4-oxo-3,4-dihydroquinazolin-2-yl)phenoxy)acetamide (376 mg, 70%) as an ocher solid. MS (ES+) m/e 446 (M+H)⁺.

Step 6

2-(3-(4-((1H-Pyrazol-3-yl)amino)-5-(2,2-difluoroethoxy)-6-methylquinazolin-2-yl)phenoxy)-N-(tert-butyl)acetamide Bis Trifluoroacetic Acid Salt

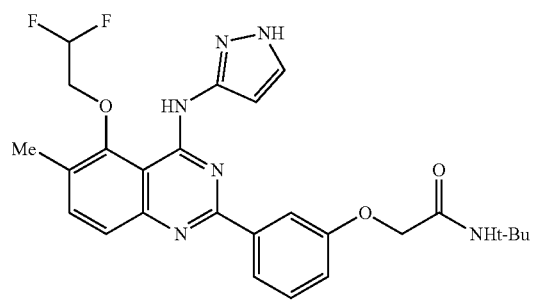

An 8 mL vial equipped with a Teflon septum and magnetic stir bar was charged with N-(tert-butyl)-2-(3-(5-(2,2-difluoroethoxy)-6-methyl-4-oxo-3,4-dihydroquinazolin-2-yl)phenoxy)acetamide (59 mg, 132 µmol) and BOP (88 mg, 199 µmol) followed by dry NMP (0.66 mL) and DBU (50 µL, 331 µmol). The reaction mixture was stirred at room temperature for 60 minutes after which, LC-MS showed complete conversion to Bt-activated substrate ([M+H]⁺ =563). The reaction mixture was diluted with 10 mL of 1:1 hexane/EtOAc and passed through a 12 g silica-cartridge using the same eluent. The collected solution was evaporated under reduced pressure and the purified Bt-activated substrate was dissolved in dry DMA (331 µL) before 1-((2-(trimethylsilyl)ethoxy)methyl)-1H-pyrazol-3-amine (57 mg, 265 µmol) and DIPEA (58 µL, 331 µmol) were added. Stirring was continued for 12 h at 90° C., after which LC-MS showed no Bt activated substrate left and a large UV peak with the desired m/z. The reaction mixture was cooled down to room temperature, evaporated to dryness under reduced pressure and subjected to flash column chromatography (0% to 90% EtOAc in hexane). The desired fractions were collected and the residue from evaporation was dissolved in 6 mL of DCE followed by 4 mL of TFA. After 12 h, LCMS indicated that complete SEM deprotection had occurred. Volatiles were removed under reduced pressure and the crude residue was purified by HPLC to afford 2-(3-(4-((1H-pyrazol-3-yl)amino)-5-(2,2-difluoroethoxy)-6-methylquinazolin-2-yl)phenoxy)-N-(tert-butyl)acetamide bis trifluoroacetic acid salt (4 mg, 5%) as a bright yellow powder. MS (ES+) m/e 511 (M+H)⁺.

Example 267

2-(3-(4-((1H-pyrazol-4-yl)amino)-5-(2,2-difluoro-ethoxy)-6-methylquinazolin-2-yl)phenoxy)-N-(tert-butyl)acetamide Bis Trifluoroacetic Acid Salt

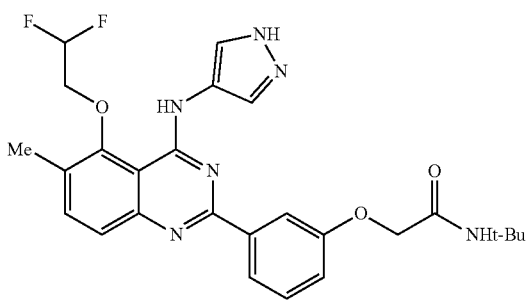

Following the synthetic sequence described for Example 266, 1-(tetrahydro-2H-pyran-2-yl)-1H-pyrazol-4-amine was used in step 6 and THP deprotection was carried out similarly (2 h reaction time) to afford the desired compound (25.4 mg, 29%) as a bright yellow powder. MS (ES+) m/e 511 (M+H)$^+$.

Example 268

N-(tert-Butyl)-2-(3-(5-(2,2-difluoroethoxy)-6-methyl-4-((1-methyl-1H-pyrazol-4-yl)amino)quinazolin-2-yl)phenoxy)acetamide Bis Trifluoroacetic Acid Salt

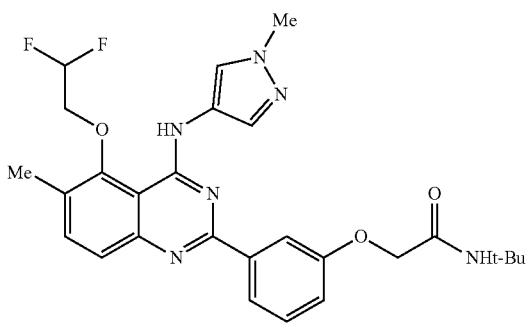

Following the synthetic sequence described for Example 266, 1-methyl-1H-pyrazol-3-amine was used in step 6 and no deprotection was necessary to afford the desired compound (61.4 mg, 68%) as a bright yellow powder. MS (ES+) m/e 525 (M+H)$^+$.

Example 269

2-(3-(4-((1H-Pyrazol-3-yl)amino)-5-(cyclopropyl-methoxy)-6-methylquinazolin-2-yl)phenoxy)-N-(tert-butyl)acetamide Bis Trifluoroacetic Acid Salt

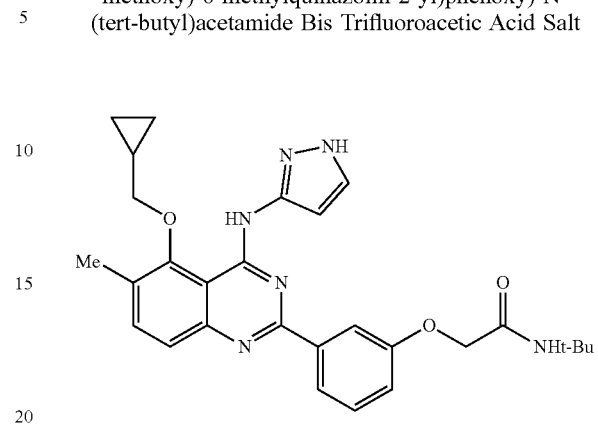

Step 1

Methyl 2-(cyclopropylmethoxy)-3-methylbenzoate

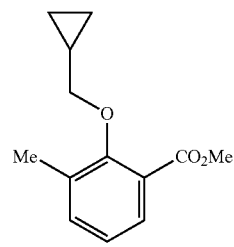 [SMILES: COC(=O)c1cccc(C)c1OCC1CC1]

Following the synthetic sequence described for Example 266, step 1, K$_2$CO$_3$ (3.12 g, 22.6 mmol), methyl 3-methylsalicylate (2.5 g, 15.0 mmol) and (bromomethyl)cyclopropane (2.2 mL, 22.57 mmol) in DMSO (15.0 mL) were used to afford methyl 2-(cyclopropylmethoxy)-3-methylbenzoate (3.19 g, 96%) as a colorless liquid. $^1$H NMR (500 MHz, Chloroform-d) δ 7.62 (dd, J=7.8, 1.3 Hz, 1H), 7.33 (d, J=7.4 Hz, 1H), 7.04 (t, J=7.6 Hz, 1H), 3.90 (s, 2H), 3.74 (d, J=7.1 Hz, 1H), 2.33 (s, 2H), 1.30 (dtd, J=11.8, 7.5, 2.7 Hz, 1H), 0.63-0.58 (m, 2H), 0.31 (q, J=4.8 Hz, 2H).

Step 2

2-(Cyclopropylmethoxy)-3-methylbenzoic Acid

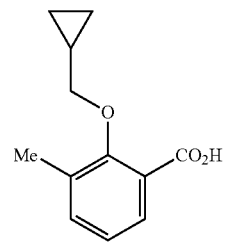 [SMILES: Cc1cccc(C(=O)O)c1OCC1CC1]

Following the synthetic sequence described for Example 266, step 2, 2-(cyclopropylmethoxy)-3-methylbenzoic acid was obtained (2.9 g, 99%) as a pale yellow powder. MS (ES−) m/e 205 (M−H)−.

Step 3

2-(Cyclopropylmethoxy)-6-((ethoxycarbonyl) amino)-3-methylbenzoic Acid

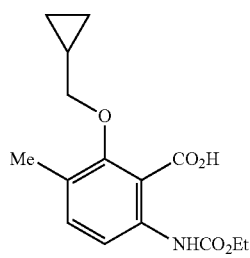

Following the synthetic sequence described for Example 266, step 3, 2-(cyclopropylmethoxy)-6-((ethoxycarbonyl) amino)-3-methylbenzoic acid was obtained (1.2 g, 99%) as a dark red thick oil. MS (ES−) m/e 292 (M−H)−.

Step 4

5-(Cyclopropylmethoxy)-6-methyl-2H-benzo[d][1,3]oxazine-2,4(1H)-dione

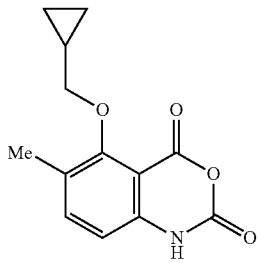 [SMILES: Cc1ccc2[nH]c(=O)oc(=O)c2c1OCC1CC1]

Following the synthetic sequence described for Example 266, step 4, 5-(cyclopropylmethoxy)-6-methyl-2H-benzo[d][1,3]oxazine-2,4(1H)-dione was obtained (757 mg, 77%) as a light brown powder. MS (ES−) m/e 246 (M−H)−.

Step 5

N-(tert-Butyl)-2-(3-(5-(cyclopropylmethoxy)-6-methyl-4-oxo-3,4-dihydroquinazolin-2-yl)phenoxy)acetamide

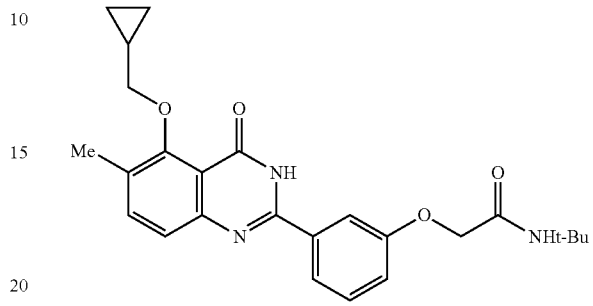

Following the synthetic sequence described for Example 266, step 5, N-(tert-butyl)-2-(3-(5-(cyclopropylmethoxy)-6-methyl-4-oxo-3,4-dihydroquinazolin-2-yl)-phenoxy)acetamide was obtained (394 mg, 75%) as a brown solid. MS (ES+) m/e 436 (M+H)+.

Step 6

2-(3-(4-((1H-Pyrazol-3-yl)amino)-5-(cyclopropylmethoxy)-6-methylquinazolin-2-yl)phenoxy)-N-(tert-butyl)acetamide Bis Trifluoroacetic Acid

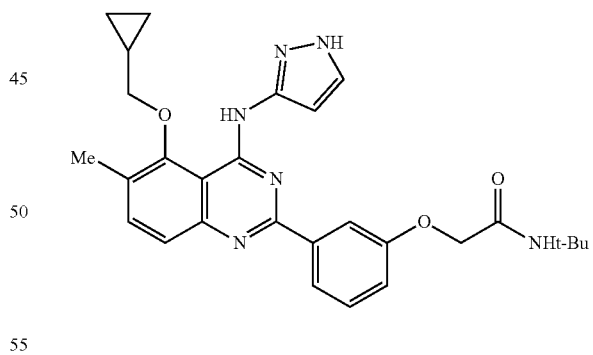

Following the synthetic sequence described for Example 266, step 6, 2-(3-(4-((1H-pyrazol-3-yl)amino)-5-(cyclopropylmethoxy)-6-methylquinazolin-2-yl)-phenoxy)-N-(tert-butyl)acetamide bis trifluoroacetic acid was obtained (13.7 mg, 13%) as a bright yellow powder. MS (ES+) m/e 501 (M+H)+.

Example 270

2-(3-(4-((1H-Pyrazol-4-yl)amino)-5-(cyclopropyl-methoxy)-6-methylquinazolin-2-yl)phenoxy)-N-(tert-butyl)acetamide Bis Trifluoroacetic Acid Salt

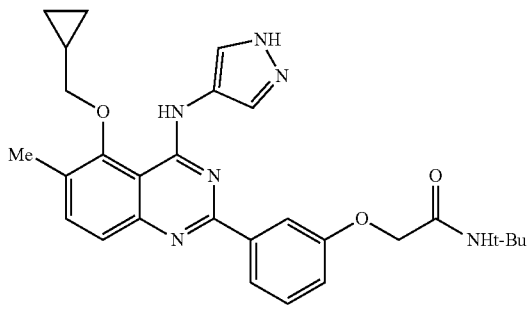

Following the synthetic sequence described for Example 269, 1-(tetrahydro-2H-pyran-2-yl)-1H-pyrazol-4-amine was used in step 6 and THP deprotection was carried out similarly (2 h reaction time) to afford the desired compound (34.8 mg, 36%) as a bright yellow powder. MS (ES+) m/e 501 (M+H)$^+$.

Example 271

N-(tert-Butyl)-2-(3-(5-(cyclopropylmethoxy)-6-methyl-4-((1-methyl-1H-pyrazol-4-yl)amino)quinazolin-2-yl)phenoxy)acetamide Bis Trifluoroacetic Acid Salt

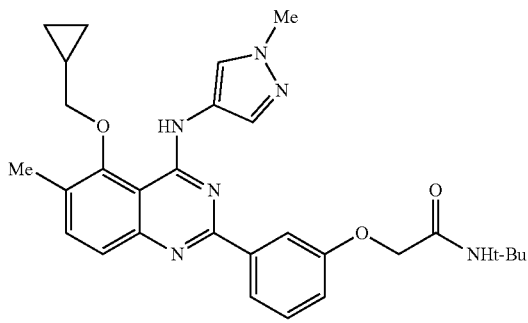

Following the synthetic sequence described for Example 269, 1-methyl-1H-pyrazol-3-amine was used in step 6 and no deprotection was necessary to afford the desired compound (29.1 mg, 29%) as a bright yellow powder. MS (ES+) m/e 515 (M+H)$^+$.

Example 272

2-(3-(4-((1H-Pyrazol-3-yl)amino)-5-isobutoxy-6-methylquinazolin-2-yl)-phenoxy)-N-(tert-butyl)acetamide Bis Trifluoroacetic Acid Salt

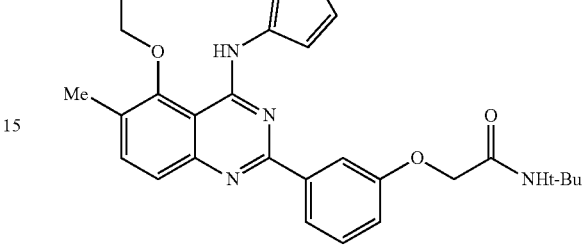

Step 1

Methyl 2-isobutoxy-3-methylbenzoate

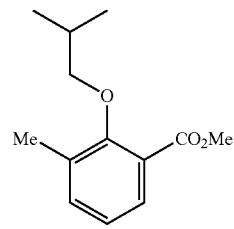 [SMILES: COC(=O)c1cccc(C)c1OCC(C)C]

Following the synthetic sequence described for Example 266, step 1, K$_2$CO$_3$ (3.12 g, 22.6 mmol), methyl 3-methylsalicylate (2.5 g, 15.0 mmol) and isobutyliodide (2.6 mL, 22.57 mmol) in DMSO (15.0 mL) were used to afford methyl 2-isobutoxy-3-methylbenzoate (2.21 g, 66%) as a colorless liquid. $^1$H NMR (500 MHz, Chloroform-d) δ 7.60 (d, J=7.5 Hz, 1H), 7.32 (d, J=7.4 Hz, 1H), 7.03 (t, J=7.6 Hz, 1H), 3.90 (d, J=0.8 Hz, 3H), 3.64 (d, J=6.4 Hz, 2H), 2.31 (s, 3H), 2.12 (dp, J=13.2, 6.6 Hz, 1H), 1.05 (d, J=6.7 Hz, 5H).

Step 2

2-Isobutoxy-3-methylbenzoic Acid

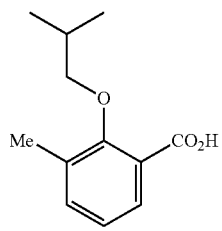

Following the synthetic sequence described for Example 266, step 2, 2-isobutoxy-3-methylbenzoic acid was obtained (2.1 g, 99%) as a yellow oil. MS (ES−) m/e 207 (M−H)$^−$.

Step 3

6-((Ethoxycarbonyl)amino)-2-isobutoxy-3-methylbenzoic Acid

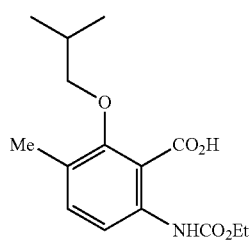

Following the synthetic sequence described for Example 266, step 3, 6-((ethoxycarbonyl)amino)-2-isobutoxy-3-methylbenzoic acid was obtained (1.2 g, 99%) as a dark red thick oil. MS (ES−) m/e 294 (M−H)⁻.

Step 4

5-Isobutoxy-6-methyl-2H-benzo[d][1,3]oxazine-2,4(1H)-dione

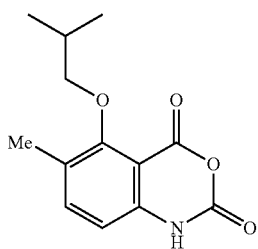 [SMILES: Cc1ccc2[nH]c(=O)oc(=O)c2c1OCC(C)C]

Following the synthetic sequence described for Example 266, step 4, 5-isobutoxy-6-methyl-2H-benzo[d][1,3]oxazine-2,4(1H)-dione was obtained (627 mg, 63%) as a tan powder. MS (ES−) m/e 248 (M−H)⁻.

Step 5

N-(tert-Butyl)-2-(3-(5-isobutoxy-6-methyl-4-oxo-3,4-dihydroquinazolin-2-yl)-phenoxy)acetamide

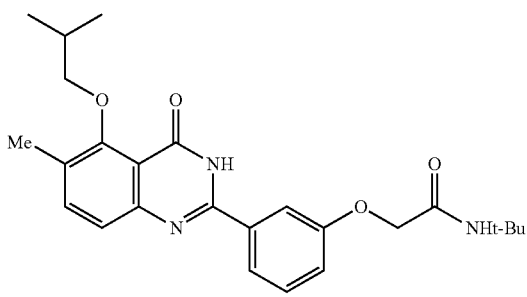

Following the synthetic sequence described for Example 266, step 5, N-(tert-butyl)-2-(3-(5-isobutoxy-6-methyl-4-oxo-3,4-dihydroquinazolin-2-yl)phenoxy)-acetamide was obtained (389 mg, 74%) as a pale yellow solid. MS (ES+) m/e 438 (M+H)⁺.

Step 6

2-(3-(4-((1H-Pyrazol-3-yl)amino)-5-isobutoxy-6-methylquinazolin-2-yl)-phenoxy)-N-(tert-butyl)acetamide Bis Trifluoroacetic Acid Salt

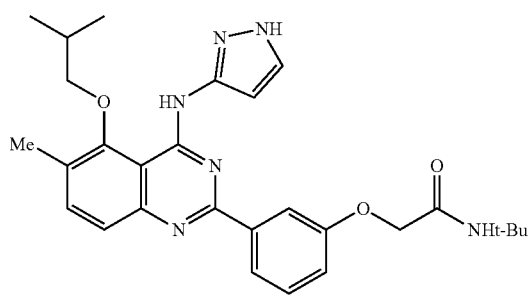

Following the synthetic sequence described for Example 266, step 6, 2-(3-(4-((1H-pyrazol-3-yl)amino)-5-isobutoxy-6-methylquinazolin-2-yl)phenoxy)-N-(tert-butyl)acetamide bis trifluoroacetic acid salt was obtained (9.7 mg, 7%) as a bright yellow powder. MS (ES+) m/e 503 (M+H)⁺.

Example 273

2-(3-(4-((1H-Pyrazol-4-yl)amino)-5-isobutoxy-6-methylquinazolin-2-yl)-phenoxy)-N-(tert-butyl)acetamide Bis Trifluoroacetic Acid Salt

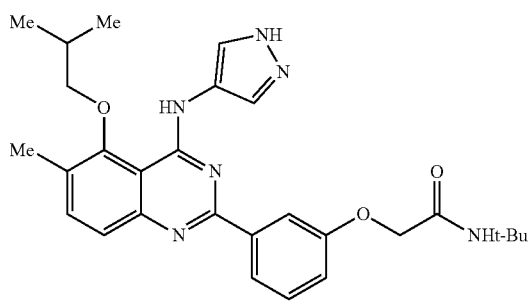

Following the synthetic sequence described for Example 272, 1-(tetrahydro-2H-pyran-2-yl)-1H-pyrazol-4-amine was used in step 6 and THP deprotection was carried out similarly (2 h reaction time) to afford the desired compound (42.6 mg, 30%) as a bright yellow powder. MS (ES+) m/e 503 (M+H)⁺.

Example 274

2-(3-(4-((1H-Pyrazol-3-yl)amino)-6-methyl-5-((3-methyloxetan-3-yl)methoxy)-quinazolin-2-yl)phenoxy)-N-(tert-butyl)acetamide Bis Trifluoroacetic Acid Salt

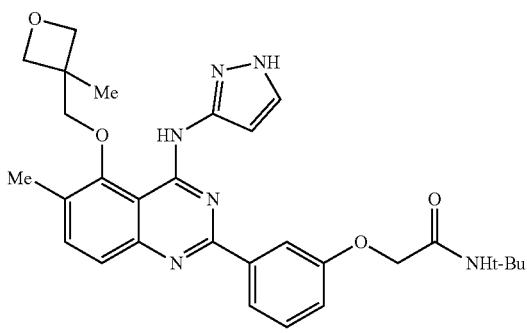

Step 1

Methyl 3-methyl-2-((3-methyloxetan-3-yl)methoxy)benzoate

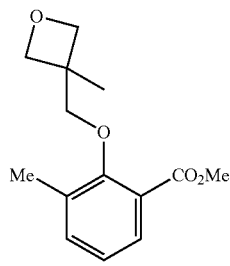 [SMILES: COC(=O)c1cccc(C)c1OCC1(C)COC1]

Following the synthetic sequence described for Example 266, step 1, $K_2CO_3$ (3.33 g, 24.1 mmol), methyl 3-methylsalicylate (2.0 g, 12.0 mmol) and (bromomethyl)-3-methyloxetane (2.4 g, 24.1 mmol) in DMSO (12.0 mL) were used to afford methyl 3-methyl-2-((3-methyloxetan-3-yl)methoxy)benzoate (2.85 g, 99%) as a colorless liquid. $^1$H NMR (500 MHz, Chloroform-d) δ 7.63 (dd, J=7.8, 1.2 Hz, 1H), 7.34 (td, 1H), 7.07 (t, J=7.6 Hz, 1H), 4.73 (d, J=5.8 Hz, 2H), 4.47 (d, J=5.8 Hz, 2H), 3.98 (s, 2H), 3.89 (d, J=0.7 Hz, 2H), 2.33 (s, 2H), 1.49 (s, 2H).

Step 2

3-Methyl-2-((3-methyloxetan-3-yl)methoxy)benzoic Acid

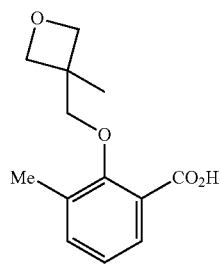 [SMILES: Cc1cccc(C(=O)O)c1OCC1(C)COC1]

Following the synthetic sequence described for Example 266, step 2, 3-methyl-2-((3-methyloxetan-3-yl)methoxy)benzoic acid was obtained (2.9 g, 99%) as a yellow thick oil. MS (ES−) m/e 235 (M−H)⁻.

Step 3

6-((Ethoxycarbonyl)amino)-3-methyl-2-((3-methyloxetan-3-yl)methoxy)-benzoic Acid

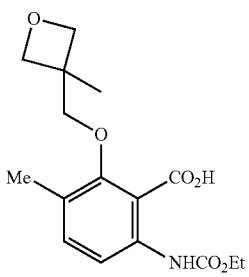

Following the synthetic sequence described for Example 266, step 3, 6-((ethoxycarbonyl)amino)-3-methyl-2-((3-methyloxetan-3-yl)methoxy)benzoic acid was obtained (1.3 g, 97%) as a dark red thick oil. MS (ES−) m/e 322 (M−H)⁻.

Step 4

5-(3-Chloro-2-(hydroxymethyl)-2-methylpropoxy)-6-methyl-2H-benzo[d][1,3]oxazine-2,4(1H)-dione

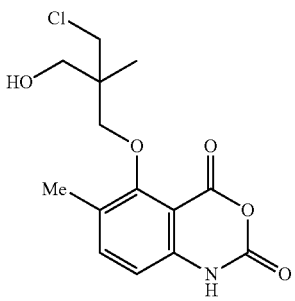 [SMILES: Cc1ccc2[nH]c(=O)oc(=O)c2c1OCC(C)(CO)CCl]

Following the synthetic sequence described for Example 266, step 4, 5-(3-chloro-2-(hydroxymethyl)-2-methylpropoxy)-6-methyl-2H-benzo[d][1,3]oxazine-2,4(1H)-dione was obtained (1.2 g, 83% purity) as a dark brown thick oil. MS (ES−) m/e 312 ($^{35}$Cl M−H)⁻, 314 ($^{37}$Cl M−H)⁻.

Step 5

N-(tert-Butyl)-2-(3-(5-(3-chloro-2-(hydroxymethyl)-2-methylpropoxy)-6-methyl-4-oxo-3,4-dihydroquinazolin-2-yl)phenoxy)acetamide

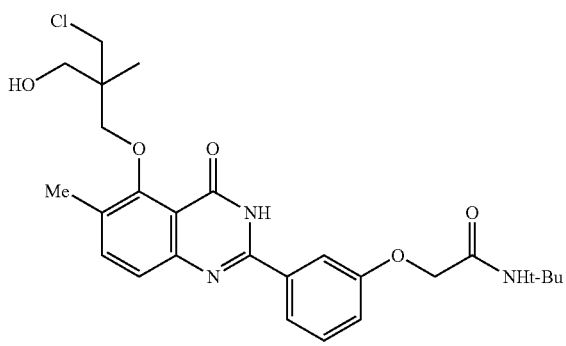

Following the synthetic sequence described for Example 266, step 5, N-(tert-butyl)-2-(3-(5-(3-chloro-2-(hydroxymethyl)-2-methylpropoxy)-6-methyl-4-oxo-3,4-dihydroquinazolin-2-yl)phenoxy)acetamide was obtained (561 mg, 44%) as a light brown powder. MS (ES+) m/e 502 ($^{35}$Cl M+H)$^+$, 504 ($^{37}$Cl M+H)$^+$.

Step 6

N-(tert-Butyl)-2-(3-(6-methyl-5-((3-methyloxetan-3-yl)methoxy)-4-oxo-3,4-dihydroquinazolin-2-yl)phenoxy)acetamide

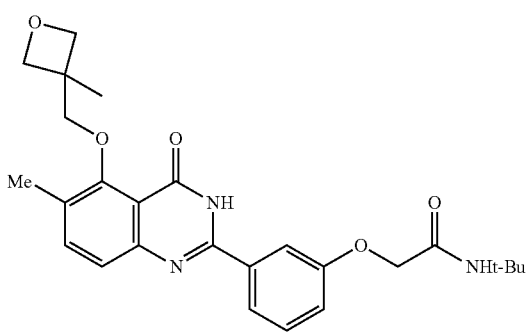

A 40 mL vial equipped with a magnetic stir bar was charged with N-(tert-butyl)-2-(3-(5-(3-chloro-2-(hydroxymethyl)-2-methylpropoxy)-6-methyl-4-oxo-3,4-di hydroquinazolin-2-yl)phenoxy)acetamide (565 mg, 1.13 mmol) and anhydrous THF (11.3 mL) under inert atmosphere and cooled down to 0° C. Potassium tert-butoxide in THF (2.8 mL, 1.6 M) was added dropwise to the reaction mixture which was slowly warmed up and stirred at 25° C. for 18 h. After 18 h, LC-MS showed >90% conversion to a major UV peak with the desired m/z. The reaction mixture was poured into sat. aq. NaHCO$_3$(50 mL) and extracted with EtOAc (2×50 mL). The combined organic layers were washed with sat. aq. NaCl, dried over Na$_2$SO$_4$ and evaporated under reduced pressure. The crude residue was purified by flash column chromatography (0% to 15% MeOH in DCM, R$_f$=0.32 @ 10% MeOH in DCM) to afford N-(tert-butyl)-2-(3-(6-methyl-5-((3-methyloxetan-3-yl)methoxy)-4-oxo-3,4-dihydroquinazolin-2-yl)phenoxy)acetamide (424 mg, 81%) as a thick orange oil that slowly solidifies at room temperature. MS (ES+) m/e 466 (M+H)$^+$.

Step 7

2-(3-(4-((1H-Pyrazol-3-yl)amino)-6-methyl-5-((3-methyloxetan-3-yl)methoxy)-quinazolin-2-yl)phenoxy)-N-(tert-butyl)acetamide Bis Trifluoroacetic Acid Salt

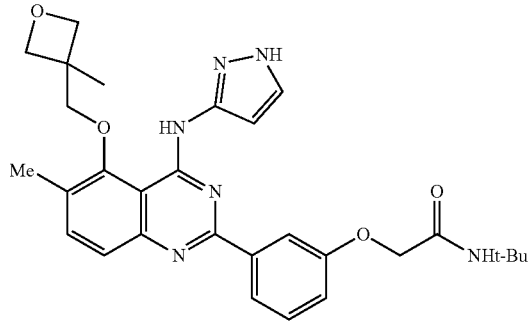

Following the synthetic sequence described for Example 266, step 6, 2-(3-(4-((1H-pyrazol-3-yl)amino)-6-methyl-5-((3-methyloxetan-3-yl)methoxy)quinazolin-2-yl)phenoxy)-N-(tert-butyl)acetamide bis trifluoroacetic acid salt was obtained (14.2 mg, 9%) as a bright yellow powder. MS (ES+) m/e 531 (M+H)$^+$.

Example 275

2-(3-(4-((1H-Pyrazol-4-yl)amino)-6-methyl-5-((3-methyloxetan-3-yl)methoxy)-quinazolin-2-yl)phenoxy)-N-(tert-butyl)acetamide Bis Trifluoroacetic Acid Salt

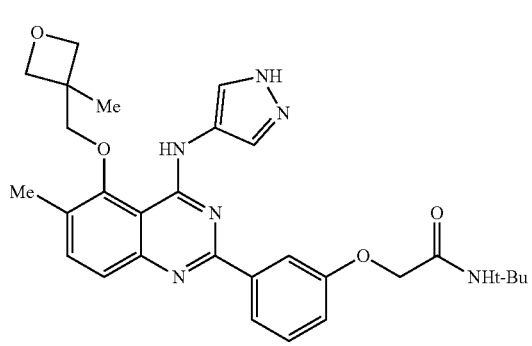

Following the synthetic sequence described for Example 274, 1-(tetrahydro-2H-pyran-2-yl)-1H-pyrazol-4-amine was used in step 7 and THP deprotection was carried out similarly (2 h reaction time) to afford 2-(3-(4-((1H-pyrazol-4-yl)amino)-6-methyl-5-((3-methyloxetan-3-yl)methoxy)quinazolin-2-yl)phenoxy)-N-(tert-butyl)-acetamide bis trifluoroacetic acid salt (12.8 mg, 8%) as a bright yellow powder. MS (ES+) m/e 531 (M+H)$^+$.

Example 276

2-(3-(4-((1H-Pyrazol-4-yl)amino)-6-(pyrrolidin-1-yl)quinazolin-2-yl)phenoxy)-N-(tert-butyl)acetamide Tris Trifluoroacetic Acid Salt

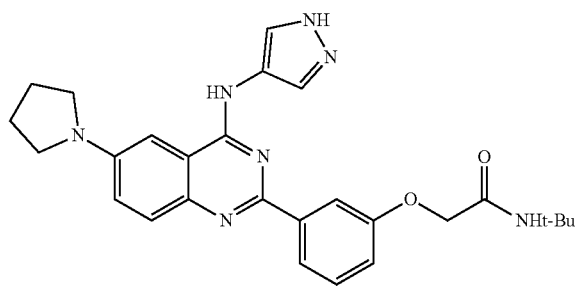

Step 1

2-Nitro-5-(pyrrolidin-1-yl)benzamide

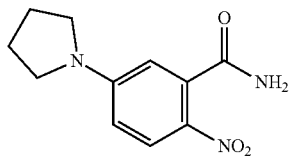 [SMILES: NC(=O)c1cc(N2CCCC2)ccc1[N+](=O)[O-]]

To a solution of 5-chloro-2-nitrobenzamide (5.0 g, 24.9 mmol) in DMF (25 mL) was added pyrrolidine (4.6 mL, 54.8 mmol). The reaction was stirred at 110° C. for 2.5 hours. LCMS showed that starting materials were consumed completely and the desired compound was the major product. the reaction mixture was poured into water (150 mL) and the precipitated solid was filtered and washed with water (1×100 mL). The solid was dried at 50° C. for 24 hours to afford 2-nitro-5-(pyrrolidin-1-yl)benzamide (5.18 g, 88%) as a bright yellow powder. MS (ES+) m/e 277 (M+H+MeCN)+. $^1$H NMR (500 MHz, DMSO-$d_6$) δ 7.97 (d, J=9.3 Hz, 1H), 7.81 (s, 1H), 7.49 (s, 1H), 6.59 (dd, J=9.3, 2.8 Hz, 1H), 6.43 (d, J=2.7 Hz, 1H), 3.44-3.33 (m, 4H), 2.04-1.88 (m, 4H).

Step 2

2-Amino-5-(pyrrolidin-1-yl)benzamide

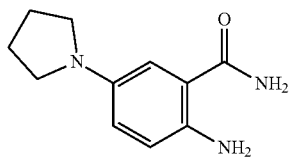

A 500 mL round-bottom flask equipped with a Teflon septum and magnetic stir bar was charged with 2-nitro-5-(pyrrolidin-1-yl)benzamide (5.1 g, 21.7 mmol) and absolute ethanol (150 mL). The reaction flask was placed under a nitrogen atmosphere before Pd/C (510 mg, 10% w/w) was added. After 5 minutes at 90° C., a solution of ammonium formate (4.1 g, 65.0 mmol) in water (4.3 mL) was added over 1 minute. The reaction mixture was then stirred for 2 h at 90° C., after which LC-MS showed complete consumption of the starting material and a major UV peak with the desired m/z. The reaction mixture was cooled down to room temperature and filtered through Celite using MeOH. Volatiles were evaporated under reduced pressure and the crude residue was triturated with MeCN to afford 2-amino-5-(pyrrolidin-1-yl)benzamide (1.13 g, 25%) as a dark brown powder. MS (ES+) m/e 206 (M+H)+. $^1$H NMR (500 MHz, DMSO-$d_6$) δ 7.71 (s, 1H), 7.02 (s, 1H), 6.69 (d, J=2.2 Hz, 1H), 6.59 (s, 1H), 6.58 (d, J=2.4 Hz, 1H), 5.71 (s, 2H), 3.12 (t, J=6.4 Hz, 4H), 1.94-1.85 (m, 5H).

Step 3

3-(2-(tert-Butylamino)-2-oxoethoxy)-N-(2-carbamoyl-4-(pyrrolidin-1-yl)-phenyl)benzamide

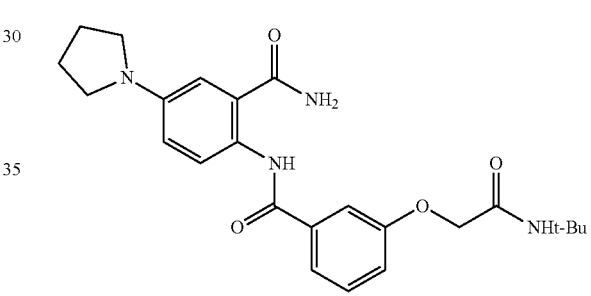

To a stirred solution of 2-amino-5-(pyrrolidin-1-yl)benzamide (500 mg, 2.44 mmol) and 3-(2-(tert-butylamino)-2-oxoethoxy)benzoic acid (673 mg, 2.68 mmol) in DMF (6.1 mL) was added DIPEA (1.3 mL, 7.3 mmol) and the reaction mixture was stirred at room temperature for 5 minutes. 1-Propanephosphonic anhydride (2.7 mL, 4.39 mmol) was added dropwise to the reaction mixture as a 50% w/w solution in DMF. The reaction mixture was stirred for an additional 60 minutes at room temperature. Upon completion of the reaction, as judged by LC-MS, the reaction mixture was diluted with water and a dark solid was filtered out and taken up in acetonitrile. The aqueous phase of the filtrate was further extracted with 10% i-PrOH in EtOAc (2×50 mL). The combined organic layers were washed with sat. aq. NaCl (1×20 mL), dried over $Na_2SO_4$ and filtered. Volatiles were evaporated and the crude residue was purified by flash column chromatography (15% to 100% EtOAc in hexane, $R_f$=0.79 @ 100% EtOAc) to afford 3-(2-(tert-butylamino)-2-oxoethoxy)-N-(2-carbamoyl-4-(pyrrolidin-1-yl)phenyl)benzamide (675 mg, 39%). The material was used in the next step without further purification. MS (ES+) m/e 439 (M+H)+.

Step 4

N-(tert-butyl)-2-(3-(4-oxo-6-(pyrrolidin-1-yl)-3,4-dihydroquinazolin-2-yl)-phenoxy)acetamide

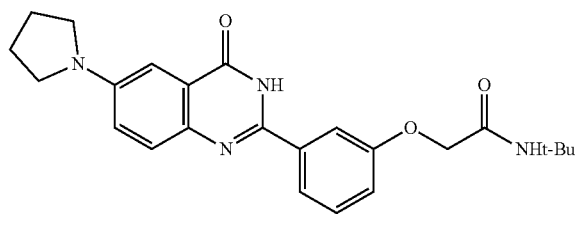

A 0.5 N aq. NaOH solution (31 mL) was added to a vial containing 3-(2-(tert-butylamino)-2-oxoethoxy)-N-(2-carbamoyl-4-(pyrrolidin-1-yl)phenyl)benzamide (675 mg, 60% purity) and the reaction mixture was heated up to 70° C. for 4 h after which, LC-MS showed that starting material had been partially cyclized to the desired product. Heating was extended for 3 h until completion of the reaction. The reaction mixture was cooled down to room temperature and acidified to pH 2 with 12 N hydrochloric acid. The precipitate was filtered and dried to afford of N-(tert-butyl)-2-(3-(4-oxo-6-(pyrrolidin-1-yl)-3,4-dihydroquinazolin-2-yl)phenoxy)acetamide (307 mg, 79%) as a yellow-brown powder. MS (ES+) m/e 421 (M+H)$^+$.

Step 5

2-(3-(4-((1H-pyrazol-4-yl)amino)-6-(pyrrolidin-1-yl)quinazolin-2-yl)-phenoxy)-N-(tert-butyl)acetamide Tris Trifluoroacetic Acid Salt

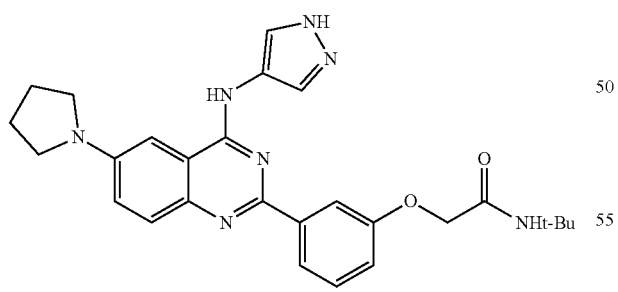

Following the synthetic sequence described for Example 261, step 6, 2-(3-(4-((1H-pyrazol-4-yl)amino)-6-(pyrrolidin-1-yl)quinazolin-2-yl)phenoxy)-N-(tert-butyl)acetamide tris trifluoroacetic acid salt was obtained (7.8 mg, 4%) as a dark orange powder. MS (ES+) m/e 486 (M+H)$^+$.

Example 277

2-(3-(4-((1H-Pyrazol-4-yl)amino)-6-(dimethylamino)quinazolin-2-yl)phenoxy)-N-(tert-butyl)acetamide Tris Trifluoroacetic Acid Salt

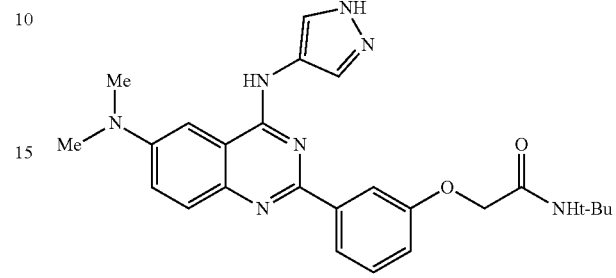

Step 1

5-(Dimethylamino)-2-nitrobenzamide

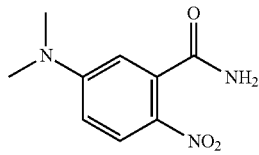

Following the synthetic sequence described for Example 276, step 1, starting from dimethylamine hydrochloride (5.7 g, 69.8 mmol) and DIPEA (6.1 mL, 34.9 mmol), 5-(dimethylamino)-2-nitrobenzamide was obtained (2.7 g, 75%) as a yellow-brown powder. MS (ES+) m/e 210 (M+H)$^+$. $^1$H NMR (500 MHz, DMSO-d$_6$) δ 7.97 (d, J=9.4 Hz, 1H), 7.83 (s, 1H), 7.50 (s, 1H), 6.75 (dd, J=9.4, 2.9 Hz, 1H), 6.58 (d, J=2.8 Hz, 1H), 3.08 (s, 6H).

Step 2

2-Amino-5-(dimethylamino)benzamide

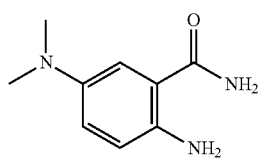

Following the synthetic sequence described for Example 276, step 2, 2-amino-5-(dimethylamino)benzamide was obtained (2.08 g, 88%) as a yellow-green powder. MS (ES+) m/e 178 (M+H)$^+$.

Step 3

3-(2-(tert-Butylamino)-2-oxoethoxy)-N-(2-carbamoyl-4-(dimethylamino)-phenyl)benzamide

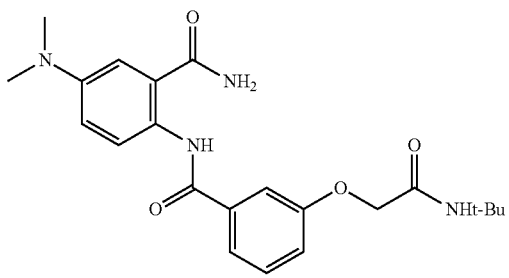

Following the synthetic sequence described for Example 276, step 3, 3-(2-(tert-butylamino)-2-oxoethoxy)-N-(2-carbamoyl-4-(dimethylamino)phenyl)benzamide was obtained (885 mg, 85%) as a yellow powder. MS (ES+) m/e 413 (M+H)$^+$.

Step 4

N-(tert-butyl)-2-(3-(6-(dimethylamino)-4-oxo-3,4-dihydroquinazolin-2-yl)-phenoxy)acetamide

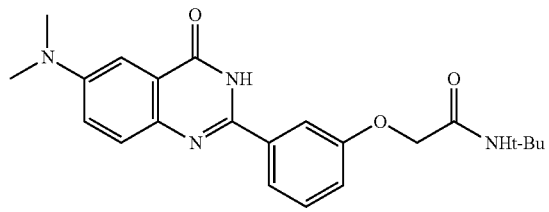

Following the synthetic sequence described for Example 276, step 4, N-(tert-butyl)-2-(3-(6-(dimethylamino)-4-oxo-3,4-dihydroquinazolin-2-yl)phenoxy)acetamide was obtained (286 mg, 34%) as a yellow powder. MS (ES+) m/e 395 (M+H)$^+$.

Step 5

2-(3-(4-((1H-pyrazol-4-yl)amino)-6-(dimethylamino)quinazolin-2-yl)-phenoxy)-N-(tert-butyl)acetamide Tris Trifluoroacetic Acid Salt

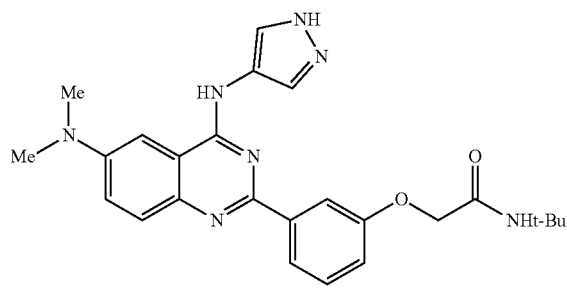

Following the synthetic sequence described for Example 276, step 6, 2-(3-(4-((1H-pyrazol-4-yl)amino)-6-(dimethylamino)quinazolin-2-yl)phenoxy)-N-(tert-butyl)acetamide tris trifluoroacetic acid salt was obtained (14.6 mg, 16%) as a bright orange powder. MS (ES+) m/e 460 (M+H)$^+$.

Example 278

2-(3-(4-((1H-Pyrazol-4-yl)amino)-6-ethoxy-7-methylquinazolin-2-yl)-phenoxy)-N-(tert-butyl)acetamide Bis Trifluoroacetic Acid Salt

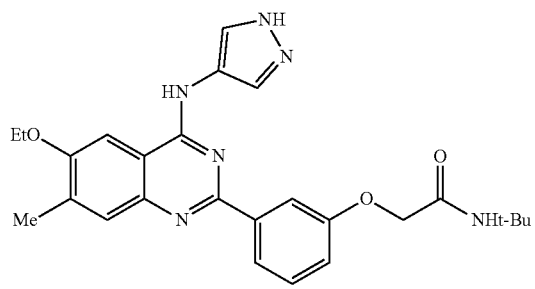

Step 1

Ethyl 3-fluoro-4-methyl-5-nitrobenzoate

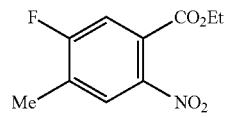

To a mixture of 3-fluoro-4-methylbenzoic acid (3.7 g, 24.0 mmol) in 18N aq. H$_2$SO$_4$ (31 mL) cooled down to 0° C. was added 70% aq. HNO$_3$ (2.14 mL, 48.0 mmol) dropwise. Once the addition of HNO$_3$ was complete, the mixture was allowed to warm to room temperature and stirred for 1 h and LC-MS confirmed the disappearance of the starting material with a new major peak. The mixture was cooled down to 0° C. once again and EtOH (62 mL) was added carefully. The ice bath was removed and the mixture was heated to 100° C. and stirred for about 5 hours. The mixture was carefully diluted into cold water. Solid NaHCO$_3$ was added until pH>8 and the aqueous layer was extracted with EtOAc (3×100 mL). The combined organic layers were washed with sat. aq. NaCl (1×100 mL), dried over Na$_2$SO$_4$, filtered through a pad of silica and concentrated under reduced pressure. The crude residue was purified by flash column chromatography (1% to 20% EtOAc in hexane, R$_f$=0.55 @ 20% EtOAc in hexane) to give ethyl 3-fluoro-4-methyl-5-nitrobenzoate (4.55 g, 83%) of as a yellow liquid. $^1$H NMR (500 MHz, Chloroform-d) δ 7.81 (d, J=6.3 Hz, 1H), 7.34 (d, J=8.6 Hz, 1H), 4.38 (q, J=7.1 Hz, 2H), 2.38 (d, J=2.1 Hz, 3H), 1.35 (t, J=7.2 Hz, 3H).

Step 2

Ethyl 5-ethoxy-4-methyl-2-nitrobenzoate

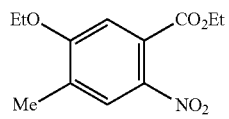

To a solution of ethyl 5-fluoro-4-methyl-2-nitrobenzoate (4.55 g, 20.0 mmol) in THF (100 mL) at −78° C. was added EtONa (1.50 g, 22.0 mmol). The reaction mixture was stirred and left in the dry ice bath to warm up overnight to room temperature. After 14 h, LC-MS showed 85:15 product to starting material ratio. The reaction mixture was quenched with 1N aq. HCl (100 mL) and extracted with EtOAc (3×75 mL). The combined organic layers were washed with sat. aq. NaCl (100 mL), dried over $Na_2SO_4$, filtered and evaporated under reduced pressure. The crude residue was purified by flash column chromatography (5% to 25% EtOAc in hexane, $R_f$=0.38 @ 20% EtOAc in hexane) to afford ethyl 5-ethoxy-4-methyl-2-nitrobenzoate (3.82 g, 75%) as a yellow crystalline solid. $^1$H NMR (500 MHz, Chloroform-d) δ 7.84 (d, J=0.9 Hz, 1H), 6.94 (s, 1H), 4.38 (q, J=7.2 Hz, 2H), 4.14 (q, J=7.0 Hz, 2H), 2.28 (s, 3H), 1.48 (t, J=7.0 Hz, 3H), 1.35 (t, J=7.2 Hz, 3H).

Step 3

Ethyl 2-amino-5-ethoxybenzoate

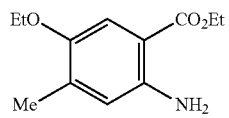

Ethyl 5-ethoxy-2-nitrobenzoate (3.82 g, 15.1 mmol) and ammonium chloride (3.23 g, 60.4 mmol) in water (21.0 mL) and ethanol (21.0 mL) were heated to 85° C. for 5 minutes before iron powder (3.37 g, 60.4 mmol) was added. The reaction mixture was heated to 85° C. for 60 min, after which TLC (SM $R_f$=0.38, pdt $R_f$=0.52 @ 20% EtOAc in hexanes) showed that the reaction was complete. The reaction mass was cooled to 30° C. and filtered through a celite bed; the bed was washed with methanol thoroughly and the solvent was evaporated. Water (50 mL) was added and it was extracted with EtOAc (3×50 mL). The combined organic layers were washed with sat. aq. NaCl (100 mL), filtered through a pad of silica and concentrated under reduced pressure. The crude residue was purified by flash column chromatography (2% to 20% EtOAc in hexane) to afford ethyl 2-amino-5-ethoxybenzoate (3.11 g, 92%) as a pale yellow powder. MS (ES+) m/e 265 (M+H+MeCN)$^+$. $^1$H NMR (500 MHz, Chloroform-d) δ 7.28 (s, 1H), 6.56 (d, J=0.9 Hz, 1H), 4.35 (q, J=7.1 Hz, 2H), 3.99 (q, J=7.0 Hz, 2H), 2.21 (d, J=0.9 Hz, 3H), 1.44-1.38 (m, 6H).

Step 4

6-Ethoxy-7-methylquinazoline-2,4-diol

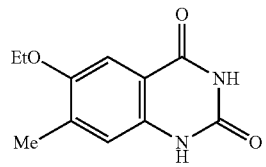

A solution of sodium hydroxide (3.89 g, 97 mmol) in water (75 mL) was added to a solution of ethyl 2-amino-5-ethoxy-4-methylbenzoate (3.10 g, 13.9 mmol) in EtOH (56 mL) and the reaction mixture was refluxed for 3 h, at which point LC-MS showed complete conversion to the desired anthranilic acid intermediate. The reaction mixture was cooled down to room temperature and evaporated to dryness. The crude residue was taken up in water (56 mL) and acidified to pH 5 with 6 N aq. HCl. Acetic acid (1.20 mL, 20.8 mmol) was added followed by a solution of potassium cyanate (2.82 g, 34.7 mmol in 35 mL) over an hour. The reaction mixture was stirred for an extra hour at room temperature once the addition was complete. LCMS showed that starting material had disappeared and that the desired intermediate was the major peak. The reaction mixture was cooled in an ice bath before sodium hydroxide pellets were added until pH>12 while maintaining the internal temperature below 50° C. (the solution went clear then a creamy solid formed and LC-MS showed some conversion to the desired quinazoline-2,4-diol). The reaction was heated up to 50° C. and stirred overnight. LC-MS showed complete conversion to the quinazoline-2,4-diol. The suspension was cooled to 0-5° C. and the precipitate was collected by filtration and washed twice with water (15 mL). The solid was poured in water (250 mL) and was acidified with concentrated aq. HCl until pH<2. The solid was collected by filtration, washed twice with water (50 mL) and dried at 50° C. under vacuum for 24 hours to provide 6-ethoxy-7-methylquinazoline-2,4-diol (2.54 g, 83%) as an off-white powder. MS (ES+) m/e 262 (M+H+MeCN)$^+$. $^1$H NMR (500 MHz, DMSO-d$_6$) δ 11.18 (d, J=1.7 Hz, 1H), 10.97 (d, J=1.9 Hz, 1H), 7.24 (s, 1H), 6.96 (s, 1H), 4.04 (q, J=6.9 Hz, 2H), 2.21 (s, 3H), 1.35 (t, J=6.9 Hz, 3H).

Step 5

2,4-Dichloro-6-ethoxy-7-methylquinazoline

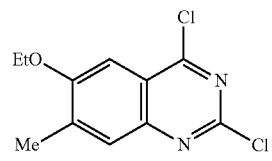 [SMILES: CCOc1cc2c(Cl)nc(Cl)nc2cc1C]

To a suspension of 6-ethoxy-7-methylquinazoline-2,4-diol (2.54 g, 11.6 mmol) in POCl$_3$ (10.8 mL, 115.5 mmol) at 70° C. was added DIPEA (4.4 mL, 25.4 mmol) and the reaction mixture was stirred at that temperature for 20 min. After 20 min, LCMS showed 2:1 starting material to product so more DIPEA (4.4 mL, 25.4 mmol) was added to the reaction mixture. After 20 more minutes at 70° C., LC-MS showed 1:5 starting material to product so one last portion of DIPEA (2.2 mL, 12.7 mmol) was added and the reaction mixture was stirred at 70° C. for 30 min. The heating was stopped and the reaction vial was stirred while cooling down to room temperature very slowly overnight. After 14 h, LC-MS showed complete conversion with less than 10% of mono-chloro intermediate. The reaction mixture was slowly added, with stirring, to a mixture of cracked ice and excess solid sodium bicarbonate. The aqueous phase was extracted with EtOAc (3×200 mL) and the combined organic layers were washed with sat. aq. NaCl, dried over $Na_2SO_4$ and filtered through a large pad of silica, eluting with EtOAc. The filtrate was evaporated under reduced pressure to afford 2,4-dichloro-6-ethoxy-7-methylquinazoline (1.80 g, 61%) as pale yellow flakes that were used in the next step without further purification. MS (ES+) m/e 298 ($^{35}$Cl M+H)$^+$, 300 ($^{37}$Cl M+H)$^+$. $^1$H NMR (500 MHz, Chloroform-d) δ 7.74 (d, J=1.1 Hz, 1H), 7.30 (s, 1H), 4.22 (q, J=7.0 Hz, 2H), 2.46 (d, J=1.0 Hz, 3H), 1.55 (t, J=6.9 Hz, 3H).

Step 6

2-Chloro-6-ethoxy-7-methyl-N-(1-(tetrahydro-2H-pyran-2-yl)-1H-pyrazol-4-yl)quinazolin-4-amine

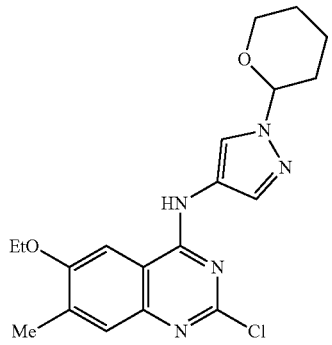

To a solution of 2,4-dichloro-6-ethoxy-7-methylquinazoline (350 mg, 1.36 mmol) in DMF (5.4 mL) were successively added DIPEA (474 μL, 2.72 mmol) and 1-(tetrahydro-2H-pyran-2-yl)-1H-pyrazol-4-amine (228 mg, 1.36 mmol). The reaction was stirred at 25° C. for 15 hours. LCMS showed that starting materials were consumed completely and the desired compound was the major product. the reaction mixture was poured into water (75 mL) and the aqueous phase was extracted with EtOAc (3×40 mL). The organic layers were washed with sat. aq. NaCl, dried over $Na_2SO_4$, filtered through a pad of silica and the solvents were evaporated under reduced pressure. The crude residue was triturated with MTBE to give 2-chloro-6-ethoxy-7-methyl-N-(1-(tetrahydro-2H-pyran-2-yl)-1H-pyrazol-4-yl)-quinazolin-4-amine (403 mg, 76%) as a pale pink powder. MS (ES+) m/e 388 ($^{35}$Cl M+H)$^+$, 390 ($^{37}$Cl M+H)$^+$.

Step 7

2-(3-(4-((1H-pyrazol-4-yl)amino)-6-ethoxy-7-methylquinazolin-2-yl)phenoxy)-N-(tert-butyl)acetamide Bis Trifluoroacetic Acid Salt

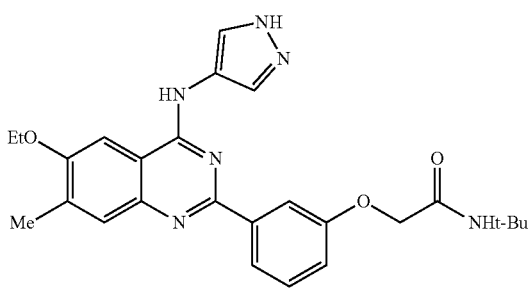

2-Chloro-6-ethoxy-7-methyl-N-(1-(tetrahydro-2H-pyran-2-yl)-1H-pyrazol-4-yl)quinazolin-4-amine (120 mg, 309 μmol), N-(tert-butyl)-2-(3-(4,4,5,5-tetramethyl-1,3,2-dioxaborolan-2-yl)phenoxy)acetamide (129 mg, 387 μmol) and Pd(dppf)Cl$_2$·CH$_2$Cl$_2$ (38 mg, 46 μmol) were weighed out in a microwave vial equipped with a stirbar. 1,2-Dimethoxyethane (12.4 mL) was added and the reaction mixture was purged with N$_2$ for 2 minutes before a 0.33 M aqueous solution of Na$_2$CO$_3$ (3.1 mL) was added. The reaction mixture was purged for 3 more minutes and the vial was sealed. The vial was irradiated for 60 min at 120° C. in a microwave oven. LCMS showed that starting material had been completely consumed. Volatiles were removed under reduced pressure and the residue was purified by flash column chromatography (20% to 100% EtOAc in hexane, R$_f$=0.50 @ 100% EtOAc). The purified material was dissolved in 10 mL of 4.0 N HCl in dioxane and stirred at room temperature for 30 min. LCMS showed that the product had been completely deprotected so volatiles were evaporated under reduced pressure. The crude residue was purified by HPLC to provide 2-(3-(4-(1H-pyrazol-4-yl)amino)-6-ethoxy-7-methylquinazolin-2-yl)phenoxy)-N-(tert-butyl)acetamide bis-trifluoroacetic acid salt (79 mg, 36%) as a bright yellow powder. MS (ES+) m/e 475 (M+H)$^+$. $^1$H NMR (500 MHz, DMSO-d$_6$) δ 8.17 (s, 2H), 7.98 (s, 1H), 7.90 (d, J=7.8 Hz, 1H), 7.86 (s, 1H), 7.80 (s, 1H), 7.62 (s, 1H), 7.59 (d, J=7.8 Hz, 1H), 7.26-7.21 (m, 1H), 4.56 (s, 2H), 4.27 (qd, J=7.0, 2.2 Hz, 2H), 2.40 (d, J=1.9 Hz, 3H), 1.49 (td, J=7.0, 1.7 Hz, 3H), 1.29 (s, 9H).

Example 279

2-(3-(4-((1H-Pyrazol-3-yl)amino)-6-ethoxy-7-methylquinazolin-2-yl)phenoxy)-N-(tert-butyl)acetamide Bis Trifluoroacetic Acid Salt

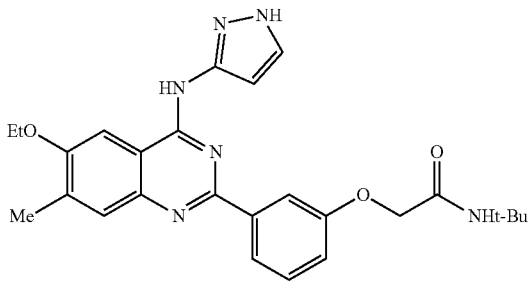

Following the synthetic sequence described for Example 278, 1-((2-(trimethylsilyl)ethoxy)methyl)-1H-pyrazol-3-amine was used in step 7 and SEM deprotection was carried out similarly (16 h reaction time) to afford 2-(3-(4-((1H-pyrazol-3-yl)-amino)-6-methyl-5-((3-methyloxetan-3-yl)methoxy)quinazolin-2-yl)phenoxy)-N-(tert-butyl)acetamide bis trifluoroacetic acid salt (42.9 mg, 32%) as a bright yellow powder. MS (ES+) m/e 531 (M+H)+.

Example 280

2-(3-(4-((1H-Pyrazol-4-yl)amino)-7-chloro-6-ethoxyquinazolin-2-yl)phenoxy)-N-(tert-butyl)acetamide Bis Trifluoroacetic Acid Salt

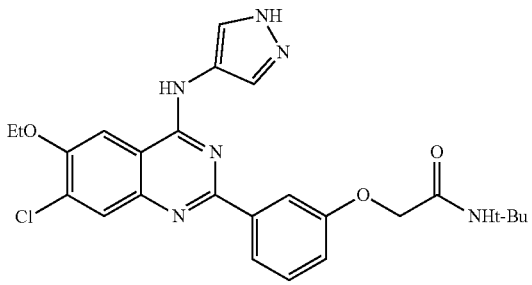

Step 1

Ethyl 4-chloro-5-fluoro-nitrobenzoate

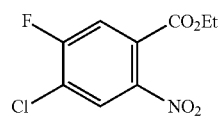

Following the synthetic sequence described for Example 278, step 1, 4-chloro-3-fluorobenzoic acid (2.0 g, 11.5 mmol), HNO$_3$ (1.53 mL, 34.4 mmol), 18N aq. H$_2$SO$_4$ (14.7 mL, 275 mmol) and EtOH (29.4 mL) were used to afford ethyl 4-chloro-5-fluoro-nitrobenzoate (2.80 g, 68%) as a yellow oil. $^1$H NMR (500 MHz, Chloroform-d) δ 8.04 (d, J=6.2 Hz, 1H), 7.51 (d, J=8.0 Hz, 1H), 4.40 (q, J=7.2 Hz, 2H), 1.36 (t, J=7.2 Hz, 3H).

Step 2

Ethyl 4-chloro-5-ethoxy-2-nitrobenzoate

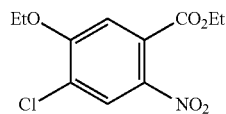

Following the synthetic sequence described for Example 278, step 2, ethyl 4-chloro-5-ethoxy-2-nitrobenzoate was obtained (1.88 g, 61%) as a yellow powder. $^1$H NMR (500 MHz, Chloroform-d) δ 8.09 (s, 1H), 7.07 (s, 1H), 4.40 (q, J=7.2 Hz, 2H), 4.22 (q, J=7.0 Hz, 2H), 1.53 (t, J=7.0 Hz, 3H), 1.36 (t, J=7.2 Hz, 3H).

Step 3

Ethyl 2-amino-4-chloro-5-ethoxybenzoate

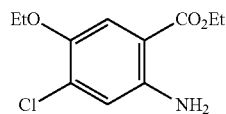

Following the synthetic sequence described for Example 278, step 3, ethyl 2-amino-4-chloro-5-ethoxybenzoate was obtained (1.37 g, 82%) as a yellow oil which solidified upon standing. MS (ES+) m/e 285 ($^{35}$Cl M+MeCN+H)+, 287 ($^{37}$Cl M+MeCN+H)+.

Step 4

7-Chloro-6-ethoxyquinazoline-2,4-diol

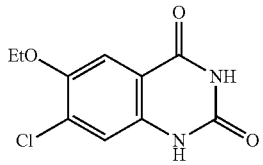

Following the synthetic sequence described for Example 278, step 4, 7-chloro-6-ethoxyquinazoline-2,4-diol was obtained (1.17 g, 88%) as an off-white powder. MS (ES+) m/e 282 ($^{35}$Cl M+MeCN+H)+, 284 ($^{37}$Cl M+MeCN+H)+. $^1$H NMR (500 MHz, DMSO-d$_6$) δ 11.24 (s, 2H), 7.44 (s, 1H), 7.23 (s, 1H), 4.14 (q, J=6.9 Hz, 2H), 1.36 (t, J=6.9 Hz, 3H).

301

Step 5

2,4,7-Trichloro-6-ethoxyquinazoline

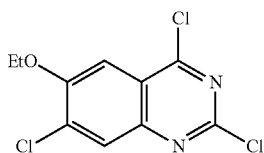 [SMILES: CCOc1cc2c(Cl)nc(Cl)nc2cc1Cl]

Following the synthetic sequence described for Example 278, step 5, crude 2,4,7-trichloro-6-ethoxyquinazoline was obtained (1.55 g, 99%) as a light orange powder. MS (ES+) m/e 318 ($^{35}$Cl/$^{35}$Cl/$^{35}$Cl M+MeCN+H)$^+$, 320 ($^{35}$Cl/$^{35}$Cl/$^{37}$Cl M+MeCN+H)$^+$, 320 ($^{35}$Cl/$^{37}$Cl/$^{37}$Cl M+MeCN+H)$^+$.

Step 6

2-Chloro-6-ethoxy-7-methyl-N-(1-(tetrahydro-2H-pyran-2-yl)-1H-pyrazol-4-yl) quinazolin-4-amine

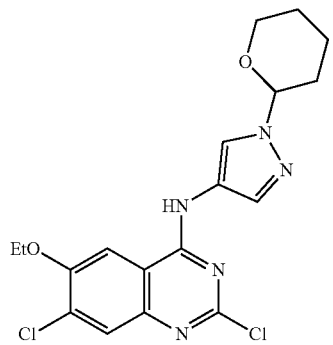 [SMILES: CCOc1cc2c(Nc3cnn(C4CCCCO4)c3)nc(Cl)nc2cc1Cl]

Following the synthetic sequence described for Example 278, step 6, 2-chloro-6-ethoxy-7-methyl-N-(1-(tetrahydro-2H-pyran-2-yl)-1H-pyrazol-4-yl)quinazolin-4-amine was obtained (94 mg, 18%) as a dark green thick oil. MS (ES+) m/e 408 ($^{35}$Cl/$^{35}$Cl M+H)$^+$, 410 ($^{35}$Cl/$^{37}$Cl M+H)$^+$.

Step 7

2-(3-(4-((1H-pyrazol-4-yl)amino)-7-chloro-6-ethoxyquinazolin-2-yl)phenoxy)-N-(tert-butyl)acetamide Bis Trifluoroacetic Acid Salt

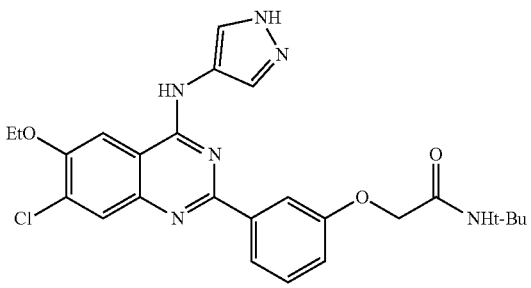

302

Following the synthetic sequence described for Example 278, step 7, 2-(3-(4-((1H-pyrazol-4-yl)amino)-7-chloro-6-ethoxyquinazolin-2-yl)phenoxy)-N-(tert-butyl)acetamide bis-trifluoroacetic acid salt was obtained (25.0 mg, 15%) as a bright yellow powder. MS (ES+) m/e 495 ($^{35}$Cl M+H)$^+$, 497 ($^{37}$Cl M+H)$^+$.

Example 281

2-(3-(4-((1H-Pyrazol-4-yl)amino)-7-chloro-6-ethoxyquinazolin-2-yl)phenoxy)-N-(tert-butyl)acetamide Bis Trifluoroacetic Acid Salt

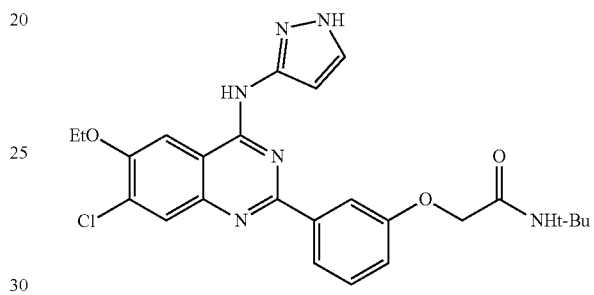

Following the synthetic sequence described for Example 279, 1-((2-(trimethylsilyl)-ethoxy)methyl)-1H-pyrazol-3-amine was used in step 7 and SEM deprotection was carried out similarly (16 h reaction time) to afford 2-(3-(4-((1H-pyrazol-3-yl)amino)-7-chloro-6-ethoxyquinazolin-2-yl)phenoxy)-N-(tert-butyl)acetamide bis-trifluoroacetic acid salt (26.8 mg, 13%) as a bright yellow powder. MS (ES+) m/e 495 ($^{35}$Cl M+H)$^+$, 497 ($^{37}$Cl M+H)$^+$.

Example 282

2-(3-(4-((1H-Pyrazol-4-yl)amino)-6-(trifluoromethoxy)quinazolin-2-yl)-phenoxy)-N-(tert-butyl)acetamide Bis-Trifluoroacetic Acid Salt

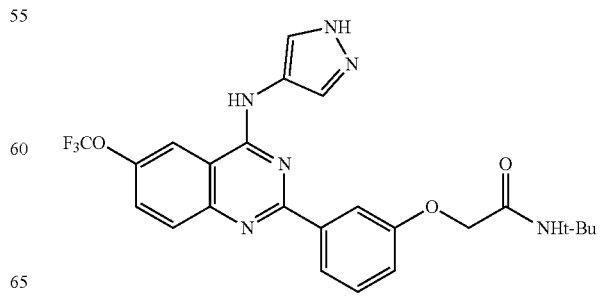

Step 1

6-(Trifluoromethoxy)quinazoline-2,4-diol

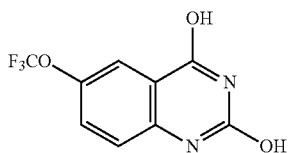 [SMILES: Oc1nc(O)c2cc(OC(F)(F)F)ccc2n1]

To a stirred solution of 2-amino-5-(trifluoromethoxy) benzoic acid (10.0 g, 45.2 mmol) and acetic acid (3.88 mL, 67.8 mmol) in water (175 mL) was added over 1 h an aqueous solution of potassium cyanate (9.17 g, 113.1 mmol in 100 mL). The reaction mixture was stirred for an extra hour at room temperature once the addition was complete. LCMS showed that starting material had disappeared and that the desired compound was the major peak. The reaction mixture was cooled to 0° C. in an ice bath before sodium hydroxide pellets were added until pH>12 while maintaining the internal temperature below 50° C. The suspension was cooled to 0-5° C. and the precipitate was collected by filtration and washed twice with water (20 mL). The solid was poured in water (100 mL) and was acidified with concentrated aq. HCl until pH<2. The solid was collected by filtration, washed with water (20 mL) and dried at 50° C. under vacuum for 24 hours to provide 6-(trifluoromethoxy) quinazoline-2,4-diol (9.25 g, 83%) as a white powder that was used directly in the next step without further purification. $^1$H NMR (500 MHz, DMSO-$d_6$) δ 11.52 (s, 1H), 11.47-11.26 (m, 1H), 7.74 (d, J=2.7 Hz, 1H), 7.68 (dd, J=8.9, 2.8 Hz, 1H), 7.27 (d, J=8.9 Hz, 1H).

Step 2

2,4-Dichloro-6-(trifluoromethoxy)quinazoline

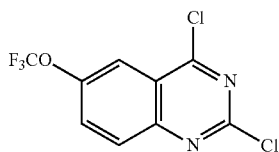 [SMILES: FC(F)(F)Oc1ccc2nc(Cl)nc(Cl)c2c1]

To a suspension of 5-trifluromethoxyquinazoline-2,4-diol (3.00 g, 12.2 mmol) in POCl$_3$ (11.4 mL, 121.9 mmol) at 70° C. was added DIPEA (2.12 mL, 12.2 mmol) and the reaction mixture was stirred at that temperature for 1 h. After 1 h and 2 h, 1 additional equivalent of DIPEA was added dropwise (for a total of 3 eq, 6.37 mL) and the reaction mixture was maintained at 70° C. for a total of 3 h. LCMS showed almost complete conversion (less than 10% combined of starting material and mono-chloro intermediate) so the reaction mixture was cooled down to room temperature and then evaporated to dryness under reduced pressure. The residue was diluted with sat. aq. NaHCO$_3$ at 0° C. to pH>10. The mixture was extracted with EtOAc (5×20 mL). The organic layers were dried over Na$_2$SO$_4$, filtered, and concentrated under reduced pressure. The crude residue was azeotroped once with toluene before being purified by flash column chromatography (1% to 25% EtOAc in hexane) to give 2,4-dichloro-6-(trifluoromethoxy)quinazoline (1.72 g, 50%) as a pale yellow solid. $^1$H NMR (500 MHz, Chloroform-d) δ 8.08 (d, J=9.3 Hz, 1H), 8.07 (d, J=1.1 Hz, 1H), 7.85 (ddd, J=9.2, 2.7, 0.8 Hz, 1H).

Step 3

2-Chloro-6-(trifluoromethoxy)-N-(1-(tetrahydro-2H-pyran-2-yl)-1H-pyrazol-4-yl)quinazolin-4-amine

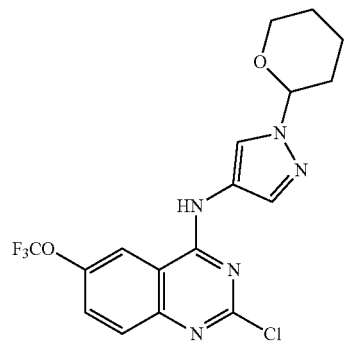 [SMILES: FC(F)(F)Oc1ccc2nc(Cl)nc(Nc3cnn(C4CCCCO4)c3)c2c1]

To a solution of 2,4-dichloro-6-trifluoromethoxyquinazoline (200 mg, 0.71 mmol) in DMF (1.4 mL) were successively added DIPEA (250 µL, 1.4 mmol) and 1-(tetrahydro-2H-pyran-2-yl)-1H-pyrazol-4-amine (118 mg, 0.71 mmol). The reaction was stirred at 50° C. for 3 hours. LCMS showed that starting materials were consumed completely and the desired compound was the major product. Water (25 mL) was added to the reaction mixture with stirring and the precipitate was extracted with 10% iPrOH in EtOAc (2×35 mL). The combined organic layers were washed with sat. aq. NaCl (2×25 mL), dried over Na$_2$SO$_4$, filtered and the solvents were evaporated under reduced pressure. The crude residue was purified by flash column chromatography (10% to 85% EtOAc in hexane, R$_f$=0.35 @ 50% EtOAc in hexane) to give 2-chloro-6-(trifluoromethoxy)-N-(1-(tetrahydro-2H-pyran-2-yl)-1H-pyrazol-4-yl)quinazolin-4-amine (174 mg, 60%) as a peach powder. MS (ES+) m/e 414 ($^{35}$Cl M+H)$^+$, 416 ($^{37}$Cl M+H)$^+$. $^1$H NMR (500 MHz, DMSO-$d_6$) δ 10.68 (s, 1H), 8.53 (d, J=2.5 Hz, 1H), 8.32 (s, 1H), 7.89 (dd, J=8.9, 2.4 Hz, 1H), 7.84 (d, J=9.1 Hz, 1H), 7.82 (s, 1H), 5.48 (dd, J=9.8, 2.2 Hz, 1H), 3.94 (ddd, J=11.4, 4.7, 3.0 Hz, 1H), 3.68 (ddd, J=11.5, 8.1, 5.9 Hz, 1H), 2.15-2.05 (m, 1H), 2.01-1.93 (m, 2H), 1.70 (ddt, J=15.8, 11.6, 7.9 Hz, 1H), 1.56 (dq, J=9.2, 5.1, 4.5 Hz, 2H).

Step 4

2-(3-(4-((1H-pyrazol-4-yl)amino)-6-(trifluoromethoxy)quinazolin-2-yl)-phenoxy)-N-(tert-butyl)acetamide Bis-Trifluoroacetic Acid Salt

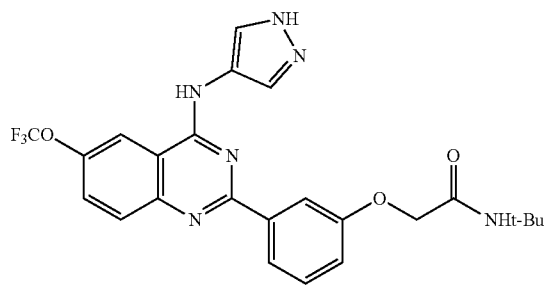

2-Chloro-N-(1-(tetrahydro-2H-pyran-2-yl)-1H-pyrazol-4-yl)-6-(trifluoromethoxy)quinazolin-4-amine (35 mg, 85 µmol), N-(tert-butyl)-2-(3-(4,4,5,5-tetramethyl-1,3,2-dioxaborolan-2-yl)phenoxy)acetamide (31 mg, 93 µmol) and Pd(dppf)Cl$_2$·CH$_2$Cl$_2$ (10 mg, 13 µmol) were weighed out in a microwave vial equipped with a stirbar. 1,2-Dimethoxyethane (3.4 mL) was added and the reaction mixture was purged with N$_2$ for 2 minutes before a 0.33 M aqueous solution of Na$_2$CO$_3$ (0.85 mL) was added. The reaction mixture was purged for 3 more minutes and the vial was sealed. The vial was irradiated for 60 min at 100° C. in a microwave oven. LCMS showed that starting material had been completely consumed. Volatiles were removed under reduced pressure and the residue was purified by flash column chromatography (20% to 100% EtOAc in hexane, R$_f$=0.37 @ 50% EtOAc in hexane). The purified material was dissolved in 10 mL of 4.0 N HCl in dioxane and stirred at room temperature for 20 min. LCMS showed that the product had been completely deprotected so volatiles were evaporated under reduced pressure. The crude residue was purified by HPLC to provide 2-(3-(4-((1H-pyrazol-4-yl)amino)-6-(trifluoromethoxy)quinazolin-2-yl)-phenoxy)-N-(tert-butyl)acetamide bis-trifluoroacetic acid salt (93 mg, 30%) as a bright yellow solid. MS (ES+) m/e 501 (M+H)$^+$. $^1$H NMR (500 MHz, DMSO-d$_6$) δ 8.61 (d, J=2.5 Hz, 1H), 8.16 (s, 2H), 8.05-7.91 (m, 4H), 7.62 (s, 1H), 7.53 (t, J=8.0 Hz, 1H), 7.17 (dd, J=8.0, 1.4 Hz, 1H), 4.54 (s, 2H), 1.30 (s, 9H).

Example 283

2-(3-(4-((1H-Pyrazol-3-yl)amino)-6-(trifluoromethoxy)quinazolin-2-yl)phenoxy)-N-(tert-butyl)acetamide Bis-Trifluoroacetic Acid Salt

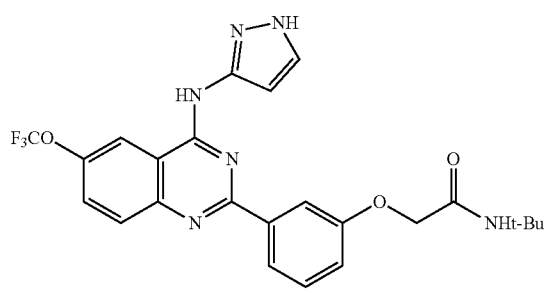

Step 1

2-Chloro-6-(trifluoromethoxy)-N-(1-((2-(trimethylsilyl)ethoxy)methyl)-1H-pyrazol-3-yl)quinazolin-4-amine

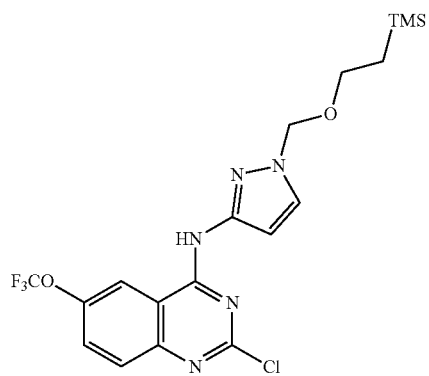 [SMILES: C[Si](C)(C)CCOCn1ccc(Nc2nc(Cl)nc3ccc(OC(F)(F)F)cc23)n1]

Following the synthetic sequence from Example 282, 1-((2-(trimethylsilyl)-ethoxy)methyl)-1H-pyrazol-3-amine was used in step 3 to afford 2-chloro-6-(trifluoromethoxy)-N-(1-(tetrahydro-2H-pyran-2-yl)-1H-pyrazol-4-yl)-quinazolin-4-amine (132 mg, 27%) as an orange solid. MS (ES+) m/e 460 ($^{35}$Cl M+H)$^+$, 462 ($^{37}$Cl M+H)$^+$. $^1$H NMR (500 MHz, DMSO-d$_6$) δ 11.35 (s, 1H), 8.82 (d, J=2.4 Hz, 1H), 7.95 (d, J=2.4 Hz, 1H), 7.89 (dd, J=9.0, 2.4 Hz, 1H), 7.84 (d, J=9.1 Hz, 1H), 6.91 (d, J=2.4 Hz, 1H), 5.40 (s, 2H), 3.55 (dd, J=8.7, 7.6 Hz, 2H), 1.25 (dd, J=18.3, 6.4 Hz, 1H), 0.86 (dd, J=8.7, 7.5 Hz, 2H), −0.03 (s, 9H).

Step 2

2-(3-(4-((1H-pyrazol-3-yl)amino)-6-(trifluoromethoxy)quinazolin-2-yl)-phenoxy)-N-(tert-butyl)acetamide Bis-Trifluoroacetic Acid Salt

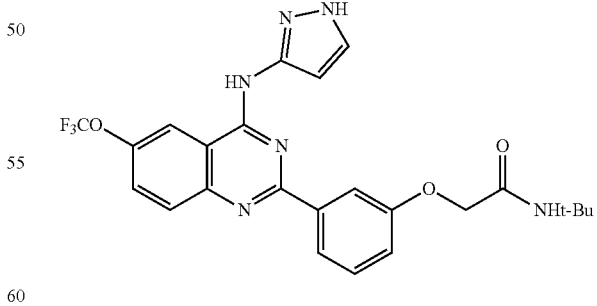

Following the synthetic sequence from Example 282, step 4, SEM deprotection was carried out similarly (16 h reaction time) to afford 2-(3-(4-((1H-pyrazol-3-yl)-amino)-7-chloro-6-ethoxyquinazolin-2-yl)phenoxy)-N-(tert-butyl)acetamide bis-trifluoroacetic acid salt (72.6 mg, 35%) as a bright yellow powder. MS (ES+) m/e 501 (M+H)$^+$.

Example 284

2-(3-(4-((1H-Pyrazol-4-yl)amino)-6-(cyclopentyloxy)quinazolin-2-yl)phenoxy)-N-(tert-butyl)acetamide Bis-Trifluoroacetic Acid Salt

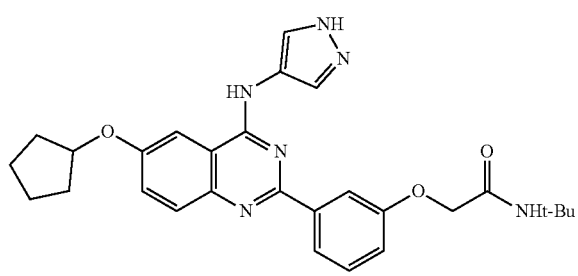

Step 1

Cyclopentyl 5-(cyclopentyloxy)-2-nitrobenzoate

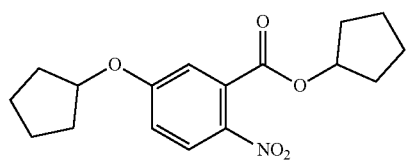

Following the synthetic sequence for Example 6, step 1, 5-hydroxy-2-nitrobenzoic acid (2.0 g, 10.9 mmol), bromocyclopentane (4.4 mL, 43.7 mmol), K$_2$CO$_3$ (4.53 g, 32.8 mmol), KI (907 mg, 5.5 mmol) and DMF (21.8 mL) were used to furnish cyclopentyl 5-(cyclopentyloxy)-2-nitrobenzoate (3.35 g, 96%) as a pale yellow solid. $^1$H NMR (500 MHz, Chloroform-d) δ 7.99 (d, J=9.1 Hz, 1H), 6.99 (d, J=2.7 Hz, 1H), 6.94 (dd, J=9.1, 2.7 Hz, 1H), 5.43 (tt, J=5.9, 3.0 Hz, 1H), 4.85 (tt, J=5.8, 2.5 Hz, 1H), 2.07-1.55 (m, 16H).

Step 2

Cyclopentyl 2-amino-5-(cyclopentyloxy)benzoate

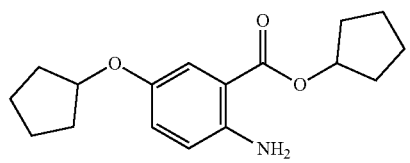 [SMILES: O=C(OC1CCCC1)c1cc(OC2CCCC2)ccc1[N+](=O)[O-]]

Following the synthetic sequence for Example 278, step 3, cyclopentyl 2-amino-5-(cyclopentyloxy)benzoate was obtained (2.9 g, 94%) as a yellow oil. $^1$H NMR (500 MHz, Chloroform-d) δ 7.33 (d, J=3.0 Hz, 1H), 6.90 (dd, J=8.9, 3.0 Hz, 1H), 6.60 (d, J=8.8 Hz, 1H), 5.36 (tt, J=6.1, 2.7 Hz, 1H), 4.64 (tt, J=5.7, 3.1 Hz, 1H), 1.99-1.54 (m, 16H).

Step 3

6-(Cyclopentyloxy)quinazoline-2,4-diol

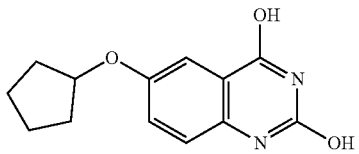 [SMILES: Oc1nc(O)c2cc(OC3CCCC3)ccc2n1]

Following the synthetic sequence for Example 6, step 3, 6-(cyclopentyloxy)-quinazoline-2,4-diol was obtained (2.67 g, 70%) as an off-white solid. $^1$H NMR (500 MHz, DMSO-d$_6$) δ 7.28 (d, J=2.9 Hz, 1H), 7.23 (dd, J=8.8, 2.9 Hz, 1H), 7.10 (d, J=8.8 Hz, 1H), 6.80 (s, 1H), 5.40 (s, 1H), 4.82 (td, J=5.8, 2.9 Hz, 1H), 1.96-1.83 (m, 2H), 1.75-1.53 (m, 6H).

Step 4

2,4-Dichloro-6-(cyclopentyloxy)quinazoline

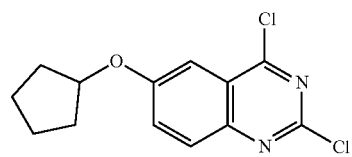 [SMILES: Clc1nc(Cl)c2cc(OC3CCCC3)ccc2n1]

Following the synthetic sequence for Example 6, step 4, 2,4-dichloro-6-(cyclopentyloxy)quinazoline was obtained (2.2 g, 99%) as a yellow solid. MS (ES+) m/e 324 ($^{35}$Cl M+MeCN+H)$^+$, 326 ($^{37}$Cl M+MeCN+H)$^+$. $^1$H NMR (500 MHz, Chloroform-d) δ 7.88 (d, J=9.2 Hz, 1H), 7.56 (dd, J=9.2, 2.7 Hz, 1H), 7.40 (d, J=2.7 Hz, 1H), 4.95 (tt, J=5.9, 2.7 Hz, 1H), 2.10-1.99 (m, 2H), 1.98-1.89 (m, 2H), 1.89-1.78 (m, 2H), 1.76-1.65 (m, 2H).

Step 5

2-Chloro-6-(cyclopentyloxy)-N-(1-(tetrahydro-2H-pyran-2-yl)-1H-pyrazol-4-yl)quinazolin-4-amine

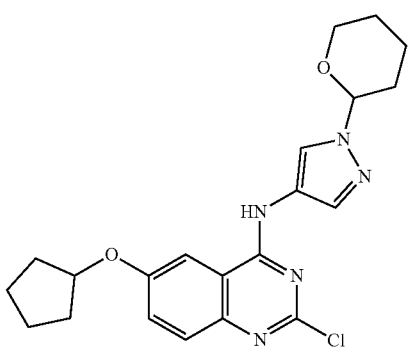 [SMILES: Clc1nc(Nc2cnn(C3CCCCO3)c2)c2cc(OC3CCCC3)ccc2n1]

Following the synthetic sequence for Example 278, step 6, 2-chloro-6-(cyclopentyloxy)-N-(1-(tetrahydro-2H-pyran-2-yl)-1H-pyrazol-4-yl)-quinazolin-4-amine was obtained (64 mg, 29%) as a pale red oil. MS (ES+) m/e 414 ($^{35}$Cl

309

M+H)⁺, 416 (³⁷Cl M+H)⁺. ¹H NMR (500 MHz, DMSO-d₆) δ 10.26 (s, 1H), 8.30 (s, 1H), 7.84 (d, J=2.7 Hz, 1H), 7.81 (s, 1H), 7.64 (d, J=9.0 Hz, 1H), 7.49 (dd, J=9.1, 2.6 Hz, 1H), 5.46 (dd, J=9.8, 2.1 Hz, 1H), 5.02 (td, J=5.6, 2.7 Hz, 1H), 3.94 (dt, J=11.6, 3.8 Hz, 1H), 3.67 (ddd, J=11.5, 8.0, 5.8 Hz, 1H), 2.20-1.87 (m, 3H), 1.98-1.92 (m, 2H), 1.86-1.46 (m, 7H), 1.55 (dt, J=8.5, 4.2 Hz, 2H).

Step 6

2-(3-(4-((1H-pyrazol-4-yl)amino)-6-(cyclopentyloxy)quinazolin-2-yl)-phenoxy)-N-(tert-butyl)acetamide Bis-Trifluoroacetic Acid Salt

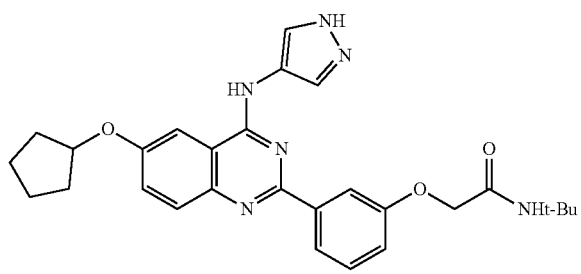

Following the synthetic sequence for Example 278, step 7, 2-(3-(4-((1H-pyrazol-4-yl)amino)-6-(cyclopentyloxy)quinazolin-2-yl)phenoxy)-N-(tert-butyl)acetamide bis-trifluoroacetic acid salt was obtained (25.6 mg, 42%) as a bright yellow powder. MS (ES+) m/e 501 (M+H)⁺. ¹H NMR (500 MHz, DMSO-d₆) δ 8.18 (s, 2H), 8.03 (s, 1H), 7.95 (d, J=8.1 Hz, 2H), 7.91 (s, 1H), 7.62 (s, 2H), 7.57 (s, 1H), 7.21 (s, 1H), 5.09 (dq, J=6.2, 3.4, 2.9 Hz, 1H), 4.55 (s, 2H), 2.07 (tq, J=10.2, 6.0, 5.5 Hz, 2H), 1.87-1.72 (m, 4H), 1.67 (dtt, J=7.1, 4.7, 2.6 Hz, 2H), 1.30 (s, 9H).

Example 285

2-(3-(4-((1H-Pyrazol-3-yl)amino)-6-(cyclopentyloxy)quinazolin-2-yl)-phenoxy)-N-(tert-butyl)acetamide Bis-Trifluoroacetic Acid Salt

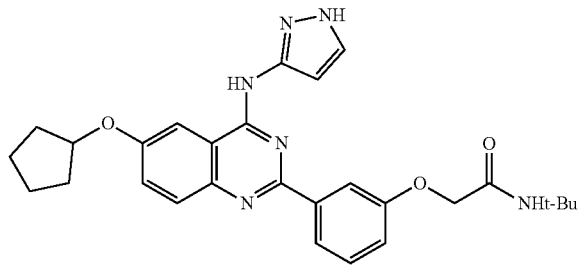

310

Step 1

2-Chloro-6-(cyclopentyloxy)-N-(1-((2-(trimethylsilyl)ethoxy)methyl)-1H-pyrazol-3-yl)quinazolin-4-amine

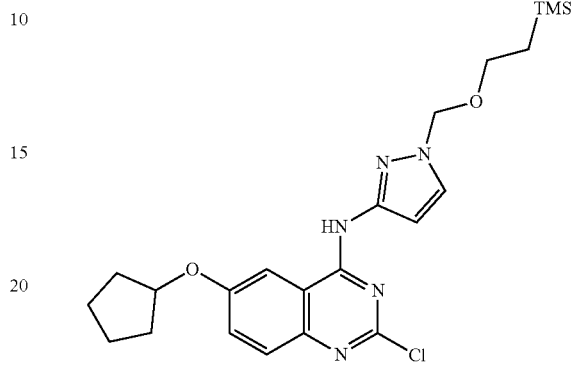

Following the synthetic sequence for Example 284, 1-((2-(trimethylsilyl)ethoxy)methyl)-1H-pyrazol-3-amine was used in step 5 to obtain 2-chloro-6-(cyclopentyloxy)-N-(1-((2-(trimethylsilyl)ethoxy)methyl)-1H-pyrazol-3-yl)-quinazolin-4-amine (100 mg, 41%) as a pale yellow solid. MS (ES+) m/e 460 (³⁵Cl M+H)⁺, 462 (³⁷Cl M+H)⁺. ¹H NMR (500 MHz, Chloroform-d) δ 7.77 (d, J=9.1 Hz, 1H), 7.57 (d, J=2.5 Hz, 1H), 7.41 (dd, J=9.2, 2.5 Hz, 1H), 7.24 (s, 1H), 5.37 (s, 2H), 4.90 (s, 1H), 3.65-3.50 (m, 2H), 2.12-1.96 (m, 1H), 1.96-1.78 (m, 3H), 1.69 (tt, J=7.2, 2.5 Hz, 2H), 1.32-1.16 (m, 2H), 1.04-0.85 (m, 2H), −0.01 (s, 9H).

Step 2

2-(3-(4-((1H-pyrazol-3-yl)amino)-6-(cyclopentyloxy)quinazolin-2-yl)-phenoxy)-N-(tert-butyl)acetamide Bis-Trifluoroacetic Acid Salt

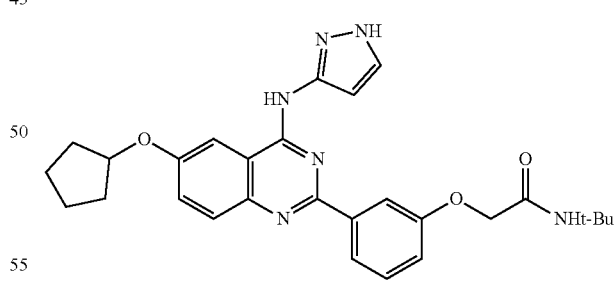

Following the synthetic sequence for Example 284, step 6, deprotection was run for 16 h to furnish 2-(3-(4-((1H-pyrazol-3-yl)amino)-6-(cyclopentyloxy)quinazolin-2-yl)-phenoxy)-N-(tert-butyl)acetamide bis-trifluoroacetic acid salt (27 mg, 17%) as a bright yellow powder. MS (ES+) m/e 501 (M+H)⁺. ¹H NMR (500 MHz, DMSO-d₆) δ 8.14 (s, 1H), 7.98 (d, J=7.5 Hz, 1H), 7.95 (s, 1H), 7.86 (s, 2H), 7.60 (s, 1H), 7.52 (s, 2H), 7.14 (s, 1H), 7.00 (s, 1H), 5.11 (t, J=6.0 Hz, 1H), 4.52 (s, 2H), 2.08 (q, J=10.2, 7.7 Hz, 2H), 1.77 (q, J=8.1, 6.4 Hz, 4H), 1.70-1.61 (m, 2H), 1.30 (s, 9H).

Example 286

2-(3-(4-((1H-Pyrazol-4-yl)amino)-6-(cyclopentyloxy)quinazolin-2-yl)-phenoxy)-N-isopropylacetamide Bis-Trifluoroacetic Acid Salt

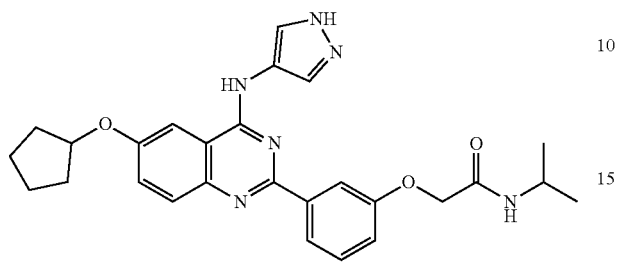

Following the synthetic sequence for Example 284, N-isopropyl-2-(3-(4,4,5,5-tetramethyl-1,3,2-dioxaborolan-2-yl)phenoxy)acetamide was used in step 6 to afford 2-(3-(4-((1H-pyrazol-4-yl)amino)-6-(cyclopentyloxy)quinazolin-2-yl)phenoxy)-N-isopropylacetamide bis-trifluoroacetic acid salt (15.3 mg, 9%) as a bright yellow powder. MS (ES+) m/e 487 (M+H)+. $^1$H NMR (500 MHz, DMSO-$d_6$) δ 8.18 (s, 2H), 8.08-7.98 (m, 2H), 7.98-7.87 (m, 3H), 7.74-7.54 (m, 2H), 7.25 (s, 1H), 5.09 (td, J=5.8, 2.8 Hz, 1H), 4.59 (s, 2H), 3.97 (dq, J=13.2, 6.7 Hz, 1H), 2.13-2.01 (m, 2H), 1.85-1.58 (m, 4H), 1.73-1.58 (m, 2H), 1.09 (d, J=6.6 Hz, 6H).

Example 287

2-(3-(4-((1H-Pyrazol-4-yl)amino)-6-(cyclopentyloxy)quinazolin-2-yl)-phenoxy)-N-cyclobutylacetamide Bis-Trifluoroacetic Acid Salt

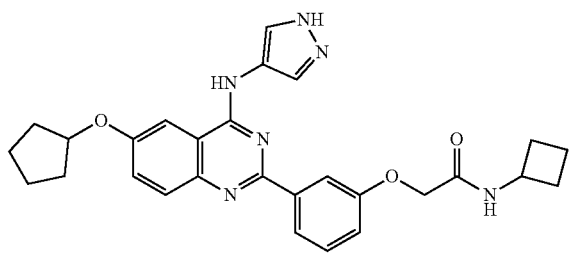 [SMILES: O=C(COc1cccc(-c2nc(Nc3cn[nH]c3)c3cc(OC4CCCC4)ccc3n2)c1)NC1CCC1]

Following the synthetic sequence for Example 284, N-cyclobutyl-2-(3-(4,4,5,5-tetramethyl-1,3,2-dioxaborolan-2-yl)phenoxy)acetamide was used in step 6 to afford 2-(3-(4-((1H-pyrazol-4-yl)amino)-6-(cyclopentyloxy)quinazolin-2-yl)phenoxy)-N-cyclobutylacetamide bis-trifluoroacetic acid salt (60.5 mg, 56%) as a bright yellow powder. MS (ES+) m/e 499 (M+H)+. $^1$H NMR (500 MHz, DMSO-$d_6$) δ 8.42 (d, J=8.0 Hz, 1H), 8.18 (s, 2H), 8.05 (s, 1H), 8.01-7.84 (m, 3H), 7.66 (d, J=9.3 Hz, 1H), 7.60 (t, J=8.0 Hz, 1H), 7.26 (d, J=8.2 Hz, 1H), 5.09 (dt, J=6.0, 3.3 Hz, 1H), 4.59 (s, 2H), 4.30 (h, J=8.2 Hz, 1H), 2.22-1.93 (m, 2H), 2.11-2.03 (m, 2H), 2.03-1.95 (m, 2H), 1.85-1.73 (m, 4H), 1.73-1.56 (m, 4H).

Example 288

N-(tert-Butyl)-2-(3-(6-methoxy-7-methyl-4-((1-methyl-1H-pyrazol-4-yl)-amino)quinazolin-2-yl)phenoxy)acetamide Trifluoroacetic Acid Salt

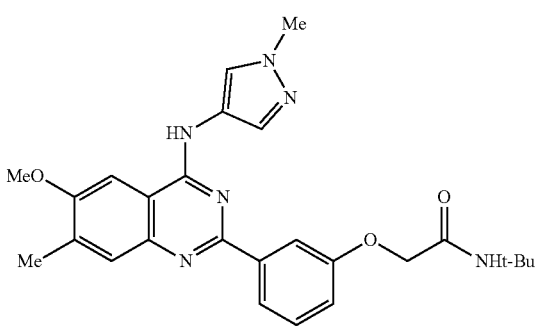

Step 1

Methyl 5-methoxy-4-methyl-2-nitrobenzoate

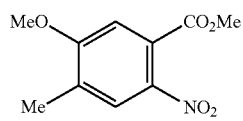 [SMILES: COC(=O)c1cc(OC)c(C)cc1[N+](=O)[O-]]

Following the synthetic sequence for Example 6, step 1, 5-methoxy-4-methyl-2-nitrobenzoic acid (800 mg, 3.8 mmol), iodomethane (940 μL, 15.2 mmol), $K_2CO_3$ (1.05 g, 7.6 mmol) and DMF (9.5 mL) were used to furnish methyl 5-methoxy-4-methyl-2-nitrobenzoate (752 mg, 88%) as a pale yellow solid. $^1$H NMR (500 MHz, Chloroform-d) δ 7.83 (d, J=0.8 Hz, 1H), 6.98 (s, 1H), 3.94 (s, 3H), 3.92 (s, 3H), 2.28 (d, J=0.8 Hz, 3H).

Step 2

Methyl 2-amino-5-methoxy-4-methylbenzoate

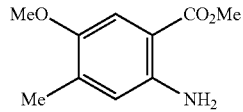

Following the synthetic sequence for Example 480, step 3, methyl 2-amino-5-methoxy-4-methylbenzoate was obtained (568 mg, 87%) as a pale yellow solid.

Step 3

6-Methoxy-7-methylquinazoline-2,4-diol

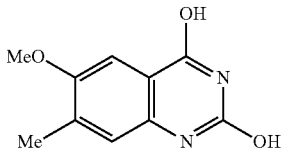 [SMILES: COc1cc2c(O)nc(O)nc2cc1C]

Following the synthetic sequence for Example 6, step 3, 6-methoxy-7-methyl-quinazoline-2,4-diol was obtained as an off-white solid. MS (ES+) m/e 248 ($^3$M+MeCN+H)$^+$.

Step 4

2,4-Dichloro-6-methoxy-7-methylquinazoline

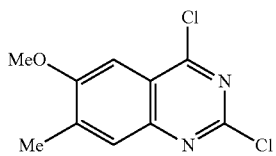 [SMILES: COc1cc2c(Cl)nc(Cl)nc2cc1C]

Following the synthetic sequence for Example 6, step 4, 2,4-dichloro-6-methoxy-7-methylquinazoline was obtained (364 mg, 53% over two steps) as a pale yellow solid. MS (ES+) m/e 284 ($^{35}$Cl/$^{35}$Cl M+MeCN+H)$^+$, 286 ($^{35}$Cl/$^{37}$Cl M+MeCN+H)$^+$, 288 ($^{37}$Cl/$^{37}$Cl M+MeCN+H)$^+$. $^1$H NMR (500 MHz, Chloroform-d) δ 7.74 (d, J=1.1 Hz, 1H), 7.32 (s, 1H), 4.02 (s, 3H), 2.45 (d, J=1.1 Hz, 3H).

Step 5

2-Chloro-6-methoxy-7-methyl-N-(1-methyl-1H-pyrazol-4-yl)quinazolin-4-amine

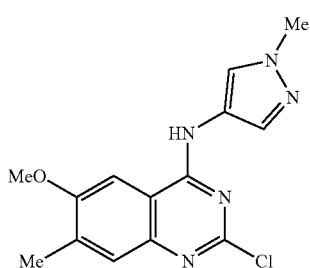 [SMILES: COc1cc2c(Nc3cnn(C)c3)nc(Cl)nc2cc1C]

Following the synthetic sequence for Example 278, step 6, 1-methyl-1H-pyrazol-4-amine was used to obtain 2-chloro-6-methoxy-7-methyl-N-(1-methyl-1H-pyrazol-4-yl)quinazolin-4-amine (194 mg, 86%) as a slightly purple powder. MS (ES+) m/e 304 ($^{35}$Cl M+H)$^+$, 306 ($^{37}$Cl M+H)$^+$. $^1$H NMR (500 MHz, DMSO-d$_6$) δ 10.18 (s, 1H), 8.14 (s, 1H), 7.78 (s, 1H), 7.71 (s, 1H), 7.51 (d, J=1.1 Hz, 1H), 3.97 (s, 3H), 3.89 (s, 3H), 2.32 (d, J=1.0 Hz, 3H).

Step 6

N-(tert-butyl)-2-(3-(6-methoxy-7-methyl-4-((1-methyl-1H-pyrazol-4-yl)-amino)quinazolin-2-yl)phenoxy)acetamide Trifluoroacetic Acid Salt

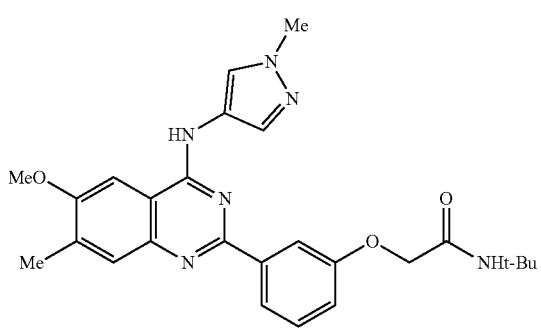

Following the synthetic sequence for Example 278, step 7, N-(tert-butyl)-2-(3-(6-methoxy-7-methyl-4-((1-methyl-1H-pyrazol-4-yl)amino)quinazolin-2-yl)phenoxy)acetamide trifluoroacetic acid salt was obtained (22.7 mg, 39%) as a bright yellow powder. MS (ES+) m/e 475 (M+H)$^+$. $^1$H NMR (500 MHz, DMSO-d$_6$) δ 8.31 (s, 1H), 8.00-7.86 (m, 4H), 7.78 (s, 1H), 7.57 (s, 2H), 7.23 (s, 1H), 4.56 (s, 2H), 4.03 (s, 3H), 3.96 (s, 3H), 2.40 (s, 3H), 1.31 (s, 9H).

Example 289

N-(tert-Butyl)-2-(3-(6-methoxy-7-methyl-4-((1-methyl-1H-pyrazol-3-yl)-amino)quinazolin-2-yl)phenoxy)acetamide Trifluoroacetic Acid Salt

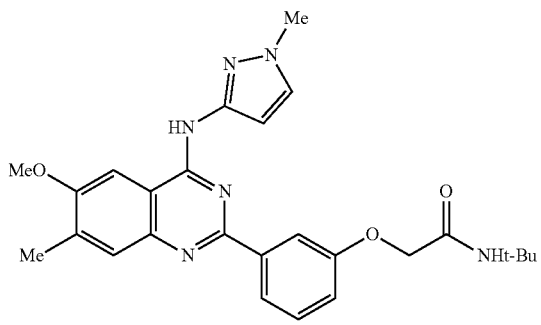

Step 1

2-Chloro-6-methoxy-7-methyl-N-(1-methyl-1H-pyrazol-3-yl)quinazolin-4-amine

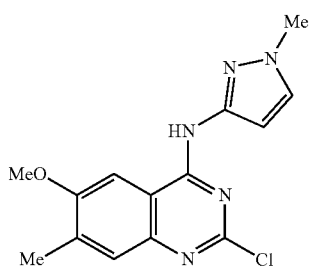 [SMILES: COc1cc2c(Nc3ccn(C)n3)nc(Cl)nc2cc1C]

Following the synthetic sequence for Example 288, 1-methyl-1H-pyrazole-3-amine was used to obtain 2-chloro-6-methoxy-7-methyl-N-(1-methyl-1H-pyrazol-3-yl)-quinazolin-4-amine (175 mg, 78%) as an off-white solid. MS (ES+) m/e 304 ($^{35}$Cl M+H)$^+$, 306 ($^{37}$Cl M+H)$^+$. $^1$H NMR (500 MHz, DMSO-d$_6$) δ 10.82 (s, 1H), 8.02 (s, 1H), 7.69 (d, J=2.2 Hz, 1H), 7.52 (d, J=1.1 Hz, 1H), 6.80 (d, J=2.3 Hz, 1H), 3.95 (s, 3H), 3.84 (s, 3H), 2.32 (d, J=0.9 Hz, 3H).

Step 2

N-(tert-butyl)-2-(3-(6-methoxy-7-methyl-4-((1-methyl-1H-pyrazol-3-yl)-amino)quinazolin-2-yl) phenoxy)acetamide Trifluoroacetic Acid Salt

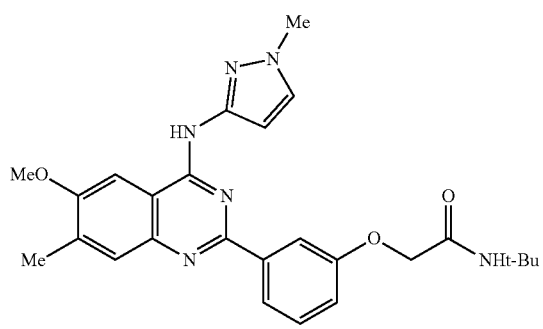

Following the synthetic sequence for Example 278, step 7, N-(tert-butyl)-2-(3-(6-methoxy-7-methyl-4-((1-methyl-1H-pyrazol-3-yl)amino)-quinazolin-2-yl)phenoxy)acetamide trifluoroacetic acid salt was obtained (23.7 mg, 41%) as a bright yellow powder. MS (ES+) m/e 475 (M+H)$^+$. $^1$H NMR (500 MHz, DMSO-d$_6$) δ 8.15 (s, 1H), 7.99-7.88 (m, 2H), 7.80 (s, 1H), 7.76 (s, 1H), 7.61-7.48 (m, 2H), 7.17 (d, J=7.6 Hz, 1H), 6.97 (d, J=2.2 Hz, 1H), 4.53 (s, 2H), 4.00 (s, 3H), 3.89 (s, 3H), 2.39 (s, 3H), 1.30 (s, 9H).

Example 290

N-(tert-Butyl)-2-(3-(6-methoxy-5-methyl-4-((1-methyl-1H-pyrazol-4-yl)-amino)quinazolin-2-yl) phenoxy)acetamide Trifluoroacetic Acid Salt

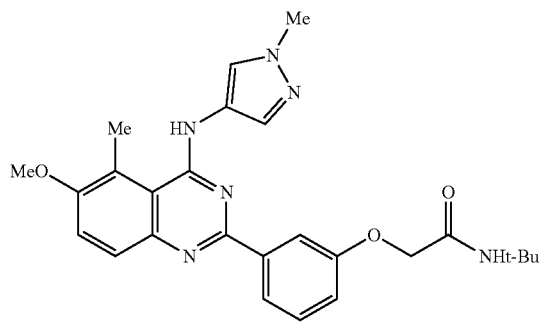

Step 1

Methyl 3-methoxy-2-methyl-6-nitrobenzoate

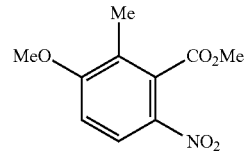

To a stirred solution of methyl 3-methoxy-2-methylbenzoate (1.00 g, 5.55 mmol) in glacial acetic acid (3.0 mL) was added conc. HNO$_3$ (1.0 mL) dropwise at room temperature. The resulting mixture was stirred at 70° C. for 2 h. After completion of the reaction (TLC: 15% EtOAc in hexanes), the reaction mixture was diluted with cold water (10 mL) and the aqueous layer was extracted with EtOAc (2×8 mL). The organic layer was washed with water (5 mL), 0.5M NaOH (5 mL), and sat. aq. NaCl (5 mL), and was dried over Na$_2$SO$_4$. The solvent was evaporated under reduced pressure and the crude material was purified by column chromatography (R$_f$=0.3 @ 15% EtOAc in Hexanes) to afford methyl 3-methoxy-2-methyl-6-nitrobenzoate (806 mg, 64%) as a viscous yellow oil that slowly solidifies.

Step 2

Methyl 6-amino-3-methoxy-2-methylbenzoate

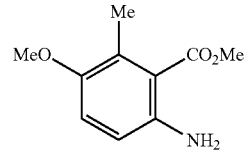 [SMILES: COC(=O)c1c([N+](=O)[O-])ccc(OC)c1C]

Following the synthetic sequence for Example 278, step 3, methyl 6-amino-3-methoxy-2-methylbenzoate (473 mg, 68%) as a yellow oil.

Step 3

6-Methoxy-5-methylquinazoline-2,4-diol

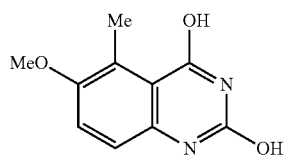

Following the synthetic sequence for Example 6, step 3, 6-methoxy-5-methyl-quinazoline-2,4-diol was obtained (387 mg, 77%) as a light brown solid. MS (ES+) m/e 248 (M+H+MeCN)$^+$. $^1$H NMR (500 MHz, DMSO-d$_6$) δ 10.92 (s, 2H), 7.34 (d, J=8.9 Hz, 1H), 7.01 (d, J=8.9 Hz, 1H), 3.78 (s, 3H), 2.56 (s, 3H).

Step 4

2,4-Dichloro-6-methoxy-5-methylquinazoline

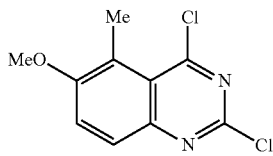 [SMILES: COc1ccc2nc(Cl)nc(Cl)c2c1C]

Following the synthetic sequence for Example 6, step 4, 2,4-dichloro-6-methoxy-5-methylquinazoline was obtained (49 mg, 11%) as a pale yellow solid. MS (ES+) m/e 284 ($^{35}$Cl/$^{35}$Cl M+MeCN+H)$^+$, 286 ($^{35}$Cl/$^{37}$Cl M+MeCN+H)$^+$, 288 ($^{37}$Cl/$^{37}$Cl M+MeCN+H)$^+$. $^1$H NMR (500 MHz, Chloroform-d) δ 7.90 (d, J=9.2 Hz, 1H), 7.70 (d, J=9.2 Hz, 1H), 4.00 (s, 3H), 2.87 (s, 3H).

Step 5

2-Chloro-6-methoxy-5-methyl-N-(1-methyl-1H-pyrazol-4-yl)quinazolin-4-amine

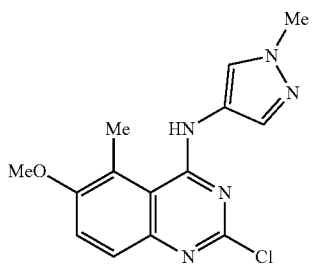 [SMILES: COc1ccc2nc(Cl)nc(Nc3cnn(C)c3)c2c1C]

Following the synthetic sequence for Example 278, Step 6, 1-methyl-1H-pyrazol-4-amine was used to obtain 2-chloro-6-methoxy-5-methyl-N-(1-methyl-1H-pyrazol-4-yl)quinazolin-4-amine (46 mg, 75%) as a light brown solid. MS (ES+) m/e 304 ($^{35}$Cl M+H)$^+$, 306 ($^{37}$Cl M+H)$^+$. $^1$H NMR (500 MHz, DMSO-d$_6$) δ 9.08 (s, 1H), 8.11 (s, 1H), 7.72 (s, 1H), 7.66 (d, J=9.1 Hz, 1H), 7.57 (d, J=9.0 Hz, 1H), 3.92 (s, 3H), 3.88 (s, 3H), 2.73 (s, 3H).

Step 6

N-(tert-butyl)-2-(3-(6-methoxy-5-methyl-4-((1-methyl-1H-pyrazol-4-yl)amino)quinazolin-2-yl)phenoxy)acetamide Trifluoroacetic Acid Salt

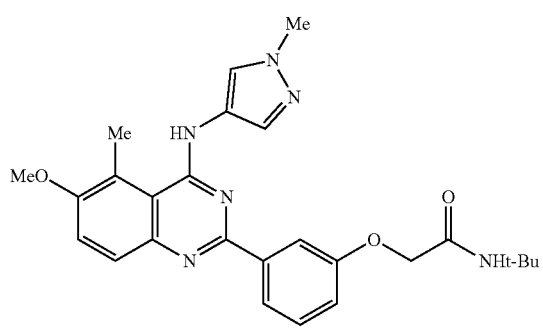

Following the synthetic sequence for Example 278, step 7, N-(tert-butyl)-2-(3-(6-methoxy-5-methyl-4-((1-methyl-1H-pyrazol-4-yl)amino)-quinazolin-2-yl)phenoxy)acetamide trifluoroacetic acid salt was obtained (26.6 mg, 30%) as a bright yellow powder. MS (ES+) m/e 475 (M+H)$^+$. $^1$H NMR (500 MHz, DMSO-d$_6$) δ 8.27 (s, 1H), 7.98-7.88 (m, 2H), 7.83 (d, J=18.3 Hz, 1H), 7.58 (s, 1H), 7.42-7.34 (m, 2H), 7.28-7.23 (m, 1H), 6.96 (dd, J=8.1, 2.0 Hz, 1H), 4.38 (s, 2H), 3.98 (s, 3H), 3.95 (s, 3H), 2.76 (s, 3H), 1.32 (s, 9H).

Example 291

N-(tert-Butyl)-2-(3-(7-chloro-6-methoxy-4-((1-methyl-1H-pyrazol-4-yl)-amino)quinazolin-2-yl)phenoxy)acetamide Trifluoroacetic Acid Salt

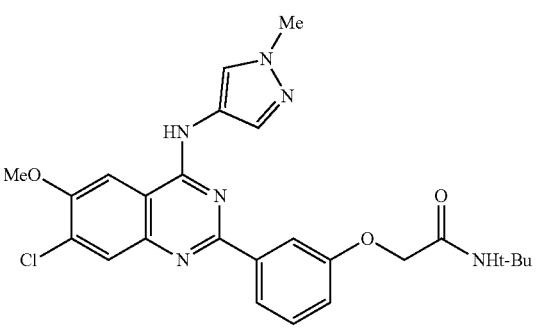

Step 1

7-Chloro-6-methoxyquinazoline-2,4-diol

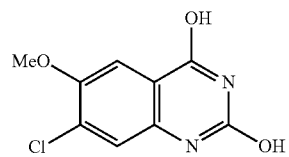

Following the synthetic sequence for Example 6, step 3, methyl 2-amino-4-chloro-5-methoxybenzoate (250 mg, 1.16 mmol) was used to obtain 7-chloro-6-methoxyquinazoline-2,4-diol (228 mg, 87%) as a slightly brown powder. MS (ES+) m/e 257 ($^{35}$Cl M+MeCN+H)$^+$, 259 ($^{37}$Cl M+MeCN+H)$^+$. $^1$H NMR (500 MHz, DMSO-d$_6$) δ 7.46 (s, 1H), 7.24 (s, 1H), 3.89 (s, 3H).

Step 2

2,4,7-Trichloro-6-methoxyquinazoline

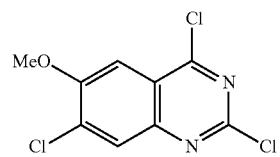 [SMILES: COc1cc2c(Cl)nc(Cl)nc2cc1Cl]

Following the synthetic sequence for Example 6, step 4, 2,4,7-trichloro-6-methoxyquinazoline was obtained (201 mg, 76%) as an ocher solid.

Step 3

2,7-Dichloro-6-methoxy-N-(1-methyl-1H-pyrazol-4-yl)quinazolin-4-amine

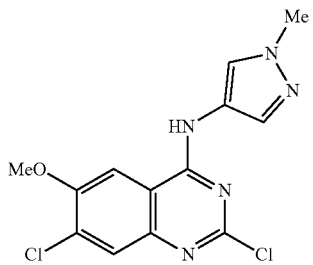 [SMILES: COc1cc2c(Nc3cnn(C)c3)nc(Cl)nc2cc1Cl]

Following the synthetic sequence for Example 278, step 6, 1-methyl-1H-pyrazol-4-amine was used to obtain 2,7-dichloro-6-methoxy-N-(1-methyl-1H-pyrazol-4-yl)quinazolin-4-amine (186 mg, 75%) as an ocher powder. MS (ES+) m/e 324 ($^{35}$Cl/$^{35}$Cl M+H)$^+$, 326 ($^{35}$Cl/$^{37}$Cl M+H)$^+$, 328 ($^{37}$Cl/$^{37}$Cl M+H)$^+$. $^1$H NMR (500 MHz, DMSO-d$_6$) δ 10.40 (s, 1H), 8.15 (s, 1H), 8.00 (s, 1H), 7.84 (s, 1H), 7.73 (s, 1H), 4.04 (s, 3H), 3.90 (s, 3H).

Step 4

N-(tert-butyl)-2-(3-(7-chloro-6-methoxy-4-((1-methyl-1H-pyrazol-4-yl)-amino)quinazolin-2-yl) phenoxy)acetamide Trifluoroacetic Acid Salt

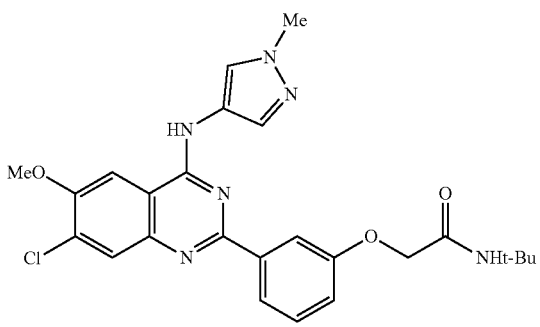

Following the synthetic sequence for Example 278, step 7, N-(tert-butyl)-2-(3-(7-chloro-6-methoxy-4-((1-methyl-1H-pyrazol-4-yl)amino)-quinazolin-2-yl)phenoxy)acetamide trifluoroacetic acid salt was obtained (20.9 mg, 28%) as a bright yellow powder. MS (ES+) m/e 495 ($^{35}$Cl-M+H)$^+$, 497 ($^{37}$Cl M+H)$^+$. 1H NMR (500 MHz, DMSO-d6) δ 8.30 (s, 1H), 8.07 (s, 1H), 8.02 (d, J=7.8 Hz, 1H), 7.99 (s, 1H), 7.95 (s, 1H), 7.85 (s, 1H), 7.55 (s, 1H), 7.14 (d, J=7.5 Hz, 1H), 4.54 (s, 2H), 4.07 (s, 3H), 3.95 (s, 3H), 1.31 (s, 9H).

Example 292

N-(tert-Butyl)-2-(3-(5-chloro-6-methoxy-4-((1-methyl-1H-pyrazol-4-yl)-amino)quinazolin-2-yl) phenoxy)acetamide Trifluoroacetic Acid Salt

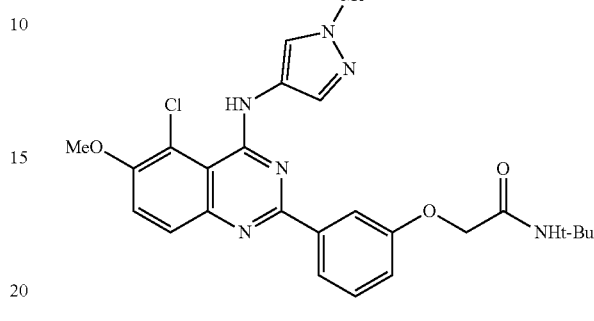

Step 1

Methyl 2-chloro-3-methoxybenzoate

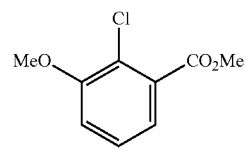 [SMILES: COC(=O)c1cccc(OC)c1Cl]

Following the synthetic sequence for Example 6, step 1, 2-chloro-3-hydroxybenzoic acid (400 mg, 2.3 mmol), K$_2$CO$_3$ (641 mg, 4.6 mmol), iodomethane (580 μL, 9.27 mmol) and DMF (2.9 mL) were used to obtain methyl 3-chloro-2-methoxybenzoate (357 mg, 77%) as a white solid.

Step 2

Methyl 2-chloro-3-methoxy-6-nitrobenzoate

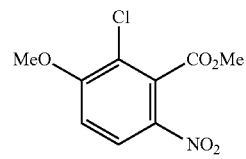

To a stirred solution of methyl 2-chloro-3-methoxybenzoate (357 mg, 1.78 mmol) in glacial acetic acid (1.0 mL) was added conc. HNO$_3$ (320 μL) dropwise at room temperature. The resulting mixture was stirred at 70° C. for 2 h. An additional 1.5 mL of conc. HNO$_3$ were added and the reaction mixture was stirred for 4 h. The reaction mixture was diluted with cold water (10 mL) and the aqueous layer was extracted with EtOAc (2×8 mL). The organic layer was washed with water (10 mL), 0.5M NaOH (10 mL), and sat. aq. NaCl (10 mL), and was dried over Na$_2$SO$_4$. The solvent was evaporated under reduced pressure and the crude material was purified by column chromatography (R$_f$=0.20 @

20% EtOAc in hexanes) to give methyl 2-chloro-3-methoxy-6-nitrobenzoate (261 mg, 60%) as a yellow solid. $^1$H NMR (500 MHz, Chloroform-d) δ 8.21 (d, J=9.2 Hz, 1H), 7.04 (d, J=9.3 Hz, 1H), 4.04 (s, 3H), 4.02 (s, 3H).

Step 3

Methyl 6-amino-2-chloro-3-methoxybenzoate

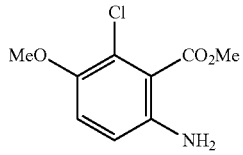 [SMILES: COC(=O)c1c([N+](=O)[O-])ccc(OC)c1Cl]

Following the synthetic sequence for Example 278, step 3, methyl 6-amino-2-chloro-3-methoxybenzoate was obtained (124 mg, 54%) as an orange oil. $^1$H NMR (500 MHz, Chloroform-d) δ 6.89 (d, J=8.9 Hz, 1H), 6.60 (d, J=8.9 Hz, 1H), 3.94 (s, 3H), 3.82 (s, 3H).

Step 4

5-Chloro-6-methoxyquinazoline-2,4-diol

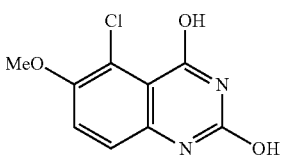

Following the synthetic sequence for Example 6, step 3, 5-chloro-6-methoxyquinazoline-2,4-diol was obtained (192 mg) as a brown solid. $^1$H (500 MHz, DMSO-$d_6$) δ 11.18 (s, 1H), 11.05 (s, 1H), 7.52 (d, J=9.1 Hz, 1H), 7.12 (d, J=9.0 Hz, 1H), 3.85 (s, 3H).

Step 5

2,4,5-Trichloro-6-methoxyquinazoline

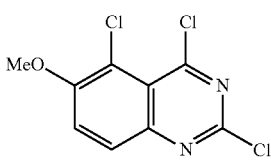 [SMILES: COc1ccc2nc(Cl)nc(Cl)c2c1Cl]

Following the synthetic sequence for Example 6, step 4, give 2,4,5-trichloro-6-methoxyquinazoline was obtained (100 mg, 58%) as an ocher solid. $^1$H NMR (500 MHz, DMSO-$d_6$) δ 7.68 (d, J=9.1 Hz, 1H), 7.58 (d, J=9.0 Hz, 1H), 3.94 (s, 3H).

Step 6

2,5-Dichloro-6-methoxy-N-(1-methyl-1H-pyrazol-4-yl)quinazolin-4-amine

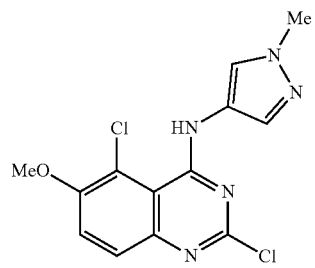 [SMILES: COc1ccc2nc(Cl)nc(Nc3cnn(C)c3)c2c1Cl]

Following the synthetic sequence for Example 278, step 6, 1-methyl-1H-pyrazol-4-amine was used to obtain 2,5-dichloro-6-methoxy-N-(1-methyl-1H-pyrazol-4-yl)quinazolin-4-amine (73 mg, 59%) as a light brown solid. MS (ES+) m/e 324 ($^{35}$Cl/$^{35}$Cl M+H)$^+$, 326 ($^{35}$Cl/$^{37}$Cl M+H)$^+$, 328 ($^{37}$Cl/$^{37}$Cl M+H)$^+$. $^1$H NMR (500 MHz, DMSO-$d_6$) δ 9.94 (s, 1H), 8.17 (s, 1H), 7.85 (d, J=9.3 Hz, 1H), 7.82 (s, 1H), 7.74 (d, J=9.1 Hz, 1H), 4.01 (s, 3H), 3.88 (s, 3H).

Step 7

N-(tert-butyl)-2-(3-(5-chloro-6-methoxy-4-((1-methyl-1H-pyrazol-4-yl)-amino)quinazolin-2-yl)phenoxy)acetamide Trifluoroacetic Acid Salt

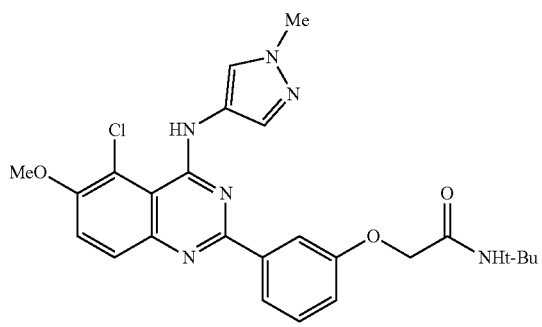

Following the synthetic sequence for Example 278, step 7, N-(tert-butyl)-2-(3-(5-chloro-6-methoxy-4-((1-methyl-1H-pyrazol-4-yl)amino)-quinazolin-2-yl)phenoxy)acetamide trifluoroacetic acid salt was obtained (19.6 mg, 28%) as a bright yellow powder. MS (ES+) m/e 495 ($^{35}$Cl-M+H)$^+$, 497 ($^{37}$Cl M+H)$^+$. $^1$H NMR (500 MHz, DMSO-$d_6$) δ 8.29 (s, 1H), 7.99 (d, J=7.8 Hz, 1H), 7.95 (s, 1H), 7.94-7.86 (m, 2H), 7.56 (s, 1H), 7.51 (t, J=7.9 Hz, 1H), 7.16 (dd, J=8.1, 2.0 Hz, 1H), 4.54 (s, 2H), 4.03 (s, 3H), 3.93 (s, 3H), 1.31 (s, 9H).

Example 293

2-(3-(4-((1H-Pyrazol-4-yl)amino)-6-ethoxy-7-fluoroquinazolin-2-yl)-phenoxy)-N-(tert-butyl)acetamide Bis-Trifluoroacetic Acid Salt

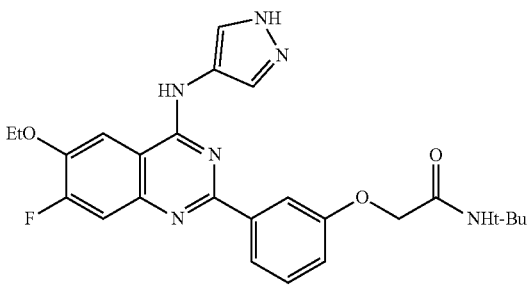

Following the synthetic sequence for Example 292, starting from 4-fluoro-3-hydroxybenzoic acid (3.0 g, 16.4 mmol), 2-(3-(4-((1H-pyrazol-4-yl)amino)-6-ethoxy-7-fluoroquinazolin-2-yl)phenoxy)-N-(tert-butyl)acetamide bis-trifluoroacetic acid salt was obtained (28 mg, 13%) as a bright yellow powder. MS (ES+) m/e 479 (M+H)$^+$. $^1$H NMR (500 MHz, DMSO-d$_6$) δ 8.19-8.09 (m, 3H), 7.98 (d, J=7.8 Hz, 1H), 7.93 (s, 1H), 7.67 (d, J=11.7 Hz, 1H), 7.60 (s, 1H), 7.50 (t, J=7.8 Hz, 1H), 7.12 (d, J=8.3 Hz, 1H), 4.52 (s, 2H), 4.32 (q, J=7.0 Hz, 2H), 1.49 (t, J=7.0 Hz, 3H), 1.30 (s, 9H).

Example 294

N-(tert-Butyl)-2-(3-(6-ethoxy-4-((5-fluoro-1H-pyrazol-3-yl)amino)-quinazolin-2-yl)phenoxy)acetamide

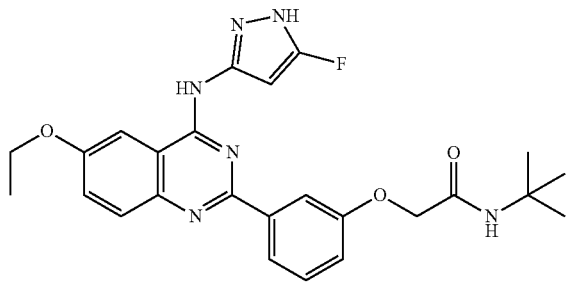

Step 1

3-(2-(tert-Butylamino)-2-oxoethoxy)-N-(2-carbamoyl-4-ethoxyphenyl)-benzamide

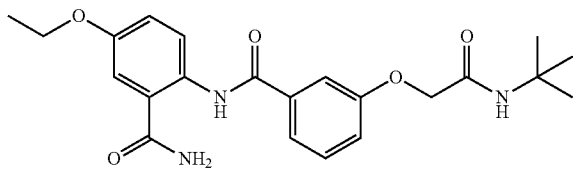 [SMILES: CCOc1ccc(NC(=O)c2cccc(OCC(=O)NC(C)(C)C)c2)c(C(N)=O)c1]

A mixture of 3-(2-(tert-butylamino)-2-oxoethoxy)benzoic acid (56.0 g, 223 mmol, 1.00 eq) and HATU (169 g, 445 mmol, 2.00 eq) in DMF (500 mL) was added 2-amino-5-ethoxybenzamide (40.2 g, 223 mmol, 1.00 eq) and DIEA (86.4 g, 669 mmol, 116 mL, 3.00 eq) and then the mixture was stirred at 25° C. for 4 h. LCMS showed desired MS was detected. The reaction mixture was extracted with ethyl acetate (700 mL×3). The combined organic layers dried over Na$_2$SO$_4$, filtered and concentrated under reduced pressure to give a residue. The residue was purified by column chromatography (SiO$_2$, Petroleum ether:Ethyl acetate=50:1 to 1:1). TLC (SiO$_2$, Petroleum ether:Ethyl acetate=1:1, P1 R$_f$=0.20) to provide the title compound (70.0 g, 76.0% yield) as a yellow solid. $^1$H NMR (400 MHz, DMSO-d$_6$) δ 12.64-12.55 (m, 1H), 8.63-8.54 (m, 1H), 8.41 (br s, 1H), 7.83 (br s, 1H), 7.57 (s, 1H), 7.52-7.46 (m, 3H), 7.44 (d, J=2.9 Hz, 1H), 7.21-7.14 (m, 2H), 4.49 (s, 2H), 4.09 (q, J=7.0 Hz, 2H), 1.35 (t, J=7.0 Hz, 3H), 1.31 (s, 9H). MS (ES+) m/e 436.1 (M+H)$^+$.

Step 2

N-(tert-Butyl)-2-(3-(6-ethoxy-4-oxo-3,4-dihydroquinazolin-2-yl)phenoxy)-acetamide

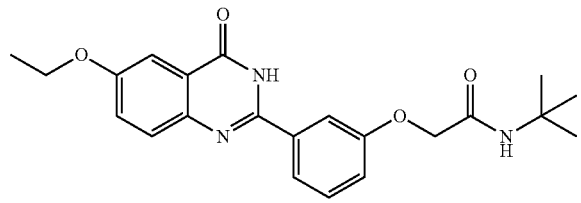 [SMILES: CCOc1ccc2nc(-c3cccc(OCC(=O)NC(C)(C)C)c3)[nH]c(=O)c2c1]

To a solution of 3-(2-(tert-butylamino)-2-oxoethoxy)-N-(2-carbamoyl-4-ethoxyphenyl)benzamide (70.0 g, 169 mmol, 1.00 eq) in EtOH (350 mL) and H$_2$O (350 mL) was added K$_2$CO$_3$ (84.2 g, 609 mmol, 3.60 eq). The mixture was stirred at 80° C. for 2 hr. LCMS showed desired MS was detected. The reaction mixture was concentrated under reduced pressure to remove the solvent. The residue was diluted with water (500 mL) and extracted with ethyl acetate (300 mL×3). The combined organic layers were dried over Na$_2$SO$_4$, filtered and concentrated under reduced pressure to give the title compound (65.0 g, 97.1% yield) as a yellow solid. $^1$H NMR (400 MHz, DMSO-d$_6$) δ 12.46 (s, 1H), 7.81-7.74 (m, 2H), 7.68 (d, J=8.8 Hz, 1H), 7.55-7.50 (m, 2H), 7.48-7.42 (m, 2H), 7.15 (dd, J=2.1, 8.0 Hz, 1H), 4.52 (s, 2H), 4.18 (q, J=6.9 Hz, 2H), 1.40 (t, J=7.0 Hz, 3H), 1.32 (s, 9H). MS (ES+) m/e 396.1 (M+H)$^+$.

Step 3

N-(tert-Butyl)-2-(3-(4-chloro-6-ethoxyquinazolin-2-yl)phenoxy)acetamide

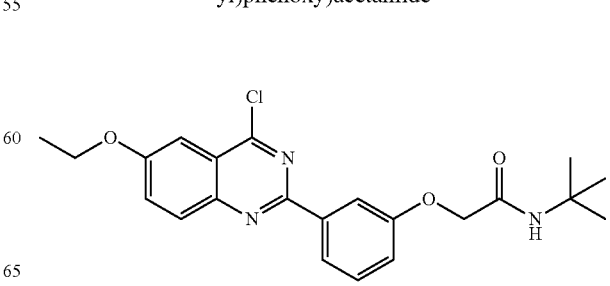

To a solution of N-(tert-butyl)-2-(3-(6-ethoxy-4-oxo-3,4-dihydroquinazolin-2-yl)phenoxy)acetamide (65.0 g, 164 mmol, 1.00 eq) in DMF (500 mL) was added SOCl$_2$ (29.3 g, 247 mmol, 17.9 mL, 1.50 eq) at 0° C. and the reaction was stirred for 2 h. LCMS showed desired MS was detected. The reaction mixture was quenched by addition water 600 mL at 0° C., and then the mixture was extracted with ethyl acetate (1000 mL×2). The combined organic layers dried over Na$_2$SO$_4$, filtered and concentrated under reduced pressure to give a residue. The crude product was triturated with DMSO (500 mL) at 25° C. for 30 min and filtered to provide the title compound (40.3 g, 58.1% yield) as a white solid. $^1$H NMR (400 MHz, DMSO-d$_6$) δ=8.12-7.96 (m, 3H), 7.84-7.73 (m, 1H), 7.67 (s, 1H), 7.52-7.45 (m, 2H), 7.14 (dd, J=2.0, 8.1 Hz, 1H), 4.53 (s, 2H), 4.28 (q, J=6.8 Hz, 2H), 1.44 (t, J=6.9 Hz, 3H), 1.34 (s, 9H). MS (ES+) m/e 414.1 (M+H)$^+$.

Step 4

N-(tert-Butyl)-2-(3-(6-ethoxy-4-(5-fluoro-1H-pyrazol-3-yl)amino)-quinazolin-2-yl)phenoxy)acetamide

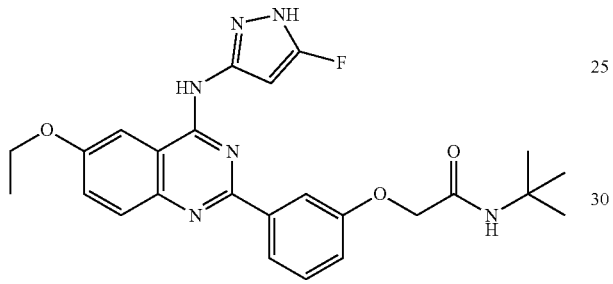

To a 1-dram vial was added N-(tert-butyl)-2-(3-(4-chloro-6-ethoxy-quinazolin-2-yl)phenoxy)acetamide (31 mg, 0.075 mmol), 5-fluoro-1H-pyrazol-3-amine (7.57, 0.075 mmol), and DIEA (19 mg, 0.15 mmol, 0.026 mL) in DMSO (0.075 mL). The reaction mixture was heated at 100° C. for 2.5 h. The mixture was diluted with DMSO/MeOH (3 mL/0.4 mL), filtered and subjected to HPLC purification to provide the title compound (13.3 mg, 30%) as a light yellow solid. MS (ES+) m/e 479 (M+H)$^+$.

Examples 295

N-(tert-Butyl)-2-(3-(6-ethoxy-4-((5-methoxy-1H-pyrazol-3-yl)amino)-quinazolin-2-yl)phenoxy)acetamide

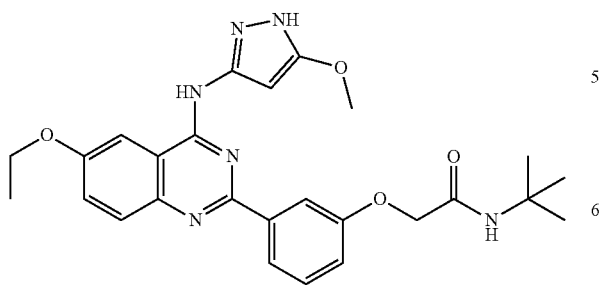

The title compound was synthesized following the synthetic sequence and the procedures described for Example 294. MS (ES+) m/e 491 (M+H)$^+$ Examples 296

2-(3-(4-(3-Amino-5-methoxy-1H-pyrazol-1-yl)-6-ethoxyquinazolin-2-yl)-phenoxy)-N-(tert-butyl)acetamide

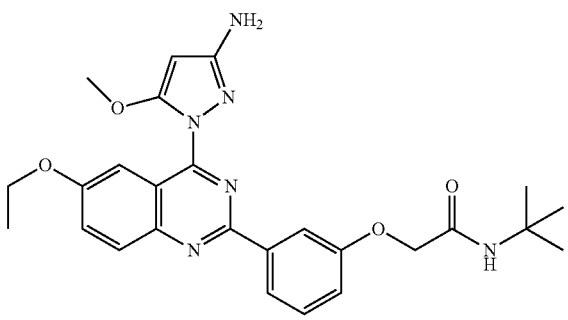 [SMILES: CCOc1ccc2nc(-c3cccc(OCC(=O)NC(C)(C)C)c3)nc(-n3nc(N)cc3OC)c2c1]

The title compound was synthesized following the synthetic sequence and the procedures described for Example 294. MS (ES+) m/e 491 (M+H)$^+$ Example 297

N-(tert-Butyl)-2-(3-(6-ethoxy-4-((5-ethyl-1H-pyrazol-3-yl)amino)-quinazolin-2-yl)phenoxy)acetamide

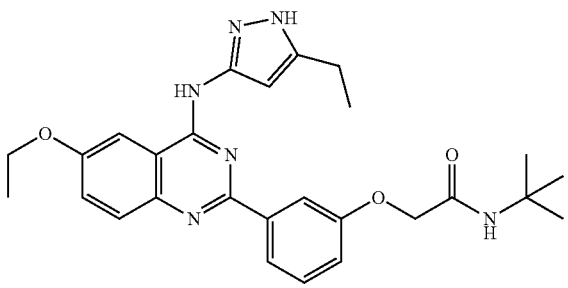 [SMILES: CCOc1ccc2nc(-c3cccc(OCC(=O)NC(C)(C)C)c3)nc(Nc3cc(CC)[nH]n3)c2c1]

The title compound was synthesized following the synthetic sequence and the procedures described for Example 294. MS (ES+) m/e 489 (M+H)$^+$.

Examples 298

N-(tert-Butyl)-2-(3-(6-ethoxy-4-((4-methyl-1H-pyrazol-3-yl)amino)-quinazolin-2-yl)phenoxy)acetamide

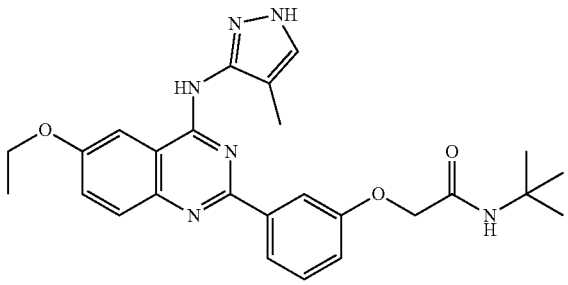 [SMILES: CCOc1ccc2nc(-c3cccc(OCC(=O)NC(C)(C)C)c3)nc(Nc3n[nH]cc3C)c2c1]

The title compound was synthesized following the synthetic sequence and the procedures described for Example 294. MS (ES+) m/e 475 (M+H)⁺.

Examples 299

2-(3-(4-(3-Amino-4-methyl-1H-pyrazol-1-yl)-6-ethoxyquinazolin-2-yl)-phenoxy)-N-(tert-butyl)acetamide

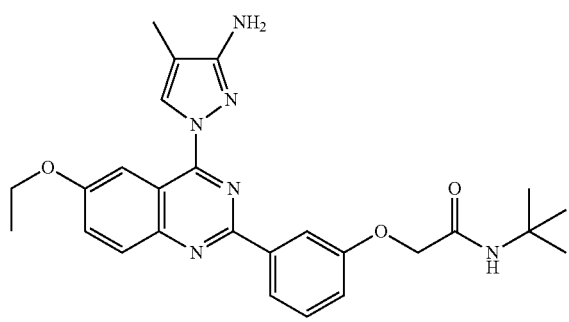 [SMILES: CCOc1ccc2nc(-c3cccc(OCC(=O)NC(C)(C)C)c3)nc(-n3cc(C)c(N)n3)c2c1]

The title compound was synthesized following the synthetic sequence and the procedures described for Example 294. MS (ES+) m/e 475 (M+H)⁺.

Example 300

N-(tert-Butyl)-2-(3-(4-((4,5-dimethyl-1H-pyrazol-3-yl)amino)-6-ethoxyquinazolin-2-yl)phenoxy)acetamide

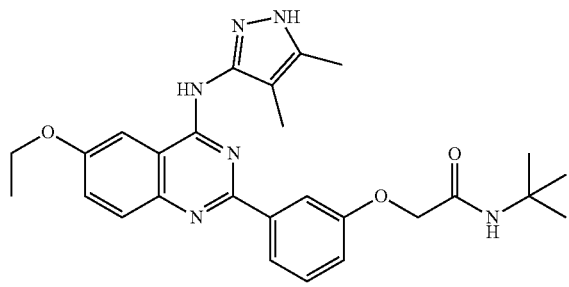 [SMILES: CCOc1ccc2nc(-c3cccc(OCC(=O)NC(C)(C)C)c3)nc(Nc3n[nH]c(C)c3C)c2c1]

The title compound was synthesized following the synthetic sequence and the procedures described for Example 294. MS (ES+) m/e 489 (M+H)⁺.

Example 301

N-(tert-Butyl)-2-(3-(4-((5-cyclobutyl-1H-pyrazol-3-yl)amino)-6-ethoxyquinazolin-2-yl)phenoxy)acetamide

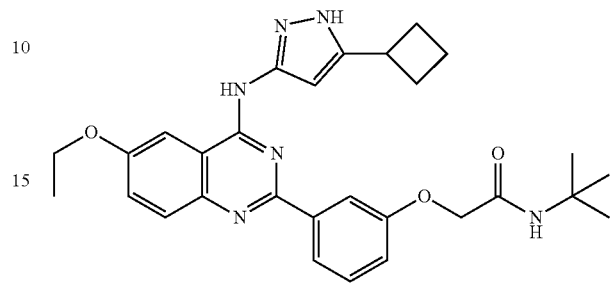

The title compound was synthesized following the synthetic sequence and the procedures described for Example 294. MS (ES+) m/e 515 (M+H)⁺.

Example 302

N-(tert-Butyl)-2-(3-(4-((5-(difluoromethyl)-1H-pyrazol-3-yl)amino)-6-ethoxyquinazolin-2-yl)phenoxy)acetamide

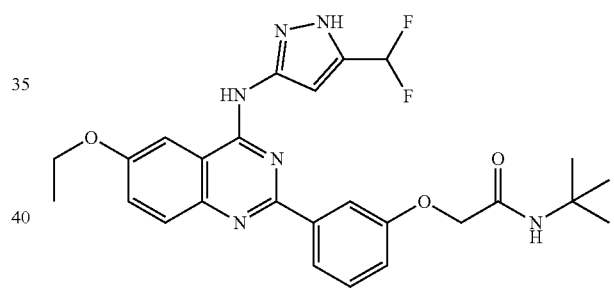

The title compound was synthesized following the synthetic sequence and the procedures described for Example 294. MS (ES+) m/e 511 (M+H)⁺.

Examples 303

N-(tert-Butyl)-2-(3-(4-((4-chloro-1H-pyrazol-3-yl)amino)-6-ethoxyquinazolin-2-yl)phenoxy)acetamide

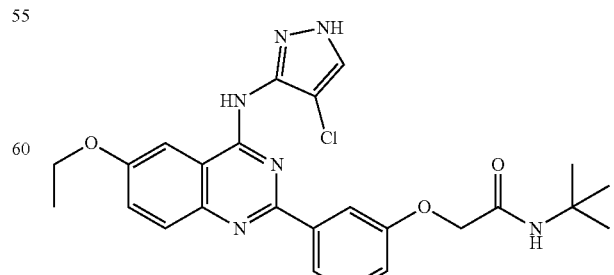

The title compound was synthesized following the synthetic sequence and the procedures described for Example 294. MS (ES+) m/e 495/497 (M+H)+.

Examples 304

2-(3-(4-(3-Amino-4-chloro-1H-pyrazol-1-yl)-6-ethoxyquinazolin-2-yl)-phenoxy)-N-(tert-butyl)acetamide

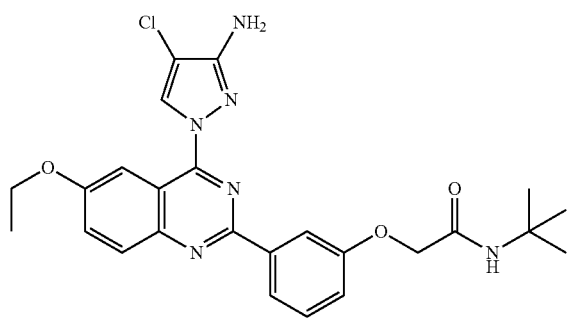

The title compound was synthesized following the synthetic sequence and the procedures described for Example 294. MS (ES+) m/e 495/497 (M+H)+.

Example 305

N-(tert-Butyl)-2-(3-(6-ethoxy-4-((1-methyl-1H-pyrazol-3-yl)amino)-quinazolin-2-yl)phenoxy)acetamide

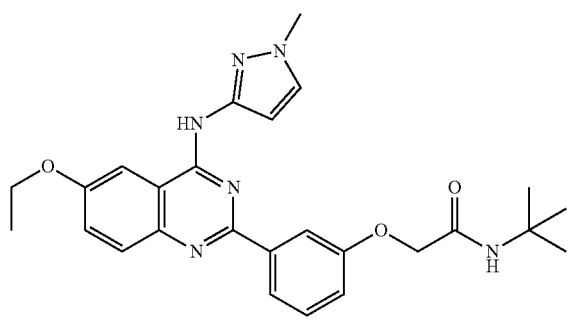 [SMILES: CCOc1ccc2nc(-c3cccc(OCC(=O)NC(C)(C)C)c3)nc(Nc3ccn(C)n3)c2c1]

The title compound was synthesized following the synthetic sequence and the procedures described for Example 294. MS (ES+) m/e 475 (M+H)+.

Examples 306

N-(tert-Butyl)-2-(3-(4-((4-cyclopropyl-1H-pyrazol-3-yl)amino)-6-ethoxyquinazolin-2-yl)phenoxy)acetamide

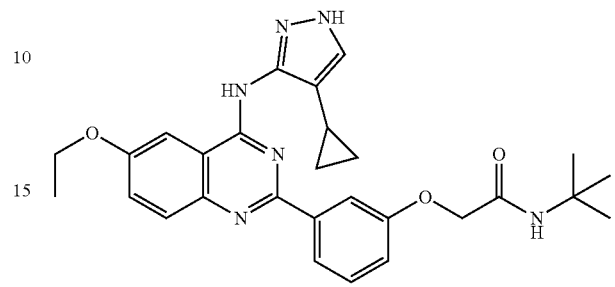

The title compound was synthesized following the synthetic sequence and the procedures described for Example 294. MS (ES+) m/e 501 (M+H)+.

Examples 307

2-(3-(4-(3-Amino-4-cyclopropyl-1H-pyrazol-1-yl)-6-ethoxyquinazolin-2-yl)-phenoxy)-N-(tert-butyl)acetamide

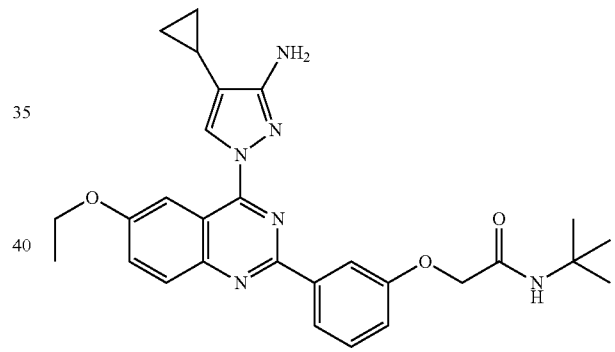

The title compound was synthesized following the synthetic sequence and the procedures described for Example 294. MS (ES+) m/e 501 (M+H)+.

Example 308

N-(tert-Butyl)-2-(3-(4-((3-chloro-5-methyl-1H-pyrazol-4-yl)amino)-6-ethoxyquinazolin-2-yl)phenoxy)acetamide

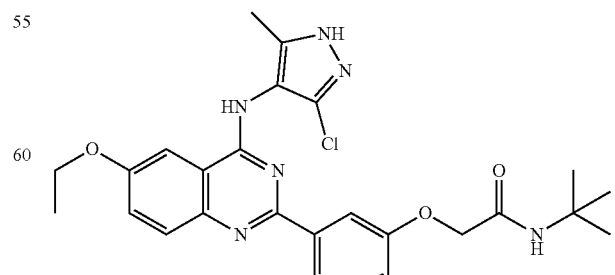

The title compound was synthesized following the synthetic sequence and the procedures described for Example 294. MS (ES+) m/e 509 (M+H)⁺.

Examples 309

N-(tert-Butyl)-2-(3-(6-ethoxy-4-((4-(trifluoromethyl)-1H-pyrazol-3-yl)amino)-quinazolin-2-yl)phenoxy)acetamide

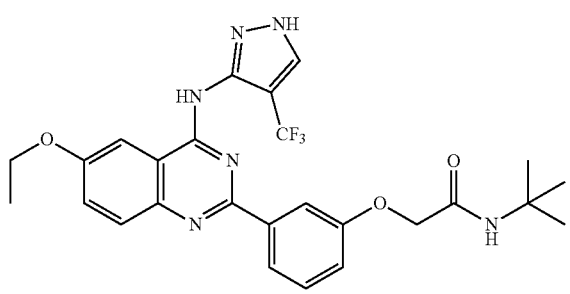 [SMILES: CCOc1ccc2nc(-c3cccc(OCC(=O)NC(C)(C)C)c3)nc(Nc3n[nH]cc3C(F)(F)F)c2c1]

The title compound was synthesized following the synthetic sequence and the procedures described for Example 294. MS (ES+) m/e 529 (M+H)⁺.

Examples 310

2-(3-(4-(3-Amino-4-(trifluoromethyl)-1H-pyrazol-1-yl)-6-ethoxy-quinazolin-2-yl)phenoxy)-N-(tert-butyl)acetamide

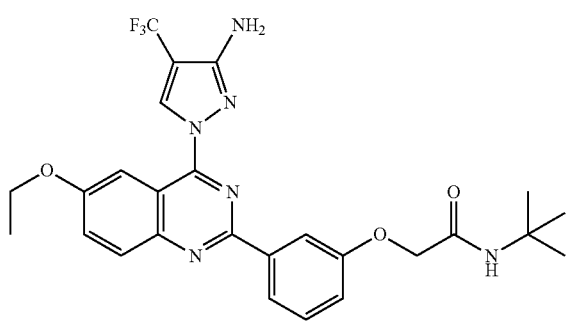

The title compound was synthesized following the synthetic sequence and the procedures described for Example 294. MS (ES+) m/e 529 (M+H)⁺.

Example 311

N-(tert-Butyl)-2-(3-(4-((3-cyclopropyl-1H-pyrazol-4-yl)amino)-6-ethoxyquinazolin-2-yl)phenoxy)acetamide

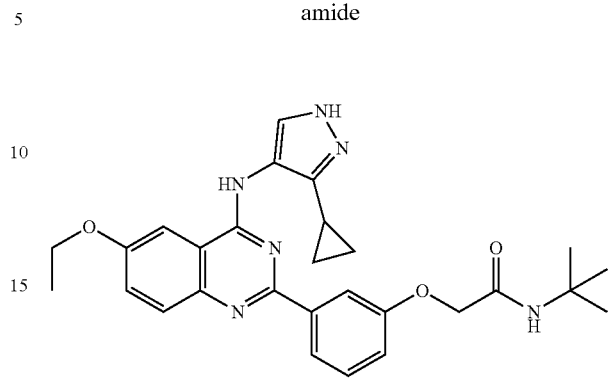

The title compound was synthesized following the synthetic sequence and the procedures described for Example 294. MS (ES+) m/e 501 (M+H)⁺.

Example 312

N-(tert-Butyl)-2-(3-(4-((5-cyclopropyl-1H-pyrazol-3-yl)amino)-6-ethoxyquinazolin-2-yl)phenoxy)acetamide

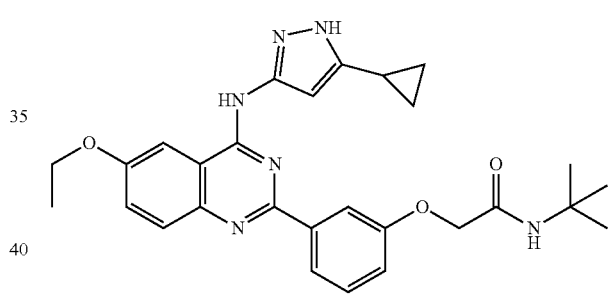

The title compound was synthesized following the synthetic sequence and the procedures described for Example 294. MS (ES+) m/e 501 (M+H)⁺.

Example 313

N-(tert-Butyl)-2-(3-(4-((1-cyclopropyl-1H-pyrazol-4-yl)amino)-6-ethoxyquinazolin-2-yl)phenoxy)acetamide

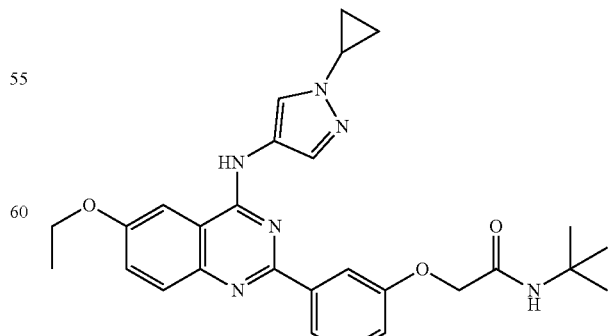

The title compound was synthesized following the synthetic sequence and the procedures described for Example 294. MS (ES+) m/e 501 (M+H)+.

Example 314

N-(tert-Butyl)-2-(3-(4-((5-chloro-1H-pyrazol-4-yl)amino)-6-ethoxyquinazolin-2-yl)phenoxy)acetamide

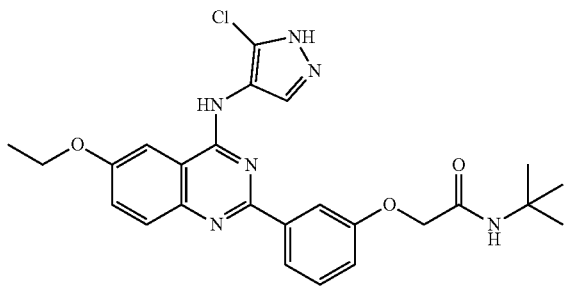 [SMILES: CCOc1ccc2nc(-c3cccc(OCC(=O)NC(C)(C)C)c3)nc(Nc3cn[nH]c3Cl)c2c1]

The title compound was synthesized following the synthetic sequence and the procedures described for Example 294. MS (ES+) m/e 495/497 (M+H)+.

Example 315

N-(tert-Butyl)-2-(3-(6-ethoxy-4-((5-(trifluoromethyl)-1H-pyrazol-4-yl)amino)-quinazolin-2-yl)phenoxy)acetamide

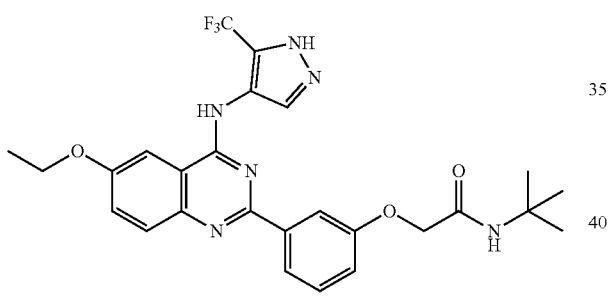

The title compound was synthesized following the synthetic sequence and the procedures described for Example 294. MS (ES+) m/e 529 (M+H)+.

Example 316

N-(tert-Butyl)-2-(3-(6-ethoxy-4-((5-methyl-1H-pyrazol-3-yl)amino)-quinazolin-2-yl)phenoxy)acetamide

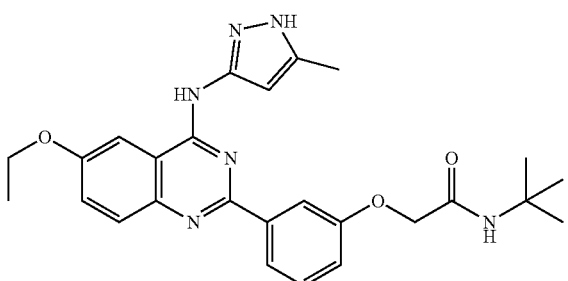

The title compound was synthesized following the synthetic sequence and the procedures described for Example 294. MS (ES+) m/e 475 (M+H)+.

Example 317

N-(tert-Butyl)-2-(3-(6-ethoxy-4-((tetrahydro-2H-pyran-4-yl)amino)-quinazolin-2-yl)phenoxy)acetamide

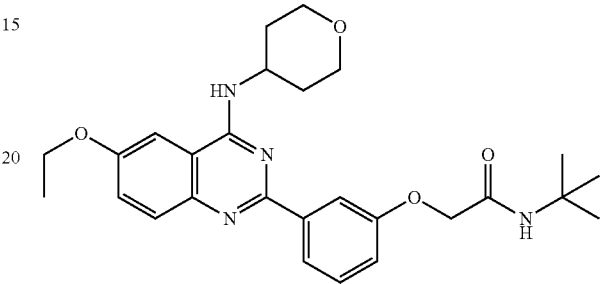

The title compound was synthesized following the synthetic sequence and the procedures described for Example 294. MS (ES+) m/e 479 (M+H)+.

Example 318

4-((2-(3-(2-(tert-Butylamino)-2-oxoethoxy)phenyl)-6-ethoxy-quinazolin-4-yl)amino)benzoic Acid

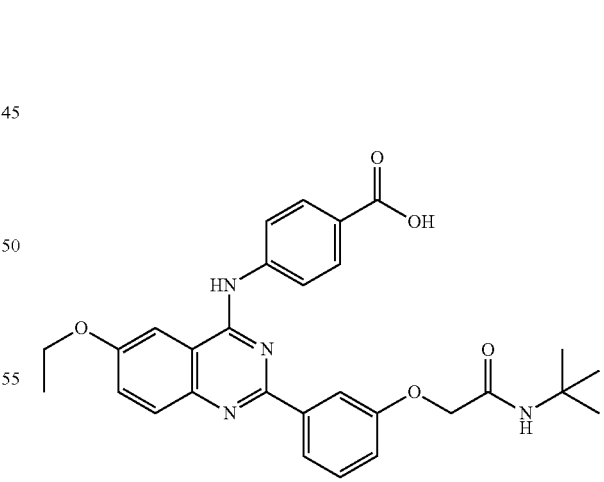

The title compound was synthesized following the synthetic sequence and the procedures described for Example 294. MS (ES+) m/e 513 (M+H)+.

Example 319

3-((2-(3-(2-(tert-Butylamino)-2-oxoethoxy)phenyl)-6-ethoxy-quinazolin-4-yl)amino)benzoic Acid

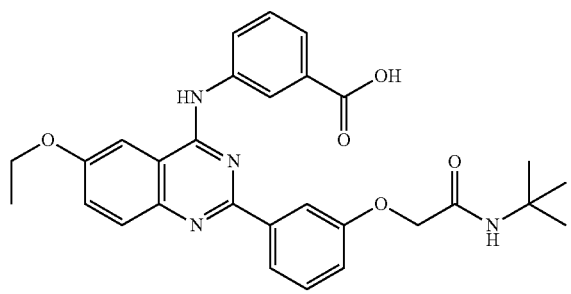 [SMILES: CCOc1ccc2nc(-c3cccc(OCC(=O)NC(C)(C)C)c3)nc(Nc3cccc(C(=O)O)c3)c2c1]

The title compound was synthesized following the synthetic sequence and the procedures described for Example 294. MS (ES+) m/e 515 (M+H)⁺.

Example 320

2-(3-(4-((1H-Imidazol-2-yl)amino)-6-ethoxyquinazolin-2-yl)phenoxy)-N-(tert-butyl)acetamide

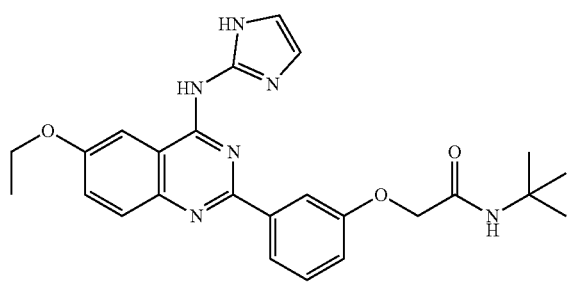 [SMILES: CCOc1ccc2nc(-c3cccc(OCC(=O)NC(C)(C)C)c3)nc(Nc3ncc[nH]3)c2c1]

The title compound was synthesized following the synthetic sequence and the procedures described for Example 294. MS (ES+) m/e 461 (M+H)⁺.

Example 321

N-(tert-Butyl)-2-(3-(6-ethoxy-4-((5-fluoropyridin-2-yl)amino)-quinazolin-2-yl)phenoxy)acetamide

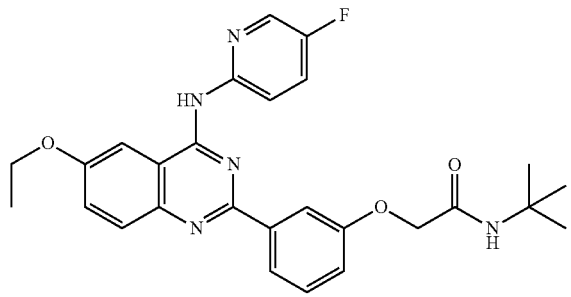 [SMILES: CCOc1ccc2nc(-c3cccc(OCC(=O)NC(C)(C)C)c3)nc(Nc3ccc(F)cn3)c2c1]

The title compound was synthesized following the synthetic sequence and the procedures described for Example 294. MS (ES+) m/e 490 (M+H)+.

Example 322

N-(tert-Butyl)-2-(3-(4-((6-cyanopyridin-3-yl)amino)-6-ethoxy-quinazolin-2-yl)phenoxy)acetamide

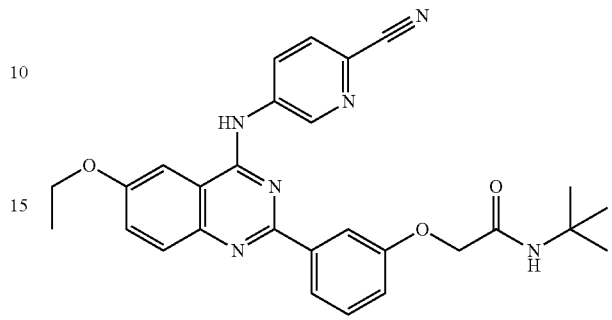

The title compound was synthesized following the synthetic sequence and the procedures described for Example 294. MS (ES+) m/e 497 (M+H)⁺.

Example 323

2-(3-(4-((1,2,4-Thiadiazol-5-yl)amino)-6-ethoxyquinazolin-2-yl)phenoxy)-N-(tert-butyl)acetamide

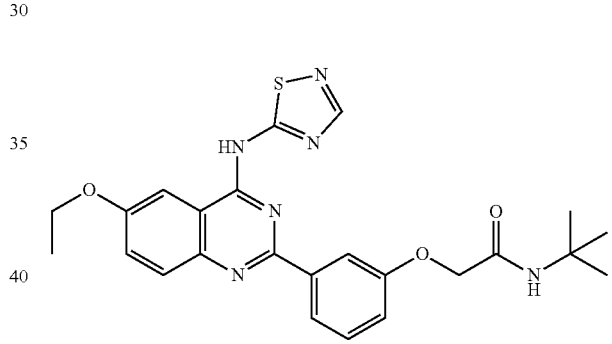

The title compound was synthesized following the synthetic sequence and the procedures described for Example 294. MS (ES+) m/e 479 (M+H)⁺.

Example 324

N-(tert-Butyl)-2-(3-(6-ethoxy-4-(thiazol-2-ylamino)quinazolin-2-yl)-phenoxy)acetamide

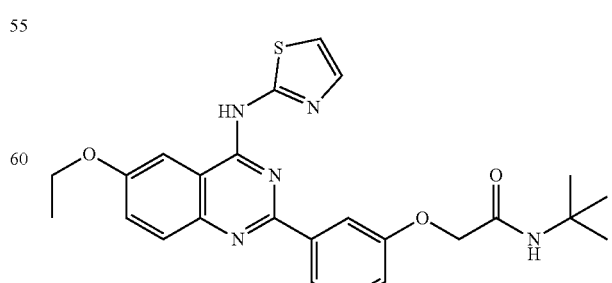

The title compound was synthesized following the synthetic sequence and the procedures described for Example 294. MS (ES+) m/e 478 (M+H)+.

Example 325

2-(3-(4-((2-Aminopyridin-4-yl)amino)-6-ethoxyquinazolin-2-yl)phenoxy)-N-(tert-butyl)acetamide

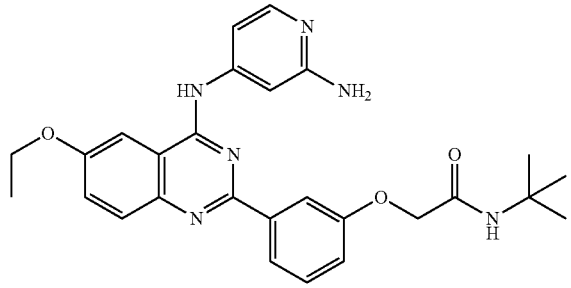 [SMILES: CCOc1ccc2nc(-c3cccc(OCC(=O)NC(C)(C)C)c3)nc(Nc3ccnc(N)c3)c2c1]

The title compound was synthesized following the synthetic sequence and the procedures described for Example 294. MS (ES+) m/e 487 (M+H)+.

Example 326

2-(3-(4-(((1H-Pyrazol-5-yl)methyl)amino)-6-ethoxy-quinazolin-2-yl)-phenoxy)-N-(tert-butyl)acetamide

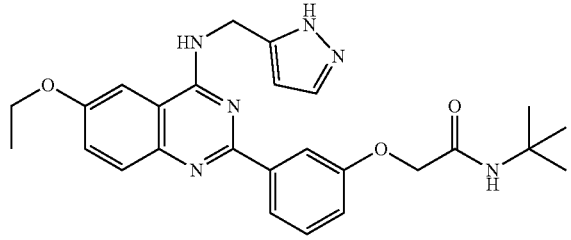 [SMILES: CCOc1ccc2nc(-c3cccc(OCC(=O)NC(C)(C)C)c3)nc(NCc3ccn[nH]3)c2c1]

The title compound was synthesized following the synthetic sequence and the procedures described for Example 294. MS (ES+) m/e 475 (M+H)+.

Example 327

N-(tert-Butyl)-2-(3-(6-ethoxy-4-(((1-methyl-1H-pyrazol-4-yl)methyl)amino)-quinazolin-2-yl)phenoxy)acetamide

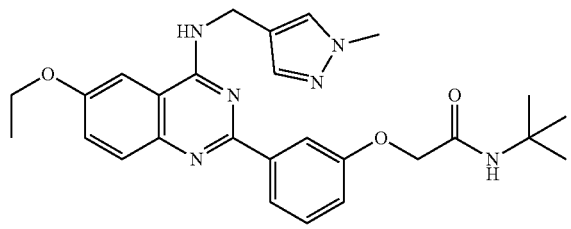 [SMILES: CCOc1ccc2nc(-c3cccc(OCC(=O)NC(C)(C)C)c3)nc(NCc3cnn(C)c3)c2c1]

The title compound was synthesized following the synthetic sequence and the procedures described for Example 294. MS (ES+) m/e 489 (M+H)+.

Example 328

2-(3-(4-(((1H-Pyrazol-4-yl)methyl)amino)-6-ethoxy-quinazolin-2-yl)phenoxy)-N-(tert-butyl)acetamide

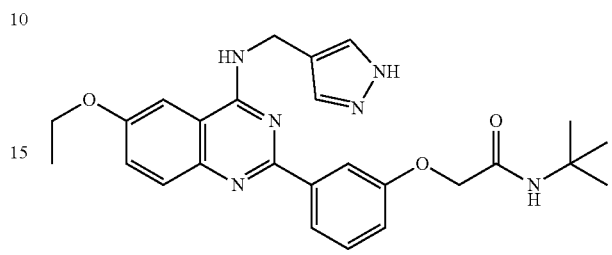

The title compound was synthesized following the synthetic sequence and the procedures described for Example 294. MS (ES+) m/e 475 (M+H)+.

Example 329

N-(tert-Butyl)-2-(3-(6-ethoxy-4-(((1-methyl-1H-pyrazol-3-yl)methyl)amino)-quinazolin-2-yl)phenoxy)acetamide

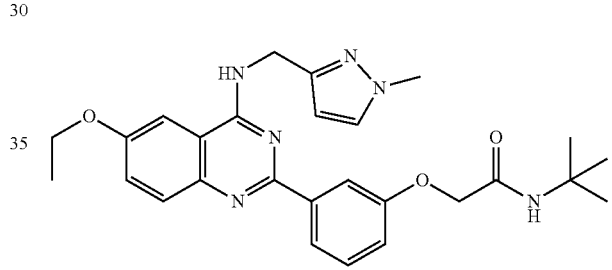

The title compound was synthesized following the synthetic sequence and the procedures described for Example 294. MS (ES+) m/e 489 (M+H)+.

Example 330

2-((2-(3-(2-(tert-Butylamino)-2-oxoethoxy)phenyl)-6-ethoxyquinazolin-4-yl)-amino)thiophene-3-carboxamide

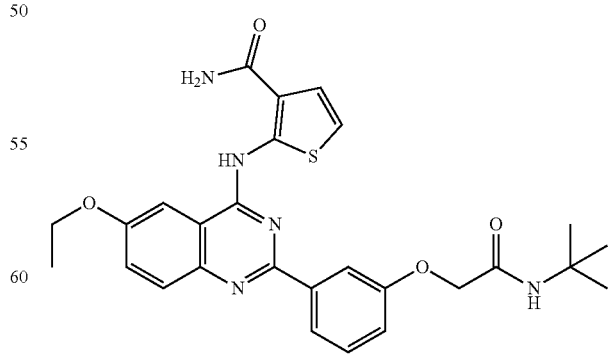

The title compound was synthesized following the synthetic sequence and the procedures described for Example 294. MS (ES+) m/e 520 (M+H)+.

Example 331

1-((2-(3-(2-(tert-Butylamino)-2-oxoethoxy)phenyl)-6-ethoxyquinazolin-4-yl)-amino)cyclopentane-1-carboxamide

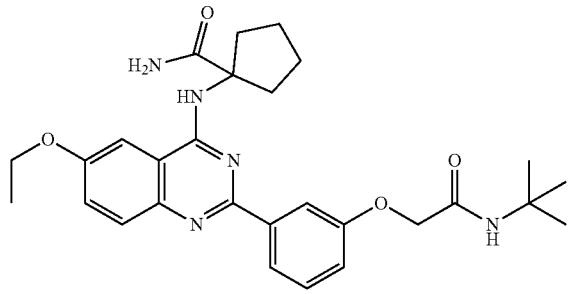 [SMILES: CCOc1ccc2nc(-c3cccc(OCC(=O)NC(C)(C)C)c3)nc(NC3(C(N)=O)CCCC3)c2c1]

The title compound was synthesized following the synthetic sequence and the procedures described for Example 294. MS (ES+) m/e 506 (M+H)+.

Example 332

3-((2-(3-(2-(tert-Butylamino)-2-oxoethoxy)phenyl)-6-ethoxyquinazolin-4-yl)-amino)benzamide

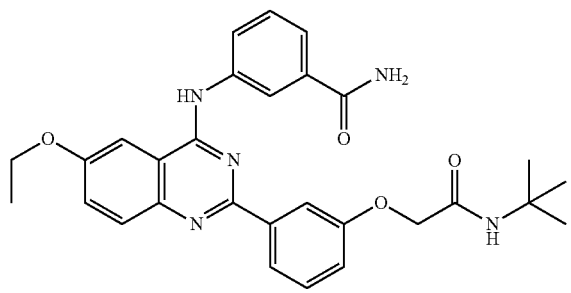 [SMILES: CCOc1ccc2nc(-c3cccc(OCC(=O)NC(C)(C)C)c3)nc(Nc3cccc(C(N)=O)c3)c2c1]

The title compound was synthesized following the synthetic sequence and the procedures described for Example 294. MS (ES+) m/e 513 (M+H)+.

Example 333

2-(3-(4-((2H-1,2,3-Triazol-4-yl)amino)-6-ethoxyquinazolin-2-yl)phenoxy)-N-(tert-butyl)acetamide

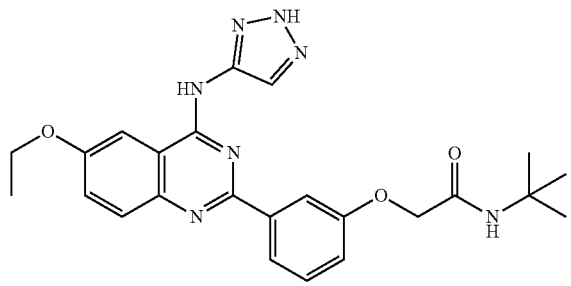 [SMILES: CCOc1ccc2nc(-c3cccc(OCC(=O)NC(C)(C)C)c3)nc(Nc3cn[nH]n3)c2c1]

The title compound was synthesized following the synthetic sequence and the procedures described for Example 294. MS (ES+) m/e 462 (M+H)+.

Example 334

2-(3-(4-((1H-Pyrazol-4-yl)amino)-6-(trifluoromethyl)quinazolin-2-yl)-phenoxy)-N-(tert-butyl)acetamide

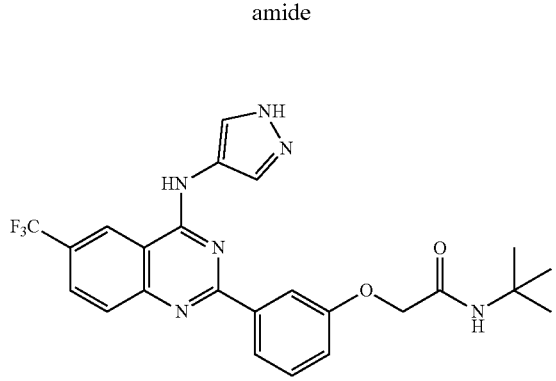

Step 1

2-Chloro-N-(1H-pyrazol-4-yl)-6-(trifluoromethyl)quinazolin-4-amine

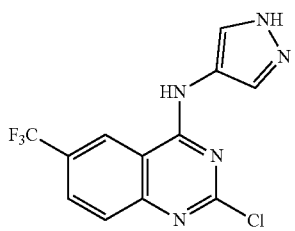 [SMILES: FC(F)(F)c1ccc2nc(Cl)nc(Nc3cn[nH]c3)c2c1]

To a solution of 4-Aminopyrazole (111 mg, 1.00 mmol) in DMF (3.3 mL) in a 20 mL vial was added 2,4-Dichloro-6-trifluoromethylquinazoline (200 mg, 1.00 mmol) and DIEA (258 mg, 2.00 mmol, 0.348 mL). The mixture was heated at 100° C. overnight, cooled to rt and poured into water. The precipitate that was formed was filtered and washed with water, dried on the filter for 1 h then in a desiccator overnight to give 227 mg of a grey solid that was used as is in the next step. MS (ES+) m/e 314/316 (M+H)+.

Step 2

2-(3-(4-((1H-Pyrazol-4-yl)amino)-6-(trifluoromethyl)quinazolin-2-yl)-phenoxy)-N-(tert-butyl)acetamide

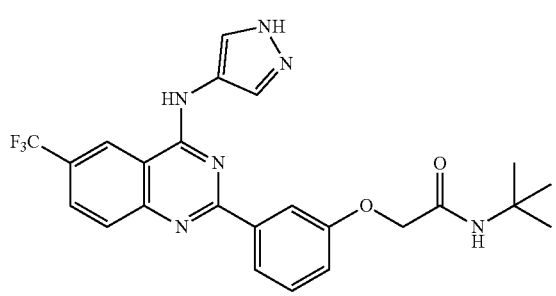 [SMILES: CC(C)(C)NC(=O)COc1cccc(-c2nc(Nc3cn[nH]c3)c3cc(C(F)(F)F)ccc3n2)c1]

To N-isopropyl-2-(3-(4,4,5,5-tetramethyl-1,3,2-dioxaborolan-2-yl)phenoxy) acetamide (INT-5, 33.3 mg, 0.100 mmol) in a 10 mL microwave vessel was added 2-chloro-N-(1H-pyrazol-4-yl)-6-(trifluoromethyl)quinazolin-4-amine (30 mg, 0.100 mmol), Pd(PPh$_3$)$_4$ (11.6 mg, 0.0100 mmol) and dioxane (1 mL). Then a solution of aqueous sodium carbonate (2M, 0.100 mL, 0.200 mmol) and water (0.100 mL) were added. The vessel was flushed with nitrogen then it was irradiated at 180° C. for 2 h. After the reaction was cooled to rt, the mixture was concentrated and purified by HPLC to give 6.5 mg, 11%, of the title compound as an olive green solid. MS (ES+) m/e 485 (M+H)$^+$.

Example 335

2-(3-(4-((1H-Pyrazol-4-yl)amino)-7-(trifluoromethyl)quinazolin-2-yl)-phenoxy)-N-(tert-butyl)acetamide

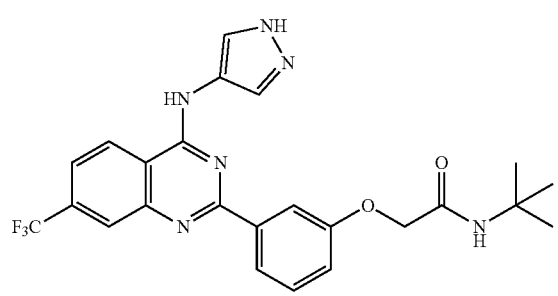 [SMILES: CC(C)(C)NC(=O)COc1cccc(-c2nc(Nc3cn[nH]c3)c3ccc(C(F)(F)F)cc3n2)c1]

The title compound was synthesized following the synthetic sequence and the procedures described for Example 334. MS (ES+) m/e 485 (M+H)$^+$.

Example 336

2-(3-(4-((1H-Pyrazol-4-yl)amino)-8-(trifluoromethyl)quinazolin-2-yl)-phenoxy)-N-(tert-butyl)acetamide

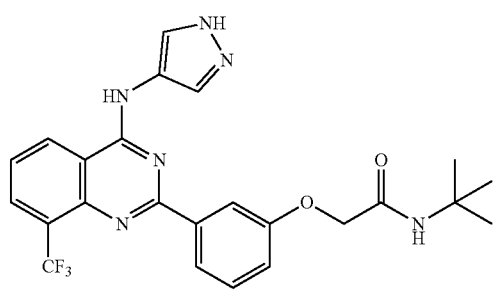 [SMILES: CC(C)(C)NC(=O)COc1cccc(-c2nc(Nc3cn[nH]c3)c3cccc(C(F)(F)F)c3n2)c1]

The title compound was synthesized following the synthetic sequence and the procedures described for Example 334. MS (ES+) m/e 485 (M+H)$^+$.

Example 337

2-(3-(4-((1H-Pyrazol-4-yl)amino)-7-fluoro-6-methoxyquinazolin-2-yl)-phenoxy)-N-(tert-butyl) acetamide

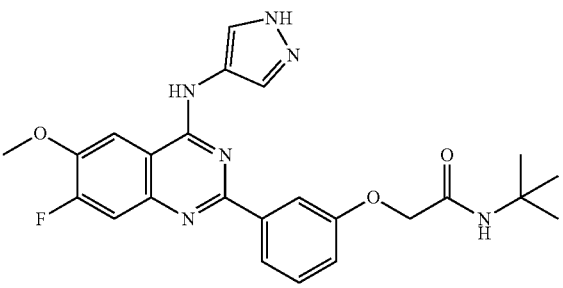 [SMILES: COc1cc2c(Nc3cn[nH]c3)nc(-c3cccc(OCC(=O)NC(C)(C)C)c3)nc2cc1F]

The title compound was synthesized following the synthetic sequence and the procedures described for Example 334. MS (ES+) m/e 465 (M+H)$^+$.

Example 338

N-(3-(6-Ethoxy-4-((1-methyl-1H-pyrazol-4-yl)amino)quinazolin-2-yl)-benzyl)pivalamide

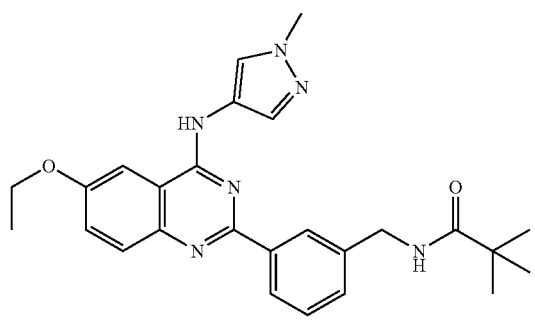 [SMILES: CCOc1ccc2nc(-c3cccc(CNC(=O)C(C)(C)C)c3)nc(Nc3cnn(C)c3)c2c1]

The title compound was synthesized following the synthetic sequence and the procedures described for Example 334. MS (ES+) m/e 459 (M+H)$^+$.

Example 339

6-Ethoxy-N-(1-methyl-1H-pyrazol-4-yl)-2-(3-morpholinophenyl)-quinazolin-4-amine

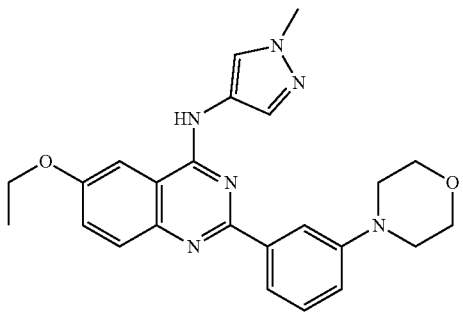 [SMILES: CCOc1ccc2nc(-c3cccc(N4CCOCC4)c3)nc(Nc3cnn(C)c3)c2c1]

The title compound was synthesized following the synthetic sequence and the procedures described for Example 334. MS (ES+) m/e 431 (M+H)$^+$.

Example 340

6-Ethoxy-N-(1-methyl-1H-pyrazol-4-yl)-2-(2-morpholinopyridin-4-yl)-quinazolin-4-amine

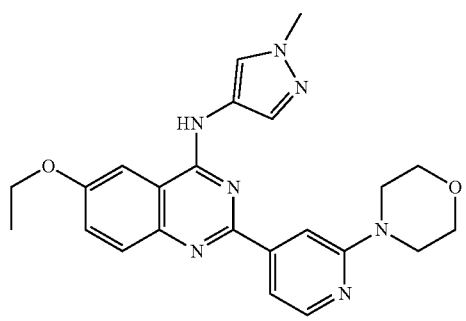 [SMILES: CCOc1ccc2nc(-c3ccnc(N4CCOCC4)c3)nc(Nc3cnn(C)c3)c2c1]

The title compound was synthesized following the synthetic sequence and the procedures described for Example 334. MS (ES+) m/e 432 (M+H)⁺.

Example 341

6-Ethoxy-N-(1-methyl-1H-pyrazol-4-yl)-2-(2-(4-methylpiperazin-1-yl)-pyridin-4-yl)quinazolin-4-amine

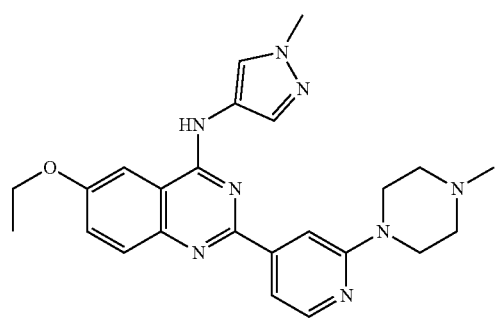 [SMILES: CCOc1ccc2nc(-c3ccnc(N4CCN(C)CC4)c3)nc(Nc3cnn(C)c3)c2c1]

The title compound was synthesized following the synthetic sequence and the procedures described for Example 334. MS (ES+) m/e 445 (M+H)⁺.

Example 342

4-(4-(6-Ethoxy-4-((1-methyl-1H-pyrazol-4-yl)amino)quinazolin-2-yl)-pyridin-2-yl)piperazin-2-one

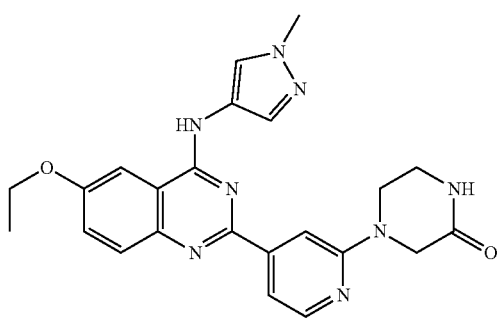 [SMILES: CCOc1ccc2nc(-c3ccnc(N4CCNC(=O)C4)c3)nc(Nc3cnn(C)c3)c2c1]

Step 1

6-Ethoxy-2-(2-fluoropyridin-4-yl)-N-(1-methyl-1H-pyrazol-4-yl)-quinazolin-4-amine

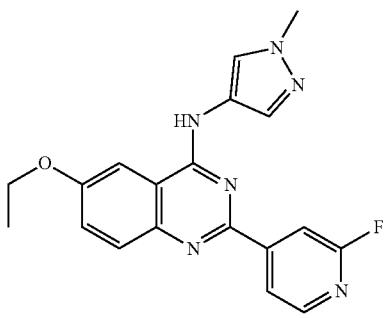 [SMILES: CCOc1ccc2nc(-c3ccnc(F)c3)nc(Nc3cnn(C)c3)c2c1]

To a mixture of 2-chloro-6-ethoxy-N-(1-methyl-1H-pyrazol-4-yl)-quinazolin-4-amine (25 mg, 0.082 mmol), 2-fluoropyridine-4-boronic acid (11.6 mg, 0.082 mmol), and Pd(PPh$_3$)$_4$ (9.5 mg, 0.0082 mmol) in a 10 mL microwave vessel was added dioxane (0.82 mL) followed by a solution of sodium carbonate (2M, 0.165 mmol, 0.082 mL), and water (0.082 mL). The vessel was flushed with nitrogen then the vessel was irradiated at 150° C. for 30 min. The mixture was diluted with water and extracted with EtOAc twice. The combined organic layers were washed with water once, saturated NaCl once, dried over sodium sulfate, decanted, and concentrated in vacuo to give an orange oil. The oil was dissolved in EtOAc and methanol and absorbed onto 4 g of Celite. The Celite was eluted on a 24 g silica gel column using 10% EtOAc/Hexanes to EtOAc gradient solvent system. This yielded 234 mg, 64%, of the product as a yellow solid.

Step 2

4-(4-(6-Ethoxy-4-((1-methyl-1H-pyrazol-4-yl)amino)quinazolin-2-yl)-pyridin-2-yl)piperazin-2-one

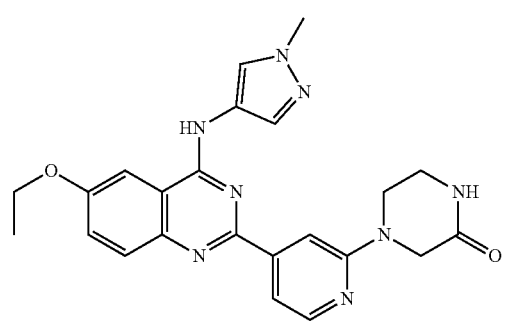 [SMILES: CCOc1ccc2nc(-c3ccnc(N4CCNC(=O)C4)c3)nc(Nc3cnn(C)c3)c2c1]

A solution of 6-ethoxy-2-(2-fluoropyridin-4-yl)-N-(1-methyl-1H-pyrazol-4-yl)-quinazolin-4-amine (15.2 mg, 0.050 mmol), and piperazin-2-one (25.0 mg, 0.250 mmol) in EtOH (0.100 mL) in a 1 dram vial was irradiated at 180° C. for 30 min in the microwave. The cooled mixture was dissolved in DMSO/MeOH (1.5 mL/0.2 mL), filtered, and subjected to HPLC to give 10.6 mg, 38%, of the title compound as a red-orange solid. MS (ES+) m/e 445 (M+H)⁺.

Example 343

1-(4-(6-Ethoxy-4-((1-methyl-1H-pyrazol-4-yl)amino)quinazolin-2-yl)-pyridin-2-yl)pyrrolidin-3-ol

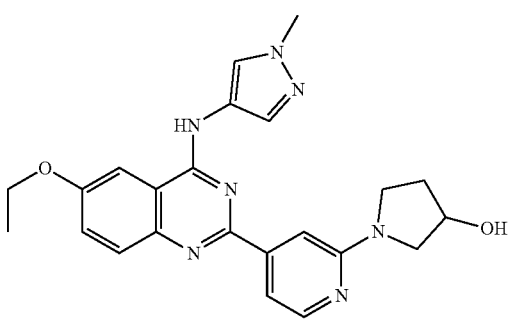 [SMILES: CCOc1ccc2nc(-c3ccnc(N4CCC(O)C4)c3)nc(Nc3cnn(C)c3)c2c1]

The title compound was synthesized following the synthetic sequence and the procedures described for Example 342. MS (ES+) m/e 432 (M+H)⁺.

Example 344

1-(4-(6-Ethoxy-4-((1-methyl-1H-pyrazol-4-yl)amino)quinazolin-2-yl)-pyridin-2-yl)piperidin-4-ol

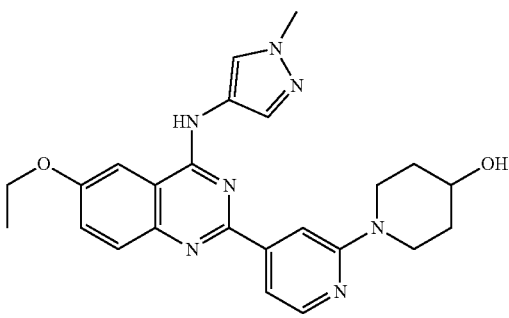 [SMILES: CCOc1ccc2nc(-c3ccnc(N4CCC(O)CC4)c3)nc(Nc3cnn(C)c3)c2c1]

The title compound was synthesized following the synthetic sequence and the procedures described for Example 342. MS (ES+) m/e 446 (M+H)⁺.

Example 345

1-(4-(6-Ethoxy-4-((1-methyl-1H-pyrazol-4-yl)amino)quinazolin-2-yl)-pyridin-2-yl)-4-methylpiperidin-4-ol

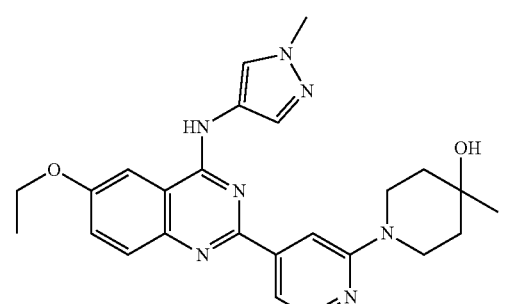

The title compound was synthesized following the synthetic sequence and the procedures described for Example 342. MS (ES+) m/e 460 (M+H)⁺.

Example 346

6-Ethoxy-N-(1-methyl-1H-pyrazol-4-yl)-2-(2-(2-methylmorpholino)-pyridin-4-yl)quinazolin-4-amine

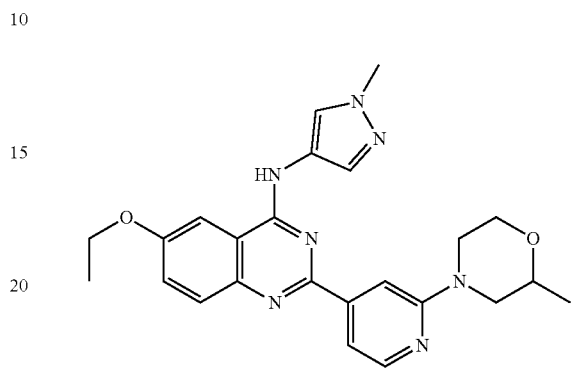

The title compound was synthesized following the synthetic sequence and the procedures described for Example 342. MS (ES+) m/e 446 (M+H)⁺.

Example 347

6-Ethoxy-2-(3-((1-methyl-1H-pyrazol-4-yl)methoxy)phenyl)-N-(1H-pyrazol-3-yl)quinazolin-4-amine

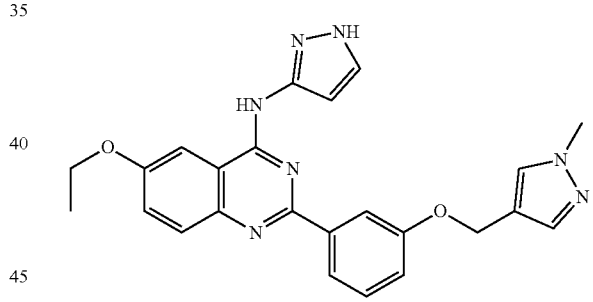

Step 1

1-Methyl-4-((3-(4,4,5,5-tetramethyl-1,3,2-dioxaborolan-2-yl)phenoxy)-methyl)-1H-pyrazole

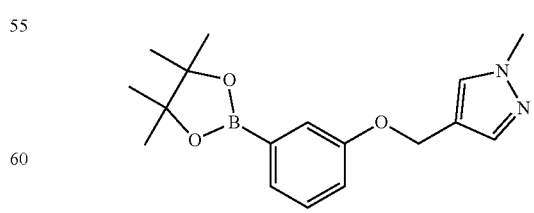

To a solution of 3-(4,4,5,5-Tetramethyl-1,3,2-dioxaborolan-2-yl)phenol (250 mg, 1.14 mmol) in DMF (3.8 mL) was added K₂CO₃ (314 mg, 2.27 mmol) followed by 4-(Chloromethyl)-1-methyl-1H-pyrazole (190 mg, 1.14 mmol). The reaction mixture was heated at 65° C. overnight. To the cooled mixture was added EtOAc and the mixture was then extracted with water. The organic layer was washed with water twice and brine once, dried over sodium sulfate, and concentrated in vacuo to provide 124 mg, 35%, of the product as a yellow oil. The product is used as is in the next step. MS (ES+) m/e 315 (M+H)+.

Step 2

6-Ethoxy-2-(3-((1-methyl-1H-pyrazol-4-yl)methoxy) phenyl)-N-(1H-pyrazol-3-yl)quinazolin-4-amine

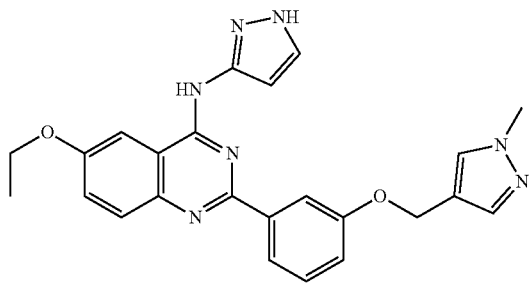 [SMILES: CCOc1ccc2nc(-c3cccc(OCc4cnn(C)c4)c3)nc(Nc3cc[nH]n3)c2c1]

The title compound was made in a similar manner by using the procedure in Example 334. MS (ES+) m/e 442 (M+H)+.

Example 348

6-Ethoxy-2-(3-((5-methyl-1,3,4-oxadiazol-2-yl) methoxy)phenyl)-N-(1H-pyrazol-3-yl)quinazolin-4-amine

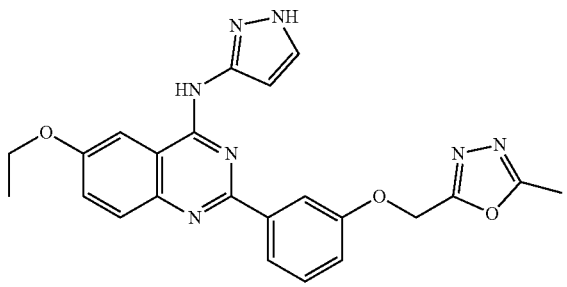 [SMILES: CCOc1ccc2nc(-c3cccc(OCc4nnc(C)o4)c3)nc(Nc3cc[nH]n3)c2c1]

The title compound was synthesized following the synthetic sequence and the procedures described for Example 347. MS (ES+) m/e 444 (M+H)+.

Example 349

6-Ethoxy-2-(3-((5-methylisoxazol-3-yl)methoxy) phenyl)-N-(1H-pyrazol-3-yl)quinazolin-4-amine

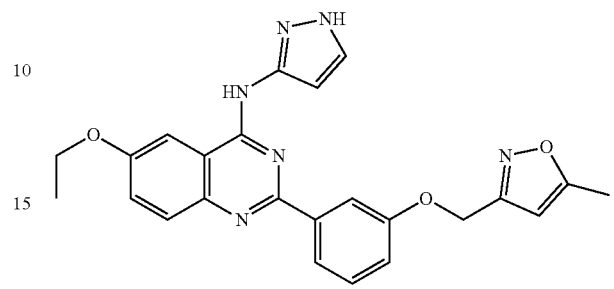

The title compound was synthesized following the synthetic sequence and the procedures described for Example 347. MS (ES+) m/e 443 (M+H)+.

Example 350

N-(3-(4-((1H-Pyrazol-3-yl)amino)-6-ethoxyquinazolin-2-yl)phenyl)-tetrahydrofuran-3-carboxamide

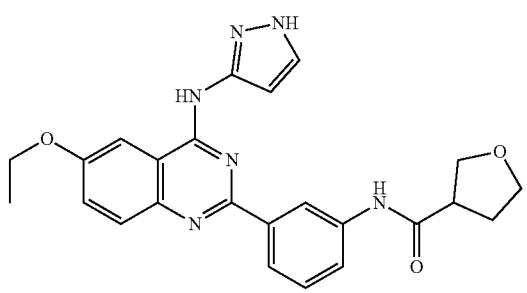 [SMILES: CCOc1ccc2nc(-c3cccc(NC(=O)C4CCOC4)c3)nc(Nc3cc[nH]n3)c2c1]

The title compound was synthesized following the synthetic sequence and the procedures described for Example 347. MS (ES+) m/e 445 (M+H)+.

Example 351

N-(3-(4-((1H-Pyrazol-3-yl)amino)-6-ethoxyquinazolin-2-yl)phenyl)-furan-3-carboxamide

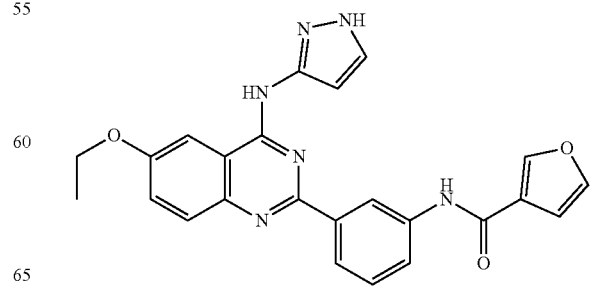

The title compound was synthesized following the synthetic sequence and the procedures described for Example 347. MS (ES+) m/e 441 (M+H)+.

Example 352

2-(3-(4-((1H-Pyrazol-4-yl)amino)-6-ethoxyquinazolin-2-yl)phenoxy)-N-isopropylacetamide

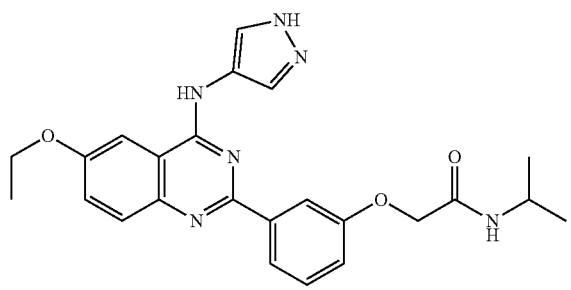 [SMILES: CCOc1ccc2nc(-c3cccc(OCC(=O)NC(C)C)c3)nc(Nc3cn[nH]c3)c2c1]

The title compound was synthesized following the synthetic sequence and the procedures described for Example 334. MS (ES+) m/e 447 (M+H)+.

Example 353

(S)-2-(3-(4-((1H-Pyrazol-4-yl)amino)-6-ethoxyquinazolin-2-yl)phenoxy)-N-(sec-butyl)acetamide

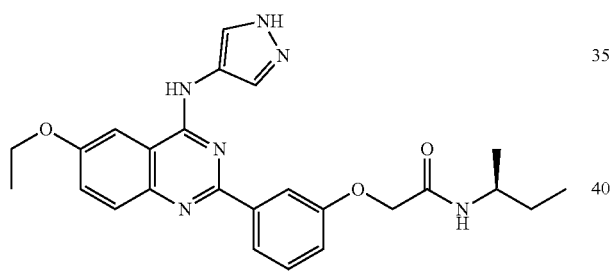

The title compound was synthesized following the synthetic sequence and the procedures described for Example 334. MS (ES+) m/e 461 (M+H)+.

Example 354

2-(3-(4-((1H-Pyrazol-4-yl)amino)-6-ethoxyquinazolin-2-yl)phenoxy)-N-cyclobutylacetamide

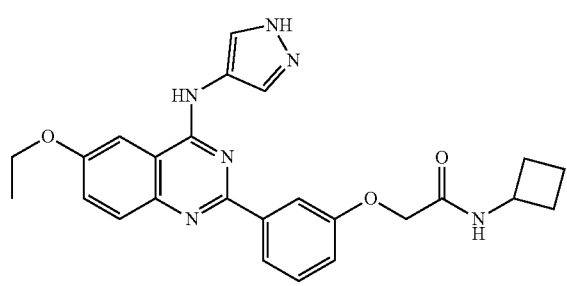 [SMILES: CCOc1ccc2nc(-c3cccc(OCC(=O)NC4CCC4)c3)nc(Nc3cn[nH]c3)c2c1]

The title compound was synthesized following the synthetic sequence and the procedures described for Example 334. MS (ES+) m/e 459 (M+H)+.

Example 355

(R)-2-(3-(4-((1H-Pyrazol-4-yl)amino)-6-ethoxyquinazolin-2-yl)phenoxy)-N-(sec-butyl)acetamide

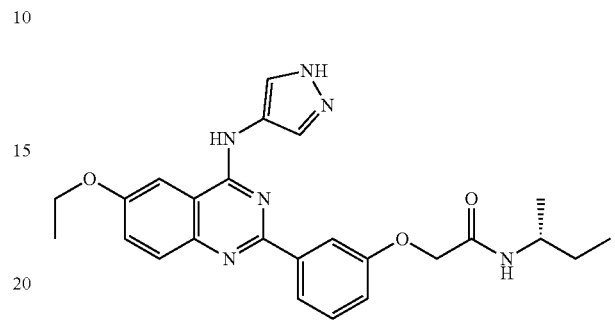

The title compound was synthesized following the synthetic sequence and the procedures described for Example 334. MS (ES+) m/e 461 (M+H)+.

Example 356

2-(3-(4-((1H-Pyrazol-4-yl)amino)-7,8-dihydro-5H-pyrano[4,3-d]pyrimidin-2-yl)phenoxy)-N-(tert-butyl)acetamide

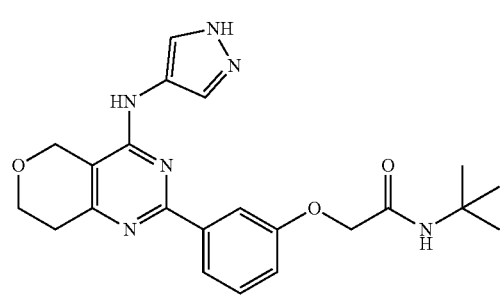 [SMILES: CC(C)(C)NC(=O)COc1cccc(-c2nc3c(c(Nc4cn[nH]c4)n2)COCC3)c1]

Step 1

2-Chloro-N-(1-(tetrahydro-2H-pyran-2-yl)-1H-pyrazol-4-yl)-7,8-dihydro-5H-pyrano[4,3-d]pyrimidin-4-amine

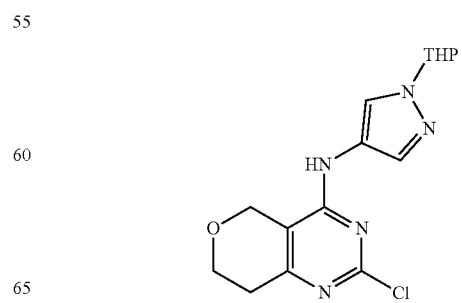

351

To a solution of 2,4-dichloro-7,8-dihydro-5H-pyrano[4,3-d]pyrimidine (251 mg, 1.22 mmol) in DMF (3.5 mL) in a 20 mL vial was added 1-(tetrahydro-2H-pyran-2-yl)-1H-pyrazol-4-amine (205 mg, 1.22 mmol) followed by DIEA (316 mg, 2.45 mmol, 0.426 mL). The reaction was heated at 100° C. overnight. While the reaction mixture was still hot, water was poured into the vial (about 12 mL) and the mixture was cooled to rt. No precipitation took place so the mixture was extracted with EtOAc once and the aqueous layer was separated. The aqueous layer was extracted once more with EtOAc. The combined organic layers were washed twice with water then once with saturated NaCl, dried over sodium sulfate, decanted from the drying agent and concentrated in vacuo to give an oil. Column chromatography (20% EtOAc/80% Hexanes to EtOAc gradient) gave 266 mg, 65%, of the product as a lavender colored solid. MS (ES+) m/e 336/338 (M+H)$^+$.

Step 2

2-(3-(4-((1H-Pyrazol-4-yl)amino)-7,8-dihydro-5H-pyrano[4,3-d]pyrimidin-2-yl)phenoxy)-N-(tert-butyl)acetamide

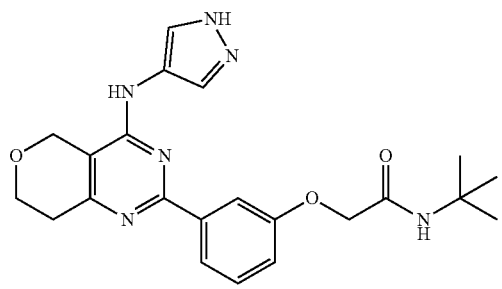 [SMILES: CC(C)(C)NC(=O)COc1cccc(-c2nc3c(c(Nc4cn[nH]c4)n2)COCC3)c1]

To N-(tert-butyl)-2-(3-(4,4,5,5-tetramethyl-1,3,2-dioxaborolan-2-yl)phenoxy) acetamide (26.6 mg, 0.080 mmol) in a 10 mL microwave vessel was added 2-chloro-N-(1-(tetrahydro-2H-pyran-2-yl)-1H-pyrazol-4-yl)-7,8-dihydro-5H-pyrano[4,3-d]pyrimidin-4-amine (26.8 mg, 0.080 mmol), Pd(PPh$_3$)$_4$ (9.2 mg, 0.0080 mmol) and dioxane (0.800 mL). Then a solution of aqueous sodium carbonate (2M, 0.080 mL, 0.160 mmol) and water (0.080 mL) were added. The vessel was flushed with nitrogen then it was irradiated at 150° C. for 1 h 15 min. After the reaction was cooled to rt, an additional amount of the boronic ester (6.8 mg) was added along with additional catalyst (4.0 mg). The reaction was irradiated 30 min at the same temperature. The cooled reaction mixture was transferred to a 20 mL vial with the aid of dioxane. The solvent was removed in vacuo. Then DCM (0.300 mL) and TFA (0.305 mL, 455 mg, 3.99 mmol, 50 eq) were added to the vial. The mixture was stirred at rt for 1 h. The DCM and excess TFA were removed in vacuo to give a residue that was stirred in DMSO/MeOH (1.5 mL/0.2 mL) for 30 min. Filtration and HPLC gave 19.2 mg, 45%, of the title compound as a yellow solid. MS (ES+) m/e 423 (M+H)$^+$.

352

Example 357

2-(3-(4-((1H-Pyrazol-4-yl)amino)-5,7-dihydrofuro[3,4-d]pyrimidin-2-yl)-phenoxy)-N-(tert-butyl)acetamide

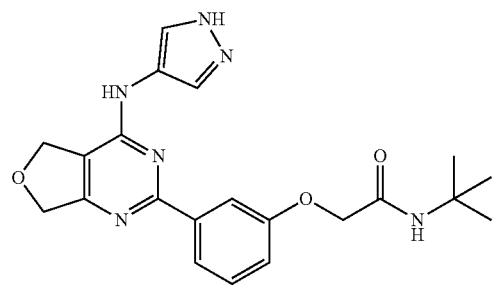 [SMILES: CC(C)(C)NC(=O)COc1cccc(-c2nc3c(c(Nc4cn[nH]c4)n2)COC3)c1]

The title compound was synthesized following the procedures described for Example 356. MS (ES+) m/e 409 (M+H)$^+$.

Example 358

2-(3-(4-((1H-Pyrazol-4-yl)amino)thieno[3,2-d]pyrimidin-2-yl)phenoxy)-N-(tert-butyl)acetamide

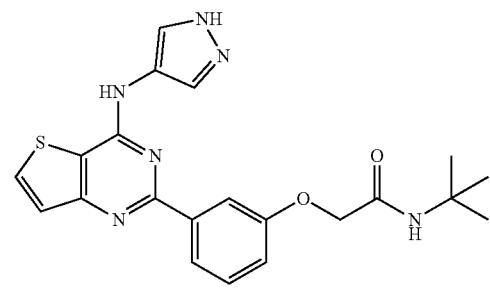 [SMILES: CC(C)(C)NC(=O)COc1cccc(-c2nc(Nc3cn[nH]c3)c3sccc3n2)c1]

The title compound was synthesized following the synthetic procedures described for Example 334. MS (ES+) m/e 423 (M+H)$^+$.

Example 359

2-(3-(4-((1H-Pyrazol-3-yl)amino)-6-ethoxyquinazolin-2-yl)phenoxy)-N-isopropylacetamide

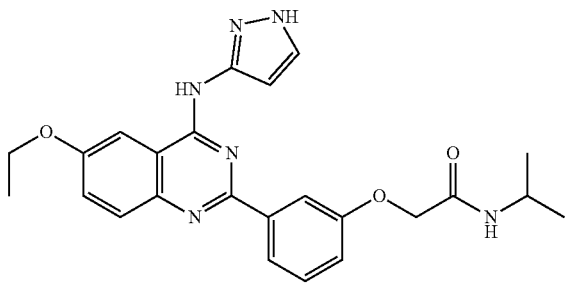 [SMILES: CCOc1ccc2nc(-c3cccc(OCC(=O)NC(C)C)c3)nc(Nc3cc[nH]n3)c2c1]

The title compound was synthesized following the synthetic procedures described for Example 334. MS (ES+) m/e 447 (M+H)⁺.

Example 360

2-(3-(4-((1H-Pyrazol-3-yl)amino)-6-ethoxyquinazolin-2-yl)phenoxy)-N-(1-methylcyclopropyl)acetamide

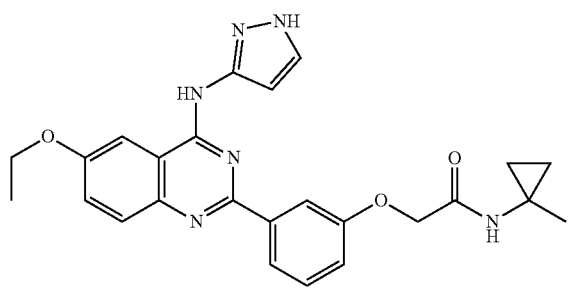 [SMILES: CCOc1ccc2nc(-c3cccc(OCC(=O)NC4(C)CC4)c3)nc(Nc3cc[nH]n3)c2c1]

The title compound was synthesized following the synthetic procedures described for Example 334. MS (ES+) m/e 459 (M+H)⁺.

Example 361

2-(3-(4-((1H-Pyrazol-3-yl)amino)-6-ethoxyquinazolin-2-yl)phenoxy)-N-cyclobutylacetamide

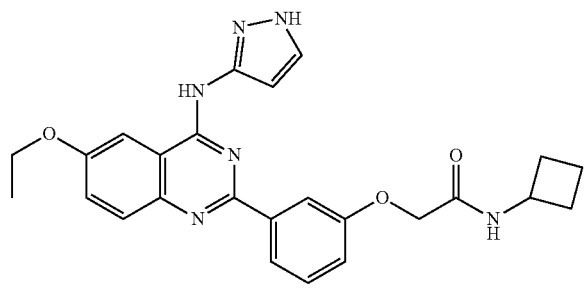 [SMILES: CCOc1ccc2nc(-c3cccc(OCC(=O)NC4CCC4)c3)nc(Nc3cc[nH]n3)c2c1]

The title compound was synthesized following the synthetic procedures described for Example 334. MS (ES+) m/e 459 (M+H)⁺.

Example 362

2-(3-(4-((1H-Pyrazol-3-yl)amino)-6-ethoxyquinazolin-2-yl)phenoxy)-N-(sec-butyl)acetamide

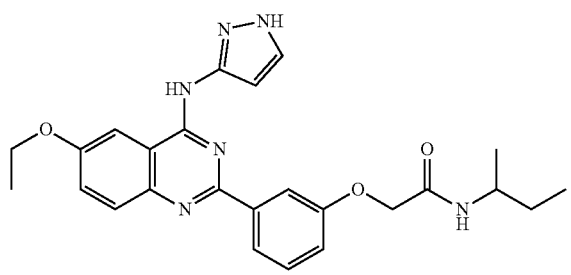 [SMILES: CCOc1ccc2nc(-c3cccc(OCC(=O)NC(C)CC)c3)nc(Nc3cc[nH]n3)c2c1]

The title compound was synthesized following the synthetic procedures described for Example 334. MS (ES+) m/e 461 (M+H)⁺.

Example 363

2-(3-(4-((1H-Pyrazol-3-yl)amino)-6-ethoxyquinazolin-2-yl)phenoxy)-N-cyclopentylacetamide

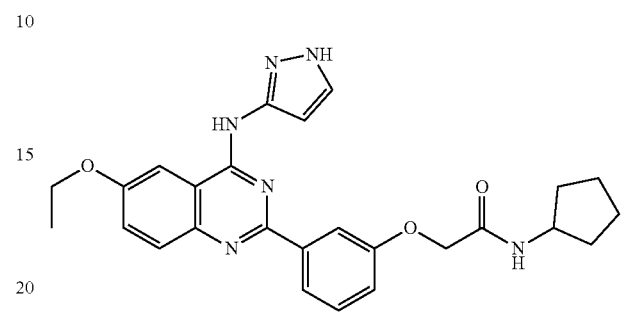

The title compound was synthesized following the synthetic procedures described for Example 334. MS (ES+) m/e 473 (M+H)⁺.

Example 364

2-(3-(4-((1H-Pyrazol-3-yl)amino)-6-ethoxyquinazolin-2-yl)phenoxy)-N-(tert-pentyl)acetamide

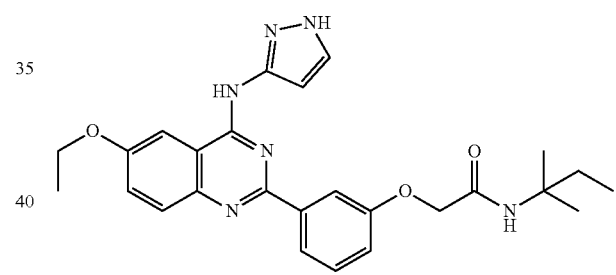

The title compound was synthesized following the synthetic procedures described for Example 334. MS (ES+) m/e 473 (M+H)⁺.

Example 365

2-(3-(4-((1H-Pyrazol-3-yl)amino)-6-ethoxyquinazolin-2-yl)phenoxy)-N-(1,3-difluoropropan-2-yl)acetamide

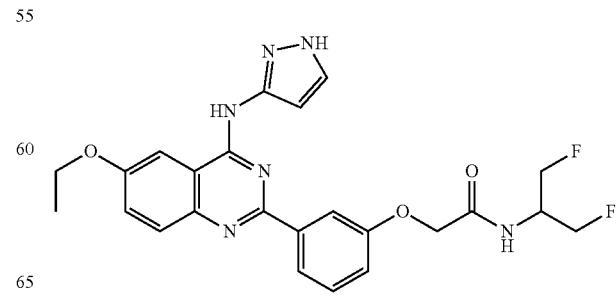

The title compound was synthesized following the synthetic procedures described for Example 334. MS (ES+) m/e 483 (M+H)⁺.

Example 366

2-(3-(4-((1H-Pyrazol-3-yl)amino)-6-ethoxyquinazolin-2-yl)phenoxy)-N-(3,3-difluorocyclobutyl)acetamide

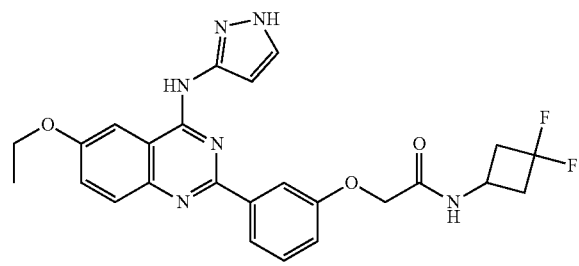 [SMILES: CCOc1ccc2nc(-c3cccc(OCC(=O)NC4CC(F)(F)C4)c3)nc(Nc3cc[nH]n3)c2c1]

The title compound was synthesized following the synthetic procedures described for Example 334. MS (ES+) m/e 495 (M+H)⁺.

Example 367

2-(3-(4-((1H-Pyrazol-4-yl)amino)-6-ethoxyquinazolin-2-yl)phenoxy)-N-isopropylacetamide

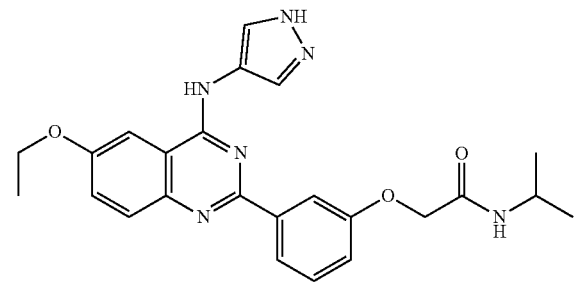 [SMILES: CCOc1ccc2nc(-c3cccc(OCC(=O)NC(C)C)c3)nc(Nc3cn[nH]c3)c2c1]

The title compound was synthesized following the synthetic procedures described for Example 334. MS (ES+) m/e 459 (M+H)⁺.

Example 368

2-(3-(4-((1H-Pyrazol-4-yl)amino)-6-ethoxyquinazolin-2-yl)phenoxy)-N-(sec-butyl)acetamide

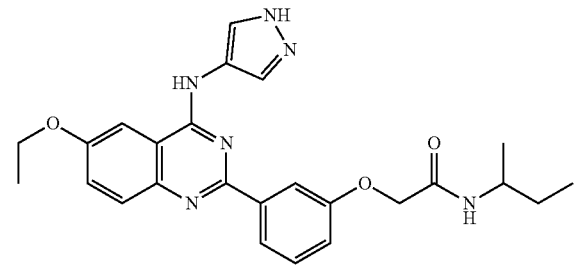 [SMILES: CCOc1ccc2nc(-c3cccc(OCC(=O)NC(C)CC)c3)nc(Nc3cn[nH]c3)c2c1]

The title compound was synthesized following the synthetic procedures described for Example 334. MS (ES+) m/e 461 (M+H)⁺.

Example 369

2-(3-(4-((1H-Pyrazol-4-yl)amino)-6-ethoxyquinazolin-2-yl)phenoxy)-N-cyclopentyl-acetamide

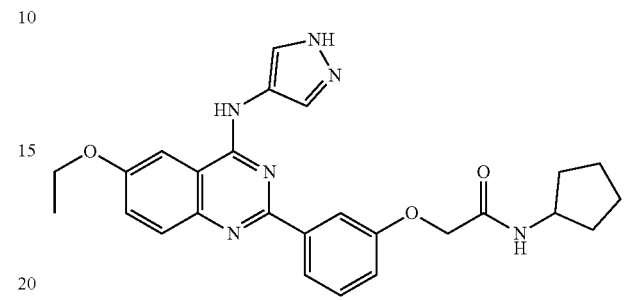

The title compound was synthesized following the synthetic procedures described for Example 334. MS (ES+) m/e 473 (M+H)⁺.

Example 370

2-(3-(4-((1H-Pyrazol-4-yl)amino)-6-ethoxyquinazolin-2-yl)phenoxy)-N-(1,3-difluoropropan-2-yl)acetamide

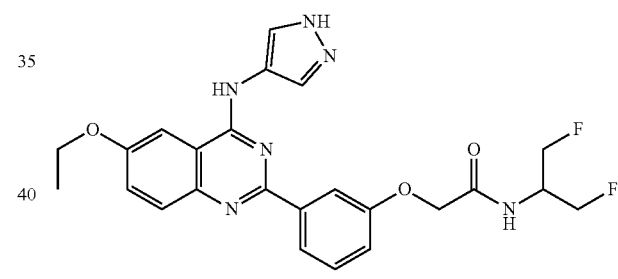

The title compound was synthesized following the synthetic procedures described for Example 334. MS (ES+) m/e 483 (M+H)⁺.

Example 371

2-(3-(4-((1H-Pyrazol-4-yl)amino)-6-ethoxyquinazolin-2-yl)phenoxy)-N-(3,3-difluorocyclobutyl)acetamide

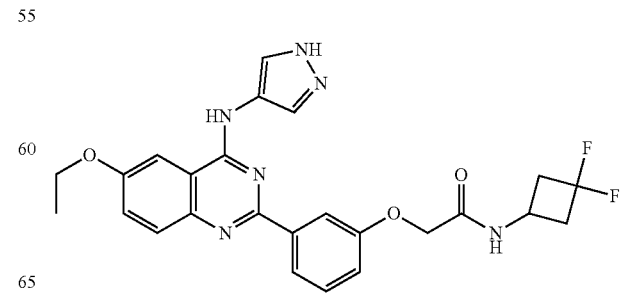

Example 372

2-(3-(4-((1H-Pyrazol-3-yl)amino)-6-ethoxyquinazo-
lin-2-yl)phenoxy)-N-(1-cyclopropylethyl)acetamide

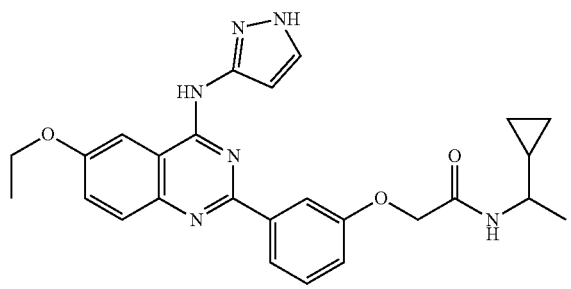 [SMILES: CCOc1ccc2nc(-c3cccc(OCC(=O)NC(C)C4CC4)c3)nc(Nc3cc[nH]n3)c2c1]

The title compound was synthesized following the synthetic procedures described for Example 334. MS (ES+) m/e 473 (M+H)⁺.

Example 373

2-(3-(4-((1H-Pyrazol-4-yl)amino)-6-ethoxyquinazo-
lin-2-yl)phenoxy)-N-(1-cyclopropylethyl)acetamide

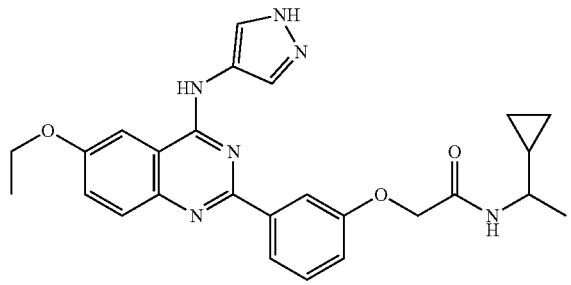 [SMILES: CCOc1ccc2nc(-c3cccc(OCC(=O)NC(C)C4CC4)c3)nc(Nc3cn[nH]c3)c2c1]

The title compound was synthesized following the synthetic procedures described for Example 334. MS (ES+) m/e 473 (M+H)⁺.

Example 374

N-(3-(4-((1H-Pyrazol-4-yl)amino)-6-ethoxyquinazo-
lin-2-yl)benzyl)furan-3-carboxamide

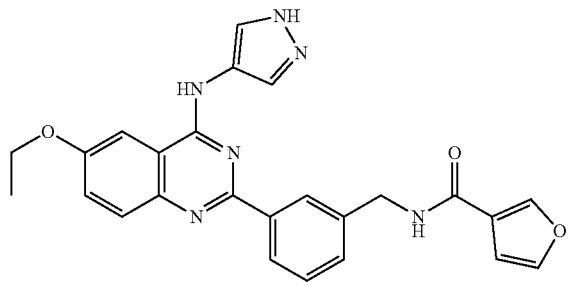 [SMILES: CCOc1ccc2nc(-c3cccc(CNC(=O)c4ccoc4)c3)nc(Nc3cn[nH]c3)c2c1]

The title compound was synthesized following the synthetic procedures described for Example 334. MS (ES+) m/e 495 (M+H)⁺.

Example 375

N-(3-(4-((1H-Pyrazol-4-yl)amino)-6-ethoxyquinazo-
lin-2-yl)phenyl)furan-3-carboxamide

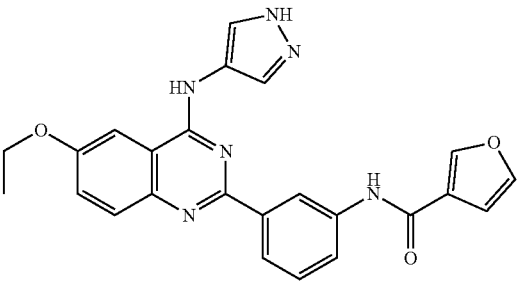 [SMILES: CCOc1ccc2nc(-c3cccc(NC(=O)c4ccoc4)c3)nc(Nc3cn[nH]c3)c2c1]

The title compound was synthesized following the synthetic procedures described for Example 334. MS (ES+) m/e 441 (M+H)⁺.

Example 376

N-(3-(4-((1H-Pyrazol-4-yl)amino)-6-ethoxyquinazo-
lin-2-yl)phenyl)-tetrahydrofuran-3-carboxamide

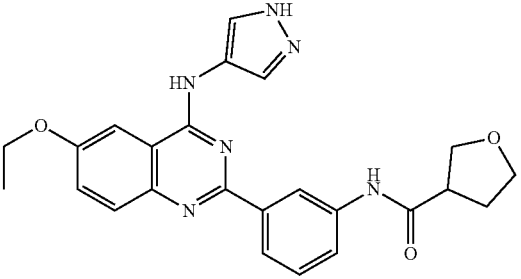 [SMILES: CCOc1ccc2nc(-c3cccc(NC(=O)C4CCOC4)c3)nc(Nc3cn[nH]c3)c2c1]

The title compound was synthesized following the synthetic procedures described for Example 334. MS (ES+) m/e 445 (M+H)⁺.

Example 377

N-(3-(4-((1H-Pyrazol-4-yl)amino)-6-ethoxyquinazo-
lin-2-yl)phenyl)-1-methylpyrrolidine-3-carboxamide

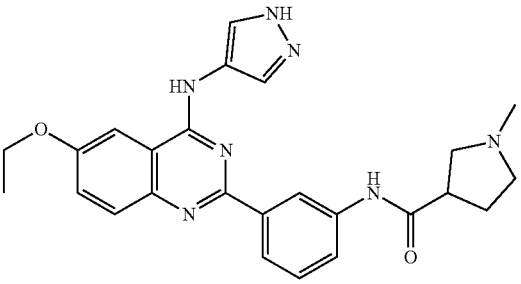 [SMILES: CCOc1ccc2nc(-c3cccc(NC(=O)C4CCN(C)C4)c3)nc(Nc3cn[nH]c3)c2c1]

The title compound was synthesized following the synthetic procedures described for Example 334. MS (ES+) m/e 458 (M+H)+.

Example 378

2-(5-(4-((1H-Pyrazol-4-yl)amino)-6-ethoxyquinazolin-2-yl)-2-fluorophenoxy)-N-isopropylacetamide

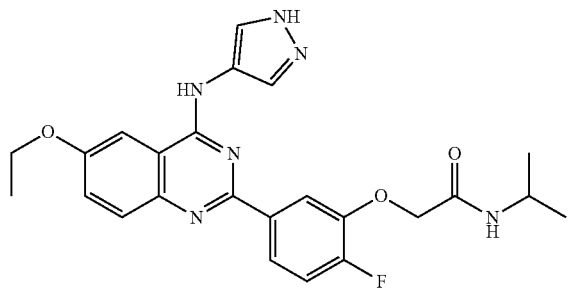 [SMILES: CCOc1ccc2nc(-c3ccc(F)c(OCC(=O)NC(C)C)c3)nc(Nc3cn[nH]c3)c2c1]

Step 1

2-(5-Bromo-2-fluorophenoxy)-N-isopropylacetamide

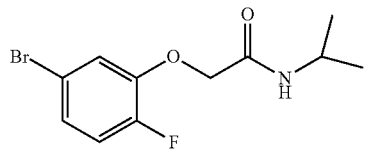 [SMILES: CC(C)NC(=O)COc1cc(Br)ccc1F]

Into a 40 mL vial was added 5-bromo-2-fluorophenol (764 mg, 4.00 mmol), DMF (13.3 mL), and K$_2$CO$_3$ (829 mg, 6.00 mmol). The mixture was then heated overnight at 70° C. The mixture was cooled to rt and poured into water. The aqueous mixture was extracted with EtOAc twice. The combined organic layers were washed with water twice followed by saturated NaCl, dried over sodium sulfate, decanted from the drying agent, and concentrated in vacuo to give 1.08 g, 62%, of the product as a white solid. MS (ES+) m/e 290/292 (M+H)+.

Step 2

2-(2-Fluoro-5-(4,4,5,5-tetramethyl-1,3,2-dioxaborolan-2-yl)phenoxy)-N-isopropylacetamide

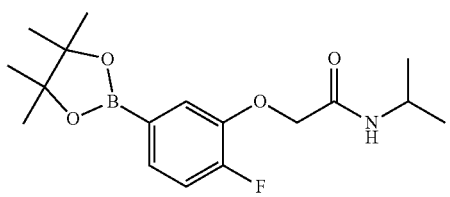 [SMILES: CC(C)NC(=O)COc1cc(B2OC(C)(C)C(C)(C)O2)ccc1F]

To a solution of 2-(5-bromo-2-fluorophenoxy)-N-isopropylacetamide (580 mg, 2.00 mmol) in 1,4-dioxane (13.3 mL) in a 100 mL RBF was added bis(pinacolato)diboron (1.02 g, 4.00 mmol), and KOAc (829 mg, 6.00 mmol). Then PdCl$_2$(dppf)·CH$_2$Cl$_2$ (163 mg, 0.200 mmol) was added and the flask was flushed with nitrogen. The reaction was heated at 110° C. for 2 h after which LC-MS showed the reaction was about 50% complete. An additional amount of KOAc (830 mg, 6.00 mmol), bis(pinacolato)diboron (1.02 g, 4.00 mmol), and catalyst (83 mg, 0.100 mmol) were added to the flask and the reaction mixture was heated at 110° C. for 1 h after which the SM was gone by LC-MS. There was some dimer present by LC-MS as well. The reaction mixture was cooled to rt and diluted with water. The aqueous mixture was extracted with EtOAc. The aqueous layer was separated and extracted once with EtOAc. The organic layers were combined, washed with saturated NaCl, and dried over sodium sulfate. The solution was decanted from the drying agent and concentrated in vacuo to give 2.5 g of a dark brown semisolid. Column chromatography (Hexanes to 40% Hexanes/60% EtOAc gradient) gave 786 mg, 117%, of a light yellow oil. By LC-MS, there was a minor amount of starting bromide present. The oil is used as is in the next step. MS (ES+) m/e 338 (M+H)+.

Step 3

2-(5-(4-((1H-Pyrazol-4-yl)amino)-6-ethoxyquinazolin-2-yl)-2-fluorophenoxy)-N-isopropylacetamide

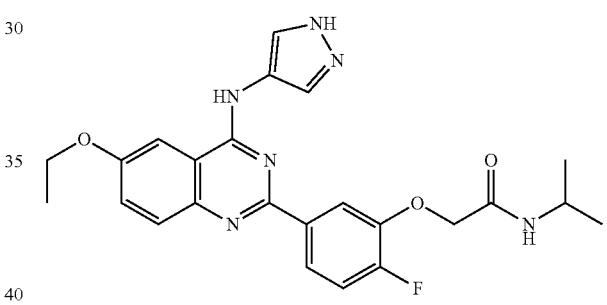

The title compound was synthesized following the synthetic procedure described for Example 334. MS (ES+) m/e 465 (M+H)+.

Example 379

2-(3-(4-((1H-Pyrazol-4-yl)amino)-6-ethoxyquinazolin-2-yl)-2-fluorophenoxy)-N-(tert-butyl)acetamide

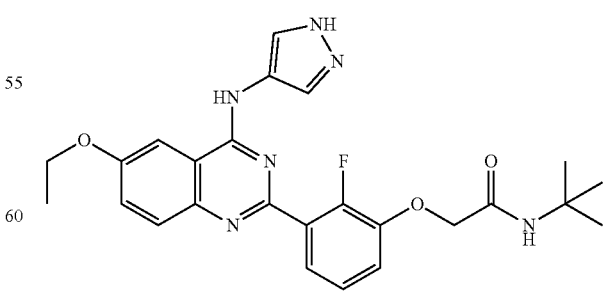

The title compound was synthesized following the synthetic procedures described for Example 334. MS (ES+) m/e 479 (M+H)+.

Example 380

2-(5-(4-((1H-Pyrazol-4-yl)amino)-6-ethoxyquinazolin-2-yl)-2-fluorophenoxy)-N-(tert-butyl)acetamide

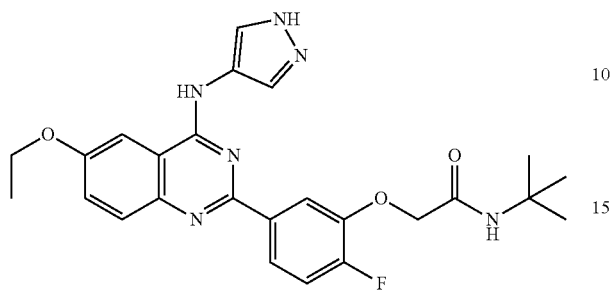

The title compound was synthesized following the synthetic procedures described for Example 334. MS (ES+) m/e 479 (M+H)⁺.

Example 381

2-(3-(4-((6-Aminopyridin-3-yl)amino)-5-methoxypyrimidin-2-yl)phenoxy)-N-(tert-butyl)acetamide

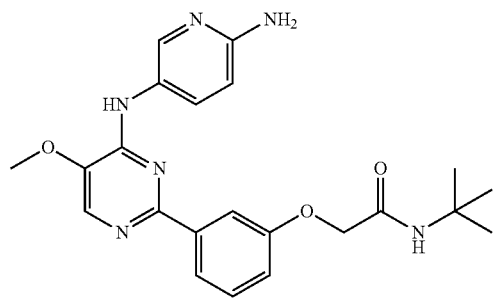 [SMILES: COc1cnc(-c2cccc(OCC(=O)NC(C)(C)C)c2)nc1Nc1ccc(N)nc1]

The title compound was synthesized following the synthetic procedures described for Example 334. MS (ES+) m/e 423 (M+H)⁺.

Example 382

2-(3-(6-((1H-Pyrazol-4-yl)amino)-7-methyl-7H-purin-2-yl)phenoxy)-N-(tert-butyl)acetamide

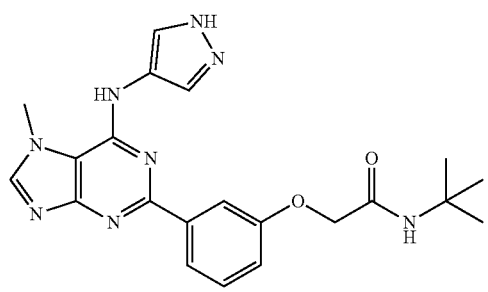 [SMILES: Cn1cnc2nc(-c3cccc(OCC(=O)NC(C)(C)C)c3)nc(Nc3cn[nH]c3)c21]

The title compound was synthesized following the synthetic procedures described for Example 334. MS (ES+) m/e 421 (M+H)⁺.

Example 383

2-(3-(4-((1H-Pyrazol-4-yl)amino)pyrrolo[2,1-f][1,2,4]triazin-2-yl)phenoxy)-N-(tert-butyl)acetamide

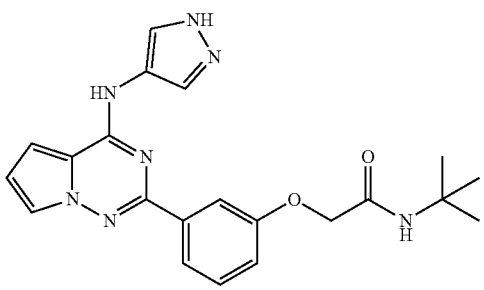 [SMILES: CC(C)(C)NC(=O)COc1cccc(-c2nc(Nc3cn[nH]c3)c3cccn3n2)c1]

The title compound was synthesized following the synthetic procedures described for Example 334. MS (ES+) m/e 406 (M+H)⁺.

Example 384

2-(3-(4-((1H-Pyrazol-4-yl)amino)-1H-pyrazolo[3,4-d]pyrimidin-6-yl)-phenoxy)-N-(tert-butyl)acetamide

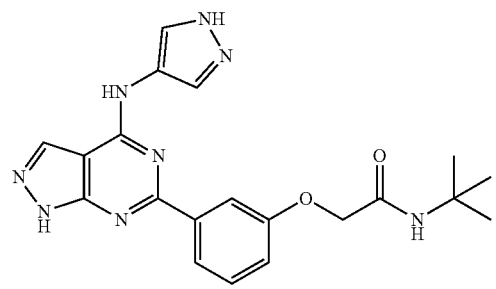 [SMILES: CC(C)(C)NC(=O)COc1cccc(-c2nc(Nc3cn[nH]c3)c3cn[nH]c3n2)c1]

The title compound was synthesized following the synthetic procedures described for Example 334. MS (ES+) m/e 407 (M+H)⁺.

Example 385

2-(3-(4-((1H-Pyrazol-4-yl)amino)-7H-pyrrolo[2,3-d]pyrimidin-2-yl)-phenoxy)-N-(tert-butyl)acetamide

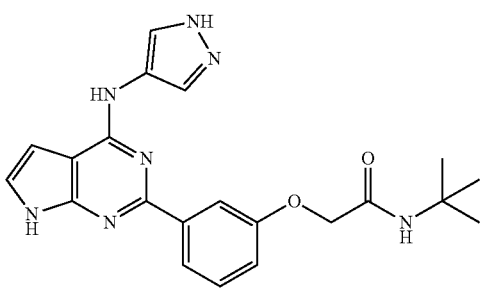 [SMILES: CC(C)(C)NC(=O)COc1cccc(-c2nc(Nc3cn[nH]c3)c3cc[nH]c3n2)c1]

The title compound was synthesized following the synthetic procedures described for Example 334. MS (ES+) m/e 406 (M+H)+.

Example 386

2-(3-(4-((1H-Pyrazol-4-yl)amino)-1-methyl-1H-pyrazolo[3,4-d]pyrimidin-6-yl)phenoxy)-N-(tert-butyl)acetamide

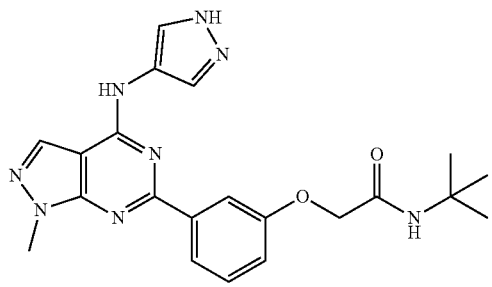 [SMILES: Cn1ncc2c(Nc3cn[nH]c3)nc(-c3cccc(OCC(=O)NC(C)(C)C)c3)nc21]

The title compound was synthesized following the synthetic procedures described for Example 334. MS (ES+) m/e 421 (M+H)+.

Example 387

2-(3-(4-((1H-Pyrazol-3-yl)amino)-6-cyclopropoxyquinazolin-2-yl)phenoxy)-N-(tert-butyl)acetamide

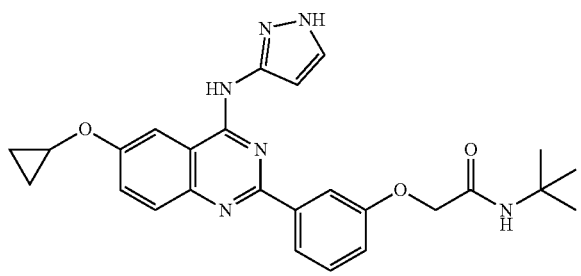 [SMILES: CC(C)(C)NC(=O)COc1cccc(-c2nc(Nc3cc[nH]n3)c3cc(OC4CC4)ccc3n2)c1]

To a solution of N-(tert-butyl)-2-(3-(4-chloro-6-cyclopropoxyquinazolin-2-yl)-phenoxy)acetamide (1.0 g, crude) and 1H-pyrazol-3-amine (195.09 mg, 2.35 mmol) in DMF (8 mL) was added DIEA (607.44 mg, 4.70 mmol, 818.66 μL) at 25° C., and then the reaction mixture was heated to 60° C. and stirred for 12 hours. The mixture was poured into H$_2$O (60 mL) and the aqueous layer was extracted with EtOAc (30 mL×3). The combined organic phases were washed with brine (30 mL×2), dried over anhydrous Na$_2$SO$_4$, filtered and concentrated under reduced pressure. The residue was purified by prep-HPLC to give pure free amine (40 mg) as a white solid. $^1$H NMR (400 MHz, DMSO-d$_6$) δ 12.02 (br s, 1H), 8.54 (d, J=2.0 Hz, 1H), 8.34 (d, J=9.2 Hz, 1H), 8.07-7.99 (m, 2H), 7.91 (d, J=2.4 Hz, 1H), 7.73 (dd, J=2.4, 9.2 Hz, 1H), 7.66 (s, 1H), 7.59 (t, J=8.0 Hz, 1H), 7.28 (dd, J=2.0, 8.0 Hz, 1H), 6.96 (d, J=2.4 Hz, 1H), 4.60 (s, 2H), 4.13-4.06 (m, 1H), 1.29 (s, 9H), 1.00-0.93 (m, 2H), 0.81-0.74 (m, 2H). MS (ES+) m/e 473.3 (M+H)+.

Example 388 (Assays)

The combination of inhibitors of both oxidative phosphorylation and glycolysis synergistically suppress cellular ATP levels. Therefore, our assay utilizes the combination of our glucose uptake inhibitors with oligomycin, a well-characterized inhibitor of ATP synthase. Because oligomycin inhibits ATP derived from oxidative phosphorylation, any remaining ATP production is derived from glycolysis. By reading out cellular ATP levels using the Promega.

Titer Glo kit, we can assess the extent of glycolysis inhibition by our glucose uptake inhibitors. Using this experimental set-up in HT1080 cancer cells, we determined the IC50 of glycolysis inhibition for the compounds.

Example 389 (GLUT1/3 Selectivity)

The GLUT selectivity of the compounds disclosed herein was determined by analyzing the ability of these compounds to inhibit glycolysis in DLD1 WT or DLD GLUT-/- cancer cells that rely on GLUT1 and GLUT3, respectively, for glucose uptake (see FIG. 1.). This assay revealed that the compounds disclosed herein inhibit both GLUT1 and GLUT3, while Bay876 is selective for GLUT1. A control compound thought to inhibit both GLUT1 and GLUT3 was shown to do so in this assay. Using this experimental set-up, it was determined the IC$_{50}$ of glycolysis inhibition for the compounds listed in the table below.

Example 390

T cell assays: Human CD4 T cells were purified using RossetteSep Human CD4 T cell Enrichment Cocktail. Resting T cells were activated with 5 μg/mL plate-bound anti-CD3 and anti-CD28. The previously described glycolysis assay was performed 24 hours post-activation. IL-17 levels in the culture supernatant were measured after 5 days of activation in the presence of 10 ng/mL each of IL-1β, TGF-β and IL-6 on a MAGPIX xMAP instrument (Luminex) using a MILLIPLEX Human IL17A kit (EMD Millipore). To quantify the levels of multiple secreted cytokines, T cells were activated with 5 μg/mL plate-bound anti-CD3 and anti-CD28 for 3 days and the culture supernatant was analyzed on a MAGPIX xMAP instrument using the MILLIPLEX Human Cytokine Premixed 29 Plex Kit. (EMD Millipore).

| Example # | GLUT (nM) HT1080 cells | GLUT1 IC50 (nM) DLD1-WT cells | GLUT3 (% inh) DLD1-KO cells | GLUT3 IC50 (nM) DLD1-KO cells |
|---|---|---|---|---|
| Ex. 8 | 4199 | 0 | 65.7 | |
| Ex. 9 | 5600 | 0 | 8.5 | |
| Ex. 10 | 6210 | 0 | 41.3 | |
| Ex. 11 | 9800 | 0 | 28.8 | |
| Ex. 12 | 6250 | 0 | 20.8 | |
| Ex. 13 | 6790 | 0 | 30.7 | |
| Ex. 14 | >10000 | 0 | 16.7 | |
| Ex. 15 | 8890 | 0 | 21.1 | |
| Ex. 16 | 3560 | 0 | 56.6 | |
| Ex. 17 | 7320 | 0 | 51.5 | |
| Ex. 18 | 5460 | 0 | 47.2 | 697.1 |
| Ex. 19 | 5980 | 0 | 18.9 | |
| Ex. 20 | 4310 | 0 | 45.7 | 560.9 |
| Ex. 21 | 2000 | 0 | 72.3 | 204.9 |
| Ex. 22 | >10000 | 0 | 26.5 | |
| Ex. 23 | 1260 | 0 | 45.1 | 201 |
| Ex. 24 | 1340 | 2.5 | 82.2 | 116 |

| Example # | GLUT (nM) HT1080 cells | GLUT1 IC50 (nM) DLD1-WT cells | GLUT3 (% inh) DLD1-KO cells | GLUT3 IC50 (nM) DLD1-KO cells |
|---|---|---|---|---|
| Ex. 25 | >10000 | | | 2884 |
| Ex. 26 | 2161 | | | 668.4 |
| Ex. 27 | 9853 | | | 1616 |
| Ex. 28 | >10000 | | | 2047 |
| Ex. 30 | >10000 | | | 4890 |
| Ex. 31 | >10000 | | | 2970 |
| Ex. 32 | >10000 | | | 1624 |
| Ex. 33 | >10000 | | | 3579 |
| Ex. 34 | 5361 | | | 309.1 |
| Ex. 35 | 3806 | | | 169.5 |
| Ex. 36 | >10000 | | | 2063 |
| Ex. 37 | 5048 | | | 93 |
| Ex. 38 | 483 | | | 62.2 |
| Ex. 39 | 3508 | | | 175.3 |
| Ex. 40 | 2339 | | | 136.2 |
| Ex. 41 | 8213 | | | 633.9 |
| Ex. 42 | >10000 | | | 2130 |
| Ex. 43 | 2986 | | | 168.1 |
| Ex. 44 | >10000 | | | 621.6 |
| Ex. 45 | 1013 | | | 39.5 |
| Ex. 46 | 1974 | | | 88 |
| Ex. 47 | 3963 | | | 121 |
| Ex. 48 | >10000 | | | 1360 |
| Ex. 49 | >10000 | | | 525 |
| Ex. 50 | 4493 | | | 752 |
| Ex. 51 | 2849 | | | 672 |
| Ex. 52 | 4331 | | | 762 |
| Ex. 53 | >10000 | | | 2980 |
| Ex. 54 | 901 | | | 269 |
| Ex. 55 | 2418 | | | 296 |
| Ex. 56 | 4049 | | | 233 |
| Ex. 57 | 2526 | | | 45 |
| Ex. 58 | 2603 | | | 38 |
| Ex. 59 | >10000 | | | 727 |
| Ex. 60 | 2669 | | | 437 |
| Ex. 61 | >10000 | | | 2339 |
| Ex. 62 | 1916 | | | 303 |
| Ex. 63 | 4505 | | | 568 |
| Ex. 64 | 1254 | | | 106 |
| Ex. 65 | 1206 | | | 94 |
| Ex. 66 | 3145 | | | 268 |
| Ex. 67 | 3827 | | | 189 |
| Ex. 68 | 487 | | | 77 |
| Ex. 69 | 4413 | | | 88 |
| Ex. 70 | 4893 | | | 338 |
| Ex. 71 | 1963 | | | 151 |
| Ex. 72 | 2022 | | | 367 |
| Ex. 73 | 8663 | | | 659.5 |
| Ex. 74 | 2400 | | | 42 |
| Ex. 75 | 1606 | | | 20.5 |
| Ex. 76 | 2737 | | | 685.2 |
| Ex. 77 | 9674 | | | 1661 |
| Ex. 78 | 262 | | | 24.1 |
| Ex. 79 | 767 | | | 10.5 |
| Ex. 80 | >10000 | | | 1493 |
| Ex. 81 | 6486 | | | 956.5 |
| Ex. 82 | 1367 | | | 438.8 |
| Ex. 83 | 1445 | | | 176.3 |
| Ex. 84 | 1997 | | | 197.5 |
| Ex. 85 | 2294 | | | 711.2 |
| Ex. 86 | >10000 | | | 1080 |
| Ex. 87 | 8166 | | | 625.7 |
| Ex. 88 | 669 | | | 51.3 |
| Ex. 89 | 2095 | | | 396.8 |
| Ex. 90 | 7376 | | | 2285 |
| Ex. 91 | >10000 | | | 3986 |
| Ex. 92 | 957 | | | 164.2 |
| Ex. 93 | 721 | | | 14.61 |
| Ex. 94 | 781 | | | 15.27 |
| Ex. 95 | 2254 | | | 231.1 |
| Ex. 96 | 2675 | | | 144.9 |
| Ex. 97 | 1630 | | | 63.51 |
| Ex. 98 | 775 | | | 45.19 |
| Ex. 99 | >10000 | | | 9201 |
| Ex. 100 | >10000 | | | 6891 |
| Ex. 101 | >10000 | | | 6158 |
| Ex. 102 | 2038 | | | 712.1 |
| Ex. 103 | 8459 | | | 2506 |
| Ex. 104 | >10000 | | | 36996 |
| Ex. 105 | 7182 | | | 330.2 |
| Ex. 106 | 1087 | | | 260.1 |
| Ex. 107 | 2306 | | | 132.9 |
| Ex. 108 | 4689 | | | 381.4 |
| Ex. 109 | >10000 | | | 30444 |
| Ex. 110 | >10000 | 105400 | | 343.5 |
| Ex. 111 | 1712 | | | 87.9 |
| Ex. 112 | 2309 | | | 22.91 |
| Ex. 113 | 3586 | | | 84.23 |
| Ex. 114 | 2243 | 16960 | | 174.5 |
| Ex. 115 | 1184 | 9170 | | 82.94 |
| Ex. 116 | 1342 | 6645 | | 93.4 |
| Ex. 117 | 1355 | 5159 | | 106.5 |
| Ex. 118 | 1044 | 5001 | | 67.7 |
| Ex. 119 | 2473 | 12040 | | 149.1 |
| Ex. 120 | 9805 | 27960 | | 380.7 |
| Ex. 121 | 2190 | 7702 | | 204.2 |
| Ex. 122 | 1688 | 5745 | | 58 |
| Ex. 123 | 2169 | 9022 | | 598.1 |
| Ex. 124 | 7790 | 38890 | | 993.9 |
| Ex. 125 | 6647 | 21360 | | 1560 |
| Ex. 126 | 1265 | 4647 | | 173 |
| Ex. 127 | 2702 | 9898 | | 256.2 |
| Ex. 128 | 1806 | 7132 | | 279.3 |
| Ex. 129 | 3244 | 11590 | | 712.7 |
| Ex. 130 | 6452 | 13060 | | 304.9 |
| Ex. 131 | 4789 | 9269 | | 501.9 |
| Ex. 132 | 4810 | 9827 | | 613.1 |
| Ex. 133 | 4868 | 9708 | | 709.1 |
| Ex. 134 | 2514 | 4101 | | 68.9 |
| Ex. 135 | 2988 | 4860 | | 98.7 |
| Ex. 136 | 3230 | 7820 | | 298.2 |
| Ex. 137 | 5252 | 21649 | | 569.8 |
| Ex. 138 | 5202 | >30000 | | 91.5 |
| Ex. 139 | 4179 | 11647 | | 462.9 |
| Ex. 140 | 2892 | >30000 | | 45.4 |
| Ex. 141 | 2425 | 7989 | | 355.5 |
| Ex. 142 | 7544 | | | 285 |
| Ex. 143 | 12520 | | | 320.8 |
| Ex. 144 | 5514 | | | 101.8 |
| Ex. 145 | 1656 | | | 54 |
| Ex. 146 | 3928 | | | 485.1 |
| Ex. 147 | 83870 | | | 180.5 |
| Ex. 148 | 1728 | 4689 | | 3.525 |
| Ex. 149 | 4406 | | | 786.2 |
| Ex. 150 | 11700 | 20050 | | 470.6 |
| Ex. 151 | 5378 | 12200 | | 242.5 |
| Ex. 152 | 13450 | 22640 | | 1845 |
| Ex. 153 | i.a | i.a. | | 70374 |
| Ex. 154 | 37720 | i.a. | | 7735 |
| Ex. 155 | i.a | i.a. | | 3923 |
| Ex. 156 | 16070 | 21650 | | 2777 |
| Ex. 157 | i.a. | i.a. | | 40769 |
| Ex. 158 | 6182 | 15290 | | 199.7 |
| Ex. 159 | 11290 | 28030 | | 783.2 |
| Ex. 160 | 6977 | 13580 | | 247.9 |
| Ex. 161 | 3513 | 5976 | | 71.91 |
| Ex. 162 | 3814 | 6671 | | 416.4 |
| Ex. 163 | 2550 | 4276 | | 104.1 |
| Ex. 164 | 904.6 | 1059 | | 887.9 |
| Ex. 165 | 8546 | 25730 | | 494.3 |
| Ex. 166 | 4294 | 9638 | | 153.1 |
| Ex. 167 | 1683 | 2736 | | 53.7 |
| Ex. 168 | 13280 | 12430 | | 791.5 |
| Ex. 169 | 2673 | 4466 | | 46.08 |
| Ex. 170 | 3530 | 5442 | | 64.43 |
| Ex. 171 | 2498 | 4061 | | 39.92 |
| Ex. 172 | 3810 | 6530 | | 70.5 |
| Ex. 173 | 748.6 | 1512 | | 10.1 |

| Example # | GLUT (nM) HT1080 cells | GLUT1 IC50 (nM) DLD1-WT cells | GLUT3 (% inh) DLD1-KO cells | GLUT3 IC50 (nM) DLD1-KO cells |
|---|---|---|---|---|
| Ex. 174 | 29800 | 28650 | | 467.5 |
| Ex. 175 | 2439 | 2094 | | 20.72 |
| Ex. 176 | i.a. | i.a. | | 3529 |
| Ex. 177 | 3646 | 4903 | | 88.81 |
| Ex. 178 | 886.3 | 1561 | | 53.18 |
| Ex. 179 | 3675 | 6709 | | 164.1 |
| Ex. 180 | 2888 | 5683 | | 295.4 |
| Ex. 181 | | | | |
| Ex. 182 | | | | |
| Ex. 183 | 2229 | 2773 | | 191.6 |
| Ex. 184 | 1929 | 2808 | | 22.27 |
| Ex. 185 | 7090 | 8839 | | 165.4 |
| Ex. 186 | 2316 | 3047 | | 29.96 |
| Ex. 187 | 2616 | 3917 | | 20.47 |
| Ex. 188 | 2615 | 4692 | | 104.6 |
| Ex. 189 | i.a. | i.a. | | 12496 |
| Ex. 190 | i.a. | i.a. | | 62.46? |
| Ex. 191 | 1545 | 3332 | | 101.2 |
| Ex. 192 | 3133 | 5111 | | 515.4 |
| Ex. 193 | 546.1 | 1031 | | 139.6 |
| Ex. 194 | 1116 | 1275 | | 59.26 |
| Ex. 195 | 1672 | 1808 | | 87.88 |
| Ex. 196 | 2179 | 2267 | | 181.8 |
| Ex. 197 | 2275 | 6104 | | 128.5 |
| Ex. 198 | 1295 | 2798 | | 174.4 |
| Ex. 199 | 12980 | 23970 | | 743.3 |
| Ex. 200 | 3985 | 11340 | | 1341 |
| Ex. 201 | 1218 | 2908 | | 65.61 |
| Ex. 202 | 2320 | 3912 | | 99.78 |
| Ex. 203 | 10380 | 12700 | | 1223 |
| Ex. 204 | 6757 | 8017 | | 1054 |
| Ex. 205 | 8108 | 10950 | | 1832 |
| Ex. 206 | 9237 | 16640 | | 1053 |
| Ex. 207 | 6776 | 11690 | | 906.2 |
| Ex. 208 | 9899 | 16050 | | 1691 |
| Ex. 209 | 6311 | 14710 | | 610 |
| Ex. 210 | 3161 | 19910 | | 114.3 |
| Ex. 211 | | | | 134.1 |
| Ex. 212 | | | | 4902 |
| Ex. 213 | | | | 178.6 |
| Ex. 214 | 567 | 1006 | | 6.5 |
| Ex. 215 | 718.2 | 1409 | | 8.527 |
| Ex. 216 | 3450 | 7638 | | 56.02 |
| Ex. 217 | 2658 | 2083 | | 166.3 |
| Ex. 218 | 2333 | 2073 | | 110.3 |
| Ex. 219 | 2411 | 2296 | | 57.47 |
| Ex. 220 | 3674, 4903 | 2248 | | 143.6 |
| Ex. 221 | 7604 | 6683 | | 975.7 |
| Ex. 222 | 2149 | 2771 | | 82.49 |
| Ex. 223 | 3996, 5992 | 3771 | | 97.31 |
| Ex. 224 | 1368 | 1138 | | 57.15 |
| Ex. 225 | 3779 | 2541 | | 29.32 |
| Ex. 226 | 10980 | 12650 | | 36.86 |
| Ex. 227 | 3392, 2909 | 4619 | | 151.5 |
| Ex. 228 | 2904, 2614 | 4580 | | 30.69 |
| Ex. 229 | 6323, 4947 | 7318 | | 85.48 |
| Ex. 230 | 9946 | 20780 | | 95.62 |
| Ex. 231 | 1649 | 4163 | | 316.1 |
| Ex. 232 | 1846 | 3994 | | 263.3 |
| Ex. 233 | 2059 | 4055 | | 304.9 |
| Ex. 234 | 611.9 | 1610 | | 100 |
| Ex. 235 | 2247 | 5101 | | 165.8 |
| Ex. 236 | 2329 | 4685 | | 153.8 |
| Ex. 237 | 948 | 2465 | | 75.88 |
| Ex. 238 | 2959 | 4331 | | 64.32 |
| Ex. 239 | 1210 | 2992 | | 31.31 |
| Ex. 240 | 2145 | 4082 | | 44.16 |
| Ex. 241 | 2254 | 4931 | | 44.54 |
| Ex. 242 | 1378 | 3612 | | 143.5 |
| Ex. 243 | 1675 | 4447 | | 41.71 |
| Ex. 244 | 3499 | 7614 | | 43.58 |
| Ex. 245 | 3474 | 7420 | | 78.5 |
| Ex. 246 | 3234 | 5882 | | 121.2 |
| Ex. 247 | 7371 | 6741 | | 71.18 |
| Ex. 248 | 2580 | 5629 | | 97.36 |
| Ex. 249 | 2372 | 2613 | | 68.63 |
| Ex. 250 | 4014 | 7014 | | 133.6 |
| Ex. 251 | 2778 | 5057 | | 173 |
| Ex. 252 | 3710 | 10370 | | 608.1 |
| Ex. 253 | 4613 | 6467 | | 27.35 |
| Ex. 254 | 5453 | 10420 | | 142.8 |
| Ex. 255 | 4103 | 19330 | | 67.4 |
| Ex. 256 | 3127 | 18840 | | 33.52 |
| Ex. 257 | 1034 | 2549 | | 21.73 |
| Ex. 258 | 1306 | 6292 | | 153.3 |
| Ex. 334 | 22360 | 22470 | | 4197 |
| Ex. 335 | i.a. | 164400 | | 291.2 |
| Ex. 295 | 874.4 | 1115 | | 89.48 |
| Ex. 296 | 15550 | 21340 | | 482.8 |
| Ex. 336 | i.a. | i.a. | | 3475 |
| Ex. 337 | 10190 | 37520 | | 252.6 |
| Ex. 316 | 3260 | 5244 | | 85.38 |
| Ex. 294 | 4492 | 7281 | | 303 |
| Ex. 297 | 2990 | 4906 | | 219.4 |
| Ex. 298 | 12370 | 19820 | | 243.8 |
| Ex. 299 | 4171 | 6659 | | 99.2 |
| Ex. 300 | 8812 | 13380 | | 178.4 |
| Ex. 302 | 2437 | 3808 | | 191 |
| Ex. 305 | 2796 | 4310 | | 90.88 |
| Ex. 301 | 3439 | 4902 | | 148.8 |
| Ex. 303 | 5813 | 11510 | | 72.35 |
| Ex. 304 | 42030 | 34860 | | 163.6 |
| Ex. 306 | 6952 | 11030 | | 178.6 |
| Ex. 307 | 8109 | 10820 | | 193 |
| Ex. 308 | i.a. | i.a. | | 9797 |
| Ex. 309 | 5925 | 10610 | | 312.2 |
| Ex. 310 | 17480 | 23370 | | 683.9 |
| Ex. 311 | 3989 | 6009 | | 183 |
| Ex. 317 | 2725 | 3467 | | 781.4 |
| Ex. 312 | 2870 | 4576 | | 104.9 |
| Ex. 313 | 2724 | 1754 | | 123.7 |
| Ex. 338 | i.a. | 19280 | | 914.8 |
| Ex. 339 | 7859 | 7012 | | 496.8 |
| Ex. 340 | 1502 | 1579 | | 346.1 |
| Ex. 341 | i.a. | i.a. | | 2215 |
| Ex. 342 | 5119 | 2546 | | 258.6 |
| Ex. 343 | i.a. | 11440 | | 846.8 |
| Ex. 344 | 10370 | 4076 | | 681.9 |
| Ex. 288 | 5377 | 2351 | | 506 |
| Ex. 289 | 4385 | 2484 | | 451.4 |
| Ex. 290 | 8819 | 4722 | | 611.3 |
| Ex. 291 | 8982 | 3193 | | 547 |
| Ex. 292 | 7913 | 2691 | | 219.3 |
| Ex. 345 | 3632 | 2439 | | 644.8 |
| Ex. 346 | 7270 | 9489 | | 606.6 |
| Ex. 318 | i.a. | 32050 | | 1424 |
| Ex. 319 | 24540 | 16050 | | 469.3 |
| Ex. 347 | 27980 | 18710 | | 821.4 |
| Ex. 349 | 35280 | 34690 | | 990.1 |
| Ex. 350 | 11310 | 6418 | | 186.1 |
| Ex. 351 | 5039 | 3585 | | 148.6 |
| Ex. 352 | 2940 | 2365 | | 64.89 |
| Ex. 353 | 3206 | 2411 | | 114.7 |
| Ex. 354 | 2254 | 1800 | | 33.44 |
| Ex. 314 | 4380 | 3342 | | 64.22 |
| Ex. 355 | 2471 | 2107 | | 33.03 |
| Ex. 356 | 13880 | 7527 | | 905.5 |
| Ex. 357 | 13880 | 9276 | | 1275 |
| Ex. 358 | 11120 | 16190 | | 418 |
| Ex. 320 | 11120 | 16190 | | 633.7 |
| Ex. 321 | 6133 | 10150 | | 69.56 |
| Ex. 322 | 1357, 1437 | 3168 | | 40.97 |
| Ex. 323 | i.a. | i.a. | | 31.12 |
| Ex. 324 | 4085 | 8076 | | 25.44 |
| Ex. 359 | 7785 | 15530 | | 80.26 |
| Ex. 360 | 5239, 4977 | 8724 | | 44.71 |
| Ex. 361 | 5863, 5726 | 11130 | | 51.72 |
| Ex. 362 | 10020, 9084 | 18770 | | 114.6 |

| Example # | GLUT (nM) HT1080 cells | GLUT1 IC50 (nM) DLD1-WT cells | GLUT3 (% inh) DLD1-KO cells | GLUT3 IC50 (nM) DLD1-KO cells |
|---|---|---|---|---|
| Ex. 363 | 6762 | 13100 | | 81.4 |
| Ex. 364 | 8005 | 10560 | | 80.54 |
| Ex. 365 | 8095 | 10560 | | 138.1 |
| Ex. 366 | 6991 | 8884 | | 50.86 |
| Ex. 325 | i.a. | i.a. | | 904.9 |
| Ex. 326 | i.a. | i.a. | | 369.2 |
| Ex. 327 | i.a. | i.a. | | 290.2 |
| Ex. 328 | i.a. | i.a. | | 901.1 |
| Ex. 329 | i.a. | i.a. | | 651.5 |
| Ex. 330 | 4168 | 6868 | | 60.55 |
| Ex. 331 | i.a. | i.a. | | 1313 |
| Ex. 332 | 2403, 1893 | 3477 | | 23.11 |
| Ex. 367 | 2342, 1874 | 5019 | | 42.39 |
| Ex. 368 | 3794, 3400 | 7972 | | 78.62 |
| Ex. 369 | 3859, 3220 | 6331 | | 62.63 |
| Ex. 370 | 3287, 2817 | 6560 | | 77.15 |
| Ex. 371 | 4323, 3240 | 9005 | | 58.42 |
| Ex. 284 | 2651 | 5027 | | 126.1 |
| Ex. 285 | 5893 | 9719 | | 152.3 |
| Ex. 282 | 6031 | 9684 | | 130.3 |
| Ex. 283 | 36530 | 23300 | | 150.1 |
| Ex. 293 | 6280 | 12930 | | 145.8 |
| Ex. 372 | 7130 | 13050 | | 167.8 |
| Ex. 373 | 2693 | 6016 | | 66.83 |
| Ex. 278 | 13590 | 21750 | | 147.1 |
| Ex. 260 | 4167 | 7656 | | 19.78 |
| Ex. 286 | 2089 | 4089 | | 291.8 |
| Ex. 287 | 2882 | 5045 | | 206.4 |
| Ex. 279 | 15480 | 22560 | | 281.7 |
| Ex. 374 | 10860 | 21190 | | 910.6 |
| Ex. 375 | 3681 | 6771 | | 211.1 |
| Ex. 276 | 2485 | 5113 | | 20.28 |
| Ex. 376 | 5762 | 11130 | | 297.4 |
| Ex. 377 | i.a. | i.a. | | i.a. |
| Ex. 280 | 22290 | i.a. | | 608.3 |
| Ex. 281 | 13960 | 19210 | | 342.7 |
| Ex. 277 | 1963 | 4677 | | 30.39 |
| Ex. 378 | 10360 | 18700 | | 112.9 |
| Ex. 379 | 2271 | 5219 | | 298.7 |
| Ex. 380 | 5481 | 12030 | | 42.95 |
| Ex. 261 | 2074 | 5576 | | 15.67 |
| Ex. 262 | 2135 | 5107 | | 29.3 |
| Ex. 263 | 4437 | 10150 | | 33.05 |
| Ex. 264 | 5640 | 14710 | | 12.13 |
| Ex. 333 | 3038 | 13660 | | 20.12 |
| Ex. 381 | 2614 | 7819 | | 124.2 |
| Ex. 265 | 3919 | 7925 | | 22.22 |
| Ex. 273 | 6073 | 10580 | | 45.84 |
| Ex. 270 | 3755 | 6833 | | 18.14 |
| Ex. 267 | 4541 | 7768 | | 12.65 |
| Ex. 271 | 4739 | 8414 | | 65.26 |
| Ex. 382 | i.a. | i.a. | | 5796 |
| Ex. 383 | 20380 | 85240 | | 1085 |
| Ex. 384 | 3623 | 9113 | | 894.4 |
| Ex. 275 | 1793 | 5412 | | 53.46 |
| Ex. 272 | 4053 | 11750 | | 164.6 |
| Ex. 269 | 2906 | 9755 | | 98 |
| Ex. 266 | 2715 | 7189 | | 27.48 |
| Ex. 274 | 2406 | 5731 | | 111.1 |
| Ex. 268 | 3022 | 10720 | | 18.89 |
| Ex. 385 | 6812 | 15740 | | 508.4 |
| Ex. 386 | 8849 | 25910 | | 674.9 |

The invention claimed is:
1. A compound that is:
2-(3-(4-((1H-pyrazol-4-yl)amino)-6-ethoxyquinazolin-2-yl)phenoxy)-N-(tert-butyl)acetamide;
2-(3-(4-((1H-pyrazol-4-yl)amino)-6-fluoroquinazolin-2-yl)phenoxy)-N-isopropylacetamide;
2-(3-(4-((1H-pyrazol-4-yl)amino)-6-fluoroquinazolin-2-yl)phenoxy)-N-(tert-butyl)acetamide;
2-(3-(4-((1H-pyrazol-4-yl)amino)quinazolin-2-yl)phenoxy)-N-(tert-butyl) acetamide;
2-(3-(4-((1H-pyrazol-4-yl)amino)-7-fluoroquinazolin-2-yl)phenoxy)-N-(tert-butyl)acetamide;
2-(3-(4-((1H-pyrazol-4-yl)amino)-5-fluoroquinazolin-2-yl)phenoxy)-N-(tert-butyl)acetamide;
2-(3-(4-((1H-pyrazol-4-yl)amino)-6-methoxyquinazolin-2-yl)phenoxy)-N-(tert-butyl)acetamide;
N-(tert-butyl)-2-(3-(6-ethoxy-4-((5-methyl-1H-pyrazol-4-yl)amino) quinazolin-2-yl)phenoxy)acetamide;
2-(3-(4-((1H-pyrazol-4-yl)amino)-7-methoxyquinazolin-2-yl)phenoxy)-N-(tert-butyl)acetamide;
2-(3-(4-((1H-pyrazol-3-yl)amino)-6-ethoxyquinazolin-2-yl)phenoxy)-N-(tert-butyl)acetamide;
2-(3-(4-((1H-pyrazol-4-yl)amino)-5-ethoxyquinazolin-2-yl)phenoxy)-N-(tert-butyl)acetamide;
2-(3-(4-((1H-pyrazol-4-yl)amino)-6-ethoxy-5-fluoroquinazolin-2-yl)phenoxy)-N-(tert-butyl)acetamide;
2-(3-(4-((1H-pyrazol-4-yl)amino)-5-methoxyquinazolin-2-yl)phenoxy)-N-(tert-butyl)acetamide;
2-(3-(4-((1H-pyrazol-4-yl)amino)-6-ethoxyquinazolin-2-yl)phenoxy)-N-(tert-pentyl)acetamide;
N-(tert-butyl)-2-(3-(4-((3,5-dimethyl-1H-pyrazol-4-yl)amino)-6-ethoxyquinazolin-2-yl)phenoxy)acetamide;
N-(tert-butyl)-2-(3-(6-ethoxy-4-((5-phenyl-1H-pyrazol-3-yl)amino)quinazolin-2-yl)phenoxy)acetamide;
N-(tert-butyl)-2-(3-(6-ethoxy-4-((5-isopropyl-1H-pyrazol-3-yl)amino)quinazolin-2-yl)phenoxy)acetamide;
2-(3-(4-((5-benzyl-1H-pyrazol-3-yl)amino)-6-ethoxyquinazolin-2-yl) phenoxy)-N-(tert-butyl)acetamide;
2-(3-(4-((1H-pyrazol-4-yl)amino)-6-(2-methoxyethoxy) quinazolin-2-yl) phenoxy)-N-(tert-butyl)acetamide;
2-(3-(4-((1H-pyrazol-4-yl)amino)-6-isopropoxyquinazolin-2-yl)phenoxy)-N-(tert-butyl)acetamide;
2-(3-(4-((1H-pyrazol-4-yl)amino)-5-(2-methoxyethoxy) quinazolin-2-yl)-phenoxy)-N-(tert-butyl)acetamide;
2-(3-(4-((1H-pyrazol-4-yl)amino)-5-(2-fluoroethoxy)quinazolin-2-yl)phenoxy)-N-(tert-butyl)acetamide;
2-(3-(4-((1H-pyrazol-3-yl)amino)-6-methoxyquinazolin-2-yl)phenoxy)-N-(tert-butyl)acetamide;
2-(3-(4-((1H-pyrazol-3-yl)amino)-6-isopropoxyquinazolin-2-yl)phenoxy)-N-(tert-butyl)acetamide;
2-(3-(4-((1H-pyrazol-4-yl)amino)-6-propoxyquinazolin-2-yl)phenoxy)-N-(tert-butyl)acetamide;
2-(3-(4-((1H-pyrazol-3-yl)amino)-6-propoxyquinazolin-2-yl)phenoxy)-N-(tert-butyl)acetamide;
2-(3-(4-((1H-pyrazol-4-yl)amino)-6-cyclopropoxyquinazolin-2-yl)phenoxy)-N-(tert-butyl)acetamide;
2-(3-(4-((1H-pyrazol-4-yl)amino)-5-chloro-6-ethoxyquinazolin-2-yl)phenoxy)-N-(tert-butyl)acetamide;
2-(3-(4-((1H-pyrazol-4-yl)amino)-6-chloro-5-methoxyquinazolin-2-yl)-phenoxy)-N-(tert-butyl)acetamide;
2-(3-(4-((1H-pyrazol-4-yl)amino)-6-cyclobutoxyquinazolin-2-yl)phenoxy)-N-(tert-butyl)acetamide;
2-(3-(4-((1H-pyrazol-4-yl)amino)-5-isopropoxyquinazolin-2-yl)phenoxy)-N-(tert-butyl)acetamide;
2-(3-(4-((1H-pyrazol-3-yl)amino)-5-chloro-6-ethoxyquinazolin-2-yl)phenoxy)-N-(tert-butyl)acetamide;
2-(3-(4-((1H-pyrazol-3-yl)amino)-6-cyclobutoxyquinazolin-2-yl)phenoxy)-N-(tert-butyl)acetamide;
2-(3-(4-((1H-pyrazol-4-yl)amino)-6-isopropoxyquinazolin-2-yl)phenoxy)-N-isopropylacetamide;
2-(3-(4-((1H-pyrazol-4-yl)amino)-6-isopropoxyquinazolin-2-yl)phenoxy)-N-cyclobutylacetamide;
2-(3-(4-((1H-pyrazol-4-yl)amino)-6-isopropoxyquinazolin-2-yl)phenoxy)-N-cyclopentylacetamide;
2-(3-(4-((1H-pyrazol-4-yl)amino)-6-isopropoxyquinazolin-2-yl)phenoxy)-N-(1-methylcyclopropyl)acetamide;

2-(3-(4-((1H-pyrazol-4-yl)amino)-6-cyclobutoxyquinazolin-2-yl)phenoxy)-N-isopropylacetamide;
2-(3-(4-((1H-pyrazol-4-yl)amino)-6-cyclobutoxyquinazolin-2-yl)phenoxy)-N-(sec-butyl)acetamide;
2-(3-(4-((1H-pyrazol-4-yl)amino)-6-cyclobutoxyquinazolin-2-yl)phenoxy)-N-(1-methylcyclopropyl)acetamide;
2-(3-(4-((1H-pyrazol-4-yl)amino)-6-propoxyquinazolin-2-yl)phenoxy)-N-isopropylacetamide;
2-(3-(4-((1H-pyrazol-4-yl)amino)-6-propoxyquinazolin-2-yl)phenoxy)-N-(1-methylcyclopropyl)acetamide;
2-(3-(4-((1H-pyrazol-4-yl)amino)-6-propoxyquinazolin-2-yl)phenoxy)-N-cyclopentylacetamide;
2-(3-(4-((1H-pyrazol-4-yl)amino)-6-propoxyquinazolin-2-yl)phenoxy)-N-(1-fluoro-2-methylpropan-2-yl)acetamide;
2-(3-(4-((1H-pyrazol-4-yl)amino)-6-isopropoxyquinazolin-2-yl)phenoxy)-N-(1-fluoro-2-methylpropan-2-yl)acetamide;
2-(3-(4-((1H-pyrazol-4-yl)amino)-6-ethoxyquinazolin-2-yl)phenoxy)-N-(1-fluoro-2-methylpropan-2-yl)acetamide;
2-(3-(4-((1H-pyrazol-3-yl)amino)-6-ethoxyquinazolin-2-yl)phenoxy)-N-(1-fluoro-2-methylpropan-2-yl)acetamide;
2-(3-(4-((1H-pyrazol-4-yl)amino)-6-propoxyquinazolin-2-yl)phenoxy)-N-(sec-butyl)acetamide;
2-(3-(4-((1H-pyrazol-4-yl)amino)-6-isopropoxyquinazolin-2-yl)phenoxy)-N-(1-fluoro-2-methylpropan-2-yl)acetamide;
2-(3-(4-((1H-pyrazol-4-yl)amino)-6-(methylthio)quinazolin-2-yl)phenoxy)-N-(tert-butyl)acetamide;
2-(3-(4-((1H-pyrazol-4-yl)amino)-6-(methylthio)quinazolin-2-yl)phenoxy)-N-isopropylacetamide;
2-(3-(4-((1H-pyrazol-3-yl)amino)-5-isopropoxyquinazolin-2-yl)phenoxy)-N-(tert-butyl)acetamide;
2-(3-(4-((1H-pyrazol-4-yl)amino)-6-(2,2,2-trifluoroethoxy)quinazolin-2-yl)-phenoxy)-N-(tert-butyl)acetamide;
2-(3-(4-((1H-pyrazol-4-yl)amino)-6-(methylsulfonyl)quinazolin-2-yl)phenoxy)-N-(tert-butyl)acetamide;
2-(3-(4-((1H-pyrazol-4-yl)amino)-6-(methylsulfonyl)quinazolin-2-yl)phenoxy)-N-isopropylacetamide;
2-(3-(4-((1H-pyrazol-4-yl)amino)-6-ethoxy-5-methylquinazolin-2-yl)phenoxy)-N-(tert-butyl)acetamide;
2-(3-(4-((1H-pyrazol-3-yl)amino)-6-(2,2,2-trifluoroethoxy)quinazolin-2-yl)-phenoxy)-N-(tert-butyl)acetamide;
2-(3-(4-((1H-pyrazol-3-yl)amino)-5-ethoxyquinazolin-2-yl)phenoxy)-N-(tert-butyl)acetamide;
2-(3-(4-((1H-pyrazol-4-yl)amino)-6-cyclopropoxyquinazolin-2-yl)phenoxy)-N-isopropylacetamide;
2-(3-(4-((1H-pyrazol-4-yl)amino)-5-ethoxy-6-methylquinazolin-2-yl)phenoxy)-N-(tert-butyl)acetamide;
2-(3-(4-((1H-pyrazol-4-yl)amino)-5-ethoxy-7-methylquinazolin-2-yl)phenoxy)-N-(tert-butyl)acetamide bis trifluoroacetic acid salt;
2-(3-(4-((1H-pyrazol-3-yl)amino)-5-ethoxy-7-methylquinazolin-2-yl)phenoxy)-N-(tert-butyl)acetamide bis trifluoroacetic acid salt;
2-(3-(4-((1H-pyrazol-4-yl)amino)-6-chloro-5-ethoxyquinazolin-2-yl)phenoxy)-N-(tert-butyl)acetamide bis trifluoroacetic acid salt;
2-(3-(4-((1H-pyrazol-4-yl)amino)-5-ethoxy-6-fluoroquinazolin-2-yl)phenoxy)-N-(tert-butyl)acetamide bis trifluoroacetic acid salt;
2-(3-(4-((1H-pyrazol-4-yl)amino)-5-ethoxy-7-fluoroquinazolin-2-yl)phenoxy)-N-(tert-butyl)acetamide bis trifluoroacetic acid salt;
2-(3-(4-((1H-pyrazol-3-yl)amino)-5-(2,2-difluoroethoxy)-6-methylquinazolin-2-yl)phenoxy)-N-(tert-butyl)acetamide bis trifluoroacetic acid salt;
2-(3-(4-((1H-pyrazol-4-yl)amino)-5-(2,2-difluoroethoxy)-6-methylquinazolin-2-yl)phenoxy)-N-(tert-butyl)acetamide bis trifluoroacetic acid salt;
2-(3-(4-((1H-pyrazol-3-yl)amino)-5-(cyclopropylmethoxy)-6-methylquinazolin-2-yl)phenoxy)-N-(tert-butyl)acetamide bis trifluoroacetic acid salt;
2-(3-(4-((1H-pyrazol-4-yl)amino)-5-(cyclopropylmethoxy)-6-methylquinazolin-2-yl)phenoxy)-N-(tert-butyl)acetamide bis trifluoroacetic acid salt;
2-(3-(4-((1H-pyrazol-3-yl)amino)-5-isobutoxy-6-methylquinazolin-2-yl)-phenoxy)-N-(tert-butyl)acetamide bis trifluoroacetic acid salt;
2-(3-(4-((1H-pyrazol-4-yl)amino)-5-isobutoxy-6-methylquinazolin-2-yl)-phenoxy)-N-(tert-butyl)acetamide bis trifluoroacetic acid salt;
2-(3-(4-((1H-pyrazol-3-yl)amino)-6-methyl-5-((3-methyloxetan-3-yl)methoxy)-quinazolin-2-yl)phenoxy)-N-(tert-butyl)acetamide bis trifluoroacetic acid salt;
2-(3-(4-((1H-pyrazol-4-yl)amino)-6-methyl-5-((3-methyloxetan-3-yl)methoxy)-quinazolin-2-yl)phenoxy)-N-(tert-butyl)acetamide bis trifluoroacetic acid salt;
2-(3-(4-((1H-pyrazol-4-yl)amino)-6-(pyrrolidin-1-yl)quinazolin-2-yl)phenoxy)-N-(tert-butyl)acetamide tris trifluoroacetic acid salt;
2-(3-(4-((1H-pyrazol-4-yl)amino)-6-(dimethylamino)quinazolin-2-yl)phenoxy)-N-(tert-butyl)acetamide tris trifluoroacetic acid salt;
2-(3-(4-((1H-pyrazol-4-yl)amino)-6-ethoxy-7-methylquinazolin-2-yl)-phenoxy)-N-(tert-butyl)acetamide bis trifluoroacetic acid salt;
2-(3-(4-((1H-pyrazol-3-yl)amino)-6-ethoxy-7-methylquinazolin-2-yl)-phenoxy)-N-(tert-butyl)acetamide bis trifluoroacetic acid salt;
2-(3-(4-((1H-pyrazol-4-yl)amino)-7-chloro-6-ethoxyquinazolin-2-yl)phenoxy)-N-(tert-butyl)acetamide bis trifluoroacetic acid salt;
2-(3-(4-((1H-pyrazol-3-yl)amino)-7-chloro-6-ethoxyquinazolin-2-yl)phenoxy)-N-(tert-butyl)acetamide bis trifluoroacetic acid salt;
2-(3-(4-((1H-pyrazol-4-yl)amino)-6-(trifluoromethoxy)quinazolin-2-yl)-phenoxy)-N-(tert-butyl)acetamide bis-trifluoroacetic acid salt;
2-(3-(4-((1H-pyrazol-3-yl)amino)-6-(trifluoromethoxy)quinazolin-2-yl)phenoxy)-N-(tert-butyl)acetamide bis-trifluoroacetic acid salt;
2-(3-(4-((1H-pyrazol-4-yl)amino)-6-(cyclopentyloxy)quinazolin-2-yl)phenoxy)-N-(tert-butyl)acetamide bis-trifluoroacetic acid salt;
2-(3-(4-((1H-pyrazol-3-yl)amino)-6-(cyclopentyloxy)quinazolin-2-yl)-phenoxy)-N-(tert-butyl)acetamide bis-trifluoroacetic acid salt;
2-(3-(4-((1H-pyrazol-4-yl)amino)-6-(cyclopentyloxy)quinazolin-2-yl)-phenoxy)-N-isopropylacetamide bis-trifluoroacetic acid salt;
2-(3-(4-((1H-pyrazol-4-yl)amino)-6-(cyclopentyloxy)quinazolin-2-yl)-phenoxy)-N-cyclobutylacetamide bis-trifluoroacetic acid salt;
2-(3-(4-((1H-pyrazol-4-yl)amino)-6-ethoxy-7-fluoroquinazolin-2-yl)-phenoxy)-N-(tert-butyl)acetamide bis-trifluoroacetic acid salt;

N-(tert-butyl)-2-(3-(6-ethoxy-4-((5-fluoro-1H-pyrazol-3-yl)amino)-quinazolin-2-yl)phenoxy)acetamide;
N-(tert-butyl)-2-(3-(6-ethoxy-4-((5-methoxy-1H-pyrazol-3-yl)amino)-quinazolin-2-yl)phenoxy)acetamide;
N-(tert-butyl)-2-(3-(6-ethoxy-4-((5-ethyl-1H-pyrazol-3-yl)amino)-quinazolin-2-yl)phenoxy)acetamide;
N-(tert-butyl)-2-(3-(6-ethoxy-4-((4-methyl-1H-pyrazol-3-yl)amino)-quinazolin-2-yl)phenoxy)acetamide;
N-(tert-butyl)-2-(3-(4-((4,5-dimethyl-1H-pyrazol-3-yl)amino)-6-ethoxyquinazolin-2-yl)phenoxy)acetamide;
N-(tert-butyl)-2-(3-(4-((5-cyclobutyl-1H-pyrazol-3-yl)amino)-6-ethoxyquinazolin-2-yl)phenoxy)acetamide;
N-(tert-butyl)-2-(3-(4-((5-(difluoromethyl)-1H-pyrazol-3-yl)amino)-6-ethoxyquinazolin-2-yl)phenoxy)acetamide;
N-(tert-butyl)-2-(3-(4-((4-chloro-1H-pyrazol-3-yl)amino)-6-ethoxyquinazolin-2-yl)phenoxy)acetamide;
N-(tert-butyl)-2-(3-(4-((4-cyclopropyl-1H-pyrazol-3-yl)amino)-6-ethoxyquinazolin-2-yl)phenoxy)acetamide;
N-(tert-butyl)-2-(3-(4-((3-chloro-5-methyl-1H-pyrazol-4-yl)amino)-6-ethoxyquinazolin-2-yl)phenoxy)acetamide;
N-(tert-butyl)-2-(3-(6-ethoxy-4-((4-(trifluoromethyl)-1H-pyrazol-3-yl)amino)-quinazolin-2-yl)phenoxy)acetamide;
N-(tert-butyl)-2-(3-(4-((3-cyclopropyl-1H-pyrazol-4-yl)amino)-6-ethoxyquinazolin-2-yl)phenoxy)acetamide;
N-(tert-butyl)-2-(3-(4-((5-cyclopropyl-1H-pyrazol-3-yl)amino)-6-ethoxyquinazolin-2-yl)phenoxy)acetamide;
N-(tert-butyl)-2-(3-(4-((5-chloro-1H-pyrazol-4-yl)amino)-6-ethoxyquinazolin-2-yl)phenoxy)acetamide;
N-(tert-butyl)-2-(3-(6-ethoxy-4-((5-(trifluoromethyl)-1H-pyrazol-4-yl)amino)-quinazolin-2-yl)phenoxy)acetamide;
N-(tert-butyl)-2-(3-(6-ethoxy-4-((5-methyl-1H-pyrazol-3-yl)amino)-quinazolin-2-yl)phenoxy)acetamide;
2-(3-(4-((1H-pyrazol-4-yl)amino)-6-(trifluoromethyl)quinazolin-2-yl)-phenoxy)-N-(tert-butyl)acetamide;
2-(3-(4-((1H-pyrazol-4-yl)amino)-7-(trifluoromethyl)quinazolin-2-yl)-phenoxy)-N-(tert-butyl)acetamide;
2-(3-(4-((1H-pyrazol-4-yl)amino)-8-(trifluoromethyl)quinazolin-2-yl)-phenoxy)-N-(tert-butyl)acetamide;
2-(3-(4-((1H-pyrazol-4-yl)amino)-7-fluoro-6-methoxyquinazolin-2-yl)-phenoxy)-N-(tert-butyl)acetamide;
2-(3-(4-((1H-pyrazol-4-yl)amino)-6-ethoxyquinazolin-2-yl)phenoxy)-N-isopropylacetamide;
(S)-2-(3-(4-((1H-pyrazol-4-yl)amino)-6-ethoxyquinazolin-2-yl)phenoxy)-N-(sec-butyl)acetamide;
2-(3-(4-((1H-pyrazol-4-yl)amino)-6-ethoxyquinazolin-2-yl)phenoxy)-N-cyclobutylacetamide;
(R)-2-(3-(4-((1H-pyrazol-4-yl)amino)-6-ethoxyquinazolin-2-yl)phenoxy)-N-(sec-butyl)acetamide;
2-(3-(4-((1H-pyrazol-3-yl)amino)-6-ethoxyquinazolin-2-yl)phenoxy)-N-isopropylacetamide;
2-(3-(4-((1H-pyrazol-3-yl)amino)-6-ethoxyquinazolin-2-yl)phenoxy)-N-(1-methylcyclopropyl)acetamide;
2-(3-(4-((1H-pyrazol-3-yl)amino)-6-ethoxyquinazolin-2-yl)phenoxy)-N-cyclobutylacetamide;
2-(3-(4-((1H-pyrazol-3-yl)amino)-6-ethoxyquinazolin-2-yl)phenoxy)-N-(sec-butyl)acetamide;
2-(3-(4-((1H-pyrazol-3-yl)amino)-6-ethoxyquinazolin-2-yl)phenoxy)-N-cyclopentylacetamide;
2-(3-(4-((1H-pyrazol-3-yl)amino)-6-ethoxyquinazolin-2-yl)phenoxy)-N-(tert-pentyl)acetamide;
2-(3-(4-((1H-pyrazol-3-yl)amino)-6-ethoxyquinazolin-2-yl)phenoxy)-N-(1,3-difluoropropan-2-yl)acetamide;
2-(3-(4-((1H-pyrazol-3-yl)amino)-6-ethoxyquinazolin-2-yl)phenoxy)-N-(3,3-difluorocyclobutyl)acetamide;
2-(3-(4-((1H-pyrazol-4-yl)amino)-6-ethoxyquinazolin-2-yl)phenoxy)-N-isopropylacetamide;
2-(3-(4-((1H-pyrazol-4-yl)amino)-6-ethoxyquinazolin-2-yl)phenoxy)-N-(sec-butyl)acetamide;
2-(3-(4-((1H-pyrazol-4-yl)amino)-6-ethoxyquinazolin-2-yl)phenoxy)-N-cyclopentyl-acetamide;
2-(3-(4-((1H-pyrazol-4-yl)amino)-6-ethoxyquinazolin-2-yl)phenoxy)-N-(1,3-difluoropropan-2-yl)acetamide;
2-(3-(4-((1H-pyrazol-4-yl)amino)-6-ethoxyquinazolin-2-yl)phenoxy)-N-(3,3-difluorocyclobutyl)acetamide;
2-(3-(4-((1H-pyrazol-3-yl)amino)-6-ethoxyquinazolin-2-yl)phenoxy)-N-(1-cyclopropylethyl)acetamide;
2-(3-(4-((1H-pyrazol-4-yl)amino)-6-ethoxyquinazolin-2-yl)phenoxy)-N-(1-cyclopropylethyl)acetamide;
2-(3-(4-((1H-pyrazol-3-yl)amino)-6-cyclopropoxyquinazolin-2-yl)phenoxy)-N-(tert-butyl)acetamide;
6-ethoxy-2-(3-(2-(3-methylmorpholino)ethoxy)phenyl)-N-(1H-pyrazol-4-yl)quinazolin-4-amine;
6-ethoxy-2-(3-(3-methylmorpholino)propoxy)phenyl)-N-(1H-pyrazol-4-yl)quinazolin-4-amine;
6-fluoro-2-(3-(3-morpholinopropoxy)phenyl)-N-(1H-pyrazol-4-yl)quinazolin-4-amine;
N-(2-(3-(4-((1H-pyrazol-4-yl)amino)-6-fluoroquinazolin-2-yl)phenoxy)ethyl)pivalamide;
N-(2-(3-(4-((1H-pyrazol-4-yl)amino)-6-ethoxyquinazolin-2-yl)phenoxy)ethyl)pivalamide;
6-ethoxy-N-(5-methyl-1H-pyrazol-4-yl)-2-(3-(3-morpholinopropoxy)phenyl)quinazolin-4-amine;
6-ethoxy-2-(3-((1-methyl-1H-pyrazol-4-yl)methoxy)phenyl)-N-(1H-pyrazol-3-yl)quinazolin-4-amine;
6-ethoxy-2-(3-((5-methyl-1,3,4-oxadiazol-2-yl)methoxy)phenyl)-N-(1H-pyrazol-3-yl)quinazolin-4-amine;
6-ethoxy-2-(3-((5-methylisoxazol-3-yl)methoxy)phenyl)-N-(1H-pyrazol-3-yl)quinazolin-4-amine;
N-(3-(4-((1H-pyrazol-3-yl)amino)-6-ethoxyquinazolin-2-yl)phenyl)-tetrahydrofuran-3-carboxamide;
N-(3-(4-((1H-pyrazol-3-yl)amino)-6-ethoxyquinazolin-2-yl)phenyl)-furan-3-carboxamide;
N-(3-(4-((1H-pyrazol-4-yl)amino)-6-ethoxyquinazolin-2-yl)benzyl)furan-3-carboxamide;
N-(3-(4-((1H-pyrazol-4-yl)amino)-6-ethoxyquinazolin-2-yl)phenyl)furan-3-carboxamide;
N-(3-(4-((1H-pyrazol-4-yl)amino)-6-ethoxyquinazolin-2-yl)phenyl)-tetrahydrofuran-3-carboxamide;
N-(3-(4-((1H-pyrazol-4-yl)amino)-6-ethoxyquinazolin-2-yl)phenyl)-1-methylpyrrolidine-3-carboxamide;
2-(3-(4-((1H-pyrazol-4-yl)amino)thieno[3,2-d]pyrimidin-2-yl)phenoxy)-N-isopropylacetamide;
2-(3-(4-((1H-pyrazol-4-yl)amino)-7,8-dihydro-5H-pyrano[4,3-d]pyrimidin-2-yl)phenoxy)-N-(tert-butyl)acetamide;
2-(3-(4-((1H-pyrazol-4-yl)amino)-5,7-dihydrofuro[3,4-d]pyrimidin-2-yl)-phenoxy)-N-(tert-butyl)acetamide;
2-(3-(4-((1H-pyrazol-4-yl)amino)thieno[3,2-d]pyrimidin-2-yl)phenoxy)-N-(tert-butyl)acetamide;
2-(3-(6-((1H-pyrazol-4-yl)amino)-7-methyl-7H-purin-2-yl)phenoxy)-N-(tert-butyl)acetamide;
2-(3-(4-((1H-pyrazol-4-yl)amino)-1H-pyrazolo[3,4-d]pyrimidin-6-yl)-phenoxy)-N-(tert-butyl)acetamide;
2-(3-(4-((1H-pyrazol-4-yl)amino)-7H-pyrrolo[2,3-d]pyrimidin-2-yl)-phenoxy)-N-(tert-butyl)acetamide;
2-(3-(4-((1H-pyrazol-4-yl)amino)-1-methyl-1H-pyrazolo[3,4-d]pyrimidin-6-yl)phenoxy)-N-(tert-butyl)acetamide;
or a pharmaceutically acceptable salt thereof.

2. A pharmaceutical dosage form comprising a compound according to claim 1 and a pharmaceutically acceptable excipient.

* * * * *